(12) United States Patent
Cannizzaro et al.

(10) Patent No.: US 7,741,345 B2
(45) Date of Patent: Jun. 22, 2010

(54) AZA-PEPTIDE PROTEASE INHIBITORS

(75) Inventors: Carina E. Cannizzaro, Foster City, CA (US); James M. Chen, San Ramon, CA (US); Manoj C. Desai, Pleasant Hill, CA (US); Michael L. Mitchell, Hayward, CA (US); Sundaramoorthi Swaminathan, Burlingame, CA (US); Lianhong Xu, Palo Alto, CA (US)

(73) Assignee: Gilead Sciences, Inc., Foster City, CA (US)

( * ) Notice: Subject to any disclaimer, the term of this patent is extended or adjusted under 35 U.S.C. 154(b) by 235 days.

(21) Appl. No.: 11/880,067

(22) Filed: Jul. 19, 2007

(65) Prior Publication Data

US 2009/0099096 A1 Apr. 16, 2009

Related U.S. Application Data

(60) Provisional application No. 60/832,459, filed on Jul. 21, 2006.

(51) Int. Cl.
*A61K 31/4427* (2006.01)
*A61K 31/443* (2006.01)
*C07D 405/02* (2006.01)

(52) U.S. Cl. .................. 514/338; 546/283.7; 546/284.1

(58) Field of Classification Search ............. 546/283.7, 546/284.1; 514/338
See application file for complete search history.

(56) References Cited

U.S. PATENT DOCUMENTS

| | | | |
|---|---|---|---|
| 4,816,570 | A | 3/1989 | Farquhar |
| 4,968,788 | A | 11/1990 | Farquhar |
| 5,461,067 | A | 10/1995 | Norbeck et al. |
| 5,663,159 | A | 9/1997 | Starrett, Jr. et al. |
| 5,792,756 | A | 8/1998 | Starrett, Jr. et al. |
| 5,912,352 | A | 6/1999 | Fassler et al. |
| 2004/0100960 | A1 | 5/2004 | Mehta |
| 2005/0159469 | A1 | 7/2005 | Randolph et al. |

FOREIGN PATENT DOCUMENTS

WO WO-2005/061487 7/2005
WO WO-2005064008 7/2005

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
Bold, G.-et al. (1998) "New Aza-Dipeptide Analogues as Potent and Orally Absorbed HIV-1 Protease Inhibitors: Candidates for Clinical Development" *J. Med. Chem.* 41:3387-3401.
Ermolieff, J. et al. (1997) "Kinetic Properties of Saquinavir-Resistant Mutants of HIV Type 1 Protease and their Implications in Drug Resistance in Vivo" *Biochemistry* 36:12364-12370.
Farquhar, D. et al. (1983) "Biologically Reversible Phosphate-Protective Groups" *J. Pharm. Sci.* 72(3):324-325.
Miller, J. (2004) "Novel arylsuflonamides possessing sub-picomolar HIV protease activities and potent anti-HIV activity against wild-type and drug-resistant viral strains" *Bioorg. Med. Chem. Ltr.* 14:959-963.
Toth, M. et al (1990) "A simple, continuous fluorometric assay for HIV protease" *Int. J. Peptide Protein Res.* 36:544-550.
Weislow, O., et al. (1989) "New Soluble-Formazan Assay for HIV-1 Cytopathic Effects: Application to High-Flux Screening of Synthetic and Natural Products for AIDS-Antiviral Activity" *J. of the Nat'l. Cancer Inst.* 81(8) 577-586.

* cited by examiner

*Primary Examiner*—Kamal A Saeed
*Assistant Examiner*—Samantha L Shterengarts
(74) *Attorney, Agent, or Firm*—Cynthia H. Zhang

(57) ABSTRACT

The invention is related to compounds of Formula I:

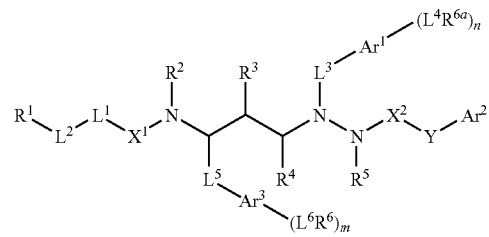

Formula I or a pharmaceutically acceptable salt, solvate, ester, and/or phosphonate thereof, compositions containing such compounds, and therapeutic methods that include the administration of such compounds.

21 Claims, No Drawings

AZA-PEPTIDE PROTEASE INHIBITORS

CROSS-REFERENCE TO RELATED APPLICATIONS

This application claims priority to U.S. Provisional Application Ser. No. 60/832,459, filed Jul. 21, 2006. The content of this provisional application is herein incorporated by reference in its entirety for all purposes.

FIELD OF THE INVENTION

This invention relates to novel HIV protease inhibitors, pharmaceutical compositions thereof, processes for making the novel HIV protease inhibitors, and methods for inhibiting and treating an HIV infection.

BACKGROUND OF THE INVENTION

In recent years, inhibitors of HIV protease have become an important class of therapeutic agents for inhibition and treatment of HIV infection in humans. HIV protease inhibitors are especially effective when administered in combination with other classes of HIV therapeutic agents, especially inhibitors of HIV reverse transcriptase, e.g. in "cocktails" of two or more HIV therapeutic agents.

On-going treatment of HIV-infected individuals with compounds that inhibit HIV protease has led to the development of mutant viruses that possess proteases that are resistant to the inhibitory effect of approved, commercially available HIV therapeutic agents currently in clinical use. Thus, to be effective, new HIV protease inhibitors must be effective not only against wild-type strains of HIV, but must also demonstrate efficacy against the newly emerging mutant strains that are resistant to the commercially available protease inhibitors. Accordingly, there continues to be a need for new HIV protease inhibitors, for example those targeting the HIV protease in both wild type and mutant strains of HIV.

SUMMARY OF THE INVENTION

Accordingly, in one embodiment, the present application provides novel HIV protease inhibitor compounds of Formula (I):

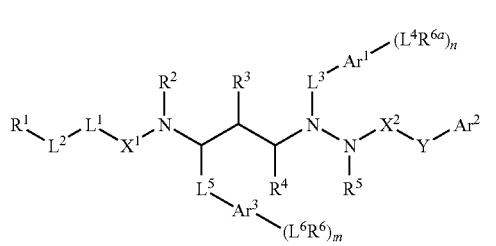

(I)

wherein, $X^1$ and $X^2$ are each independently —C(O)—, —C(S)—, —S(O)—, or —S(O)$_n$—;

Y is —O—, —NR$^7$—, or —S—;

$L^1$ is —O—, alkylene, substituted alkylene, alkenylene, substituted alkenylene, alkynylene, or substituted alkynylene;

$L^2$ is a covalent bond or —NR$^8$—;

with the proviso that when $L^1$ is alkylene and $L^2$ is a covalent bond, $R^1$ is not a substituted heterocyclyl selected from the group of heterocyclyls consisting of:

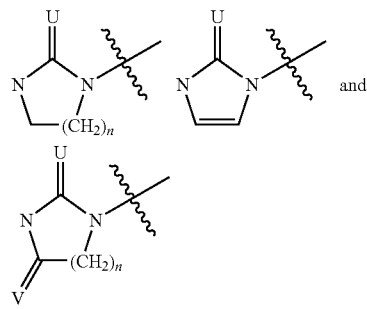

wherein U and V are independently O, S, or NH; n is 1 or 2;

$L^3$ and $L^5$ are each independently a covalent bond, alkylene or substituted alkylene;

$L^4$ and $L^6$ are each independently a bond, —O—, —CH$_2$—, —NR$^7$— or —OCH$_2$—, —CH$_2$O—;

$Ar^1$, $Ar^2$, and $Ar^3$ are each independently cycloalkyl, substituted cycloalkyl, cycloalkenyl, substituted cycloalkenyl, aryl, substituted aryl, heterocyclyl, or substituted heterocyclyl;

$R^1$ is cycloalkyl, substituted cycloalkyl, cycloalkenyl, substituted cycloalkenyl, aryl, substituted aryl, heterocyclyl, or substituted heterocyclyl, —C(O)R$^9$, and —C(O)OR$^9$;

$R^2$ is H, alkyl, or substituted alkyl;

$R^3$ is —OH or —O-PG wherein PG is a protecting group;

$R^4$ is H, alkyl, or substituted alkyl;

$R^5$ is H, alkyl, or substituted alkyl;

$R^6$ and $R^{6a}$ are each independently H, halo, cyano, alkyl, substituted alkyl, haloalkyl, substituted haloalkyl, alkenyl, substituted alkenyl, alkynyl, substituted alkynyl, cycloalkyl, substituted cycloalkyl, cycloalkenyl, substituted cycloalkenyl, heterocyclyl, substituted heterocyclyl, aryl, or substituted aryl;

each $R^7$ is H, alkyl, or substituted alkyl;

$R^8$ is H, alkyl, or substituted alkyl;

$R^9$ is H, alkyl, substituted alkyl, alkenyl, substituted alkenyl, alkynyl, substituted alkynyl, cycloalkyl, substituted cycloalkyl, cycloalkenyl, substituted cycloalkenyl, heterocyclyl, substituted heterocyclyl, aryl, or substituted aryl;

m is 0, 1, 2, 3, 4, or 5;

n is 0, 1, 2, 3, 4, or 5;

or a pharmaceutically acceptable salt, solvate, and/or ester thereof.

In another embodiment, the present invention provides a pharmaceutical composition comprising a pharmaceutically acceptable carrier and a therapeutically effective amount of a compound of Formula I or pharmaceutically acceptable salt, solvate, and/or ester thereof.

In another embodiment, the present application provides a method for treating HIV infections which comprises administering to a patient in need of such treatment a therapeutically effective amount of at least one compound of Formula I, or a pharmaceutically acceptable salt, solvate, and/or ester thereof.

In another embodiment, the present application provides a method for treating HIV infections which comprises administering to a patient in need of such treatment a therapeutically effective combination of (a) one or more compounds of Formula I and (b) another therapeutic agent (e.g., one or more compounds selected from HIV reverse transcriptase inhibitors and HIV protease inhibitors).

In another embodiment, the present invention provides a method of treating HIV infection which comprises administering to a patient in need thereof a therapeutically effective amount of: (a) a compound of Formula I; and, (b) at least one compound selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, $CXCR^4$ inhibitors, entry inhibitors, gp120 inhibitors, G6PD and NADH-oxidase inhibitors, CCR5 inhibitors, other drugs for treating HIV, and mixtures thereof.

In another embodiment, the present invention provides a kit or container comprising a compound of Formula (I) in an amount effective for use as a standard or reagent in a test or assay for determining the ability of a potential pharmaceutical compound to inhibit HIV protease and/or HIV growth.

DETAILED DESCRIPTION

Reference will now be made in detail to certain claims of the invention, examples of which are illustrated in the accompanying structures and formulas. While the invention will be described in conjunction with the enumerated claims, it will be understood that they are not intended the invention to those claims. On the contrary, the invention is intended to cover all alternatives, modifications, and equivalents, which may be included within the scope of the present invention as defined by the claims.

Unless stated otherwise, the following terms and phrases as used herein are intended to have the following meanings:

When trade names are used herein, applicants intend to independently include the tradename product and the active pharmaceutical ingredient(s) of the tradename product.

In accordance with a convention used in the art,

is used in structural formulas herein to depict the bond that is the point of attachment of the moiety or substituent to the core or backbond structure.

As used herein, "a compound of the invention" or "a compound of formula (I)" means a compound of formula (I) or a pharmaceutically acceptable salt, solvate, or physiologically functional derivative thereof. Similarly, with respect to isolatable intermediates such as for example, compounds of formula (IX), the phrase "a compound of formula (number)" means a compound of that formula and pharmaceutically acceptable salts, solvates and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)$ $CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH$ $(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH$ $(CH_3)CH_2CH_2CH_2CH_3$), 3-hexyl (—$CH(CH_2CH_3)$ $(CH_2CH_2CH_3)$), 2-methyl-2-pentyl (—$C(CH_3)_2$ $CH_2CH_2CH_3$), 3-methyl-2-pentyl (—$CH(CH_3)CH(CH_3)$ $CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ $(CH_3)_2CH(CH_3)_2$), 3,3-dimethyl-2-butyl (—$CH(CH_3)C$ $(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH$ $(CH_3)$—), 1,3-propyl (—$CH_2CH_2CH_2$—), 1,4-butyl (—$CH_2CF2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH═CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, etc., for example, "substituted alkyl", "substituted alkylene", "substituted aryl", "substituted arylalkyl", "substituted heterocyclyl", and "substituted carbocyclyl" means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O$^-$, ═O, —OR, —SR, —S$^-$, —NR$_2$, —N$^+$R$_3$, ═NR, —CX$_3$, —CN, —OCN, —SCN, —N═C═O, —NCS, —NO, —NO$_2$, ═N$_2$, —N$_3$, —NHC(═O)R, —C(═O)R, —C(═O)NRR—S(═O)$_2$O$^-$, —S(═O)$_2$OH, —S(═O)$_2$R, —OS(═O)$_2$OR, —S(═O)$_2$NR, —S(═O)R, —OP(═O)(OR)$_2$, —N(═O)(OR)$_2$, —N(═O)(O—)$_2$, —N(═O)(OH)$_2$, —N(O)(OR)(O—), —C(═O)R, —C(═O)X, —C(S)R, —C(O)OR, —C(O)O$^-$, —C(S)OR, —C(O)SR, —C(S)SR, —C(O)NRR, —C(S)NRR, —C(═NR)NRR, where each X is independently a halogen: F, Cl, Br, or I; and each R is independently H, alkyl, aryl, arylalkyl, a heterocycle, or a protecting group or prodrug moiety. Alkylene, alkenylene, and alkynylene groups may also be similarly substituted.

"Bioavailability" is the degree to which the pharmaceutically active agent becomes available to the target tissue after the agent's introduction into the body. Enhancement of the bioavailability of a pharmaceutically active agent can provide a more efficient and effective treatment for patients because, for a given dose, more of the pharmaceutically active agent will be available at the targeted tissue sites.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_1$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

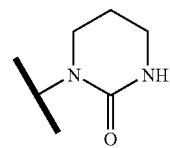

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, p-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

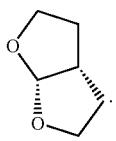

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in Principles of Modern Heterocyclic Chemistry. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 6 to 20 carbon atoms, e.g., the alkyl portion of the arylalkyl group is 1 to 6 carbon atoms and the heterocyclyl moiety is 5 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in Principles of Modern Heterocyclic Chemistry, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 6 to 20 carbon atoms, e.g., the alkenyl portion of the heterocyclyl alkenyl group is 1 to 6 carbon atoms and the heterocyclyl moiety is 5 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in Principles of Modern Heterocyclic Chemistry, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 6 to 20 carbon atoms, e.g., the alkynyl portion of the heterocyclyl alkynyl group is 1 to 6 carbon atoms and the heterocyclyl moiety is 5 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-5-aryl, -alkylene-5-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The term "optionally substituted" in reference to a particular moiety of the compound of Formula I (e.g., an optionally substituted aryl group) refers to a moiety having 0, 1, 2, or more substituents.

"Ac" means acetyl (—$C(O)CH_3$).
"$Ac_2O$" means acetic anhydride.
"DCM" means dichloromethane ($CH_2Cl_2$).
"DIBAL" means diisobutylaluminum hydride.
"DMAP" means dimethylaminopyridine.
"EDC" means 1-(3-Dimethylaminopropyl)-3-ethylcarbodiimide.
"Et" means ethyl.
"EtOAc" means ethylacetate.
"HOBt" means N-hydroxybenzotriazole.
"Me" means methyl (—$CH_3$).
"MeOH" means methanol.
"MeCN" means acetonitrile.
"Pr" means propyl.
"i-Pr" means isopropyl (—$CH(CH_3)_2$).
"i-PrOH" means isopropanol.
"room temperature" means room temperature.
"TFA" means trifluoroacetic acid.
"THF" means tetrahydrofuran.
"PG" means protecting group.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. N. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and I or (+) and (–) are employed to designate the sign of rotation of plane-polarized light by the compound, with (–) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Linker" or "link" refers to a chemical moiety comprising a covalent bond or a chain or group of atoms that covalently attaches a phosphonate group to a drug. Linkers include portions of substituents $A^1$ and $A^3$, which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

The terms "phosphonate" and "phosphonate group" include functional groups or moieties within a molecule that comprises a phosphorous that is 1) single-bonded to a carbon, 2) double-bonded to a heteroatom, 3) single-bonded to a heteroatom, and 4) single-bonded to another heteroatom, wherein each heteroatom can be the same or different. The terms "phosphonate" and "phosphonate group" also include functional groups or moieties that comprise a phosphorous in the same oxidation state as the phosphorous described above, as well as functional groups or moieties that comprise a prodrug moiety that can separate from a compound so that the compound retains a phosphorous having the characteristics described above. For example, the terms "phosphonate" and "phosphonate group" include phosphonic acid, phosphonic monoester, phosphonic diester, phosphonamidate, and phosphonthioate functional groups. In one specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen, and 4) single-bonded to another oxygen, as well as functional groups or moieties that comprise a prodrug moiety that can separate from a compound so that the compound retains a phosphorous having such characteristics. In another specific embodiment of the invention, the terms "phosphonate" and "phosphonate group" include functional groups or moieties within a molecule that comprises a phosphorous that is 1) single-bonded to a carbon, 2) double-bonded to an oxygen, 3) single-bonded to an oxygen or nitrogen, and 4) single-bonded to another oxygen or nitrogen, as well as functional groups or moieties that comprise a prodrug moiety that can separate from a compound so that the compound retains a phosphorous having such characteristics.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

"Prodrug moiety" refers to a labile functional group which separates from the active compound during metabolism, systemically, inside a cell, by hydrolysis, enzymatic cleavage, or by some other process (Bundgaard, Hans, "Design and Application of Prodrugs" in *A Textbook of Drug Design and Development* (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

Exemplary prodrug moieties include the hydrolytically sensitive or labile acyloxymethyl esters —$CH_2C(=O)R^a$ and acyloxymethyl carbonates —$CH_2OC(=O)OR^a$ where $R^1$ is $C_1$-$C_6$ alkyl, $C_1$-$C_6$ substituted alkyl, $C_6$-$C_{20}$ aryl or $C_6$-$C_{20}$ substituted aryl. The acyloxyalkyl ester was first used as a prodrug strategy for carboxylic acids and then applied to phosphates and phosphonates by Farquhar et al. (1983) *J. Pharm. Sci.* 72: 324; also U.S. Pat. Nos. 4,816,570, 4,968,788, 5,663,159 and 5792756. Subsequently, the acyloxyalkyl ester was used to deliver phosphonic acids across cell membranes and to enhance oral bioavailability. A close variant of the acyloxyalkyl ester, the alkoxycarbonyloxyalkyl ester (carbonate), may also enhance oral bioavailability as a prodrug moiety in the compounds of the combinations of the invention. An exemplary acyloxymethyl ester is pivaloyloxymethoxy, (POM) —$CH_2C(=O)C(CH_3)_3$. An exemplary acyloxymethyl carbonate prodrug moiety is pivaloyloxymethylcarbonate (POC)—$CH_2C(=O)OC(CH_3)_3$.

The phosphonate group may be a phosphonate prodrug moiety. The prodrug moiety may be sensitive to hydrolysis, such as, but not limited to a pivaloyloxymethyl carbonate (POC) or POM group. Alternatively, the prodrug moiety may be sensitive to enzymatic potentiated cleavage, such as a lactate ester or a phosphonamidate-ester group.

One skilled in the art will recognize that substituents and other moieties of the compounds of Formula I should be selected in order to provide a compound which is sufficiently stable to provide a pharmaceutically useful compound which can be formulated into an acceptably stable pharmaceutical composition. Compounds of Formula I which have such stability are contemplated as falling within the scope of the present invention.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), which is incorporated by reference in its entirety herein. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 155-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur ester-forming groups, such as sulphonate, sulfate, and sulfinate.

Metabolites of the Compounds of the Invention

Also falling within the scope of this invention are the in vivo metabolic products of the compounds described herein. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled (e.g., $C^{14}$ or $H^3$) compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no anti-infective activity of their own.

Compounds of Formula I

In one embodiment, the present application provides compounds according to Formula I, as described herein.

In another embodiment of the compounds of Formula I, the protecting group (PG) is —$PO_3^{2-}$, —$CH_2$—O—C(O)$R^{3a}$, —$CH_2$—O—C(O)O$R^{3a}$, —$CH_2OPO_3^{2-}$ or —$PO_3CH_2CF_3^{1-}$, wherein $R^{3a}$ is alkyl or substituted alkyl.

In still another embodiment of the compounds of Formula I, $L^3$ and $L^5$ are independently methylene, ethylene, or propylene.

In still another embodiment of the compounds of Formula I, $L^3$ and/or $L^5$ are a covalent bond.

In still another embodiment of the compounds of Formula I, $Ar^3$ is phenyl, naphthyl, isoxazolyl, imidazolyl, pyridyl, furyl, thiazolyl, or isothiazolyl, thiophenyl.

In still another embodiment of the compounds of Formula I, -$L^5$-$Ar^3$ is

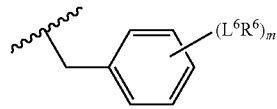

wherein $L^6$ is a covalent bond, —O—, —$CH_2$—, —$NR^7$— or —$OCH_2$—; $R^6$ is H, halo, nitro, cyano, formyl, alkyl, substituted alkyl, alkenyl, substituted alkenyl, alkynyl, substituted alkynyl, alkoxy, substituted alkoxy, cycloalkyl, substituted cycloalkyl, cycloalkenyl, substituted cycloalkenyl, heterocyclyl, substituted heterocyclyl, aryl, or substituted aryl; and m is 0, 1, 2, 3, 4, or 5.

In still another embodiment of the compounds of Formula I, -$L^5$-$Ar^3$ is

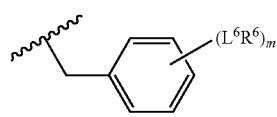

wherein $L^6$ is a covalent bond, —O—, —$CH_2$—, —$NR^7$— or OCH$_2$—; $R^6$ is H, halo, nitro, cyano, formyl, alkyl, substituted alkyl, alkenyl, substituted alkenyl, alkynyl, substituted alkynyl, alkoxy, substituted alkoxy, cycloalkyl, substituted cycloalkyl, cycloalkenyl, substituted cycloalkenyl, heterocyclyl, substituted heterocyclyl, aryl, or substituted aryl; and m is 0, 1, 2, 3, 4, or 5; $L^6$ is —O—$CH_2$—; $R^6$ is cycloalkyl, substituted cycloalkyl, cycloalkenyl, substituted cycloalkenyl, aryl, substituted aryl, heterocyclyl, substituted heterocyclyl, —NHS(O)$_2$R, —C(O)—R, —S(O)$_2$R, —C(O)NHR, —S(O)$_2$NHR (where R is H, alkyl, or substituted alkyl).

In still another embodiment of the compounds of Formula I, In still another embodiment of the compounds of Formula I, -$L^5$-$Ar^3$ is

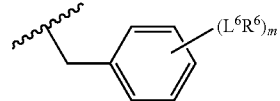

wherein $L^6$ is a covalent bond, —O—, —$CH_2$—, —$NR^7$— or —$OCH_2$—; $R^6$ is H, halo, nitro, cyano, formyl, alkyl, substituted alkyl, alkenyl, substituted alkenyl, alkynyl, substituted alkynyl, alkoxy, substituted alkoxy, cycloalkyl, substituted cycloalkyl, cycloalkenyl, substituted cycloalkenyl, heterocyclyl, substituted heterocyclyl, aryl, or substituted aryl; and m is 0, 1, 2, 3, 4, or 5; $L^6$ is —O—$CH_2$—; $R^6$ is phenyl.

In still another embodiment of the compounds of Formula I, -$L^5$-$Ar^3$ is

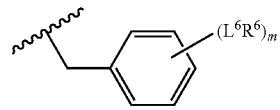

wherein $L^6$ is a covalent bond, —O—, —$CH_2$—, —$NR^7$— or —$OCH_2$—; $R^6$ is H, halo, nitro, cyano, formyl, alkyl, substituted alkyl, alkenyl, substituted alkenyl, alkynyl, substituted alkynyl, alkoxy, substituted alkoxy, cycloalkyl, substituted cycloalkyl, cycloalkenyl, substituted cycloalkenyl, heterocyclyl, substituted heterocyclyl, aryl, or substituted aryl; and m is 0, 1, 2, 3, 4, or 5; $L^6$ is —O—; $R^6$ is alkyl or substituted alkyl.

In still another embodiment of the compounds of Formula I, $L^3$ is alkylene; $Ar^1$ is aryl or substituted aryl.

In still another embodiment of the compounds of Formula I, $L^3$ is alkylene; $Ar^1$ is aryl or substituted aryl; $R^{6a}$ is a 5- or 6-membered aromatic, nonaromatic dihydro, or nonaromatic tetrahydro heterocyclyl having from 1 to 3 heteroatoms.

In still another embodiment of the compounds of Formula I, $L^3$ is alkylene; $Ar^1$ is aryl or substituted aryl; $R^{6a}$ is a carbocyclyl or heterocyclyl having the following structure:

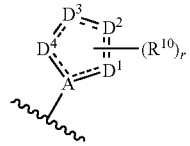

wherein A is $CR^{10}$ or N; $D^1$, $D^2$, $D^3$, and $D^4$ are independently selected from the group consisting of C, N, O, and S; each $R^{10}$ is independently H, alkyl, substituted alkyl, alkenyl, substituted alkenyl, alkynyl, substituted alkynyl, —O-alkyl, —O-(substituted alkyl), aryl, substituted aryl, with the proviso that in each occurrence of ($R^{10}$)$_r$, r is 0 or an integer from 1 to 8, whereby carbon is tetravalent, nitrogen is trivalent, and sulfur and oxygen are divalent; and ===== is a single or double bond.

In still another embodiment of the compounds of Formula I, $L^3$ is alkylene; $Ar^1$ is aryl or substituted aryl; $R^{6a}$ is a carbocyclyl or heterocyclyl having the following structure:

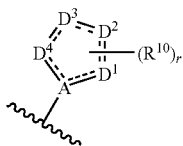

wherein A is N; $D^1$ is N; $D^2$ is C; $D^3$ is N; $D^4$ is C; each $R^{10}$ is independently H, alkyl, substituted alkyl, alkenyl, substituted alkenyl, alkynyl, substituted alkynyl, —O-alkyl, —O-(substituted alkyl), aryl, substituted aryl, with the proviso that in each occurrence of $(R^{10})_r$, r is 0 or an integer from 1 to 8, whereby carbon is tetravalent, nitrogen is trivalent, and sulfur and oxygen are divalent; and ----- is a single or double bond.

In still another embodiment of the compounds of Formula I, $L^3$ is alkylene; $Ar^1$ is aryl or substituted aryl; $R^{6a}$ is

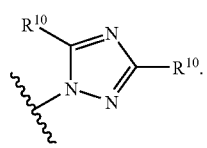

In still another embodiment of the compounds of Formula I, $L^3$ is alkylene; $Ar^1$ is aryl or substituted aryl; $R^{6a}$ is

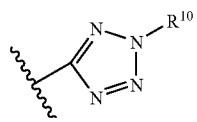

In still another embodiment of the compounds of Formula I, $L^3$ is alkylene; $Ar^1$ is aryl or substituted aryl; $R^{6a}$ is a carbocyclyl or heterocyclyl having the following structure:

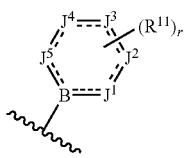

wherein B is $CR^{11}$ or N; $J^1$, $J^2$, $J^3$, $J^4$, and $J^5$ are independently selected from the group consisting of C, N, O, and S; each $R^{11}$ is independently H, alkyl, substituted alkyl, alkenyl, substituted alkenyl, alkynyl, substituted alkynyl, —O-alkyl, —O-(substituted alkyl), aryl, substituted aryl, with the proviso that in each occurrence of $(R^{11})_r$, r is 0 or an integer from 1 to 10 whereby carbon is tetravalent, nitrogen is trivalent, and sulfur and oxygen are divalent; and ----- is a single or double bond.

In still another embodiment of the compounds of Formula I, $L^3$ is alkylene; $Ar^1$ is aryl or substituted aryl; $R^{6a}$ is a carbocyclyl or heterocyclyl having the following structure:

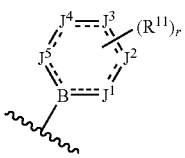

wherein B is C; $J^1$ is C; $J^2$ is C or N, $J^3$ is C or N, $J^4$ is C; $J^5$ is C or N.

In still another embodiment of the compounds of Formula I, $R^{6a}$ is

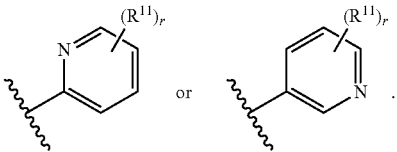

In still another embodiment of the compounds of Formula I, $L^3$ is alkylene; $Ar^1$ is aryl or substituted aryl; $R^{6a}$ is a carbocyclyl or heterocyclyl having the following structure:

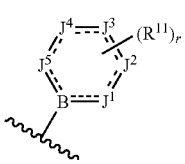

wherein B is N; $J^1$ is C; $J^2$ is C; $J^3$ is O, $J^4$ is C; $J^5$ is C.

In still another embodiment of the compounds of Formula I, $R^{6a}$ is

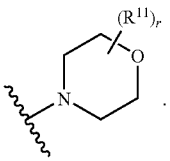

In still another embodiment of the compounds of Formula I, $R^{6a}$ is haloalkyl or substituted haloalkyl.

In still another embodiment of the compounds of Formula I, $Ar^2$ is cycloalkyl, substituted cycloalkyl, cycloalkenyl, substituted cycloalkenyl, aryl, substituted aryl, heterocyclyl, substituted heterocyclyl.

In still another embodiment of the compounds of Formula I, $Ar^2$ is mono-heterocyclyl having carbon atoms and from 1 to 3 heteroatoms selected from O, N, and S.

In still another embodiment of the compounds of Formula I, $Ar^2$ is

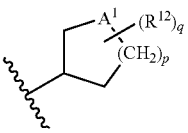

wherein $A^1$ is O, S, S(O), or S(O)$_2$; $R^{12}$ is H, alkyl, substituted haloalkyl, substituted haloalkyl, hydroxyalkyl, substituted hydroxyalkyl, alkoxyalkyl or substituted alkoxyalkyl; p is 1 or 2; and q is 0, 1, 2, or 3.

In still another embodiment of the compounds of Formula I, Ar² is bicyclic-heterocyclyl having from 1 to 3 heteroatoms selected from O, S, and N.

In still another embodiment of the compounds of Formula I, Ar² is

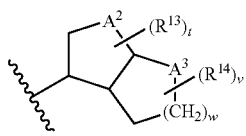

wherein, A² and A³ are each independently O or S; R¹³ and R¹⁴ are each independently H, alkyl, substituted haloalkyl, substituted haloalkyl, hydroxyalkyl, substituted hydroxyalkyl, alkoxyalkyl or substituted alkoxyalkyl; t is 1, 2, or 3; v is 1, 2, 3, or 4; and w is 1 or 2.

In still another embodiment of the compounds of Formula I, R¹ is a non-aromatic heterocyclyl having from 1 to 3 heteroatoms selected from O, N, and S.

In still another embodiment of the compounds of Formula I, R¹ is

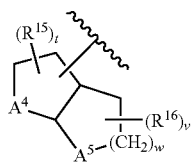

wherein A⁴ and A⁵ are each independently O or S; R¹⁵ and R¹⁶ are each independently H, alkyl, substituted haloalkyl, substituted haloalkyl, hydroxyalkyl, substituted hydroxyalkyl, alkoxyalkyl or substituted alkoxyalkyl; t is 1, 2, or 3; v is 1, 2, 3, or 4; and w is 1 or 2.

In still another embodiment of the compounds of Formula I, R¹-L²-L¹-X¹— is

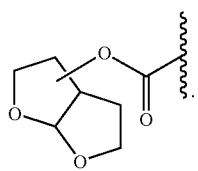

In still another embodiment of the compounds of Formula I, L¹ is substituted alkylene, L² is N(R⁸) wherein R⁸ is H or alkyl; R¹ is —C(O)OR⁹ wherein R⁹ is alkyl.

In still another embodiment of the compounds of Formula I, R¹-L²-L¹- is

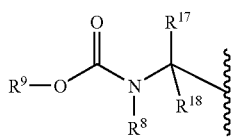

wherein R⁹ is alkyl; R⁸ and R¹⁷ are independently H, alkyl, or substituted alkyl, or R¹⁷ and R¹⁸ taken together with the carbon atom to which they are shown attached form a heterocyclyl or a substituted heterocyclyl.

In still another embodiment of the compounds of Formula I, R¹-L²-L¹- is

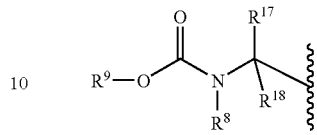

wherein R⁹ is alkyl; R⁸ and R¹⁷ is methyl, ethyl, propyl, isopropyl, n-butyl, sec-butyl or tert-butyl.

In still another embodiment of the compounds of Formula I, X¹ and X² are independently —C(O)—, —S(O)₂—, or —S(O)—.

In still another embodiment of the compounds of Formula I, X¹ and X² are the same, i.e., X¹ and X² are both —C(O)—.

In still another embodiment of the compounds of Formula I, X¹ and X² are different, i.e., X¹ is —C(O)— and X² is —S(O)₂—, or —S(O)—; X¹ is —S(O)₂—, or —S(O)— and X² is —C(O)—.

In still another embodiment of the compounds of Formula I, Y is —S— or —O—; Ar² is heterocyclyl or substituted heterocyclyl. Non-limiting examples of heterocycles include pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, tetrahydrofuranyl, tetrahydroquinolinyl, tetrahydroisoquinolinyl, decahydroquinolinyl, thienyl, thianthrenyl, pyranyl, isobenzofuranyl, chromenyl, xanthenyl, phenoxathinyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

In still another embodiment of the compounds of Formula I, Y is —O—; Ar² is

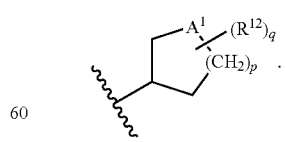

wherein A¹ is O, S, S(O), or S(O)₂, R¹² is H, alkyl, substituted haloalkyl, substituted haloalkyl, hydroxyalkyl, substituted hydroxyalkyl, alkoxyalkyl or substituted alkoxyalkyl, p is 1 or 2, and q is 0, 1, 2, or 3.

In still another embodiment of the compounds of Formula I, Y is —O—; Ar² is

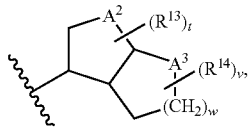

wherein, A² and A³ are each independently O or S; R¹³ and R¹⁴ are each independently H, alkyl, substituted haloalkyl, substituted haloalkyl, hydroxyalkyl, substituted hydroxyalkyl, alkoxyalkyl or substituted alkoxyalkyl, t is 1, 2, or 3, v is 1, 2, 3, or 4; and w is 1 or 2.

In still another embodiment of the compounds of Formula I, L¹ is alkylene, substituted alkylene, alkenylene, substituted, alkenylene, alkynylene, or substituted alkynylene. Non-limiting examples of alkylene include —CH₂—, —CH(CH₃)—, —CH(—CH₂CH₃)—, —CH(—CH₂CH₂CH₃)—, —CH(—CH(CH₃)₂)—, —CH(—CH₂CH₂CH₂CH₃)—, —CH(—CH₂CH(CH₃)₂)—, —CH(—CH(CH₃)CH₂CH₃)—, —CH(—C(CH₃)₃)—, —C(CH₃)₂—, —CH(OCH₃)—, —CH(CH₂OH)—, —CH(CH₂CH₂OH)—, etc. In one particular embodiment, L¹ is methylene substituted with an alkyl group, wherein the alkyl group is selected from the group consisting of methyl, ethyl, n-propyl, 2-propyl, n-butyl, 2-butyl, tert-butyl, and 2,2-dimethylpropyl.

In still another embodiment of the compounds of Formula I, L¹ is alkylene or substituted alkylene, L² is —NR⁸—, wherein R⁸ is H, alkyl, or substituted alkyl; wherein said alkyl or substituted alkyl is any alkyl or substituted alkyl defined or exemplified herein.

In still another embodiment of the compounds of Formula I, L³ and L⁵ are independently alkylene or substituted alkylene. Non-limiting examples of alkylene and substituted alkylene include any of the alkylenes or substituted alkylenes defined or disclosed herein. For example, substituted alkylenes include alkylenes substituted with one or more —OH group, alkylenes substituted with one or more ether group, e.g., a —O-Bn group, alkylenes substituted with one or more halogen, or alkylenes substituted with combinations of two or more substituents (e.g., —OH and halogen, halogen and ether, etc.).

In still another embodiment of the compounds of Formula I, L³ and L⁵ are the same, i.e., L³ and L⁵ are the same alkylene or substituted alkylene group.

In still another embodiment of the compounds of Formula I, L³ and L⁵ are different, i.e., L³ is an alkylene and L⁵ is a substituted alkylene, L³ is an alkylene and L⁵ is a different alkylene, or L³ is a substituted alkylene, and L⁵ is a different substituted alkylene.

In still another embodiment of the compounds of Formula I, L⁴ and L⁶ are independently selected from the group consisting of a covalent bond, —O—, —CH₂—, —NR⁷—OCH₂—, or —CH₂O—.

In still another embodiment of the compounds of Formula I, L⁴ and L⁶ are different. For example, L⁴ is a covalent bond and L⁶ is —O—; L⁴ is a covalent bond and L⁶ is —NH—; L⁴ is a —O—, L⁶ is —NH—.

In still another embodiment of the compounds of Formula I, L³ is —H₂— and n is 0.

In still another embodiment of the compounds of Formula I, L³ is —CH₂— and m is 0.

In still another embodiment of the compounds of Formula I, L⁵ is —CH₂— and n is 0.

In still another embodiment of the compounds of Formula I, L⁵ is —CH₂— and m is 0.

In still another embodiment of the compounds of Formula I, Ar¹ is substituted or unsubstituted aryl, wherein aryl is any aryl defined or exemplified herein, and, when present, the substituents on said aryl include one or more of any substituents defined or exemplified herein. Non-limiting examples of aryl include phenyl, substituted benzene, naphthalene, anthracene, biphenyl, and the like. In a particular embodiment, Ar¹ is phenyl.

In still another embodiment of the compounds of Formula I, Ar¹ is substituted or unsubstituted heteroaryl, wherein heteroaryl is any heteroaryl defined or exemplified herein, and, when present, the substituents on said heteroaryl include one or more of any substituents defined or exemplified herein.

In still another embodiment of the compounds of Formula I, R⁶ᵃ is substituted or unsubstituted aryl, wherein aryl is any aryl defined or exemplified herein, and, when present, the substituents on said aryl include one or more of any substituents defined or exemplified herein.

In still another embodiment of the compounds of Formula I, R⁶ᵃ is substituted or unsubstituted heteroaryl, wherein heteroaryl is any heteroaryl defined or exemplified herein. Non-limiting examples of heteroaryl include thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, Ar³ is substituted or unsubstituted aryl, wherein aryl is any aryl defined or exemplified herein, and, when present, the substituents on said aryl include one or more of any substituents defined or exemplified herein. In a particular embodiment, Ar³ is phenyl or substituted phenyl.

In still another embodiment of the compounds of Formula I, Ar³ is substituted or unsubstituted heteroaryl, wherein heteroaryl is any heteroaryl defined or exemplified herein, and, when present, the substituents on said heteroaryl include one or more of any substituents defined or exemplified herein. Non-limiting examples of heteroaryl include thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, R⁶ is substituted or unsubstituted aryl, wherein aryl is any aryl defined or exemplified herein, and, when present, the substituents on said aryl include one or more of any substituents defined or exemplified herein.

In still another embodiment of the compounds of Formula I, R⁶ is substituted or unsubstituted heteroaryl, wherein heteroaryl is any heteroaryl defined or exemplified herein. Non-limiting examples of heteroaryl include thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, L³ is alkylene, Ar¹ is substituted or unsubstituted aryl, wherein aryl is any aryl defined or exemplified herein, and the substituents on said aryl are any substituents defined and exemplified herein. In a particular embodiment, Ar¹ is phenyl or substituted phenyl.

In still another embodiment of the compounds of Formula I, L³ is alkylene and Ar¹ is substituted or unsubstituted heteroaryl, wherein heteroaryl is any heteroaryl defined or exemplified herein, and, when present, the substituents on said heteroaryl include one or more of any substituent defined or exemplified herein. Non-limiting examples of heteroaryl include thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, $L^5$ is substituted or unsubstituted alkylene, and $Ar^3$ is substituted or unsubstituted aryl, wherein alkylene and aryl are any alkylene or aryl defined or exemplified herein, and, when present, the substituents on said alkylene or aryl include one or more of any substituents defined or exemplified herein.

In still another embodiment of the compounds of Formula I, $L^5$ is substituted or unsubstituted alkylene, and $Ar^3$ is substituted or unsubstituted heteroaryl, wherein alkylene and heteroaryl are any alkylene or heteroaryl defined or exemplified herein, and, when present, the substituents on said alkylene or heteroaryl include one or more of any substituents defined or exemplified herein. Non-limiting examples of heteroaryl include thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, $Ar^1$ is substituted or unsubstituted aryl, and $Ar^3$ is substituted or unsubstituted heteroaryl, wherein aryl and heteroaryl are any aryl or heteroaryl defined or exemplified herein, and, when present, the substituents on said aryl or heteroaryl include one or more of any substituents defined or exemplified herein.

In still another embodiment of the compounds of Formula I, $Ar^3$ is substituted or unsubstituted aryl, and $Ar^1$ is substituted or unsubstituted heteroaryl, wherein aryl and heteroaryl are any aryl or heteroaryl defined or exemplified herein, and, when present, the substituents on said aryl or heteroaryl include one or more of any substituents defined or exemplified herein.

In still another embodiment of the compounds of Formula I, both $Ar^1$ and $Ar^3$ are substituted or unsubstituted aryl, wherein aryl is any aryl defined or exemplified herein, and, when present, the substituents on said aryl include one or more of any substituents defined or exemplified herein.

In still another embodiment of the compounds of Formula I, $L^4$ is a covalent bond, $R^{6a}$ is aryl, substituted aryl, wherein the aryl is any aryl defined or exemplified herein, and, when present, the substituents on the aryl include one or more of any substituents defined or exemplified herein.

In still another embodiment of the compounds of Formula I, $L^4$ is a covalent bond, $R^{6a}$ is heteroaryl, or substituted heteroaryl, wherein the heteroaryl is selected from the group consisting of thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, n is 0, and $Ar^1$ is unsubstituted aryl.

In still another embodiment of the compounds of Formula I, n is 1, and $Ar^1$ is aryl, $L^4$ is —O—, $R^{6a}$ is alkyl or substituted alkyl wherein alkyl or substituted alkyl is any alkyl or substituted alkyl defined or exemplified herein. In one particular embodiment, $R^{6a}$ is methyl.

In still another embodiment of the compounds of Formula I, two of the $Ar^1$, $Ar^3$, $R^6$, or $R^{6'''}$ are the same and the remaining two are different, e.g. two of $Ar^1$, $Ar^3$, $R^6$, or $R^{6a}$ are substituted or unsubstituted aryls and the other two of $Ar^1$, $Ar^3$, $R^6$, or $R^{6a}$ are substituted or unsubstituted heteroaryls, wherein aryl and heteroaryl are any aryl or heteroaryl defined or exemplified herein, and, when present, the substituents on the aryl or heteroaryl include one or more of any substituents defined or exemplified herein.

In still another embodiment of the compounds of Formula I, m is 0, and $Ar^3$ is unsubstituted aryl.

In still another embodiment of the compounds of Formula I, m is 1; $L^6$ is —O—$CH_2$; $R^6$ is aryl, wherein aryl is any aryl defined or exemplified herein.

In still another embodiment of the compounds of Formula I, m is 1; $L^6$ is —O—; $R^6$ is alkyl or substituted alkyl, wherein alkyl or substituted alkyl is any alkyl or substituted alkyl defined or exemplified herein. In one particular embodiment, $R^6$ is methyl.

In still another embodiment of the compounds of Formula I, m is 1, $L^4$ is O-alkylene (wherein the alkylene portion of the O-alkylene group is attached to either $Ar^1$ or $R^{6a}$), $R^{6a}$ is heteroaryl, or substituted heteroaryl, and wherein the heteroaryl is selected from the group consisting of thienyl, furyl, oxazolyl, isoxazolyl, thiazolyl, triazolyl, tetrazolyl, pyridyl, pyridazinyl, indazolyl, imidazopyridinyl, indolyl, benzimidazolyl, isoquinolinyl and quinolinyl.

In still another embodiment of the compounds of Formula I, $L^1$ is —O, $L^2$ is a covalent bond, and $R^1$ is aryl or substituted aryl, wherein the aryl and the substituted aryl are any aryl and substituted aryl defined or exemplified herein.

In still another embodiment of the compounds of Formula I, $L^1$ is —O, $L^2$ is a covalent bond, and $R^1$ is heterocyclyl, or substituted heterocyclyl, wherein the heterocyclyl and substituted heterocyclyl are any heterocyclyl and substituted heterocyclyl defined or exemplified herein. Non-limiting examples of heterocycles include pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, tetrahydrofuranyl, tetrahydroquinolinyl, tetrahydroisoquinolinyl, decahydroquinolinyl, thienyl, thianthrenyl, pyranyl, isobenzofuranyl, chromenyl, xanthenyl, phenoxathinyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, α-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

In still another embodiment of the compounds of Formula I, $R^1$ is —C(O)$R^9$ or —C(O)O$R^9$, wherein $R^9$ is H, alkyl, substituted alkyl, alkenyl. Non-limiting examples of alkyl or substituted alkyl include —$CH_3$, —CH$(CH_3)_2$, —C$(CH_3)_3$, —CH(alkyl), —CH(substituted alkyl), —CH(heteroalkyl), —C(alkyl)$_2$, —C(substituted alkyl)$_2$, —C(heteroalkyl)$_2$, —C(alkyl)(substituted alkyl), —C(heteroalkyl)(substituted alkyl), and —C(alkyl)(heteroalkyl), wherein alkyl, substituted alkyl, and heteroalkyl are as defined and exemplified herein.

In still another embodiment of the compounds of Formula I, $R^2$, $R^4$, and $R^5$ are each the same. In a particular embodiment $R^2$, $R^4$, and $R^5$ are each H. In another particular embodiment $R^2$, $R^4$, and $R^5$ are each alkyl, e.g. one of the alkyl groups defined or disclosed herein.

In still another embodiment of the compounds of Formula I, $R^2$, $R^4$, and $R^5$ are each different.

In still another embodiment of the compounds of Formula I, two of $R^2$, $R^4$, and $R^5$ are the same, and the other is different.

In still another embodiment of the compounds of Formula I, n is 0, m is 1, $R^2$, $R^4$, and $R^5$ are each independently selected from the group consisting of H, alkyl, and substituted alkyl, wherein alkyl or substituted alkyl is any alkyl or substituted alkyl, defined or disclosed herein.

In still another embodiment of the compounds of Formula I, n is 1, m is 0, $R^2$, $R^4$, and $R^5$ are each independently selected from the group consisting of H, alkyl, and substituted alkyl, wherein alkyl or substituted alkyl is any alkyl or substituted alkyl, defined or disclosed herein.

In still another embodiment of the compounds of Formula I, m and n are both 1, and $R^2$ is H; $R^3$ is OH.

In still another embodiment of the compounds of Formula I, m and n are both 1, and $R^4$ is H; $R^3$ is OH.

In still another embodiment of the compounds of Formula I, m and n are both 1, and $R^5$ is H; $R^3$ is OH.

In still another embodiment of the compounds of Formula I, n is 0, m is 1, and $R^2$ is H; $R^3$ is OH.

In still another embodiment of the compounds of Formula I, n is 0, m is 1, and $R^4$ is H; $R^3$ is OH.

In still another embodiment of the compounds of Formula I, n is 0, m is 1, and $R^5$ is H; $R^3$ is OH.

In still another embodiment of the compounds of Formula I, n is 1, m is 0, and $R^2$ is H; $R^3$ is OH.

In still another embodiment of the compounds of Formula I, n is 1, m is 0, and $R^4$ is H; $R^3$ is OH.

In still another embodiment of the compounds of Formula I, n is 1, m is 0, and $R^5$ is H; $R^3$ is OH.

In yet another embodiment of the compounds of Formula I, m is 0, the -$L^5$-$Ar^3$-$(L^6$-$R^6)_m$ moiety is an -alkylene-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, m is 1, the -$L^5$-$Ar^3$-$(L^6$-$R^6)_m$ moiety is an -alkylene-aryl-heteroaryl group, wherein said alkylene, aryl, and heteroaryl moieties are any alkylene, aryl, and heteroaryl moieties defined or exemplified herein, optionally substituted with one or more of any substituents defined or exemplified herein.

In yet another embodiment of the compounds of Formula I, m is 1, the -$L^5$-$Ar^3$-$(L^6$-$R^6)_m$ moiety is an -alkylene-O-alkyl group, wherein said alkylene, alkyl, aryl, and heteroaryl moieties are any alkylene, alkyl aryl, and heteroaryl moieties defined or exemplified herein, optionally substituted with one or more of any substituents defined or exemplified herein. In one particular embodiment, one substituent on the alkyl is halogen.

In yet another embodiment of the compounds of Formula I, m is 1, the -$L^5$-$Ar^3$-$(L^6$-$R^6)_m$ moiety is an -alkylene-aryl-O—CH$_2$-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, m is 1, the -$L^5$-$Ar^3$-$(L^6$-$R^6)_m$ moiety is an -alkylene-aryl-CH$_2$—O-heteroaryl group, wherein said alkylene, aryl, and heteroaryl moieties are any alkylene, aryl, and heteroaryl moieties defined or exemplified herein, optionally substituted on the alkylene, heteroaryl, and/or aryl with one or more of any substituents defined or exemplified herein.

In yet another embodiment of the compounds of Formula I, m is 1, the -$L^5$-$Ar^3$-$(L^6$-$R^6)_m$ moiety is an -alkylene-aryl-O—CH$_2$-heteroaryl group, wherein said alkylene, aryl, and heteroaryl moieties are any alkylene, aryl and heteroaryl moieties defined or exemplified herein, optionally substituted with one or more of any substituents defined or exemplified herein.

In yet another embodiment of the compounds of Formula I, m is 1, the -$L^5$-$Ar^3$-$(L^6$-$R^6)_m$ moiety is an -alkylene-aryl-O-alkylene-NH—C(O)—O-alkyl group, wherein said alkylene, alkyl and aryl moieties are any alkylene, alkyl, and aryl moieties defined or exemplified herein, optionally substituted with one or more of any substituents defined or exemplified herein.

In yet another embodiment of the compounds of Formula I, m is 1, the -$L^5$-$Ar^3$-$(L^6$-$R^6)_m$ moiety is an -alkylene-aryl-O-alkylene-NH—S(O)$_2$-alkyl group, wherein said alkylene, and aryl moieties are any alkylene, and aryl moieties defined or exemplified herein, optionally substituted with one or more of any substituents defined or exemplified herein.

In yet another embodiment of the compounds of Formula I, m is 1, the -$L^5$-$Ar^3$-$(L^6$-$R^6)_m$ moiety is an -alkylene-aryl-O-alkylene-NH—C(O)-heterocyclyl group, wherein said alkylene, aryl, and heterocyclyl moieties are any alkylene, aryl, and heterocyclyl moieties defined or exemplified herein, optionally substituted with one or more of any substituents defined or exemplified herein.

In yet another embodiment of the compounds of Formula I, m is 1, the -$L^5$-$Ar^3$-$(L^6$-$R^6)_m$ moiety is an -alkylene-aryl-O-alkylene-PO$_3$(alkyl)$_2$ group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, n is 0, the -$L^3$-$Ar^1$-$(L^4$-$R^{6a})_n$ moiety is an -alkylene-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, n is 1, 2, or 3; $L^4$ is a covalent bond; $L^3$ is alkylene; $Ar^1$ is aryl; each $R^{6a}$ is independently halo, cyano, haloalkyl, or —O-haloalkyl. Preferably, each halo is independently F or Cl.

In yet another embodiment of the compounds of Formula I, the -$L^3$-$Ar^1$-$(L^4$-$R^{6a})_n$ moiety is an -alkylene-(substituted aryl) group, wherein the substituents on the substituted aryl are one or more moieties selected from the group consisting of halo, cyano, haloalkyl, or —O-haloalkyl.

In yet another embodiment of the compounds of Formula I, n is 1, 2, or 3; $L^4$ is a covalent bond; $L^3$ is alkylene; $Ar^1$ is aryl; each $R^{6f}$ is independently halo, cyano, haloalkyl, or —O-haloalkyl; m is 1; $L^6$ is a covalent bond; the -$L^5$-$Ar^3$-$(L^6$-$R^6)_m$ moiety is an -alkylene-aryl-heterocyclyl group, wherein said alkylene, aryl, and heterocyclyl moieties are any alkylene and aryl moieties defined or exemplified herein, optionally substituted on the alkylene and/or aryl with one or more of any substituents defined or exemplified herein. Preferably, the -$L^5$-$Ar^3$-$(L^6$-$R^6)_m$ moiety is an -alkylene-aryl-heteroaryl group, wherein said alkylene, aryl, and heteroaryl moieties are any alkylene and aryl moieties defined or exemplified herein, optionally substituted on the alkylene and/or aryl with one or more of any substituents defined or exemplified herein.

In yet another embodiment of the compounds of Formula I, n is 1, the -$L^3$-$Ar^1$-$(L^4$-$R^{6a})_n$ moiety is an -alkylene-aryl-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-O-alkylene-heterocyclyl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ is an -alkylene-aryl-O-haloalkyl group, wherein said alkylene, haloalkyl, and aryl moieties are any alkylene, haloalkyl, and aryl moieties defined or exemplified herein, optionally substituted with one or more of any substituents defined or exemplified herein.

In yet another embodiment of the compounds of Formula I, n is 0, the -$L^3$-$Ar^1$-($L^4$-$R^{6a}$)$_n$ moiety is an -alkylene-aryl group, m is 1, the -$L^5$-$Ar^3$-($L^6$-$R^6$)$_m$ moiety is an -alkylene-aryl-heteroaryl group, wherein said alkylene, aryl, and heteroaryl moieties are any alkylene, aryl, and heteroaryl moieties defined or exemplified herein, optionally substituted on the alkylene, aryl and/or heteroaryl with one or more of any substituents defined or exemplified herein.

In yet another embodiment of the compounds of Formula I, n is 0, the -$L^3$-$Ar^1$-($L^4$-$R^{6a}$)$_n$ moiety is an -alkylene-aryl group, m is 1, the -$L^5$-$Ar^3$-($L^6$-$R^6$)$_m$ moiety is an -alkylene-aryl-O—CH$_2$-heteroaryl group, wherein said alkylene, aryl; and heteroaryl moieties are any alkylene, aryl; and heteroaryl moieties defined or exemplified herein, optionally substituted on the alkylene, aryl and/or heteroaryl with one or more of any substituents defined or exemplified herein.

In yet another embodiment of the compounds of Formula I, n is 0, the -$L^3$-$Ar^1$-($L^4$-$R^{6a}$)$_n$ moiety is α-alkylene-aryl group, m is 1, the -$L^5$-$Ar^3$-($L^6$-$R^6$)$_m$ moiety is an -alkylene-aryl-aryl group, wherein said alkylene and aryl moieties are any alkylene and aryl moieties defined or exemplified herein, optionally substituted on the alkylene and/or aryl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene-aryl group, wherein said alkylene, heterocyclyl and aryl moieties are any alkylene, heterocyclyl, and aryl moieties defined or exemplified herein, optionally substituted with one or more of any substituents defined or exemplified.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-alkyl group, wherein said alkylene, alkyl, heterocyclyl and aryl moieties are any alkylene, alkyl, heterocyclyl, and aryl moieties defined or exemplified herein, optionally substituted with one or more of any substituents defined or exemplified.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O—CH$_2$-aryl group, wherein said alkylene, heterocyclyl and aryl moieties are any alkylene, heterocyclyl, and aryl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O—CH$_2$-heterocyclyl group, wherein said alkylene, heterocyclyl, and aryl moieties are any alkylene, heterocyclyl, and aryl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—C(O)—O-alkyl group, wherein said alkylene, alkyl, heterocyclyl, and aryl moieties are any alkylene, alkyl, heterocyclyl, and, and aryl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—S(O)$_2$—O-alkyl group, wherein said alkylene, alkyl, heterocyclyl, and aryl moieties are any alkylene, alkyl, heterocyclyl, and, and aryl moieties defined or exemplified herein, optionally substituted with one or more of any substituents defined or exemplified herein.

In yet another embodiment of the compounds of Formula I, n is 1, the -$L^3$-$Ar^1$-($L^4$-$R^6$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—C(O)-heteroaryl group, wherein said alkylene, alkyl, heterocyclyl, aryl, and heteroaryl moieties are any alkylene, alkyl, heterocyclyl, aryl, and heteroaryl moieties defined or exemplified herein, optionally substituted with one or more of any substituents defined or exemplified herein.

In yet another embodiment of the compounds of Formula I, n is 1, the -$L^3$-$Ar^1$-($L^4$-$R^6$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-PO$_3$(alkyl)$_2$ group, wherein said alkylene, alkyl, heterocyclyl, and aryl moieties are any alkylene, alkyl, heterocyclyl, and aryl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-O-alkylene-heterocyclyl group, m is 0, the -$L^5$-$Ar^3$-($L^6$-$R^6$)$_m$ moiety is an -alkylene-aryl group, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-O-haloalkyl, m is 1, the -$L^5$-$Ar^3$-($L^6$-$R^6$)$_m$ moiety is an -alkylene-aryl-heteroaryl group, wherein said alkylene, haloalkyl, aryl, and heteroaryl moieties are any alkylene, haloalkyl, aryl, and heteroaryl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_m$ moiety is an -alkylene-aryl-O-haloalkyl group, m is 0, the -$L^5$-$Ar^3$-($L^6$-$R^6$)$_m$ moiety is an -alkylene-aryl-O-alkyl group, wherein said alkylene, alkyl, haloalkyl, and aryl, moieties are any alkylene, alkyl, haloalkyl, and aryl heterocyclyl moieties defined or exemplified herein, optionally substituted with one or more of any substituents defined or exemplified herein.

In yet another embodiment of the compounds of Formula I, n is 0, the -$L^3$-$Ar^1$-($L^4$-$R^{6a}$)$_n$ moiety is an -alkylene-aryl group, m is 1, the -$L^5$-$Ar^3$-($L^6$-$R^6$)$_m$ moiety is an -alkylene-aryl-heteroaryl group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, heterocyclyl, aryl, and heteroaryl moieties are any alkylene, alkyl, heterocyclyl, aryl, and heteroaryl moieties defined or exemplified herein, optionally substituted with one or more of any substituents defined or exemplified herein.

In yet another embodiment of the compounds of Formula I, n is 0, the -$L^3$-$Ar^1$-($L^4$-$R^{6a}$)$_n$ moiety is an -alkylene-aryl group, m is 1, the -$L^5$-$Ar^3$-($L^6$-$R^6$)$_m$ moiety is an -alkylene-aryl-O—CH$_2$-heteroaryl group, $L^1$-$L^2$-$R^1$ is —O—$R^1$, wherein $R^1$ is heterocyclyl or substituted heterocyclyl, wherein said alkylene, heterocyclyl, aryl, heteroaryl, heterocyclyl moieties are any alkylene, heterocyclyl, aryl, heteroaryl, heterocyclyl moieties defined or exemplified herein, optionally substituted with one or more of any substituents defined or exemplified herein.

In yet another embodiment of the compounds of Formula I, n is 0, the -$L^3$-$Ar^1$-($L^4$-$R^{6a}$)$_n$ moiety is an -alkylene-aryl group, m is 1, the -$L^5$-$Ar^3$-($L^6$-$R^6$)$_m$ moiety is an -alkylene-aryl-aryl group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene-aryl group, $L^1$-$L^2$-$R^1$ is —O—$R^1$, wherein $R^1$ is alkyl or substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene-aryl group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene-aryl group, -$L^1$-$L^2$-$R^1$ is —C($R^{17}R^{18}$)—$NR^8$—C(O)—O—$R^9$ wherein $R^8$, $R^{17}$, and $R^1$ are independently H, alkyl, or substituted alkyl, and $R^9$ is alkyl or substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0; the -$L^5$-$Ar^3$-($L^6$-$R^6$)$_m$ moiety is an -alkylene-aryl group, -$L^1$-$L^2$-$R^1$ is —C($R^{17}R^{18}$)—$NR^8$—C(O)—O—$R^9$ wherein $R^{17}$ and $R^{18}$ taken together with the carbon atom to which they are shown attached form a heterocyclyl or a substituted heterocyclyl, $R^8$ is H, alkyl, or substituted alkyl, and $R^9$ is alkyl or substituted alkyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, -$L^5$-$Ar^3$-($L^6$-$R^6$)$_m$ moiety is an -alkylene-aryl-O—CH$_2$-aryl group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O—CH$_2$-aryl group, $L^1$-$L^2$-$R^1$ is —($R^{17}R^{18}$)—$NR^8$—C(O)—O—$R^9$ wherein $R^8$, $R^{17}$, and $R^{18}$ are independently H, alkyl, or substituted alkyl, and $R^9$ is alkyl or substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O—CH$_2$-heterocyclyl group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heteroaryl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—C(O)—O-alkyl group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—S(O)$_2$—O-alkyl group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—C(O)-heteroaryl group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-PO$_3$(alkyl)$_2$ group, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-$PO_3$(alkyl)$_2$ group, -$L^1$-$L^2$-$R^1$ is —C($R^{17}R^{18}$)—$NR^8$—C(O)—O—$R^9$ wherein $R^8$, $R^{17}$, and $R^{18}$ are independently H, alkyl, or substituted alkyl, and $R^9$ is alkyl or substituted alkyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-O-alkylene-heterocyclyl group, m is 0, the -$L^5$-$Ar^3$-($L^6$-$R^6$)$_m$ moiety is an -alkylene-aryl group, -$L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-O-haloalkyl, m is 1, the -$L^5$-$Ar^3$-($L^6$-$R^6$)$_m$ moiety is an -alkylene-aryl-heteroaryl group, -$L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-O-haloalkyl, m is 0, the -$L^5$-$Ar^3$-($L^6$-$R^6$)$_m$ moiety is α-alkylene-aryl, $L^1$-$L^2$-$R^1$ is —O—$R^1$, wherein $R^1$ is heterocyclyl, substituted heterocyclyl, heterocyclylalkyl, or substituted heterocyclylalkyl, wherein said alkylene, alkyl, aryl, and heterocyclyl moieties are any alkylene, alkyl, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, n is 0, the -$L^3$-$Ar^1$-($L^4$-$R^{6a}$)$_n$ moiety is an -alkylene-aryl group, m is 1, the -$L^5$-$Ar^3$-($L^6$-$R^6$)$_m$ moiety is an -alkylene-aryl-heteroaryl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-heteroaryl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted on the alkylene, aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene-aryl group, -$L^1$-$L^2$-$R^1$ is —C($R^{17}R^{18}$)—$NR^8$—C(O)—O—$R^9$ wherein $R^8$, $R^{17}$, and $R^1$ are independently H, alkyl, or substituted alkyl, and $R^9$ is alkyl or substituted alkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene-aryl group, -$L^1$-$L^2$-$R^1$ is —C($R^{17}R^{18}$)—$NR^8$—C(O)—O—$R^9$ wherein $R^{17}$ and $R^{18}$ taken together with the carbon atom to which they are shown attached form a heterocyclyl or a substituted heterocyclyl, $R^8$ is H, alkyl, or substituted alkyl, and $R^9$ is alkyl or substituted alkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O—$CH_2$-aryl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—C(O)—O-alkyl group, $L^1$-$L^2$-$R^1$ is —O—$R^1$, wherein $R^1$ is heterocyclyl, substituted heterocyclyl, heterocyclylalkyl, or substituted heterocyclylalkyl, )—, $X^2$ is —(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—S(O)$_2$—O-alkyl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-NH—C(O)-heteroaryl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-$PO_3$(alkyl)$_2$ group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkylene-$PO_3$(alkyl)$_2$ group, -$L^1$-$L^2$-$R^1$ is —C($R^{17}R^{18}$)—$NR^8$—C(O)—O—$R^9$ wherein $R^8$, and $R^{17}$ are independently H, alkyl, or substituted alkyl, and $R^9$ is alkyl or substituted alkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_m$ moiety is an -alkylene-aryl-heterocyclyl group, m is 1, the -$L^5$-$Ar^3$-($L^6$-$R^6$)$_m$ moiety is an -alkylene-aryl-O-aryl group, -$L^1$-$L^2$-$R^1$ is —C($R^{17}R^{18}$)—$NR^8$—C(O)—O—$R^9$ wherein $R^8$, $R^{17}$, and $R^{18}$ are independently H, alkyl, or substituted alkyl, and $R^9$ is alkyl or substituted alkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 1, the -$L^5$-$Ar^3$-($L^6$-$R^6$)$_m$ moiety is an -alkylene-aryl-O-alkyl group, -$L^1$-$L^2$-$R^1$ is —C($R^{17}R^{18}$)—$NR^8$—C(O)—O—$R^9$ wherein $R^8$, $R^{17}$, and $R^{18}$ are independently H, alkyl, or substituted alkyl, and $R^9$ is alkyl or substituted alkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^6$)$_n$ moiety is an -alkylene-aryl-heterocyclyl group, m is 1, the -$L^5$-$Ar^3$-($L^6$-$R^6$)$_m$ moiety is an -alkylene-aryl-O-heteroaryl group, -$L^1$-$L^2$-$R^1$ is —C($R^{17}R^{18}$)—$NR^8$—C(O)—O—$R^9$ wherein $R^8$, $R^{17}$, and $R^{18}$ are independently H, alkyl, or substituted alkyl, and $R^9$ is alkyl or substituted alkyl, $X^2$ is —C(O)—, Y is —O—, $Ar^2$ is heterocyclyl or substituted heterocyclyl, wherein said alkylene, alkyl, aryl, heteroaryl, and heterocyclyl moieties are any alkylene, alkyl, aryl, heteroaryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene group, -$L^1$-$L^2$-$R^1$ is —C($R^{17}R^{18}$)—$NR^8$—C(O)—O—$R^9$ wherein $R^8$, $R^{17}$, and $R^{18}$ are independently H, alkyl, or substituted alkyl, and $R^9$ is alkyl or substituted alkyl, $X^2$ is —C(O)—, Y is —O—, $Ar^2$ is heterocyclyl or substituted heterocyclyl, wherein said alkylene, alkyl, aryl, heteroaryl, and heterocyclyl moieties are any alkylene, alkyl, aryl, heteroaryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-O-alkylene-heterocyclyl group, m is 0, -$L^5$-$Ar^3$-($L^6$-$R^6$)$_m$ moiety is α-alkylene-aryl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —(O)—, Y is —O—, $Ar^2$ is heterocyclyl or substituted heterocyclyl, wherein said alkylene, aryl, and heterocyclyl moieties are any alkylene, aryl, and heterocyclyl moieties defined or exemplified herein, optionally substituted on the alkylene and/or aryl and/or heterocyclyl with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene-aryl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$); moiety is an -alkylene-aryl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —C(O)—, Y is —O—, $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, n is 1, the -$L^3$-$Ar^1$-($L^4$-$R^{6a}$)$_n$ moiety is an -alkylene-aryl-heterocyclyl group, m is 0, the -$L^5$-$Ar^3$-($L^6$-$R^6$)$_m$ moiety is an -alkylene-aryl group, $L^1$-$L^2$-$R^1$ is —O—$R^1$, wherein $R^1$ is heterocyclyl, substituted heterocyclyl, heterocyclylalkyl, or substituted heterocyclylalkyl, $X^2$ is —(O)—, Y is —S—, and $Ar^2$ is heterocyclyl or substituted heterocyclyl, wherein said alkylene, alkyl, aryl, and heterocyclyl moieties are any alkylene, alkyl, aryl, and heterocyclyl moieties defined or exemplified herein, optionally substituted with one or more of any substituents defined or exemplified herein.

In yet another embodiment of the compounds of Formula I, the compounds are selected from the group consisting of
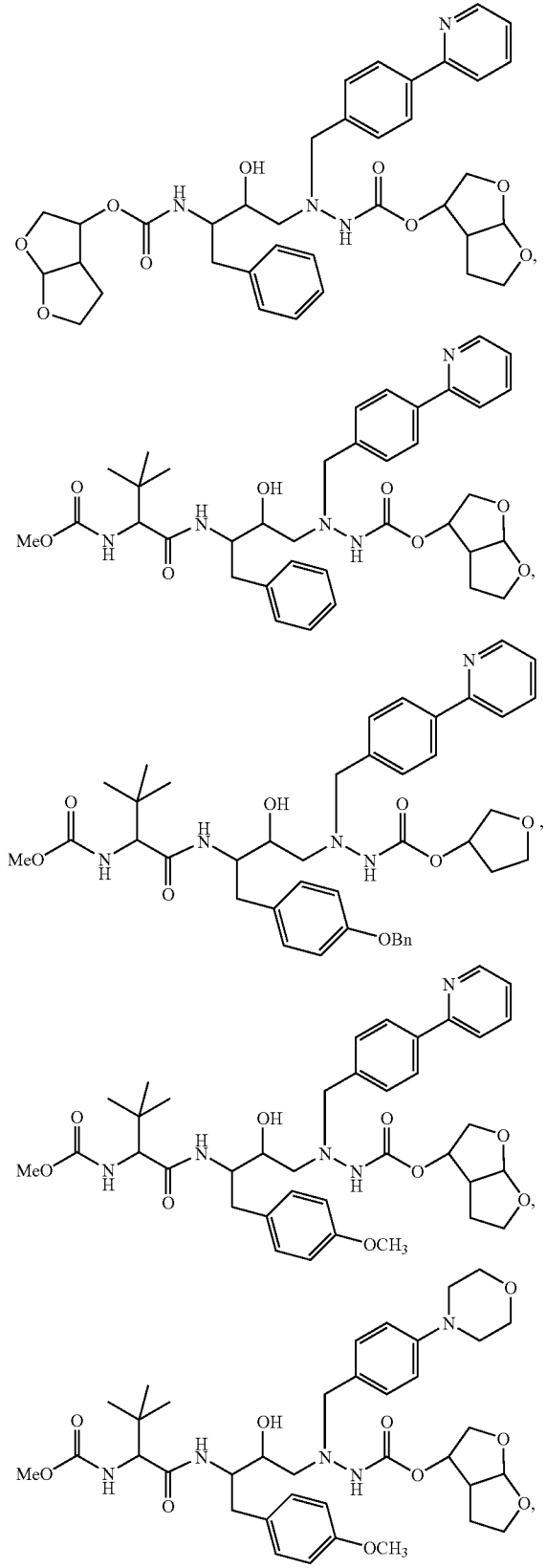
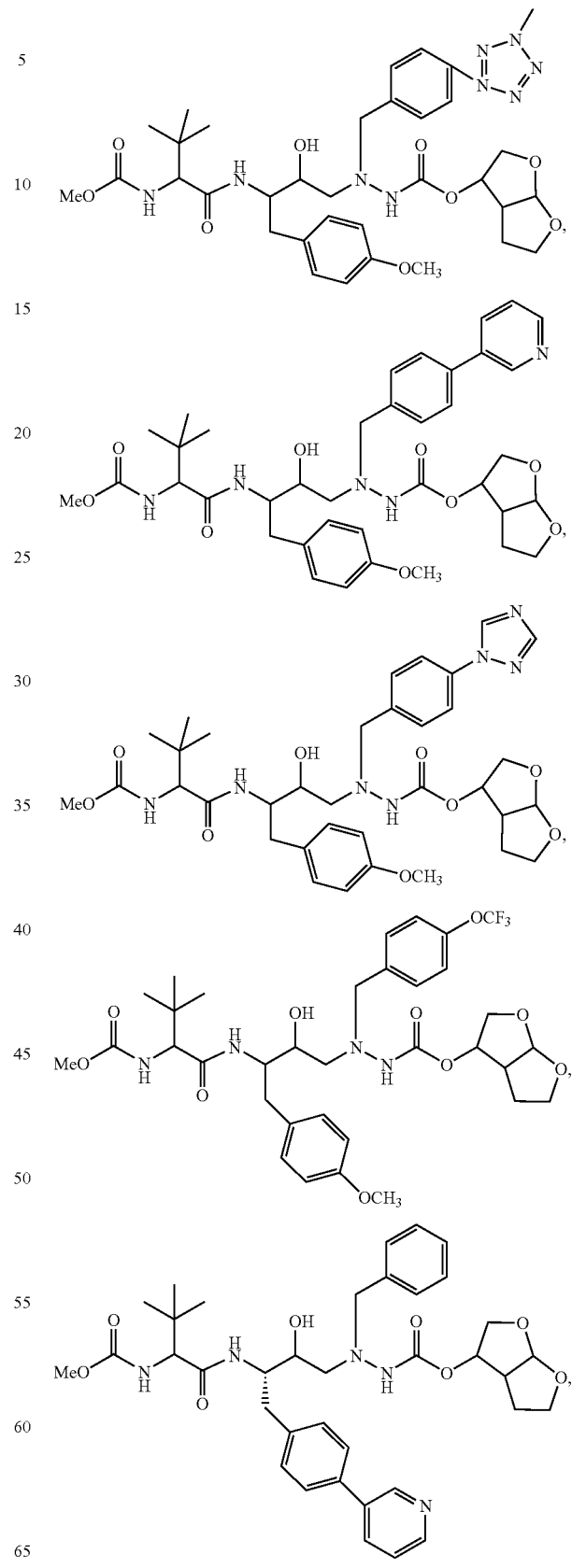

-continued
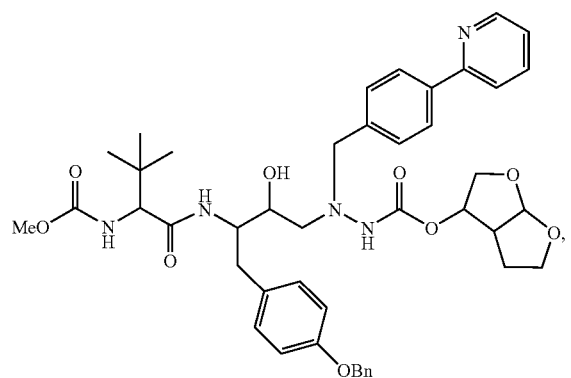
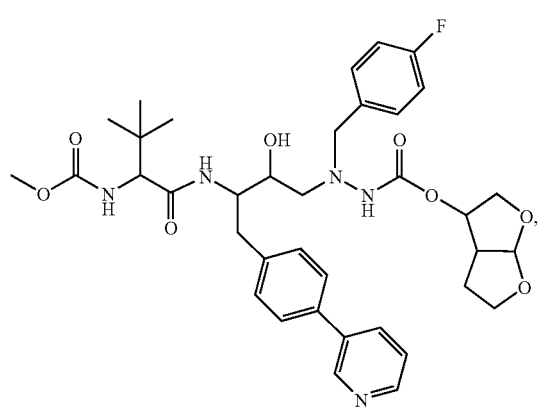
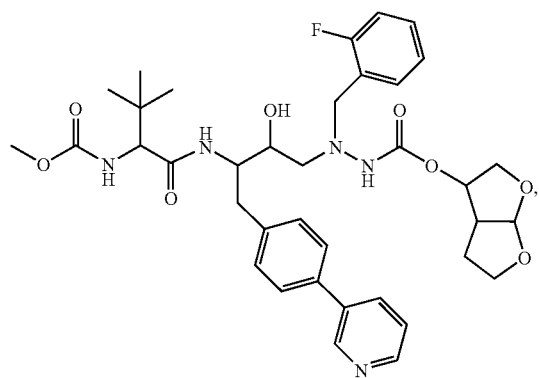
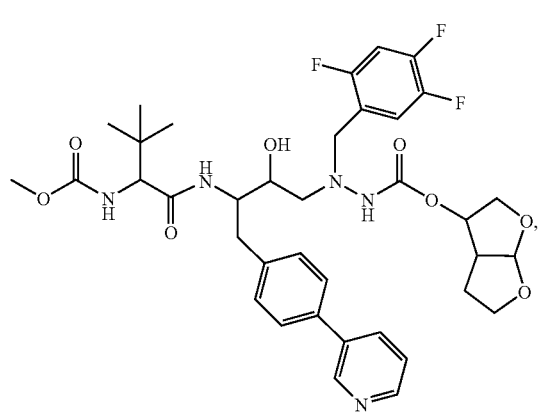
-continued
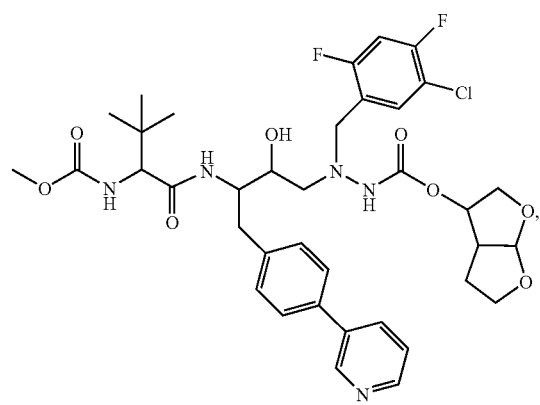
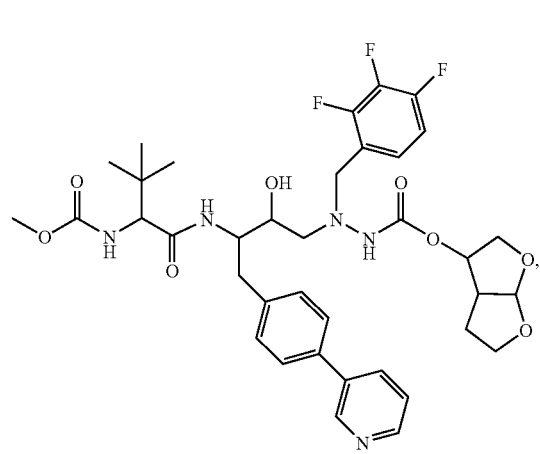
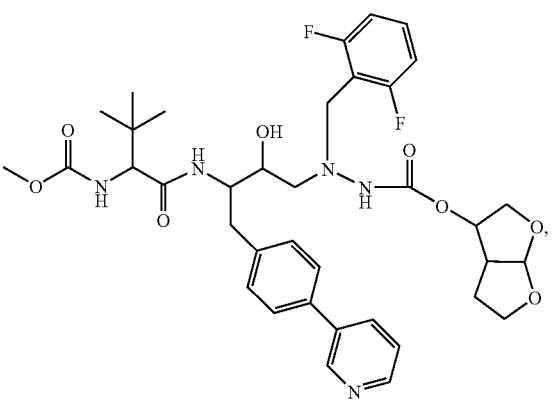
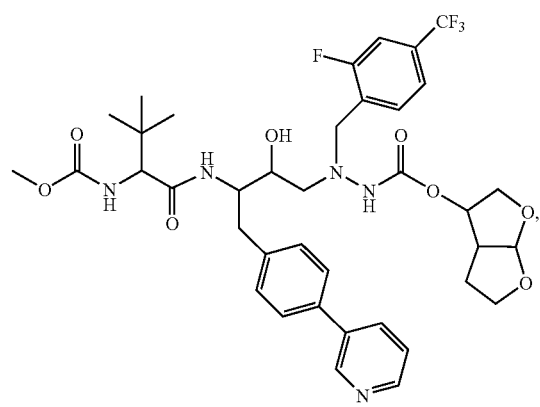

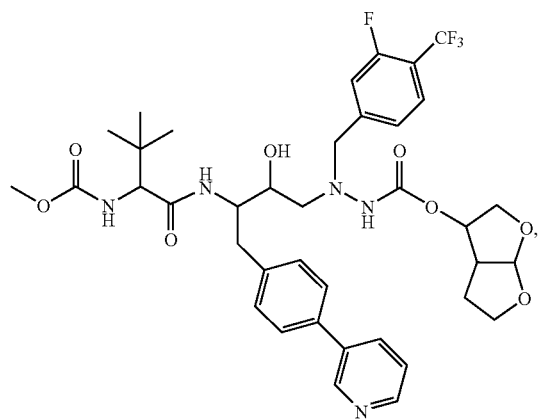
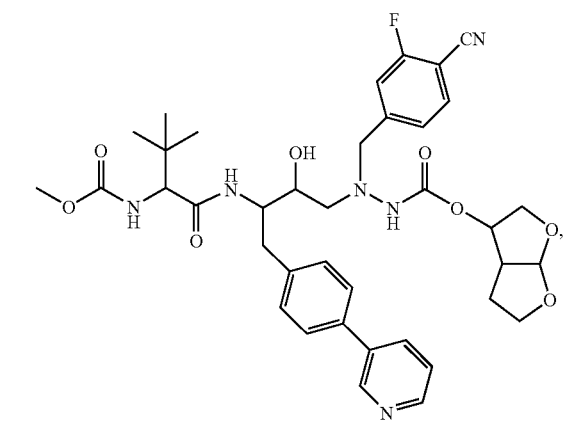
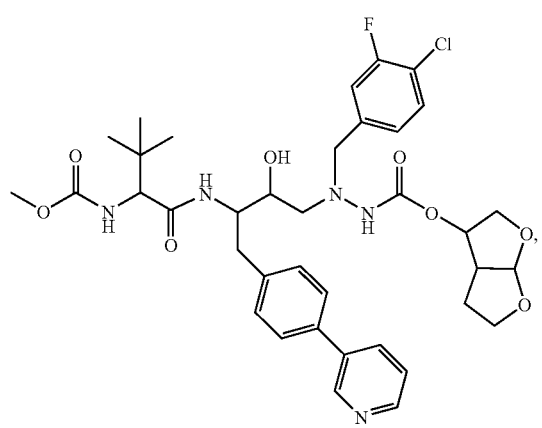
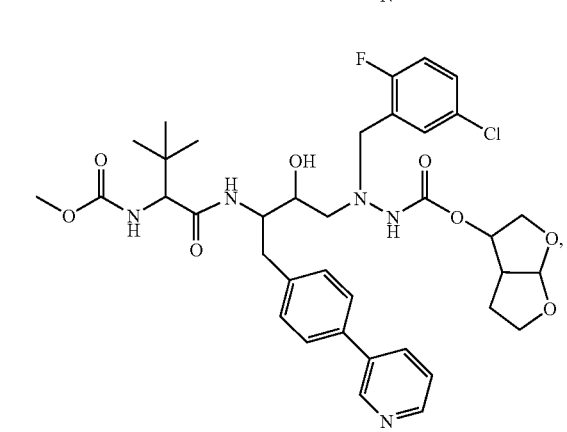
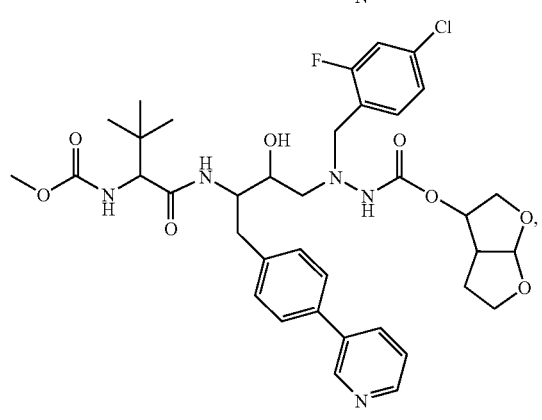
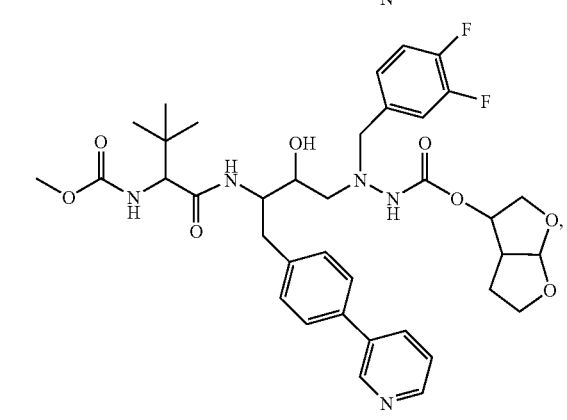
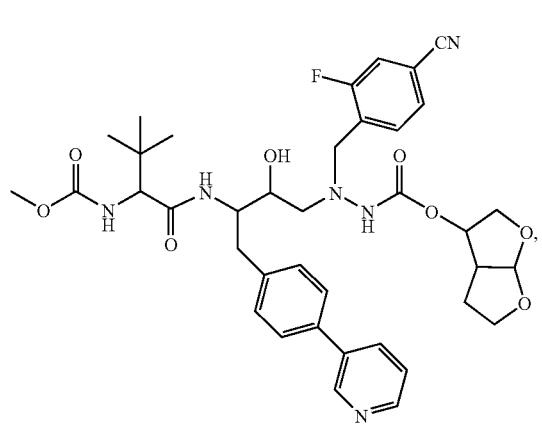
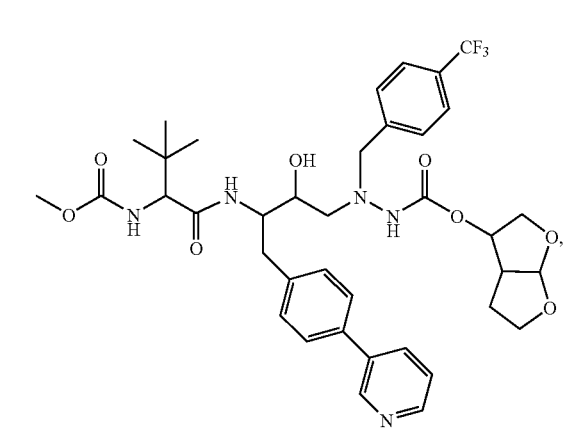

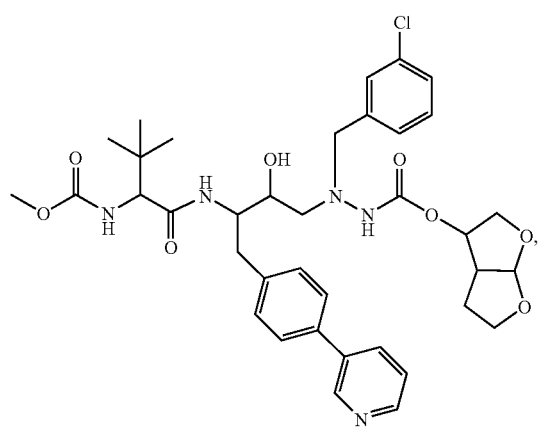
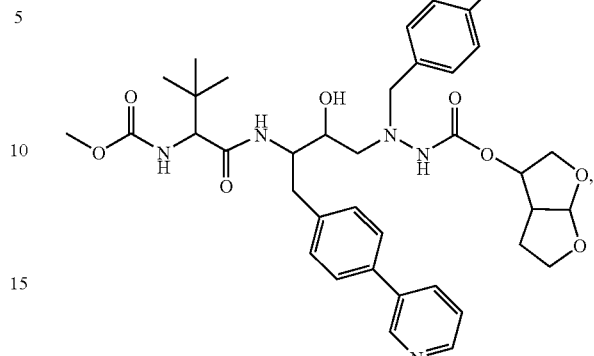
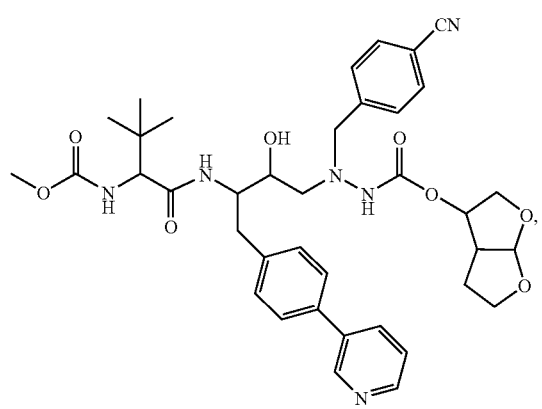
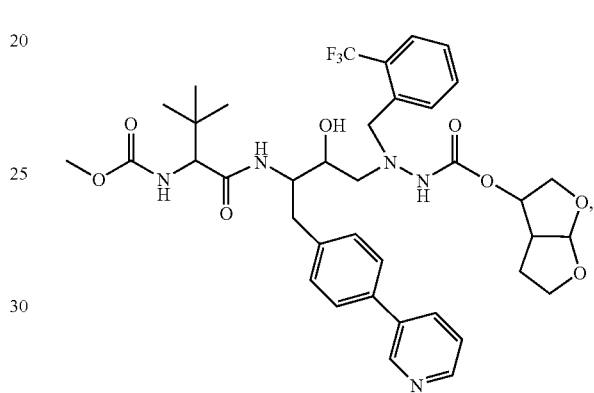
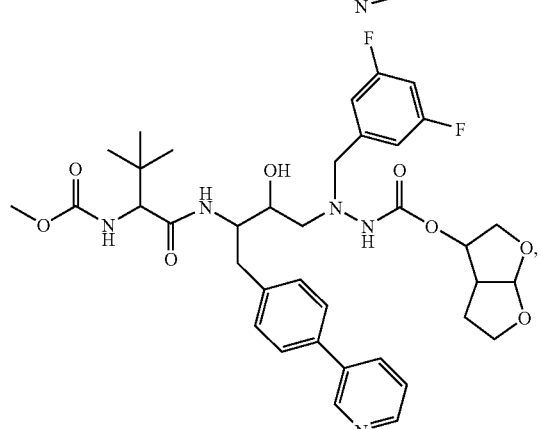
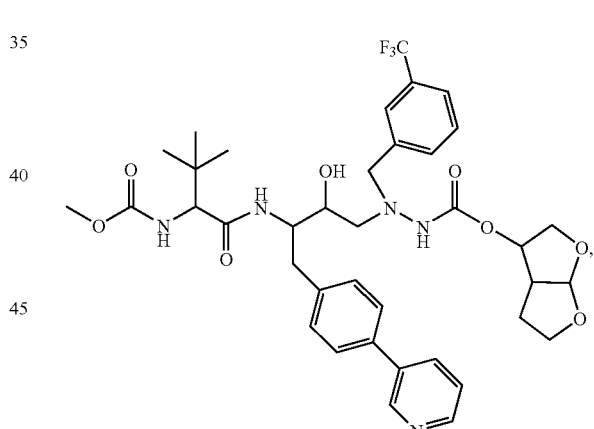
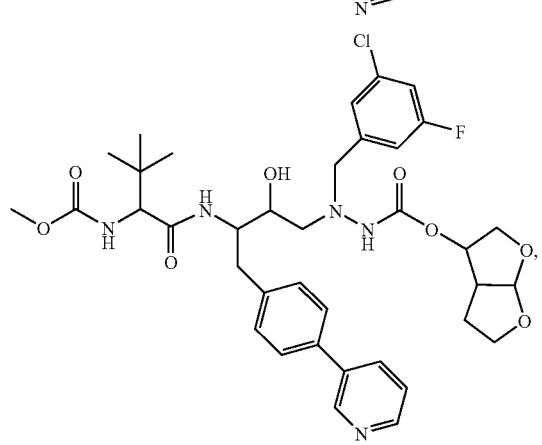
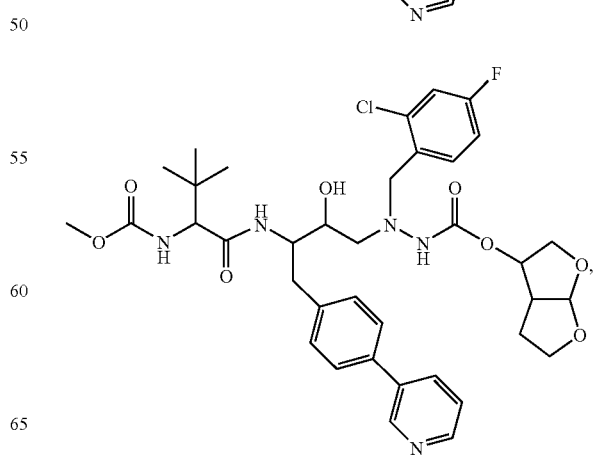

-continued
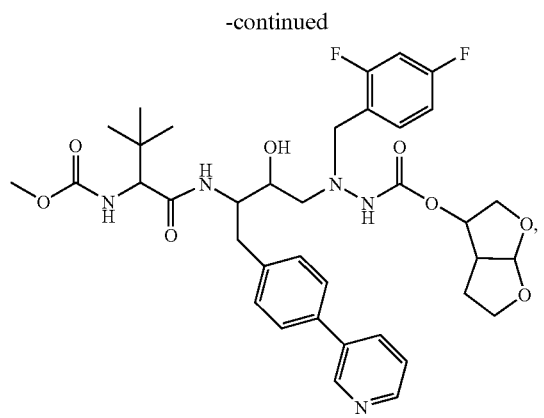
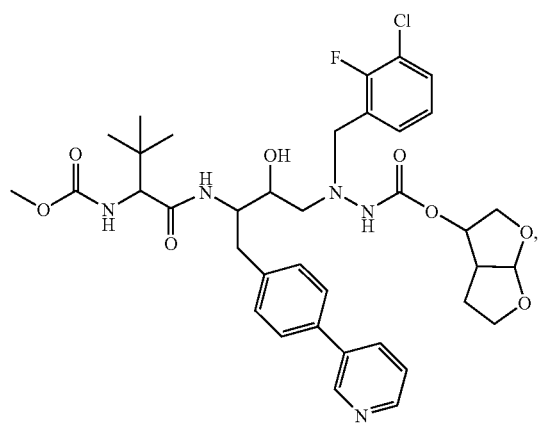
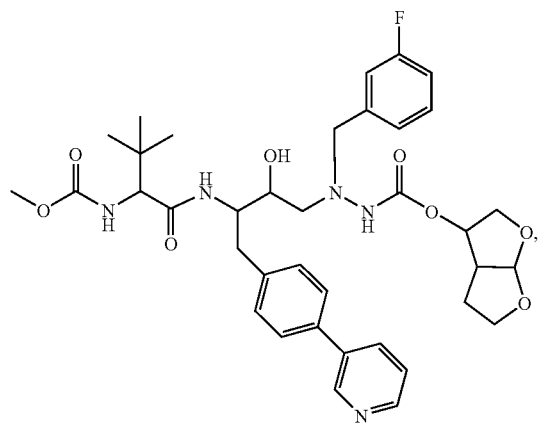
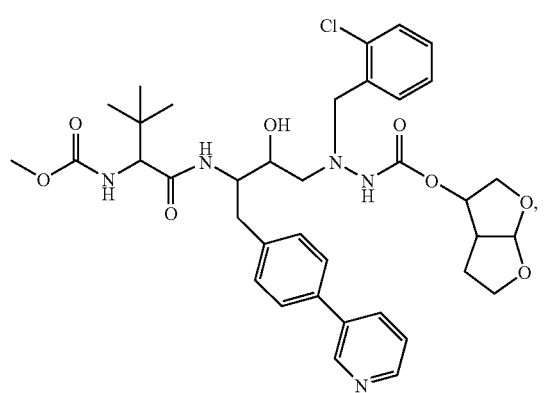
-continued
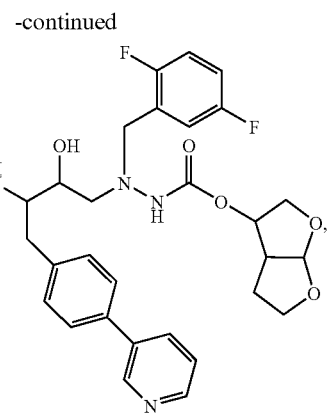
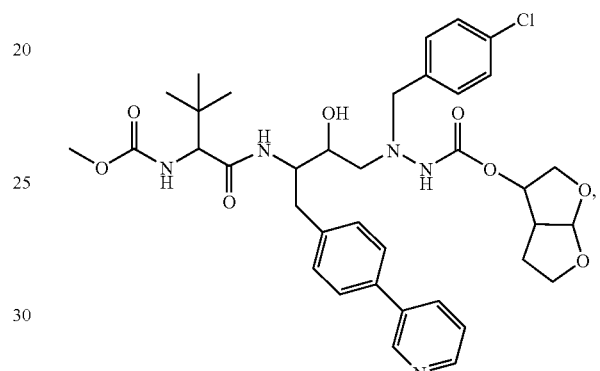
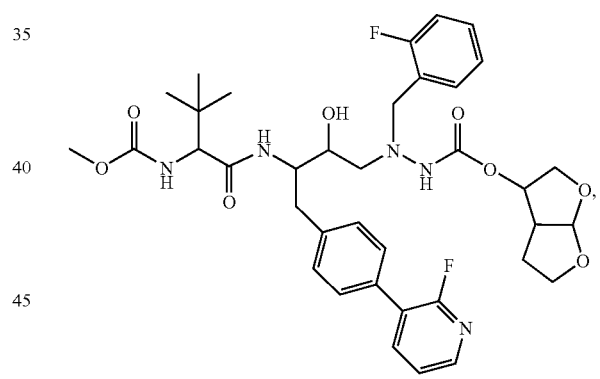
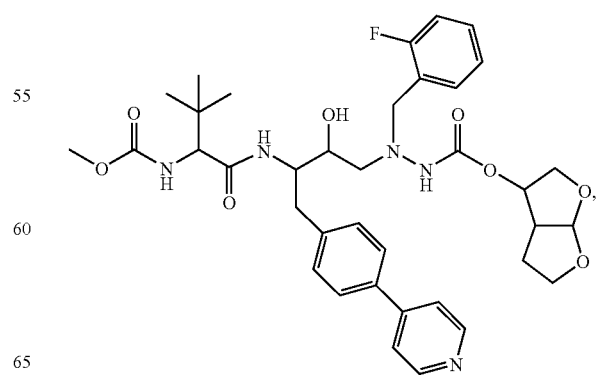

-continued

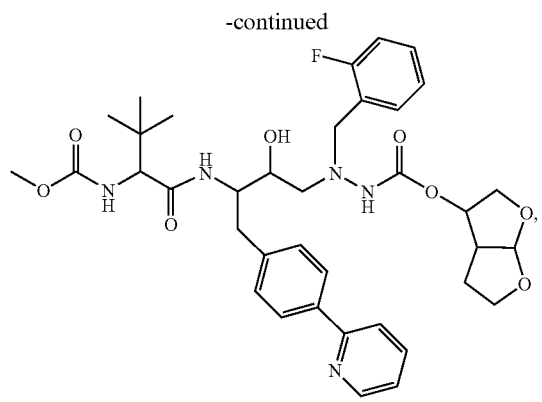

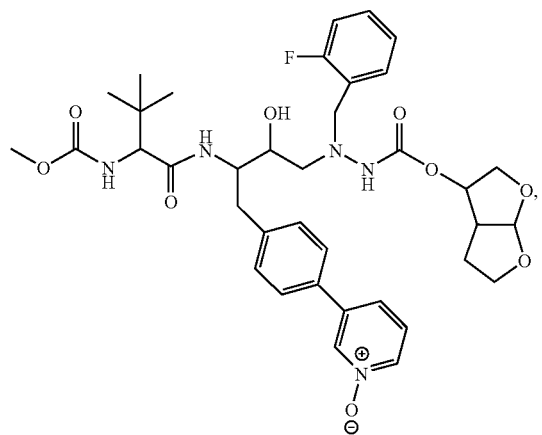

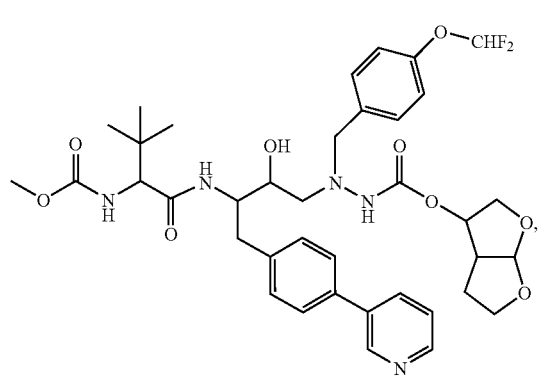

-continued

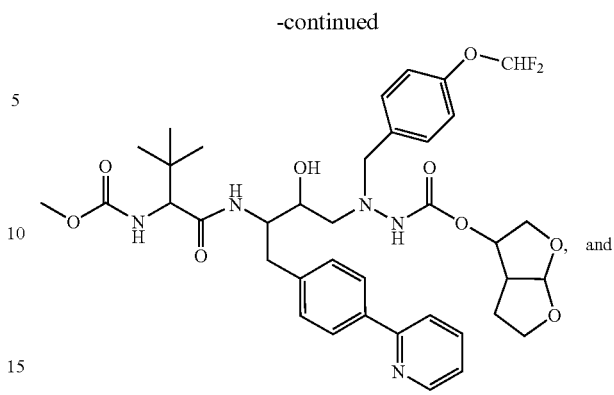

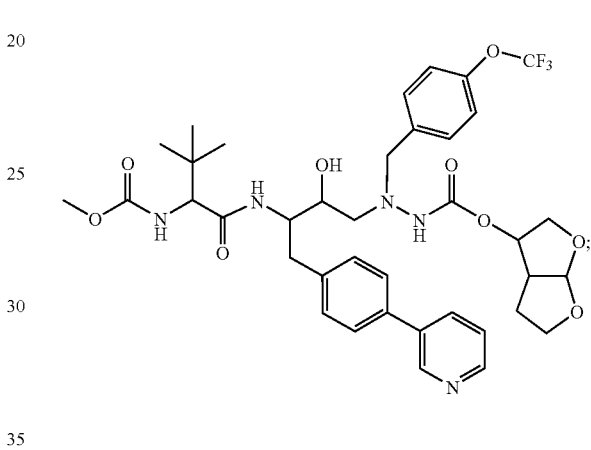

or a pharmaceutically acceptable salt, solvate and/or ester thereof.

In still yet another embodiment, compounds of Formula I are named below in tabular format (Table 6) as compounds of general Formula II:

Formula II

Compounds of general formula II are depicted as a "core" structure (Z) substituted with four moieties T1, T2, X1 and X2. The core structures Z are depicted in Table 1. The points of attachment of T1, T2, X1 and X2 are indicated on each of the core structures depicted in Table 1. Tables 2-5, respectively, show the structures of the T1, T2, X1 and X2 moieties. The point of attachment of the core structure Z is indicated in each of the structures of T1, T2, X1 and X2. Each core structure Z in Table 1, and each substituent T1, T2, $X^1$ and $X^2$ and Tables 2-5 is represented by a "code" comprising a letter and a number. Each structure of a compound of Formula II can be designated in tabular form by combining the "code" representing each structural moiety using the following syntax: Z.T1.T2.X1.X2. Thus, for example, Z1.T1A.T2A.X1A.X2A represents the following structure:

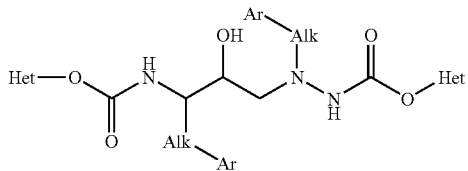

In the structures depicted in Tables 1-5, the term "Alk" means a substituted or unsubstituted alkyl or alkylene group, wherein the terms "alkyl" and "alkylene" are as defined herein. "Alk" means an alkyl group when depicted as monovalent, and an alkylene group when depicted as divalent. "Het" is a substituted or unsubstituted heterocyclyl or heterocyclylene group, wherein the term "heterocyclyl" is as defined herein, and the term "heterocyclylene" means a heterocyclyl group as defined herein, in which a hydrogen atom has been replaced by an open valence (in analogy to alkylene), thereby defining a divalent heterocyclyl. "Het" is a heterocyclyl when depicted as monovalent, and heterocyclylene when depicted as divalent. "Ar" is a substitute or unsubstituted aryl or arylene group, wherein the term "aryl" is as defined herein, and the term "arylene" means an aryl group as defined herein, in which a hydrogen atom has been replaced by an open valence (in analogy to alkylene), thereby defining a divalent aryl. "Ar" is aryl when depicted as monovalent, and arylene when depicted as divalent. When substituted, "Alk", "Het", and "Ar" can be substituted with any of the substituents defined or exemplified herein. For example, substituents of "Alk" can include ether, halogen, —OH, amide, amine, etc., substituents of "Het" can include alkyl, aryl, carbonyl, —OH, halogen, and substituents of "Ar" can include alkyl, aryl, —OH, halogen, etc., with the proviso that the resulting structure is chemically reasonable, and would provide compounds which are sufficiently stable for formulation in a pharmaceutically acceptable composition.

TABLE 1

Core Structures

| Code | Subgenus Structure |
|------|--------------------|
| Z1 | (structure) |
| Z2 | (structure) |
| Z3 | (structure) |

TABLE 1-continued

Core Structures

| Code | Subgenus Structure |
|------|--------------------|
| Z4 | (structure) |
| Z5 | (structure) |

TABLE 2

T1 Structures

| Code | T1 Structure |
|------|--------------|
| T1A | —O-Het |
| T1B | —O—Ar |
| T1C | —O-Alk-Ar |
| T1D | —O-Alk-Het |
| T1E | -Alk-NH—C(O)—O-Alk |
| T1F | -Alk-Het |

TABLE 3

T2 Structures

| Code | T2 Structure |
|------|--------------|
| T2A | —O-Het |
| T2B | —O—Ar |
| T2C | —O-Alk-Ar |
| T2D | —O-Alk-Het |

TABLE 4

X1 Structures

| Code | X1 Structure |
|------|--------------|
| X1A | —Ar |
| X1B | —Ar—Ar |
| X1C | —Ar-Het |
| X1D | —Ar—O-Het |
| X1E | —Ar—O-Alk-Het |
| X1F | —Ar—NH-Het |

TABLE 5

X2 Structures

| Code | X2 Structure |
|------|--------------|
| X2A | —Ar |
| X2B | —Ar—Ar |
| X2C | —Ar-Het |
| X2D | —Ar—O-Het |

TABLE 5-continued

X2 Structures

| Code | X2 Structure |
| --- | --- |
| X2E | —Ar—O-Alk-Het |
| X2F | —Ar—NH-Het |

TABLE 6

List of Compound Structure of Formula II

Z1.T1A.T2A.X1A.X2A, Z2.T1A.T2A.X1A.X2A,
Z3.T1A.T2A.X1A.X2A,
Z4.T1A.T2A.X1A.X2A, Z5.T1A.T2A.X1A.X2A,
Z1.T1B.T2A.X1A.X2A,
Z2.T1B.T2A.X1A.X2A, Z3.T1B.T2A.X1A.X2A,
Z4.T1B.T2A.X1A.X2A,
Z5.T1B.T2A.X1A.X2A, Z1.T1C.T2A.X1A.X2A,
Z2.T1C.T2A.X1A.X2A,
Z3.T1C.T2A.X1A.X2A, Z4.T1C.T2A.X1A.X2A,
Z5.T1C.T2A.X1A.X2A,
Z1.T1D.T2A.X1A.X2A, Z2.T1D.T2A.X1A.X2A,
Z3.T1D.T2A.X1A.X2A,
Z4.T1D.T2A.X1A.X2A, Z5.T1D.T2A.X1A.X2A,
Z1.T1E.T2A.X1A.X2A,
Z2.T1E.T2A.X1A.X2A, Z3.T1E.T2A.X1A.X2A,
Z4.T1E.T2A.X1A.X2A,
Z5.T1E.T2A.X1A.X2A, Z1.T1F.T2A.X1A.X2A,
Z2.T1F.T2A.X1A.X2A,
Z3.T1F.T2A.X1A.X2A, Z4.T1F.T2A.X1A.X2A,
Z5.T1F.T2A.X1A.X2A,
Z1.T1A.T2B.X1A.X2A, Z2.T1A.T2B.X1A.X2A,
Z3.T1A.T2B.X1A.X2A,
Z4.T1A.T2B.X1A.X2A, Z5.T1A.T2B.X1A.X2A,
Z1.T1B.T2B.X1A.X2A,
Z2.T1B.T2B.X1A.X2A, Z3.T1B.T2B.X1A.X2A,
Z4.T1B.T2B.X1A.X2A,
Z5.T1B.T2B.X1A.X2A, Z1.T1C.T2B.X1A.X2A,
Z2.T1C.T2B.X1A.X2A,
Z3.T1C.T2B.X1A.X2A, Z4.T1C.T2B.X1A.X2A,
Z5.T1C.T2B.X1A.X2A,
Z1.T1D.T2B.X1A.X2A, Z2.T1D.T2B.X1A.X2A,
Z3.T1D.T2B.X1A.X2A,
Z4.T1D.T2B.X1A.X2A, Z5.T1D.T2B.X1A.X2A,
Z1.T1E.T2B.X1A.X2A,
Z2.T1E.T2B.X1A.X2A, Z3.T1E.T2B.X1A.X2A,
Z4.T1E.T2B.X1A.X2A,
Z5.T1E.T2B.X1A.X2A, Z1.T1F.T2B.X1A.X2A,
Z2.T1F.T2B.X1A.X2A,
Z3.T1F.T2B.X1A.X2A, Z4.T1F.T2B.X1A.X2A,
Z5.T1F.T2B.X1A.X2A,
Z1.T1A.T2C.X1A.X2A, Z2.T1A.T2C.X1A.X2A,
Z3.T1A.T2C.X1A.X2A,
Z4.T1A.T2C.X1A.X2A, Z5.T1A.T2C.X1A.X2A,
Z1.T1B.T2C.X1A.X2A,
Z2.T1B.T2C.X1A.X2A, Z3.T1B.T2C.X1A.X2A,
Z4.T1B.T2C.X1A.X2A,
Z5.T1B.T2C.X1A.X2A, Z1.T1C.T2C.X1A.X2A,
Z2.T1C.T2C.X1A.X2A,
Z3.T1C.T2C.X1A.X2A, Z4.T1C.T2C.X1A.X2A,
Z5.T1C.T2C.X1A.X2A,
Z1.T1D.T2C.X1A.X2A, Z2.T1D.T2C.X1A.X2A,
Z3.T1D.T2C.X1A.X2A,
Z4.T1D.T2C.X1A.X2A, Z5.T1D.T2C.X1A.X2A,
Z1.T1E.T2C.X1A.X2A,
Z2.T1E.T2C.X1A.X2A, Z3.T1E.T2C.X1A.X2A,
Z4.T1E.T2C.X1A.X2A,
Z5.T1E.T2C.X1A.X2A, Z1.T1F.T2C.X1A.X2A,
Z2.T1F.T2C.X1A.X2A,
Z3.T1F.T2C.X1A.X2A, Z4.T1F.T2C.X1A.X2A,
Z5.T1F.T2C.X1A.X2A,
Z1.T1A.T2D.X1A.X2A, Z2.T1A.T2D.X1A.X2A,
Z3.T1A.T2D.X1A.X2A,
Z4.T1A.T2D.X1A.X2A, Z5.T1A.T2D.X1A.X2A,
Z1.T1B.T2D.X1A.X2A,
Z2.T1B.T2D.X1A.X2A, Z3.T1B.T2D.X1A.X2A,
Z4.T1B.T2D.X1A.X2A,
Z5.T1B.T2D.X1A.X2A, Z1.T1C.T2D.X1A.X2A,
Z2.T1C.T2D.X1A.X2A,
Z3.T1C.T2D.X1A.X2A, Z4.T1C.T2D.X1A.X2A,
Z5.T1C.T2D.X1A.X2A,
Z1.T1D.T2D.X1A.X2A, Z2.T1D.T2D.X1A.X2A,
Z3.T1D.T2D.X1A.X2A,
Z4.T1D.T2D.X1A.X2A, Z5.T1D.T2D.X1A.X2A,
Z1.T1E.T2D.X1A.X2A,
Z2.T1E.T2D.X1A.X2A, Z3.T1E.T2D.X1A.X2A,
Z4.T1E.T2D.X1A.X2A,
Z5.T1E.T2D.X1A.X2A, Z1.T1F.T2D.X1A.X2A,
Z2.T1F.T2D.X1A.X2A,
Z3.T1F.T2D.X1A.X2A, Z4.T1F.T2D.X1A.X2A,
Z5.T1F.T2D.X1A.X2A,
Z1.T1A.T2A.X1B.X2A, Z2.T1A.T2A.X1B.X2A,
Z3.T1A.T2A.X1B.X2A,
Z4.T1A.T2A.X1B.X2A, Z5.T1A.T2A.X1B.X2A,
Z1.T1B.T2A.X1B.X2A,
Z2.T1B.T2A.X1B.X2A, Z3.T1B.T2A.X1B.X2A,
Z4.T1B.T2A.X1B.X2A,
Z5.T1B.T2A.X1B.X2A, Z1.T1C.T2A.X1B.X2A,
Z2.T1C.T2A.X1B.X2A,
Z3.T1C.T2A.X1B.X2A, Z4.T1C.T2A.X1B.X2A,
Z5.T1C.T2A.X1B.X2A,
Z1.T1D.T2A.X1B.X2A, Z2.T1D.T2A.X1B.X2A,
Z3.T1D.T2A.X1B.X2A,
Z4.T1D.T2A.X1B.X2A, Z5.T1D.T2A.X1B.X2A,
Z1.T1E.T2A.X1B.X2A,
Z2.T1E.T2A.X1B.X2A, Z3.T1E.T2A.X1B.X2A,
Z4.T1E.T2A.X1B.X2A,
Z5.T1E.T2A.X1B.X2A, Z1.T1F.T2A.X1B.X2A,
Z2.T1F.T2A.X1B.X2A,
Z3.T1F.T2A.X1B.X2A, Z4.T1F.T2A.X1B.X2A,
Z5.T1F.T2A.X1B.X2A,
Z1.T1A.T2B.X1B.X2A, Z2.T1A.T2B.X1B.X2A,
Z3.T1A.T2B.X1B.X2A,
Z4.T1A.T2B.X1B.X2A, Z5.T1A.T2B.X1B.X2A,
Z1.T1B.T2B.X1B.X2A,
Z2.T1B.T2B.X1B.X2A, Z3.T1B.T2B.X1B.X2A,
Z4.T1B.T2B.X1B.X2A,
Z5.T1B.T2B.X1B.X2A, Z1.T1C.T2B.X1B.X2A,
Z2.T1C.T2B.X1B.X2A,
Z3.T1C.T2B.X1B.X2A, Z4.T1C.T2B.X1B.X2A,
Z5.T1C.T2B.X1B.X2A,
Z1.T1D.T2B.X1B.X2A, Z2.T1D.T2B.X1B.X2A,
Z3.T1D.T2B.X1B.X2A,
Z4.T1D.T2B.X1B.X2A, Z5.T1D.T2B.X1B.X2A,
Z1.T1E.T2B.X1B.X2A,
Z2.T1E.T2B.X1B.X2A, Z3.T1E.T2B.X1B.X2A,
Z4.T1E.T2B.X1B.X2A,
Z5.T1E.T2B.X1B.X2A, Z1.T1F.T2B.X1B.X2A,
Z2.T1F.T2B.X1B.X2A,
Z3.T1F.T2B.X1B.X2A, Z4.T1F.T2B.X1B.X2A,
Z5.T1F.T2B.X1B.X2A,
Z1.T1A.T2C.X1B.X2A, Z2.T1A.T2C.X1B.X2A,
Z3.T1A.T2C.X1B.X2A,
Z4.T1A.T2C.X1B.X2A, Z5.T1A.T2C.X1B.X2A,
Z1.T1B.T2C.X1B.X2A,
Z2.T1B.T2C.X1B.X2A, Z3.T1B.T2C.X1B.X2A,
Z4.T1B.T2C.X1B.X2A,
Z5.T1B.T2C.X1B.X2A, Z1.T1C.T2C.X1B.X2A,
Z2.T1C.T2C.X1B.X2A,
Z3.T1C.T2C.X1B.X2A, Z4.T1C.T2C.X1B.X2A,
Z5.T1C.T2C.X1B.X2A,
Z1.T1D.T2C.X1B.X2A, Z2.T1D.T2C.X1B.X2A,
Z3.T1D.T2C.X1B.X2A,
Z4.T1D.T2C.X1B.X2A, Z5.T1D.T2C.X1B.X2A,
Z1.T1E.T2C.X1B.X2A,
Z2.T1E.T2C.X1B.X2A, Z3.T1E.T2C.X1B.X2A,
Z4.T1E.T2C.X1B.X2A,
Z5.T1E.T2C.X1B.X2A, Z1.T1F.T2C.X1B.X2A,
Z2.T1F.T2C.X1B.X2A,
Z3.T1F.T2C.X1B.X2A, Z4.T1F.T2C.X1B.X2A,
Z5.T1F.T2C.X1B.X2A,

TABLE 6-continued

List of Compound Structure of Formula II

Z1.T1A.T2D.X1B.X2A, Z2.T1A.T2D.X1B.X2A, Z3.T1A.T2D.X1B.X2A,
Z4.T1A.T2D.X1B.X2A, Z5.T1A.T2D.X1B.X2A, Z1.T1B.T2D.X1B.X2A,
Z2.T1B.T2D.X1B.X2A, Z3.T1B.T2D.X1B.X2A, Z4.T1B.T2D.X1B.X2A,
Z5.T1B.T2D.X1B.X2A, Z1.T1C.T2D.X1B.X2A, Z2.T1C.T2D.X1B.X2A,
Z3.T1C.T2D.X1B.X2A, Z4.T1C.T2D.X1B.X2A, Z5.T1C.T2D.X1B.X2A,
Z1.T1D.T2D.X1B.X2A, Z2.T1D.T2D.X1B.X2A, Z3.T1D.T2D.X1B.X2A,
Z4.T1D.T2D.X1B.X2A, Z5.T1D.T2D.X1B.X2A, Z1.T1E.T2D.X1B.X2A,
Z2.T1E.T2D.X1B.X2A, Z3.T1E.T2D.X1B.X2A, Z4.T1E.T2D.X1B.X2A,
Z5.T1E.T2D.X1B.X2A, Z1.T1F.T2D.X1B.X2A, Z2.T1F.T2D.X1B.X2A,
Z3.T1F.T2D.X1B.X2A, Z4.T1F.T2D.X1B.X2A, Z5.T1F.T2D.X1B.X2A,
Z1.T1A.T2A.X1C.X2A, Z2.T1A.T2A.X1C.X2A, Z3.T1A.T2A.X1C.X2A,
Z4.T1A.T2A.X1C.X2A, Z5.T1A.T2A.X1C.X2A, Z1.T1B.T2A.X1C.X2A,
Z2.T1B.T2A.X1C.X2A, Z3.T1B.T2A.X1C.X2A, Z4.T1B.T2A.X1C.X2A,
Z5.T1B.T2A.X1C.X2A, Z1.T1C.T2A.X1C.X2A, Z2.T1C.T2A.X1C.X2A,
Z3.T1C.T2A.X1C.X2A, Z4.T1C.T2A.X1C.X2A, Z5.T1C.T2A.X1C.X2A,
Z1.T1D.T2A.X1C.X2A, Z2.T1D.T2A.X1C.X2A, Z3.T1D.T2A.X1C.X2A,
Z4.T1D.T2A.X1C.X2A, Z5.T1D.T2A.X1C.X2A, Z1.T1E.T2A.X1C.X2A,
Z2.T1E.T2A.X1C.X2A, Z3.T1E.T2A.X1C.X2A, Z4.T1E.T2A.X1C.X2A,
Z5.T1E.T2A.X1C.X2A, Z1.T1F.T2A.X1C.X2A, Z2.T1F.T2A.X1C.X2A,
Z3.T1F.T2A.X1C.X2A, Z4.T1F.T2A.X1C.X2A, Z5.T1F.T2A.X1C.X2A,
Z1.T1A.T2B.X1C.X2A, Z2.T1A.T2B.X1C.X2A, Z3.T1A.T2B.X1C.X2A,
Z4.T1A.T2B.X1C.X2A, Z5.T1A.T2B.X1C.X2A, Z1.T1B.T2B.X1C.X2A,
Z2.T1B.T2B.X1C.X2A, Z3.T1B.T2B.X1C.X2A, Z4.T1B.T2B.X1C.X2A,
Z5.T1B.T2B.X1C.X2A, Z1.T1C.T2B.X1C.X2A, Z2.T1C.T2B.X1C.X2A,
Z3.T1C.T2B.X1C.X2A, Z4.T1C.T2B.X1C.X2A, Z5.T1C.T2B.X1C.X2A,
Z1.T1D.T2B.X1C.X2A, Z2.T1D.T2B.X1C.X2A, Z3.T1D.T2B.X1C.X2A,
Z4.T1D.T2B.X1C.X2A, Z5.T1D.T2B.X1C.X2A, Z1.T1E.T2B.X1C.X2A,
Z2.T1E.T2B.X1C.X2A, Z3.T1E.T2B.X1C.X2A, Z4.T1E.T2B.X1C.X2A,
Z5.T1E.T2B.X1C.X2A, Z1.T1F.T2B.X1C.X2A, Z2.T1F.T2B.X1C.X2A,
Z3.T1F.T2B.X1C.X2A, Z4.T1F.T2B.X1C.X2A, Z5.T1F.T2B.X1C.X2A,
Z1.T1A.T2C.X1C.X2A, Z2.T1A.T2C.X1C.X2A, Z3.T1A.T2C.X1C.X2A,
Z4.T1A.T2C.X1C.X2A, Z5.T1A.T2C.X1C.X2A, Z1.T1B.T2C.X1C.X2A,
Z2.T1B.T2C.X1C.X2A, Z3.T1B.T2C.X1C.X2A, Z4.T1B.T2C.X1C.X2A,
Z5.T1B.T2C.X1C.X2A, Z1.T1C.T2C.X1C.X2A, Z2.T1C.T2C.X1C.X2A,
Z3.T1C.T2C.X1C.X2A, Z4.T1C.T2C.X1C.X2A, Z5.T1C.T2C.X1C.X2A,
Z1.T1D.T2C.X1C.X2A, Z2.T1D.T2C.X1C.X2A, Z3.T1D.T2C.X1C.X2A,
Z4.T1D.T2C.X1C.X2A, Z5.T1D.T2C.X1C.X2A, Z1.T1E.T2C.X1C.X2A,
Z2.T1E.T2C.X1C.X2A, Z3.T1E.T2C.X1C.X2A, Z4.T1E.T2C.X1C.X2A,
Z5.T1E.T2C.X1C.X2A, Z1.T1F.T2C.X1C.X2A, Z2.T1F.T2C.X1C.X2A,
Z3.T1F.T2C.X1C.X2A, Z4.T1F.T2C.X1C.X2A, Z5.T1F.T2C.X1C.X2A,
Z1.T1A.T2D.X1C.X2A, Z2.T1A.T2D.X1C.X2A, Z3.T1A.T2D.X1C.X2A,
Z4.T1A.T2D.X1C.X2A, Z5.T1A.T2D.X1C.X2A, Z1.T1B.T2D.X1C.X2A,
Z2.T1B.T2D.X1C.X2A, Z3.T1B.T2D.X1C.X2A, Z4.T1B.T2D.X1C.X2A,
Z5.T1B.T2D.X1C.X2A, Z1.T1C.T2D.X1C.X2A, Z2.T1C.T2D.X1C.X2A,
Z3.T1C.T2D.X1C.X2A, Z4.T1C.T2D.X1C.X2A, Z5.T1C.T2D.X1C.X2A,
Z1.T1D.T2D.X1C.X2A, Z2.T1D.T2D.X1C.X2A, Z3.T1D.T2D.X1C.X2A,
Z4.T1D.T2D.X1C.X2A, Z5.T1D.T2D.X1C.X2A, Z1.T1E.T2D.X1C.X2A,
Z2.T1E.T2D.X1C.X2A, Z3.T1E.T2D.X1C.X2A, Z4.T1E.T2D.X1C.X2A,
Z5.T1E.T2D.X1C.X2A, Z1.T1F.T2D.X1C.X2A, Z2.T1F.T2D.X1C.X2A,
Z3.T1F.T2D.X1C.X2A, Z4.T1F.T2D.X1C.X2A, Z5.T1F.T2D.X1C.X2A,
Z1.T1A.T2A.X1D.X2A, Z2.T1A.T2A.X1D.X2A, Z3.T1A.T2A.X1D.X2A,
Z4.T1A.T2A.X1D.X2A, Z5.T1A.T2A.X1D.X2A, Z1.T1B.T2A.X1D.X2A,
Z2.T1B.T2A.X1D.X2A, Z3.T1B.T2A.X1D.X2A, Z4.T1B.T2A.X1D.X2A,
Z5.T1B.T2A.X1D.X2A, Z1.T1C.T2A.X1D.X2A, Z2.T1C.T2A.X1D.X2A,
Z3.T1C.T2A.X1D.X2A, Z4.T1C.T2A.X1D.X2A, Z5.T1C.T2A.X1D.X2A,
Z1.T1D.T2A.X1D.X2A, Z2.T1D.T2A.X1D.X2A, Z3.T1D.T2A.X1D.X2A,
Z4.T1D.T2A.X1D.X2A, Z5.T1D.T2A.X1D.X2A, Z1.T1E.T2A.X1D.X2A,
Z2.T1E.T2A.X1D.X2A, Z3.T1E.T2A.X1D.X2A, Z4.T1E.T2A.X1D.X2A,
Z5.T1E.T2A.X1D.X2A, Z1.T1F.T2A.X1D.X2A, Z2.T1F.T2A.X1D.X2A,
Z3.T1F.T2A.X1D.X2A, Z4.T1F.T2A.X1D.X2A, Z5.T1F.T2A.X1D.X2A,
Z1.T1A.T2B.X1D.X2A, Z2.T1A.T2B.X1D.X2A, Z3.T1A.T2B.X1D.X2A,
Z4.T1A.T2B.X1D.X2A, Z5.T1A.T2B.X1D.X2A, Z1.T1B.T2B.X1D.X2A,
Z2.T1B.T2B.X1D.X2A, Z3.T1B.T2B.X1D.X2A, Z4.T1B.T2B.X1D.X2A,
Z5.T1B.T2B.X1D.X2A, Z1.T1C.T2B.X1D.X2A, Z2.T1C.T2B.X1D.X2A,
Z3.T1C.T2B.X1D.X2A, Z4.T1C.T2B.X1D.X2A, Z5.T1C.T2B.X1D.X2A,
Z1.T1D.T2B.X1D.X2A, Z2.T1D.T2B.X1D.X2A, Z3.T1D.T2B.X1D.X2A,
Z4.T1D.T2B.X1D.X2A, Z5.T1D.T2B.X1D.X2A, Z1.T1E.T2B.X1D.X2A,
Z2.T1E.T2B.X1D.X2A, Z3.T1E.T2B.X1D.X2A, Z4.T1E.T2B.X1D.X2A,
Z5.T1E.T2B.X1D.X2A, Z1.T1F.T2B.X1D.X2A, Z2.T1F.T2B.X1D.X2A,
Z3.T1F.T2B.X1D.X2A, Z4.T1F.T2B.X1D.X2A, Z5.T1F.T2B.X1D.X2A,
Z1.T1A.T2C.X1D.X2A, Z2.T1A.T2C.X1D.X2A, Z3.T1A.T2C.X1D.X2A,
Z4.T1A.T2C.X1D.X2A, Z5.T1A.T2C.X1D.X2A, Z1.T1B.T2C.X1D.X2A,
Z2.T1B.T2C.X1D.X2A, Z3.T1B.T2C.X1D.X2A, Z4.T1B.T2C.X1D.X2A,
Z5.T1B.T2C.X1D.X2A, Z1.T1C.T2C.X1D.X2A, Z2.T1C.T2C.X1D.X2A,
Z3.T1C.T2C.X1D.X2A, Z4.T1C.T2C.X1D.X2A, Z5.T1C.T2C.X1D.X2A,
Z1.T1D.T2C.X1D.X2A, Z2.T1D.T2C.X1D.X2A, Z3.T1D.T2C.X1D.X2A,
Z4.T1D.T2C.X1D.X2A, Z5.T1D.T2C.X1D.X2A, Z1.T1E.T2C.X1D.X2A,

TABLE 6-continued

List of Compound Structure of Formula II

Z2.T1E.T2C.X1D.X2A, Z3.T1E.T2C.X1D.X2A,
Z4.T1E.T2C.X1D.X2A,
Z5.T1E.T2C.X1D.X2A, Z1.T1F.T2C.X1D.X2A,
Z2.T1F.T2C.X1D.X2A,
Z3.T1F.T2C.X1D.X2A, Z4.T1F.T2C.X1D.X2A,
Z5.T1F.T2C.X1D.X2A,
Z1.T1A.T2D.X1D.X2A, Z2.T1A.T2D.X1D.X2A,
Z3.T1A.T2D.X1D.X2A,
Z4.T1A.T2D.X1D.X2A, Z5.T1A.T2D.X1D.X2A,
Z1.T1B.T2D.X1D.X2A,
Z2.T1B.T2D.X1D.X2A, Z3.T1B.T2D.X1D.X2A,
Z4.T1B.T2D.X1D.X2A,
Z5.T1B.T2D.X1D.X2A, Z1.T1C.T2D.X1D.X2A,
Z2.T1C.T2D.X1D.X2A,
Z3.T1C.T2D.X1D.X2A, Z4.T1C.T2D.X1D.X2A,
Z5.T1C.T2D.X1D.X2A,
Z1.T1D.T2D.X1D.X2A, Z2.T1D.T2D.X1D.X2A,
Z3.T1D.T2D.X1D.X2A,
Z4.T1D.T2D.X1D.X2A, Z5.T1D.T2D.X1D.X2A,
Z1.T1E.T2D.X1D.X2A,
Z2.T1E.T2D.X1D.X2A, Z3.T1E.T2D.X1D.X2A,
Z4.T1E.T2D.X1D.X2A,
Z5.T1E.T2D.X1D.X2A, Z1.T1F.T2D.X1D.X2A,
Z2.T1F.T2D.X1D.X2A,
Z3.T1F.T2D.X1D.X2A, Z4.T1F.T2D.X1D.X2A,
Z5.T1F.T2D.X1D.X2A,
Z1.T1A.T2A.X1E.X2A, Z2.T1A.T2A.X1E.X2A,
Z3.T1A.T2A.X1E.X2A,
Z4.T1A.T2A.X1E.X2A, Z5.T1A.T2A.X1E.X2A,
Z1.T1B.T2A.X1E.X2A,
Z2.T1B.T2A.X1E.X2A, Z3.T1B.T2A.X1E.X2A,
Z4.T1B.T2A.X1E.X2A,
Z5.T1B.T2A.X1E.X2A, Z1.T1C.T2A.X1E.X2A,
Z2.T1C.T2A.X1E.X2A,
Z3.T1C.T2A.X1E.X2A, Z4.T1C.T2A.X1E.X2A,
Z5.T1C.T2A.X1E.X2A,
Z1.T1D.T2A.X1E.X2A, Z2.T1D.T2A.X1E.X2A,
Z3.T1D.T2A.X1E.X2A,
Z4.T1D.T2A.X1E.X2A, Z5.T1D.T2A.X1E.X2A,
Z1.T1E.T2A.X1E.X2A,
Z2.T1E.T2A.X1E.X2A, Z3.T1E.T2A.X1E.X2A,
Z4.T1E.T2A.X1E.X2A,
Z5.T1E.T2A.X1E.X2A, Z1.T1F.T2A.X1E.X2A,
Z2.T1F.T2A.X1E.X2A,
Z3.T1F.T2A.X1E.X2A, Z4.T1F.T2A.X1E.X2A,
Z5.T1F.T2A.X1E.X2A,
Z1.T1A.T2B.X1E.X2A, Z2.T1A.T2B.X1E.X2A,
Z3.T1A.T2B.X1E.X2A,
Z4.T1A.T2B.X1E.X2A, Z5.T1A.T2B.X1E.X2A,
Z1.T1B.T2B.X1E.X2A,
Z2.T1B.T2B.X1E.X2A, Z3.T1B.T2B.X1E.X2A,
Z4.T1B.T2B.X1E.X2A,
Z5.T1B.T2B.X1E.X2A, Z1.T1C.T2B.X1E.X2A,
Z2.T1C.T2B.X1E.X2A,
Z3.T1C.T2B.X1E.X2A, Z4.T1C.T2B.X1E.X2A,
Z5.T1C.T2B.X1E.X2A,
Z1.T1D.T2B.X1E.X2A, Z2.T1D.T2B.X1E.X2A,
Z3.T1D.T2B.X1E.X2A,
Z4.T1D.T2B.X1E.X2A, Z5.T1D.T2B.X1E.X2A,
Z1.T1E.T2B.X1E.X2A,
Z2.T1E.T2B.X1E.X2A, Z3.T1E.T2B.X1E.X2A,
Z4.T1E.T2B.X1E.X2A,
Z5.T1E.T2B.X1E.X2A, Z1.T1F.T2B.X1E.X2A,
Z2.T1F.T2B.X1E.X2A,
Z3.T1F.T2B.X1E.X2A, Z4.T1F.T2B.X1E.X2A,
Z5.T1F.T2B.X1E.X2A,
Z1.T1A.T2C.X1E.X2A, Z2.T1A.T2C.X1E.X2A,
Z3.T1A.T2C.X1E.X2A,
Z4.T1A.T2C.X1E.X2A, Z5.T1A.T2C.X1E.X2A,
Z1.T1B.T2C.X1E.X2A,
Z2.T1B.T2C.X1E.X2A, Z3.T1B.T2C.X1E.X2A,
Z4.T1B.T2C.X1E.X2A,
Z5.T1B.T2C.X1E.X2A, Z1.T1C.T2C.X1E.X2A,
Z2.T1C.T2C.X1E.X2A,
Z3.T1C.T2C.X1E.X2A, Z4.T1C.T2C.X1E.X2A,
Z5.T1C.T2C.X1E.X2A,
Z1.T1D.T2C.X1E.X2A, Z2.T1D.T2C.X1E.X2A,
Z3.T1D.T2C.X1E.X2A,
Z4.T1D.T2C.X1E.X2A, Z5.T1D.T2C.X1E.X2A,
Z1.T1E.T2C.X1E.X2A,
Z2.T1E.T2C.X1E.X2A, Z3.T1E.T2C.X1E.X2A,
Z4.T1E.T2C.X1E.X2A,
Z5.T1E.T2C.X1E.X2A, Z1.T1F.T2C.X1E.X2A,
Z2.T1F.T2C.X1E.X2A,
Z3.T1F.T2C.X1E.X2A, Z4.T1F.T2C.X1E.X2A,
Z5.T1F.T2C.X1E.X2A,
Z1.T1A.T2D.X1E.X2A, Z2.T1A.T2D.X1E.X2A,
Z3.T1A.T2D.X1E.X2A,
Z4.T1A.T2D.X1E.X2A, Z5.T1A.T2D.X1E.X2A,
Z1.T1B.T2D.X1E.X2A,
Z2.T1B.T2D.X1E.X2A, Z3.T1B.T2D.X1E.X2A,
Z4.T1B.T2D.X1E.X2A,
Z5.T1B.T2D.X1E.X2A, Z1.T1C.T2D.X1E.X2A,
Z2.T1C.T2D.X1E.X2A,
Z3.T1C.T2D.X1E.X2A, Z4.T1C.T2D.X1E.X2A,
Z5.T1C.T2D.X1E.X2A,
Z1.T1D.T2D.X1E.X2A, Z2.T1D.T2D.X1E.X2A,
Z3.T1D.T2D.X1E.X2A,
Z4.T1D.T2D.X1E.X2A, Z5.T1D.T2D.X1E.X2A,
Z1.T1E.T2D.X1E.X2A,
Z2.T1E.T2D.X1E.X2A, Z3.T1E.T2D.X1E.X2A,
Z4.T1E.T2D.X1E.X2A,
Z5.T1E.T2D.X1E.X2A, Z1.T1F.T2D.X1E.X2A,
Z2.T1F.T2D.X1E.X2A,
Z3.T1F.T2D.X1E.X2A, Z4.T1F.T2D.X1E.X2A,
Z5.T1F.T2D.X1E.X2A,
Z1.T1A.T2A.X1F.X2A, Z2.T1A.T2A.X1F.X2A,
Z3.T1A.T2A.X1F.X2A,
Z4.T1A.T2A.X1F.X2A, Z5.T1A.T2A.X1F.X2A,
Z1.T1B.T2A.X1F.X2A,
Z2.T1B.T2A.X1F.X2A, Z3.T1B.T2A.X1F.X2A,
Z4.T1B.T2A.X1F.X2A,
Z5.T1B.T2A.X1F.X2A, Z1.T1C.T2A.X1F.X2A,
Z2.T1C.T2A.X1F.X2A,
Z3.T1C.T2A.X1F.X2A, Z4.T1C.T2A.X1F.X2A,
Z5.T1C.T2A.X1F.X2A,
Z1.T1D.T2A.X1F.X2A, Z2.T1D.T2A.X1F.X2A,
Z3.T1D.T2A.X1F.X2A,
Z4.T1D.T2A.X1F.X2A, Z5.T1D.T2A.X1F.X2A,
Z1.T1E.T2A.X1F.X2A,
Z2.T1E.T2A.X1F.X2A, Z3.T1E.T2A.X1F.X2A,
Z4.T1E.T2A.X1F.X2A,
Z5.T1E.T2A.X1F.X2A, Z1.T1F.T2A.X1F.X2A,
Z2.T1F.T2A.X1F.X2A,
Z3.T1F.T2A.X1F.X2A, Z4.T1F.T2A.X1F.X2A,
Z5.T1F.T2A.X1F.X2A,
Z1.T1A.T2B.X1F.X2A, Z2.T1A.T2B.X1F.X2A,
Z3.T1A.T2B.X1F.X2A,
Z4.T1A.T2B.X1F.X2A, Z5.T1A.T2B.X1F.X2A,
Z1.T1B.T2B.X1F.X2A,
Z2.T1B.T2B.X1F.X2A, Z3.T1B.T2B.X1F.X2A,
Z4.T1B.T2B.X1F.X2A,
Z5.T1B.T2B.X1F.X2A, Z1.T1C.T2B.X1F.X2A,
Z2.T1C.T2B.X1F.X2A,
Z3.T1C.T2B.X1F.X2A, Z4.T1C.T2B.X1F.X2A,
Z5.T1C.T2B.X1F.X2A,
Z1.T1D.T2B.X1F.X2A, Z2.T1D.T2B.X1F.X2A,
Z3.T1D.T2B.X1F.X2A,
Z4.T1D.T2B.X1F.X2A, Z5.T1D.T2B.X1F.X2A,
Z1.T1E.T2B.X1F.X2A,
Z2.T1E.T2B.X1F.X2A, Z3.T1E.T2B.X1F.X2A,
Z4.T1E.T2B.X1F.X2A,
Z5.T1E.T2B.X1F.X2A, Z1.T1F.T2B.X1F.X2A,
Z2.T1F.T2B.X1F.X2A,
Z3.T1F.T2B.X1F.X2A, Z4.T1F.T2B.X1F.X2A,
Z5.T1F.T2B.X1F.X2A,
Z1.T1A.T2C.X1F.X2A, Z2.T1A.T2C.X1F.X2A,
Z3.T1A.T2C.X1F.X2A,
Z4.T1A.T2C.X1F.X2A, Z5.T1A.T2C.X1F.X2A,
Z1.T1B.T2C.X1F.X2A,
Z2.T1B.T2C.X1F.X2A, Z3.T1B.T2C.X1F.X2A,
Z4.T1B.T2C.X1F.X2A,
Z5.T1B.T2C.X1F.X2A, Z1.T1C.T2C.X1F.X2A,
Z2.T1C.T2C.X1F.X2A,

TABLE 6-continued

List of Compound Structure of Formula II

Z3.T1C.T2C.X1F.X2A, Z4.T1C.T2C.X1F.X2A,
Z5.T1C.T2C.X1F.X2A,
Z1.T1D.T2C.X1F.X2A, Z2.T1D.T2C.X1F.X2A,
Z3.T1D.T2C.X1F.X2A,
Z4.T1D.T2C.X1F.X2A, Z5.T1D.T2C.X1F.X2A,
Z1.T1E.T2C.X1F.X2A,
Z2.T1E.T2C.X1F.X2A, Z3.T1E.T2C.X1F.X2A,
Z4.T1E.T2C.X1F.X2A,
Z5.T1E.T2C.X1F.X2A, Z1.T1F.T2C.X1F.X2A,
Z2.T1F.T2C.X1F.X2A,
Z3.T1F.T2C.X1F.X2A, Z4.T1F.T2C.X1F.X2A,
Z5.T1F.T2C.X1F.X2A,
Z1.T1A.T2D.X1F.X2A, Z2.T1A.T2D.X1F.X2A,
Z3.T1A.T2D.X1F.X2A,
Z4.T1A.T2D.X1F.X2A, Z5.T1A.T2D.X1F.X2A,
Z1.T1B.T2D.X1F.X2A,
Z2.T1B.T2D.X1F.X2A, Z3.T1B.T2D.X1F.X2A,
Z4.T1B.T2D.X1F.X2A,
Z5.T1B.T2D.X1F.X2A, Z1.T1C.T2D.X1F.X2A,
Z2.T1C.T2D.X1F.X2A,
Z3.T1C.T2D.X1F.X2A, Z4.T1C.T2D.X1F.X2A,
Z5.T1C.T2D.X1F.X2A,
Z1.T1D.T2D.X1F.X2A, Z2.T1D.T2D.X1F.X2A,
Z3.T1D.T2D.X1F.X2A,
Z4.T1D.T2D.X1F.X2A, Z5.T1D.T2D.X1F.X2A,
Z1.T1E.T2D.X1F.X2A,
Z2.T1E.T2D.X1F.X2A, Z3.T1E.T2D.X1F.X2A,
Z4.T1E.T2D.X1F.X2A,
Z5.T1E.T2D.X1F.X2A, Z1.T1F.T2D.X1F.X2A,
Z2.T1F.T2D.X1F.X2A,
Z3.T1F.T2D.X1F.X2A, Z4.T1F.T2D.X1F.X2A,
Z5.T1F.T2D.X1F.X2A,
Z1.T1A.T2A.X1A.X2B, Z2.T1A.T2A.X1A.X2B,
Z3.T1A.T2A.X1A.X2B,
Z4.T1A.T2A.X1A.X2B, Z5.T1A.T2A.X1A.X2B,
Z1.T1B.T2A.X1A.X2B,
Z2.T1B.T2A.X1A.X2B, Z3.T1B.T2A.X1A.X2B,
Z4.T1B.T2A.X1A.X2B,
Z5.T1B.T2A.X1A.X2B, Z1.T1C.T2A.X1A.X2B,
Z2.T1C.T2A.X1A.X2B,
Z3.T1C.T2A.X1A.X2B, Z4.T1C.T2A.X1A.X2B,
Z5.T1C.T2A.X1A.X2B,
Z1.T1D.T2A.X1A.X2B, Z2.T1D.T2A.X1A.X2B,
Z3.T1D.T2A.X1A.X2B,
Z4.T1D.T2A.X1A.X2B, Z5.T1D.T2A.X1A.X2B,
Z1.T1E.T2A.X1A.X2B,
Z2.T1E.T2A.X1A.X2B, Z3.T1E.T2A.X1A.X2B,
Z4.T1E.T2A.X1A.X2B,
Z5.T1E.T2A.X1A.X2B, Z1.T1F.T2A.X1A.X2B,
Z2.T1F.T2A.X1A.X2B,
Z3.T1F.T2A.X1A.X2B, Z4.T1F.T2A.X1A.X2B,
Z5.T1F.T2A.X1A.X2B,
Z1.T1A.T2B.X1A.X2B, Z2.T1A.T2B.X1A.X2B,
Z3.T1A.T2B.X1A.X2B,
Z4.T1A.T2B.X1A.X2B, Z5.T1A.T2B.X1A.X2B,
Z1.T1B.T2B.X1A.X2B,
Z2.T1B.T2B.X1A.X2B, Z3.T1B.T2B.X1A.X2B,
Z4.T1B.T2B.X1A.X2B,
Z5.T1B.T2B.X1A.X2B, Z1.T1C.T2B.X1A.X2B,
Z2.T1C.T2B.X1A.X2B,
Z3.T1C.T2B.X1A.X2B, Z4.T1C.T2B.X1A.X2B,
Z5.T1C.T2B.X1A.X2B,
Z1.T1D.T2B.X1A.X2B, Z2.T1D.T2B.X1A.X2B,
Z3.T1D.T2B.X1A.X2B,
Z4.T1D.T2B.X1A.X2B, Z5.T1D.T2B.X1A.X2B,
Z1.T1E.T2B.X1A.X2B,
Z2.T1E.T2B.X1A.X2B, Z3.T1E.T2B.X1A.X2B,
Z4.T1E.T2B.X1A.X2B,
Z5.T1E.T2B.X1A.X2B, Z1.T1F.T2B.X1A.X2B,
Z2.T1F.T2B.X1A.X2B,
Z3.T1F.T2B.X1A.X2B, Z4.T1F.T2B.X1A.X2B,
Z5.T1F.T2B.X1A.X2B,
Z1.T1A.T2C.X1A.X2B, Z2.T1A.T2C.X1A.X2B,
Z3.T1A.T2C.X1A.X2B,
Z4.T1A.T2C.X1A.X2B, Z5.T1A.T2C.X1A.X2B,
Z1.T1B.T2C.X1A.X2B,

Z2.T1B.T2C.X1A.X2B, Z3.T1B.T2C.X1A.X2B,
Z4.T1B.T2C.X1A.X2B,
Z5.T1B.T2C.X1A.X2B, Z1.T1C.T2C.X1A.X2B,
Z2.T1C.T2C.X1A.X2B,
Z3.T1C.T2C.X1A.X2B, Z4.T1C.T2C.X1A.X2B,
Z5.T1C.T2C.X1A.X2B,
Z1.T1D.T2C.X1A.X2B, Z2.T1D.T2C.X1A.X2B,
Z3.T1D.T2C.X1A.X2B,
Z4.T1D.T2C.X1A.X2B, Z5.T1D.T2C.X1A.X2B,
Z1.T1E.T2C.X1A.X2B,
Z2.T1E.T2C.X1A.X2B, Z3.T1E.T2C.X1A.X2B,
Z4.T1E.T2C.X1A.X2B,
Z5.T1E.T2C.X1A.X2B, Z1.T1F.T2C.X1A.X2B,
Z2.T1F.T2C.X1A.X2B,
Z3.T1F.T2C.X1A.X2B, Z4.T1F.T2C.X1A.X2B,
Z5.T1F.T2C.X1A.X2B,
Z1.T1A.T2D.X1A.X2B, Z2.T1A.T2D.X1A.X2B,
Z3.T1A.T2D.X1A.X2B,
Z4.T1A.T2D.X1A.X2B, Z5.T1A.T2D.X1A.X2B,
Z1.T1B.T2D.X1A.X2B,
Z2.T1B.T2D.X1A.X2B, Z3.T1B.T2D.X1A.X2B,
Z4.T1B.T2D.X1A.X2B,
Z5.T1B.T2D.X1A.X2B, Z1.T1C.T2D.X1A.X2B,
Z2.T1C.T2D.X1A.X2B,
Z3.T1C.T2D.X1A.X2B, Z4.T1C.T2D.X1A.X2B,
Z5.T1C.T2D.X1A.X2B,
Z1.T1D.T2D.X1A.X2B, Z2.T1D.T2D.X1A.X2B,
Z3.T1D.T2D.X1A.X2B,
Z4.T1D.T2D.X1A.X2B, Z5.T1D.T2D.X1A.X2B,
Z1.T1E.T2D.X1A.X2B,
Z2.T1E.T2D.X1A.X2B, Z3.T1E.T2D.X1A.X2B,
Z4.T1E.T2D.X1A.X2B,
Z5.T1E.T2D.X1A.X2B, Z1.T1F.T2D.X1A.X2B,
Z2.T1F.T2D.X1A.X2B,
Z3.T1F.T2D.X1A.X2B, Z4.T1F.T2D.X1A.X2B,
Z5.T1F.T2D.X1A.X2B,
Z1.T1A.T2A.X1B.X2B, Z2.T1A.T2A.X1B.X2B,
Z3.T1A.T2A.X1B.X2B,
Z4.T1A.T2A.X1B.X2B, Z5.T1A.T2A.X1B.X2B,
Z1.T1B.T2A.X1B.X2B,
Z2.T1B.T2A.X1B.X2B, Z3.T1B.T2A.X1B.X2B,
Z4.T1B.T2A.X1B.X2B,
Z5.T1B.T2A.X1B.X2B, Z1.T1C.T2A.X1B.X2B,
Z2.T1C.T2A.X1B.X2B,
Z3.T1C.T2A.X1B.X2B, Z4.T1C.T2A.X1B.X2B,
Z5.T1C.T2A.X1B.X2B,
Z1.T1D.T2A.X1B.X2B, Z2.T1D.T2A.X1B.X2B,
Z3.T1D.T2A.X1B.X2B,
Z4.T1D.T2A.X1B.X2B, Z5.T1D.T2A.X1B.X2B,
Z1.T1E.T2A.X1B.X2B,
Z2.T1E.T2A.X1B.X2B, Z3.T1E.T2A.X1B.X2B,
Z4.T1E.T2A.X1B.X2B,
Z5.T1E.T2A.X1B.X2B, Z1.T1F.T2A.X1B.X2B,
Z2.T1F.T2A.X1B.X2B,
Z3.T1F.T2A.X1B.X2B, Z4.T1F.T2A.X1B.X2B,
Z5.T1F.T2A.X1B.X2B,
Z1.T1A.T2B.X1B.X2B, Z2.T1A.T2B.X1B.X2B,
Z3.T1A.T2B.X1B.X2B,
Z4.T1A.T2B.X1B.X2B, Z5.T1A.T2B.X1B.X2B,
Z1.T1B.T2B.X1B.X2B,
Z2.T1B.T2B.X1B.X2B, Z3.T1B.T2B.X1B.X2B,
Z4.T1B.T2B.X1B.X2B,
Z5.T1B.T2B.X1B.X2B, Z1.T1C.T2B.X1B.X2B,
Z2.T1C.T2B.X1B.X2B,
Z3.T1C.T2B.X1B.X2B, Z4.T1C.T2B.X1B.X2B,
Z5.T1C.T2B.X1B.X2B,
Z1.T1D.T2B.X1B.X2B, Z2.T1D.T2B.X1B.X2B,
Z3.T1D.T2B.X1B.X2B,
Z4.T1D.T2B.X1B.X2B, Z5.T1D.T2B.X1B.X2B,
Z1.T1E.T2B.X1B.X2B,
Z2.T1E.T2B.X1B.X2B, Z3.T1E.T2B.X1B.X2B,
Z4.T1E.T2B.X1B.X2B,
Z5.T1E.T2B.X1B.X2B, Z1.T1F.T2B.X1B.X2B,
Z2.T1F.T2B.X1B.X2B,
Z3.T1F.T2B.X1B.X2B, Z4.T1F.T2B.X1B.X2B,
Z5.T1F.T2B.X1B.X2B,
Z1.T1A.T2C.X1B.X2B, Z2.T1A.T2C.X1B.X2B,
Z3.T1A.T2C.X1B.X2B,

TABLE 6-continued

List of Compound Structure of Formula II

Z4.T1A.T2C.X1B.X2B, Z5.T1A.T2C.X1B.X2B,
Z1.T1B.T2C.X1B.X2B,
Z2.T1B.T2C.X1B.X2B, Z3.T1B.T2C.X1B.X2B,
Z4.T1B.T2C.X1B.X2B,
Z5.T1B.T2C.X1B.X2B, Z1.T1C.T2C.X1B.X2B,
Z2.T1C.T2C.X1B.X2B,
Z3.T1C.T2C.X1B.X2B, Z4.T1C.T2C.X1B.X2B,
Z5.T1C.T2C.X1B.X2B,
Z1.T1D.T2C.X1B.X2B, Z2.T1D.T2C.X1B.X2B,
Z3.T1D.T2C.X1B.X2B,
Z4.T1D.T2C.X1B.X2B, Z5.T1D.T2C.X1B.X2B,
Z1.T1E.T2C.X1B.X2B,
Z2.T1E.T2C.X1B.X2B, Z3.T1E.T2C.X1B.X2B,
Z4.T1E.T2C.X1B.X2B,
Z5.T1E.T2C.X1B.X2B, Z1.T1F.T2C.X1B.X2B,
Z2.T1F.T2C.X1B.X2B,
Z3.T1F.T2C.X1B.X2B, Z4.T1F.T2C.X1B.X2B,
Z5.T1F.T2C.X1B.X2B,
Z1.T1A.T2D.X1B.X2B, Z2.T1A.T2D.X1B.X2B,
Z3.T1A.T2D.X1B.X2B,
Z4.T1A.T2D.X1B.X2B, Z5.T1A.T2D.X1B.X2B,
Z1.T1B.T2D.X1B.X2B,
Z2.T1B.T2D.X1B.X2B, Z3.T1B.T2D.X1B.X2B,
Z4.T1B.T2D.X1B.X2B,
Z5.T1B.T2D.X1B.X2B, Z1.T1C.T2D.X1B.X2B,
Z2.T1C.T2D.X1B.X2B,
Z3.T1C.T2D.X1B.X2B, Z4.T1C.T2D.X1B.X2B,
Z5.T1C.T2D.X1B.X2B,
Z1.T1D.T2D.X1B.X2B, Z2.T1D.T2D.X1B.X2B,
Z3.T1D.T2D.X1B.X2B,
Z4.T1D.T2D.X1B.X2B, Z5.T1D.T2D.X1B.X2B,
Z1.T1E.T2D.X1B.X2B,
Z2.T1E.T2D.X1B.X2B, Z3.T1E.T2D.X1B.X2B,
Z4.T1E.T2D.X1B.X2B,
Z5.T1E.T2D.X1B.X2B, Z1.T1F.T2D.X1B.X2B,
Z2.T1F.T2D.X1B.X2B,
Z3.T1F.T2D.X1B.X2B, Z4.T1F.T2D.X1B.X2B,
Z5.T1F.T2D.X1B.X2B,
Z1.T1A.T2A.X1C.X2B, Z2.T1A.T2A.X1C.X2B,
Z3.T1A.T2A.X1C.X2B,
Z4.T1A.T2A.X1C.X2B, Z5.T1A.T2A.X1C.X2B,
Z1.T1B.T2A.X1C.X2B,
Z2.T1B.T2A.X1C.X2B, Z3.T1B.T2A.X1C.X2B,
Z4.T1B.T2A.X1C.X2B,
Z5.T1B.T2A.X1C.X2B, Z1.T1C.T2A.X1C.X2B,
Z2.T1C.T2A.X1C.X2B,
Z3.T1C.T2A.X1C.X2B, Z4.T1C.T2A.X1C.X2B,
Z5.T1C.T2A.X1C.X2B,
Z1.T1D.T2A.X1C.X2B, Z2.T1D.T2A.X1C.X2B,
Z3.T1D.T2A.X1C.X2B,
Z4.T1D.T2A.X1C.X2B, Z5.T1D.T2A.X1C.X2B,
Z1.T1E.T2A.X1C.X2B,
Z2.T1E.T2A.X1C.X2B, Z3.T1E.T2A.X1C.X2B,
Z4.T1E.T2A.X1C.X2B,
Z5.T1E.T2A.X1C.X2B, Z1.T1F.T2A.X1C.X2B,
Z2.T1F.T2A.X1C.X2B,
Z3.T1F.T2A.X1C.X2B, Z4.T1F.T2A.X1C.X2B,
Z5.T1F.T2A.X1C.X2B,
Z1.T1A.T2B.X1C.X2B, Z2.T1A.T2B.X1C.X2B,
Z3.T1A.T2B.X1C.X2B,
Z4.T1A.T2B.X1C.X2B, Z5.T1A.T2B.X1C.X2B,
Z1.T1B.T2B.X1C.X2B,
Z2.T1B.T2B.X1C.X2B, Z3.T1B.T2B.X1C.X2B,
Z4.T1B.T2B.X1C.X2B,
Z5.T1B.T2B.X1C.X2B, Z1.T1C.T2B.X1C.X2B,
Z2.T1C.T2B.X1C.X2B,
Z3.T1C.T2B.X1C.X2B, Z4.T1C.T2B.X1C.X2B,
Z5.T1C.T2B.X1C.X2B,
Z1.T1D.T2B.X1C.X2B, Z2.T1D.T2B.X1C.X2B,
Z3.T1D.T2B.X1C.X2B,
Z4.T1D.T2B.X1C.X2B, Z5.T1D.T2B.X1C.X2B,
Z1.T1E.T2B.X1C.X2B,
Z2.T1E.T2B.X1C.X2B, Z3.T1E.T2B.X1C.X2B,
Z4.T1E.T2B.X1C.X2B,
Z5.T1E.T2B.X1C.X2B, Z1.T1F.T2B.X1C.X2B,
Z2.T1F.T2B.X1C.X2B,
Z3.T1F.T2B.X1C.X2B, Z4.T1F.T2B.X1C.X2B,
Z5.T1F.T2B.X1C.X2B,
Z1.T1A.T2C.X1C.X2B, Z2.T1A.T2C.X1C.X2B,
Z3.T1A.T2C.X1C.X2B,
Z4.T1A.T2C.X1C.X2B, Z5.T1A.T2C.X1C.X2B,
Z1.T1B.T2C.X1C.X2B,
Z2.T1B.T2C.X1C.X2B, Z3.T1B.T2C.X1C.X2B,
Z4.T1B.T2C.X1C.X2B,
Z5.T1B.T2C.X1C.X2B, Z1.T1C.T2C.X1C.X2B,
Z2.T1C.T2C.X1C.X2B,
Z3.T1C.T2C.X1C.X2B, Z4.T1C.T2C.X1C.X2B,
Z5.T1C.T2C.X1C.X2B,
Z1.T1D.T2C.X1C.X2B, Z2.T1D.T2C.X1C.X2B,
Z3.T1D.T2C.X1C.X2B,
Z4.T1D.T2C.X1C.X2B, Z5.T1D.T2C.X1C.X2B,
Z1.T1E.T2C.X1C.X2B,
Z2.T1E.T2C.X1C.X2B, Z3.T1E.T2C.X1C.X2B,
Z4.T1E.T2C.X1C.X2B,
Z5.T1E.T2C.X1C.X2B, Z1.T1F.T2C.X1C.X2B,
Z2.T1F.T2C.X1C.X2B,
Z3.T1F.T2C.X1C.X2B, Z4.T1F.T2C.X1C.X2B,
Z5.T1F.T2C.X1C.X2B,
Z1.T1A.T2D.X1C.X2B, Z2.T1A.T2D.X1C.X2B,
Z3.T1A.T2D.X1C.X2B,
Z4.T1A.T2D.X1C.X2B, Z5.T1A.T2D.X1C.X2B,
Z1.T1B.T2D.X1C.X2B,
Z2.T1B.T2D.X1C.X2B, Z3.T1B.T2D.X1C.X2B,
Z4.T1B.T2D.X1C.X2B,
Z5.T1B.T2D.X1C.X2B, Z1.T1C.T2D.X1C.X2B,
Z2.T1C.T2D.X1C.X2B,
Z3.T1C.T2D.X1C.X2B, Z4.T1C.T2D.X1C.X2B,
Z5.T1C.T2D.X1C.X2B,
Z1.T1D.T2D.X1C.X2B, Z2.T1D.T2D.X1C.X2B,
Z3.T1D.T2D.X1C.X2B,
Z4.T1D.T2D.X1C.X2B, Z5.T1D.T2D.X1C.X2B,
Z1.T1E.T2D.X1C.X2B,
Z2.T1E.T2D.X1C.X2B, Z3.T1E.T2D.X1C.X2B,
Z4.T1E.T2D.X1C.X2B,
Z5.T1E.T2D.X1C.X2B, Z1.T1F.T2D.X1C.X2B,
Z2.T1F.T2D.X1C.X2B,
Z3.T1F.T2D.X1C.X2B, Z4.T1F.T2D.X1C.X2B,
Z5.T1F.T2D.X1C.X2B,
Z1.T1A.T2A.X1D.X2B, Z2.T1A.T2A.X1D.X2B,
Z3.T1A.T2A.X1D.X2B,
Z4.T1A.T2A.X1D.X2B, Z5.T1A.T2A.X1D.X2B,
Z1.T1B.T2A.X1D.X2B,
Z2.T1B.T2A.X1D.X2B, Z3.T1B.T2A.X1D.X2B,
Z4.T1B.T2A.X1D.X2B,
Z5.T1B.T2A.X1D.X2B, Z1.T1C.T2A.X1D.X2B,
Z2.T1C.T2A.X1D.X2B,
Z3.T1C.T2A.X1D.X2B, Z4.T1C.T2A.X1D.X2B,
Z5.T1C.T2A.X1D.X2B,
Z1.T1D.T2A.X1D.X2B, Z2.T1D.T2A.X1D.X2B,
Z3.T1D.T2A.X1D.X2B,
Z4.T1D.T2A.X1D.X2B, Z5.T1D.T2A.X1D.X2B,
Z1.T1E.T2A.X1D.X2B,
Z2.T1E.T2A.X1D.X2B, Z3.T1E.T2A.X1D.X2B,
Z4.T1E.T2A.X1D.X2B,
Z5.T1E.T2A.X1D.X2B, Z1.T1F.T2A.X1D.X2B,
Z2.T1F.T2A.X1D.X2B,
Z3.T1F.T2A.X1D.X2B, Z4.T1F.T2A.X1D.X2B,
Z5.T1F.T2A.X1D.X2B,
Z1.T1A.T2B.X1D.X2B, Z2.T1A.T2B.X1D.X2B,
Z3.T1A.T2B.X1D.X2B,
Z4.T1A.T2B.X1D.X2B, Z5.T1A.T2B.X1D.X2B,
Z1.T1B.T2B.X1D.X2B,
Z2.T1B.T2B.X1D.X2B, Z3.T1B.T2B.X1D.X2B,
Z4.T1B.T2B.X1D.X2B,
Z5.T1B.T2B.X1D.X2B, Z1.T1C.T2B.X1D.X2B,
Z2.T1C.T2B.X1D.X2B,
Z3.T1C.T2B.X1D.X2B, Z4.T1C.T2B.X1D.X2B,
Z5.T1C.T2B.X1D.X2B,
Z1.T1D.T2B.X1D.X2B, Z2.T1D.T2B.X1D.X2B,
Z3.T1D.T2B.X1D.X2B,
Z4.T1D.T2B.X1D.X2B, Z5.T1D.T2B.X1D.X2B,
Z1.T1E.T2B.X1D.X2B,
Z2.T1E.T2B.X1D.X2B, Z3.T1E.T2B.X1D.X2B,
Z4.T1E.T2B.X1D.X2B,

TABLE 6-continued

List of Compound Structure of Formula II

Z5.T1E.T2B.X1D.X2B, Z1.T1F.T2B.X1D.X2B,
Z2.T1F.T2B.X1D.X2B,
Z3.T1F.T2B.X1D.X2B, Z4.T1F.T2B.X1D.X2B,
Z5.T1F.T2B.X1D.X2B,
Z1.T1A.T2C.X1D.X2B, Z2.T1A.T2C.X1D.X2B,
Z3.T1A.T2C.X1D.X2B,
Z4.T1A.T2C.X1D.X2B, Z5.T1A.T2C.X1D.X2B,
Z1.T1B.T2C.X1D.X2B,
Z2.T1B.T2C.X1D.X2B, Z3.T1B.T2C.X1D.X2B,
Z4.T1B.T2C.X1D.X2B,
Z5.T1B.T2C.X1D.X2B, Z1.T1C.T2C.X1D.X2B,
Z2.T1C.T2C.X1D.X2B,
Z3.T1C.T2C.X1D.X2B, Z4.T1C.T2C.X1D.X2B,
Z5.T1C.T2C.X1D.X2B,
Z1.T1D.T2C.X1D.X2B, Z2.T1D.T2C.X1D.X2B,
Z3.T1D.T2C.X1D.X2B,
Z4.T1D.T2C.X1D.X2B, Z5.T1D.T2C.X1D.X2B,
Z1.T1E.T2C.X1D.X2B,
Z2.T1E.T2C.X1D.X2B, Z3.T1E.T2C.X1D.X2B,
Z4.T1E.T2C.X1D.X2B,
Z5.T1E.T2C.X1D.X2B, Z1.T1F.T2C.X1D.X2B,
Z2.T1F.T2C.X1D.X2B,
Z3.T1F.T2C.X1D.X2B, Z4.T1F.T2C.X1D.X2B,
Z5.T1F.T2C.X1D.X2B,
Z1.T1A.T2D.X1D.X2B, Z2.T1A.T2D.X1D.X2B,
Z3.T1A.T2D.X1D.X2B,
Z4.T1A.T2D.X1D.X2B, Z5.T1A.T2D.X1D.X2B,
Z1.T1B.T2D.X1D.X2B,
Z2.T1B.T2D.X1D.X2B, Z3.T1B.T2D.X1D.X2B,
Z4.T1B.T2D.X1D.X2B,
Z5.T1B.T2D.X1D.X2B, Z1.T1C.T2D.X1D.X2B,
Z2.T1C.T2D.X1D.X2B,
Z3.T1C.T2D.X1D.X2B, Z4.T1C.T2D.X1D.X2B,
Z5.T1C.T2D.X1D.X2B,
Z1.T1D.T2D.X1D.X2B, Z2.T1D.T2D.X1D.X2B,
Z3.T1D.T2D.X1D.X2B,
Z4.T1D.T2D.X1D.X2B, Z5.T1D.T2D.X1D.X2B,
Z1.T1E.T2D.X1D.X2B,
Z2.T1E.T2D.X1D.X2B, Z3.T1E.T2D.X1D.X2B,
Z4.T1E.T2D.X1D.X2B,
Z5.T1E.T2D.X1D.X2B, Z1.T1F.T2D.X1D.X2B,
Z2.T1F.T2D.X1D.X2B,
Z3.T1F.T2D.X1D.X2B, Z4.T1F.T2D.X1D.X2B,
Z5.T1F.T2D.X1D.X2B,
Z1.T1A.T2A.X1E.X2B, Z2.T1A.T2A.X1E.X2B,
Z3.T1A.T2A.X1E.X2B,
Z4.T1A.T2A.X1E.X2B, Z5.T1A.T2A.X1E.X2B,
Z1.T1B.T2A.X1E.X2B,
Z2.T1B.T2A.X1E.X2B, Z3.T1B.T2A.X1E.X2B,
Z4.T1B.T2A.X1E.X2B,
Z5.T1B.T2A.X1E.X2B, Z1.T1C.T2A.X1E.X2B,
Z2.T1C.T2A.X1E.X2B,
Z3.T1C.T2A.X1E.X2B, Z4.T1C.T2A.X1E.X2B,
Z5.T1C.T2A.X1E.X2B,
Z1.T1D.T2A.X1E.X2B, Z2.T1D.T2A.X1E.X2B,
Z3.T1D.T2A.X1E.X2B,
Z4.T1D.T2A.X1E.X2B, Z5.T1D.T2A.X1E.X2B,
Z1.T1E.T2A.X1E.X2B,
Z2.T1E.T2A.X1E.X2B, Z3.T1E.T2A.X1E.X2B,
Z4.T1E.T2A.X1E.X2B,
Z5.T1E.T2A.X1E.X2B, Z1.T1F.T2A.X1E.X2B,
Z2.T1F.T2A.X1E.X2B,
Z3.T1F.T2A.X1E.X2B, Z4.T1F.T2A.X1E.X2B,
Z5.T1F.T2A.X1E.X2B,
Z1.T1A.T2B.X1E.X2B, Z2.T1A.T2B.X1E.X2B,
Z3.T1A.T2B.X1E.X2B,
Z4.T1A.T2B.X1E.X2B, Z5.T1A.T2B.X1E.X2B,
Z1.T1B.T2B.X1E.X2B,
Z2.T1B.T2B.X1E.X2B, Z3.T1B.T2B.X1E.X2B,
Z4.T1B.T2B.X1E.X2B,
Z5.T1B.T2B.X1E.X2B, Z1.T1C.T2B.X1E.X2B,
Z2.T1C.T2B.X1E.X2B,
Z3.T1C.T2B.X1E.X2B, Z4.T1C.T2B.X1E.X2B,
Z5.T1C.T2B.X1E.X2B,
Z1.T1D.T2B.X1E.X2B, Z2.T1D.T2B.X1E.X2B,
Z3.T1D.T2B.X1E.X2B,
Z4.T1D.T2B.X1E.X2B, Z5.T1D.T2B.X1E.X2B,
Z1.T1E.T2B.X1E.X2B,
Z2.T1E.T2B.X1E.X2B, Z3.T1E.T2B.X1E.X2B,
Z4.T1E.T2B.X1E.X2B,
Z5.T1E.T2B.X1E.X2B, Z1.T1F.T2B.X1E.X2B,
Z2.T1F.T2B.X1E.X2B,
Z3.T1F.T2B.X1E.X2B, Z4.T1F.T2B.X1E.X2B,
Z5.T1F.T2B.X1E.X2B,
Z1.T1A.T2C.X1E.X2B, Z2.T1A.T2C.X1E.X2B,
Z3.T1A.T2C.X1E.X2B,
Z4.T1A.T2C.X1E.X2B, Z5.T1A.T2C.X1E.X2B,
Z1.T1B.T2C.X1E.X2B,
Z2.T1B.T2C.X1E.X2B, Z3.T1B.T2C.X1E.X2B,
Z4.T1B.T2C.X1E.X2B,
Z5.T1B.T2C.X1E.X2B, Z1.T1C.T2C.X1E.X2B,
Z2.T1C.T2C.X1E.X2B,
Z3.T1C.T2C.X1E.X2B, Z4.T1C.T2C.X1E.X2B,
Z5.T1C.T2C.X1E.X2B,
Z1.T1D.T2C.X1E.X2B, Z2.T1D.T2C.X1E.X2B,
Z3.T1D.T2C.X1E.X2B,
Z4.T1D.T2C.X1E.X2B, Z5.T1D.T2C.X1E.X2B,
Z1.T1E.T2C.X1E.X2B,
Z2.T1E.T2C.X1E.X2B, Z3.T1E.T2C.X1E.X2B,
Z4.T1E.T2C.X1E.X2B,
Z5.T1E.T2C.X1E.X2B, Z1.T1F.T2C.X1E.X2B,
Z2.T1F.T2C.X1E.X2B,
Z3.T1F.T2C.X1E.X2B, Z4.T1F.T2C.X1E.X2B,
Z5.T1F.T2C.X1E.X2B,
Z1.T1A.T2D.X1E.X2B, Z2.T1A.T2D.X1E.X2B,
Z3.T1A.T2D.X1E.X2B,
Z4.T1A.T2D.X1E.X2B, Z5.T1A.T2D.X1E.X2B,
Z1.T1B.T2D.X1E.X2B,
Z2.T1B.T2D.X1E.X2B, Z3.T1B.T2D.X1E.X2B,
Z4.T1B.T2D.X1E.X2B,
Z5.T1B.T2D.X1E.X2B, Z1.T1C.T2D.X1E.X2B,
Z2.T1C.T2D.X1E.X2B,
Z3.T1C.T2D.X1E.X2B, Z4.T1C.T2D.X1E.X2B,
Z5.T1C.T2D.X1E.X2B,
Z1.T1D.T2D.X1E.X2B, Z2.T1D.T2D.X1E.X2B,
Z3.T1D.T2D.X1E.X2B,
Z4.T1D.T2D.X1E.X2B, Z5.T1D.T2D.X1E.X2B,
Z1.T1E.T2D.X1E.X2B,
Z2.T1E.T2D.X1E.X2B, Z3.T1E.T2D.X1E.X2B,
Z4.T1E.T2D.X1E.X2B,
Z5.T1E.T2D.X1E.X2B, Z1.T1F.T2D.X1E.X2B,
Z2.T1F.T2D.X1E.X2B,
Z3.T1F.T2D.X1E.X2B, Z4.T1F.T2D.X1E.X2B,
Z5.T1F.T2D.X1E.X2B,
Z1.T1A.T2A.X1F.X2B, Z2.T1A.T2A.X1F.X2B,
Z3.T1A.T2A.X1F.X2B,
Z4.T1A.T2A.X1F.X2B, Z5.T1A.T2A.X1F.X2B,
Z1.T1B.T2A.X1F.X2B,
Z2.T1B.T2A.X1F.X2B, Z3.T1B.T2A.X1F.X2B,
Z4.T1B.T2A.X1F.X2B,
Z5.T1B.T2A.X1F.X2B, Z1.T1C.T2A.X1F.X2B,
Z2.T1C.T2A.X1F.X2B,
Z3.T1C.T2A.X1F.X2B, Z4.T1C.T2A.X1F.X2B,
Z5.T1C.T2A.X1F.X2B,
Z1.T1D.T2A.X1F.X2B, Z2.T1D.T2A.X1F.X2B,
Z3.T1D.T2A.X1F.X2B,
Z4.T1D.T2A.X1F.X2B, Z5.T1D.T2A.X1F.X2B,
Z1.T1E.T2A.X1F.X2B,
Z2.T1E.T2A.X1F.X2B, Z3.T1E.T2A.X1F.X2B,
Z4.T1E.T2A.X1F.X2B,
Z5.T1E.T2A.X1F.X2B, Z1.T1F.T2A.X1F.X2B,
Z2.T1F.T2A.X1F.X2B,
Z3.T1F.T2A.X1F.X2B, Z4.T1F.T2A.X1F.X2B,
Z5.T1F.T2A.X1F.X2B,
Z1.T1A.T2B.X1F.X2B, Z2.T1A.T2B.X1F.X2B,
Z3.T1A.T2B.X1F.X2B,
Z4.T1A.T2B.X1F.X2B, Z5.T1A.T2B.X1F.X2B,
Z1.T1B.T2B.X1F.X2B,
Z2.T1B.T2B.X1F.X2B, Z3.T1B.T2B.X1F.X2B,
Z4.T1B.T2B.X1F.X2B,
Z5.T1B.T2B.X1F.X2B, Z1.T1C.T2B.X1F.X2B,
Z2.T1C.T2B.X1F.X2B,
Z3.T1C.T2B.X1F.X2B, Z4.T1C.T2B.X1F.X2B,
Z5.T1C.T2B.X1F.X2B,

TABLE 6-continued

List of Compound Structure of Formula II

Z1.T1D.T2B.X1F.X2B, Z2.T1D.T2B.X1F.X2B, Z3.T1D.T2B.X1F.X2B,
Z4.T1D.T2B.X1F.X2B, Z5.T1D.T2B.X1F.X2B, Z1.T1E.T2B.X1F.X2B,
Z2.T1E.T2B.X1F.X2B, Z3.T1E.T2B.X1F.X2B, Z4.T1E.T2B.X1F.X2B,
Z5.T1E.T2B.X1F.X2B, Z1.T1F.T2B.X1F.X2B, Z2.T1F.T2B.X1F.X2B,
Z3.T1F.T2B.X1F.X2B, Z4.T1F.T2B.X1F.X2B, Z5.T1F.T2B.X1F.X2B,
Z1.T1A.T2C.X1F.X2B, Z2.T1A.T2C.X1F.X2B, Z3.T1A.T2C.X1F.X2B,
Z4.T1A.T2C.X1F.X2B, Z5.T1A.T2C.X1F.X2B, Z1.T1B.T2C.X1F.X2B,
Z2.T1B.T2C.X1F.X2B, Z3.T1B.T2C.X1F.X2B, Z4.T1B.T2C.X1F.X2B,
Z5.T1B.T2C.X1F.X2B, Z1.T1C.T2C.X1F.X2B, Z2.T1C.T2C.X1F.X2B,
Z3.T1C.T2C.X1F.X2B, Z4.T1C.T2C.X1F.X2B, Z5.T1C.T2C.X1F.X2B,
Z1.T1D.T2C.X1F.X2B, Z2.T1D.T2C.X1F.X2B, Z3.T1D.T2C.X1F.X2B,
Z4.T1D.T2C.X1F.X2B, Z5.T1D.T2C.X1F.X2B, Z1.T1E.T2C.X1F.X2B,
Z2.T1E.T2C.X1F.X2B, Z3.T1E.T2C.X1F.X2B, Z4.T1E.T2C.X1F.X2B,
Z5.T1E.T2C.X1F.X2B, Z1.T1F.T2C.X1F.X2B, Z2.T1F.T2C.X1F.X2B,
Z3.T1F.T2C.X1F.X2B, Z4.T1F.T2C.X1F.X2B, Z5.T1F.T2C.X1F.X2B,
Z1.T1A.T2D.X1F.X2B, Z2.T1A.T2D.X1F.X2B, Z3.T1A.T2D.X1F.X2B,
Z4.T1A.T2D.X1F.X2B, Z5.T1A.T2D.X1F.X2B, Z1.T1B.T2D.X1F.X2B,
Z2.T1B.T2D.X1F.X2B, Z3.T1B.T2D.X1F.X2B, Z4.T1B.T2D.X1F.X2B,
Z5.T1B.T2D.X1F.X2B, Z1.T1C.T2D.X1F.X2B, Z2.T1C.T2D.X1F.X2B,
Z3.T1C.T2D.X1F.X2B, Z4.T1C.T2D.X1F.X2B, Z5.T1C.T2D.X1F.X2B,
Z1.T1D.T2D.X1F.X2B, Z2.T1D.T2D.X1F.X2B, Z3.T1D.T2D.X1F.X2B,
Z4.T1D.T2D.X1F.X2B, Z5.T1D.T2D.X1F.X2B, Z1.T1E.T2D.X1F.X2B,
Z2.T1E.T2D.X1F.X2B, Z3.T1E.T2D.X1F.X2B, Z4.T1E.T2D.X1F.X2B,
Z5.T1E.T2D.X1F.X2B, Z1.T1F.T2D.X1F.X2B, Z2.T1F.T2D.X1F.X2B,
Z3.T1F.T2D.X1F.X2B, Z4.T1F.T2D.X1F.X2B, Z5.T1F.T2D.X1F.X2B,
Z1.T1A.T2A.X1A.X2C, Z2.T1A.T2A.X1A.X2C, Z3.T1A.T2A.X1A.X2C,
Z4.T1A.T2A.X1A.X2C, Z5.T1A.T2A.X1A.X2C, Z1.T1B.T2A.X1A.X2C,
Z2.T1B.T2A.X1A.X2C, Z3.T1B.T2A.X1A.X2C, Z4.T1B.T2A.X1A.X2C,
Z5.T1B.T2A.X1A.X2C, Z1.T1C.T2A.X1A.X2C, Z2.T1C.T2A.X1A.X2C,
Z3.T1C.T2A.X1A.X2C, Z4.T1C.T2A.X1A.X2C, Z5.T1C.T2A.X1A.X2C,
Z1.T1D.T2A.X1A.X2C, Z2.T1D.T2A.X1A.X2C, Z3.T1D.T2A.X1A.X2C,
Z4.T1D.T2A.X1A.X2C, Z5.T1D.T2A.X1A.X2C, Z1.T1E.T2A.X1A.X2C,
Z2.T1E.T2A.X1A.X2C, Z3.T1E.T2A.X1A.X2C, Z4.T1E.T2A.X1A.X2C,
Z5.T1E.T2A.X1A.X2C, Z1.T1F.T2A.X1A.X2C, Z2.T1F.T2A.X1A.X2C,
Z3.T1F.T2A.X1A.X2C, Z4.T1F.T2A.X1A.X2C, Z5.T1F.T2A.X1A.X2C,
Z1.T1A.T2B.X1A.X2C, Z2.T1A.T2B.X1A.X2C, Z3.T1A.T2B.X1A.X2C,
Z4.T1A.T2B.X1A.X2C, Z5.T1A.T2B.X1A.X2C, Z1.T1B.T2B.X1A.X2C,
Z2.T1B.T2B.X1A.X2C, Z3.T1B.T2B.X1A.X2C, Z4.T1B.T2B.X1A.X2C,
Z5.T1B.T2B.X1A.X2C, Z1.T1C.T2B.X1A.X2C, Z2.T1C.T2B.X1A.X2C,
Z3.T1C.T2B.X1A.X2C, Z4.T1C.T2B.X1A.X2C, Z5.T1C.T2B.X1A.X2C,
Z1.T1D.T2B.X1A.X2C, Z2.T1D.T2B.X1A.X2C, Z3.T1D.T2B.X1A.X2C,
Z4.T1D.T2B.X1A.X2C, Z5.T1D.T2B.X1A.X2C, Z1.T1E.T2B.X1A.X2C,
Z2.T1E.T2B.X1A.X2C, Z3.T1E.T2B.X1A.X2C, Z4.T1E.T2B.X1A.X2C,
Z5.T1E.T2B.X1A.X2C, Z1.T1F.T2B.X1A.X2C, Z2.T1F.T2B.X1A.X2C,
Z3.T1F.T2B.X1A.X2C, Z4.T1F.T2B.X1A.X2C, Z5.T1F.T2B.X1A.X2C,
Z1.T1A.T2C.X1A.X2C, Z2.T1A.T2C.X1A.X2C, Z3.T1A.T2C.X1A.X2C,
Z4.T1A.T2C.X1A.X2C, Z5.T1A.T2C.X1A.X2C, Z1.T1B.T2C.X1A.X2C,
Z2.T1B.T2C.X1A.X2C, Z3.T1B.T2C.X1A.X2C, Z4.T1B.T2C.X1A.X2C,
Z5.T1B.T2C.X1A.X2C, Z1.T1C.T2C.X1A.X2C, Z2.T1C.T2C.X1A.X2C,
Z3.T1C.T2C.X1A.X2C, Z4.T1C.T2C.X1A.X2C, Z5.T1C.T2C.X1A.X2C,
Z1.T1D.T2C.X1A.X2C, Z2.T1D.T2C.X1A.X2C, Z3.T1D.T2C.X1A.X2C,
Z4.T1D.T2C.X1A.X2C, Z5.T1D.T2C.X1A.X2C, Z1.T1E.T2C.X1A.X2C,
Z2.T1E.T2C.X1A.X2C, Z3.T1E.T2C.X1A.X2C, Z4.T1E.T2C.X1A.X2C,
Z5.T1E.T2C.X1A.X2C, Z1.T1F.T2C.X1A.X2C, Z2.T1F.T2C.X1A.X2C,
Z3.T1F.T2C.X1A.X2C, Z4.T1F.T2C.X1A.X2C, Z5.T1F.T2C.X1A.X2C,
Z1.T1A.T2D.X1A.X2C, Z2.T1A.T2D.X1A.X2C, Z3.T1A.T2D.X1A.X2C,
Z4.T1A.T2D.X1A.X2C, Z5.T1A.T2D.X1A.X2C, Z1.T1B.T2D.X1A.X2C,
Z2.T1B.T2D.X1A.X2C, Z3.T1B.T2D.X1A.X2C, Z4.T1B.T2D.X1A.X2C,
Z5.T1B.T2D.X1A.X2C, Z1.T1C.T2D.X1A.X2C, Z2.T1C.T2D.X1A.X2C,
Z3.T1C.T2D.X1A.X2C, Z4.T1C.T2D.X1A.X2C, Z5.T1C.T2D.X1A.X2C,
Z1.T1D.T2D.X1A.X2C, Z2.T1D.T2D.X1A.X2C, Z3.T1D.T2D.X1A.X2C,
Z4.T1D.T2D.X1A.X2C, Z5.T1D.T2D.X1A.X2C, Z1.T1E.T2D.X1A.X2C,
Z2.T1E.T2D.X1A.X2C, Z3.T1E.T2D.X1A.X2C, Z4.T1E.T2D.X1A.X2C,
Z5.T1E.T2D.X1A.X2C, Z1.T1F.T2D.X1A.X2C, Z2.T1F.T2D.X1A.X2C,
Z3.T1F.T2D.X1A.X2C, Z4.T1F.T2D.X1A.X2C, Z5.T1F.T2D.X1A.X2C,
Z1.T1A.T2A.X1B.X2C, Z2.T1A.T2A.X1B.X2C, Z3.T1A.T2A.X1B.X2C,
Z4.T1A.T2A.X1B.X2C, Z5.T1A.T2A.X1B.X2C, Z1.T1B.T2A.X1B.X2C,
Z2.T1B.T2A.X1B.X2C, Z3.T1B.T2A.X1B.X2C, Z4.T1B.T2A.X1B.X2C,
Z5.T1B.T2A.X1B.X2C, Z1.T1C.T2A.X1B.X2C, Z2.T1C.T2A.X1B.X2C,
Z3.T1C.T2A.X1B.X2C, Z4.T1C.T2A.X1B.X2C, Z5.T1C.T2A.X1B.X2C,
Z1.T1D.T2A.X1B.X2C, Z2.T1D.T2A.X1B.X2C, Z3.T1D.T2A.X1B.X2C,
Z4.T1D.T2A.X1B.X2C, Z5.T1D.T2A.X1B.X2C, Z1.T1E.T2A.X1B.X2C,
Z2.T1E.T2A.X1B.X2C, Z3.T1E.T2A.X1B.X2C, Z4.T1E.T2A.X1B.X2C,
Z5.T1E.T2A.X1B.X2C, Z1.T1F.T2A.X1B.X2C, Z2.T1F.T2A.X1B.X2C,
Z3.T1F.T2A.X1B.X2C, Z4.T1F.T2A.X1B.X2C, Z5.T1F.T2A.X1B.X2C,
Z1.T1A.T2B.X1B.X2C, Z2.T1A.T2B.X1B.X2C, Z3.T1A.T2B.X1B.X2C,

TABLE 6-continued

List of Compound Structure of Formula II

Z4.T1A.T2B.X1B.X2C, Z5.T1A.T2B.X1B.X2C, Z1.T1B.T2B.X1B.X2C,
Z2.T1B.T2B.X1B.X2C, Z3.T1B.T2B.X1B.X2C, Z4.T1B.T2B.X1B.X2C,
Z5.T1B.T2B.X1B.X2C, Z1.T1C.T2B.X1B.X2C, Z2.T1C.T2B.X1B.X2C,
Z3.T1C.T2B.X1B.X2C, Z4.T1C.T2B.X1B.X2C, Z5.T1C.T2B.X1B.X2C,
Z1.T1D.T2B.X1B.X2C, Z2.T1D.T2B.X1B.X2C, Z3.T1D.T2B.X1B.X2C,
Z4.T1D.T2B.X1B.X2C, Z5.T1D.T2B.X1B.X2C, Z1.T1E.T2B.X1B.X2C,
Z2.T1E.T2B.X1B.X2C, Z3.T1E.T2B.X1B.X2C, Z4.T1E.T2B.X1B.X2C,
Z5.T1E.T2B.X1B.X2C, Z1.T1F.T2B.X1B.X2C, Z2.T1F.T2B.X1B.X2C,
Z3.T1F.T2B.X1B.X2C, Z4.T1F.T2B.X1B.X2C, Z5.T1F.T2B.X1B.X2C,
Z1.T1A.T2C.X1B.X2C, Z2.T1A.T2C.X1B.X2C, Z3.T1A.T2C.X1B.X2C,
Z4.T1A.T2C.X1B.X2C, Z5.T1A.T2C.X1B.X2C, Z1.T1B.T2C.X1B.X2C,
Z2.T1B.T2C.X1B.X2C, Z3.T1B.T2C.X1B.X2C, Z4.T1B.T2C.X1B.X2C,
Z5.T1B.T2C.X1B.X2C, Z1.T1C.T2C.X1B.X2C, Z2.T1C.T2C.X1B.X2C,
Z3.T1C.T2C.X1B.X2C, Z4.T1C.T2C.X1B.X2C, Z5.T1C.T2C.X1B.X2C,
Z1.T1D.T2C.X1B.X2C, Z2.T1D.T2C.X1B.X2C, Z3.T1D.T2C.X1B.X2C,
Z4.T1D.T2C.X1B.X2C, Z5.T1D.T2C.X1B.X2C, Z1.T1E.T2C.X1B.X2C,
Z2.T1E.T2C.X1B.X2C, Z3.T1E.T2C.X1B.X2C, Z4.T1E.T2C.X1B.X2C,
Z5.T1E.T2C.X1B.X2C, Z1.T1F.T2C.X1B.X2C, Z2.T1F.T2C.X1B.X2C,
Z3.T1F.T2C.X1B.X2C, Z4.T1F.T2C.X1B.X2C, Z5.T1F.T2C.X1B.X2C,
Z1.T1A.T2D.X1B.X2C, Z2.T1A.T2D.X1B.X2C, Z3.T1A.T2D.X1B.X2C,
Z4.T1A.T2D.X1B.X2C, Z5.T1A.T2D.X1B.X2C, Z1.T1B.T2D.X1B.X2C,
Z2.T1B.T2D.X1B.X2C, Z3.T1B.T2D.X1B.X2C, Z4.T1B.T2D.X1B.X2C,
Z5.T1B.T2D.X1B.X2C, Z1.T1C.T2D.X1B.X2C, Z2.T1C.T2D.X1B.X2C,
Z3.T1C.T2D.X1B.X2C, Z4.T1C.T2D.X1B.X2C, Z5.T1C.T2D.X1B.X2C,
Z1.T1D.T2D.X1B.X2C, Z2.T1D.T2D.X1B.X2C, Z3.T1D.T2D.X1B.X2C,
Z4.T1D.T2D.X1B.X2C, Z5.T1D.T2D.X1B.X2C, Z1.T1E.T2D.X1B.X2C,
Z2.T1E.T2D.X1B.X2C, Z3.T1E.T2D.X1B.X2C, Z4.T1E.T2D.X1B.X2C,
Z5.T1E.T2D.X1B.X2C, Z1.T1F.T2D.X1B.X2C, Z2.T1F.T2D.X1B.X2C,
Z3.T1F.T2D.X1B.X2C, Z4.T1F.T2D.X1B.X2C, Z5.T1F.T2D.X1B.X2C,
Z1.T1A.T2A.X1C.X2C, Z2.T1A.T2A.X1C.X2C, Z3.T1A.T2A.X1C.X2C,
Z4.T1A.T2A.X1C.X2C, Z5.T1A.T2A.X1C.X2C, Z1.T1B.T2A.X1C.X2C,
Z2.T1B.T2A.X1C.X2C, Z3.T1B.T2A.X1C.X2C, Z4.T1B.T2A.X1C.X2C,
Z5.T1B.T2A.X1C.X2C, Z1.T1C.T2A.X1C.X2C, Z2.T1C.T2A.X1C.X2C,
Z3.T1C.T2A.X1C.X2C, Z4.T1C.T2A.X1C.X2C, Z5.T1C.T2A.X1C.X2C,
Z1.T1D.T2A.X1C.X2C, Z2.T1D.T2A.X1C.X2C, Z3.T1D.T2A.X1C.X2C,
Z4.T1D.T2A.X1C.X2C, Z5.T1D.T2A.X1C.X2C, Z1.T1E.T2A.X1C.X2C,
Z2.T1E.T2A.X1C.X2C, Z3.T1E.T2A.X1C.X2C, Z4.T1E.T2A.X1C.X2C,
Z5.T1E.T2A.X1C.X2C, Z1.T1F.T2A.X1C.X2C, Z2.T1F.T2A.X1C.X2C,
Z3.T1F.T2A.X1C.X2C, Z4.T1F.T2A.X1C.X2C, Z5.T1F.T2A.X1C.X2C,
Z1.T1A.T2B.X1C.X2C, Z2.T1A.T2B.X1C.X2C, Z3.T1A.T2B.X1C.X2C,
Z4.T1A.T2B.X1C.X2C, Z5.T1A.T2B.X1C.X2C, Z1.T1B.T2B.X1C.X2C,
Z2.T1B.T2B.X1C.X2C, Z3.T1B.T2B.X1C.X2C, Z4.T1B.T2B.X1C.X2C,
Z5.T1B.T2B.X1C.X2C, Z1.T1C.T2B.X1C.X2C, Z2.T1C.T2B.X1C.X2C,
Z3.T1C.T2B.X1C.X2C, Z4.T1C.T2B.X1C.X2C, Z5.T1C.T2B.X1C.X2C,
Z1.T1D.T2B.X1C.X2C, Z2.T1D.T2B.X1C.X2C, Z3.T1D.T2B.X1C.X2C,
Z4.T1D.T2B.X1C.X2C, Z5.T1D.T2B.X1C.X2C, Z1.T1E.T2B.X1C.X2C,
Z2.T1E.T2B.X1C.X2C, Z3.T1E.T2B.X1C.X2C, Z4.T1E.T2B.X1C.X2C,
Z5.T1E.T2B.X1C.X2C, Z1.T1F.T2B.X1C.X2C, Z2.T1F.T2B.X1C.X2C,
Z3.T1F.T2B.X1C.X2C, Z4.T1F.T2B.X1C.X2C, Z5.T1F.T2B.X1C.X2C,
Z1.T1A.T2C.X1C.X2C, Z2.T1A.T2C.X1C.X2C, Z3.T1A.T2C.X1C.X2C,
Z4.T1A.T2C.X1C.X2C, Z5.T1A.T2C.X1C.X2C, Z1.T1B.T2C.X1C.X2C,
Z2.T1B.T2C.X1C.X2C, Z3.T1B.T2C.X1C.X2C, Z4.T1B.T2C.X1C.X2C,
Z5.T1B.T2C.X1C.X2C, Z1.T1C.T2C.X1C.X2C, Z2.T1C.T2C.X1C.X2C,
Z3.T1C.T2C.X1C.X2C, Z4.T1C.T2C.X1C.X2C, Z5.T1C.T2C.X1C.X2C,
Z1.T1D.T2C.X1C.X2C, Z2.T1D.T2C.X1C.X2C, Z3.T1D.T2C.X1C.X2C,
Z4.T1D.T2C.X1C.X2C, Z5.T1D.T2C.X1C.X2C, Z1.T1E.T2C.X1C.X2C,
Z2.T1E.T2C.X1C.X2C, Z3.T1E.T2C.X1C.X2C, Z4.T1E.T2C.X1C.X2C,
Z5.T1E.T2C.X1C.X2C, Z1.T1F.T2C.X1C.X2C, Z2.T1F.T2C.X1C.X2C,
Z3.T1F.T2C.X1C.X2C, Z4.T1F.T2C.X1C.X2C, Z5.T1F.T2C.X1C.X2C,
Z1.T1A.T2D.X1C.X2C, Z2.T1A.T2D.X1C.X2C, Z3.T1A.T2D.X1C.X2C,
Z4.T1A.T2D.X1C.X2C, Z5.T1A.T2D.X1C.X2C, Z1.T1B.T2D.X1C.X2C,
Z2.T1B.T2D.X1C.X2C, Z3.T1B.T2D.X1C.X2C, Z4.T1B.T2D.X1C.X2C,
Z5.T1B.T2D.X1C.X2C, Z1.T1C.T2D.X1C.X2C, Z2.T1C.T2D.X1C.X2C,
Z3.T1C.T2D.X1C.X2C, Z4.T1C.T2D.X1C.X2C, Z5.T1C.T2D.X1C.X2C,
Z1.T1D.T2D.X1C.X2C, Z2.T1D.T2D.X1C.X2C, Z3.T1D.T2D.X1C.X2C,
Z4.T1D.T2D.X1C.X2C, Z5.T1D.T2D.X1C.X2C, Z1.T1E.T2D.X1C.X2C,
Z2.T1E.T2D.X1C.X2C, Z3.T1E.T2D.X1C.X2C, Z4.T1E.T2D.X1C.X2C,
Z5.T1E.T2D.X1C.X2C, Z1.T1F.T2D.X1C.X2C, Z2.T1F.T2D.X1C.X2C,
Z3.T1F.T2D.X1C.X2C, Z4.T1F.T2D.X1C.X2C, Z5.T1F.T2D.X1C.X2C,
Z1.T1A.T2A.X1D.X2C, Z2.T1A.T2A.X1D.X2C, Z3.T1A.T2A.X1D.X2C,
Z4.T1A.T2A.X1D.X2C, Z5.T1A.T2A.X1D.X2C, Z1.T1B.T2A.X1D.X2C,
Z2.T1B.T2A.X1D.X2C, Z3.T1B.T2A.X1D.X2C, Z4.T1B.T2A.X1D.X2C,
Z5.T1B.T2A.X1D.X2C, Z1.T1C.T2A.X1D.X2C, Z2.T1C.T2A.X1D.X2C,
Z3.T1C.T2A.X1D.X2C, Z4.T1C.T2A.X1D.X2C, Z5.T1C.T2A.X1D.X2C,
Z1.T1D.T2A.X1D.X2C, Z2.T1D.T2A.X1D.X2C, Z3.T1D.T2A.X1D.X2C,
Z4.T1D.T2A.X1D.X2C, Z5.T1D.T2A.X1D.X2C, Z1.T1E.T2A.X1D.X2C,
Z2.T1E.T2A.X1D.X2C, Z3.T1E.T2A.X1D.X2C, Z4.T1E.T2A.X1D.X2C,

TABLE 6-continued

List of Compound Structure of Formula II

Z5.T1E.T2A.X1D.X2C, Z1.T1F.T2A.X1D.X2C,
Z2.T1F.T2A.X1D.X2C,
Z3.T1F.T2A.X1D.X2C, Z4.T1F.T2A.X1D.X2C,
Z5.T1F.T2A.X1D.X2C,
Z1.T1A.T2B.X1D.X2C, Z2.T1A.T2B.X1D.X2C,
Z3.T1A.T2B.X1D.X2C,
Z4.T1A.T2B.X1D.X2C, Z5.T1A.T2B.X1D.X2C,
Z1.T1B.T2B.X1D.X2C,
Z2.T1B.T2B.X1D.X2C, Z3.T1B.T2B.X1D.X2C,
Z4.T1B.T2B.X1D.X2C,
Z5.T1B.T2B.X1D.X2C, Z1.T1C.T2B.X1D.X2C,
Z2.T1C.T2B.X1D.X2C,
Z3.T1C.T2B.X1D.X2C, Z4.T1C.T2B.X1D.X2C,
Z5.T1C.T2B.X1D.X2C,
Z1.T1D.T2B.X1D.X2C, Z2.T1D.T2B.X1D.X2C,
Z3.T1D.T2B.X1D.X2C,
Z4.T1D.T2B.X1D.X2C, Z5.T1D.T2B.X1D.X2C,
Z1.T1E.T2B.X1D.X2C,
Z2.T1E.T2B.X1D.X2C, Z3.T1E.T2B.X1D.X2C,
Z4.T1E.T2B.X1D.X2C,
Z5.T1E.T2B.X1D.X2C, Z1.T1F.T2B.X1D.X2C,
Z2.T1F.T2B.X1D.X2C,
Z3.T1F.T2B.X1D.X2C, Z4.T1F.T2B.X1D.X2C,
Z5.T1F.T2B.X1D.X2C,
Z1.T1A.T2C.X1D.X2C, Z2.T1A.T2C.X1D.X2C,
Z3.T1A.T2C.X1D.X2C,
Z4.T1A.T2C.X1D.X2C, Z5.T1A.T2C.X1D.X2C,
Z1.T1B.T2C.X1D.X2C,
Z2.T1B.T2C.X1D.X2C, Z3.T1B.T2C.X1D.X2C,
Z4.T1B.T2C.X1D.X2C,
Z5.T1B.T2C.X1D.X2C, Z1.T1C.T2C.X1D.X2C,
Z2.T1C.T2C.X1D.X2C,
Z3.T1C.T2C.X1D.X2C, Z4.T1C.T2C.X1D.X2C,
Z5.T1C.T2C.X1D.X2C,
Z1.T1D.T2C.X1D.X2C, Z2.T1D.T2C.X1D.X2C,
Z3.T1D.T2C.X1D.X2C,
Z4.T1D.T2C.X1D.X2C, Z5.T1D.T2C.X1D.X2C,
Z1.T1E.T2C.X1D.X2C,
Z2.T1E.T2C.X1D.X2C, Z3.T1E.T2C.X1D.X2C,
Z4.T1E.T2C.X1D.X2C,
Z5.T1E.T2C.X1D.X2C, Z1.T1F.T2C.X1D.X2C,
Z2.T1F.T2C.X1D.X2C,
Z3.T1F.T2C.X1D.X2C, Z4.T1F.T2C.X1D.X2C,
Z5.T1F.T2C.X1D.X2C,
Z1.T1A.T2D.X1D.X2C, Z2.T1A.T2D.X1D.X2C,
Z3.T1A.T2D.X1D.X2C,
Z4.T1A.T2D.X1D.X2C, Z5.T1A.T2D.X1D.X2C,
Z1.T1B.T2D.X1D.X2C,
Z2.T1B.T2D.X1D.X2C, Z3.T1B.T2D.X1D.X2C,
Z4.T1B.T2D.X1D.X2C,
Z5.T1B.T2D.X1D.X2C, Z1.T1C.T2D.X1D.X2C,
Z2.T1C.T2D.X1D.X2C,
Z3.T1C.T2D.X1D.X2C, Z4.T1C.T2D.X1D.X2C,
Z5.T1C.T2D.X1D.X2C,
Z1.T1D.T2D.X1D.X2C, Z2.T1D.T2D.X1D.X2C,
Z3.T1D.T2D.X1D.X2C,
Z4.T1D.T2D.X1D.X2C, Z5.T1D.T2D.X1D.X2C,
Z1.T1E.T2D.X1D.X2C,
Z2.T1E.T2D.X1D.X2C, Z3.T1E.T2D.X1D.X2C,
Z4.T1E.T2D.X1D.X2C,
Z5.T1E.T2D.X1D.X2C, Z1.T1F.T2D.X1D.X2C,
Z2.T1F.T2D.X1D.X2C,
Z3.T1F.T2D.X1D.X2C, Z4.T1F.T2D.X1D.X2C,
Z5.T1F.T2D.X1D.X2C,
Z1.T1A.T2A.X1E.X2C, Z2.T1A.T2A.X1E.X2C,
Z3.T1A.T2A.X1E.X2C,
Z4.T1A.T2A.X1E.X2C, Z5.T1A.T2A.X1E.X2C,
Z1.T1B.T2A.X1E.X2C,
Z2.T1B.T2A.X1E.X2C, Z3.T1B.T2A.X1E.X2C,
Z4.T1B.T2A.X1E.X2C,
Z5.T1B.T2A.X1E.X2C, Z1.T1C.T2A.X1E.X2C,
Z2.T1C.T2A.X1E.X2C,
Z3.T1C.T2A.X1E.X2C, Z4.T1C.T2A.X1E.X2C,
Z5.T1C.T2A.X1E.X2C,
Z1.T1D.T2A.X1E.X2C, Z2.T1D.T2A.X1E.X2C,
Z3.T1D.T2A.X1E.X2C,
Z4.T1D.T2A.X1E.X2C, Z5.T1D.T2A.X1E.X2C,
Z1.T1E.T2A.X1E.X2C,
Z2.T1E.T2A.X1E.X2C, Z3.T1E.T2A.X1E.X2C,
Z4.T1E.T2A.X1E.X2C,
Z5.T1E.T2A.X1E.X2C, Z1.T1F.T2A.X1E.X2C,
Z2.T1F.T2A.X1E.X2C,
Z3.T1F.T2A.X1E.X2C, Z4.T1F.T2A.X1E.X2C,
Z5.T1F.T2A.X1E.X2C,
Z1.T1A.T2B.X1E.X2C, Z2.T1A.T2B.X1E.X2C,
Z3.T1A.T2B.X1E.X2C,
Z4.T1A.T2B.X1E.X2C, Z5.T1A.T2B.X1E.X2C,
Z1.T1B.T2B.X1E.X2C,
Z2.T1B.T2B.X1E.X2C, Z3.T1B.T2B.X1E.X2C,
Z4.T1B.T2B.X1E.X2C,
Z5.T1B.T2B.X1E.X2C, Z1.T1C.T2B.X1E.X2C,
Z2.T1C.T2B.X1E.X2C,
Z3.T1C.T2B.X1E.X2C, Z4.T1C.T2B.X1E.X2C,
Z5.T1C.T2B.X1E.X2C,
Z1.T1D.T2B.X1E.X2C, Z2.T1D.T2B.X1E.X2C,
Z3.T1D.T2B.X1E.X2C,
Z4.T1D.T2B.X1E.X2C, Z5.T1D.T2B.X1E.X2C,
Z1.T1E.T2B.X1E.X2C,
Z2.T1E.T2B.X1E.X2C, Z3.T1E.T2B.X1E.X2C,
Z4.T1E.T2B.X1E.X2C,
Z5.T1E.T2B.X1E.X2C, Z1.T1F.T2B.X1E.X2C,
Z2.T1F.T2B.X1E.X2C,
Z3.T1F.T2B.X1E.X2C, Z4.T1F.T2B.X1E.X2C,
Z5.T1F.T2B.X1E.X2C,
Z1.T1A.T2C.X1E.X2C, Z2.T1A.T2C.X1E.X2C,
Z3.T1A.T2C.X1E.X2C,
Z4.T1A.T2C.X1E.X2C, Z5.T1A.T2C.X1E.X2C,
Z1.T1B.T2C.X1E.X2C,
Z2.T1B.T2C.X1E.X2C, Z3.T1B.T2C.X1E.X2C,
Z4.T1B.T2C.X1E.X2C,
Z5.T1B.T2C.X1E.X2C, Z1.T1C.T2C.X1E.X2C,
Z2.T1C.T2C.X1E.X2C,
Z3.T1C.T2C.X1E.X2C, Z4.T1C.T2C.X1E.X2C,
Z5.T1C.T2C.X1E.X2C,
Z1.T1D.T2C.X1E.X2C, Z2.T1D.T2C.X1E.X2C,
Z3.T1D.T2C.X1E.X2C,
Z4.T1D.T2C.X1E.X2C, Z5.T1D.T2C.X1E.X2C,
Z1.T1E.T2C.X1E.X2C,
Z2.T1E.T2C.X1E.X2C, Z3.T1E.T2C.X1E.X2C,
Z4.T1E.T2C.X1E.X2C,
Z5.T1E.T2C.X1E.X2C, Z1.T1F.T2C.X1E.X2C,
Z2.T1F.T2C.X1E.X2C,
Z3.T1F.T2C.X1E.X2C, Z4.T1F.T2C.X1E.X2C,
Z5.T1F.T2C.X1E.X2C,
Z1.T1A.T2D.X1E.X2C, Z2.T1A.T2D.X1E.X2C,
Z3.T1A.T2D.X1E.X2C,
Z4.T1A.T2D.X1E.X2C, Z5.T1A.T2D.X1E.X2C,
Z1.T1B.T2D.X1E.X2C,
Z2.T1B.T2D.X1E.X2C, Z3.T1B.T2D.X1E.X2C,
Z4.T1B.T2D.X1E.X2C,
Z5.T1B.T2D.X1E.X2C, Z1.T1C.T2D.X1E.X2C,
Z2.T1C.T2D.X1E.X2C,
Z3.T1C.T2D.X1E.X2C, Z4.T1C.T2D.X1E.X2C,
Z5.T1C.T2D.X1E.X2C,
Z1.T1D.T2D.X1E.X2C, Z2.T1D.T2D.X1E.X2C,
Z3.T1D.T2D.X1E.X2C,
Z4.T1D.T2D.X1E.X2C, Z5.T1D.T2D.X1E.X2C,
Z1.T1E.T2D.X1E.X2C,
Z2.T1E.T2D.X1E.X2C, Z3.T1E.T2D.X1E.X2C,
Z4.T1E.T2D.X1E.X2C,
Z5.T1E.T2D.X1E.X2C, Z1.T1F.T2D.X1E.X2C,
Z2.T1F.T2D.X1E.X2C,
Z3.T1F.T2D.X1E.X2C, Z4.T1F.T2D.X1E.X2C,
Z5.T1F.T2D.X1E.X2C,
Z1.T1A.T2A.X1F.X2C, Z2.T1A.T2A.X1F.X2C,
Z3.T1A.T2A.X1F.X2C,
Z4.T1A.T2A.X1F.X2C, Z5.T1A.T2A.X1F.X2C,
Z1.T1B.T2A.X1F.X2C,
Z2.T1B.T2A.X1F.X2C, Z3.T1B.T2A.X1F.X2C,
Z4.T1B.T2A.X1F.X2C,
Z5.T1B.T2A.X1F.X2C, Z1.T1C.T2A.X1F.X2C,
Z2.T1C.T2A.X1F.X2C,
Z3.T1C.T2A.X1F.X2C, Z4.T1C.T2A.X1F.X2C,
Z5.T1C.T2A.X1F.X2C,

TABLE 6-continued

List of Compound Structure of Formula II

Z1.T1D.T2A.X1F.X2C, Z2.T1D.T2A.X1F.X2C,
Z3.T1D.T2A.X1F.X2C,
Z4.T1D.T2A.X1F.X2C, Z5.T1D.T2A.X1F.X2C,
Z1.T1E.T2A.X1F.X2C,
Z2.T1E.T2A.X1F.X2C, Z3.T1E.T2A.X1F.X2C,
Z4.T1E.T2A.X1F.X2C,
Z5.T1E.T2A.X1F.X2C, Z1.T1F.T2A.X1F.X2C,
Z2.T1F.T2A.X1F.X2C,
Z3.T1F.T2A.X1F.X2C, Z4.T1F.T2A.X1F.X2C,
Z5.T1F.T2A.X1F.X2C,
Z1.T1A.T2B.X1F.X2C, Z2.T1A.T2B.X1F.X2C,
Z3.T1A.T2B.X1F.X2C,
Z4.T1A.T2B.X1F.X2C, Z5.T1A.T2B.X1F.X2C,
Z1.T1B.T2B.X1F.X2C,
Z2.T1B.T2B.X1F.X2C, Z3.T1B.T2B.X1F.X2C,
Z4.T1B.T2B.X1F.X2C,
Z5.T1B.T2B.X1F.X2C, Z1.T1C.T2B.X1F.X2C,
Z2.T1C.T2B.X1F.X2C,
Z3.T1C.T2B.X1F.X2C, Z4.T1C.T2B.X1F.X2C,
Z5.T1C.T2B.X1F.X2C,
Z1.T1D.T2B.X1F.X2C, Z2.T1D.T2B.X1F.X2C,
Z3.T1D.T2B.X1F.X2C,
Z4.T1D.T2B.X1F.X2C, Z5.T1D.T2B.X1F.X2C,
Z1.T1E.T2B.X1F.X2C,
Z2.T1E.T2B.X1F.X2C, Z3.T1E.T2B.X1F.X2C,
Z4.T1E.T2B.X1F.X2C,
Z5.T1E.T2B.X1F.X2C, Z1.T1F.T2B.X1F.X2C,
Z2.T1F.T2B.X1F.X2C,
Z3.T1F.T2B.X1F.X2C, Z4.T1F.T2B.X1F.X2C,
Z5.T1F.T2B.X1F.X2C,
Z1.T1A.T2C.X1F.X2C, Z2.T1A.T2C.X1F.X2C,
Z3.T1A.T2C.X1F.X2C,
Z4.T1A.T2C.X1F.X2C, Z5.T1A.T2C.X1F.X2C,
Z1.T1B.T2C.X1F.X2C,
Z2.T1B.T2C.X1F.X2C, Z3.T1B.T2C.X1F.X2C,
Z4.T1B.T2C.X1F.X2C,
Z5.T1B.T2C.X1F.X2C, Z1.T1C.T2C.X1F.X2C,
Z2.T1C.T2C.X1F.X2C,
Z3.T1C.T2C.X1F.X2C, Z4.T1C.T2C.X1F.X2C,
Z5.T1C.T2C.X1F.X2C,
Z1.T1D.T2C.X1F.X2C, Z2.T1D.T2C.X1F.X2C,
Z3.T1D.T2C.X1F.X2C,
Z4.T1D.T2C.X1F.X2C, Z5.T1D.T2C.X1F.X2C,
Z1.T1E.T2C.X1F.X2C,
Z2.T1E.T2C.X1F.X2C, Z3.T1E.T2C.X1F.X2C,
Z4.T1E.T2C.X1F.X2C,
Z5.T1E.T2C.X1F.X2C, Z1.T1F.T2C.X1F.X2C,
Z2.T1F.T2C.X1F.X2C,
Z3.T1F.T2C.X1F.X2C, Z4.T1F.T2C.X1F.X2C,
Z5.T1F.T2C.X1F.X2C,
Z1.T1A.T2D.X1F.X2C, Z2.T1A.T2D.X1F.X2C,
Z3.T1A.T2D.X1F.X2C,
Z4.T1A.T2D.X1F.X2C, Z5.T1A.T2D.X1F.X2C,
Z1.T1B.T2D.X1F.X2C,
Z2.T1B.T2D.X1F.X2C, Z3.T1B.T2D.X1F.X2C,
Z4.T1B.T2D.X1F.X2C,
Z5.T1B.T2D.X1F.X2C, Z1.T1C.T2D.X1F.X2C,
Z2.T1C.T2D.X1F.X2C,
Z3.T1C.T2D.X1F.X2C, Z4.T1C.T2D.X1F.X2C,
Z5.T1C.T2D.X1F.X2C,
Z1.T1D.T2D.X1F.X2C, Z2.T1D.T2D.X1F.X2C,
Z3.T1D.T2D.X1F.X2C,
Z4.T1D.T2D.X1F.X2C, Z5.T1D.T2D.X1F.X2C,
Z1.T1E.T2D.X1F.X2C,
Z2.T1E.T2D.X1F.X2C, Z3.T1E.T2D.X1F.X2C,
Z4.T1E.T2D.X1F.X2C,
Z5.T1E.T2D.X1F.X2C, Z1.T1F.T2D.X1F.X2C,
Z2.T1F.T2D.X1F.X2C,
Z3.T1F.T2D.X1F.X2C, Z4.T1F.T2D.X1F.X2C,
Z5.T1F.T2D.X1F.X2C,
Z1.T1A.T2A.X1A.X2D, Z2.T1A.T2A.X1A.X2D,
Z3.T1A.T2A.X1A.X2D,
Z4.T1A.T2A.X1A.X2D, Z5.T1A.T2A.X1A.X2D,
Z1.T1B.T2A.X1A.X2D,
Z2.T1B.T2A.X1A.X2D, Z3.T1B.T2A.X1A.X2D,
Z4.T1B.T2A.X1A.X2D,
Z5.T1B.T2A.X1A.X2D, Z1.T1C.T2A.X1A.X2D,
Z2.T1C.T2A.X1A.X2D,
Z3.T1C.T2A.X1A.X2D, Z4.T1C.T2A.X1A.X2D,
Z5.T1C.T2A.X1A.X2D,
Z1.T1D.T2A.X1A.X2D, Z2.T1D.T2A.X1A.X2D,
Z3.T1D.T2A.X1A.X2D,
Z4.T1D.T2A.X1A.X2D, Z5.T1D.T2A.X1A.X2D,
Z1.T1E.T2A.X1A.X2D,
Z2.T1E.T2A.X1A.X2D, Z3.T1E.T2A.X1A.X2D,
Z4.T1E.T2A.X1A.X2D,
Z5.T1E.T2A.X1A.X2D, Z1.T1F.T2A.X1A.X2D,
Z2.T1F.T2A.X1A.X2D,
Z3.T1F.T2A.X1A.X2D, Z4.T1F.T2A.X1A.X2D,
Z5.T1F.T2A.X1A.X2D,
Z1.T1A.T2B.X1A.X2D, Z2.T1A.T2B.X1A.X2D,
Z3.T1A.T2B.X1A.X2D,
Z4.T1A.T2B.X1A.X2D, Z5.T1A.T2B.X1A.X2D,
Z1.T1B.T2B.X1A.X2D,
Z2.T1B.T2B.X1A.X2D, Z3.T1B.T2B.X1A.X2D,
Z4.T1B.T2B.X1A.X2D,
Z5.T1B.T2B.X1A.X2D, Z1.T1C.T2B.X1A.X2D,
Z2.T1C.T2B.X1A.X2D,
Z3.T1C.T2B.X1A.X2D, Z4.T1C.T2B.X1A.X2D,
Z5.T1C.T2B.X1A.X2D,
Z1.T1D.T2B.X1A.X2D, Z2.T1D.T2B.X1A.X2D,
Z3.T1D.T2B.X1A.X2D,
Z4.T1D.T2B.X1A.X2D, Z5.T1D.T2B.X1A.X2D,
Z1.T1E.T2B.X1A.X2D,
Z2.T1E.T2B.X1A.X2D, Z3.T1E.T2B.X1A.X2D,
Z4.T1E.T2B.X1A.X2D,
Z5.T1E.T2B.X1A.X2D, Z1.T1F.T2B.X1A.X2D,
Z2.T1F.T2B.X1A.X2D,
Z3.T1F.T2B.X1A.X2D, Z4.T1F.T2B.X1A.X2D,
Z5.T1F.T2B.X1A.X2D,
Z1.T1A.T2C.X1A.X2D, Z2.T1A.T2C.X1A.X2D,
Z3.T1A.T2C.X1A.X2D,
Z4.T1A.T2C.X1A.X2D, Z5.T1A.T2C.X1A.X2D,
Z1.T1B.T2C.X1A.X2D,
Z2.T1B.T2C.X1A.X2D, Z3.T1B.T2C.X1A.X2D,
Z4.T1B.T2C.X1A.X2D,
Z5.T1B.T2C.X1A.X2D, Z1.T1C.T2C.X1A.X2D,
Z2.T1C.T2C.X1A.X2D,
Z3.T1C.T2C.X1A.X2D, Z4.T1C.T2C.X1A.X2D,
Z5.T1C.T2C.X1A.X2D,
Z1.T1D.T2C.X1A.X2D, Z2.T1D.T2C.X1A.X2D,
Z3.T1D.T2C.X1A.X2D,
Z4.T1D.T2C.X1A.X2D, Z5.T1D.T2C.X1A.X2D,
Z1.T1E.T2C.X1A.X2D,
Z2.T1E.T2C.X1A.X2D, Z3.T1E.T2C.X1A.X2D,
Z4.T1E.T2C.X1A.X2D,
Z5.T1E.T2C.X1A.X2D, Z1.T1F.T2C.X1A.X2D,
Z2.T1F.T2C.X1A.X2D,
Z3.T1F.T2C.X1A.X2D, Z4.T1F.T2C.X1A.X2D,
Z5.T1F.T2C.X1A.X2D,
Z1.T1A.T2D.X1A.X2D, Z2.T1A.T2D.X1A.X2D,
Z3.T1A.T2D.X1A.X2D,
Z4.T1A.T2D.X1A.X2D, Z5.T1A.T2D.X1A.X2D,
Z1.T1B.T2D.X1A.X2D,
Z2.T1B.T2D.X1A.X2D, Z3.T1B.T2D.X1A.X2D,
Z4.T1B.T2D.X1A.X2D,
Z5.T1B.T2D.X1A.X2D, Z1.T1C.T2D.X1A.X2D,
Z2.T1C.T2D.X1A.X2D,
Z3.T1C.T2D.X1A.X2D, Z4.T1C.T2D.X1A.X2D,
Z5.T1C.T2D.X1A.X2D,
Z1.T1D.T2D.X1A.X2D, Z2.T1D.T2D.X1A.X2D,
Z3.T1D.T2D.X1A.X2D,
Z4.T1D.T2D.X1A.X2D, Z5.T1D.T2D.X1A.X2D,
Z1.T1E.T2D.X1A.X2D,
Z2.T1E.T2D.X1A.X2D, Z3.T1E.T2D.X1A.X2D,
Z4.T1E.T2D.X1A.X2D,
Z5.T1E.T2D.X1A.X2D, Z1.T1F.T2D.X1A.X2D,
Z2.T1F.T2D.X1A.X2D,
Z3.T1F.T2D.X1A.X2D, Z4.T1F.T2D.X1A.X2D,
Z5.T1F.T2D.X1A.X2D,
Z1.T1A.T2A.X1B.X2D, Z2.T1A.T2A.X1B.X2D,
Z3.T1A.T2A.X1B.X2D,
Z4.T1A.T2A.X1B.X2D, Z5.T1A.T2A.X1B.X2D,
Z1.T1B.T2A.X1B.X2D,

TABLE 6-continued

List of Compound Structure of Formula II

Z2.T1B.T2A.X1B.X2D, Z3.T1B.T2A.X1B.X2D,
Z4.T1B.T2A.X1B.X2D,
Z5.T1B.T2A.X1B.X2D, Z1.T1C.T2A.X1B.X2D,
Z2.T1C.T2A.X1B.X2D,
Z3.T1C.T2A.X1B.X2D, Z4.T1C.T2A.X1B.X2D,
Z5.T1C.T2A.X1B.X2D,
Z1.T1D.T2A.X1B.X2D, Z2.T1D.T2A.X1B.X2D,
Z3.T1D.T2A.X1B.X2D,
Z4.T1D.T2A.X1B.X2D, Z5.T1D.T2A.X1B.X2D,
Z1.T1E.T2A.X1B.X2D,
Z2.T1E.T2A.X1B.X2D, Z3.T1E.T2A.X1B.X2D,
Z4.T1E.T2A.X1B.X2D,
Z5.T1E.T2A.X1B.X2D, Z1.T1F.T2A.X1B.X2D,
Z2.T1F.T2A.X1B.X2D,
Z3.T1F.T2A.X1B.X2D, Z4.T1F.T2A.X1B.X2D,
Z5.T1F.T2A.X1B.X2D,
Z1.T1A.T2B.X1B.X2D, Z2.T1A.T2B.X1B.X2D,
Z3.T1A.T2B.X1B.X2D,
Z4.T1A.T2B.X1B.X2D, Z5.T1A.T2B.X1B.X2D,
Z1.T1B.T2B.X1B.X2D,
Z2.T1B.T2B.X1B.X2D, Z3.T1B.T2B.X1B.X2D,
Z4.T1B.T2B.X1B.X2D,
Z5.T1B.T2B.X1B.X2D, Z1.T1C.T2B.X1B.X2D,
Z2.T1C.T2B.X1B.X2D,
Z3.T1C.T2B.X1B.X2D, Z4.T1C.T2B.X1B.X2D,
Z5.T1C.T2B.X1B.X2D,
Z1.T1D.T2B.X1B.X2D, Z2.T1D.T2B.X1B.X2D,
Z3.T1D.T2B.X1B.X2D,
Z4.T1D.T2B.X1B.X2D, Z5.T1D.T2B.X1B.X2D,
Z1.T1E.T2B.X1B.X2D,
Z2.T1E.T2B.X1B.X2D, Z3.T1E.T2B.X1B.X2D,
Z4.T1E.T2B.X1B.X2D,
Z5.T1E.T2B.X1B.X2D, Z1.T1F.T2B.X1B.X2D,
Z2.T1F.T2B.X1B.X2D,
Z3.T1F.T2B.X1B.X2D, Z4.T1F.T2B.X1B.X2D,
Z5.T1F.T2B.X1B.X2D,
Z1.T1A.T2C.X1B.X2D, Z2.T1A.T2C.X1B.X2D,
Z3.T1A.T2C.X1B.X2D,
Z4.T1A.T2C.X1B.X2D, Z5.T1A.T2C.X1B.X2D,
Z1.T1B.T2C.X1B.X2D,
Z2.T1B.T2C.X1B.X2D, Z3.T1B.T2C.X1B.X2D,
Z4.T1B.T2C.X1B.X2D,
Z5.T1B.T2C.X1B.X2D, Z1.T1C.T2C.X1B.X2D,
Z2.T1C.T2C.X1B.X2D,
Z3.T1C.T2C.X1B.X2D, Z4.T1C.T2C.X1B.X2D,
Z5.T1C.T2C.X1B.X2D,
Z1.T1D.T2C.X1B.X2D, Z2.T1D.T2C.X1B.X2D,
Z3.T1D.T2C.X1B.X2D,
Z4.T1D.T2C.X1B.X2D, Z5.T1D.T2C.X1B.X2D,
Z1.T1E.T2C.X1B.X2D,
Z2.T1E.T2C.X1B.X2D, Z3.T1E.T2C.X1B.X2D,
Z4.T1E.T2C.X1B.X2D,
Z5.T1E.T2C.X1B.X2D, Z1.T1F.T2C.X1B.X2D,
Z2.T1F.T2C.X1B.X2D,
Z3.T1F.T2C.X1B.X2D, Z4.T1F.T2C.X1B.X2D,
Z5.T1F.T2C.X1B.X2D,
Z1.T1A.T2D.X1B.X2D, Z2.T1A.T2D.X1B.X2D,
Z3.T1A.T2D.X1B.X2D,
Z4.T1A.T2D.X1B.X2D, Z5.T1A.T2D.X1B.X2D,
Z1.T1B.T2D.X1B.X2D,
Z2.T1B.T2D.X1B.X2D, Z3.T1B.T2D.X1B.X2D,
Z4.T1B.T2D.X1B.X2D,
Z5.T1B.T2D.X1B.X2D, Z1.T1C.T2D.X1B.X2D,
Z2.T1C.T2D.X1B.X2D,
Z3.T1C.T2D.X1B.X2D, Z4.T1C.T2D.X1B.X2D,
Z5.T1C.T2D.X1B.X2D,
Z1.T1D.T2D.X1B.X2D, Z2.T1D.T2D.X1B.X2D,
Z3.T1D.T2D.X1B.X2D,
Z4.T1D.T2D.X1B.X2D, Z5.T1D.T2D.X1B.X2D,
Z1.T1E.T2D.X1B.X2D,
Z2.T1E.T2D.X1B.X2D, Z3.T1E.T2D.X1B.X2D,
Z4.T1E.T2D.X1B.X2D,
Z5.T1E.T2D.X1B.X2D, Z1.T1F.T2D.X1B.X2D,
Z2.T1F.T2D.X1B.X2D,
Z3.T1F.T2D.X1B.X2D, Z4.T1F.T2D.X1B.X2D,
Z5.T1F.T2D.X1B.X2D,

TABLE 6-continued

List of Compound Structure of Formula II

Z1.T1A.T2A.X1C.X2D, Z2.T1A.T2A.X1C.X2D,
Z3.T1A.T2A.X1C.X2D,
Z4.T1A.T2A.X1C.X2D, Z5.T1A.T2A.X1C.X2D,
Z1.T1B.T2A.X1C.X2D,
Z2.T1B.T2A.X1C.X2D, Z3.T1B.T2A.X1C.X2D,
Z4.T1B.T2A.X1C.X2D,
Z5.T1B.T2A.X1C.X2D, Z1.T1C.T2A.X1C.X2D,
Z2.T1C.T2A.X1C.X2D,
Z3.T1C.T2A.X1C.X2D, Z4.T1C.T2A.X1C.X2D,
Z5.T1C.T2A.X1C.X2D,
Z1.T1D.T2A.X1C.X2D, Z2.T1D.T2A.X1C.X2D,
Z3.T1D.T2A.X1C.X2D,
Z4.T1D.T2A.X1C.X2D, Z5.T1D.T2A.X1C.X2D,
Z1.T1E.T2A.X1C.X2D,
Z2.T1E.T2A.X1C.X2D, Z3.T1E.T2A.X1C.X2D,
Z4.T1E.T2A.X1C.X2D,
Z5.T1E.T2A.X1C.X2D, Z1.T1F.T2A.X1C.X2D,
Z2.T1F.T2A.X1C.X2D,
Z3.T1F.T2A.X1C.X2D, Z4.T1F.T2A.X1C.X2D,
Z5.T1F.T2A.X1C.X2D,
Z1.T1A.T2B.X1C.X2D, Z2.T1A.T2B.X1C.X2D,
Z3.T1A.T2B.X1C.X2D,
Z4.T1A.T2B.X1C.X2D, Z5.T1A.T2B.X1C.X2D,
Z1.T1B.T2B.X1C.X2D,
Z2.T1B.T2B.X1C.X2D, Z3.T1B.T2B.X1C.X2D,
Z4.T1B.T2B.X1C.X2D,
Z5.T1B.T2B.X1C.X2D, Z1.T1C.T2B.X1C.X2D,
Z2.T1C.T2B.X1C.X2D,
Z3.T1C.T2B.X1C.X2D, Z4.T1C.T2B.X1C.X2D,
Z5.T1C.T2B.X1C.X2D,
Z1.T1D.T2B.X1C.X2D, Z2.T1D.T2B.X1C.X2D,
Z3.T1D.T2B.X1C.X2D,
Z4.T1D.T2B.X1C.X2D, Z5.T1D.T2B.X1C.X2D,
Z1.T1E.T2B.X1C.X2D,
Z2.T1E.T2B.X1C.X2D, Z3.T1E.T2B.X1C.X2D,
Z4.T1E.T2B.X1C.X2D,
Z5.T1E.T2B.X1C.X2D, Z1.T1F.T2B.X1C.X2D,
Z2.T1F.T2B.X1C.X2D,
Z3.T1F.T2B.X1C.X2D, Z4.T1F.T2B.X1C.X2D,
Z5.T1F.T2B.X1C.X2D,
Z1.T1A.T2C.X1C.X2D, Z2.T1A.T2C.X1C.X2D,
Z3.T1A.T2C.X1C.X2D,
Z4.T1A.T2C.X1C.X2D, Z5.T1A.T2C.X1C.X2D,
Z1.T1B.T2C.X1C.X2D,
Z2.T1B.T2C.X1C.X2D, Z3.T1B.T2C.X1C.X2D,
Z4.T1B.T2C.X1C.X2D,
Z5.T1B.T2C.X1C.X2D, Z1.T1C.T2C.X1C.X2D,
Z2.T1C.T2C.X1C.X2D,
Z3.T1C.T2C.X1C.X2D, Z4.T1C.T2C.X1C.X2D,
Z5.T1C.T2C.X1C.X2D,
Z1.T1D.T2C.X1C.X2D, Z2.T1D.T2C.X1C.X2D,
Z3.T1D.T2C.X1C.X2D,
Z4.T1D.T2C.X1C.X2D, Z5.T1D.T2C.X1C.X2D,
Z1.T1E.T2C.X1C.X2D,
Z2.T1E.T2C.X1C.X2D, Z3.T1E.T2C.X1C.X2D,
Z4.T1E.T2C.X1C.X2D,
Z5.T1E.T2C.X1C.X2D, Z1.T1F.T2C.X1C.X2D,
Z2.T1F.T2C.X1C.X2D,
Z3.T1F.T2C.X1C.X2D, Z4.T1F.T2C.X1C.X2D,
Z5.T1F.T2C.X1C.X2D,
Z1.T1A.T2D.X1C.X2D, Z2.T1A.T2D.X1C.X2D,
Z3.T1A.T2D.X1C.X2D,
Z4.T1A.T2D.X1C.X2D, Z5.T1A.T2D.X1C.X2D,
Z1.T1B.T2D.X1C.X2D,
Z2.T1B.T2D.X1C.X2D, Z3.T1B.T2D.X1C.X2D,
Z4.T1B.T2D.X1C.X2D,
Z5.T1B.T2D.X1C.X2D, Z1.T1C.T2D.X1C.X2D,
Z2.T1C.T2D.X1C.X2D,
Z3.T1C.T2D.X1C.X2D, Z4.T1C.T2D.X1C.X2D,
Z5.T1C.T2D.X1C.X2D,
Z1.T1D.T2D.X1C.X2D, Z2.T1D.T2D.X1C.X2D,
Z3.T1D.T2D.X1C.X2D,
Z4.T1D.T2D.X1C.X2D, Z5.T1D.T2D.X1C.X2D,
Z1.T1E.T2D.X1C.X2D,
Z2.T1E.T2D.X1C.X2D, Z3.T1E.T2D.X1C.X2D,
Z4.T1E.T2D.X1C.X2D,
Z5.T1E.T2D.X1C.X2D, Z1.T1F.T2D.X1C.X2D,
Z2.T1F.T2D.X1C.X2D,

TABLE 6-continued

List of Compound Structure of Formula II

Z3.T1F.T2D.X1C.X2D, Z4.T1F.T2D.X1C.X2D,
Z5.T1F.T2D.X1C.X2D,
Z1.T1A.T2A.X1D.X2D, Z2.T1A.T2A.X1D.X2D,
Z3.T1A.T2A.X1D.X2D,
Z4.T1A.T2A.X1D.X2D, Z5.T1A.T2A.X1D.X2D,
Z1.T1B.T2A.X1D.X2D,
Z2.T1B.T2A.X1D.X2D, Z3.T1B.T2A.X1D.X2D,
Z4.T1B.T2A.X1D.X2D,
Z5.T1B.T2A.X1D.X2D, Z1.T1C.T2A.X1D.X2D,
Z2.T1C.T2A.X1D.X2D,
Z3.T1C.T2A.X1D.X2D, Z4.T1C.T2A.X1D.X2D,
Z5.T1C.T2A.X1D.X2D,
Z1.T1D.T2A.X1D.X2D, Z2.T1D.T2A.X1D.X2D,
Z3.T1D.T2A.X1D.X2D,
Z4.T1D.T2A.X1D.X2D, Z5.T1D.T2A.X1D.X2D,
Z1.T1E.T2A.X1D.X2D,
Z2.T1E.T2A.X1D.X2D, Z3.T1E.T2A.X1D.X2D,
Z4.T1E.T2A.X1D.X2D,
Z5.T1E.T2A.X1D.X2D, Z1.T1F.T2A.X1D.X2D,
Z2.T1F.T2A.X1D.X2D,
Z3.T1F.T2A.X1D.X2D, Z4.T1F.T2A.X1D.X2D,
Z5.T1F.T2A.X1D.X2D,
Z1.T1A.T2B.X1D.X2D, Z2.T1A.T2B.X1D.X2D,
Z3.T1A.T2B.X1D.X2D,
Z4.T1A.T2B.X1D.X2D, Z5.T1A.T2B.X1D.X2D,
Z1.T1B.T2B.X1D.X2D,
Z2.T1B.T2B.X1D.X2D, Z3.T1B.T2B.X1D.X2D,
Z4.T1B.T2B.X1D.X2D,
Z5.T1B.T2B.X1D.X2D, Z1.T1C.T2B.X1D.X2D,
Z2.T1C.T2B.X1D.X2D,
Z3.T1C.T2B.X1D.X2D, Z4.T1C.T2B.X1D.X2D,
Z5.T1C.T2B.X1D.X2D,
Z1.T1D.T2B.X1D.X2D, Z2.T1D.T2B.X1D.X2D,
Z3.T1D.T2B.X1D.X2D,
Z4.T1D.T2B.X1D.X2D, Z5.T1D.T2B.X1D.X2D,
Z1.T1E.T2B.X1D.X2D,
Z2.T1E.T2B.X1D.X2D, Z3.T1E.T2B.X1D.X2D,
Z4.T1E.T2B.X1D.X2D,
Z5.T1E.T2B.X1D.X2D, Z1.T1F.T2B.X1D.X2D,
Z2.T1F.T2B.X1D.X2D,
Z3.T1F.T2B.X1D.X2D, Z4.T1F.T2B.X1D.X2D,
Z5.T1F.T2B.X1D.X2D,
Z1.T1A.T2C.X1D.X2D, Z2.T1A.T2C.X1D.X2D,
Z3.T1A.T2C.X1D.X2D,
Z4.T1A.T2C.X1D.X2D, Z5.T1A.T2C.X1D.X2D,
Z1.T1B.T2C.X1D.X2D,
Z2.T1B.T2C.X1D.X2D, Z3.T1B.T2C.X1D.X2D,
Z4.T1B.T2C.X1D.X2D,
Z5.T1B.T2C.X1D.X2D, Z1.T1C.T2C.X1D.X2D,
Z2.T1C.T2C.X1D.X2D,
Z3.T1C.T2C.X1D.X2D, Z4.T1C.T2C.X1D.X2D,
Z5.T1C.T2C.X1D.X2D,
Z1.T1D.T2C.X1D.X2D, Z2.T1D.T2C.X1D.X2D,
Z3.T1D.T2C.X1D.X2D,
Z4.T1D.T2C.X1D.X2D, Z5.T1D.T2C.X1D.X2D,
Z1.T1E.T2C.X1D.X2D,
Z2.T1E.T2C.X1D.X2D, Z3.T1E.T2C.X1D.X2D,
Z4.T1E.T2C.X1D.X2D,
Z5.T1E.T2C.X1D.X2D, Z1.T1F.T2C.X1D.X2D,
Z2.T1F.T2C.X1D.X2D,
Z3.T1F.T2C.X1D.X2D, Z4.T1F.T2C.X1D.X2D,
Z5.T1F.T2C.X1D.X2D,
Z1.T1A.T2D.X1D.X2D, Z2.T1A.T2D.X1D.X2D,
Z3.T1A.T2D.X1D.X2D,
Z4.T1A.T2D.X1D.X2D, Z5.T1A.T2D.X1D.X2D,
Z1.T1B.T2D.X1D.X2D,
Z2.T1B.T2D.X1D.X2D, Z3.T1B.T2D.X1D.X2D,
Z4.T1B.T2D.X1D.X2D,
Z5.T1B.T2D.X1D.X2D, Z1.T1C.T2D.X1D.X2D,
Z2.T1C.T2D.X1D.X2D,
Z3.T1C.T2D.X1D.X2D, Z4.T1C.T2D.X1D.X2D,
Z5.T1C.T2D.X1D.X2D,
Z1.T1D.T2D.X1D.X2D, Z2.T1D.T2D.X1D.X2D,
Z3.T1D.T2D.X1D.X2D,
Z4.T1D.T2D.X1D.X2D, Z5.T1D.T2D.X1D.X2D,
Z1.T1E.T2D.X1D.X2D,
Z2.T1E.T2D.X1D.X2D, Z3.T1E.T2D.X1D.X2D,
Z4.T1E.T2D.X1D.X2D,
Z5.T1E.T2D.X1D.X2D, Z1.T1F.T2D.X1D.X2D,
Z2.T1F.T2D.X1D.X2D,
Z3.T1F.T2D.X1D.X2D, Z4.T1F.T2D.X1D.X2D,
Z5.T1F.T2D.X1D.X2D,
Z1.T1A.T2A.X1E.X2D, Z2.T1A.T2A.X1E.X2D,
Z3.T1A.T2A.X1E.X2D,
Z4.T1A.T2A.X1E.X2D, Z5.T1A.T2A.X1E.X2D,
Z1.T1B.T2A.X1E.X2D,
Z2.T1B.T2A.X1E.X2D, Z3.T1B.T2A.X1E.X2D,
Z4.T1B.T2A.X1E.X2D,
Z5.T1B.T2A.X1E.X2D, Z1.T1C.T2A.X1E.X2D,
Z2.T1C.T2A.X1E.X2D,
Z3.T1C.T2A.X1E.X2D, Z4.T1C.T2A.X1E.X2D,
Z5.T1C.T2A.X1E.X2D,
Z1.T1D.T2A.X1E.X2D, Z2.T1D.T2A.X1E.X2D,
Z3.T1D.T2A.X1E.X2D,
Z4.T1D.T2A.X1E.X2D, Z5.T1D.T2A.X1E.X2D,
Z1.T1E.T2A.X1E.X2D,
Z2.T1E.T2A.X1E.X2D, Z3.T1E.T2A.X1E.X2D,
Z4.T1E.T2A.X1E.X2D,
Z5.T1E.T2A.X1E.X2D, Z1.T1F.T2A.X1E.X2D,
Z2.T1F.T2A.X1E.X2D,
Z3.T1F.T2A.X1E.X2D, Z4.T1F.T2A.X1E.X2D,
Z5.T1F.T2A.X1E.X2D,
Z1.T1A.T2B.X1E.X2D, Z2.T1A.T2B.X1E.X2D,
Z3.T1A.T2B.X1E.X2D,
Z4.T1A.T2B.X1E.X2D, Z5.T1A.T2B.X1E.X2D,
Z1.T1B.T2B.X1E.X2D,
Z2.T1B.T2B.X1E.X2D, Z3.T1B.T2B.X1E.X2D,
Z4.T1B.T2B.X1E.X2D,
Z5.T1B.T2B.X1E.X2D, Z1.T1C.T2B.X1E.X2D,
Z2.T1C.T2B.X1E.X2D,
Z3.T1C.T2B.X1E.X2D, Z4.T1C.T2B.X1E.X2D,
Z5.T1C.T2B.X1E.X2D,
Z1.T1D.T2B.X1E.X2D, Z2.T1D.T2B.X1E.X2D,
Z3.T1D.T2B.X1E.X2D,
Z4.T1D.T2B.X1E.X2D, Z5.T1D.T2B.X1E.X2D,
Z1.T1E.T2B.X1E.X2D,
Z2.T1E.T2B.X1E.X2D, Z3.T1E.T2B.X1E.X2D,
Z4.T1E.T2B.X1E.X2D,
Z5.T1E.T2B.X1E.X2D, Z1.T1F.T2B.X1E.X2D,
Z2.T1F.T2B.X1E.X2D,
Z3.T1F.T2B.X1E.X2D, Z4.T1F.T2B.X1E.X2D,
Z5.T1F.T2B.X1E.X2D,
Z1.T1A.T2C.X1E.X2D, Z2.T1A.T2C.X1E.X2D,
Z3.T1A.T2C.X1E.X2D,
Z4.T1A.T2C.X1E.X2D, Z5.T1A.T2C.X1E.X2D,
Z1.T1B.T2C.X1E.X2D,
Z2.T1B.T2C.X1E.X2D, Z3.T1B.T2C.X1E.X2D,
Z4.T1B.T2C.X1E.X2D,
Z5.T1B.T2C.X1E.X2D, Z1.T1C.T2C.X1E.X2D,
Z2.T1C.T2C.X1E.X2D,
Z3.T1C.T2C.X1E.X2D, Z4.T1C.T2C.X1E.X2D,
Z5.T1C.T2C.X1E.X2D,
Z1.T1D.T2C.X1E.X2D, Z2.T1D.T2C.X1E.X2D,
Z3.T1D.T2C.X1E.X2D,
Z4.T1D.T2C.X1E.X2D, Z5.T1D.T2C.X1E.X2D,
Z1.T1E.T2C.X1E.X2D,
Z2.T1E.T2C.X1E.X2D, Z3.T1E.T2C.X1E.X2D,
Z4.T1E.T2C.X1E.X2D,
Z5.T1E.T2C.X1E.X2D, Z1.T1F.T2C.X1E.X2D,
Z2.T1F.T2C.X1E.X2D,
Z3.T1F.T2C.X1E.X2D, Z4.T1F.T2C.X1E.X2D,
Z5.T1F.T2C.X1E.X2D,
Z1.T1A.T2D.X1E.X2D, Z2.T1A.T2D.X1E.X2D,
Z3.T1A.T2D.X1E.X2D,
Z4.T1A.T2D.X1E.X2D, Z5.T1A.T2D.X1E.X2D,
Z1.T1B.T2D.X1E.X2D,
Z2.T1B.T2D.X1E.X2D, Z3.T1B.T2D.X1E.X2D,
Z4.T1B.T2D.X1E.X2D,
Z5.T1B.T2D.X1E.X2D, Z1.T1C.T2D.X1E.X2D,
Z2.T1C.T2D.X1E.X2D,
Z3.T1C.T2D.X1E.X2D, Z4.T1C.T2D.X1E.X2D,
Z5.T1C.T2D.X1E.X2D,
Z1.T1D.T2D.X1E.X2D, Z2.T1D.T2D.X1E.X2D,
Z3.T1D.T2D.X1E.X2D,

TABLE 6-continued

List of Compound Structure of Formula II

Z4.T1D.T2D.X1E.X2D, Z5.T1D.T2D.X1E.X2D,
Z1.T1E.T2D.X1E.X2D,
Z2.T1E.T2D.X1E.X2D, Z3.T1E.T2D.X1E.X2D,
Z4.T1E.T2D.X1E.X2D,
Z5.T1E.T2D.X1E.X2D, Z1.T1F.T2D.X1E.X2D,
Z2.T1F.T2D.X1E.X2D,
Z3.T1F.T2D.X1E.X2D, Z4.T1F.T2D.X1E.X2D,
Z5.T1F.T2D.X1E.X2D,
Z1.T1A.T2A.X1F.X2D, Z2.T1A.T2A.X1F.X2D,
Z3.T1A.T2A.X1F.X2D,
Z4.T1A.T2A.X1F.X2D, Z5.T1A.T2A.X1F.X2D,
Z1.T1B.T2A.X1F.X2D,
Z2.T1B.T2A.X1F.X2D, Z3.T1B.T2A.X1F.X2D,
Z4.T1B.T2A.X1F.X2D,
Z5.T1B.T2A.X1F.X2D, Z1.T1C.T2A.X1F.X2D,
Z2.T1C.T2A.X1F.X2D,
Z3.T1C.T2A.X1F.X2D, Z4.T1C.T2A.X1F.X2D,
Z5.T1C.T2A.X1F.X2D,
Z1.T1D.T2A.X1F.X2D, Z2.T1D.T2A.X1F.X2D,
Z3.T1D.T2A.X1F.X2D,
Z4.T1D.T2A.X1F.X2D, Z5.T1D.T2A.X1F.X2D,
Z1.T1E.T2A.X1F.X2D,
Z2.T1E.T2A.X1F.X2D, Z3.T1E.T2A.X1F.X2D,
Z4.T1E.T2A.X1F.X2D,
Z5.T1E.T2A.X1F.X2D, Z1.T1F.T2A.X1F.X2D,
Z2.T1F.T2A.X1F.X2D,
Z3.T1F.T2A.X1F.X2D, Z4.T1F.T2A.X1F.X2D,
Z5.T1F.T2A.X1F.X2D,
Z1.T1A.T2B.X1F.X2D, Z2.T1A.T2B.X1F.X2D,
Z3.T1A.T2B.X1F.X2D,
Z4.T1A.T2B.X1F.X2D, Z5.T1A.T2B.X1F.X2D,
Z1.T1B.T2B.X1F.X2D,
Z2.T1B.T2B.X1F.X2D, Z3.T1B.T2B.X1F.X2D,
Z4.T1B.T2B.X1F.X2D,
Z5.T1B.T2B.X1F.X2D, Z1.T1C.T2B.X1F.X2D,
Z2.T1C.T2B.X1F.X2D,
Z3.T1C.T2B.X1F.X2D, Z4.T1C.T2B.X1F.X2D,
Z5.T1C.T2B.X1F.X2D,
Z1.T1D.T2B.X1F.X2D, Z2.T1D.T2B.X1F.X2D,
Z3.T1D.T2B.X1F.X2D,
Z4.T1D.T2B.X1F.X2D, Z5.T1D.T2B.X1F.X2D,
Z1.T1E.T2B.X1F.X2D,
Z2.T1E.T2B.X1F.X2D, Z3.T1E.T2B.X1F.X2D,
Z4.T1E.T2B.X1F.X2D,
Z5.T1E.T2B.X1F.X2D, Z1.T1F.T2B.X1F.X2D,
Z2.T1F.T2B.X1F.X2D,
Z3.T1F.T2B.X1F.X2D, Z4.T1F.T2B.X1F.X2D,
Z5.T1F.T2B.X1F.X2D,
Z1.T1A.T2C.X1F.X2D, Z2.T1A.T2C.X1F.X2D,
Z3.T1A.T2C.X1F.X2D,
Z4.T1A.T2C.X1F.X2D, Z5.T1A.T2C.X1F.X2D,
Z1.T1B.T2C.X1F.X2D,
Z2.T1B.T2C.X1F.X2D, Z3.T1B.T2C.X1F.X2D,
Z4.T1B.T2C.X1F.X2D,
Z5.T1B.T2C.X1F.X2D, Z1.T1C.T2C.X1F.X2D,
Z2.T1C.T2C.X1F.X2D,
Z3.T1C.T2C.X1F.X2D, Z4.T1C.T2C.X1F.X2D,
Z5.T1C.T2C.X1F.X2D,
Z1.T1D.T2C.X1F.X2D, Z2.T1D.T2C.X1F.X2D,
Z3.T1D.T2C.X1F.X2D,
Z4.T1D.T2C.X1F.X2D, Z5.T1D.T2C.X1F.X2D,
Z1.T1E.T2C.X1F.X2D,
Z2.T1E.T2C.X1F.X2D, Z3.T1E.T2C.X1F.X2D,
Z4.T1E.T2C.X1F.X2D,
Z5.T1E.T2C.X1F.X2D, Z1.T1F.T2C.X1F.X2D,
Z2.T1F.T2C.X1F.X2D,
Z3.T1F.T2C.X1F.X2D, Z4.T1F.T2C.X1F.X2D,
Z5.T1F.T2C.X1F.X2D,
Z1.T1A.T2D.X1F.X2D, Z2.T1A.T2D.X1F.X2D,
Z3.T1A.T2D.X1F.X2D,
Z4.T1A.T2D.X1F.X2D, Z5.T1A.T2D.X1F.X2D,
Z1.T1B.T2D.X1F.X2D,
Z2.T1B.T2D.X1F.X2D, Z3.T1B.T2D.X1F.X2D,
Z4.T1B.T2D.X1F.X2D,
Z5.T1B.T2D.X1F.X2D, Z1.T1C.T2D.X1F.X2D,
Z2.T1C.T2D.X1F.X2D,
Z3.T1C.T2D.X1F.X2D, Z4.T1C.T2D.X1F.X2D,
Z5.T1C.T2D.X1F.X2D,
Z1.T1D.T2D.X1F.X2D, Z2.T1D.T2D.X1F.X2D,
Z3.T1D.T2D.X1F.X2D,
Z4.T1D.T2D.X1F.X2D, Z5.T1D.T2D.X1F.X2D,
Z1.T1E.T2D.X1F.X2D,
Z2.T1E.T2D.X1F.X2D, Z3.T1E.T2D.X1F.X2D,
Z4.T1E.T2D.X1F.X2D,
Z5.T1E.T2D.X1F.X2D, Z1.T1F.T2D.X1F.X2D,
Z2.T1F.T2D.X1F.X2D,
Z3.T1F.T2D.X1F.X2D, Z4.T1F.T2D.X1F.X2D,
Z5.T1F.T2D.X1F.X2D,
Z1.T1A.T2A.X1A.X2E, Z2.T1A.T2A.X1A.X2E,
Z3.T1A.T2A.X1A.X2E,
Z4.T1A.T2A.X1A.X2E, Z5.T1A.T2A.X1A.X2E,
Z1.T1B.T2A.X1A.X2E,
Z2.T1B.T2A.X1A.X2E, Z3.T1B.T2A.X1A.X2E,
Z4.T1B.T2A.X1A.X2E,
Z5.T1B.T2A.X1A.X2E, Z1.T1C.T2A.X1A.X2E,
Z2.T1C.T2A.X1A.X2E,
Z3.T1C.T2A.X1A.X2E, Z4.T1C.T2A.X1A.X2E,
Z5.T1C.T2A.X1A.X2E,
Z1.T1D.T2A.X1A.X2E, Z2.T1D.T2A.X1A.X2E,
Z3.T1D.T2A.X1A.X2E,
Z4.T1D.T2A.X1A.X2E, Z5.T1D.T2A.X1A.X2E,
Z1.T1E.T2A.X1A.X2E,
Z2.T1E.T2A.X1A.X2E, Z3.T1E.T2A.X1A.X2E,
Z4.T1E.T2A.X1A.X2E,
Z5.T1E.T2A.X1A.X2E, Z1.T1F.T2A.X1A.X2E,
Z2.T1F.T2A.X1A.X2E,
Z3.T1F.T2A.X1A.X2E, Z4.T1F.T2A.X1A.X2E,
Z5.T1F.T2A.X1A.X2E,
Z1.T1A.T2B.X1A.X2E, Z2.T1A.T2B.X1A.X2E,
Z3.T1A.T2B.X1A.X2E,
Z4.T1A.T2B.X1A.X2E, Z5.T1A.T2B.X1A.X2E,
Z1.T1B.T2B.X1A.X2E,
Z2.T1B.T2B.X1A.X2E, Z3.T1B.T2B.X1A.X2E,
Z4.T1B.T2B.X1A.X2E,
Z5.T1B.T2B.X1A.X2E, Z1.T1C.T2B.X1A.X2E,
Z2.T1C.T2B.X1A.X2E,
Z3.T1C.T2B.X1A.X2E, Z4.T1C.T2B.X1A.X2E,
Z5.T1C.T2B.X1A.X2E,
Z1.T1D.T2B.X1A.X2E, Z2.T1D.T2B.X1A.X2E,
Z3.T1D.T2B.X1A.X2E,
Z4.T1D.T2B.X1A.X2E, Z5.T1D.T2B.X1A.X2E,
Z1.T1E.T2B.X1A.X2E,
Z2.T1E.T2B.X1A.X2E, Z3.T1E.T2B.X1A.X2E,
Z4.T1E.T2B.X1A.X2E,
Z5.T1E.T2B.X1A.X2E, Z1.T1F.T2B.X1A.X2E,
Z2.T1F.T2B.X1A.X2E,
Z3.T1F.T2B.X1A.X2E, Z4.T1F.T2B.X1A.X2E,
Z5.T1F.T2B.X1A.X2E,
Z1.T1A.T2C.X1A.X2E, Z2.T1A.T2C.X1A.X2E,
Z3.T1A.T2C.X1A.X2E,
Z4.T1A.T2C.X1A.X2E, Z5.T1A.T2C.X1A.X2E,
Z1.T1B.T2C.X1A.X2E,
Z2.T1B.T2C.X1A.X2E, Z3.T1B.T2C.X1A.X2E,
Z4.T1B.T2C.X1A.X2E,
Z5.T1B.T2C.X1A.X2E, Z1.T1C.T2C.X1A.X2E,
Z2.T1C.T2C.X1A.X2E,
Z3.T1C.T2C.X1A.X2E, Z4.T1C.T2C.X1A.X2E,
Z5.T1C.T2C.X1A.X2E,
Z1.T1D.T2C.X1A.X2E, Z2.T1D.T2C.X1A.X2E,
Z3.T1D.T2C.X1A.X2E,
Z4.T1D.T2C.X1A.X2E, Z5.T1D.T2C.X1A.X2E,
Z1.T1E.T2C.X1A.X2E,
Z2.T1E.T2C.X1A.X2E, Z3.T1E.T2C.X1A.X2E,
Z4.T1E.T2C.X1A.X2E,
Z5.T1E.T2C.X1A.X2E, Z1.T1F.T2C.X1A.X2E,
Z2.T1F.T2C.X1A.X2E,
Z3.T1F.T2C.X1A.X2E, Z4.T1F.T2C.X1A.X2E,
Z5.T1F.T2C.X1A.X2E,
Z1.T1A.T2D.X1A.X2E, Z2.T1A.T2D.X1A.X2E,
Z3.T1A.T2D.X1A.X2E,
Z4.T1A.T2D.X1A.X2E, Z5.T1A.T2D.X1A.X2E,
Z1.T1B.T2D.X1A.X2E,
Z2.T1B.T2D.X1A.X2E, Z3.T1B.T2D.X1A.X2E,
Z4.T1B.T2D.X1A.X2E,

TABLE 6-continued

List of Compound Structure of Formula II

Z5.T1B.T2D.X1A.X2E, Z1.T1C.T2D.X1A.X2E, Z2.T1C.T2D.X1A.X2E,
Z3.T1C.T2D.X1A.X2E, Z1.T1C.T2D.X1A.X2E, Z5.T1C.T2D.X1A.X2E,
Z1.T1D.T2D.X1A.X2E, Z2.T1D.T2D.X1A.X2E, Z3.T1D.T2D.X1A.X2E,
Z4.T1D.T2D.X1A.X2E, Z5.T1D.T2D.X1A.X2E, Z1.T1E.T2D.X1A.X2E,
Z2.T1E.T2D.X1A.X2E, Z3.T1E.T2D.X1A.X2E, Z4.T1E.T2D.X1A.X2E,
Z5.T1E.T2D.X1A.X2E, Z1.T1F.T2D.X1A.X2E, Z2.T1F.T2D.X1A.X2E,
Z3.T1F.T2D.X1A.X2E, Z4.T1F.T2D.X1A.X2E, Z5.T1F.T2D.X1A.X2E,
Z1.T1A.T2A.X1B.X2E, Z2.T1A.T2A.X1B.X2E, Z3.T1A.T2A.X1B.X2E,
Z4.T1A.T2A.X1B.X2E, Z5.T1A.T2A.X1B.X2E, Z1.T1B.T2A.X1B.X2E,
Z2.T1B.T2A.X1B.X2E, Z3.T1B.T2A.X1B.X2E, Z4.T1B.T2A.X1B.X2E,
Z5.T1B.T2A.X1B.X2E, Z1.T1C.T2A.X1B.X2E, Z2.T1C.T2A.X1B.X2E,
Z3.T1C.T2A.X1B.X2E, Z4.T1C.T2A.X1B.X2E, Z5.T1C.T2A.X1B.X2E,
Z1.T1D.T2A.X1B.X2E, Z2.T1D.T2A.X1B.X2E, Z3.T1D.T2A.X1B.X2E,
Z4.T1D.T2A.X1B.X2E, Z5.T1D.T2A.X1B.X2E, Z1.T1E.T2A.X1B.X2E,
Z2.T1E.T2A.X1B.X2E, Z3.T1E.T2A.X1B.X2E, Z4.T1E.T2A.X1B.X2E,
Z5.T1E.T2A.X1B.X2E, Z1.T1F.T2A.X1B.X2E, Z2.T1F.T2A.X1B.X2E,
Z3.T1F.T2A.X1B.X2E, Z4.T1F.T2A.X1B.X2E, Z5.T1F.T2A.X1B.X2E,
Z1.T1A.T2B.X1B.X2E, Z2.T1A.T2B.X1B.X2E, Z3.T1A.T2B.X1B.X2E,
Z4.T1A.T2B.X1B.X2E, Z5.T1A.T2B.X1B.X2E, Z1.T1B.T2B.X1B.X2E,
Z2.T1B.T2B.X1B.X2E, Z3.T1B.T2B.X1B.X2E, Z4.T1B.T2B.X1B.X2E,
Z5.T1B.T2B.X1B.X2E, Z1.T1C.T2B.X1B.X2E, Z2.T1C.T2B.X1B.X2E,
Z3.T1C.T2B.X1B.X2E, Z4.T1C.T2B.X1B.X2E, Z5.T1C.T2B.X1B.X2E,
Z1.T1D.T2B.X1B.X2E, Z2.T1D.T2B.X1B.X2E, Z3.T1D.T2B.X1B.X2E,
Z4.T1D.T2B.X1B.X2E, Z5.T1D.T2B.X1B.X2E, Z1.T1E.T2B.X1B.X2E,
Z2.T1E.T2B.X1B.X2E, Z3.T1E.T2B.X1B.X2E, Z4.T1E.T2B.X1B.X2E,
Z5.T1E.T2B.X1B.X2E, Z1.T1F.T2B.X1B.X2E, Z2.T1F.T2B.X1B.X2E,
Z3.T1F.T2B.X1B.X2E, Z4.T1F.T2B.X1B.X2E, Z5.T1F.T2B.X1B.X2E,
Z1.T1A.T2C.X1B.X2E, Z2.T1A.T2C.X1B.X2E, Z3.T1A.T2C.X1B.X2E,
Z4.T1A.T2C.X1B.X2E, Z5.T1A.T2C.X1B.X2E, Z1.T1B.T2C.X1B.X2E,
Z2.T1B.T2C.X1B.X2E, Z3.T1B.T2C.X1B.X2E, Z4.T1B.T2C.X1B.X2E,
Z5.T1B.T2C.X1B.X2E, Z1.T1C.T2C.X1B.X2E, Z2.T1C.T2C.X1B.X2E,
Z3.T1C.T2C.X1B.X2E, Z4.T1C.T2C.X1B.X2E, Z5.T1C.T2C.X1B.X2E,
Z1.T1D.T2C.X1B.X2E, Z2.T1D.T2C.X1B.X2E, Z3.T1D.T2C.X1B.X2E,
Z4.T1D.T2C.X1B.X2E, Z5.T1D.T2C.X1B.X2E, Z1.T1E.T2C.X1B.X2E,
Z2.T1E.T2C.X1B.X2E, Z3.T1E.T2C.X1B.X2E, Z4.T1E.T2C.X1B.X2E,
Z5.T1E.T2C.X1B.X2E, Z1.T1F.T2C.X1B.X2E, Z2.T1F.T2C.X1B.X2E,
Z3.T1F.T2C.X1B.X2E, Z4.T1F.T2C.X1B.X2E, Z5.T1F.T2C.X1B.X2E,
Z1.T1A.T2D.X1B.X2E, Z2.T1A.T2D.X1B.X2E, Z3.T1A.T2D.X1B.X2E,
Z4.T1A.T2D.X1B.X2E, Z5.T1A.T2D.X1B.X2E, Z1.T1B.T2D.X1B.X2E,
Z2.T1B.T2D.X1B.X2E, Z3.T1B.T2D.X1B.X2E, Z4.T1B.T2D.X1B.X2E,
Z5.T1B.T2D.X1B.X2E, Z1.T1C.T2D.X1B.X2E, Z2.T1C.T2D.X1B.X2E,
Z3.T1C.T2D.X1B.X2E, Z4.T1C.T2D.X1B.X2E, Z5.T1C.T2D.X1B.X2E,
Z1.T1D.T2D.X1B.X2E, Z2.T1D.T2D.X1B.X2E, Z3.T1D.T2D.X1B.X2E,
Z4.T1D.T2D.X1B.X2E, Z5.T1D.T2D.X1B.X2E, Z1.T1E.T2D.X1B.X2E,
Z2.T1E.T2D.X1B.X2E, Z3.T1E.T2D.X1B.X2E, Z4.T1E.T2D.X1B.X2E,
Z5.T1E.T2D.X1B.X2E, Z1.T1F.T2D.X1B.X2E, Z2.T1F.T2D.X1B.X2E,
Z3.T1F.T2D.X1B.X2E, Z4.T1F.T2D.X1B.X2E, Z5.T1F.T2D.X1B.X2E,
Z1.T1A.T2A.X1C.X2E, Z2.T1A.T2A.X1C.X2E, Z3.T1A.T2A.X1C.X2E,
Z4.T1A.T2A.X1C.X2E, Z5.T1A.T2A.X1C.X2E, Z1.T1B.T2A.X1C.X2E,
Z2.T1B.T2A.X1C.X2E, Z3.T1B.T2A.X1C.X2E, Z4.T1B.T2A.X1C.X2E,
Z5.T1B.T2A.X1C.X2E, Z1.T1C.T2A.X1C.X2E, Z2.T1C.T2A.X1C.X2E,
Z3.T1C.T2A.X1C.X2E, Z4.T1C.T2A.X1C.X2E, Z5.T1C.T2A.X1C.X2E,
Z1.T1D.T2A.X1C.X2E, Z2.T1D.T2A.X1C.X2E, Z3.T1D.T2A.X1C.X2E,
Z4.T1D.T2A.X1C.X2E, Z5.T1D.T2A.X1C.X2E, Z1.T1E.T2A.X1C.X2E,
Z2.T1E.T2A.X1C.X2E, Z3.T1E.T2A.X1C.X2E, Z4.T1E.T2A.X1C.X2E,
Z5.T1E.T2A.X1C.X2E, Z1.T1F.T2A.X1C.X2E, Z2.T1F.T2A.X1C.X2E,
Z3.T1F.T2A.X1C.X2E, Z4.T1F.T2A.X1C.X2E, Z5.T1F.T2A.X1C.X2E,
Z1.T1A.T2B.X1C.X2E, Z2.T1A.T2B.X1C.X2E, Z3.T1A.T2B.X1C.X2E,
Z4.T1A.T2B.X1C.X2E, Z5.T1A.T2B.X1C.X2E, Z1.T1B.T2B.X1C.X2E,
Z2.T1B.T2B.X1C.X2E, Z3.T1B.T2B.X1C.X2E, Z4.T1B.T2B.X1C.X2E,
Z5.T1B.T2B.X1C.X2E, Z1.T1C.T2B.X1C.X2E, Z2.T1C.T2B.X1C.X2E,
Z3.T1C.T2B.X1C.X2E, Z4.T1C.T2B.X1C.X2E, Z5.T1C.T2B.X1C.X2E,
Z1.T1D.T2B.X1C.X2E, Z2.T1D.T2B.X1C.X2E, Z3.T1D.T2B.X1C.X2E,
Z4.T1D.T2B.X1C.X2E, Z5.T1D.T2B.X1C.X2E, Z1.T1E.T2B.X1C.X2E,
Z2.T1E.T2B.X1C.X2E, Z3.T1E.T2B.X1C.X2E, Z4.T1E.T2B.X1C.X2E,
Z5.T1E.T2B.X1C.X2E, Z1.T1F.T2B.X1C.X2E, Z2.T1F.T2B.X1C.X2E,
Z3.T1F.T2B.X1C.X2E, Z4.T1F.T2B.X1C.X2E, Z5.T1F.T2B.X1C.X2E,
Z1.T1A.T2C.X1C.X2E, Z2.T1A.T2C.X1C.X2E, Z3.T1A.T2C.X1C.X2E,
Z4.T1A.T2C.X1C.X2E, Z5.T1A.T2C.X1C.X2E, Z1.T1B.T2C.X1C.X2E,
Z2.T1B.T2C.X1C.X2E, Z3.T1B.T2C.X1C.X2E, Z4.T1B.T2C.X1C.X2E,
Z5.T1B.T2C.X1C.X2E, Z1.T1C.T2C.X1C.X2E, Z2.T1C.T2C.X1C.X2E,
Z3.T1C.T2C.X1C.X2E, Z4.T1C.T2C.X1C.X2E, Z5.T1C.T2C.X1C.X2E,
Z1.T1D.T2C.X1C.X2E, Z2.T1D.T2C.X1C.X2E, Z3.T1D.T2C.X1C.X2E,
Z4.T1D.T2C.X1C.X2E, Z5.T1D.T2C.X1C.X2E, Z1.T1E.T2C.X1C.X2E,
Z2.T1E.T2C.X1C.X2E, Z3.T1E.T2C.X1C.X2E, Z4.T1E.T2C.X1C.X2E,
Z5.T1E.T2C.X1C.X2E, Z1.T1F.T2C.X1C.X2E, Z2.T1F.T2C.X1C.X2E,
Z3.T1F.T2C.X1C.X2E, Z4.T1F.T2C.X1C.X2E, Z5.T1F.T2C.X1C.X2E,

TABLE 6-continued

List of Compound Structure of Formula II

Z1.T1A.T2D.X1C.X2E, Z2.T1A.T2D.X1C.X2E,
Z3.T1A.T2D.X1C.X2E,
Z4.T1A.T2D.X1C.X2E, Z5.T1A.T2D.X1C.X2E,
Z1.T1B.T2D.X1C.X2E,
Z2.T1B.T2D.X1C.X2E, Z3.T1B.T2D.X1C.X2E,
Z4.T1B.T2D.X1C.X2E,
Z5.T1B.T2D.X1C.X2E, Z1.T1C.T2D.X1C.X2E,
Z2.T1C.T2D.X1C.X2E,
Z3.T1C.T2D.X1C.X2E, Z4.T1C.T2D.X1C.X2E,
Z5.T1C.T2D.X1C.X2E,
Z1.T1D.T2D.X1C.X2E, Z2.T1D.T2D.X1C.X2E,
Z3.T1D.T2D.X1C.X2E,
Z4.T1D.T2D.X1C.X2E, Z5.T1D.T2D.X1C.X2E,
Z1.T1E.T2D.X1C.X2E,
Z2.T1E.T2D.X1C.X2E, Z3.T1E.T2D.X1C.X2E,
Z4.T1E.T2D.X1C.X2E,
Z5.T1E.T2D.X1C.X2E, Z1.T1F.T2D.X1C.X2E,
Z2.T1F.T2D.X1C.X2E,
Z3.T1F.T2D.X1C.X2E, Z4.T1F.T2D.X1C.X2E,
Z5.T1F.T2D.X1C.X2E,
Z1.T1A.T2A.X1D.X2E, Z2.T1A.T2A.X1D.X2E,
Z3.T1A.T2A.X1D.X2E,
Z4.T1A.T2A.X1D.X2E, Z5.T1A.T2A.X1D.X2E,
Z1.T1B.T2A.X1D.X2E,
Z2.T1B.T2A.X1D.X2E, Z3.T1B.T2A.X1D.X2E,
Z4.T1B.T2A.X1D.X2E,
Z5.T1B.T2A.X1D.X2E, Z1.T1C.T2A.X1D.X2E,
Z2.T1C.T2A.X1D.X2E,
Z3.T1C.T2A.X1D.X2E, Z4.T1C.T2A.X1D.X2E,
Z5.T1C.T2A.X1D.X2E,
Z1.T1D.T2A.X1D.X2E, Z2.T1D.T2A.X1D.X2E,
Z3.T1D.T2A.X1D.X2E,
Z4.T1D.T2A.X1D.X2E, Z5.T1D.T2A.X1D.X2E,
Z1.T1E.T2A.X1D.X2E,
Z2.T1E.T2A.X1D.X2E, Z3.T1E.T2A.X1D.X2E,
Z4.T1E.T2A.X1D.X2E,
Z5.T1E.T2A.X1D.X2E, Z1.T1F.T2A.X1D.X2E,
Z2.T1F.T2A.X1D.X2E,
Z3.T1F.T2A.X1D.X2E, Z4.T1F.T2A.X1D.X2E,
Z5.T1F.T2A.X1D.X2E,
Z1.T1A.T2B.X1D.X2E, Z2.T1A.T2B.X1D.X2E,
Z3.T1A.T2B.X1D.X2E,
Z4.T1A.T2B.X1D.X2E, Z5.T1A.T2B.X1D.X2E,
Z1.T1B.T2B.X1D.X2E,
Z2.T1B.T2B.X1D.X2E, Z3.T1B.T2B.X1D.X2E,
Z4.T1B.T2B.X1D.X2E,
Z5.T1B.T2B.X1D.X2E, Z1.T1C.T2B.X1D.X2E,
Z2.T1C.T2B.X1D.X2E,
Z3.T1C.T2B.X1D.X2E, Z4.T1C.T2B.X1D.X2E,
Z5.T1C.T2B.X1D.X2E,
Z1.T1D.T2B.X1D.X2E, Z2.T1D.T2B.X1D.X2E,
Z3.T1D.T2B.X1D.X2E,
Z4.T1D.T2B.X1D.X2E, Z5.T1D.T2B.X1D.X2E,
Z1.T1E.T2B.X1D.X2E,
Z2.T1E.T2B.X1D.X2E, Z3.T1E.T2B.X1D.X2E,
Z4.T1E.T2B.X1D.X2E,
Z5.T1E.T2B.X1D.X2E, Z1.T1F.T2B.X1D.X2E,
Z2.T1F.T2B.X1D.X2E,
Z3.T1F.T2B.X1D.X2E, Z4.T1F.T2B.X1D.X2E,
Z5.T1F.T2B.X1D.X2E,
Z1.T1A.T2C.X1D.X2E, Z2.T1A.T2C.X1D.X2E,
Z3.T1A.T2C.X1D.X2E,
Z4.T1A.T2C.X1D.X2E, Z5.T1A.T2C.X1D.X2E,
Z1.T1B.T2C.X1D.X2E,
Z2.T1B.T2C.X1D.X2E, Z3.T1B.T2C.X1D.X2E,
Z4.T1B.T2C.X1D.X2E,
Z5.T1B.T2C.X1D.X2E, Z1.T1C.T2C.X1D.X2E,
Z2.T1C.T2C.X1D.X2E,
Z3.T1C.T2C.X1D.X2E, Z4.T1C.T2C.X1D.X2E,
Z5.T1C.T2C.X1D.X2E,
Z1.T1D.T2C.X1D.X2E, Z2.T1D.T2C.X1D.X2E,
Z3.T1D.T2C.X1D.X2E,
Z4.T1D.T2C.X1D.X2E, Z5.T1D.T2C.X1D.X2E,
Z1.T1E.T2C.X1D.X2E,
Z2.T1E.T2C.X1D.X2E, Z3.T1E.T2C.X1D.X2E,
Z4.T1E.T2C.X1D.X2E,
Z5.T1E.T2C.X1D.X2E, Z1.T1F.T2C.X1D.X2E,
Z2.T1F.T2C.X1D.X2E,
Z3.T1F.T2C.X1D.X2E, Z4.T1F.T2C.X1D.X2E,
Z5.T1F.T2C.X1D.X2E,
Z1.T1A.T2D.X1D.X2E, Z2.T1A.T2D.X1D.X2E,
Z3.T1A.T2D.X1D.X2E,
Z4.T1A.T2D.X1D.X2E, Z5.T1A.T2D.X1D.X2E,
Z1.T1B.T2D.X1D.X2E,
Z2.T1B.T2D.X1D.X2E, Z3.T1B.T2D.X1D.X2E,
Z4.T1B.T2D.X1D.X2E,
Z5.T1B.T2D.X1D.X2E, Z1.T1C.T2D.X1D.X2E,
Z2.T1C.T2D.X1D.X2E,
Z3.T1C.T2D.X1D.X2E, Z4.T1C.T2D.X1D.X2E,
Z5.T1C.T2D.X1D.X2E,
Z1.T1D.T2D.X1D.X2E, Z2.T1D.T2D.X1D.X2E,
Z3.T1D.T2D.X1D.X2E,
Z4.T1D.T2D.X1D.X2E, Z5.T1D.T2D.X1D.X2E,
Z1.T1E.T2D.X1D.X2E,
Z2.T1E.T2D.X1D.X2E, Z3.T1E.T2D.X1D.X2E,
Z4.T1E.T2D.X1D.X2E,
Z5.T1E.T2D.X1D.X2E, Z1.T1F.T2D.X1D.X2E,
Z2.T1F.T2D.X1D.X2E,
Z3.T1F.T2D.X1D.X2E, Z4.T1F.T2D.X1D.X2E,
Z5.T1F.T2D.X1D.X2E,
Z1.T1A.T2A.X1E.X2E, Z2.T1A.T2A.X1E.X2E,
Z3.T1A.T2A.X1E.X2E,
Z4.T1A.T2A.X1E.X2E, Z5.T1A.T2A.X1E.X2E,
Z1.T1B.T2A.X1E.X2E,
Z2.T1B.T2A.X1E.X2E, Z3.T1B.T2A.X1E.X2E,
Z4.T1B.T2A.X1E.X2E,
Z5.T1B.T2A.X1E.X2E, Z1.T1C.T2A.X1E.X2E,
Z2.T1C.T2A.X1E.X2E,
Z3.T1C.T2A.X1E.X2E, Z4.T1C.T2A.X1E.X2E,
Z5.T1C.T2A.X1E.X2E,
Z1.T1D.T2A.X1E.X2E, Z2.T1D.T2A.X1E.X2E,
Z3.T1D.T2A.X1E.X2E,
Z4.T1D.T2A.X1E.X2E, Z5.T1D.T2A.X1E.X2E,
Z1.T1E.T2A.X1E.X2E,
Z2.T1E.T2A.X1E.X2E, Z3.T1E.T2A.X1E.X2E,
Z4.T1E.T2A.X1E.X2E,
Z5.T1E.T2A.X1E.X2E, Z1.T1F.T2A.X1E.X2E,
Z2.T1F.T2A.X1E.X2E,
Z3.T1F.T2A.X1E.X2E, Z4.T1F.T2A.X1E.X2E,
Z5.T1F.T2A.X1E.X2E,
Z1.T1A.T2B.X1E.X2E, Z2.T1A.T2B.X1E.X2E,
Z3.T1A.T2B.X1E.X2E,
Z4.T1A.T2B.X1E.X2E, Z5.T1A.T2B.X1E.X2E,
Z1.T1B.T2B.X1E.X2E,
Z2.T1B.T2B.X1E.X2E, Z3.T1B.T2B.X1E.X2E,
Z4.T1B.T2B.X1E.X2E,
Z5.T1B.T2B.X1E.X2E, Z1.T1C.T2B.X1E.X2E,
Z2.T1C.T2B.X1E.X2E,
Z3.T1C.T2B.X1E.X2E, Z4.T1C.T2B.X1E.X2E,
Z5.T1C.T2B.X1E.X2E,
Z1.T1D.T2B.X1E.X2E, Z2.T1D.T2B.X1E.X2E,
Z3.T1D.T2B.X1E.X2E,
Z4.T1D.T2B.X1E.X2E, Z5.T1D.T2B.X1E.X2E,
Z1.T1E.T2B.X1E.X2E,
Z2.T1E.T2B.X1E.X2E, Z3.T1E.T2B.X1E.X2E,
Z4.T1E.T2B.X1E.X2E,
Z5.T1E.T2B.X1E.X2E, Z1.T1F.T2B.X1E.X2E,
Z2.T1F.T2B.X1E.X2E,
Z3.T1F.T2B.X1E.X2E, Z4.T1F.T2B.X1E.X2E,
Z5.T1F.T2B.X1E.X2E,
Z1.T1A.T2C.X1E.X2E, Z2.T1A.T2C.X1E.X2E,
Z3.T1A.T2C.X1E.X2E,
Z4.T1A.T2C.X1E.X2E, Z5.T1A.T2C.X1E.X2E,
Z1.T1B.T2C.X1E.X2E,
Z2.T1B.T2C.X1E.X2E, Z3.T1B.T2C.X1E.X2E,
Z4.T1B.T2C.X1E.X2E,
Z5.T1B.T2C.X1E.X2E, Z1.T1C.T2C.X1E.X2E,
Z2.T1C.T2C.X1E.X2E,
Z3.T1C.T2C.X1E.X2E, Z4.T1C.T2C.X1E.X2E,
Z5.T1C.T2C.X1E.X2E,
Z1.T1D.T2C.X1E.X2E, Z2.T1D.T2C.X1E.X2E,
Z3.T1D.T2C.X1E.X2E,
Z4.T1D.T2C.X1E.X2E, Z5.T1D.T2C.X1E.X2E,
Z1.T1E.T2C.X1E.X2E,

TABLE 6-continued

List of Compound Structure of Formula II

Z2.T1E.T2C.X1E.X2E, Z3.T1E.T2C.X1E.X2E,
Z4.T1E.T2C.X1E.X2E,
Z5.T1E.T2C.X1E.X2E, Z1.T1F.T2C.X1E.X2E,
Z2.T1F.T2C.X1E.X2E,
Z3.T1F.T2C.X1E.X2E, Z4.T1F.T2C.X1E.X2E,
Z5.T1F.T2C.X1E.X2E,
Z1.T1A.T2D.X1E.X2E, Z2.T1A.T2D.X1E.X2E,
Z3.T1A.T2D.X1E.X2E,
Z4.T1A.T2D.X1E.X2E, Z5.T1A.T2D.X1E.X2E,
Z1.T1B.T2D.X1E.X2E,
Z2.T1B.T2D.X1E.X2E, Z3.T1B.T2D.X1E.X2E,
Z4.T1B.T2D.X1E.X2E,
Z5.T1B.T2D.X1E.X2E, Z1.T1C.T2D.X1E.X2E,
Z2.T1C.T2D.X1E.X2E,
Z3.T1C.T2D.X1E.X2E, Z4.T1C.T2D.X1E.X2E,
Z5.T1C.T2D.X1E.X2E,
Z1.T1D.T2D.X1E.X2E, Z2.T1D.T2D.X1E.X2E,
Z3.T1D.T2D.X1E.X2E,
Z4.T1D.T2D.X1E.X2E, Z5.T1D.T2D.X1E.X2E,
Z1.T1E.T2D.X1E.X2E,
Z2.T1E.T2D.X1E.X2E, Z3.T1E.T2D.X1E.X2E,
Z4.T1E.T2D.X1E.X2E,
Z5.T1E.T2D.X1E.X2E, Z1.T1F.T2D.X1E.X2E,
Z2.T1F.T2D.X1E.X2E,
Z3.T1F.T2D.X1E.X2E, Z4.T1F.T2D.X1E.X2E,
Z5.T1F.T2D.X1E.X2E,
Z1.T1A.T2A.X1F.X2E, Z2.T1A.T2A.X1F.X2E,
Z3.T1A.T2A.X1F.X2E,
Z4.T1A.T2A.X1F.X2E, Z5.T1A.T2A.X1F.X2E,
Z1.T1B.T2A.X1F.X2E,
Z2.T1B.T2A.X1F.X2E, Z3.T1B.T2A.X1F.X2E,
Z4.T1B.T2A.X1F.X2E,
Z5.T1B.T2A.X1F.X2E, Z1.T1C.T2A.X1F.X2E,
Z2.T1C.T2A.X1F.X2E,
Z3.T1C.T2A.X1F.X2E, Z4.T1C.T2A.X1F.X2E,
Z5.T1C.T2A.X1F.X2E,
Z1.T1D.T2A.X1F.X2E, Z2.T1D.T2A.X1F.X2E,
Z3.T1D.T2A.X1F.X2E,
Z4.T1D.T2A.X1F.X2E, Z5.T1D.T2A.X1F.X2E,
Z1.T1E.T2A.X1F.X2E,
Z2.T1E.T2A.X1F.X2E, Z3.T1E.T2A.X1F.X2E,
Z4.T1E.T2A.X1F.X2E,
Z5.T1E.T2A.X1F.X2E, Z1.T1F.T2A.X1F.X2E,
Z2.T1F.T2A.X1F.X2E,
Z3.T1F.T2A.X1F.X2E, Z4.T1F.T2A.X1F.X2E,
Z5.T1F.T2A.X1F.X2E,
Z1.T1A.T2B.X1F.X2E, Z2.T1A.T2B.X1F.X2E,
Z3.T1A.T2B.X1F.X2E,
Z4.T1A.T2B.X1F.X2E, Z5.T1A.T2B.X1F.X2E,
Z1.T1B.T2B.X1F.X2E,
Z2.T1B.T2B.X1F.X2E, Z3.T1B.T2B.X1F.X2E,
Z4.T1B.T2B.X1F.X2E,
Z5.T1B.T2B.X1F.X2E, Z1.T1C.T2B.X1F.X2E,
Z2.T1C.T2B.X1F.X2E,
Z3.T1C.T2B.X1F.X2E, Z4.T1C.T2B.X1F.X2E,
Z5.T1C.T2B.X1F.X2E,
Z1.T1D.T2B.X1F.X2E, Z2.T1D.T2B.X1F.X2E,
Z3.T1D.T2B.X1F.X2E,
Z4.T1D.T2B.X1F.X2E, Z5.T1D.T2B.X1F.X2E,
Z1.T1E.T2B.X1F.X2E,
Z2.T1E.T2B.X1F.X2E, Z3.T1E.T2B.X1F.X2E,
Z4.T1E.T2B.X1F.X2E,
Z5.T1E.T2B.X1F.X2E, Z1.T1F.T2B.X1F.X2E,
Z2.T1F.T2B.X1F.X2E,
Z3.T1F.T2B.X1F.X2E, Z4.T1F.T2B.X1F.X2E,
Z5.T1F.T2B.X1F.X2E,
Z1.T1A.T2C.X1F.X2E, Z2.T1A.T2C.X1F.X2E,
Z3.T1A.T2C.X1F.X2E,
Z4.T1A.T2C.X1F.X2E, Z5.T1A.T2C.X1F.X2E,
Z1.T1B.T2C.X1F.X2E,
Z2.T1B.T2C.X1F.X2E, Z3.T1B.T2C.X1F.X2E,
Z4.T1B.T2C.X1F.X2E,
Z5.T1B.T2C.X1F.X2E, Z1.T1C.T2C.X1F.X2E,
Z2.T1C.T2C.X1F.X2E,
Z3.T1C.T2C.X1F.X2E, Z4.T1C.T2C.X1F.X2E,
Z5.T1C.T2C.X1F.X2E,
Z1.T1D.T2C.X1F.X2E, Z2.T1D.T2C.X1F.X2E,
Z3.T1D.T2C.X1F.X2E,
Z4.T1D.T2C.X1F.X2E, Z5.T1D.T2C.X1F.X2E,
Z1.T1E.T2C.X1F.X2E,
Z2.T1E.T2C.X1F.X2E, Z3.T1E.T2C.X1F.X2E,
Z4.T1E.T2C.X1F.X2E,
Z5.T1E.T2C.X1F.X2E, Z1.T1F.T2C.X1F.X2E,
Z2.T1F.T2C.X1F.X2E,
Z3.T1F.T2C.X1F.X2E, Z4.T1F.T2C.X1F.X2E,
Z5.T1F.T2C.X1F.X2E,
Z1.T1A.T2D.X1F.X2E, Z2.T1A.T2D.X1F.X2E,
Z3.T1A.T2D.X1F.X2E,
Z4.T1A.T2D.X1F.X2E, Z5.T1A.T2D.X1F.X2E,
Z1.T1B.T2D.X1F.X2E,
Z2.T1B.T2D.X1F.X2E, Z3.T1B.T2D.X1F.X2E,
Z4.T1B.T2D.X1F.X2E,
Z5.T1B.T2D.X1F.X2E, Z1.T1C.T2D.X1F.X2E,
Z2.T1C.T2D.X1F.X2E,
Z3.T1C.T2D.X1F.X2E, Z4.T1C.T2D.X1F.X2E,
Z5.T1C.T2D.X1F.X2E,
Z1.T1D.T2D.X1F.X2E, Z2.T1D.T2D.X1F.X2E,
Z3.T1D.T2D.X1F.X2E,
Z4.T1D.T2D.X1F.X2E, Z5.T1D.T2D.X1F.X2E,
Z1.T1E.T2D.X1F.X2E,
Z2.T1E.T2D.X1F.X2E, Z3.T1E.T2D.X1F.X2E,
Z4.T1E.T2D.X1F.X2E,
Z5.T1E.T2D.X1F.X2E, Z1.T1F.T2D.X1F.X2E,
Z2.T1F.T2D.X1F.X2E,
Z3.T1F.T2D.X1F.X2E, Z4.T1F.T2D.X1F.X2E,
Z5.T1F.T2D.X1F.X2E,
Z1.T1A.T2A.X1A.X2F, Z2.T1A.T2A.X1A.X2F,
Z3.T1A.T2A.X1A.X2F,
Z4.T1A.T2A.X1A.X2F, Z5.T1A.T2A.X1A.X2F,
Z1.T1B.T2A.X1A.X2F,
Z2.T1B.T2A.X1A.X2F, Z3.T1B.T2A.X1A.X2F,
Z4.T1B.T2A.X1A.X2F,
Z5.T1B.T2A.X1A.X2F, Z1.T1C.T2A.X1A.X2F,
Z2.T1C.T2A.X1A.X2F,
Z3.T1C.T2A.X1A.X2F, Z4.T1C.T2A.X1A.X2F,
Z5.T1C.T2A.X1A.X2F,
Z1.T1D.T2A.X1A.X2F, Z2.T1D.T2A.X1A.X2F,
Z3.T1D.T2A.X1A.X2F,
Z4.T1D.T2A.X1A.X2F, Z5.T1D.T2A.X1A.X2F,
Z1.T1E.T2A.X1A.X2F,
Z2.T1E.T2A.X1A.X2F, Z3.T1E.T2A.X1A.X2F,
Z4.T1E.T2A.X1A.X2F,
Z5.T1E.T2A.X1A.X2F, Z1.T1F.T2A.X1A.X2F,
Z2.T1F.T2A.X1A.X2F,
Z3.T1F.T2A.X1A.X2F, Z4.T1F.T2A.X1A.X2F,
Z5.T1F.T2A.X1A.X2F,
Z1.T1A.T2B.X1A.X2F, Z2.T1A.T2B.X1A.X2F,
Z3.T1A.T2B.X1A.X2F,
Z4.T1A.T2B.X1A.X2F, Z5.T1A.T2B.X1A.X2F,
Z1.T1B.T2B.X1A.X2F,
Z2.T1B.T2B.X1A.X2F, Z3.T1B.T2B.X1A.X2F,
Z4.T1B.T2B.X1A.X2F,
Z5.T1B.T2B.X1A.X2F, Z1.T1C.T2B.X1A.X2F,
Z2.T1C.T2B.X1A.X2F,
Z3.T1C.T2B.X1A.X2F, Z4.T1C.T2B.X1A.X2F,
Z5.T1C.T2B.X1A.X2F,
Z1.T1D.T2B.X1A.X2F, Z2.T1D.T2B.X1A.X2F,
Z3.T1D.T2B.X1A.X2F,
Z4.T1D.T2B.X1A.X2F, Z5.T1D.T2B.X1A.X2F,
Z1.T1E.T2B.X1A.X2F,
Z2.T1E.T2B.X1A.X2F, Z3.T1E.T2B.X1A.X2F,
Z4.T1E.T2B.X1A.X2F,
Z5.T1E.T2B.X1A.X2F, Z1.T1F.T2B.X1A.X2F,
Z2.T1F.T2B.X1A.X2F,
Z3.T1F.T2B.X1A.X2F, Z4.T1F.T2B.X1A.X2F,
Z5.T1F.T2B.X1A.X2F,
Z1.T1A.T2C.X1A.X2F, Z2.T1A.T2C.X1A.X2F,
Z3.T1A.T2C.X1A.X2F,
Z4.T1A.T2C.X1A.X2F, Z5.T1A.T2C.X1A.X2F,
Z1.T1B.T2C.X1A.X2F,
Z2.T1B.T2C.X1A.X2F, Z3.T1B.T2C.X1A.X2F,
Z4.T1B.T2C.X1A.X2F,
Z5.T1B.T2C.X1A.X2F, Z1.T1C.T2C.X1A.X2F,
Z2.T1C.T2C.X1A.X2F,

TABLE 6-continued

List of Compound Structure of Formula II

Z3.T1C.T2C.X1A.X2F, Z4.T1C.T2C.X1A.X2F, Z5.T1C.T2C.X1A.X2F,
Z1.T1D.T2C.X1A.X2F, Z2.T1D.T2C.X1A.X2F, Z3.T1D.T2C.X1A.X2F,
Z4.T1D.T2C.X1A.X2F, Z5.T1D.T2C.X1A.X2F, Z1.T1E.T2C.X1A.X2F,
Z2.T1E.T2C.X1A.X2F, Z3.T1E.T2C.X1A.X2F, Z4.T1E.T2C.X1A.X2F,
Z5.T1E.T2C.X1A.X2F, Z1.T1F.T2C.X1A.X2F, Z2.T1F.T2C.X1A.X2F,
Z3.T1F.T2C.X1A.X2F, Z4.T1F.T2C.X1A.X2F, Z5.T1F.T2C.X1A.X2F,
Z1.T1A.T2D.X1A.X2F, Z2.T1A.T2D.X1A.X2F, Z3.T1A.T2D.X1A.X2F,
Z4.T1A.T2D.X1A.X2F, Z5.T1A.T2D.X1A.X2F, Z1.T1B.T2D.X1A.X2F,
Z2.T1B.T2D.X1A.X2F, Z3.T1B.T2D.X1A.X2F, Z4.T1B.T2D.X1A.X2F,
Z5.T1B.T2D.X1A.X2F, Z1.T1C.T2D.X1A.X2F, Z2.T1C.T2D.X1A.X2F,
Z3.T1C.T2D.X1A.X2F, Z4.T1C.T2D.X1A.X2F, Z5.T1C.T2D.X1A.X2F,
Z1.T1D.T2D.X1A.X2F, Z2.T1D.T2D.X1A.X2F, Z3.T1D.T2D.X1A.X2F,
Z4.T1D.T2D.X1A.X2F, Z5.T1D.T2D.X1A.X2F, Z1.T1E.T2D.X1A.X2F,
Z2.T1E.T2D.X1A.X2F, Z3.T1E.T2D.X1A.X2F, Z4.T1E.T2D.X1A.X2F,
Z5.T1E.T2D.X1A.X2F, Z1.T1F.T2D.X1A.X2F, Z2.T1F.T2D.X1A.X2F,
Z3.T1F.T2D.X1A.X2F, Z4.T1F.T2D.X1A.X2F, Z5.T1F.T2D.X1A.X2F,
Z1.T1A.T2A.X1B.X2F, Z2.T1A.T2A.X1B.X2F, Z3.T1A.T2A.X1B.X2F,
Z4.T1A.T2A.X1B.X2F, Z5.T1A.T2A.X1B.X2F, Z1.T1B.T2A.X1B.X2F,
Z2.T1B.T2A.X1B.X2F, Z3.T1B.T2A.X1B.X2F, Z4.T1B.T2A.X1B.X2F,
Z5.T1B.T2A.X1B.X2F, Z1.T1C.T2A.X1B.X2F, Z2.T1C.T2A.X1B.X2F,
Z3.T1C.T2A.X1B.X2F, Z4.T1C.T2A.X1B.X2F, Z5.T1C.T2A.X1B.X2F,
Z1.T1D.T2A.X1B.X2F, Z2.T1D.T2A.X1B.X2F, Z3.T1D.T2A.X1B.X2F,
Z4.T1D.T2A.X1B.X2F, Z5.T1D.T2A.X1B.X2F, Z1.T1E.T2A.X1B.X2F,
Z2.T1E.T2A.X1B.X2F, Z3.T1E.T2A.X1B.X2F, Z4.T1E.T2A.X1B.X2F,
Z5.T1E.T2A.X1B.X2F, Z1.T1F.T2A.X1B.X2F, Z2.T1F.T2A.X1B.X2F,
Z3.T1F.T2A.X1B.X2F, Z4.T1F.T2A.X1B.X2F, Z5.T1F.T2A.X1B.X2F,
Z1.T1A.T2B.X1B.X2F, Z2.T1A.T2B.X1B.X2F, Z3.T1A.T2B.X1B.X2F,
Z4.T1A.T2B.X1B.X2F, Z5.T1A.T2B.X1B.X2F, Z1.T1B.T2B.X1B.X2F,
Z2.T1B.T2B.X1B.X2F, Z3.T1B.T2B.X1B.X2F, Z4.T1B.T2B.X1B.X2F,
Z5.T1B.T2B.X1B.X2F, Z1.T1C.T2B.X1B.X2F, Z2.T1C.T2B.X1B.X2F,
Z3.T1C.T2B.X1B.X2F, Z4.T1C.T2B.X1B.X2F, Z5.T1C.T2B.X1B.X2F,
Z1.T1D.T2B.X1B.X2F, Z2.T1D.T2B.X1B.X2F, Z3.T1D.T2B.X1B.X2F,
Z4.T1D.T2B.X1B.X2F, Z5.T1D.T2B.X1B.X2F, Z1.T1E.T2B.X1B.X2F,
Z2.T1E.T2B.X1B.X2F, Z3.T1E.T2B.X1B.X2F, Z4.T1E.T2B.X1B.X2F,
Z5.T1E.T2B.X1B.X2F, Z1.T1F.T2B.X1B.X2F, Z2.T1F.T2B.X1B.X2F,
Z3.T1F.T2B.X1B.X2F, Z4.T1F.T2B.X1B.X2F, Z5.T1F.T2B.X1B.X2F,
Z1.T1A.T2C.X1B.X2F, Z2.T1A.T2C.X1B.X2F, Z3.T1A.T2C.X1B.X2F,
Z4.T1A.T2C.X1B.X2F, Z5.T1A.T2C.X1B.X2F, Z1.T1B.T2C.X1B.X2F,
Z2.T1B.T2C.X1B.X2F, Z3.T1B.T2C.X1B.X2F, Z4.T1B.T2C.X1B.X2F,
Z5.T1B.T2C.X1B.X2F, Z1.T1C.T2C.X1B.X2F, Z2.T1C.T2C.X1B.X2F,
Z3.T1C.T2C.X1B.X2F, Z4.T1C.T2C.X1B.X2F, Z5.T1C.T2C.X1B.X2F,
Z1.T1D.T2C.X1B.X2F, Z2.T1D.T2C.X1B.X2F, Z3.T1D.T2C.X1B.X2F,
Z4.T1D.T2C.X1B.X2F, Z5.T1D.T2C.X1B.X2F, Z1.T1E.T2C.X1B.X2F,
Z2.T1E.T2C.X1B.X2F, Z3.T1E.T2C.X1B.X2F, Z4.T1E.T2C.X1B.X2F,
Z5.T1E.T2C.X1B.X2F, Z1.T1F.T2C.X1B.X2F, Z2.T1F.T2C.X1B.X2F,
Z3.T1F.T2C.X1B.X2F, Z4.T1F.T2C.X1B.X2F, Z5.T1F.T2C.X1B.X2F,
Z1.T1A.T2D.X1B.X2F, Z2.T1A.T2D.X1B.X2F, Z3.T1A.T2D.X1B.X2F,
Z4.T1A.T2D.X1B.X2F, Z5.T1A.T2D.X1B.X2F, Z1.T1B.T2D.X1B.X2F,
Z2.T1B.T2D.X1B.X2F, Z3.T1B.T2D.X1B.X2F, Z4.T1B.T2D.X1B.X2F,
Z5.T1B.T2D.X1B.X2F, Z1.T1C.T2D.X1B.X2F, Z2.T1C.T2D.X1B.X2F,
Z3.T1C.T2D.X1B.X2F, Z4.T1C.T2D.X1B.X2F, Z5.T1C.T2D.X1B.X2F,
Z1.T1D.T2D.X1B.X2F, Z2.T1D.T2D.X1B.X2F, Z3.T1D.T2D.X1B.X2F,
Z4.T1D.T2D.X1B.X2F, Z5.T1D.T2D.X1B.X2F, Z1.T1E.T2D.X1B.X2F,
Z2.T1E.T2D.X1B.X2F, Z3.T1E.T2D.X1B.X2F, Z4.T1E.T2D.X1B.X2F,
Z5.T1E.T2D.X1B.X2F, Z1.T1F.T2D.X1B.X2F, Z2.T1F.T2D.X1B.X2F,
Z3.T1F.T2D.X1B.X2F, Z4.T1F.T2D.X1B.X2F, Z5.T1F.T2D.X1B.X2F,
Z1.T1A.T2A.X1C.X2F, Z2.T1A.T2A.X1C.X2F, Z3.T1A.T2A.X1C.X2F,
Z4.T1A.T2A.X1C.X2F, Z5.T1A.T2A.X1C.X2F, Z1.T1B.T2A.X1C.X2F,
Z2.T1B.T2A.X1C.X2F, Z3.T1B.T2A.X1C.X2F, Z4.T1B.T2A.X1C.X2F,
Z5.T1B.T2A.X1C.X2F, Z1.T1C.T2A.X1C.X2F, Z2.T1C.T2A.X1C.X2F,
Z3.T1C.T2A.X1C.X2F, Z4.T1C.T2A.X1C.X2F, Z5.T1C.T2A.X1C.X2F,
Z1.T1D.T2A.X1C.X2F, Z2.T1D.T2A.X1C.X2F, Z3.T1D.T2A.X1C.X2F,
Z4.T1D.T2A.X1C.X2F, Z5.T1D.T2A.X1C.X2F, Z1.T1E.T2A.X1C.X2F,
Z2.T1E.T2A.X1C.X2F, Z3.T1E.T2A.X1C.X2F, Z4.T1E.T2A.X1C.X2F,
Z5.T1E.T2A.X1C.X2F, Z1.T1F.T2A.X1C.X2F, Z2.T1F.T2A.X1C.X2F,
Z3.T1F.T2A.X1C.X2F, Z4.T1F.T2A.X1C.X2F, Z5.T1F.T2A.X1C.X2F,
Z1.T1A.T2B.X1C.X2F, Z2.T1A.T2B.X1C.X2F, Z3.T1A.T2B.X1C.X2F,
Z4.T1A.T2B.X1C.X2F, Z5.T1A.T2B.X1C.X2F, Z1.T1B.T2B.X1C.X2F,
Z2.T1B.T2B.X1C.X2F, Z3.T1B.T2B.X1C.X2F, Z4.T1B.T2B.X1C.X2F,
Z5.T1B.T2B.X1C.X2F, Z1.T1C.T2B.X1C.X2F, Z2.T1C.T2B.X1C.X2F,
Z3.T1C.T2B.X1C.X2F, Z4.T1C.T2B.X1C.X2F, Z5.T1C.T2B.X1C.X2F,
Z1.T1D.T2B.X1C.X2F, Z2.T1D.T2B.X1C.X2F, Z3.T1D.T2B.X1C.X2F,
Z4.T1D.T2B.X1C.X2F, Z5.T1D.T2B.X1C.X2F, Z1.T1E.T2B.X1C.X2F,
Z2.T1E.T2B.X1C.X2F, Z3.T1E.T2B.X1C.X2F, Z4.T1E.T2B.X1C.X2F,
Z5.T1E.T2B.X1C.X2F, Z1.T1F.T2B.X1C.X2F, Z2.T1F.T2B.X1C.X2F,
Z3.T1F.T2B.X1C.X2F, Z4.T1F.T2B.X1C.X2F, Z5.T1F.T2B.X1C.X2F,
Z1.T1A.T2C.X1C.X2F, Z2.T1A.T2C.X1C.X2F, Z3.T1A.T2C.X1C.X2F,

TABLE 6-continued

List of Compound Structure of Formula II

Z4.T1A.T2C.X1C.X2F, Z5.T1A.T2C.X1C.X2F,
Z1.T1B.T2C.X1C.X2F,
Z2.T1B.T2C.X1C.X2F, Z3.T1B.T2C.X1C.X2F,
Z4.T1B.T2C.X1C.X2F,
Z5.T1B.T2C.X1C.X2F, Z1.T1C.T2C.X1C.X2F,
Z2.T1C.T2C.X1C.X2F,
Z3.T1C.T2C.X1C.X2F, Z4.T1C.T2C.X1C.X2F,
Z5.T1C.T2C.X1C.X2F,
Z1.T1D.T2C.X1C.X2F, Z2.T1D.T2C.X1C.X2F,
Z3.T1D.T2C.X1C.X2F,
Z4.T1D.T2C.X1C.X2F, Z5.T1D.T2C.X1C.X2F,
Z1.T1E.T2C.X1C.X2F,
Z2.T1E.T2C.X1C.X2F, Z3.T1E.T2C.X1C.X2F,
Z4.T1E.T2C.X1C.X2F,
Z5.T1E.T2C.X1C.X2F, Z1.T1F.T2C.X1C.X2F,
Z2.T1F.T2C.X1C.X2F,
Z3.T1F.T2C.X1C.X2F, Z4.T1F.T2C.X1C.X2F,
Z5.T1F.T2C.X1C.X2F,
Z1.T1A.T2D.X1C.X2F, Z2.T1A.T2D.X1C.X2F,
Z3.T1A.T2D.X1C.X2F,
Z4.T1A.T2D.X1C.X2F, Z5.T1A.T2D.X1C.X2F,
Z1.T1B.T2D.X1C.X2F,
Z2.T1B.T2D.X1C.X2F, Z3.T1B.T2D.X1C.X2F,
Z4.T1B.T2D.X1C.X2F,
Z5.T1B.T2D.X1C.X2F, Z1.T1C.T2D.X1C.X2F,
Z2.T1C.T2D.X1C.X2F,
Z3.T1C.T2D.X1C.X2F, Z4.T1C.T2D.X1C.X2F,
Z5.T1C.T2D.X1C.X2F,
Z1.T1D.T2D.X1C.X2F, Z2.T1D.T2D.X1C.X2F,
Z3.T1D.T2D.X1C.X2F,
Z4.T1D.T2D.X1C.X2F, Z5.T1D.T2D.X1C.X2F,
Z1.T1E.T2D.X1C.X2F,
Z2.T1E.T2D.X1C.X2F, Z3.T1E.T2D.X1C.X2F,
Z4.T1E.T2D.X1C.X2F,
Z5.T1E.T2D.X1C.X2F, Z1.T1F.T2D.X1C.X2F,
Z2.T1F.T2D.X1C.X2F,
Z3.T1F.T2D.X1C.X2F, Z4.T1F.T2D.X1C.X2F,
Z5.T1F.T2D.X1C.X2F,
Z1.T1A.T2A.X1D.X2F, Z2.T1A.T2A.X1D.X2F,
Z3.T1A.T2A.X1D.X2F,
Z4.T1A.T2A.X1D.X2F, Z5.T1A.T2A.X1D.X2F,
Z1.T1B.T2A.X1D.X2F,
Z2.T1B.T2A.X1D.X2F, Z3.T1B.T2A.X1D.X2F,
Z4.T1B.T2A.X1D.X2F,
Z5.T1B.T2A.X1D.X2F, Z1.T1C.T2A.X1D.X2F,
Z2.T1C.T2A.X1D.X2F,
Z3.T1C.T2A.X1D.X2F, Z4.T1C.T2A.X1D.X2F,
Z5.T1C.T2A.X1D.X2F,
Z1.T1D.T2A.X1D.X2F, Z2.T1D.T2A.X1D.X2F,
Z3.T1D.T2A.X1D.X2F,
Z4.T1D.T2A.X1D.X2F, Z5.T1D.T2A.X1D.X2F,
Z1.T1E.T2A.X1D.X2F,
Z2.T1E.T2A.X1D.X2F, Z3.T1E.T2A.X1D.X2F,
Z4.T1E.T2A.X1D.X2F,
Z5.T1E.T2A.X1D.X2F, Z1.T1F.T2A.X1D.X2F,
Z2.T1F.T2A.X1D.X2F,
Z3.T1F.T2A.X1D.X2F, Z4.T1F.T2A.X1D.X2F,
Z5.T1F.T2A.X1D.X2F,
Z1.T1A.T2B.X1D.X2F, Z2.T1A.T2B.X1D.X2F,
Z3.T1A.T2B.X1D.X2F,
Z4.T1A.T2B.X1D.X2F, Z5.T1A.T2B.X1D.X2F,
Z1.T1B.T2B.X1D.X2F,
Z2.T1B.T2B.X1D.X2F, Z3.T1B.T2B.X1D.X2F,
Z4.T1B.T2B.X1D.X2F,
Z5.T1B.T2B.X1D.X2F, Z1.T1C.T2B.X1D.X2F,
Z2.T1C.T2B.X1D.X2F,
Z3.T1C.T2B.X1D.X2F, Z4.T1C.T2B.X1D.X2F,
Z5.T1C.T2B.X1D.X2F,
Z1.T1D.T2B.X1D.X2F, Z2.T1D.T2B.X1D.X2F,
Z3.T1D.T2B.X1D.X2F,
Z4.T1D.T2B.X1D.X2F, Z5.T1D.T2B.X1D.X2F,
Z1.T1E.T2B.X1D.X2F,
Z2.T1E.T2B.X1D.X2F, Z3.T1E.T2B.X1D.X2F,
Z4.T1E.T2B.X1D.X2F,
Z5.T1E.T2B.X1D.X2F, Z1.T1F.T2B.X1D.X2F,
Z2.T1F.T2B.X1D.X2F,
Z3.T1F.T2B.X1D.X2F, Z4.T1F.T2B.X1D.X2F,
Z5.T1F.T2B.X1D.X2F,
Z1.T1A.T2C.X1D.X2F, Z2.T1A.T2C.X1D.X2F,
Z3.T1A.T2C.X1D.X2F,
Z4.T1A.T2C.X1D.X2F, Z5.T1A.T2C.X1D.X2F,
Z1.T1B.T2C.X1D.X2F,
Z2.T1B.T2C.X1D.X2F, Z3.T1B.T2C.X1D.X2F,
Z4.T1B.T2C.X1D.X2F,
Z5.T1B.T2C.X1D.X2F, Z1.T1C.T2C.X1D.X2F,
Z2.T1C.T2C.X1D.X2F,
Z3.T1C.T2C.X1D.X2F, Z4.T1C.T2C.X1D.X2F,
Z5.T1C.T2C.X1D.X2F,
Z1.T1D.T2C.X1D.X2F, Z2.T1D.T2C.X1D.X2F,
Z3.T1D.T2C.X1D.X2F,
Z4.T1D.T2C.X1D.X2F, Z5.T1D.T2C.X1D.X2F,
Z1.T1E.T2C.X1D.X2F,
Z2.T1E.T2C.X1D.X2F, Z3.T1E.T2C.X1D.X2F,
Z4.T1E.T2C.X1D.X2F,
Z5.T1E.T2C.X1D.X2F, Z1.T1F.T2C.X1D.X2F,
Z2.T1F.T2C.X1D.X2F,
Z3.T1F.T2C.X1D.X2F, Z4.T1F.T2C.X1D.X2F,
Z5.T1F.T2C.X1D.X2F,
Z1.T1A.T2D.X1D.X2F, Z2.T1A.T2D.X1D.X2F,
Z3.T1A.T2D.X1D.X2F,
Z4.T1A.T2D.X1D.X2F, Z5.T1A.T2D.X1D.X2F,
Z1.T1B.T2D.X1D.X2F,
Z2.T1B.T2D.X1D.X2F, Z3.T1B.T2D.X1D.X2F,
Z4.T1B.T2D.X1D.X2F,
Z5.T1B.T2D.X1D.X2F, Z1.T1C.T2D.X1D.X2F,
Z2.T1C.T2D.X1D.X2F,
Z3.T1C.T2D.X1D.X2F, Z4.T1C.T2D.X1D.X2F,
Z5.T1C.T2D.X1D.X2F,
Z1.T1D.T2D.X1D.X2F, Z2.T1D.T2D.X1D.X2F,
Z3.T1D.T2D.X1D.X2F,
Z4.T1D.T2D.X1D.X2F, Z5.T1D.T2D.X1D.X2F,
Z1.T1E.T2D.X1D.X2F,
Z2.T1E.T2D.X1D.X2F, Z3.T1E.T2D.X1D.X2F,
Z4.T1E.T2D.X1D.X2F,
Z5.T1E.T2D.X1D.X2F, Z1.T1F.T2D.X1D.X2F,
Z2.T1F.T2D.X1D.X2F,
Z3.T1F.T2D.X1D.X2F, Z4.T1F.T2D.X1D.X2F,
Z5.T1F.T2D.X1D.X2F,
Z1.T1A.T2A.X1E.X2F, Z2.T1A.T2A.X1E.X2F,
Z3.T1A.T2A.X1E.X2F,
Z4.T1A.T2A.X1E.X2F, Z5.T1A.T2A.X1E.X2F,
Z1.T1B.T2A.X1E.X2F,
Z2.T1B.T2A.X1E.X2F, Z3.T1B.T2A.X1E.X2F,
Z4.T1B.T2A.X1E.X2F,
Z5.T1B.T2A.X1E.X2F, Z1.T1C.T2A.X1E.X2F,
Z2.T1C.T2A.X1E.X2F,
Z3.T1C.T2A.X1E.X2F, Z4.T1C.T2A.X1E.X2F,
Z5.T1C.T2A.X1E.X2F,
Z1.T1D.T2A.X1E.X2F, Z2.T1D.T2A.X1E.X2F,
Z3.T1D.T2A.X1E.X2F,
Z4.T1D.T2A.X1E.X2F, Z5.T1D.T2A.X1E.X2F,
Z1.T1E.T2A.X1E.X2F,
Z2.T1E.T2A.X1E.X2F, Z3.T1E.T2A.X1E.X2F,
Z4.T1E.T2A.X1E.X2F,
Z5.T1E.T2A.X1E.X2F, Z1.T1F.T2A.X1E.X2F,
Z2.T1F.T2A.X1E.X2F,
Z3.T1F.T2A.X1E.X2F, Z4.T1F.T2A.X1E.X2F,
Z5.T1F.T2A.X1E.X2F,
Z1.T1A.T2B.X1E.X2F, Z2.T1A.T2B.X1E.X2F,
Z3.T1A.T2B.X1E.X2F,
Z4.T1A.T2B.X1E.X2F, Z5.T1A.T2B.X1E.X2F,
Z1.T1B.T2B.X1E.X2F,
Z2.T1B.T2B.X1E.X2F, Z3.T1B.T2B.X1E.X2F,
Z4.T1B.T2B.X1E.X2F,
Z5.T1B.T2B.X1E.X2F, Z1.T1C.T2B.X1E.X2F,
Z2.T1C.T2B.X1E.X2F,
Z3.T1C.T2B.X1E.X2F, Z4.T1C.T2B.X1E.X2F,
Z5.T1C.T2B.X1E.X2F,
Z1.T1D.T2B.X1E.X2F, Z2.T1D.T2B.X1E.X2F,
Z3.T1D.T2B.X1E.X2F,
Z4.T1D.T2B.X1E.X2F, Z5.T1D.T2B.X1E.X2F,
Z1.T1E.T2B.X1E.X2F,
Z2.T1E.T2B.X1E.X2F, Z3.T1E.T2B.X1E.X2F,
Z4.T1E.T2B.X1E.X2F,

TABLE 6-continued

List of Compound Structure of Formula II

Z5.T1E.T2B.X1E.X2F, Z1.T1F.T2B.X1E.X2F,
Z2.T1F.T2B.X1E.X2F,
Z3.T1F.T2B.X1E.X2F, Z4.T1F.T2B.X1E.X2F,
Z5.T1F.T2B.X1E.X2F,
Z1.T1A.T2C.X1E.X2F, Z2.T1A.T2C.X1E.X2F,
Z3.T1A.T2C.X1E.X2F,
Z4.T1A.T2C.X1E.X2F, Z5.T1A.T2C.X1E.X2F,
Z1.T1B.T2C.X1E.X2F,
Z2.T1B.T2C.X1E.X2F, Z3.T1B.T2C.X1E.X2F,
Z4.T1B.T2C.X1E.X2F,
Z5.T1B.T2C.X1E.X2F, Z1.T1C.T2C.X1E.X2F,
Z2.T1C.T2C.X1E.X2F,
Z3.T1C.T2C.X1E.X2F, Z4.T1C.T2C.X1E.X2F,
Z5.T1C.T2C.X1E.X2F,
Z1.T1D.T2C.X1E.X2F, Z2.T1D.T2C.X1E.X2F,
Z3.T1D.T2C.X1E.X2F,
Z4.T1D.T2C.X1E.X2F, Z5.T1D.T2C.X1E.X2F,
Z1.T1E.T2C.X1E.X2F,
Z2.T1E.T2C.X1E.X2F, Z3.T1E.T2C.X1E.X2F,
Z4.T1E.T2C.X1E.X2F,
Z5.T1E.T2C.X1E.X2F, Z1.T1F.T2C.X1E.X2F,
Z2.T1F.T2C.X1E.X2F,
Z3.T1F.T2C.X1E.X2F, Z4.T1F.T2C.X1E.X2F,
Z5.T1F.T2C.X1E.X2F,
Z1.T1A.T2D.X1E.X2F, Z2.T1A.T2D.X1E.X2F,
Z3.T1A.T2D.X1E.X2F,
Z4.T1A.T2D.X1E.X2F, Z5.T1A.T2D.X1E.X2F,
Z1.T1B.T2D.X1E.X2F,
Z2.T1B.T2D.X1E.X2F, Z3.T1B.T2D.X1E.X2F,
Z4.T1B.T2D.X1E.X2F,
Z5.T1B.T2D.X1E.X2F, Z1.T1C.T2D.X1E.X2F,
Z2.T1C.T2D.X1E.X2F,
Z3.T1C.T2D.X1E.X2F, Z4.T1C.T2D.X1E.X2F,
Z5.T1C.T2D.X1E.X2F,
Z1.T1D.T2D.X1E.X2F, Z2.T1D.T2D.X1E.X2F,
Z3.T1D.T2D.X1E.X2F,
Z4.T1D.T2D.X1E.X2F, Z5.T1D.T2D.X1E.X2F,
Z1.T1E.T2D.X1E.X2F,
Z2.T1E.T2D.X1E.X2F, Z3.T1E.T2D.X1E.X2F,
Z4.T1E.T2D.X1E.X2F,
Z5.T1E.T2D.X1E.X2F, Z1.T1F.T2D.X1E.X2F,
Z2.T1F.T2D.X1E.X2F,
Z3.T1F.T2D.X1E.X2F, Z4.T1F.T2D.X1E.X2F,
Z5.T1F.T2D.X1E.X2F,
Z1.T1A.T2A.X1F.X2F, Z2.T1A.T2A.X1F.X2F,
Z3.T1A.T2A.X1F.X2F,
Z4.T1A.T2A.X1F.X2F, Z5.T1A.T2A.X1F.X2F,
Z1.T1B.T2A.X1F.X2F,
Z2.T1B.T2A.X1F.X2F, Z3.T1B.T2A.X1F.X2F,
Z4.T1B.T2A.X1F.X2F,
Z5.T1B.T2A.X1F.X2F, Z1.T1C.T2A.X1F.X2F,
Z2.T1C.T2A.X1F.X2F,
Z3.T1C.T2A.X1F.X2F, Z4.T1C.T2A.X1F.X2F,
Z5.T1C.T2A.X1F.X2F,
Z1.T1D.T2A.X1F.X2F, Z2.T1D.T2A.X1F.X2F,
Z3.T1D.T2A.X1F.X2F,
Z4.T1D.T2A.X1F.X2F, Z5.T1D.T2A.X1F.X2F,
Z1.T1E.T2A.X1F.X2F,
Z2.T1E.T2A.X1F.X2F, Z3.T1E.T2A.X1F.X2F,
Z4.T1E.T2A.X1F.X2F,
Z5.T1E.T2A.X1F.X2F, Z1.T1F.T2A.X1F.X2F,
Z2.T1F.T2A.X1F.X2F,
Z3.T1F.T2A.X1F.X2F, Z4.T1F.T2A.X1F.X2F,
Z5.T1F.T2A.X1F.X2F,
Z1.T1A.T2B.X1F.X2F, Z2.T1A.T2B.X1F.X2F,
Z3.T1A.T2B.X1F.X2F,
Z4.T1A.T2B.X1F.X2F, Z5.T1A.T2B.X1F.X2F,
Z1.T1B.T2B.X1F.X2F,
Z2.T1B.T2B.X1F.X2F, Z3.T1B.T2B.X1F.X2F,
Z4.T1B.T2B.X1F.X2F,
Z5.T1B.T2B.X1F.X2F, Z1.T1C.T2B.X1F.X2F,
Z2.T1C.T2B.X1F.X2F,
Z3.T1C.T2B.X1F.X2F, Z4.T1C.T2B.X1F.X2F,
Z5.T1C.T2B.X1F.X2F,
Z1.T1D.T2B.X1F.X2F, Z2.T1D.T2B.X1F.X2F,
Z3.T1D.T2B.X1F.X2F,

TABLE 6-continued

List of Compound Structure of Formula II

Z4.T1D.T2B.X1F.X2F, Z5.T1D.T2B.X1F.X2F,
Z1.T1E.T2B.X1F.X2F,
Z2.T1E.T2B.X1F.X2F, Z3.T1E.T2B.X1F.X2F,
Z4.T1E.T2B.X1F.X2F,
Z5.T1E.T2B.X1F.X2F, Z1.T1F.T2B.X1F.X2F,
Z2.T1F.T2B.X1F.X2F,
Z3.T1F.T2B.X1F.X2F, Z4.T1F.T2B.X1F.X2F,
Z5.T1F.T2B.X1F.X2F,
Z1.T1A.T2C.X1F.X2F, Z2.T1A.T2C.X1F.X2F,
Z3.T1A.T2C.X1F.X2F,
Z4.T1A.T2C.X1F.X2F, Z5.T1A.T2C.X1F.X2F,
Z1.T1B.T2C.X1F.X2F,
Z2.T1B.T2C.X1F.X2F, Z3.T1B.T2C.X1F.X2F,
Z4.T1B.T2C.X1F.X2F,
Z5.T1B.T2C.X1F.X2F, Z1.T1C.T2C.X1F.X2F,
Z2.T1C.T2C.X1F.X2F,
Z3.T1C.T2C.X1F.X2F, Z4.T1C.T2C.X1F.X2F,
Z5.T1C.T2C.X1F.X2F,
Z1.T1D.T2C.X1F.X2F, Z2.T1D.T2C.X1F.X2F,
Z3.T1D.T2C.X1F.X2F,
Z4.T1D.T2C.X1F.X2F, Z5.T1D.T2C.X1F.X2F,
Z1.T1E.T2C.X1F.X2F,
Z2.T1E.T2C.X1F.X2F, Z3.T1E.T2C.X1F.X2F,
Z4.T1E.T2C.X1F.X2F,
Z5.T1E.T2C.X1F.X2F, Z1.T1F.T2C.X1F.X2F,
Z2.T1F.T2C.X1F.X2F,
Z3.T1F.T2C.X1F.X2F, Z4.T1F.T2C.X1F.X2F,
Z5.T1F.T2C.X1F.X2F,
Z1.T1A.T2D.X1F.X2F, Z2.T1A.T2D.X1F.X2F,
Z3.T1A.T2D.X1F.X2F,
Z4.T1A.T2D.X1F.X2F, Z5.T1A.T2D.X1F.X2F,
Z1.T1B.T2D.X1F.X2F,
Z2.T1B.T2D.X1F.X2F, Z3.T1B.T2D.X1F.X2F,
Z4.T1B.T2D.X1F.X2F,
Z5.T1B.T2D.X1F.X2F, Z1.T1C.T2D.X1F.X2F,
Z2.T1C.T2D.X1F.X2F,
Z3.T1C.T2D.X1F.X2F, Z4.T1C.T2D.X1F.X2F,
Z5.T1C.T2D.X1F.X2F,
Z1.T1D.T2D.X1F.X2F, Z2.T1D.T2D.X1F.X2F,
Z3.T1D.T2D.X1F.X2F,
Z4.T1D.T2D.X1F.X2F, Z5.T1D.T2D.X1F.X2F,
Z1.T1E.T2D.X1F.X2F,
Z2.T1E.T2D.X1F.X2F, Z3.T1E.T2D.X1F.X2F,
Z4.T1E.T2D.X1F.X2F,
Z5.T1E.T2D.X1F.X2F, Z1.T1F.T2D.X1F.X2F,
Z2.T1F.T2D.X1F.X2F,
Z3.T1F.T2D.X1F.X2F, Z4.T1F.T2D.X1F.X2F,
Z5.T1F.T2D.X1F.X2F.

In still yet another embodiment, the compounds of Formula I are named below in tabular format (Table 30.6) as compounds of general Formula III:

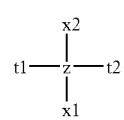

III

As discussed above, each structure of a compound of Formula III can be designated in tabular form by combining the "code" representing each structural moiety using the following syntax: z.t1.t2.x1.x2. Thus, for example, z1.t1a.t2b.x1a.x2a represents the following structure:

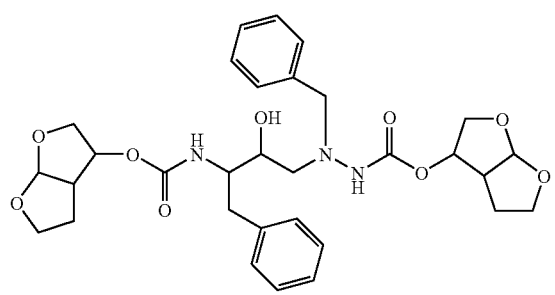
TABLE 30.1
Core Structures
| Code | Subgenus Structure |
|---|---|
| z1 | |
| z2 | |
| z3 | |
| z4 | |
| z5 | |
TABLE 30.2
t1 Structures
| Code | t1 Structure |
|---|---|
| t1a | |
| t1b | |
| t1c | |
| t1d | |
| t1e | |
TABLE 30.3
t2 Structures
| Code | t2 Structure |
|---|---|
| t2a | |
| t2b | |
| t2c | |

TABLE 30.4 x1 Structures

| Code | x1 Structure |
|---|---|
| x1a | phenyl |
| x1b | 4-fluorophenyl |
| x1c | 4-methoxyphenyl |
| x1d | 4'-fluoro-biphenyl-4-yl |
| x1e | 4-(pyridin-3-yloxy)phenyl |
| x1f | 4-(pyridin-3-yl)phenyl |
| x1g | 4-(thiazol-5-ylamino)phenyl |
| x1h | 4-((2-methylthiazol-4-yl)methoxy)phenyl |

TABLE 30.5 x2 Structures

| Code | x2 Structure |
|---|---|
| x2a | phenyl |
| x2b | 4-fluorophenyl |
| x2c | 2-fluorophenyl |
| x2d | biphenyl-4-yl |
| x2e | 4-(pyridin-2-yl)phenyl |
| x2f | 4-(pyridin-3-yloxy)phenyl |
| x2g | 4-(pyridin-2-ylamino)phenyl |
| x2h | 4-((1H-imidazol-4-yl)methoxy)phenyl |

TABLE 30.6

List of Compound Structures of Formula III z1.t1a.t2a.x1a.x2a, z1.t1a.t2a.x1a.x2b, z1.t1a.t2a.x1a.x2c, z1.t1a.t2a.x1a.x2d,
z1.t1a.t2a.x1a.x2e, z1.t1a.t2a.x1a.x2f, z1.t1a.t2a.x1a.x2g, z1.t1a.t2a.x1a.x2h,
z1.t1a.t2a.x1b.x2a, z1.t1a.t2a.x1b.x2b, z1.t1a.t2a.x1b.x2c, z1.t1a.t2a.x1b.x2d,
z1.t1a.t2a.x1b.x2e, z1.t1a.t2a.x1b.x2f, z1.t1a.t2a.x1b.x2g, z1.t1a.t2a.x1b.x2h,
z1.t1a.t2a.x1c.x2a, z1.t1a.t2a.x1c.x2b, z1.t1a.t2a.x1c.x2c, z1.t1a.t2a.x1c.x2d,
z1.t1a.t2a.x1c.x2e, z1.t1a.t2a.x1c.x2f, z1.t1a.t2a.x1c.x2g, z1.t1a.t2a.x1c.x2h,
z1.t1a.t2a.x1d.x2a, z1.t1a.t2a.x1d.x2b, z1.t1a.t2a.x1d.x2c, z1.t1a.t2a.x1d.x2d,
z1.t1a.t2a.x1d.x2e, z1.t1a.t2a.x1d.x2f, z1.t1a.t2a.x1d.x2g, z1.t1a.t2a.x1d.x2h,
z1.t1a.t2a.x1e.x2a, z1.t1a.t2a.x1e.x2b, z1.t1a.t2a.x1e.x2c, z1.t1a.t2a.x1e.x2d,
z1.t1a.t2a.x1e.x2e, z1.t1a.t2a.x1e.x2f, z1.t1a.t2a.x1e.x2g, z1.t1a.t2a.x1e.x2h,
z1.t1a.t2a.x1f.x2a, z1.t1a.t2a.x1f.x2b, z1.t1a.t2a.x1f.x2c, z1.t1a.t2a.x1f.x2d,
z1.t1a.t2a.x1f.x2e, z1.t1a.t2a.x1f.x2f, z1.t1a.t2a.x1f.x2g, z1.t1a.t2a.x1f.x2h,
z1.t1a.t2a.x1g.x2a, z1.t1a.t2a.x1g.x2b, z1.t1a.t2a.x1g.x2c, z1.t1a.t2a.x1g.x2d,
z1.t1a.t2a.x1g.x2e, z1.t1a.t2a.x1g.x2f, z1.t1a.t2a.x1g.x2g, z1.t1a.t2a.x1g.x2h,
z1.t1a.t2a.x1h.x2a, z1.t1a.t2a.x1h.x2b, z1.t1a.t2a.x1h.x2c, z1.t1a.t2a.x1h.x2d,
z1.t1a.t2a.x1h.x2e, z1.t1a.t2a.x1h.x2f, z1.t1a.t2a.x1h.x2g, z1.t1a.t2a.x1h.x2h,
z1.t1a.t2b.x1a.x2a, z1.t1a.t2b.x1a.x2b, z1.t1a.t2b.x1a.x2c, z1.t1a.t2b.x1a.x2d,
z1.t1a.t2b.x1a.x2e, z1.t1a.t2b.x1a.x2f, z1.t1a.t2b.x1a.x2g, z1.t1a.t2b.x1a.x2h,
z1.t1a.t2b.x1b.x2a, z1.t1a.t2b.x1b.x2b, z1.t1a.t2b.x1b.x2c, z1.t1a.t2b.x1b.x2d,
z1.t1a.t2b.x1b.x2e, z1.t1a.t2b.x1b.x2f, z1.t1a.t2b.x1b.x2g, z1.t1a.t2b.x1b.x2h,
z1.t1a.t2b.x1c.x2a, z1.t1a.t2b.x1c.x2b, z1.t1a.t2b.x1c.x2c, z1.t1a.t2b.x1c.x2d,
z1.t1a.t2b.x1c.x2e, z1.t1a.t2b.x1c.x2f, z1.t1a.t2b.x1c.x2g, z1.t1a.t2b.x1c.x2h,
z1.t1a.t2b.x1d.x2a, z1.t1a.t2b.x1d.x2b, z1.t1a.t2b.x1d.x2c, z1.t1a.t2b.x1d.x2d,
z1.t1a.t2b.x1d.x2e, z1.t1a.t2b.x1d.x2f, z1.t1a.t2b.x1d.x2g, z1.t1a.t2b.x1d.x2h,
z1.t1a.t2b.x1e.x2a, z1.t1a.t2b.x1e.x2b, z1.t1a.t2b.x1e.x2c, z1.t1a.t2b.x1e.x2d,
z1.t1a.t2b.x1e.x2e, z1.t1a.t2b.x1e.x2f, z1.t1a.t2b.x1e.x2g, z1.t1a.t2b.x1e.x2h,
z1.t1a.t2b.x1f.x2a, z1.t1a.t2b.x1f.x2b, z1.t1a.t2b.x1f.x2c, z1.t1a.t2b.x1f.x2d,
z1.t1a.t2b.x1f.x2e, z1.t1a.t2b.x1f.x2f, z1.t1a.t2b.x1f.x2g, z1.t1a.t2b.x1f.x2h,
z1.t1a.t2b.x1g.x2a, z1.t1a.t2b.x1g.x2b, z1.t1a.t2b.x1g.x2c, z1.t1a.t2b.x1g.x2d,
z1.t1a.t2b.x1g.x2e, z1.t1a.t2b.x1g.x2f, z1.t1a.t2b.x1g.x2g, z1.t1a.t2b.x1g.x2h,
z1.t1a.t2b.x1h.x2a, z1.t1a.t2b.x1h.x2b, z1.t1a.t2b.x1h.x2c, z1.t1a.t2b.x1h.x2d,
z1.t1a.t2b.x1h.x2e, z1.t1a.t2b.x1h.x2f, z1.t1a.t2b.x1h.x2g, z1.t1a.t2b.x1h.x2h,
z1.t1a.t2c.x1a.x2a, z1.t1a.t2c.x1a.x2b, z1.t1a.t2c.x1a.x2c, z1.t1a.t2c.x1a.x2d,
z1.t1a.t2c.x1a.x2e, z1.t1a.t2c.x1a.x2f, z1.t1a.t2c.x1a.x2g, z1.t1a.t2c.x1a.x2h,
z1.t1a.t2c.x1b.x2a, z1.t1a.t2c.x1b.x2b, z1.t1a.t2c.x1b.x2c, z1.t1a.t2c.x1b.x2d,
z1.t1a.t2c.x1b.x2e, z1.t1a.t2c.x1b.x2f, z1.t1a.t2c.x1b.x2g, z1.t1a.t2c.x1b.x2h,
z1.t1a.t2c.x1c.x2a, z1.t1a.t2c.x1c.x2b, z1.t1a.t2c.x1c.x2c, z1.t1a.t2c.x1c.x2d,
z1.t1a.t2c.x1c.x2e, z1.t1a.t2c.x1c.x2f, z1.t1a.t2c.x1c.x2g, z1.t1a.t2c.x1c.x2h,
z1.t1a.t2c.x1d.x2a, z1.t1a.t2c.x1d.x2b, z1.t1a.t2c.x1d.x2c, z1.t1a.t2c.x1d.x2d,
z1.t1a.t2c.x1d.x2e, z1.t1a.t2c.x1d.x2f, z1.t1a.t2c.x1d.x2g, z1.t1a.t2c.x1d.x2h,
z1.t1a.t2c.x1e.x2a, z1.t1a.t2c.x1e.x2b, z1.t1a.t2c.x1e.x2c, z1.t1a.t2c.x1e.x2d,
z1.t1a.t2c.x1e.x2e, z1.t1a.t2c.x1e.x2f, z1.t1a.t2c.x1e.x2g, z1.t1a.t2c.x1e.x2h,
z1.t1a.t2c.x1f.x2a, z1.t1a.t2c.x1f.x2b, z1.t1a.t2c.x1f.x2c, z1.t1a.t2c.x1f.x2d,
z1.t1a.t2c.x1f.x2e, z1.t1a.t2c.x1f.x2f, z1.t1a.t2c.x1f.x2g, z1.t1a.t2c.x1f.x2h,
z1.t1a.t2c.x1g.x2a, z1.t1a.t2c.x1g.x2b, z1.t1a.t2c.x1g.x2c, z1.t1a.t2c.x1g.x2d,
z1.t1a.t2c.x1g.x2e, z1.t1a.t2c.x1g.x2f, z1.t1a.t2c.x1g.x2g, z1.t1a.t2c.x1g.x2h,
z1.t1a.t2c.x1h.x2a, z1.t1a.t2c.x1h.x2b, z1.t1a.t2c.x1h.x2c, z1.t1a.t2c.x1h.x2d,
z1.t1a.t2c.x1h.x2e, z1.t1a.t2c.x1h.x2f, z1.t1a.t2c.x1h.x2g, z1.t1a.t2c.x1h.x2h,
z1.t1b.t2a.x1a.x2a, z1.t1b.t2a.x1a.x2b, z1.t1b.t2a.x1a.x2c, z1.t1b.t2a.x1a.x2d,
z1.t1b.t2a.x1a.x2e, z1.t1b.t2a.x1a.x2f, z1.t1b.t2a.x1a.x2g, z1.t1b.t2a.x1a.x2h,
z1.t1b.t2a.x1b.x2a, z1.t1b.t2a.x1b.x2b, z1.t1b.t2a.x1b.x2c, z1.t1b.t2a.x1b.x2d,
z1.t1b.t2a.x1b.x2e, z1.t1b.t2a.x1b.x2f, z1.t1b.t2a.x1b.x2g, z1.t1b.t2a.x1b.x2h,
z1.t1b.t2a.x1c.x2a, z1.t1b.t2a.x1c.x2b, z1.t1b.t2a.x1c.x2c, z1.t1b.t2a.x1c.x2d,
z1.t1b.t2a.x1c.x2e, z1.t1b.t2a.x1c.x2f, z1.t1b.t2a.x1c.x2g, z1.t1b.t2a.x1c.x2h,
z1.t1b.t2a.x1d.x2a, z1.t1b.t2a.x1d.x2b, z1.t1b.t2a.x1d.x2c, z1.t1b.t2a.x1d.x2d,
z1.t1b.t2a.x1d.x2e, z1.t1b.t2a.x1d.x2f, z1.t1b.t2a.x1d.x2g, z1.t1b.t2a.x1d.x2h,
z1.t1b.t2a.x1e.x2a, z1.t1b.t2a.x1e.x2b, z1.t1b.t2a.x1e.x2c, z1.t1b.t2a.x1e.x2d,
z1.t1b.t2a.x1e.x2e, z1.t1b.t2a.x1e.x2f, z1.t1b.t2a.x1e.x2g, z1.t1b.t2a.x1e.x2h,
z1.t1b.t2a.x1f.x2a, z1.t1b.t2a.x1f.x2b, z1.t1b.t2a.x1f.x2c, z1.t1b.t2a.x1f.x2d,
z1.t1b.t2a.x1f.x2e, z1.t1b.t2a.x1f.x2f, z1.t1b.t2a.x1f.x2g, z1.t1b.t2a.x1f.x2h,
z1.t1b.t2a.x1g.x2a, z1.t1b.t2a.x1g.x2b, z1.t1b.t2a.x1g.x2c, z1.t1b.t2a.x1g.x2d,
z1.t1b.t2a.x1g.x2e, z1.t1b.t2a.x1g.x2f, z1.t1b.t2a.x1g.x2g, z1.t1b.t2a.x1g.x2h,
z1.t1b.t2a.x1h.x2a, z1.t1b.t2a.x1h.x2b, z1.t1b.t2a.x1h.x2c, z1.t1b.t2a.x1h.x2d,
z1.t1b.t2a.x1h.x2e, z1.t1b.t2a.x1h.x2f, z1.t1b.t2a.x1h.x2g, z1.t1b.t2a.x1h.x2h,
z1.t1b.t2b.x1a.x2a, z1.t1b.t2b.x1a.x2b, z1.t1b.t2b.x1a.x2c, z1.t1b.t2b.x1a.x2d,
z1.t1b.t2b.x1a.x2e, z1.t1b.t2b.x1a.x2f, z1.t1b.t2b.x1a.x2g, z1.t1b.t2b.x1a.x2h,
z1.t1b.t2b.x1b.x2a, z1.t1b.t2b.x1b.x2b, z1.t1b.t2b.x1b.x2c, z1.t1b.t2b.x1b.x2d,
z1.t1b.t2b.x1b.x2e, z1.t1b.t2b.x1b.x2f, z1.t1b.t2b.x1b.x2g, z1.t1b.t2b.x1b.x2h,
z1.t1b.t2b.x1c.x2a, z1.t1b.t2b.x1c.x2b, z1.t1b.t2b.x1c.x2c, z1.t1b.t2b.x1c.x2d,
z1.t1b.t2b.x1c.x2e, z1.t1b.t2b.x1c.x2f, z1.t1b.t2b.x1c.x2g, z1.t1b.t2b.x1c.x2h,
z1.t1b.t2b.x1d.x2a, z1.t1b.t2b.x1d.x2b, z1.t1b.t2b.x1d.x2c, z1.t1b.t2b.x1d.x2d,
z1.t1b.t2b.x1d.x2e, z1.t1b.t2b.x1d.x2f, z1.t1b.t2b.x1d.x2g, z1.t1b.t2b.x1d.x2h,
z1.t1b.t2b.x1e.x2a, z1.t1b.t2b.x1e.x2b, z1.t1b.t2b.x1e.x2c, z1.t1b.t2b.x1e.x2d,
z1.t1b.t2b.x1e.x2e, z1.t1b.t2b.x1e.x2f, z1.t1b.t2b.x1e.x2g, z1.t1b.t2b.x1e.x2h,
z1.t1b.t2b.x1f.x2a, z1.t1b.t2b.x1f.x2b, z1.t1b.t2b.x1f.x2c, z1.t1b.t2b.x1f.x2d,
z1.t1b.t2b.x1f.x2e, z1.t1b.t2b.x1f.x2f, z1.t1b.t2b.x1f.x2g, z1.t1b.t2b.x1f.x2h,
z1.t1b.t2b.x1g.x2a, z1.t1b.t2b.x1g.x2b, z1.t1b.t2b.x1g.x2c, z1.t1b.t2b.x1g.x2d, TABLE 30.6-continued List of Compound Structures of Formula III z1.t1b.t2b.x1g.x2e, z1.t1b.t2b.x1g.x2f, z1.t1b.t2b.x1g.x2g,
z1.t1b.t2b.x1g.x2h,
z1.t1b.t2b.x1h.x2a, z1.t1b.t2b.x1h.x2b, z1.t1b.t2b.x1h.x2c,
z1.t1b.t2b.x1h.x2d,
z1.t1b.t2b.x1h.x2e, z1.t1b.t2b.x1h.x2f, z1.t1b.t2b.x1h.x2g,
z1.t1b.t2b.x1h.x2h,
z1.t1b.t2c.x1a.x2a, z1.t1b.t2c.x1a.x2b, z1.t1b.t2c.x1a.x2c,
z1.t1b.t2c.x1a.x2d,
z1.t1b.t2c.x1a.x2e, z1.t1b.t2c.x1a.x2f, z1.t1b.t2c.x1a.x2g,
z1.t1b.t2c.x1a.x2h,
z1.t1b.t2c.x1b.x2a, z1.t1b.t2c.x1b.x2b, z1.t1b.t2c.x1b.x2c,
z1.t1b.t2c.x1b.x2d,
z1.t1b.t2c.x1b.x2e, z1.t1b.t2c.x1b.x2f, z1.t1b.t2c.x1b.x2g,
z1.t1b.t2c.x1b.x2h,
z1.t1b.t2c.x1c.x2a, z1.t1b.t2c.x1c.x2b, z1.t1b.t2c.x1c.x2c,
z1.t1b.t2c.x1c.x2d,
z1.t1b.t2c.x1c.x2e, z1.t1b.t2c.x1c.x2f, z1.t1b.t2c.x1c.x2g,
z1.t1b.t2c.x1c.x2h,
z1.t1b.t2c.x1d.x2a, z1.t1b.t2c.x1d.x2b, z1.t1b.t2c.x1d.x2c,
z1.t1b.t2c.x1d.x2d,
z1.t1b.t2c.x1d.x2e, z1.t1b.t2c.x1d.x2f, z1.t1b.t2c.x1d.x2g,
z1.t1b.t2c.x1d.x2h,
z1.t1b.t2c.x1e.x2a, z1.t1b.t2c.x1e.x2b, z1.t1b.t2c.x1e.x2c,
z1.t1b.t2c.x1e.x2d,
z1.t1b.t2c.x1e.x2e, z1.t1b.t2c.x1e.x2f, z1.t1b.t2c.x1e.x2g,
z1.t1b.t2c.x1e.x2h,
z1.t1b.t2c.x1f.x2a, z1.t1b.t2c.x1f.x2b, z1.t1b.t2c.x1f.x2c,
z1.t1b.t2c.x1f.x2d,
z1.t1b.t2c.x1f.x2e, z1.t1b.t2c.x1f.x2f, z1.t1b.t2c.x1f.x2g,
z1.t1b.t2c.x1f.x2h,
z1.t1b.t2c.x1g.x2a, z1.t1b.t2c.x1g.x2b, z1.t1b.t2c.x1g.x2c,
z1.t1b.t2c.x1g.x2d,
z1.t1b.t2c.x1g.x2e, z1.t1b.t2c.x1g.x2f, z1.t1b.t2c.x1g.x2g,
z1.t1b.t2c.x1g.x2h,
z1.t1b.t2c.x1h.x2a, z1.t1b.t2c.x1h.x2b, z1.t1b.t2c.x1h.x2c,
z1.t1b.t2c.x1h.x2d,
z1.t1b.t2c.x1h.x2e, z1.t1b.t2c.x1h.x2f, z1.t1b.t2c.x1h.x2g,
z1.t1b.t2c.x1h.x2h,
z1.t1c.t2a.x1a.x2a, z1.t1c.t2a.x1a.x2b, z1.t1c.t2a.x1a.x2c,
z1.t1c.t2a.x1a.x2d,
z1.t1c.t2a.x1a.x2e, z1.t1c.t2a.x1a.x2f, z1.t1c.t2a.x1a.x2g,
z1.t1c.t2a.x1a.x2h,
z1.t1c.t2a.x1b.x2a, z1.t1c.t2a.x1b.x2b, z1.t1c.t2a.x1b.x2c,
z1.t1c.t2a.x1b.x2d,
z1.t1c.t2a.x1b.x2e, z1.t1c.t2a.x1b.x2f, z1.t1c.t2a.x1b.x2g,
z1.t1c.t2a.x1b.x2h,
z1.t1c.t2a.x1c.x2a, z1.t1c.t2a.x1c.x2b, z1.t1c.t2a.x1c.x2c,
z1.t1c.t2a.x1c.x2d,
z1.t1c.t2a.x1c.x2e, z1.t1c.t2a.x1c.x2f, z1.t1c.t2a.x1c.x2g,
z1.t1c.t2a.x1c.x2h,
z1.t1c.t2a.x1d.x2a, z1.t1c.t2a.x1d.x2b, z1.t1c.t2a.x1d.x2c,
z1.t1c.t2a.x1d.x2d,
z1.t1c.t2a.x1d.x2e, z1.t1c.t2a.x1d.x2f, z1.t1c.t2a.x1d.x2g,
z1.t1c.t2a.x1d.x2h,
z1.t1c.t2a.x1e.x2a, z1.t1c.t2a.x1e.x2b, z1.t1c.t2a.x1e.x2c,
z1.t1c.t2a.x1e.x2d,
z1.t1c.t2a.x1e.x2e, z1.t1c.t2a.x1e.x2f, z1.t1c.t2a.x1e.x2g,
z1.t1c.t2a.x1e.x2h,
z1.t1c.t2a.x1f.x2a, z1.t1c.t2a.x1f.x2b, z1.t1c.t2a.x1f.x2c,
z1.t1c.t2a.x1f.x2d,
z1.t1c.t2a.x1f.x2e, z1.t1c.t2a.x1f.x2f, z1.t1c.t2a.x1f.x2g,
z1.t1c.t2a.x1f.x2h,
z1.t1c.t2a.x1g.x2a, z1.t1c.t2a.x1g.x2b, z1.t1c.t2a.x1g.x2c,
z1.t1c.t2a.x1g.x2d,
z1.t1c.t2a.x1g.x2e, z1.t1c.t2a.x1g.x2f, z1.t1c.t2a.x1g.x2g,
z1.t1c.t2a.x1g.x2h,
z1.t1c.t2a.x1h.x2a, z1.t1c.t2a.x1h.x2b, z1.t1c.t2a.x1h.x2c,
z1.t1c.t2a.x1h.x2d,
z1.t1c.t2a.x1h.x2e, z1.t1c.t2a.x1h.x2f, z1.t1c.t2a.x1h.x2g,
z1.t1c.t2a.x1h.x2h,
z1.t1c.t2b.x1a.x2a, z1.t1c.t2b.x1a.x2b, z1.t1c.t2b.x1a.x2c,
z1.t1c.t2b.x1a.x2d,
z1.t1c.t2b.x1a.x2e, z1.t1c.t2b.x1a.x2f, z1.t1c.t2b.x1a.x2g,
z1.t1c.t2b.x1a.x2h,
z1.t1c.t2b.x1b.x2a, z1.t1c.t2b.x1b.x2b, z1.t1c.t2b.x1b.x2c,
z1.t1c.t2b.x1b.x2d,
z1.t1c.t2b.x1b.x2e, z1.t1c.t2b.x1b.x2f, z1.t1c.t2b.x1b.x2g,
z1.t1c.t2b.x1b.x2h,
z1.t1c.t2b.x1c.x2a, z1.t1c.t2b.x1c.x2b, z1.t1c.t2b.x1c.x2c,
z1.t1c.t2b.x1c.x2d,
z1.t1c.t2b.x1c.x2e, z1.t1c.t2b.x1c.x2f, z1.t1c.t2b.x1c.x2g,
z1.t1c.t2b.x1c.x2h,
z1.t1c.t2b.x1d.x2a, z1.t1c.t2b.x1d.x2b, z1.t1c.t2b.x1d.x2c,
z1.t1c.t2b.x1d.x2d,
z1.t1c.t2b.x1d.x2e, z1.t1c.t2b.x1d.x2f, z1.t1c.t2b.x1d.x2g,
z1.t1c.t2b.x1d.x2h,
z1.t1c.t2b.x1e.x2a, z1.t1c.t2b.x1e.x2b, z1.t1c.t2b.x1e.x2c,
z1.t1c.t2b.x1e.x2d,
z1.t1c.t2b.x1e.x2e, z1.t1c.t2b.x1e.x2f, z1.t1c.t2b.x1e.x2g,
z1.t1c.t2b.x1e.x2h,
z1.t1c.t2b.x1f.x2a, z1.t1c.t2b.x1f.x2b, z1.t1c.t2b.x1f.x2c,
z1.t1c.t2b.x1f.x2d,
z1.t1c.t2b.x1f.x2e, z1.t1c.t2b.x1f.x2f, z1.t1c.t2b.x1f.x2g,
z1.t1c.t2b.x1f.x2h,
z1.t1c.t2b.x1g.x2a, z1.t1c.t2b.x1g.x2b, z1.t1c.t2b.x1g.x2c,
z1.t1c.t2b.x1g.x2d,
z1.t1c.t2b.x1g.x2e, z1.t1c.t2b.x1g.x2f, z1.t1c.t2b.x1g.x2g,
z1.t1c.t2b.x1g.x2h,
z1.t1c.t2b.x1h.x2a, z1.t1c.t2b.x1h.x2b, z1.t1c.t2b.x1h.x2c,
z1.t1c.t2b.x1h.x2d,
z1.t1c.t2b.x1h.x2e, z1.t1c.t2b.x1h.x2f, z1.t1c.t2b.x1h.x2g,
z1.t1c.t2b.x1h.x2h,
z1.t1c.t2c.x1a.x2a, z1.t1c.t2c.x1a.x2b, z1.t1c.t2c.x1a.x2c,
z1.t1c.t2c.x1a.x2d,
z1.t1c.t2c.x1a.x2e, z1.t1c.t2c.x1a.x2f, z1.t1c.t2c.x1a.x2g,
z1.t1c.t2c.x1a.x2h,
z1.t1c.t2c.x1b.x2a, z1.t1c.t2c.x1b.x2b, z1.t1c.t2c.x1b.x2c,
z1.t1c.t2c.x1b.x2d,
z1.t1c.t2c.x1b.x2e, z1.t1c.t2c.x1b.x2f, z1.t1c.t2c.x1b.x2g,
z1.t1c.t2c.x1b.x2h,
z1.t1c.t2c.x1c.x2a, z1.t1c.t2c.x1c.x2b, z1.t1c.t2c.x1c.x2c,
z1.t1c.t2c.x1c.x2d,
z1.t1c.t2c.x1c.x2e, z1.t1c.t2c.x1c.x2f, z1.t1c.t2c.x1c.x2g,
z1.t1c.t2c.x1c.x2h,
z1.t1c.t2c.x1d.x2a, z1.t1c.t2c.x1d.x2b, z1.t1c.t2c.x1d.x2c,
z1.t1c.t2c.x1d.x2d,
z1.t1c.t2c.x1d.x2e, z1.t1c.t2c.x1d.x2f, z1.t1c.t2c.x1d.x2g,
z1.t1c.t2c.x1d.x2h,
z1.t1c.t2c.x1e.x2a, z1.t1c.t2c.x1e.x2b, z1.t1c.t2c.x1e.x2c,
z1.t1c.t2c.x1e.x2d,
z1.t1c.t2c.x1e.x2e, z1.t1c.t2c.x1e.x2f, z1.t1c.t2c.x1e.x2g,
z1.t1c.t2c.x1e.x2h,
z1.t1c.t2c.x1f.x2a, z1.t1c.t2c.x1f.x2b, z1.t1c.t2c.x1f.x2c,
z1.t1c.t2c.x1f.x2d,
z1.t1c.t2c.x1f.x2e, z1.t1c.t2c.x1f.x2f, z1.t1c.t2c.x1f.x2g,
z1.t1c.t2c.x1f.x2h,
z1.t1c.t2c.x1g.x2a, z1.t1c.t2c.x1g.x2b, z1.t1c.t2c.x1g.x2c,
z1.t1c.t2c.x1g.x2d,
z1.t1c.t2c.x1g.x2e, z1.t1c.t2c.x1g.x2f, z1.t1c.t2c.x1g.x2g,
z1.t1c.t2c.x1g.x2h,
z1.t1c.t2c.x1h.x2a, z1.t1c.t2c.x1h.x2b, z1.t1c.t2c.x1h.x2c,
z1.t1c.t2c.x1h.x2d,
z1.t1c.t2c.x1h.x2e, z1.t1c.t2c.x1h.x2f, z1.t1c.t2c.x1h.x2g,
z1.t1c.t2c.x1h.x2h,
z1.t1d.t2a.x1a.x2a, z1.t1d.t2a.x1a.x2b, z1.t1d.t2a.x1a.x2c,
z1.t1d.t2a.x1a.x2d,
z1.t1d.t2a.x1a.x2e, z1.t1d.t2a.x1a.x2f, z1.t1d.t2a.x1a.x2g,
z1.t1d.t2a.x1a.x2h,
z1.t1d.t2a.x1b.x2a, z1.t1d.t2a.x1b.x2b, z1.t1d.t2a.x1b.x2c,
z1.t1d.t2a.x1b.x2d,
z1.t1d.t2a.x1b.x2e, z1.t1d.t2a.x1b.x2f, z1.t1d.t2a.x1b.x2g,
z1.t1d.t2a.x1b.x2h,
z1.t1d.t2a.x1c.x2a, z1.t1d.t2a.x1c.x2b, z1.t1d.t2a.x1c.x2c,
z1.t1d.t2a.x1c.x2d,
z1.t1d.t2a.x1c.x2e, z1.t1d.t2a.x1c.x2f, z1.t1d.t2a.x1c.x2g,
z1.t1d.t2a.x1c.x2h,
z1.t1d.t2a.x1d.x2a, z1.t1d.t2a.x1d.x2b, z1.t1d.t2a.x1d.x2c,
z1.t1d.t2a.x1d.x2d,
z1.t1d.t2a.x1d.x2e, z1.t1d.t2a.x1d.x2f, z1.t1d.t2a.x1d.x2g,
z1.t1d.t2a.x1d.x2h,
z1.t1d.t2a.x1e.x2a, z1.t1d.t2a.x1e.x2b, z1.t1d.t2a.x1e.x2c,
z1.t1d.t2a.x1e.x2d,
z1.t1d.t2a.x1e.x2e, z1.t1d.t2a.x1e.x2f, z1.t1d.t2a.x1e.x2g,
z1.t1d.t2a.x1e.x2h,

TABLE 30.6-continued

List of Compound Structures of Formula III z1.t1d.t2a.x1f.x2a, z1.t1d.t2a.x1f.x2b, z1.t1d.t2a.x1f.x2c, z1.t1d.t2a.x1f.x2d,
z1.t1d.t2a.x1f.x2e, z1.t1d.t2a.x1f.x2f, z1.t1d.t2a.x1f.x2g, z1.t1d.t2a.x1f.x2h,
z1.t1d.t2a.x1g.x2a, z1.t1d.t2a.x1g.x2b, z1.t1d.t2a.x1g.x2c, z1.t1d.t2a.x1g.x2d,
z1.t1d.t2a.x1g.x2e, z1.t1d.t2a.x1g.x2f, z1.t1d.t2a.x1g.x2g, z1.t1d.t2a.x1g.x2h,
z1.t1d.t2a.x1h.x2a, z1.t1d.t2a.x1h.x2b, z1.t1d.t2a.x1h.x2c, z1.t1d.t2a.x1h.x2d,
z1.t1d.t2a.x1h.x2e, z1.t1d.t2a.x1h.x2f, z1.t1d.t2a.x1h.x2g, z1.t1d.t2a.x1h.x2h,
z1.t1d.t2b.x1a.x2a, z1.t1d.t2b.x1a.x2b, z1.t1d.t2b.x1a.x2c, z1.t1d.t2b.x1a.x2d,
z1.t1d.t2b.x1a.x2e, z1.t1d.t2b.x1a.x2f, z1.t1d.t2b.x1a.x2g, z1.t1d.t2b.x1a.x2h,
z1.t1d.t2b.x1b.x2a, z1.t1d.t2b.x1b.x2b, z1.t1d.t2b.x1b.x2c, z1.t1d.t2b.x1b.x2d,
z1.t1d.t2b.x1b.x2e, z1.t1d.t2b.x1b.x2f, z1.t1d.t2b.x1b.x2g, z1.t1d.t2b.x1b.x2h,
z1.t1d.t2b.x1c.x2a, z1.t1d.t2b.x1c.x2b, z1.t1d.t2b.x1c.x2c, z1.t1d.t2b.x1c.x2d,
z1.t1d.t2b.x1c.x2e, z1.t1d.t2b.x1c.x2f, z1.t1d.t2b.x1c.x2g, z1.t1d.t2b.x1c.x2h,
z1.t1d.t2b.x1d.x2a, z1.t1d.t2b.x1d.x2b, z1.t1d.t2b.x1d.x2c, z1.t1d.t2b.x1d.x2d,
z1.t1d.t2b.x1d.x2e, z1.t1d.t2b.x1d.x2f, z1.t1d.t2b.x1d.x2g, z1.t1d.t2b.x1d.x2h,
z1.t1d.t2b.x1e.x2a, z1.t1d.t2b.x1e.x2b, z1.t1d.t2b.x1e.x2c, z1.t1d.t2b.x1e.x2d,
z1.t1d.t2b.x1e.x2e, z1.t1d.t2b.x1e.x2f, z1.t1d.t2b.x1e.x2g, z1.t1d.t2b.x1e.x2h,
z1.t1d.t2b.x1f.x2a, z1.t1d.t2b.x1f.x2b, z1.t1d.t2b.x1f.x2c, z1.t1d.t2b.x1f.x2d,
z1.t1d.t2b.x1f.x2e, z1.t1d.t2b.x1f.x2f, z1.t1d.t2b.x1f.x2g, z1.t1d.t2b.x1f.x2h,
z1.t1d.t2b.x1g.x2a, z1.t1d.t2b.x1g.x2b, z1.t1d.t2b.x1g.x2c, z1.t1d.t2b.x1g.x2d,
z1.t1d.t2b.x1g.x2e, z1.t1d.t2b.x1g.x2f, z1.t1d.t2b.x1g.x2g, z1.t1d.t2b.x1g.x2h,
z1.t1d.t2b.x1h.x2a, z1.t1d.t2b.x1h.x2b, z1.t1d.t2b.x1h.x2c, z1.t1d.t2b.x1h.x2d,
z1.t1d.t2b.x1h.x2e, z1.t1d.t2b.x1h.x2f, z1.t1d.t2b.x1h.x2g, z1.t1d.t2b.x1h.x2h,
z1.t1d.t2c.x1a.x2a, z1.t1d.t2c.x1a.x2b, z1.t1d.t2c.x1a.x2c, z1.t1d.t2c.x1a.x2d,
z1.t1d.t2c.x1a.x2e, z1.t1d.t2c.x1a.x2f, z1.t1d.t2c.x1a.x2g, z1.t1d.t2c.x1a.x2h,
z1.t1d.t2c.x1b.x2a, z1.t1d.t2c.x1b.x2b, z1.t1d.t2c.x1b.x2c, z1.t1d.t2c.x1b.x2d,
z1.t1d.t2c.x1b.x2e, z1.t1d.t2c.x1b.x2f, z1.t1d.t2c.x1b.x2g, z1.t1d.t2c.x1b.x2h,
z1.t1d.t2c.x1c.x2a, z1.t1d.t2c.x1c.x2b, z1.t1d.t2c.x1c.x2c, z1.t1d.t2c.x1c.x2d,
z1.t1d.t2c.x1c.x2e, z1.t1d.t2c.x1c.x2f, z1.t1d.t2c.x1c.x2g, z1.t1d.t2c.x1c.x2h,
z1.t1d.t2c.x1d.x2a, z1.t1d.t2c.x1d.x2b, z1.t1d.t2c.x1d.x2c, z1.t1d.t2c.x1d.x2d,
z1.t1d.t2c.x1d.x2e, z1.t1d.t2c.x1d.x2f, z1.t1d.t2c.x1d.x2g, z1.t1d.t2c.x1d.x2h,
z1.t1d.t2c.x1e.x2a, z1.t1d.t2c.x1e.x2b, z1.t1d.t2c.x1e.x2c, z1.t1d.t2c.x1e.x2d,
z1.t1d.t2c.x1e.x2e, z1.t1d.t2c.x1e.x2f, z1.t1d.t2c.x1e.x2g, z1.t1d.t2c.x1e.x2h,
z1.t1d.t2c.x1f.x2a, z1.t1d.t2c.x1f.x2b, z1.t1d.t2c.x1f.x2c, z1.t1d.t2c.x1f.x2d,
z1.t1d.t2c.x1f.x2e, z1.t1d.t2c.x1f.x2f, z1.t1d.t2c.x1f.x2g, z1.t1d.t2c.x1f.x2h,
z1.t1d.t2c.x1g.x2a, z1.t1d.t2c.x1g.x2b, z1.t1d.t2c.x1g.x2c, z1.t1d.t2c.x1g.x2d,
z1.t1d.t2c.x1g.x2e, z1.t1d.t2c.x1g.x2f, z1.t1d.t2c.x1g.x2g, z1.t1d.t2c.x1g.x2h,
z1.t1d.t2c.x1h.x2a, z1.t1d.t2c.x1h.x2b, z1.t1d.t2c.x1h.x2c, z1.t1d.t2c.x1h.x2d,
z1.t1d.t2c.x1h.x2e, z1.t1d.t2c.x1h.x2f, z1.t1d.t2c.x1h.x2g, z1.t1d.t2c.x1h.x2h,
z1.t1e.t2a.x1a.x2a, z1.t1e.t2a.x1a.x2b, z1.t1e.t2a.x1a.x2c, z1.t1e.t2a.x1a.x2d,
z1.t1e.t2a.x1a.x2e, z1.t1e.t2a.x1a.x2f, z1.t1e.t2a.x1a.x2g, z1.t1e.t2a.x1a.x2h,
z1.t1e.t2a.x1b.x2a, z1.t1e.t2a.x1b.x2b, z1.t1e.t2a.x1b.x2c, z1.t1e.t2a.x1b.x2d,
z1.t1e.t2a.x1b.x2e, z1.t1e.t2a.x1b.x2f, z1.t1e.t2a.x1b.x2g, z1.t1e.t2a.x1b.x2h,
z1.t1e.t2a.x1c.x2a, z1.t1e.t2a.x1c.x2b, z1.t1e.t2a.x1c.x2c, z1.t1e.t2a.x1c.x2d,
z1.t1e.t2a.x1c.x2e, z1.t1e.t2a.x1c.x2f, z1.t1e.t2a.x1c.x2g, z1.t1e.t2a.x1c.x2h,
z1.t1e.t2a.x1d.x2a, z1.t1e.t2a.x1d.x2b, z1.t1e.t2a.x1d.x2c, z1.t1e.t2a.x1d.x2d,
z1.t1e.t2a.x1d.x2e, z1.t1e.t2a.x1d.x2f, z1.t1e.t2a.x1d.x2g, z1.t1e.t2a.x1d.x2h,
z1.t1e.t2a.x1e.x2a, z1.t1e.t2a.x1e.x2b, z1.t1e.t2a.x1e.x2c, z1.t1e.t2a.x1e.x2d,
z1.t1e.t2a.x1e.x2e, z1.t1e.t2a.x1e.x2f, z1.t1e.t2a.x1e.x2g, z1.t1e.t2a.x1e.x2h,
z1.t1e.t2a.x1f.x2a, z1.t1e.t2a.x1f.x2b, z1.t1e.t2a.x1f.x2c, z1.t1e.t2a.x1f.x2d,
z1.t1e.t2a.x1f.x2e, z1.t1e.t2a.x1f.x2f, z1.t1e.t2a.x1f.x2g, z1.t1e.t2a.x1f.x2h,
z1.t1e.t2a.x1g.x2a, z1.t1e.t2a.x1g.x2b, z1.t1e.t2a.x1g.x2c, z1.t1e.t2a.x1g.x2d,
z1.t1e.t2a.x1g.x2e, z1.t1e.t2a.x1g.x2f, z1.t1e.t2a.x1g.x2g, z1.t1e.t2a.x1g.x2h,
z1.t1e.t2a.x1h.x2a, z1.t1e.t2a.x1h.x2b, z1.t1e.t2a.x1h.x2c, z1.t1e.t2a.x1h.x2d,
z1.t1e.t2a.x1h.x2e, z1.t1e.t2a.x1h.x2f, z1.t1e.t2a.x1h.x2g, z1.t1e.t2a.x1h.x2h,
z1.t1e.t2b.x1a.x2a, z1.t1e.t2b.x1a.x2b, z1.t1e.t2b.x1a.x2c, z1.t1e.t2b.x1a.x2d,
z1.t1e.t2b.x1a.x2e, z1.t1e.t2b.x1a.x2f, z1.t1e.t2b.x1a.x2g, z1.t1e.t2b.x1a.x2h,
z1.t1e.t2b.x1b.x2a, z1.t1e.t2b.x1b.x2b, z1.t1e.t2b.x1b.x2c, z1.t1e.t2b.x1b.x2d,
z1.t1e.t2b.x1b.x2e, z1.t1e.t2b.x1b.x2f, z1.t1e.t2b.x1b.x2g, z1.t1e.t2b.x1b.x2h,
z1.t1e.t2b.x1c.x2a, z1.t1e.t2b.x1c.x2b, z1.t1e.t2b.x1c.x2c, z1.t1e.t2b.x1c.x2d,
z1.t1e.t2b.x1c.x2e, z1.t1e.t2b.x1c.x2f, z1.t1e.t2b.x1c.x2g, z1.t1e.t2b.x1c.x2h,
z1.t1e.t2b.x1d.x2a, z1.t1e.t2b.x1d.x2b, z1.t1e.t2b.x1d.x2c, z1.t1e.t2b.x1d.x2d,
z1.t1e.t2b.x1d.x2e, z1.t1e.t2b.x1d.x2f, z1.t1e.t2b.x1d.x2g, z1.t1e.t2b.x1d.x2h,
z1.t1e.t2b.x1e.x2a, z1.t1e.t2b.x1e.x2b, z1.t1e.t2b.x1e.x2c, z1.t1e.t2b.x1e.x2d,
z1.t1e.t2b.x1e.x2e, z1.t1e.t2b.x1e.x2f, z1.t1e.t2b.x1e.x2g, z1.t1e.t2b.x1e.x2h,
z1.t1e.t2b.x1f.x2a, z1.t1e.t2b.x1f.x2b, z1.t1e.t2b.x1f.x2c, z1.t1e.t2b.x1f.x2d,
z1.t1e.t2b.x1f.x2e, z1.t1e.t2b.x1f.x2f, z1.t1e.t2b.x1f.x2g, z1.t1e.t2b.x1f.x2h,
z1.t1e.t2b.x1g.x2a, z1.t1e.t2b.x1g.x2b, z1.t1e.t2b.x1g.x2c, z1.t1e.t2b.x1g.x2d,
z1.t1e.t2b.x1g.x2e, z1.t1e.t2b.x1g.x2f, z1.t1e.t2b.x1g.x2g, z1.t1e.t2b.x1g.x2h,
z1.t1e.t2b.x1h.x2a, z1.t1e.t2b.x1h.x2b, z1.t1e.t2b.x1h.x2c, z1.t1e.t2b.x1h.x2d,
z1.t1e.t2b.x1h.x2e, z1.t1e.t2b.x1h.x2f, z1.t1e.t2b.x1h.x2g, z1.t1e.t2b.x1h.x2h,
z1.t1e.t2c.x1a.x2a, z1.t1e.t2c.x1a.x2b, z1.t1e.t2c.x1a.x2c, z1.t1e.t2c.x1a.x2d,
z1.t1e.t2c.x1a.x2e, z1.t1e.t2c.x1a.x2f, z1.t1e.t2c.x1a.x2g, z1.t1e.t2c.x1a.x2h,
z1.t1e.t2c.x1b.x2a, z1.t1e.t2c.x1b.x2b, z1.t1e.t2c.x1b.x2c, z1.t1e.t2c.x1b.x2d,
z1.t1e.t2c.x1b.x2e, z1.t1e.t2c.x1b.x2f, z1.t1e.t2c.x1b.x2g, z1.t1e.t2c.x1b.x2h,
z1.t1e.t2c.x1c.x2a, z1.t1e.t2c.x1c.x2b, z1.t1e.t2c.x1c.x2c, z1.t1e.t2c.x1c.x2d,
z1.t1e.t2c.x1c.x2e, z1.t1e.t2c.x1c.x2f, z1.t1e.t2c.x1c.x2g, z1.t1e.t2c.x1c.x2h,
z1.t1e.t2c.x1d.x2a, z1.t1e.t2c.x1d.x2b, z1.t1e.t2c.x1d.x2c, z1.t1e.t2c.x1d.x2d,

TABLE 30.6-continued

List of Compound Structures of Formula III z1.t1e.t2c.x1d.x2e, z1.t1e.t2c.x1d.x2f, z1.t1e.t2c.x1d.x2g,
z1.t1e.t2c.x1d.x2h,
z1.t1e.t2c.x1e.x2a, z1.t1e.t2c.x1e.x2b, z1.t1e.t2c.x1e.x2c,
z1.t1e.t2c.x1e.x2d,
z1.t1e.t2c.x1e.x2e, z1.t1e.t2c.x1e.x2f, z1.t1e.t2c.x1e.x2g,
z1.t1e.t2c.x1e.x2h,
z1.t1e.t2c.x1f.x2a, z1.t1e.t2c.x1f.x2b, z1.t1e.t2c.x1f.x2c,
z1.t1e.t2c.x1f.x2d,
z1.t1e.t2c.x1f.x2e, z1.t1e.t2c.x1f.x2f, z1.t1e.t2c.x1f.x2g,
z1.t1e.t2c.x1f.x2h,
z1.t1e.t2c.x1g.x2a, z1.t1e.t2c.x1g.x2b, z1.t1e.t2c.x1g.x2c,
z1.t1e.t2c.x1g.x2d,
z1.t1e.t2c.x1g.x2e, z1.t1e.t2c.x1g.x2f, z1.t1e.t2c.x1g.x2g,
z1.t1e.t2c.x1g.x2h,
z1.t1e.t2c.x1h.x2a, z1.t1e.t2c.x1h.x2b, z1.t1e.t2c.x1h.x2c,
z1.t1e.t2c.x1h.x2d,
z1.t1e.t2c.x1h.x2e, z1.t1e.t2c.x1h.x2f, z1.t1e.t2c.x1h.x2g,
z1.t1e.t2c.x1h.x2h,
z2.t1a.t2a.x1a.x2a, z2.t1a.t2a.x1a.x2b, z2.t1a.t2a.x1a.x2c,
z2.t1a.t2a.x1a.x2d,
z2.t1a.t2a.x1a.x2e, z2.t1a.t2a.x1a.x2f, z2.t1a.t2a.x1a.x2g,
z2.t1a.t2a.x1a.x2h,
z2.t1a.t2a.x1b.x2a, z2.t1a.t2a.x1b.x2b, z2.t1a.t2a.x1b.x2c,
z2.t1a.t2a.x1b.x2d,
z2.t1a.t2a.x1b.x2e, z2.t1a.t2a.x1b.x2f, z2.t1a.t2a.x1b.x2g,
z2.t1a.t2a.x1b.x2h,
z2.t1a.t2a.x1c.x2a, z2.t1a.t2a.x1c.x2b, z2.t1a.t2a.x1c.x2c,
z2.t1a.t2a.x1c.x2d,
z2.t1a.t2a.x1c.x2e, z2.t1a.t2a.x1c.x2f, z2.t1a.t2a.x1c.x2g,
z2.t1a.t2a.x1c.x2h,
z2.t1a.t2a.x1d.x2a, z2.t1a.t2a.x1d.x2b, z2.t1a.t2a.x1d.x2c,
z2.t1a.t2a.x1d.x2d,
z2.t1a.t2a.x1d.x2e, z2.t1a.t2a.x1d.x2f, z2.t1a.t2a.x1d.x2g,
z2.t1a.t2a.x1d.x2h,
z2.t1a.t2a.x1e.x2a, z2.t1a.t2a.x1e.x2b, z2.t1a.t2a.x1e.x2c,
z2.t1a.t2a.x1e.x2d,
z2.t1a.t2a.x1e.x2e, z2.t1a.t2a.x1e.x2f, z2.t1a.t2a.x1e.x2g,
z2.t1a.t2a.x1e.x2h,
z2.t1a.t2a.x1f.x2a, z2.t1a.t2a.x1f.x2b, z2.t1a.t2a.x1f.x2c,
z2.t1a.t2a.x1f.x2d,
z2.t1a.t2a.x1f.x2e, z2.t1a.t2a.x1f.x2f, z2.t1a.t2a.x1f.x2g,
z2.t1a.t2a.x1f.x2h,
z2.t1a.t2a.x1g.x2a, z2.t1a.t2a.x1g.x2b, z2.t1a.t2a.x1g.x2c,
z2.t1a.t2a.x1g.x2d,
z2.t1a.t2a.x1g.x2e, z2.t1a.t2a.x1g.x2f, z2.t1a.t2a.x1g.x2g,
z2.t1a.t2a.x1g.x2h,
z2.t1a.t2a.x1h.x2a, z2.t1a.t2a.x1h.x2b, z2.t1a.t2a.x1h.x2c,
z2.t1a.t2a.x1h.x2d,
z2.t1a.t2a.x1h.x2e, z2.t1a.t2a.x1h.x2f, z2.t1a.t2a.x1h.x2g,
z2.t1a.t2a.x1h.x2h,
z2.t1a.t2b.x1a.x2a, z2.t1a.t2b.x1a.x2b, z2.t1a.t2b.x1a.x2c,
z2.t1a.t2b.x1a.x2d,
z2.t1a.t2b.x1a.x2e, z2.t1a.t2b.x1a.x2f, z2.t1a.t2b.x1a.x2g,
z2.t1a.t2b.x1a.x2h,
z2.t1a.t2b.x1b.x2a, z2.t1a.t2b.x1b.x2b, z2.t1a.t2b.x1b.x2c,
z2.t1a.t2b.x1b.x2d,
z2.t1a.t2b.x1b.x2e, z2.t1a.t2b.x1b.x2f, z2.t1a.t2b.x1b.x2g,
z2.t1a.t2b.x1b.x2h,
z2.t1a.t2b.x1c.x2a, z2.t1a.t2b.x1c.x2b, z2.t1a.t2b.x1c.x2c,
z2.t1a.t2b.x1c.x2d,
z2.t1a.t2b.x1c.x2e, z2.t1a.t2b.x1c.x2f, z2.t1a.t2b.x1c.x2g,
z2.t1a.t2b.x1c.x2h,
z2.t1a.t2b.x1d.x2a, z2.t1a.t2b.x1d.x2b, z2.t1a.t2b.x1d.x2c,
z2.t1a.t2b.x1d.x2d,
z2.t1a.t2b.x1d.x2e, z2.t1a.t2b.x1d.x2f, z2.t1a.t2b.x1d.x2g,
z2.t1a.t2b.x1d.x2h,
z2.t1a.t2b.x1e.x2a, z2.t1a.t2b.x1e.x2b, z2.t1a.t2b.x1e.x2c,
z2.t1a.t2b.x1e.x2d,
z2.t1a.t2b.x1e.x2e, z2.t1a.t2b.x1e.x2f, z2.t1a.t2b.x1e.x2g,
z2.t1a.t2b.x1e.x2h,
z2.t1a.t2b.x1f.x2a, z2.t1a.t2b.x1f.x2b, z2.t1a.t2b.x1f.x2c,
z2.t1a.t2b.x1f.x2d,
z2.t1a.t2b.x1f.x2e, z2.t1a.t2b.x1f.x2f, z2.t1a.t2b.x1f.x2g,
z2.t1a.t2b.x1f.x2h,
z2.t1a.t2b.x1g.x2a, z2.t1a.t2b.x1g.x2b, z2.t1a.t2b.x1g.x2c,
z2.t1a.t2b.x1g.x2d,

TABLE 30.6-continued

List of Compound Structures of Formula III z2.t1a.t2b.x1g.x2e, z2.t1a.t2b.x1g.x2f, z2.t1a.t2b.x1g.x2g,
z2.t1a.t2b.x1g.x2h,
z2.t1a.t2b.x1h.x2a, z2.t1a.t2b.x1h.x2b, z2.t1a.t2b.x1h.x2c,
z2.t1a.t2b.x1h.x2d,
z2.t1a.t2b.x1h.x2e, z2.t1a.t2b.x1h.x2f, z2.t1a.t2b.x1h.x2g,
z2.t1a.t2b.x1h.x2h,
z2.t1a.t2c.x1a.x2a, z2.t1a.t2c.x1a.x2b, z2.t1a.t2c.x1a.x2c,
z2.t1a.t2c.x1a.x2d,
z2.t1a.t2c.x1a.x2e, z2.t1a.t2c.x1a.x2f, z2.t1a.t2c.x1a.x2g,
z2.t1a.t2c.x1a.x2h,
z2.t1a.t2c.x1b.x2a, z2.t1a.t2c.x1b.x2b, z2.t1a.t2c.x1b.x2c,
z2.t1a.t2c.x1b.x2d,
z2.t1a.t2c.x1b.x2e, z2.t1a.t2c.x1b.x2f, z2.t1a.t2c.x1b.x2g,
z2.t1a.t2c.x1b.x2h,
z2.t1a.t2c.x1c.x2a, z2.t1a.t2c.x1c.x2b, z2.t1a.t2c.x1c.x2c,
z2.t1a.t2c.x1c.x2d,
z2.t1a.t2c.x1c.x2e, z2.t1a.t2c.x1c.x2f, z2.t1a.t2c.x1c.x2g,
z2.t1a.t2c.x1c.x2h,
z2.t1a.t2c.x1d.x2a, z2.t1a.t2c.x1d.x2b, z2.t1a.t2c.x1d.x2c,
z2.t1a.t2c.x1d.x2d,
z2.t1a.t2c.x1d.x2e, z2.t1a.t2c.x1d.x2f, z2.t1a.t2c.x1d.x2g,
z2.t1a.t2c.x1d.x2h,
z2.t1a.t2c.x1e.x2a, z2.t1a.t2c.x1e.x2b, z2.t1a.t2c.x1e.x2c,
z2.t1a.t2c.x1e.x2d,
z2.t1a.t2c.x1e.x2e, z2.t1a.t2c.x1e.x2f, z2.t1a.t2c.x1e.x2g,
z2.t1a.t2c.x1e.x2h,
z2.t1a.t2c.x1f.x2a, z2.t1a.t2c.x1f.x2b, z2.t1a.t2c.x1f.x2c,
z2.t1a.t2c.x1f.x2d,
z2.t1a.t2c.x1f.x2e, z2.t1a.t2c.x1f.x2f, z2.t1a.t2c.x1f.x2g,
z2.t1a.t2c.x1f.x2h,
z2.t1a.t2c.x1g.x2a, z2.t1a.t2c.x1g.x2b, z2.t1a.t2c.x1g.x2c,
z2.t1a.t2c.x1g.x2d,
z2.t1a.t2c.x1g.x2e, z2.t1a.t2c.x1g.x2f, z2.t1a.t2c.x1g.x2g,
z2.t1a.t2c.x1g.x2h,
z2.t1a.t2c.x1h.x2a, z2.t1a.t2c.x1h.x2b, z2.t1a.t2c.x1h.x2c,
z2.t1a.t2c.x1h.x2d,
z2.t1a.t2c.x1h.x2e, z2.t1a.t2c.x1h.x2f, z2.t1a.t2c.x1h.x2g,
z2.t1a.t2c.x1h.x2h,
z2.t1b.t2a.x1a.x2a, z2.t1b.t2a.x1a.x2b, z2.t1b.t2a.x1a.x2c,
z2.t1b.t2a.x1a.x2d,
z2.t1b.t2a.x1a.x2e, z2.t1b.t2a.x1a.x2f, z2.t1b.t2a.x1a.x2g,
z2.t1b.t2a.x1a.x2h,
z2.t1b.t2a.x1b.x2a, z2.t1b.t2a.x1b.x2b, z2.t1b.t2a.x1b.x2c,
z2.t1b.t2a.x1b.x2d,
z2.t1b.t2a.x1b.x2e, z2.t1b.t2a.x1b.x2f, z2.t1b.t2a.x1b.x2g,
z2.t1b.t2a.x1b.x2h,
z2.t1b.t2a.x1c.x2a, z2.t1b.t2a.x1c.x2b, z2.t1b.t2a.x1c.x2c,
z2.t1b.t2a.x1c.x2d,
z2.t1b.t2a.x1c.x2e, z2.t1b.t2a.x1c.x2f, z2.t1b.t2a.x1c.x2g,
z2.t1b.t2a.x1c.x2h,
z2.t1b.t2a.x1d.x2a, z2.t1b.t2a.x1d.x2b, z2.t1b.t2a.x1d.x2c,
z2.t1b.t2a.x1d.x2d,
z2.t1b.t2a.x1d.x2e, z2.t1b.t2a.x1d.x2f, z2.t1b.t2a.x1d.x2g,
z2.t1b.t2a.x1d.x2h,
z2.t1b.t2a.x1e.x2a, z2.t1b.t2a.x1e.x2b, z2.t1b.t2a.x1e.x2c,
z2.t1b.t2a.x1e.x2d,
z2.t1b.t2a.x1e.x2e, z2.t1b.t2a.x1e.x2f, z2.t1b.t2a.x1e.x2g,
z2.t1b.t2a.x1e.x2h,
z2.t1b.t2a.x1f.x2a, z2.t1b.t2a.x1f.x2b, z2.t1b.t2a.x1f.x2c,
z2.t1b.t2a.x1f.x2d,
z2.t1b.t2a.x1f.x2e, z2.t1b.t2a.x1f.x2f, z2.t1b.t2a.x1f.x2g,
z2.t1b.t2a.x1f.x2h,
z2.t1b.t2a.x1g.x2a, z2.t1b.t2a.x1g.x2b, z2.t1b.t2a.x1g.x2c,
z2.t1b.t2a.x1g.x2d,
z2.t1b.t2a.x1g.x2e, z2.t1b.t2a.x1g.x2f, z2.t1b.t2a.x1g.x2g,
z2.t1b.t2a.x1g.x2h,
z2.t1b.t2a.x1h.x2a, z2.t1b.t2a.x1h.x2b, z2.t1b.t2a.x1h.x2c,
z2.t1b.t2a.x1h.x2d,
z2.t1b.t2a.x1h.x2e, z2.t1b.t2a.x1h.x2f, z2.t1b.t2a.x1h.x2g,
z2.t1b.t2a.x1h.x2h,
z2.t1b.t2b.x1a.x2a, z2.t1b.t2b.x1a.x2b, z2.t1b.t2b.x1a.x2c,
z2.t1b.t2b.x1a.x2d,
z2.t1b.t2b.x1a.x2e, z2.t1b.t2b.x1a.x2f, z2.t1b.t2b.x1a.x2g,
z2.t1b.t2b.x1a.x2h,
z2.t1b.t2b.x1b.x2a, z2.t1b.t2b.x1b.x2b, z2.t1b.t2b.x1b.x2c,
z2.t1b.t2b.x1b.x2d,
z2.t1b.t2b.x1b.x2e, z2.t1b.t2b.x1b.x2f, z2.t1b.t2b.x1b.x2g,
z2.t1b.t2b.x1b.x2h,

TABLE 30.6-continued
List of Compound Structures of Formula III z2.t1b.t2b.x1c.x2a, z2.t1b.t2b.x1c.x2b, z2.t1b.t2b.x1c.x2c,
z2.t1b.t2b.x1c.x2d,
z2.t1b.t2b.x1c.x2e, z2.t1b.t2b.x1c.x2f, z2.t1b.t2b.x1c.x2g,
z2.t1b.t2b.x1c.x2h,
z2.t1b.t2b.x1d.x2a, z2.t1b.t2b.x1d.x2b, z2.t1b.t2b.x1d.x2c,
z2.t1b.t2b.x1d.x2d,
z2.t1b.t2b.x1d.x2e, z2.t1b.t2b.x1d.x2f, z2.t1b.t2b.x1d.x2g,
z2.t1b.t2b.x1d.x2h,
z2.t1b.t2b.x1e.x2a, z2.t1b.t2b.x1e.x2b, z2.t1b.t2b.x1e.x2c,
z2.t1b.t2b.x1e.x2d,
z2.t1b.t2b.x1e.x2e, z2.t1b.t2b.x1e.x2f, z2.t1b.t2b.x1e.x2g,
z2.t1b.t2b.x1e.x2h,
z2.t1b.t2b.x1f.x2a, z2.t1b.t2b.x1f.x2b, z2.t1b.t2b.x1f.x2c,
z2.t1b.t2b.x1f.x2d,
z2.t1b.t2b.x1f.x2e, z2.t1b.t2b.x1f.x2f, z2.t1b.t2b.x1f.x2g,
z2.t1b.t2b.x1f.x2h,
z2.t1b.t2b.x1g.x2a, z2.t1b.t2b.x1g.x2b, z2.t1b.t2b.x1g.x2c,
z2.t1b.t2b.x1g.x2d,
z2.t1b.t2b.x1g.x2e, z2.t1b.t2b.x1g.x2f, z2.t1b.t2b.x1g.x2g,
z2.t1b.t2b.x1g.x2h,
z2.t1b.t2b.x1h.x2a, z2.t1b.t2b.x1h.x2b, z2.t1b.t2b.x1h.x2c,
z2.t1b.t2b.x1h.x2d,
z2.t1b.t2b.x1h.x2e, z2.t1b.t2b.x1h.x2f, z2.t1b.t2b.x1h.x2g,
z2.t1b.t2b.x1h.x2h,
z2.t1b.t2c.x1a.x2a, z2.t1b.t2c.x1a.x2b, z2.t1b.t2c.x1a.x2c,
z2.t1b.t2c.x1a.x2d,
z2.t1b.t2c.x1a.x2e, z2.t1b.t2c.x1a.x2f, z2.t1b.t2c.x1a.x2g,
z2.t1b.t2c.x1a.x2h,
z2.t1b.t2c.x1b.x2a, z2.t1b.t2c.x1b.x2b, z2.t1b.t2c.x1b.x2c,
z2.t1b.t2c.x1b.x2d,
z2.t1b.t2c.x1b.x2e, z2.t1b.t2c.x1b.x2f, z2.t1b.t2c.x1b.x2g,
z2.t1b.t2c.x1b.x2h,
z2.t1b.t2c.x1c.x2a, z2.t1b.t2c.x1c.x2b, z2.t1b.t2c.x1c.x2c,
z2.t1b.t2c.x1c.x2d,
z2.t1b.t2c.x1c.x2e, z2.t1b.t2c.x1c.x2f, z2.t1b.t2c.x1c.x2g,
z2.t1b.t2c.x1c.x2h,
z2.t1b.t2c.x1d.x2a, z2.t1b.t2c.x1d.x2b, z2.t1b.t2c.x1d.x2c,
z2.t1b.t2c.x1d.x2d,
z2.t1b.t2c.x1d.x2e, z2.t1b.t2c.x1d.x2f, z2.t1b.t2c.x1d.x2g,
z2.t1b.t2c.x1d.x2h,
z2.t1b.t2c.x1e.x2a, z2.t1b.t2c.x1e.x2b, z2.t1b.t2c.x1e.x2c,
z2.t1b.t2c.x1e.x2d,
z2.t1b.t2c.x1e.x2e, z2.t1b.t2c.x1e.x2f, z2.t1b.t2c.x1e.x2g,
z2.t1b.t2c.x1e.x2h,
z2.t1b.t2c.x1f.x2a, z2.t1b.t2c.x1f.x2b, z2.t1b.t2c.x1f.x2c,
z2.t1b.t2c.x1f.x2d,
z2.t1b.t2c.x1f.x2e, z2.t1b.t2c.x1f.x2f, z2.t1b.t2c.x1f.x2g,
z2.t1b.t2c.x1f.x2h,
z2.t1b.t2c.x1g.x2a, z2.t1b.t2c.x1g.x2b, z2.t1b.t2c.x1g.x2c,
z2.t1b.t2c.x1g.x2d,
z2.t1b.t2c.x1g.x2e, z2.t1b.t2c.x1g.x2f, z2.t1b.t2c.x1g.x2g,
z2.t1b.t2c.x1g.x2h,
z2.t1b.t2c.x1h.x2a, z2.t1b.t2c.x1h.x2b, z2.t1b.t2c.x1h.x2c,
z2.t1b.t2c.x1h.x2d,
z2.t1b.t2c.x1h.x2e, z2.t1b.t2c.x1h.x2f, z2.t1b.t2c.x1h.x2g,
z2.t1b.t2c.x1h.x2h,
z2.t1c.t2a.x1a.x2a, z2.t1c.t2a.x1a.x2b, z2.t1c.t2a.x1a.x2c,
z2.t1c.t2a.x1a.x2d,
z2.t1c.t2a.x1a.x2e, z2.t1c.t2a.x1a.x2f, z2.t1c.t2a.x1a.x2g,
z2.t1c.t2a.x1a.x2h,
z2.t1c.t2a.x1b.x2a, z2.t1c.t2a.x1b.x2b, z2.t1c.t2a.x1b.x2c,
z2.t1c.t2a.x1b.x2d,
z2.t1c.t2a.x1b.x2e, z2.t1c.t2a.x1b.x2f, z2.t1c.t2a.x1b.x2g,
z2.t1c.t2a.x1b.x2h,
z2.t1c.t2a.x1c.x2a, z2.t1c.t2a.x1c.x2b, z2.t1c.t2a.x1c.x2c,
z2.t1c.t2a.x1c.x2d,
z2.t1c.t2a.x1c.x2e, z2.t1c.t2a.x1c.x2f, z2.t1c.t2a.x1c.x2g,
z2.t1c.t2a.x1c.x2h,
z2.t1c.t2a.x1d.x2a, z2.t1c.t2a.x1d.x2b, z2.t1c.t2a.x1d.x2c,
z2.t1c.t2a.x1d.x2d,
z2.t1c.t2a.x1d.x2e, z2.t1c.t2a.x1d.x2f, z2.t1c.t2a.x1d.x2g,
z2.t1c.t2a.x1d.x2h,
z2.t1c.t2a.x1e.x2a, z2.t1c.t2a.x1e.x2b, z2.t1c.t2a.x1e.x2c,
z2.t1c.t2a.x1e.x2d,
z2.t1c.t2a.x1e.x2e, z2.t1c.t2a.x1e.x2f, z2.t1c.t2a.x1e.x2g,
z2.t1c.t2a.x1e.x2h,
z2.t1c.t2a.x1f.x2a, z2.t1c.t2a.x1f.x2b, z2.t1c.t2a.x1f.x2c,
z2.t1c.t2a.x1f.x2d,
z2.t1c.t2a.x1f.x2e, z2.t1c.t2a.x1f.x2f, z2.t1c.t2a.x1f.x2g,
z2.t1c.t2a.x1f.x2h,
z2.t1c.t2a.x1g.x2a, z2.t1c.t2a.x1g.x2b, z2.t1c.t2a.x1g.x2c,
z2.t1c.t2a.x1g.x2d,
z2.t1c.t2a.x1g.x2e, z2.t1c.t2a.x1g.x2f, z2.t1c.t2a.x1g.x2g,
z2.t1c.t2a.x1g.x2h,
z2.t1c.t2a.x1h.x2a, z2.t1c.t2a.x1h.x2b, z2.t1c.t2a.x1h.x2c,
z2.t1c.t2a.x1h.x2d,
z2.t1c.t2a.x1h.x2e, z2.t1c.t2a.x1h.x2f, z2.t1c.t2a.x1h.x2g,
z2.t1c.t2a.x1h.x2h,
z2.t1c.t2b.x1a.x2a, z2.t1c.t2b.x1a.x2b, z2.t1c.t2b.x1a.x2c,
z2.t1c.t2b.x1a.x2d,
z2.t1c.t2b.x1a.x2e, z2.t1c.t2b.x1a.x2f, z2.t1c.t2b.x1a.x2g,
z2.t1c.t2b.x1a.x2h,
z2.t1c.t2b.x1b.x2a, z2.t1c.t2b.x1b.x2b, z2.t1c.t2b.x1b.x2c,
z2.t1c.t2b.x1b.x2d,
z2.t1c.t2b.x1b.x2e, z2.t1c.t2b.x1b.x2f, z2.t1c.t2b.x1b.x2g,
z2.t1c.t2b.x1b.x2h,
z2.t1c.t2b.x1c.x2a, z2.t1c.t2b.x1c.x2b, z2.t1c.t2b.x1c.x2c,
z2.t1c.t2b.x1c.x2d,
z2.t1c.t2b.x1c.x2e, z2.t1c.t2b.x1c.x2f, z2.t1c.t2b.x1c.x2g,
z2.t1c.t2b.x1c.x2h,
z2.t1c.t2b.x1d.x2a, z2.t1c.t2b.x1d.x2b, z2.t1c.t2b.x1d.x2c,
z2.t1c.t2b.x1d.x2d,
z2.t1c.t2b.x1d.x2e, z2.t1c.t2b.x1d.x2f, z2.t1c.t2b.x1d.x2g,
z2.t1c.t2b.x1d.x2h,
z2.t1c.t2b.x1e.x2a, z2.t1c.t2b.x1e.x2b, z2.t1c.t2b.x1e.x2c,
z2.t1c.t2b.x1e.x2d,
z2.t1c.t2b.x1e.x2e, z2.t1c.t2b.x1e.x2f, z2.t1c.t2b.x1e.x2g,
z2.t1c.t2b.x1e.x2h,
z2.t1c.t2b.x1f.x2a, z2.t1c.t2b.x1f.x2b, z2.t1c.t2b.x1f.x2c,
z2.t1c.t2b.x1f.x2d,
z2.t1c.t2b.x1f.x2e, z2.t1c.t2b.x1f.x2f, z2.t1c.t2b.x1f.x2g,
z2.t1c.t2b.x1f.x2h,
z2.t1c.t2b.x1g.x2a, z2.t1c.t2b.x1g.x2b, z2.t1c.t2b.x1g.x2c,
z2.t1c.t2b.x1g.x2d,
z2.t1c.t2b.x1g.x2e, z2.t1c.t2b.x1g.x2f, z2.t1c.t2b.x1g.x2g,
z2.t1c.t2b.x1g.x2h,
z2.t1c.t2b.x1h.x2a, z2.t1c.t2b.x1h.x2b, z2.t1c.t2b.x1h.x2c,
z2.t1c.t2b.x1h.x2d,
z2.t1c.t2b.x1h.x2e, z2.t1c.t2b.x1h.x2f, z2.t1c.t2b.x1h.x2g,
z2.t1c.t2b.x1h.x2h,
z2.t1c.t2c.x1a.x2a, z2.t1c.t2c.x1a.x2b, z2.t1c.t2c.x1a.x2c,
z2.t1c.t2c.x1a.x2d,
z2.t1c.t2c.x1a.x2e, z2.t1c.t2c.x1a.x2f, z2.t1c.t2c.x1a.x2g,
z2.t1c.t2c.x1a.x2h,
z2.t1c.t2c.x1b.x2a, z2.t1c.t2c.x1b.x2b, z2.t1c.t2c.x1b.x2c,
z2.t1c.t2c.x1b.x2d,
z2.t1c.t2c.x1b.x2e, z2.t1c.t2c.x1b.x2f, z2.t1c.t2c.x1b.x2g,
z2.t1c.t2c.x1b.x2h,
z2.t1c.t2c.x1c.x2a, z2.t1c.t2c.x1c.x2b, z2.t1c.t2c.x1c.x2c,
z2.t1c.t2c.x1c.x2d,
z2.t1c.t2c.x1c.x2e, z2.t1c.t2c.x1c.x2f, z2.t1c.t2c.x1c.x2g,
z2.t1c.t2c.x1c.x2h,
z2.t1c.t2c.x1d.x2a, z2.t1c.t2c.x1d.x2b, z2.t1c.t2c.x1d.x2c,
z2.t1c.t2c.x1d.x2d,
z2.t1c.t2c.x1d.x2e, z2.t1c.t2c.x1d.x2f, z2.t1c.t2c.x1d.x2g,
z2.t1c.t2c.x1d.x2h,
z2.t1c.t2c.x1e.x2a, z2.t1c.t2c.x1e.x2b, z2.t1c.t2c.x1e.x2c,
z2.t1c.t2c.x1e.x2d,
z2.t1c.t2c.x1e.x2e, z2.t1c.t2c.x1e.x2f, z2.t1c.t2c.x1e.x2g,
z2.t1c.t2c.x1e.x2h,
z2.t1c.t2c.x1f.x2a, z2.t1c.t2c.x1f.x2b, z2.t1c.t2c.x1f.x2c,
z2.t1c.t2c.x1f.x2d,
z2.t1c.t2c.x1f.x2e, z2.t1c.t2c.x1f.x2f, z2.t1c.t2c.x1f.x2g,
z2.t1c.t2c.x1f.x2h,
z2.t1c.t2c.x1g.x2a, z2.t1c.t2c.x1g.x2b, z2.t1c.t2c.x1g.x2c,
z2.t1c.t2c.x1g.x2d,
z2.t1c.t2c.x1g.x2e, z2.t1c.t2c.x1g.x2f, z2.t1c.t2c.x1g.x2g,
z2.t1c.t2c.x1g.x2h,
z2.t1c.t2c.x1h.x2a, z2.t1c.t2c.x1h.x2b, z2.t1c.t2c.x1h.x2c,
z2.t1c.t2c.x1h.x2d,
z2.t1c.t2c.x1h.x2e, z2.t1c.t2c.x1h.x2f, z2.t1c.t2c.x1h.x2g,
z2.t1c.t2c.x1h.x2h,
z2.t1d.t2a.x1a.x2a, z2.t1d.t2a.x1a.x2b, z2.t1d.t2a.x1a.x2c,
z2.t1d.t2a.x1a.x2d, TABLE 30.6-continued List of Compound Structures of Formula III z2.t1d.t2a.x1a.x2e, z2.t1d.t2a.x1a.x2f, z2.t1d.t2a.x1a.x2g, z2.t1d.t2a.x1a.x2h,
z2.t1d.t2a.x1b.x2a, z2.t1d.t2a.x1b.x2b, z2.t1d.t2a.x1b.x2c, z2.t1d.t2a.x1b.x2d,
z2.t1d.t2a.x1b.x2e, z2.t1d.t2a.x1b.x2f, z2.t1d.t2a.x1b.x2g, z2.t1d.t2a.x1b.x2h,
z2.t1d.t2a.x1c.x2a, z2.t1d.t2a.x1c.x2b, z2.t1d.t2a.x1c.x2c, z2.t1d.t2a.x1c.x2d,
z2.t1d.t2a.x1c.x2e, z2.t1d.t2a.x1c.x2f, z2.t1d.t2a.x1c.x2g, z2.t1d.t2a.x1c.x2h,
z2.t1d.t2a.x1d.x2a, z2.t1d.t2a.x1d.x2b, z2.t1d.t2a.x1d.x2c, z2.t1d.t2a.x1d.x2d,
z2.t1d.t2a.x1d.x2e, z2.t1d.t2a.x1d.x2f, z2.t1d.t2a.x1d.x2g, z2.t1d.t2a.x1d.x2h,
z2.t1d.t2a.x1e.x2a, z2.t1d.t2a.x1e.x2b, z2.t1d.t2a.x1e.x2c, z2.t1d.t2a.x1e.x2d,
z2.t1d.t2a.x1e.x2e, z2.t1d.t2a.x1e.x2f, z2.t1d.t2a.x1e.x2g, z2.t1d.t2a.x1e.x2h,
z2.t1d.t2a.x1f.x2a, z2.t1d.t2a.x1f.x2b, z2.t1d.t2a.x1f.x2c, z2.t1d.t2a.x1f.x2d,
z2.t1d.t2a.x1f.x2e, z2.t1d.t2a.x1f.x2f, z2.t1d.t2a.x1f.x2g, z2.t1d.t2a.x1f.x2h,
z2.t1d.t2a.x1g.x2a, z2.t1d.t2a.x1g.x2b, z2.t1d.t2a.x1g.x2c, z2.t1d.t2a.x1g.x2d,
z2.t1d.t2a.x1g.x2e, z2.t1d.t2a.x1g.x2f, z2.t1d.t2a.x1g.x2g, z2.t1d.t2a.x1g.x2h,
z2.t1d.t2a.x1h.x2a, z2.t1d.t2a.x1h.x2b, z2.t1d.t2a.x1h.x2c, z2.t1d.t2a.x1h.x2d,
z2.t1d.t2a.x1h.x2e, z2.t1d.t2a.x1h.x2f, z2.t1d.t2a.x1h.x2g, z2.t1d.t2a.x1h.x2h,
z2.t1d.t2b.x1a.x2a, z2.t1d.t2b.x1a.x2b, z2.t1d.t2b.x1a.x2c, z2.t1d.t2b.x1a.x2d,
z2.t1d.t2b.x1a.x2e, z2.t1d.t2b.x1a.x2f, z2.t1d.t2b.x1a.x2g, z2.t1d.t2b.x1a.x2h,
z2.t1d.t2b.x1b.x2a, z2.t1d.t2b.x1b.x2b, z2.t1d.t2b.x1b.x2c, z2.t1d.t2b.x1b.x2d,
z2.t1d.t2b.x1b.x2e, z2.t1d.t2b.x1b.x2f, z2.t1d.t2b.x1b.x2g, z2.t1d.t2b.x1b.x2h,
z2.t1d.t2b.x1c.x2a, z2.t1d.t2b.x1c.x2b, z2.t1d.t2b.x1c.x2c, z2.t1d.t2b.x1c.x2d,
z2.t1d.t2b.x1c.x2e, z2.t1d.t2b.x1c.x2f, z2.t1d.t2b.x1c.x2g, z2.t1d.t2b.x1c.x2h,
z2.t1d.t2b.x1d.x2a, z2.t1d.t2b.x1d.x2b, z2.t1d.t2b.x1d.x2c, z2.t1d.t2b.x1d.x2d,
z2.t1d.t2b.x1d.x2e, z2.t1d.t2b.x1d.x2f, z2.t1d.t2b.x1d.x2g, z2.t1d.t2b.x1d.x2h,
z2.t1d.t2b.x1e.x2a, z2.t1d.t2b.x1e.x2b, z2.t1d.t2b.x1e.x2c, z2.t1d.t2b.x1e.x2d,
z2.t1d.t2b.x1e.x2e, z2.t1d.t2b.x1e.x2f, z2.t1d.t2b.x1e.x2g, z2.t1d.t2b.x1e.x2h,
z2.t1d.t2b.x1f.x2a, z2.t1d.t2b.x1f.x2b, z2.t1d.t2b.x1f.x2c, z2.t1d.t2b.x1f.x2d,
z2.t1d.t2b.x1f.x2e, z2.t1d.t2b.x1f.x2f, z2.t1d.t2b.x1f.x2g, z2.t1d.t2b.x1f.x2h,
z2.t1d.t2b.x1g.x2a, z2.t1d.t2b.x1g.x2b, z2.t1d.t2b.x1g.x2c, z2.t1d.t2b.x1g.x2d,
z2.t1d.t2b.x1g.x2e, z2.t1d.t2b.x1g.x2f, z2.t1d.t2b.x1g.x2g, z2.t1d.t2b.x1g.x2h,
z2.t1d.t2b.x1h.x2a, z2.t1d.t2b.x1h.x2b, z2.t1d.t2b.x1h.x2c, z2.t1d.t2b.x1h.x2d,
z2.t1d.t2b.x1h.x2e, z2.t1d.t2b.x1h.x2f, z2.t1d.t2b.x1h.x2g, z2.t1d.t2b.x1h.x2h,
z2.t1d.t2c.x1a.x2a, z2.t1d.t2c.x1a.x2b, z2.t1d.t2c.x1a.x2c, z2.t1d.t2c.x1a.x2d,
z2.t1d.t2c.x1a.x2e, z2.t1d.t2c.x1a.x2f, z2.t1d.t2c.x1a.x2g, z2.t1d.t2c.x1a.x2h,
z2.t1d.t2c.x1b.x2a, z2.t1d.t2c.x1b.x2b, z2.t1d.t2c.x1b.x2c, z2.t1d.t2c.x1b.x2d,
z2.t1d.t2c.x1b.x2e, z2.t1d.t2c.x1b.x2f, z2.t1d.t2c.x1b.x2g, z2.t1d.t2c.x1b.x2h,
z2.t1d.t2c.x1c.x2a, z2.t1d.t2c.x1c.x2b, z2.t1d.t2c.x1c.x2c, z2.t1d.t2c.x1c.x2d,
z2.t1d.t2c.x1c.x2e, z2.t1d.t2c.x1c.x2f, z2.t1d.t2c.x1c.x2g, z2.t1d.t2c.x1c.x2h,
z2.t1d.t2c.x1d.x2a, z2.t1d.t2c.x1d.x2b, z2.t1d.t2c.x1d.x2c, z2.t1d.t2c.x1d.x2d,
z2.t1d.t2c.x1d.x2e, z2.t1d.t2c.x1d.x2f, z2.t1d.t2c.x1d.x2g, z2.t1d.t2c.x1d.x2h,
z2.t1d.t2c.x1e.x2a, z2.t1d.t2c.x1e.x2b, z2.t1d.t2c.x1e.x2c, z2.t1d.t2c.x1e.x2d,
z2.t1d.t2c.x1e.x2e, z2.t1d.t2c.x1e.x2f, z2.t1d.t2c.x1e.x2g, z2.t1d.t2c.x1e.x2h,
z2.t1d.t2c.x1f.x2a, z2.t1d.t2c.x1f.x2b, z2.t1d.t2c.x1f.x2c, z2.t1d.t2c.x1f.x2d,
z2.t1d.t2c.x1f.x2e, z2.t1d.t2c.x1f.x2f, z2.t1d.t2c.x1f.x2g, z2.t1d.t2c.x1f.x2h,
z2.t1d.t2c.x1g.x2a, z2.t1d.t2c.x1g.x2b, z2.t1d.t2c.x1g.x2c, z2.t1d.t2c.x1g.x2d,
z2.t1d.t2c.x1g.x2e, z2.t1d.t2c.x1g.x2f, z2.t1d.t2c.x1g.x2g, z2.t1d.t2c.x1g.x2h,
z2.t1d.t2c.x1h.x2a, z2.t1d.t2c.x1h.x2b, z2.t1d.t2c.x1h.x2c, z2.t1d.t2c.x1h.x2d,
z2.t1d.t2c.x1h.x2e, z2.t1d.t2c.x1h.x2f, z2.t1d.t2c.x1h.x2g, z2.t1d.t2c.x1h.x2h,
z2.t1e.t2a.x1a.x2a, z2.t1e.t2a.x1a.x2b, z2.t1e.t2a.x1a.x2c, z2.t1e.t2a.x1a.x2d,
z2.t1e.t2a.x1a.x2e, z2.t1e.t2a.x1a.x2f, z2.t1e.t2a.x1a.x2g, z2.t1e.t2a.x1a.x2h,
z2.t1e.t2a.x1b.x2a, z2.t1e.t2a.x1b.x2b, z2.t1e.t2a.x1b.x2c, z2.t1e.t2a.x1b.x2d,
z2.t1e.t2a.x1b.x2e, z2.t1e.t2a.x1b.x2f, z2.t1e.t2a.x1b.x2g, z2.t1e.t2a.x1b.x2h,
z2.t1e.t2a.x1c.x2a, z2.t1e.t2a.x1c.x2b, z2.t1e.t2a.x1c.x2c, z2.t1e.t2a.x1c.x2d,
z2.t1e.t2a.x1c.x2e, z2.t1e.t2a.x1c.x2f, z2.t1e.t2a.x1c.x2g, z2.t1e.t2a.x1c.x2h,
z2.t1e.t2a.x1d.x2a, z2.t1e.t2a.x1d.x2b, z2.t1e.t2a.x1d.x2c, z2.t1e.t2a.x1d.x2d,
z2.t1e.t2a.x1d.x2e, z2.t1e.t2a.x1d.x2f, z2.t1e.t2a.x1d.x2g, z2.t1e.t2a.x1d.x2h,
z2.t1e.t2a.x1e.x2a, z2.t1e.t2a.x1e.x2b, z2.t1e.t2a.x1e.x2c, z2.t1e.t2a.x1e.x2d,
z2.t1e.t2a.x1e.x2e, z2.t1e.t2a.x1e.x2f, z2.t1e.t2a.x1e.x2g, z2.t1e.t2a.x1e.x2h,
z2.t1e.t2a.x1f.x2a, z2.t1e.t2a.x1f.x2b, z2.t1e.t2a.x1f.x2c, z2.t1e.t2a.x1f.x2d,
z2.t1e.t2a.x1f.x2e, z2.t1e.t2a.x1f.x2f, z2.t1e.t2a.x1f.x2g, z2.t1e.t2a.x1f.x2h,
z2.t1e.t2a.x1g.x2a, z2.t1e.t2a.x1g.x2b, z2.t1e.t2a.x1g.x2c, z2.t1e.t2a.x1g.x2d,
z2.t1e.t2a.x1g.x2e, z2.t1e.t2a.x1g.x2f, z2.t1e.t2a.x1g.x2g, z2.t1e.t2a.x1g.x2h,
z2.t1e.t2a.x1h.x2a, z2.t1e.t2a.x1h.x2b, z2.t1e.t2a.x1h.x2c, z2.t1e.t2a.x1h.x2d,
z2.t1e.t2a.x1h.x2e, z2.t1e.t2a.x1h.x2f, z2.t1e.t2a.x1h.x2g, z2.t1e.t2a.x1h.x2h,
z2.t1e.t2b.x1a.x2a, z2.t1e.t2b.x1a.x2b, z2.t1e.t2b.x1a.x2c, z2.t1e.t2b.x1a.x2d,
z2.t1e.t2b.x1a.x2e, z2.t1e.t2b.x1a.x2f, z2.t1e.t2b.x1a.x2g, z2.t1e.t2b.x1a.x2h,
z2.t1e.t2b.x1b.x2a, z2.t1e.t2b.x1b.x2b, z2.t1e.t2b.x1b.x2c, z2.t1e.t2b.x1b.x2d,
z2.t1e.t2b.x1b.x2e, z2.t1e.t2b.x1b.x2f, z2.t1e.t2b.x1b.x2g, z2.t1e.t2b.x1b.x2h,
z2.t1e.t2b.x1c.x2a, z2.t1e.t2b.x1c.x2b, z2.t1e.t2b.x1c.x2c, z2.t1e.t2b.x1c.x2d,
z2.t1e.t2b.x1c.x2e, z2.t1e.t2b.x1c.x2f, z2.t1e.t2b.x1c.x2g, z2.t1e.t2b.x1c.x2h,
z2.t1e.t2b.x1d.x2a, z2.t1e.t2b.x1d.x2b, z2.t1e.t2b.x1d.x2c, z2.t1e.t2b.x1d.x2d,
z2.t1e.t2b.x1d.x2e, z2.t1e.t2b.x1d.x2f, z2.t1e.t2b.x1d.x2g, z2.t1e.t2b.x1d.x2h,
z2.t1e.t2b.x1e.x2a, z2.t1e.t2b.x1e.x2b, z2.t1e.t2b.x1e.x2c, z2.t1e.t2b.x1e.x2d,
z2.t1e.t2b.x1e.x2e, z2.t1e.t2b.x1e.x2f, z2.t1e.t2b.x1e.x2g, z2.t1e.t2b.x1e.x2h,
z2.t1e.t2b.x1f.x2a, z2.t1e.t2b.x1f.x2b, z2.t1e.t2b.x1f.x2c, z2.t1e.t2b.x1f.x2d,
z2.t1e.t2b.x1f.x2e, z2.t1e.t2b.x1f.x2f, z2.t1e.t2b.x1f.x2g, z2.t1e.t2b.x1f.x2h,
z2.t1e.t2b.x1g.x2a, z2.t1e.t2b.x1g.x2b, z2.t1e.t2b.x1g.x2c, z2.t1e.t2b.x1g.x2d,
z2.t1e.t2b.x1g.x2e, z2.t1e.t2b.x1g.x2f, z2.t1e.t2b.x1g.x2g, z2.t1e.t2b.x1g.x2h,

TABLE 30.6-continued

List of Compound Structures of Formula III z2.t1e.t2b.x1h.x2a, z2.t1e.t2b.x1h.x2b, z2.t1e.t2b.x1h.x2c, z2.t1e.t2b.x1h.x2d,
z2.t1e.t2b.x1h.x2e, z2.t1e.t2b.x1h.x2f, z2.t1e.t2b.x1h.x2g, z2.t1e.t2b.x1h.x2h,
z2.t1e.t2c.x1a.x2a, z2.t1e.t2c.x1a.x2b, z2.t1e.t2c.x1a.x2c, z2.t1e.t2c.x1a.x2d,
z2.t1e.t2c.x1a.x2e, z2.t1e.t2c.x1a.x2f, z2.t1e.t2c.x1a.x2g, z2.t1e.t2c.x1a.x2h,
z2.t1e.t2c.x1b.x2a, z2.t1e.t2c.x1b.x2b, z2.t1e.t2c.x1b.x2c, z2.t1e.t2c.x1b.x2d,
z2.t1e.t2c.x1b.x2e, z2.t1e.t2c.x1b.x2f, z2.t1e.t2c.x1b.x2g, z2.t1e.t2c.x1b.x2h,
z2.t1e.t2c.x1c.x2a, z2.t1e.t2c.x1c.x2b, z2.t1e.t2c.x1c.x2c, z2.t1e.t2c.x1c.x2d,
z2.t1e.t2c.x1c.x2e, z2.t1e.t2c.x1c.x2f, z2.t1e.t2c.x1c.x2g, z2.t1e.t2c.x1c.x2h,
z2.t1e.t2c.x1d.x2a, z2.t1e.t2c.x1d.x2b, z2.t1e.t2c.x1d.x2c, z2.t1e.t2c.x1d.x2d,
z2.t1e.t2c.x1d.x2e, z2.t1e.t2c.x1d.x2f, z2.t1e.t2c.x1d.x2g, z2.t1e.t2c.x1d.x2h,
z2.t1e.t2c.x1e.x2a, z2.t1e.t2c.x1e.x2b, z2.t1e.t2c.x1e.x2c, z2.t1e.t2c.x1e.x2d,
z2.t1e.t2c.x1e.x2e, z2.t1e.t2c.x1e.x2f, z2.t1e.t2c.x1e.x2g, z2.t1e.t2c.x1e.x2h,
z2.t1e.t2c.x1f.x2a, z2.t1e.t2c.x1f.x2b, z2.t1e.t2c.x1f.x2c, z2.t1e.t2c.x1f.x2d,
z2.t1e.t2c.x1f.x2e, z2.t1e.t2c.x1f.x2f, z2.t1e.t2c.x1f.x2g, z2.t1e.t2c.x1f.x2h,
z2.t1e.t2c.x1g.x2a, z2.t1e.t2c.x1g.x2b, z2.t1e.t2c.x1g.x2c, z2.t1e.t2c.x1g.x2d,
z2.t1e.t2c.x1g.x2e, z2.t1e.t2c.x1g.x2f, z2.t1e.t2c.x1g.x2g, z2.t1e.t2c.x1g.x2h,
z2.t1e.t2c.x1h.x2a, z2.t1e.t2c.x1h.x2b, z2.t1e.t2c.x1h.x2c, z2.t1e.t2c.x1h.x2d,
z2.t1e.t2c.x1h.x2e, z2.t1e.t2c.x1h.x2f, z2.t1e.t2c.x1h.x2g, z2.t1e.t2c.x1h.x2h,
z3.t1a.t2a.x1a.x2a, z3.t1a.t2a.x1a.x2b, z3.t1a.t2a.x1a.x2c, z3.t1a.t2a.x1a.x2d,
z3.t1a.t2a.x1a.x2e, z3.t1a.t2a.x1a.x2f, z3.t1a.t2a.x1a.x2g, z3.t1a.t2a.x1a.x2h,
z3.t1a.t2a.x1b.x2a, z3.t1a.t2a.x1b.x2b, z3.t1a.t2a.x1b.x2c, z3.t1a.t2a.x1b.x2d,
z3.t1a.t2a.x1b.x2e, z3.t1a.t2a.x1b.x2f, z3.t1a.t2a.x1b.x2g, z3.t1a.t2a.x1b.x2h,
z3.t1a.t2a.x1c.x2a, z3.t1a.t2a.x1c.x2b, z3.t1a.t2a.x1c.x2c, z3.t1a.t2a.x1c.x2d,
z3.t1a.t2a.x1c.x2e, z3.t1a.t2a.x1c.x2f, z3.t1a.t2a.x1c.x2g, z3.t1a.t2a.x1c.x2h,
z3.t1a.t2a.x1d.x2a, z3.t1a.t2a.x1d.x2b, z3.t1a.t2a.x1d.x2c, z3.t1a.t2a.x1d.x2d,
z3.t1a.t2a.x1d.x2e, z3.t1a.t2a.x1d.x2f, z3.t1a.t2a.x1d.x2g, z3.t1a.t2a.x1d.x2h,
z3.t1a.t2a.x1e.x2a, z3.t1a.t2a.x1e.x2b, z3.t1a.t2a.x1e.x2c, z3.t1a.t2a.x1e.x2d,
z3.t1a.t2a.x1e.x2e, z3.t1a.t2a.x1e.x2f, z3.t1a.t2a.x1e.x2g, z3.t1a.t2a.x1e.x2h,
z3.t1a.t2a.x1f.x2a, z3.t1a.t2a.x1f.x2b, z3.t1a.t2a.x1f.x2c, z3.t1a.t2a.x1f.x2d,
z3.t1a.t2a.x1f.x2e, z3.t1a.t2a.x1f.x2f, z3.t1a.t2a.x1f.x2g, z3.t1a.t2a.x1f.x2h,
z3.t1a.t2a.x1g.x2a, z3.t1a.t2a.x1g.x2b, z3.t1a.t2a.x1g.x2c, z3.t1a.t2a.x1g.x2d,
z3.t1a.t2a.x1g.x2e, z3.t1a.t2a.x1g.x2f, z3.t1a.t2a.x1g.x2g, z3.t1a.t2a.x1g.x2h,
z3.t1a.t2a.x1h.x2a, z3.t1a.t2a.x1h.x2b, z3.t1a.t2a.x1h.x2c, z3.t1a.t2a.x1h.x2d,
z3.t1a.t2a.x1h.x2e, z3.t1a.t2a.x1h.x2f, z3.t1a.t2a.x1h.x2g, z3.t1a.t2a.x1h.x2h,
z3.t1a.t2b.x1a.x2a, z3.t1a.t2b.x1a.x2b, z3.t1a.t2b.x1a.x2c, z3.t1a.t2b.x1a.x2d,
z3.t1a.t2b.x1a.x2e, z3.t1a.t2b.x1a.x2f, z3.t1a.t2b.x1a.x2g, z3.t1a.t2b.x1a.x2h,
z3.t1a.t2b.x1b.x2a, z3.t1a.t2b.x1b.x2b, z3.t1a.t2b.x1b.x2c, z3.t1a.t2b.x1b.x2d,
z3.t1a.t2b.x1b.x2e, z3.t1a.t2b.x1b.x2f, z3.t1a.t2b.x1b.x2g, z3.t1a.t2b.x1b.x2h,
z3.t1a.t2b.x1c.x2a, z3.t1a.t2b.x1c.x2b, z3.t1a.t2b.x1c.x2c, z3.t1a.t2b.x1c.x2d,
z3.t1a.t2b.x1c.x2e, z3.t1a.t2b.x1c.x2f, z3.t1a.t2b.x1c.x2g, z3.t1a.t2b.x1c.x2h,
z3.t1a.t2b.x1d.x2a, z3.t1a.t2b.x1d.x2b, z3.t1a.t2b.x1d.x2c, z3.t1a.t2b.x1d.x2d,
z3.t1a.t2b.x1d.x2e, z3.t1a.t2b.x1d.x2f, z3.t1a.t2b.x1d.x2g, z3.t1a.t2b.x1d.x2h,
z3.t1a.t2b.x1e.x2a, z3.t1a.t2b.x1e.x2b, z3.t1a.t2b.x1e.x2c, z3.t1a.t2b.x1e.x2d,
z3.t1a.t2b.x1e.x2e, z3.t1a.t2b.x1e.x2f, z3.t1a.t2b.x1e.x2g, z3.t1a.t2b.x1e.x2h,
z3.t1a.t2b.x1f.x2a, z3.t1a.t2b.x1f.x2b, z3.t1a.t2b.x1f.x2c, z3.t1a.t2b.x1f.x2d,
z3.t1a.t2b.x1f.x2e, z3.t1a.t2b.x1f.x2f, z3.t1a.t2b.x1f.x2g, z3.t1a.t2b.x1f.x2h,
z3.t1a.t2b.x1g.x2a, z3.t1a.t2b.x1g.x2b, z3.t1a.t2b.x1g.x2c, z3.t1a.t2b.x1g.x2d,
z3.t1a.t2b.x1g.x2e, z3.t1a.t2b.x1g.x2f, z3.t1a.t2b.x1g.x2g, z3.t1a.t2b.x1g.x2h,
z3.t1a.t2b.x1h.x2a, z3.t1a.t2b.x1h.x2b, z3.t1a.t2b.x1h.x2c, z3.t1a.t2b.x1h.x2d,
z3.t1a.t2b.x1h.x2e, z3.t1a.t2b.x1h.x2f, z3.t1a.t2b.x1h.x2g, z3.t1a.t2b.x1h.x2h,
z3.t1a.t2c.x1a.x2a, z3.t1a.t2c.x1a.x2b, z3.t1a.t2c.x1a.x2c, z3.t1a.t2c.x1a.x2d,
z3.t1a.t2c.x1a.x2e, z3.t1a.t2c.x1a.x2f, z3.t1a.t2c.x1a.x2g, z3.t1a.t2c.x1a.x2h,
z3.t1a.t2c.x1b.x2a, z3.t1a.t2c.x1b.x2b, z3.t1a.t2c.x1b.x2c, z3.t1a.t2c.x1b.x2d,
z3.t1a.t2c.x1b.x2e, z3.t1a.t2c.x1b.x2f, z3.t1a.t2c.x1b.x2g, z3.t1a.t2c.x1b.x2h,
z3.t1a.t2c.x1c.x2a, z3.t1a.t2c.x1c.x2b, z3.t1a.t2c.x1c.x2c, z3.t1a.t2c.x1c.x2d,
z3.t1a.t2c.x1c.x2e, z3.t1a.t2c.x1c.x2f, z3.t1a.t2c.x1c.x2g, z3.t1a.t2c.x1c.x2h,
z3.t1a.t2c.x1d.x2a, z3.t1a.t2c.x1d.x2b, z3.t1a.t2c.x1d.x2c, z3.t1a.t2c.x1d.x2d,
z3.t1a.t2c.x1d.x2e, z3.t1a.t2c.x1d.x2f, z3.t1a.t2c.x1d.x2g, z3.t1a.t2c.x1d.x2h,
z3.t1a.t2c.x1e.x2a, z3.t1a.t2c.x1e.x2b, z3.t1a.t2c.x1e.x2c, z3.t1a.t2c.x1e.x2d,
z3.t1a.t2c.x1e.x2e, z3.t1a.t2c.x1e.x2f, z3.t1a.t2c.x1e.x2g, z3.t1a.t2c.x1e.x2h,
z3.t1a.t2c.x1f.x2a, z3.t1a.t2c.x1f.x2b, z3.t1a.t2c.x1f.x2c, z3.t1a.t2c.x1f.x2d,
z3.t1a.t2c.x1f.x2e, z3.t1a.t2c.x1f.x2f, z3.t1a.t2c.x1f.x2g, z3.t1a.t2c.x1f.x2h,
z3.t1a.t2c.x1g.x2a, z3.t1a.t2c.x1g.x2b, z3.t1a.t2c.x1g.x2c, z3.t1a.t2c.x1g.x2d,
z3.t1a.t2c.x1g.x2e, z3.t1a.t2c.x1g.x2f, z3.t1a.t2c.x1g.x2g, z3.t1a.t2c.x1g.x2h,
z3.t1a.t2c.x1h.x2a, z3.t1a.t2c.x1h.x2b, z3.t1a.t2c.x1h.x2c, z3.t1a.t2c.x1h.x2d,
z3.t1a.t2c.x1h.x2e, z3.t1a.t2c.x1h.x2f, z3.t1a.t2c.x1h.x2g, z3.t1a.t2c.x1h.x2h,
z3.t1b.t2a.x1a.x2a, z3.t1b.t2a.x1a.x2b, z3.t1b.t2a.x1a.x2c, z3.t1b.t2a.x1a.x2d,
z3.t1b.t2a.x1a.x2e, z3.t1b.t2a.x1a.x2f, z3.t1b.t2a.x1a.x2g, z3.t1b.t2a.x1a.x2h,
z3.t1b.t2a.x1b.x2a, z3.t1b.t2a.x1b.x2b, z3.t1b.t2a.x1b.x2c, z3.t1b.t2a.x1b.x2d,
z3.t1b.t2a.x1b.x2e, z3.t1b.t2a.x1b.x2f, z3.t1b.t2a.x1b.x2g, z3.t1b.t2a.x1b.x2h,
z3.t1b.t2a.x1c.x2a, z3.t1b.t2a.x1c.x2b, z3.t1b.t2a.x1c.x2c, z3.t1b.t2a.x1c.x2d,
z3.t1b.t2a.x1c.x2e, z3.t1b.t2a.x1c.x2f, z3.t1b.t2a.x1c.x2g, z3.t1b.t2a.x1c.x2h,
z3.t1b.t2a.x1d.x2a, z3.t1b.t2a.x1d.x2b, z3.t1b.t2a.x1d.x2c, z3.t1b.t2a.x1d.x2d,
z3.t1b.t2a.x1d.x2e, z3.t1b.t2a.x1d.x2f, z3.t1b.t2a.x1d.x2g, z3.t1b.t2a.x1d.x2h,
z3.t1b.t2a.x1e.x2a, z3.t1b.t2a.x1e.x2b, z3.t1b.t2a.x1e.x2c, z3.t1b.t2a.x1e.x2d,
z3.t1b.t2a.x1e.x2e, z3.t1b.t2a.x1e.x2f, z3.t1b.t2a.x1e.x2g, z3.t1b.t2a.x1e.x2h,
z3.t1b.t2a.x1f.x2a, z3.t1b.t2a.x1f.x2b, z3.t1b.t2a.x1f.x2c, z3.t1b.t2a.x1f.x2d, TABLE 30.6-continued List of Compound Structures of Formula III z3.t1b.t2a.x1f.x2e, z3.t1b.t2a.x1f.x2f, z3.t1b.t2a.x1f.x2g,
z3.t1b.t2a.x1f.x2h,
z3.t1b.t2a.x1g.x2a, z3.t1b.t2a.x1g.x2b, z3.t1b.t2a.x1g.x2c,
z3.t1b.t2a.x1g.x2d,
z3.t1b.t2a.x1g.x2e, z3.t1b.t2a.x1g.x2f, z3.t1b.t2a.x1g.x2g,
z3.t1b.t2a.x1g.x2h,
z3.t1b.t2a.x1h.x2a, z3.t1b.t2a.x1h.x2b, z3.t1b.t2a.x1h.x2c,
z3.t1b.t2a.x1h.x2d,
z3.t1b.t2a.x1h.x2e, z3.t1b.t2a.x1h.x2f, z3.t1b.t2a.x1h.x2g,
z3.t1b.t2a.x1h.x2h,
z3.t1b.t2b.x1a.x2a, z3.t1b.t2b.x1a.x2b, z3.t1b.t2b.x1a.x2c,
z3.t1b.t2b.x1a.x2d,
z3.t1b.t2b.x1a.x2e, z3.t1b.t2b.x1a.x2f, z3.t1b.t2b.x1a.x2g,
z3.t1b.t2b.x1a.x2h,
z3.t1b.t2b.x1b.x2a, z3.t1b.t2b.x1b.x2b, z3.t1b.t2b.x1b.x2c,
z3.t1b.t2b.x1b.x2d,
z3.t1b.t2b.x1b.x2e, z3.t1b.t2b.x1b.x2f, z3.t1b.t2b.x1b.x2g,
z3.t1b.t2b.x1b.x2h,
z3.t1b.t2b.x1c.x2a, z3.t1b.t2b.x1c.x2b, z3.t1b.t2b.x1c.x2c,
z3.t1b.t2b.x1c.x2d,
z3.t1b.t2b.x1c.x2e, z3.t1b.t2b.x1c.x2f, z3.t1b.t2b.x1c.x2g,
z3.t1b.t2b.x1c.x2h,
z3.t1b.t2b.x1d.x2a, z3.t1b.t2b.x1d.x2b, z3.t1b.t2b.x1d.x2c,
z3.t1b.t2b.x1d.x2d,
z3.t1b.t2b.x1d.x2e, z3.t1b.t2b.x1d.x2f, z3.t1b.t2b.x1d.x2g,
z3.t1b.t2b.x1d.x2h,
z3.t1b.t2b.x1e.x2a, z3.t1b.t2b.x1e.x2b, z3.t1b.t2b.x1e.x2c,
z3.t1b.t2b.x1e.x2d,
z3.t1b.t2b.x1e.x2e, z3.t1b.t2b.x1e.x2f, z3.t1b.t2b.x1e.x2g,
z3.t1b.t2b.x1e.x2h,
z3.t1b.t2b.x1f.x2a, z3.t1b.t2b.x1f.x2b, z3.t1b.t2b.x1f.x2c,
z3.t1b.t2b.x1f.x2d,
z3.t1b.t2b.x1f.x2e, z3.t1b.t2b.x1f.x2f, z3.t1b.t2b.x1f.x2g,
z3.t1b.t2b.x1f.x2h,
z3.t1b.t2b.x1g.x2a, z3.t1b.t2b.x1g.x2b, z3.t1b.t2b.x1g.x2c,
z3.t1b.t2b.x1g.x2d,
z3.t1b.t2b.x1g.x2e, z3.t1b.t2b.x1g.x2f, z3.t1b.t2b.x1g.x2g,
z3.t1b.t2b.x1g.x2h,
z3.t1b.t2b.x1h.x2a, z3.t1b.t2b.x1h.x2b, z3.t1b.t2b.x1h.x2c,
z3.t1b.t2b.x1h.x2d,
z3.t1b.t2b.x1h.x2e, z3.t1b.t2b.x1h.x2f, z3.t1b.t2b.x1h.x2g,
z3.t1b.t2b.x1h.x2h,
z3.t1b.t2c.x1a.x2a, z3.t1b.t2c.x1a.x2b, z3.t1b.t2c.x1a.x2c,
z3.t1b.t2c.x1a.x2d,
z3.t1b.t2c.x1a.x2e, z3.t1b.t2c.x1a.x2f, z3.t1b.t2c.x1a.x2g,
z3.t1b.t2c.x1a.x2h,
z3.t1b.t2c.x1b.x2a, z3.t1b.t2c.x1b.x2b, z3.t1b.t2c.x1b.x2c,
z3.t1b.t2c.x1b.x2d,
z3.t1b.t2c.x1b.x2e, z3.t1b.t2c.x1b.x2f, z3.t1b.t2c.x1b.x2g,
z3.t1b.t2c.x1b.x2h,
z3.t1b.t2c.x1c.x2a, z3.t1b.t2c.x1c.x2b, z3.t1b.t2c.x1c.x2c,
z3.t1b.t2c.x1c.x2d,
z3.t1b.t2c.x1c.x2e, z3.t1b.t2c.x1c.x2f, z3.t1b.t2c.x1c.x2g,
z3.t1b.t2c.x1c.x2h,
z3.t1b.t2c.x1d.x2a, z3.t1b.t2c.x1d.x2b, z3.t1b.t2c.x1d.x2c,
z3.t1b.t2c.x1d.x2d,
z3.t1b.t2c.x1d.x2e, z3.t1b.t2c.x1d.x2f, z3.t1b.t2c.x1d.x2g,
z3.t1b.t2c.x1d.x2h,
z3.t1b.t2c.x1e.x2a, z3.t1b.t2c.x1e.x2b, z3.t1b.t2c.x1e.x2c,
z3.t1b.t2c.x1e.x2d,
z3.t1b.t2c.x1e.x2e, z3.t1b.t2c.x1e.x2f, z3.t1b.t2c.x1e.x2g,
z3.t1b.t2c.x1e.x2h,
z3.t1b.t2c.x1f.x2a, z3.t1b.t2c.x1f.x2b, z3.t1b.t2c.x1f.x2c,
z3.t1b.t2c.x1f.x2d,
z3.t1b.t2c.x1f.x2e, z3.t1b.t2c.x1f.x2f, z3.t1b.t2c.x1f.x2g,
z3.t1b.t2c.x1f.x2h,
z3.t1b.t2c.x1g.x2a, z3.t1b.t2c.x1g.x2b, z3.t1b.t2c.x1g.x2c,
z3.t1b.t2c.x1g.x2d,
z3.t1b.t2c.x1g.x2e, z3.t1b.t2c.x1g.x2f, z3.t1b.t2c.x1g.x2g,
z3.t1b.t2c.x1g.x2h,
z3.t1b.t2c.x1h.x2a, z3.t1b.t2c.x1h.x2b, z3.t1b.t2c.x1h.x2c,
z3.t1b.t2c.x1h.x2d,
z3.t1b.t2c.x1h.x2e, z3.t1b.t2c.x1h.x2f, z3.t1b.t2c.x1h.x2g,
z3.t1b.t2c.x1h.x2h,
z3.t1c.t2a.x1a.x2a, z3.t1c.t2a.x1a.x2b, z3.t1c.t2a.x1a.x2c,
z3.t1c.t2a.x1a.x2d,
z3.t1c.t2a.x1a.x2e, z3.t1c.t2a.x1a.x2f, z3.t1c.t2a.x1a.x2g,
z3.t1c.t2a.x1a.x2h,
z3.t1c.t2a.x1b.x2a, z3.t1c.t2a.x1b.x2b, z3.t1c.t2a.x1b.x2c,
z3.t1c.t2a.x1b.x2d,
z3.t1c.t2a.x1b.x2e, z3.t1c.t2a.x1b.x2f, z3.t1c.t2a.x1b.x2g,
z3.t1c.t2a.x1b.x2h,
z3.t1c.t2a.x1c.x2a, z3.t1c.t2a.x1c.x2b, z3.t1c.t2a.x1c.x2c,
z3.t1c.t2a.x1c.x2d,
z3.t1c.t2a.x1c.x2e, z3.t1c.t2a.x1c.x2f, z3.t1c.t2a.x1c.x2g,
z3.t1c.t2a.x1c.x2h,
z3.t1c.t2a.x1d.x2a, z3.t1c.t2a.x1d.x2b, z3.t1c.t2a.x1d.x2c,
z3.t1c.t2a.x1d.x2d,
z3.t1c.t2a.x1d.x2e, z3.t1c.t2a.x1d.x2f, z3.t1c.t2a.x1d.x2g,
z3.t1c.t2a.x1d.x2h,
z3.t1c.t2a.x1e.x2a, z3.t1c.t2a.x1e.x2b, z3.t1c.t2a.x1e.x2c,
z3.t1c.t2a.x1e.x2d,
z3.t1c.t2a.x1e.x2e, z3.t1c.t2a.x1e.x2f, z3.t1c.t2a.x1e.x2g,
z3.t1c.t2a.x1e.x2h,
z3.t1c.t2a.x1f.x2a, z3.t1c.t2a.x1f.x2b, z3.t1c.t2a.x1f.x2c,
z3.t1c.t2a.x1f.x2d,
z3.t1c.t2a.x1f.x2e, z3.t1c.t2a.x1f.x2f, z3.t1c.t2a.x1f.x2g,
z3.t1c.t2a.x1f.x2h,
z3.t1c.t2a.x1g.x2a, z3.t1c.t2a.x1g.x2b, z3.t1c.t2a.x1g.x2c,
z3.t1c.t2a.x1g.x2d,
z3.t1c.t2a.x1g.x2e, z3.t1c.t2a.x1g.x2f, z3.t1c.t2a.x1g.x2g,
z3.t1c.t2a.x1g.x2h,
z3.t1c.t2a.x1h.x2a, z3.t1c.t2a.x1h.x2b, z3.t1c.t2a.x1h.x2c,
z3.t1c.t2a.x1h.x2d,
z3.t1c.t2a.x1h.x2e, z3.t1c.t2a.x1h.x2f, z3.t1c.t2a.x1h.x2g,
z3.t1c.t2a.x1h.x2h,
z3.t1c.t2b.x1a.x2a, z3.t1c.t2b.x1a.x2b, z3.t1c.t2b.x1a.x2c,
z3.t1c.t2b.x1a.x2d,
z3.t1c.t2b.x1a.x2e, z3.t1c.t2b.x1a.x2f, z3.t1c.t2b.x1a.x2g,
z3.t1c.t2b.x1a.x2h,
z3.t1c.t2b.x1b.x2a, z3.t1c.t2b.x1b.x2b, z3.t1c.t2b.x1b.x2c,
z3.t1c.t2b.x1b.x2d,
z3.t1c.t2b.x1b.x2e, z3.t1c.t2b.x1b.x2f, z3.t1c.t2b.x1b.x2g,
z3.t1c.t2b.x1b.x2h,
z3.t1c.t2b.x1c.x2a, z3.t1c.t2b.x1c.x2b, z3.t1c.t2b.x1c.x2c,
z3.t1c.t2b.x1c.x2d,
z3.t1c.t2b.x1c.x2e, z3.t1c.t2b.x1c.x2f, z3.t1c.t2b.x1c.x2g,
z3.t1c.t2b.x1c.x2h,
z3.t1c.t2b.x1d.x2a, z3.t1c.t2b.x1d.x2b, z3.t1c.t2b.x1d.x2c,
z3.t1c.t2b.x1d.x2d,
z3.t1c.t2b.x1d.x2e, z3.t1c.t2b.x1d.x2f, z3.t1c.t2b.x1d.x2g,
z3.t1c.t2b.x1d.x2h,
z3.t1c.t2b.x1e.x2a, z3.t1c.t2b.x1e.x2b, z3.t1c.t2b.x1e.x2c,
z3.t1c.t2b.x1e.x2d,
z3.t1c.t2b.x1e.x2e, z3.t1c.t2b.x1e.x2f, z3.t1c.t2b.x1e.x2g,
z3.t1c.t2b.x1e.x2h,
z3.t1c.t2b.x1f.x2a, z3.t1c.t2b.x1f.x2b, z3.t1c.t2b.x1f.x2c,
z3.t1c.t2b.x1f.x2d,
z3.t1c.t2b.x1f.x2e, z3.t1c.t2b.x1f.x2f, z3.t1c.t2b.x1f.x2g,
z3.t1c.t2b.x1f.x2h,
z3.t1c.t2b.x1g.x2a, z3.t1c.t2b.x1g.x2b, z3.t1c.t2b.x1g.x2c,
z3.t1c.t2b.x1g.x2d,
z3.t1c.t2b.x1g.x2e, z3.t1c.t2b.x1g.x2f, z3.t1c.t2b.x1g.x2g,
z3.t1c.t2b.x1g.x2h,
z3.t1c.t2b.x1h.x2a, z3.t1c.t2b.x1h.x2b, z3.t1c.t2b.x1h.x2c,
z3.t1c.t2b.x1h.x2d,
z3.t1c.t2b.x1h.x2e, z3.t1c.t2b.x1h.x2f, z3.t1c.t2b.x1h.x2g,
z3.t1c.t2b.x1h.x2h,
z3.t1c.t2c.x1a.x2a, z3.t1c.t2c.x1a.x2b, z3.t1c.t2c.x1a.x2c,
z3.t1c.t2c.x1a.x2d,
z3.t1c.t2c.x1a.x2e, z3.t1c.t2c.x1a.x2f, z3.t1c.t2c.x1a.x2g,
z3.t1c.t2c.x1a.x2h,
z3.t1c.t2c.x1b.x2a, z3.t1c.t2c.x1b.x2b, z3.t1c.t2c.x1b.x2c,
z3.t1c.t2c.x1b.x2d,
z3.t1c.t2c.x1b.x2e, z3.t1c.t2c.x1b.x2f, z3.t1c.t2c.x1b.x2g,
z3.t1c.t2c.x1b.x2h,
z3.t1c.t2c.x1c.x2a, z3.t1c.t2c.x1c.x2b, z3.t1c.t2c.x1c.x2c,
z3.t1c.t2c.x1c.x2d,
z3.t1c.t2c.x1c.x2e, z3.t1c.t2c.x1c.x2f, z3.t1c.t2c.x1c.x2g,
z3.t1c.t2c.x1c.x2h,
z3.t1c.t2c.x1d.x2a, z3.t1c.t2c.x1d.x2b, z3.t1c.t2c.x1d.x2c,
z3.t1c.t2c.x1d.x2d,
z3.t1c.t2c.x1d.x2e, z3.t1c.t2c.x1d.x2f, z3.t1c.t2c.x1d.x2g,
z3.t1c.t2c.x1d.x2h,

TABLE 30.6-continued

List of Compound Structures of Formula III z3.t1c.t2c.x1e.x2a, z3.t1c.t2c.x1e.x2b, z3.t1c.t2c.x1e.x2c, z3.t1c.t2c.x1e.x2d,
z3.t1c.t2c.x1e.x2e, z3.t1c.t2c.x1e.x2f, z3.t1c.t2c.x1e.x2g, z3.t1c.t2c.x1e.x2h,
z3.t1c.t2c.x1f.x2a, z3.t1c.t2c.x1f.x2b, z3.t1c.t2c.x1f.x2c, z3.t1c.t2c.x1f.x2d,
z3.t1c.t2c.x1f.x2e, z3.t1c.t2c.x1f.x2f, z3.t1c.t2c.x1f.x2g, z3.t1c.t2c.x1f.x2h,
z3.t1c.t2c.x1g.x2a, z3.t1c.t2c.x1g.x2b, z3.t1c.t2c.x1g.x2c, z3.t1c.t2c.x1g.x2d,
z3.t1c.t2c.x1g.x2e, z3.t1c.t2c.x1g.x2f, z3.t1c.t2c.x1g.x2g, z3.t1c.t2c.x1g.x2h,
z3.t1c.t2c.x1h.x2a, z3.t1c.t2c.x1h.x2b, z3.t1c.t2c.x1h.x2c, z3.t1c.t2c.x1h.x2d,
z3.t1c.t2c.x1h.x2e, z3.t1c.t2c.x1h.x2f, z3.t1c.t2c.x1h.x2g, z3.t1c.t2c.x1h.x2h,
z3.t1d.t2a.x1a.x2a, z3.t1d.t2a.x1a.x2b, z3.t1d.t2a.x1a.x2c, z3.t1d.t2a.x1a.x2d,
z3.t1d.t2a.x1a.x2e, z3.t1d.t2a.x1a.x2f, z3.t1d.t2a.x1a.x2g, z3.t1d.t2a.x1a.x2h,
z3.t1d.t2a.x1b.x2a, z3.t1d.t2a.x1b.x2b, z3.t1d.t2a.x1b.x2c, z3.t1d.t2a.x1b.x2d,
z3.t1d.t2a.x1b.x2e, z3.t1d.t2a.x1b.x2f, z3.t1d.t2a.x1b.x2g, z3.t1d.t2a.x1b.x2h,
z3.t1d.t2a.x1c.x2a, z3.t1d.t2a.x1c.x2b, z3.t1d.t2a.x1c.x2c, z3.t1d.t2a.x1c.x2d,
z3.t1d.t2a.x1c.x2e, z3.t1d.t2a.x1c.x2f, z3.t1d.t2a.x1c.x2g, z3.t1d.t2a.x1c.x2h,
z3.t1d.t2a.x1d.x2a, z3.t1d.t2a.x1d.x2b, z3.t1d.t2a.x1d.x2c, z3.t1d.t2a.x1d.x2d,
z3.t1d.t2a.x1d.x2e, z3.t1d.t2a.x1d.x2f, z3.t1d.t2a.x1d.x2g, z3.t1d.t2a.x1d.x2h,
z3.t1d.t2a.x1e.x2a, z3.t1d.t2a.x1e.x2b, z3.t1d.t2a.x1e.x2c, z3.t1d.t2a.x1e.x2d,
z3.t1d.t2a.x1e.x2e, z3.t1d.t2a.x1e.x2f, z3.t1d.t2a.x1e.x2g, z3.t1d.t2a.x1e.x2h,
z3.t1d.t2a.x1f.x2a, z3.t1d.t2a.x1f.x2b, z3.t1d.t2a.x1f.x2c, z3.t1d.t2a.x1f.x2d,
z3.t1d.t2a.x1f.x2e, z3.t1d.t2a.x1f.x2f, z3.t1d.t2a.x1f.x2g, z3.t1d.t2a.x1f.x2h,
z3.t1d.t2a.x1g.x2a, z3.t1d.t2a.x1g.x2b, z3.t1d.t2a.x1g.x2c, z3.t1d.t2a.x1g.x2d,
z3.t1d.t2a.x1g.x2e, z3.t1d.t2a.x1g.x2f, z3.t1d.t2a.x1g.x2g, z3.t1d.t2a.x1g.x2h,
z3.t1d.t2a.x1h.x2a, z3.t1d.t2a.x1h.x2b, z3.t1d.t2a.x1h.x2c, z3.t1d.t2a.x1h.x2d,
z3.t1d.t2a.x1h.x2e, z3.t1d.t2a.x1h.x2f, z3.t1d.t2a.x1h.x2g, z3.t1d.t2a.x1h.x2h,
z3.t1d.t2b.x1a.x2a, z3.t1d.t2b.x1a.x2b, z3.t1d.t2b.x1a.x2c, z3.t1d.t2b.x1a.x2d,
z3.t1d.t2b.x1a.x2e, z3.t1d.t2b.x1a.x2f, z3.t1d.t2b.x1a.x2g, z3.t1d.t2b.x1a.x2h,
z3.t1d.t2b.x1b.x2a, z3.t1d.t2b.x1b.x2b, z3.t1d.t2b.x1b.x2c, z3.t1d.t2b.x1b.x2d,
z3.t1d.t2b.x1b.x2e, z3.t1d.t2b.x1b.x2f, z3.t1d.t2b.x1b.x2g, z3.t1d.t2b.x1b.x2h,
z3.t1d.t2b.x1c.x2a, z3.t1d.t2b.x1c.x2b, z3.t1d.t2b.x1c.x2c, z3.t1d.t2b.x1c.x2d,
z3.t1d.t2b.x1c.x2e, z3.t1d.t2b.x1c.x2f, z3.t1d.t2b.x1c.x2g, z3.t1d.t2b.x1c.x2h,
z3.t1d.t2b.x1d.x2a, z3.t1d.t2b.x1d.x2b, z3.t1d.t2b.x1d.x2c, z3.t1d.t2b.x1d.x2d,
z3.t1d.t2b.x1d.x2e, z3.t1d.t2b.x1d.x2f, z3.t1d.t2b.x1d.x2g, z3.t1d.t2b.x1d.x2h,
z3.t1d.t2b.x1e.x2a, z3.t1d.t2b.x1e.x2b, z3.t1d.t2b.x1e.x2c, z3.t1d.t2b.x1e.x2d,
z3.t1d.t2b.x1e.x2e, z3.t1d.t2b.x1e.x2f, z3.t1d.t2b.x1e.x2g, z3.t1d.t2b.x1e.x2h,
z3.t1d.t2b.x1f.x2a, z3.t1d.t2b.x1f.x2b, z3.t1d.t2b.x1f.x2c, z3.t1d.t2b.x1f.x2d,
z3.t1d.t2b.x1f.x2e, z3.t1d.t2b.x1f.x2f, z3.t1d.t2b.x1f.x2g, z3.t1d.t2b.x1f.x2h,
z3.t1d.t2b.x1g.x2a, z3.t1d.t2b.x1g.x2b, z3.t1d.t2b.x1g.x2c, z3.t1d.t2b.x1g.x2d,
z3.t1d.t2b.x1g.x2e, z3.t1d.t2b.x1g.x2f, z3.t1d.t2b.x1g.x2g, z3.t1d.t2b.x1g.x2h,
z3.t1d.t2b.x1h.x2a, z3.t1d.t2b.x1h.x2b, z3.t1d.t2b.x1h.x2c, z3.t1d.t2b.x1h.x2d,
z3.t1d.t2b.x1h.x2e, z3.t1d.t2b.x1h.x2f, z3.t1d.t2b.x1h.x2g, z3.t1d.t2b.x1h.x2h,
z3.t1d.t2c.x1a.x2a, z3.t1d.t2c.x1a.x2b, z3.t1d.t2c.x1a.x2c, z3.t1d.t2c.x1a.x2d,
z3.t1d.t2c.x1a.x2e, z3.t1d.t2c.x1a.x2f, z3.t1d.t2c.x1a.x2g, z3.t1d.t2c.x1a.x2h,
z3.t1d.t2c.x1b.x2a, z3.t1d.t2c.x1b.x2b, z3.t1d.t2c.x1b.x2c, z3.t1d.t2c.x1b.x2d,
z3.t1d.t2c.x1b.x2e, z3.t1d.t2c.x1b.x2f, z3.t1d.t2c.x1b.x2g, z3.t1d.t2c.x1b.x2h,
z3.t1d.t2c.x1c.x2a, z3.t1d.t2c.x1c.x2b, z3.t1d.t2c.x1c.x2c, z3.t1d.t2c.x1c.x2d,
z3.t1d.t2c.x1c.x2e, z3.t1d.t2c.x1c.x2f, z3.t1d.t2c.x1c.x2g, z3.t1d.t2c.x1c.x2h,
z3.t1d.t2c.x1d.x2a, z3.t1d.t2c.x1d.x2b, z3.t1d.t2c.x1d.x2c, z3.t1d.t2c.x1d.x2d,
z3.t1d.t2c.x1d.x2e, z3.t1d.t2c.x1d.x2f, z3.t1d.t2c.x1d.x2g, z3.t1d.t2c.x1d.x2h,
z3.t1d.t2c.x1e.x2a, z3.t1d.t2c.x1e.x2b, z3.t1d.t2c.x1e.x2c, z3.t1d.t2c.x1e.x2d,
z3.t1d.t2c.x1e.x2e, z3.t1d.t2c.x1e.x2f, z3.t1d.t2c.x1e.x2g, z3.t1d.t2c.x1e.x2h,
z3.t1d.t2c.x1f.x2a, z3.t1d.t2c.x1f.x2b, z3.t1d.t2c.x1f.x2c, z3.t1d.t2c.x1f.x2d,
z3.t1d.t2c.x1f.x2e, z3.t1d.t2c.x1f.x2f, z3.t1d.t2c.x1f.x2g, z3.t1d.t2c.x1f.x2h,
z3.t1d.t2c.x1g.x2a, z3.t1d.t2c.x1g.x2b, z3.t1d.t2c.x1g.x2c, z3.t1d.t2c.x1g.x2d,
z3.t1d.t2c.x1g.x2e, z3.t1d.t2c.x1g.x2f, z3.t1d.t2c.x1g.x2g, z3.t1d.t2c.x1g.x2h,
z3.t1d.t2c.x1h.x2a, z3.t1d.t2c.x1h.x2b, z3.t1d.t2c.x1h.x2c, z3.t1d.t2c.x1h.x2d,
z3.t1d.t2c.x1h.x2e, z3.t1d.t2c.x1h.x2f, z3.t1d.t2c.x1h.x2g, z3.t1d.t2c.x1h.x2h,
z3.t1e.t2a.x1a.x2a, z3.t1e.t2a.x1a.x2b, z3.t1e.t2a.x1a.x2c, z3.t1e.t2a.x1a.x2d,
z3.t1e.t2a.x1a.x2e, z3.t1e.t2a.x1a.x2f, z3.t1e.t2a.x1a.x2g, z3.t1e.t2a.x1a.x2h,
z3.t1e.t2a.x1b.x2a, z3.t1e.t2a.x1b.x2b, z3.t1e.t2a.x1b.x2c, z3.t1e.t2a.x1b.x2d,
z3.t1e.t2a.x1b.x2e, z3.t1e.t2a.x1b.x2f, z3.t1e.t2a.x1b.x2g, z3.t1e.t2a.x1b.x2h,
z3.t1e.t2a.x1c.x2a, z3.t1e.t2a.x1c.x2b, z3.t1e.t2a.x1c.x2c, z3.t1e.t2a.x1c.x2d,
z3.t1e.t2a.x1c.x2e, z3.t1e.t2a.x1c.x2f, z3.t1e.t2a.x1c.x2g, z3.t1e.t2a.x1c.x2h,
z3.t1e.t2a.x1d.x2a, z3.t1e.t2a.x1d.x2b, z3.t1e.t2a.x1d.x2c, z3.t1e.t2a.x1d.x2d,
z3.t1e.t2a.x1d.x2e, z3.t1e.t2a.x1d.x2f, z3.t1e.t2a.x1d.x2g, z3.t1e.t2a.x1d.x2h,
z3.t1e.t2a.x1e.x2a, z3.t1e.t2a.x1e.x2b, z3.t1e.t2a.x1e.x2c, z3.t1e.t2a.x1e.x2d,
z3.t1e.t2a.x1e.x2e, z3.t1e.t2a.x1e.x2f, z3.t1e.t2a.x1e.x2g, z3.t1e.t2a.x1e.x2h,
z3.t1e.t2a.x1f.x2a, z3.t1e.t2a.x1f.x2b, z3.t1e.t2a.x1f.x2c, z3.t1e.t2a.x1f.x2d,
z3.t1e.t2a.x1f.x2e, z3.t1e.t2a.x1f.x2f, z3.t1e.t2a.x1f.x2g, z3.t1e.t2a.x1f.x2h,
z3.t1e.t2a.x1g.x2a, z3.t1e.t2a.x1g.x2b, z3.t1e.t2a.x1g.x2c, z3.t1e.t2a.x1g.x2d,
z3.t1e.t2a.x1g.x2e, z3.t1e.t2a.x1g.x2f, z3.t1e.t2a.x1g.x2g, z3.t1e.t2a.x1g.x2h,
z3.t1e.t2a.x1h.x2a, z3.t1e.t2a.x1h.x2b, z3.t1e.t2a.x1h.x2c, z3.t1e.t2a.x1h.x2d,
z3.t1e.t2a.x1h.x2e, z3.t1e.t2a.x1h.x2f, z3.t1e.t2a.x1h.x2g, z3.t1e.t2a.x1h.x2h,
z3.t1e.t2b.x1a.x2a, z3.t1e.t2b.x1a.x2b, z3.t1e.t2b.x1a.x2c, z3.t1e.t2b.x1a.x2d,
z3.t1e.t2b.x1a.x2e, z3.t1e.t2b.x1a.x2f, z3.t1e.t2b.x1a.x2g, z3.t1e.t2b.x1a.x2h,
z3.t1e.t2b.x1b.x2a, z3.t1e.t2b.x1b.x2b, z3.t1e.t2b.x1b.x2c, z3.t1e.t2b.x1b.x2d,
z3.t1e.t2b.x1b.x2e, z3.t1e.t2b.x1b.x2f, z3.t1e.t2b.x1b.x2g, z3.t1e.t2b.x1b.x2h,
z3.t1e.t2b.x1c.x2a, z3.t1e.t2b.x1c.x2b, z3.t1e.t2b.x1c.x2c, z3.t1e.t2b.x1c.x2d,

TABLE 30.6-continued

List of Compound Structures of Formula III z3.t1e.t2b.x1c.x2e, z3.t1e.t2b.x1c.x2f, z3.t1e.t2b.x1c.x2g,
z3.t1e.t2b.x1c.x2h,
z3.t1e.t2b.x1d.x2a, z3.t1e.t2b.x1d.x2b, z3.t1e.t2b.x1d.x2c,
z3.t1e.t2b.x1d.x2d,
z3.t1e.t2b.x1d.x2e, z3.t1e.t2b.x1d.x2f, z3.t1e.t2b.x1d.x2g,
z3.t1e.t2b.x1d.x2h,
z3.t1e.t2b.x1e.x2a, z3.t1e.t2b.x1e.x2b, z3.t1e.t2b.x1e.x2c,
z3.t1e.t2b.x1e.x2d,
z3.t1e.t2b.x1e.x2e, z3.t1e.t2b.x1e.x2f, z3.t1e.t2b.x1e.x2g,
z3.t1e.t2b.x1e.x2h,
z3.t1e.t2b.x1f.x2a, z3.t1e.t2b.x1f.x2b, z3.t1e.t2b.x1f.x2c,
z3.t1e.t2b.x1f.x2d,
z3.t1e.t2b.x1f.x2e, z3.t1e.t2b.x1f.x2f, z3.t1e.t2b.x1f.x2g,
z3.t1e.t2b.x1f.x2h,
z3.t1e.t2b.x1g.x2a, z3.t1e.t2b.x1g.x2b, z3.t1e.t2b.x1g.x2c,
z3.t1e.t2b.x1g.x2d,
z3.t1e.t2b.x1g.x2e, z3.t1e.t2b.x1g.x2f, z3.t1e.t2b.x1g.x2g,
z3.t1e.t2b.x1g.x2h,
z3.t1e.t2b.x1h.x2a, z3.t1e.t2b.x1h.x2b, z3.t1e.t2b.x1h.x2c,
z3.t1e.t2b.x1h.x2d,
z3.t1e.t2b.x1h.x2e, z3.t1e.t2b.x1h.x2f, z3.t1e.t2b.x1h.x2g,
z3.t1e.t2b.x1h.x2h,
z3.t1e.t2c.x1a.x2a, z3.t1e.t2c.x1a.x2b, z3.t1e.t2c.x1a.x2c,
z3.t1e.t2c.x1a.x2d,
z3.t1e.t2c.x1a.x2e, z3.t1e.t2c.x1a.x2f, z3.t1e.t2c.x1a.x2g,
z3.t1e.t2c.x1a.x2h,
z3.t1e.t2c.x1b.x2a, z3.t1e.t2c.x1b.x2b, z3.t1e.t2c.x1b.x2c,
z3.t1e.t2c.x1b.x2d,
z3.t1e.t2c.x1b.x2e, z3.t1e.t2c.x1b.x2f, z3.t1e.t2c.x1b.x2g,
z3.t1e.t2c.x1b.x2h,
z3.t1e.t2c.x1c.x2a, z3.t1e.t2c.x1c.x2b, z3.t1e.t2c.x1c.x2c,
z3.t1e.t2c.x1c.x2d,
z3.t1e.t2c.x1c.x2e, z3.t1e.t2c.x1c.x2f, z3.t1e.t2c.x1c.x2g,
z3.t1e.t2c.x1c.x2h,
z3.t1e.t2c.x1d.x2a, z3.t1e.t2c.x1d.x2b, z3.t1e.t2c.x1d.x2c,
z3.t1e.t2c.x1d.x2d,
z3.t1e.t2c.x1d.x2e, z3.t1e.t2c.x1d.x2f, z3.t1e.t2c.x1d.x2g,
z3.t1e.t2c.x1d.x2h,
z3.t1e.t2c.x1e.x2a, z3.t1e.t2c.x1e.x2b, z3.t1e.t2c.x1e.x2c,
z3.t1e.t2c.x1e.x2d,
z3.t1e.t2c.x1e.x2e, z3.t1e.t2c.x1e.x2f, z3.t1e.t2c.x1e.x2g,
z3.t1e.t2c.x1e.x2h,
z3.t1e.t2c.x1f.x2a, z3.t1e.t2c.x1f.x2b, z3.t1e.t2c.x1f.x2c,
z3.t1e.t2c.x1f.x2d,
z3.t1e.t2c.x1f.x2e, z3.t1e.t2c.x1f.x2f, z3.t1e.t2c.x1f.x2g,
z3.t1e.t2c.x1f.x2h,
z3.t1e.t2c.x1g.x2a, z3.t1e.t2c.x1g.x2b, z3.t1e.t2c.x1g.x2c,
z3.t1e.t2c.x1g.x2d,
z3.t1e.t2c.x1g.x2e, z3.t1e.t2c.x1g.x2f, z3.t1e.t2c.x1g.x2g,
z3.t1e.t2c.x1g.x2h,
z3.t1e.t2c.x1h.x2a, z3.t1e.t2c.x1h.x2b, z3.t1e.t2c.x1h.x2c,
z3.t1e.t2c.x1h.x2d,
z3.t1e.t2c.x1h.x2e, z3.t1e.t2c.x1h.x2f, z3.t1e.t2c.x1h.x2g,
z3.t1e.t2c.x1h.x2h,
z4.t1a.t2a.x1a.x2a, z4.t1a.t2a.x1a.x2b, z4.t1a.t2a.x1a.x2c,
z4.t1a.t2a.x1a.x2d,
z4.t1a.t2a.x1a.x2e, z4.t1a.t2a.x1a.x2f, z4.t1a.t2a.x1a.x2g,
z4.t1a.t2a.x1a.x2h,
z4.t1a.t2a.x1b.x2a, z4.t1a.t2a.x1b.x2b, z4.t1a.t2a.x1b.x2c,
z4.t1a.t2a.x1b.x2d,
z4.t1a.t2a.x1b.x2e, z4.t1a.t2a.x1b.x2f, z4.t1a.t2a.x1b.x2g,
z4.t1a.t2a.x1b.x2h,
z4.t1a.t2a.x1c.x2a, z4.t1a.t2a.x1c.x2b, z4.t1a.t2a.x1c.x2c,
z4.t1a.t2a.x1c.x2d,
z4.t1a.t2a.x1c.x2e, z4.t1a.t2a.x1c.x2f, z4.t1a.t2a.x1c.x2g,
z4.t1a.t2a.x1c.x2h,
z4.t1a.t2a.x1d.x2a, z4.t1a.t2a.x1d.x2b, z4.t1a.t2a.x1d.x2c,
z4.t1a.t2a.x1d.x2d,
z4.t1a.t2a.x1d.x2e, z4.t1a.t2a.x1d.x2f, z4.t1a.t2a.x1d.x2g,
z4.t1a.t2a.x1d.x2h,
z4.t1a.t2a.x1e.x2a, z4.t1a.t2a.x1e.x2b, z4.t1a.t2a.x1e.x2c,
z4.t1a.t2a.x1e.x2d,
z4.t1a.t2a.x1e.x2e, z4.t1a.t2a.x1e.x2f, z4.t1a.t2a.x1e.x2g,
z4.t1a.t2a.x1e.x2h,
z4.t1a.t2a.x1f.x2a, z4.t1a.t2a.x1f.x2b, z4.t1a.t2a.x1f.x2c,
z4.t1a.t2a.x1f.x2d,
z4.t1a.t2a.x1f.x2e, z4.t1a.t2a.x1f.x2f, z4.t1a.t2a.x1f.x2g,
z4.t1a.t2a.x1f.x2h,
z4.t1a.t2a.x1g.x2a, z4.t1a.t2a.x1g.x2b, z4.t1a.t2a.x1g.x2c,
z4.t1a.t2a.x1g.x2d,
z4.t1a.t2a.x1g.x2e, z4.t1a.t2a.x1g.x2f, z4.t1a.t2a.x1g.x2g,
z4.t1a.t2a.x1g.x2h,
z4.t1a.t2a.x1h.x2a, z4.t1a.t2a.x1h.x2b, z4.t1a.t2a.x1h.x2c,
z4.t1a.t2a.x1h.x2d,
z4.t1a.t2a.x1h.x2e, z4.t1a.t2a.x1h.x2f, z4.t1a.t2a.x1h.x2g,
z4.t1a.t2a.x1h.x2h,
z4.t1a.t2b.x1a.x2a, z4.t1a.t2b.x1a.x2b, z4.t1a.t2b.x1a.x2c,
z4.t1a.t2b.x1a.x2d,
z4.t1a.t2b.x1a.x2e, z4.t1a.t2b.x1a.x2f, z4.t1a.t2b.x1a.x2g,
z4.t1a.t2b.x1a.x2h,
z4.t1a.t2b.x1b.x2a, z4.t1a.t2b.x1b.x2b, z4.t1a.t2b.x1b.x2c,
z4.t1a.t2b.x1b.x2d,
z4.t1a.t2b.x1b.x2e, z4.t1a.t2b.x1b.x2f, z4.t1a.t2b.x1b.x2g,
z4.t1a.t2b.x1b.x2h,
z4.t1a.t2b.x1c.x2a, z4.t1a.t2b.x1c.x2b, z4.t1a.t2b.x1c.x2c,
z4.t1a.t2b.x1c.x2d,
z4.t1a.t2b.x1c.x2e, z4.t1a.t2b.x1c.x2f, z4.t1a.t2b.x1c.x2g,
z4.t1a.t2b.x1c.x2h,
z4.t1a.t2b.x1d.x2a, z4.t1a.t2b.x1d.x2b, z4.t1a.t2b.x1d.x2c,
z4.t1a.t2b.x1d.x2d,
z4.t1a.t2b.x1d.x2e, z4.t1a.t2b.x1d.x2f, z4.t1a.t2b.x1d.x2g,
z4.t1a.t2b.x1d.x2h,
z4.t1a.t2b.x1e.x2a, z4.t1a.t2b.x1e.x2b, z4.t1a.t2b.x1e.x2c,
z4.t1a.t2b.x1e.x2d,
z4.t1a.t2b.x1e.x2e, z4.t1a.t2b.x1e.x2f, z4.t1a.t2b.x1e.x2g,
z4.t1a.t2b.x1e.x2h,
z4.t1a.t2b.x1f.x2a, z4.t1a.t2b.x1f.x2b, z4.t1a.t2b.x1f.x2c,
z4.t1a.t2b.x1f.x2d,
z4.t1a.t2b.x1f.x2e, z4.t1a.t2b.x1f.x2f, z4.t1a.t2b.x1f.x2g,
z4.t1a.t2b.x1f.x2h,
z4.t1a.t2b.x1g.x2a, z4.t1a.t2b.x1g.x2b, z4.t1a.t2b.x1g.x2c,
z4.t1a.t2b.x1g.x2d,
z4.t1a.t2b.x1g.x2e, z4.t1a.t2b.x1g.x2f, z4.t1a.t2b.x1g.x2g,
z4.t1a.t2b.x1g.x2h,
z4.t1a.t2b.x1h.x2a, z4.t1a.t2b.x1h.x2b, z4.t1a.t2b.x1h.x2c,
z4.t1a.t2b.x1h.x2d,
z4.t1a.t2b.x1h.x2e, z4.t1a.t2b.x1h.x2f, z4.t1a.t2b.x1h.x2g,
z4.t1a.t2b.x1h.x2h,
z4.t1a.t2c.x1a.x2a, z4.t1a.t2c.x1a.x2b, z4.t1a.t2c.x1a.x2c,
z4.t1a.t2c.x1a.x2d,
z4.t1a.t2c.x1a.x2e, z4.t1a.t2c.x1a.x2f, z4.t1a.t2c.x1a.x2g,
z4.t1a.t2c.x1a.x2h,
z4.t1a.t2c.x1b.x2a, z4.t1a.t2c.x1b.x2b, z4.t1a.t2c.x1b.x2c,
z4.t1a.t2c.x1b.x2d,
z4.t1a.t2c.x1b.x2e, z4.t1a.t2c.x1b.x2f, z4.t1a.t2c.x1b.x2g,
z4.t1a.t2c.x1b.x2h,
z4.t1a.t2c.x1c.x2a, z4.t1a.t2c.x1c.x2b, z4.t1a.t2c.x1c.x2c,
z4.t1a.t2c.x1c.x2d,
z4.t1a.t2c.x1c.x2e, z4.t1a.t2c.x1c.x2f, z4.t1a.t2c.x1c.x2g,
z4.t1a.t2c.x1c.x2h,
z4.t1a.t2c.x1d.x2a, z4.t1a.t2c.x1d.x2b, z4.t1a.t2c.x1d.x2c,
z4.t1a.t2c.x1d.x2d,
z4.t1a.t2c.x1d.x2e, z4.t1a.t2c.x1d.x2f, z4.t1a.t2c.x1d.x2g,
z4.t1a.t2c.x1d.x2h,
z4.t1a.t2c.x1e.x2a, z4.t1a.t2c.x1e.x2b, z4.t1a.t2c.x1e.x2c,
z4.t1a.t2c.x1e.x2d,
z4.t1a.t2c.x1e.x2e, z4.t1a.t2c.x1e.x2f, z4.t1a.t2c.x1e.x2g,
z4.t1a.t2c.x1e.x2h,
z4.t1a.t2c.x1f.x2a, z4.t1a.t2c.x1f.x2b, z4.t1a.t2c.x1f.x2c,
z4.t1a.t2c.x1f.x2d,
z4.t1a.t2c.x1f.x2e, z4.t1a.t2c.x1f.x2f, z4.t1a.t2c.x1f.x2g,
z4.t1a.t2c.x1f.x2h,
z4.t1a.t2c.x1g.x2a, z4.t1a.t2c.x1g.x2b, z4.t1a.t2c.x1g.x2c,
z4.t1a.t2c.x1g.x2d,
z4.t1a.t2c.x1g.x2e, z4.t1a.t2c.x1g.x2f, z4.t1a.t2c.x1g.x2g,
z4.t1a.t2c.x1g.x2h,
z4.t1a.t2c.x1h.x2a, z4.t1a.t2c.x1h.x2b, z4.t1a.t2c.x1h.x2c,
z4.t1a.t2c.x1h.x2d,
z4.t1a.t2c.x1h.x2e, z4.t1a.t2c.x1h.x2f, z4.t1a.t2c.x1h.x2g,
z4.t1a.t2c.x1h.x2h,
z4.t1b.t2a.x1a.x2a, z4.t1b.t2a.x1a.x2b, z4.t1b.t2a.x1a.x2c,
z4.t1b.t2a.x1a.x2d,
z4.t1b.t2a.x1a.x2e, z4.t1b.t2a.x1a.x2f, z4.t1b.t2a.x1a.x2g,
z4.t1b.t2a.x1a.x2h,

TABLE 30.6-continued

List of Compound Structures of Formula III z4.t1b.t2a.x1b.x2a, z4.t1b.t2a.x1b.x2b, z4.t1b.t2a.x1b.x2c,
z4.t1b.t2a.x1b.x2d,
z4.t1b.t2a.x1b.x2e, z4.t1b.t2a.x1b.x2f, z4.t1b.t2a.x1b.x2g,
z4.t1b.t2a.x1b.x2h,
z4.t1b.t2a.x1c.x2a, z4.t1b.t2a.x1c.x2b, z4.t1b.t2a.x1c.x2c,
z4.t1b.t2a.x1c.x2d,
z4.t1b.t2a.x1c.x2e, z4.t1b.t2a.x1c.x2f, z4.t1b.t2a.x1c.x2g,
z4.t1b.t2a.x1c.x2h,
z4.t1b.t2a.x1d.x2a, z4.t1b.t2a.x1d.x2b, z4.t1b.t2a.x1d.x2c,
z4.t1b.t2a.x1d.x2d,
z4.t1b.t2a.x1d.x2e, z4.t1b.t2a.x1d.x2f, z4.t1b.t2a.x1d.x2g,
z4.t1b.t2a.x1d.x2h,
z4.t1b.t2a.x1e.x2a, z4.t1b.t2a.x1e.x2b, z4.t1b.t2a.x1e.x2c,
z4.t1b.t2a.x1e.x2d,
z4.t1b.t2a.x1e.x2e, z4.t1b.t2a.x1e.x2f, z4.t1b.t2a.x1e.x2g,
z4.t1b.t2a.x1e.x2h,
z4.t1b.t2a.x1f.x2a, z4.t1b.t2a.x1f.x2b, z4.t1b.t2a.x1f.x2c,
z4.t1b.t2a.x1f.x2d,
z4.t1b.t2a.x1f.x2e, z4.t1b.t2a.x1f.x2f, z4.t1b.t2a.x1f.x2g,
z4.t1b.t2a.x1f.x2h,
z4.t1b.t2a.x1g.x2a, z4.t1b.t2a.x1g.x2b, z4.t1b.t2a.x1g.x2c,
z4.t1b.t2a.x1g.x2d,
z4.t1b.t2a.x1g.x2e, z4.t1b.t2a.x1g.x2f, z4.t1b.t2a.x1g.x2g,
z4.t1b.t2a.x1g.x2h,
z4.t1b.t2a.x1h.x2a, z4.t1b.t2a.x1h.x2b, z4.t1b.t2a.x1h.x2c,
z4.t1b.t2a.x1h.x2d,
z4.t1b.t2a.x1h.x2e, z4.t1b.t2a.x1h.x2f, z4.t1b.t2a.x1h.x2g,
z4.t1b.t2a.x1h.x2h,
z4.t1b.t2b.x1a.x2a, z4.t1b.t2b.x1a.x2b, z4.t1b.t2b.x1a.x2c,
z4.t1b.t2b.x1a.x2d,
z4.t1b.t2b.x1a.x2e, z4.t1b.t2b.x1a.x2f, z4.t1b.t2b.x1a.x2g,
z4.t1b.t2b.x1a.x2h,
z4.t1b.t2b.x1b.x2a, z4.t1b.t2b.x1b.x2b, z4.t1b.t2b.x1b.x2c,
z4.t1b.t2b.x1b.x2d,
z4.t1b.t2b.x1b.x2e, z4.t1b.t2b.x1b.x2f, z4.t1b.t2b.x1b.x2g,
z4.t1b.t2b.x1b.x2h,
z4.t1b.t2b.x1c.x2a, z4.t1b.t2b.x1c.x2b, z4.t1b.t2b.x1c.x2c,
z4.t1b.t2b.x1c.x2d,
z4.t1b.t2b.x1c.x2e, z4.t1b.t2b.x1c.x2f, z4.t1b.t2b.x1c.x2g,
z4.t1b.t2b.x1c.x2h,
z4.t1b.t2b.x1d.x2a, z4.t1b.t2b.x1d.x2b, z4.t1b.t2b.x1d.x2c,
z4.t1b.t2b.x1d.x2d,
z4.t1b.t2b.x1d.x2e, z4.t1b.t2b.x1d.x2f, z4.t1b.t2b.x1d.x2g,
z4.t1b.t2b.x1d.x2h,
z4.t1b.t2b.x1e.x2a, z4.t1b.t2b.x1e.x2b, z4.t1b.t2b.x1e.x2c,
z4.t1b.t2b.x1e.x2d,
z4.t1b.t2b.x1e.x2e, z4.t1b.t2b.x1e.x2f, z4.t1b.t2b.x1e.x2g,
z4.t1b.t2b.x1e.x2h,
z4.t1b.t2b.x1f.x2a, z4.t1b.t2b.x1f.x2b, z4.t1b.t2b.x1f.x2c,
z4.t1b.t2b.x1f.x2d,
z4.t1b.t2b.x1f.x2e, z4.t1b.t2b.x1f.x2f, z4.t1b.t2b.x1f.x2g,
z4.t1b.t2b.x1f.x2h,
z4.t1b.t2b.x1g.x2a, z4.t1b.t2b.x1g.x2b, z4.t1b.t2b.x1g.x2c,
z4.t1b.t2b.x1g.x2d,
z4.t1b.t2b.x1g.x2e, z4.t1b.t2b.x1g.x2f, z4.t1b.t2b.x1g.x2g,
z4.t1b.t2b.x1g.x2h,
z4.t1b.t2b.x1h.x2a, z4.t1b.t2b.x1h.x2b, z4.t1b.t2b.x1h.x2c,
z4.t1b.t2b.x1h.x2d,
z4.t1b.t2b.x1h.x2e, z4.t1b.t2b.x1h.x2f, z4.t1b.t2b.x1h.x2g,
z4.t1b.t2b.x1h.x2h,
z4.t1b.t2c.x1a.x2a, z4.t1b.t2c.x1a.x2b, z4.t1b.t2c.x1a.x2c,
z4.t1b.t2c.x1a.x2d,
z4.t1b.t2c.x1a.x2e, z4.t1b.t2c.x1a.x2f, z4.t1b.t2c.x1a.x2g,
z4.t1b.t2c.x1a.x2h,
z4.t1b.t2c.x1b.x2a, z4.t1b.t2c.x1b.x2b, z4.t1b.t2c.x1b.x2c,
z4.t1b.t2c.x1b.x2d,
z4.t1b.t2c.x1b.x2e, z4.t1b.t2c.x1b.x2f, z4.t1b.t2c.x1b.x2g,
z4.t1b.t2c.x1b.x2h,
z4.t1b.t2c.x1c.x2a, z4.t1b.t2c.x1c.x2b, z4.t1b.t2c.x1c.x2c,
z4.t1b.t2c.x1c.x2d,
z4.t1b.t2c.x1c.x2e, z4.t1b.t2c.x1c.x2f, z4.t1b.t2c.x1c.x2g,
z4.t1b.t2c.x1c.x2h,
z4.t1b.t2c.x1d.x2a, z4.t1b.t2c.x1d.x2b, z4.t1b.t2c.x1d.x2c,
z4.t1b.t2c.x1d.x2d,
z4.t1b.t2c.x1d.x2e, z4.t1b.t2c.x1d.x2f, z4.t1b.t2c.x1d.x2g,
z4.t1b.t2c.x1d.x2h,
z4.t1b.t2c.x1e.x2a, z4.t1b.t2c.x1e.x2b, z4.t1b.t2c.x1e.x2c,
z4.t1b.t2c.x1e.x2d,
z4.t1b.t2c.x1e.x2e, z4.t1b.t2c.x1e.x2f, z4.t1b.t2c.x1e.x2g,
z4.t1b.t2c.x1e.x2h,
z4.t1b.t2c.x1f.x2a, z4.t1b.t2c.x1f.x2b, z4.t1b.t2c.x1f.x2c,
z4.t1b.t2c.x1f.x2d,
z4.t1b.t2c.x1f.x2e, z4.t1b.t2c.x1f.x2f, z4.t1b.t2c.x1f.x2g,
z4.t1b.t2c.x1f.x2h,
z4.t1b.t2c.x1g.x2a, z4.t1b.t2c.x1g.x2b, z4.t1b.t2c.x1g.x2c,
z4.t1b.t2c.x1g.x2d,
z4.t1b.t2c.x1g.x2e, z4.t1b.t2c.x1g.x2f, z4.t1b.t2c.x1g.x2g,
z4.t1b.t2c.x1g.x2h,
z4.t1b.t2c.x1h.x2a, z4.t1b.t2c.x1h.x2b, z4.t1b.t2c.x1h.x2c,
z4.t1b.t2c.x1h.x2d,
z4.t1b.t2c.x1h.x2e, z4.t1b.t2c.x1h.x2f, z4.t1b.t2c.x1h.x2g,
z4.t1b.t2c.x1h.x2h,
z4.t1c.t2a.x1a.x2a, z4.t1c.t2a.x1a.x2b, z4.t1c.t2a.x1a.x2c,
z4.t1c.t2a.x1a.x2d,
z4.t1c.t2a.x1a.x2e, z4.t1c.t2a.x1a.x2f, z4.t1c.t2a.x1a.x2g,
z4.t1c.t2a.x1a.x2h,
z4.t1c.t2a.x1b.x2a, z4.t1c.t2a.x1b.x2b, z4.t1c.t2a.x1b.x2c,
z4.t1c.t2a.x1b.x2d,
z4.t1c.t2a.x1b.x2e, z4.t1c.t2a.x1b.x2f, z4.t1c.t2a.x1b.x2g,
z4.t1c.t2a.x1b.x2h,
z4.t1c.t2a.x1c.x2a, z4.t1c.t2a.x1c.x2b, z4.t1c.t2a.x1c.x2c,
z4.t1c.t2a.x1c.x2d,
z4.t1c.t2a.x1c.x2e, z4.t1c.t2a.x1c.x2f, z4.t1c.t2a.x1c.x2g,
z4.t1c.t2a.x1c.x2h,
z4.t1c.t2a.x1d.x2a, z4.t1c.t2a.x1d.x2b, z4.t1c.t2a.x1d.x2c,
z4.t1c.t2a.x1d.x2d,
z4.t1c.t2a.x1d.x2e, z4.t1c.t2a.x1d.x2f, z4.t1c.t2a.x1d.x2g,
z4.t1c.t2a.x1d.x2h,
z4.t1c.t2a.x1e.x2a, z4.t1c.t2a.x1e.x2b, z4.t1c.t2a.x1e.x2c,
z4.t1c.t2a.x1e.x2d,
z4.t1c.t2a.x1e.x2e, z4.t1c.t2a.x1e.x2f, z4.t1c.t2a.x1e.x2g,
z4.t1c.t2a.x1e.x2h,
z4.t1c.t2a.x1f.x2a, z4.t1c.t2a.x1f.x2b, z4.t1c.t2a.x1f.x2c,
z4.t1c.t2a.x1f.x2d,
z4.t1c.t2a.x1f.x2e, z4.t1c.t2a.x1f.x2f, z4.t1c.t2a.x1f.x2g,
z4.t1c.t2a.x1f.x2h,
z4.t1c.t2a.x1g.x2a, z4.t1c.t2a.x1g.x2b, z4.t1c.t2a.x1g.x2c,
z4.t1c.t2a.x1g.x2d,
z4.t1c.t2a.x1g.x2e, z4.t1c.t2a.x1g.x2f, z4.t1c.t2a.x1g.x2g,
z4.t1c.t2a.x1g.x2h,
z4.t1c.t2a.x1h.x2a, z4.t1c.t2a.x1h.x2b, z4.t1c.t2a.x1h.x2c,
z4.t1c.t2a.x1h.x2d,
z4.t1c.t2a.x1h.x2e, z4.t1c.t2a.x1h.x2f, z4.t1c.t2a.x1h.x2g,
z4.t1c.t2a.x1h.x2h,
z4.t1c.t2b.x1a.x2a, z4.t1c.t2b.x1a.x2b, z4.t1c.t2b.x1a.x2c,
z4.t1c.t2b.x1a.x2d,
z4.t1c.t2b.x1a.x2e, z4.t1c.t2b.x1a.x2f, z4.t1c.t2b.x1a.x2g,
z4.t1c.t2b.x1a.x2h,
z4.t1c.t2b.x1b.x2a, z4.t1c.t2b.x1b.x2b, z4.t1c.t2b.x1b.x2c,
z4.t1c.t2b.x1b.x2d,
z4.t1c.t2b.x1b.x2e, z4.t1c.t2b.x1b.x2f, z4.t1c.t2b.x1b.x2g,
z4.t1c.t2b.x1b.x2h,
z4.t1c.t2b.x1c.x2a, z4.t1c.t2b.x1c.x2b, z4.t1c.t2b.x1c.x2c,
z4.t1c.t2b.x1c.x2d,
z4.t1c.t2b.x1c.x2e, z4.t1c.t2b.x1c.x2f, z4.t1c.t2b.x1c.x2g,
z4.t1c.t2b.x1c.x2h,
z4.t1c.t2b.x1d.x2a, z4.t1c.t2b.x1d.x2b, z4.t1c.t2b.x1d.x2c,
z4.t1c.t2b.x1d.x2d,
z4.t1c.t2b.x1d.x2e, z4.t1c.t2b.x1d.x2f, z4.t1c.t2b.x1d.x2g,
z4.t1c.t2b.x1d.x2h,
z4.t1c.t2b.x1e.x2a, z4.t1c.t2b.x1e.x2b, z4.t1c.t2b.x1e.x2c,
z4.t1c.t2b.x1e.x2d,
z4.t1c.t2b.x1e.x2e, z4.t1c.t2b.x1e.x2f, z4.t1c.t2b.x1e.x2g,
z4.t1c.t2b.x1e.x2h,
z4.t1c.t2b.x1f.x2a, z4.t1c.t2b.x1f.x2b, z4.t1c.t2b.x1f.x2c,
z4.t1c.t2b.x1f.x2d,
z4.t1c.t2b.x1f.x2e, z4.t1c.t2b.x1f.x2f, z4.t1c.t2b.x1f.x2g,
z4.t1c.t2b.x1f.x2h,
z4.t1c.t2b.x1g.x2a, z4.t1c.t2b.x1g.x2b, z4.t1c.t2b.x1g.x2c,
z4.t1c.t2b.x1g.x2d,
z4.t1c.t2b.x1g.x2e, z4.t1c.t2b.x1g.x2f, z4.t1c.t2b.x1g.x2g,
z4.t1c.t2b.x1g.x2h,
z4.t1c.t2b.x1h.x2a, z4.t1c.t2b.x1h.x2b, z4.t1c.t2b.x1h.x2c,
z4.t1c.t2b.x1h.x2d, TABLE 30.6-continued List of Compound Structures of Formula III z4.t1c.t2b.x1h.x2e, z4.t1c.t2b.x1h.x2f, z4.t1c.t2b.x1h.x2g,
z4.t1c.t2b.x1h.x2h,
z4.t1c.t2c.x1a.x2a, z4.t1c.t2c.x1a.x2b, z4.t1c.t2c.x1a.x2c,
z4.t1c.t2c.x1a.x2d,
z4.t1c.t2c.x1a.x2e, z4.t1c.t2c.x1a.x2f, z4.t1c.t2c.x1a.x2g,
z4.t1c.t2c.x1a.x2h,
z4.t1c.t2c.x1b.x2a, z4.t1c.t2c.x1b.x2b, z4.t1c.t2c.x1b.x2c,
z4.t1c.t2c.x1b.x2d,
z4.t1c.t2c.x1b.x2e, z4.t1c.t2c.x1b.x2f, z4.t1c.t2c.x1b.x2g,
z4.t1c.t2c.x1b.x2h,
z4.t1c.t2c.x1c.x2a, z4.t1c.t2c.x1c.x2b, z4.t1c.t2c.x1c.x2c,
z4.t1c.t2c.x1c.x2d,
z4.t1c.t2c.x1c.x2e, z4.t1c.t2c.x1c.x2f, z4.t1c.t2c.x1c.x2g,
z4.t1c.t2c.x1c.x2h,
z4.t1c.t2c.x1d.x2a, z4.t1c.t2c.x1d.x2b, z4.t1c.t2c.x1d.x2c,
z4.t1c.t2c.x1d.x2d,
z4.t1c.t2c.x1d.x2e, z4.t1c.t2c.x1d.x2f, z4.t1c.t2c.x1d.x2g,
z4.t1c.t2c.x1d.x2h,
z4.t1c.t2c.x1e.x2a, z4.t1c.t2c.x1e.x2b, z4.t1c.t2c.x1e.x2c,
z4.t1c.t2c.x1e.x2d,
z4.t1c.t2c.x1e.x2e, z4.t1c.t2c.x1e.x2f, z4.t1c.t2c.x1e.x2g,
z4.t1c.t2c.x1e.x2h,
z4.t1c.t2c.x1f.x2a, z4.t1c.t2c.x1f.x2b, z4.t1c.t2c.x1f.x2c,
z4.t1c.t2c.x1f.x2d,
z4.t1c.t2c.x1f.x2e, z4.t1c.t2c.x1f.x2f, z4.t1c.t2c.x1f.x2g,
z4.t1c.t2c.x1f.x2h,
z4.t1c.t2c.x1g.x2a, z4.t1c.t2c.x1g.x2b, z4.t1c.t2c.x1g.x2c,
z4.t1c.t2c.x1g.x2d,
z4.t1c.t2c.x1g.x2e, z4.t1c.t2c.x1g.x2f, z4.t1c.t2c.x1g.x2g,
z4.t1c.t2c.x1g.x2h,
z4.t1c.t2c.x1h.x2a, z4.t1c.t2c.x1h.x2b, z4.t1c.t2c.x1h.x2c,
z4.t1c.t2c.x1h.x2d,
z4.t1c.t2c.x1h.x2e, z4.t1c.t2c.x1h.x2f, z4.t1c.t2c.x1h.x2g,
z4.t1c.t2c.x1h.x2h,
z4.t1d.t2a.x1a.x2a, z4.t1d.t2a.x1a.x2b, z4.t1d.t2a.x1a.x2c,
z4.t1d.t2a.x1a.x2d,
z4.t1d.t2a.x1a.x2e, z4.t1d.t2a.x1a.x2f, z4.t1d.t2a.x1a.x2g,
z4.t1d.t2a.x1a.x2h,
z4.t1d.t2a.x1b.x2a, z4.t1d.t2a.x1b.x2b, z4.t1d.t2a.x1b.x2c,
z4.t1d.t2a.x1b.x2d,
z4.t1d.t2a.x1b.x2e, z4.t1d.t2a.x1b.x2f, z4.t1d.t2a.x1b.x2g,
z4.t1d.t2a.x1b.x2h,
z4.t1d.t2a.x1c.x2a, z4.t1d.t2a.x1c.x2b, z4.t1d.t2a.x1c.x2c,
z4.t1d.t2a.x1c.x2d,
z4.t1d.t2a.x1c.x2e, z4.t1d.t2a.x1c.x2f, z4.t1d.t2a.x1c.x2g,
z4.t1d.t2a.x1c.x2h,
z4.t1d.t2a.x1d.x2a, z4.t1d.t2a.x1d.x2b, z4.t1d.t2a.x1d.x2c,
z4.t1d.t2a.x1d.x2d,
z4.t1d.t2a.x1d.x2e, z4.t1d.t2a.x1d.x2f, z4.t1d.t2a.x1d.x2g,
z4.t1d.t2a.x1d.x2h,
z4.t1d.t2a.x1e.x2a, z4.t1d.t2a.x1e.x2b, z4.t1d.t2a.x1e.x2c,
z4.t1d.t2a.x1e.x2d,
z4.t1d.t2a.x1e.x2e, z4.t1d.t2a.x1e.x2f, z4.t1d.t2a.x1e.x2g,
z4.t1d.t2a.x1e.x2h,
z4.t1d.t2a.x1f.x2a, z4.t1d.t2a.x1f.x2b, z4.t1d.t2a.x1f.x2c,
z4.t1d.t2a.x1f.x2d,
z4.t1d.t2a.x1f.x2e, z4.t1d.t2a.x1f.x2f, z4.t1d.t2a.x1f.x2g,
z4.t1d.t2a.x1f.x2h,
z4.t1d.t2a.x1g.x2a, z4.t1d.t2a.x1g.x2b, z4.t1d.t2a.x1g.x2c,
z4.t1d.t2a.x1g.x2d,
z4.t1d.t2a.x1g.x2e, z4.t1d.t2a.x1g.x2f, z4.t1d.t2a.x1g.x2g,
z4.t1d.t2a.x1g.x2h,
z4.t1d.t2a.x1h.x2a, z4.t1d.t2a.x1h.x2b, z4.t1d.t2a.x1h.x2c,
z4.t1d.t2a.x1h.x2d,
z4.t1d.t2a.x1h.x2e, z4.t1d.t2a.x1h.x2f, z4.t1d.t2a.x1h.x2g,
z4.t1d.t2a.x1h.x2h,
z4.t1d.t2b.x1a.x2a, z4.t1d.t2b.x1a.x2b, z4.t1d.t2b.x1a.x2c,
z4.t1d.t2b.x1a.x2d,
z4.t1d.t2b.x1a.x2e, z4.t1d.t2b.x1a.x2f, z4.t1d.t2b.x1a.x2g,
z4.t1d.t2b.x1a.x2h,
z4.t1d.t2b.x1b.x2a, z4.t1d.t2b.x1b.x2b, z4.t1d.t2b.x1b.x2c,
z4.t1d.t2b.x1b.x2d,
z4.t1d.t2b.x1b.x2e, z4.t1d.t2b.x1b.x2f, z4.t1d.t2b.x1b.x2g,
z4.t1d.t2b.x1b.x2h,
z4.t1d.t2b.x1c.x2a, z4.t1d.t2b.x1c.x2b, z4.t1d.t2b.x1c.x2c,
z4.t1d.t2b.x1c.x2d,
z4.t1d.t2b.x1c.x2e, z4.t1d.t2b.x1c.x2f, z4.t1d.t2b.x1c.x2g,
z4.t1d.t2b.x1c.x2h,
z4.t1d.t2b.x1d.x2a, z4.t1d.t2b.x1d.x2b, z4.t1d.t2b.x1d.x2c,
z4.t1d.t2b.x1d.x2d,
z4.t1d.t2b.x1d.x2e, z4.t1d.t2b.x1d.x2f, z4.t1d.t2b.x1d.x2g,
z4.t1d.t2b.x1d.x2h,
z4.t1d.t2b.x1e.x2a, z4.t1d.t2b.x1e.x2b, z4.t1d.t2b.x1e.x2c,
z4.t1d.t2b.x1e.x2d,
z4.t1d.t2b.x1e.x2e, z4.t1d.t2b.x1e.x2f, z4.t1d.t2b.x1e.x2g,
z4.t1d.t2b.x1e.x2h,
z4.t1d.t2b.x1f.x2a, z4.t1d.t2b.x1f.x2b, z4.t1d.t2b.x1f.x2c,
z4.t1d.t2b.x1f.x2d,
z4.t1d.t2b.x1f.x2e, z4.t1d.t2b.x1f.x2f, z4.t1d.t2b.x1f.x2g,
z4.t1d.t2b.x1f.x2h,
z4.t1d.t2b.x1g.x2a, z4.t1d.t2b.x1g.x2b, z4.t1d.t2b.x1g.x2c,
z4.t1d.t2b.x1g.x2d,
z4.t1d.t2b.x1g.x2e, z4.t1d.t2b.x1g.x2f, z4.t1d.t2b.x1g.x2g,
z4.t1d.t2b.x1g.x2h,
z4.t1d.t2b.x1h.x2a, z4.t1d.t2b.x1h.x2b, z4.t1d.t2b.x1h.x2c,
z4.t1d.t2b.x1h.x2d,
z4.t1d.t2b.x1h.x2e, z4.t1d.t2b.x1h.x2f, z4.t1d.t2b.x1h.x2g,
z4.t1d.t2b.x1h.x2h,
z4.t1d.t2c.x1a.x2a, z4.t1d.t2c.x1a.x2b, z4.t1d.t2c.x1a.x2c,
z4.t1d.t2c.x1a.x2d,
z4.t1d.t2c.x1a.x2e, z4.t1d.t2c.x1a.x2f, z4.t1d.t2c.x1a.x2g,
z4.t1d.t2c.x1a.x2h,
z4.t1d.t2c.x1b.x2a, z4.t1d.t2c.x1b.x2b, z4.t1d.t2c.x1b.x2c,
z4.t1d.t2c.x1b.x2d,
z4.t1d.t2c.x1b.x2e, z4.t1d.t2c.x1b.x2f, z4.t1d.t2c.x1b.x2g,
z4.t1d.t2c.x1b.x2h,
z4.t1d.t2c.x1c.x2a, z4.t1d.t2c.x1c.x2b, z4.t1d.t2c.x1c.x2c,
z4.t1d.t2c.x1c.x2d,
z4.t1d.t2c.x1c.x2e, z4.t1d.t2c.x1c.x2f, z4.t1d.t2c.x1c.x2g,
z4.t1d.t2c.x1c.x2h,
z4.t1d.t2c.x1d.x2a, z4.t1d.t2c.x1d.x2b, z4.t1d.t2c.x1d.x2c,
z4.t1d.t2c.x1d.x2d,
z4.t1d.t2c.x1d.x2e, z4.t1d.t2c.x1d.x2f, z4.t1d.t2c.x1d.x2g,
z4.t1d.t2c.x1d.x2h,
z4.t1d.t2c.x1e.x2a, z4.t1d.t2c.x1e.x2b, z4.t1d.t2c.x1e.x2c,
z4.t1d.t2c.x1e.x2d,
z4.t1d.t2c.x1e.x2e, z4.t1d.t2c.x1e.x2f, z4.t1d.t2c.x1e.x2g,
z4.t1d.t2c.x1e.x2h,
z4.t1d.t2c.x1f.x2a, z4.t1d.t2c.x1f.x2b, z4.t1d.t2c.x1f.x2c,
z4.t1d.t2c.x1f.x2d,
z4.t1d.t2c.x1f.x2e, z4.t1d.t2c.x1f.x2f, z4.t1d.t2c.x1f.x2g,
z4.t1d.t2c.x1f.x2h,
z4.t1d.t2c.x1g.x2a, z4.t1d.t2c.x1g.x2b, z4.t1d.t2c.x1g.x2c,
z4.t1d.t2c.x1g.x2d,
z4.t1d.t2c.x1g.x2e, z4.t1d.t2c.x1g.x2f, z4.t1d.t2c.x1g.x2g,
z4.t1d.t2c.x1g.x2h,
z4.t1d.t2c.x1h.x2a, z4.t1d.t2c.x1h.x2b, z4.t1d.t2c.x1h.x2c,
z4.t1d.t2c.x1h.x2d,
z4.t1d.t2c.x1h.x2e, z4.t1d.t2c.x1h.x2f, z4.t1d.t2c.x1h.x2g,
z4.t1d.t2c.x1h.x2h,
z4.t1e.t2a.x1a.x2a, z4.t1e.t2a.x1a.x2b, z4.t1e.t2a.x1a.x2c,
z4.t1e.t2a.x1a.x2d,
z4.t1e.t2a.x1a.x2e, z4.t1e.t2a.x1a.x2f, z4.t1e.t2a.x1a.x2g,
z4.t1e.t2a.x1a.x2h,
z4.t1e.t2a.x1b.x2a, z4.t1e.t2a.x1b.x2b, z4.t1e.t2a.x1b.x2c,
z4.t1e.t2a.x1b.x2d,
z4.t1e.t2a.x1b.x2e, z4.t1e.t2a.x1b.x2f, z4.t1e.t2a.x1b.x2g,
z4.t1e.t2a.x1b.x2h,
z4.t1e.t2a.x1c.x2a, z4.t1e.t2a.x1c.x2b, z4.t1e.t2a.x1c.x2c,
z4.t1e.t2a.x1c.x2d,
z4.t1e.t2a.x1c.x2e, z4.t1e.t2a.x1c.x2f, z4.t1e.t2a.x1c.x2g,
z4.t1e.t2a.x1c.x2h,
z4.t1e.t2a.x1d.x2a, z4.t1e.t2a.x1d.x2b, z4.t1e.t2a.x1d.x2c,
z4.t1e.t2a.x1d.x2d,
z4.t1e.t2a.x1d.x2e, z4.t1e.t2a.x1d.x2f, z4.t1e.t2a.x1d.x2g,
z4.t1e.t2a.x1d.x2h,
z4.t1e.t2a.x1e.x2a, z4.t1e.t2a.x1e.x2b, z4.t1e.t2a.x1e.x2c,
z4.t1e.t2a.x1e.x2d,
z4.t1e.t2a.x1e.x2e, z4.t1e.t2a.x1e.x2f, z4.t1e.t2a.x1e.x2g,
z4.t1e.t2a.x1e.x2h,
z4.t1e.t2a.x1f.x2a, z4.t1e.t2a.x1f.x2b, z4.t1e.t2a.x1f.x2c,
z4.t1e.t2a.x1f.x2d,
z4.t1e.t2a.x1f.x2e, z4.t1e.t2a.x1f.x2f, z4.t1e.t2a.x1f.x2g,
z4.t1e.t2a.x1f.x2h,

TABLE 30.6-continued

List of Compound Structures of Formula III z4.t1e.t2a.x1g.x2a, z4.t1e.t2a.x1g.x2b, z4.t1e.t2a.x1g.x2c, z4.t1e.t2a.x1g.x2d,
z4.t1e.t2a.x1g.x2e, z4.t1e.t2a.x1g.x2f, z4.t1e.t2a.x1g.x2g, z4.t1e.t2a.x1g.x2h,
z4.t1e.t2a.x1h.x2a, z4.t1e.t2a.x1h.x2b, z4.t1e.t2a.x1h.x2c, z4.t1e.t2a.x1h.x2d,
z4.t1e.t2a.x1h.x2e, z4.t1e.t2a.x1h.x2f, z4.t1e.t2a.x1h.x2g, z4.t1e.t2a.x1h.x2h,
z4.t1e.t2b.x1a.x2a, z4.t1e.t2b.x1a.x2b, z4.t1e.t2b.x1a.x2c, z4.t1e.t2b.x1a.x2d,
z4.t1e.t2b.x1a.x2e, z4.t1e.t2b.x1a.x2f, z4.t1e.t2b.x1a.x2g, z4.t1e.t2b.x1a.x2h,
z4.t1e.t2b.x1b.x2a, z4.t1e.t2b.x1b.x2b, z4.t1e.t2b.x1b.x2c, z4.t1e.t2b.x1b.x2d,
z4.t1e.t2b.x1b.x2e, z4.t1e.t2b.x1b.x2f, z4.t1e.t2b.x1b.x2g, z4.t1e.t2b.x1b.x2h,
z4.t1e.t2b.x1c.x2a, z4.t1e.t2b.x1c.x2b, z4.t1e.t2b.x1c.x2c, z4.t1e.t2b.x1c.x2d,
z4.t1e.t2b.x1c.x2e, z4.t1e.t2b.x1c.x2f, z4.t1e.t2b.x1c.x2g, z4.t1e.t2b.x1c.x2h,
z4.t1e.t2b.x1d.x2a, z4.t1e.t2b.x1d.x2b, z4.t1e.t2b.x1d.x2c, z4.t1e.t2b.x1d.x2d,
z4.t1e.t2b.x1d.x2e, z4.t1e.t2b.x1d.x2f, z4.t1e.t2b.x1d.x2g, z4.t1e.t2b.x1d.x2h,
z4.t1e.t2b.x1e.x2a, z4.t1e.t2b.x1e.x2b, z4.t1e.t2b.x1e.x2c, z4.t1e.t2b.x1e.x2d,
z4.t1e.t2b.x1e.x2e, z4.t1e.t2b.x1e.x2f, z4.t1e.t2b.x1e.x2g, z4.t1e.t2b.x1e.x2h,
z4.t1e.t2b.x1f.x2a, z4.t1e.t2b.x1f.x2b, z4.t1e.t2b.x1f.x2c, z4.t1e.t2b.x1f.x2d,
z4.t1e.t2b.x1f.x2e, z4.t1e.t2b.x1f.x2f, z4.t1e.t2b.x1f.x2g, z4.t1e.t2b.x1f.x2h,
z4.t1e.t2b.x1g.x2a, z4.t1e.t2b.x1g.x2b, z4.t1e.t2b.x1g.x2c, z4.t1e.t2b.x1g.x2d,
z4.t1e.t2b.x1g.x2e, z4.t1e.t2b.x1g.x2f, z4.t1e.t2b.x1g.x2g, z4.t1e.t2b.x1g.x2h,
z4.t1e.t2b.x1h.x2a, z4.t1e.t2b.x1h.x2b, z4.t1e.t2b.x1h.x2c, z4.t1e.t2b.x1h.x2d,
z4.t1e.t2b.x1h.x2e, z4.t1e.t2b.x1h.x2f, z4.t1e.t2b.x1h.x2g, z4.t1e.t2b.x1h.x2h,
z4.t1e.t2c.x1a.x2a, z4.t1e.t2c.x1a.x2b, z4.t1e.t2c.x1a.x2c, z4.t1e.t2c.x1a.x2d,
z4.t1e.t2c.x1a.x2e, z4.t1e.t2c.x1a.x2f, z4.t1e.t2c.x1a.x2g, z4.t1e.t2c.x1a.x2h,
z4.t1e.t2c.x1b.x2a, z4.t1e.t2c.x1b.x2b, z4.t1e.t2c.x1b.x2c, z4.t1e.t2c.x1b.x2d,
z4.t1e.t2c.x1b.x2e, z4.t1e.t2c.x1b.x2f, z4.t1e.t2c.x1b.x2g, z4.t1e.t2c.x1b.x2h,
z4.t1e.t2c.x1c.x2a, z4.t1e.t2c.x1c.x2b, z4.t1e.t2c.x1c.x2c, z4.t1e.t2c.x1c.x2d,
z4.t1e.t2c.x1c.x2e, z4.t1e.t2c.x1c.x2f, z4.t1e.t2c.x1c.x2g, z4.t1e.t2c.x1c.x2h,
z4.t1e.t2c.x1d.x2a, z4.t1e.t2c.x1d.x2b, z4.t1e.t2c.x1d.x2c, z4.t1e.t2c.x1d.x2d,
z4.t1e.t2c.x1d.x2e, z4.t1e.t2c.x1d.x2f, z4.t1e.t2c.x1d.x2g, z4.t1e.t2c.x1d.x2h,
z4.t1e.t2c.x1e.x2a, z4.t1e.t2c.x1e.x2b, z4.t1e.t2c.x1e.x2c, z4.t1e.t2c.x1e.x2d,
z4.t1e.t2c.x1e.x2e, z4.t1e.t2c.x1e.x2f, z4.t1e.t2c.x1e.x2g, z4.t1e.t2c.x1e.x2h,
z4.t1e.t2c.x1f.x2a, z4.t1e.t2c.x1f.x2b, z4.t1e.t2c.x1f.x2c, z4.t1e.t2c.x1f.x2d,
z4.t1e.t2c.x1f.x2e, z4.t1e.t2c.x1f.x2f, z4.t1e.t2c.x1f.x2g, z4.t1e.t2c.x1f.x2h,
z4.t1e.t2c.x1g.x2a, z4.t1e.t2c.x1g.x2b, z4.t1e.t2c.x1g.x2c, z4.t1e.t2c.x1g.x2d,
z4.t1e.t2c.x1g.x2e, z4.t1e.t2c.x1g.x2f, z4.t1e.t2c.x1g.x2g, z4.t1e.t2c.x1g.x2h,
z4.t1e.t2c.x1h.x2a, z4.t1e.t2c.x1h.x2b, z4.t1e.t2c.x1h.x2c, z4.t1e.t2c.x1h.x2d,
z4.t1e.t2c.x1h.x2e, z4.t1e.t2c.x1h.x2f, z4.t1e.t2c.x1h.x2g, z4.t1e.t2c.x1h.x2h,
z5.t1a.t2a.x1a.x2a, z5.t1a.t2a.x1a.x2b, z5.t1a.t2a.x1a.x2c, z5.t1a.t2a.x1a.x2d,
z5.t1a.t2a.x1a.x2e, z5.t1a.t2a.x1a.x2f, z5.t1a.t2a.x1a.x2g, z5.t1a.t2a.x1a.x2h,
z5.t1a.t2a.x1b.x2a, z5.t1a.t2a.x1b.x2b, z5.t1a.t2a.x1b.x2c, z5.t1a.t2a.x1b.x2d,
z5.t1a.t2a.x1b.x2e, z5.t1a.t2a.x1b.x2f, z5.t1a.t2a.x1b.x2g, z5.t1a.t2a.x1b.x2h,
z5.t1a.t2a.x1c.x2a, z5.t1a.t2a.x1c.x2b, z5.t1a.t2a.x1c.x2c, z5.t1a.t2a.x1c.x2d,
z5.t1a.t2a.x1c.x2e, z5.t1a.t2a.x1c.x2f, z5.t1a.t2a.x1c.x2g, z5.t1a.t2a.x1c.x2h,
z5.t1a.t2a.x1d.x2a, z5.t1a.t2a.x1d.x2b, z5.t1a.t2a.x1d.x2c, z5.t1a.t2a.x1d.x2d,
z5.t1a.t2a.x1d.x2e, z5.t1a.t2a.x1d.x2f, z5.t1a.t2a.x1d.x2g, z5.t1a.t2a.x1d.x2h,
z5.t1a.t2a.x1e.x2a, z5.t1a.t2a.x1e.x2b, z5.t1a.t2a.x1e.x2c, z5.t1a.t2a.x1e.x2d,
z5.t1a.t2a.x1e.x2e, z5.t1a.t2a.x1e.x2f, z5.t1a.t2a.x1e.x2g, z5.t1a.t2a.x1e.x2h,
z5.t1a.t2a.x1f.x2a, z5.t1a.t2a.x1f.x2b, z5.t1a.t2a.x1f.x2c, z5.t1a.t2a.x1f.x2d,
z5.t1a.t2a.x1f.x2e, z5.t1a.t2a.x1f.x2f, z5.t1a.t2a.x1f.x2g, z5.t1a.t2a.x1f.x2h,
z5.t1a.t2a.x1g.x2a, z5.t1a.t2a.x1g.x2b, z5.t1a.t2a.x1g.x2c, z5.t1a.t2a.x1g.x2d,
z5.t1a.t2a.x1g.x2e, z5.t1a.t2a.x1g.x2f, z5.t1a.t2a.x1g.x2g, z5.t1a.t2a.x1g.x2h,
z5.t1a.t2a.x1h.x2a, z5.t1a.t2a.x1h.x2b, z5.t1a.t2a.x1h.x2c, z5.t1a.t2a.x1h.x2d,
z5.t1a.t2a.x1h.x2e, z5.t1a.t2a.x1h.x2f, z5.t1a.t2a.x1h.x2g, z5.t1a.t2a.x1h.x2h,
z5.t1a.t2b.x1a.x2a, z5.t1a.t2b.x1a.x2b, z5.t1a.t2b.x1a.x2c, z5.t1a.t2b.x1a.x2d,
z5.t1a.t2b.x1a.x2e, z5.t1a.t2b.x1a.x2f, z5.t1a.t2b.x1a.x2g, z5.t1a.t2b.x1a.x2h,
z5.t1a.t2b.x1b.x2a, z5.t1a.t2b.x1b.x2b, z5.t1a.t2b.x1b.x2c, z5.t1a.t2b.x1b.x2d,
z5.t1a.t2b.x1b.x2e, z5.t1a.t2b.x1b.x2f, z5.t1a.t2b.x1b.x2g, z5.t1a.t2b.x1b.x2h,
z5.t1a.t2b.x1c.x2a, z5.t1a.t2b.x1c.x2b, z5.t1a.t2b.x1c.x2c, z5.t1a.t2b.x1c.x2d,
z5.t1a.t2b.x1c.x2e, z5.t1a.t2b.x1c.x2f, z5.t1a.t2b.x1c.x2g, z5.t1a.t2b.x1c.x2h,
z5.t1a.t2b.x1d.x2a, z5.t1a.t2b.x1d.x2b, z5.t1a.t2b.x1d.x2c, z5.t1a.t2b.x1d.x2d,
z5.t1a.t2b.x1d.x2e, z5.t1a.t2b.x1d.x2f, z5.t1a.t2b.x1d.x2g, z5.t1a.t2b.x1d.x2h,
z5.t1a.t2b.x1e.x2a, z5.t1a.t2b.x1e.x2b, z5.t1a.t2b.x1e.x2c, z5.t1a.t2b.x1e.x2d,
z5.t1a.t2b.x1e.x2e, z5.t1a.t2b.x1e.x2f, z5.t1a.t2b.x1e.x2g, z5.t1a.t2b.x1e.x2h,
z5.t1a.t2b.x1f.x2a, z5.t1a.t2b.x1f.x2b, z5.t1a.t2b.x1f.x2c, z5.t1a.t2b.x1f.x2d,
z5.t1a.t2b.x1f.x2e, z5.t1a.t2b.x1f.x2f, z5.t1a.t2b.x1f.x2g, z5.t1a.t2b.x1f.x2h,
z5.t1a.t2b.x1g.x2a, z5.t1a.t2b.x1g.x2b, z5.t1a.t2b.x1g.x2c, z5.t1a.t2b.x1g.x2d,
z5.t1a.t2b.x1g.x2e, z5.t1a.t2b.x1g.x2f, z5.t1a.t2b.x1g.x2g, z5.t1a.t2b.x1g.x2h,
z5.t1a.t2b.x1h.x2a, z5.t1a.t2b.x1h.x2b, z5.t1a.t2b.x1h.x2c, z5.t1a.t2b.x1h.x2d,
z5.t1a.t2b.x1h.x2e, z5.t1a.t2b.x1h.x2f, z5.t1a.t2b.x1h.x2g, z5.t1a.t2b.x1h.x2h,
z5.t1a.t2c.x1a.x2a, z5.t1a.t2c.x1a.x2b, z5.t1a.t2c.x1a.x2c, z5.t1a.t2c.x1a.x2d,
z5.t1a.t2c.x1a.x2e, z5.t1a.t2c.x1a.x2f, z5.t1a.t2c.x1a.x2g, z5.t1a.t2c.x1a.x2h,
z5.t1a.t2c.x1b.x2a, z5.t1a.t2c.x1b.x2b, z5.t1a.t2c.x1b.x2c, z5.t1a.t2c.x1b.x2d,
z5.t1a.t2c.x1b.x2e, z5.t1a.t2c.x1b.x2f, z5.t1a.t2c.x1b.x2g, z5.t1a.t2c.x1b.x2h,
z5.t1a.t2c.x1c.x2a, z5.t1a.t2c.x1c.x2b, z5.t1a.t2c.x1c.x2c, z5.t1a.t2c.x1c.x2d,
z5.t1a.t2c.x1c.x2e, z5.t1a.t2c.x1c.x2f, z5.t1a.t2c.x1c.x2g, z5.t1a.t2c.x1c.x2h,
z5.t1a.t2c.x1d.x2a, z5.t1a.t2c.x1d.x2b, z5.t1a.t2c.x1d.x2c, z5.t1a.t2c.x1d.x2d,
z5.t1a.t2c.x1d.x2e, z5.t1a.t2c.x1d.x2f, z5.t1a.t2c.x1d.x2g, z5.t1a.t2c.x1d.x2h,
z5.t1a.t2c.x1e.x2a, z5.t1a.t2c.x1e.x2b, z5.t1a.t2c.x1e.x2c, z5.t1a.t2c.x1e.x2d,

TABLE 30.6-continued

List of Compound Structures of Formula III z5.t1a.t2c.x1e.x2e, z5.t1a.t2c.x1e.x2f, z5.t1a.t2c.x1e.x2g, z5.t1a.t2c.x1e.x2h,
z5.t1a.t2c.x1f.x2a, z5.t1a.t2c.x1f.x2b, z5.t1a.t2c.x1f.x2c, z5.t1a.t2c.x1f.x2d,
z5.t1a.t2c.x1f.x2e, z5.t1a.t2c.x1f.x2f, z5.t1a.t2c.x1f.x2g, z5.t1a.t2c.x1f.x2h,
z5.t1a.t2c.x1g.x2a, z5.t1a.t2c.x1g.x2b, z5.t1a.t2c.x1g.x2c, z5.t1a.t2c.x1g.x2d,
z5.t1a.t2c.x1g.x2e, z5.t1a.t2c.x1g.x2f, z5.t1a.t2c.x1g.x2g, z5.t1a.t2c.x1g.x2h,
z5.t1a.t2c.x1h.x2a, z5.t1a.t2c.x1h.x2b, z5.t1a.t2c.x1h.x2c, z5.t1a.t2c.x1h.x2d,
z5.t1a.t2c.x1h.x2e, z5.t1a.t2c.x1h.x2f, z5.t1a.t2c.x1h.x2g, z5.t1a.t2c.x1h.x2h,
z5.t1b.t2a.x1a.x2a, z5.t1b.t2a.x1a.x2b, z5.t1b.t2a.x1a.x2c, z5.t1b.t2a.x1a.x2d,
z5.t1b.t2a.x1a.x2e, z5.t1b.t2a.x1a.x2f, z5.t1b.t2a.x1a.x2g, z5.t1b.t2a.x1a.x2h,
z5.t1b.t2a.x1b.x2a, z5.t1b.t2a.x1b.x2b, z5.t1b.t2a.x1b.x2c, z5.t1b.t2a.x1b.x2d,
z5.t1b.t2a.x1b.x2e, z5.t1b.t2a.x1b.x2f, z5.t1b.t2a.x1b.x2g, z5.t1b.t2a.x1b.x2h,
z5.t1b.t2a.x1c.x2a, z5.t1b.t2a.x1c.x2b, z5.t1b.t2a.x1c.x2c, z5.t1b.t2a.x1c.x2d,
z5.t1b.t2a.x1c.x2e, z5.t1b.t2a.x1c.x2f, z5.t1b.t2a.x1c.x2g, z5.t1b.t2a.x1c.x2h,
z5.t1b.t2a.x1d.x2a, z5.t1b.t2a.x1d.x2b, z5.t1b.t2a.x1d.x2c, z5.t1b.t2a.x1d.x2d,
z5.t1b.t2a.x1d.x2e, z5.t1b.t2a.x1d.x2f, z5.t1b.t2a.x1d.x2g, z5.t1b.t2a.x1d.x2h,
z5.t1b.t2a.x1e.x2a, z5.t1b.t2a.x1e.x2b, z5.t1b.t2a.x1e.x2c, z5.t1b.t2a.x1e.x2d,
z5.t1b.t2a.x1e.x2e, z5.t1b.t2a.x1e.x2f, z5.t1b.t2a.x1e.x2g, z5.t1b.t2a.x1e.x2h,
z5.t1b.t2a.x1f.x2a, z5.t1b.t2a.x1f.x2b, z5.t1b.t2a.x1f.x2c, z5.t1b.t2a.x1f.x2d,
z5.t1b.t2a.x1f.x2e, z5.t1b.t2a.x1f.x2f, z5.t1b.t2a.x1f.x2g, z5.t1b.t2a.x1f.x2h,
z5.t1b.t2a.x1g.x2a, z5.t1b.t2a.x1g.x2b, z5.t1b.t2a.x1g.x2c, z5.t1b.t2a.x1g.x2d,
z5.t1b.t2a.x1g.x2e, z5.t1b.t2a.x1g.x2f, z5.t1b.t2a.x1g.x2g, z5.t1b.t2a.x1g.x2h,
z5.t1b.t2a.x1h.x2a, z5.t1b.t2a.x1h.x2b, z5.t1b.t2a.x1h.x2c, z5.t1b.t2a.x1h.x2d,
z5.t1b.t2a.x1h.x2e, z5.t1b.t2a.x1h.x2f, z5.t1b.t2a.x1h.x2g, z5.t1b.t2a.x1h.x2h,
z5.t1b.t2b.x1a.x2a, z5.t1b.t2b.x1a.x2b, z5.t1b.t2b.x1a.x2c, z5.t1b.t2b.x1a.x2d,
z5.t1b.t2b.x1a.x2e, z5.t1b.t2b.x1a.x2f, z5.t1b.t2b.x1a.x2g, z5.t1b.t2b.x1a.x2h,
z5.t1b.t2b.x1b.x2a, z5.t1b.t2b.x1b.x2b, z5.t1b.t2b.x1b.x2c, z5.t1b.t2b.x1b.x2d,
z5.t1b.t2b.x1b.x2e, z5.t1b.t2b.x1b.x2f, z5.t1b.t2b.x1b.x2g, z5.t1b.t2b.x1b.x2h,
z5.t1b.t2b.x1c.x2a, z5.t1b.t2b.x1c.x2b, z5.t1b.t2b.x1c.x2c, z5.t1b.t2b.x1c.x2d,
z5.t1b.t2b.x1c.x2e, z5.t1b.t2b.x1c.x2f, z5.t1b.t2b.x1c.x2g, z5.t1b.t2b.x1c.x2h,
z5.t1b.t2b.x1d.x2a, z5.t1b.t2b.x1d.x2b, z5.t1b.t2b.x1d.x2c, z5.t1b.t2b.x1d.x2d,
z5.t1b.t2b.x1d.x2e, z5.t1b.t2b.x1d.x2f, z5.t1b.t2b.x1d.x2g, z5.t1b.t2b.x1d.x2h,
z5.t1b.t2b.x1e.x2a, z5.t1b.t2b.x1e.x2b, z5.t1b.t2b.x1e.x2c, z5.t1b.t2b.x1e.x2d,
z5.t1b.t2b.x1e.x2e, z5.t1b.t2b.x1e.x2f, z5.t1b.t2b.x1e.x2g, z5.t1b.t2b.x1e.x2h,
z5.t1b.t2b.x1f.x2a, z5.t1b.t2b.x1f.x2b, z5.t1b.t2b.x1f.x2c, z5.t1b.t2b.x1f.x2d,
z5.t1b.t2b.x1f.x2e, z5.t1b.t2b.x1f.x2f, z5.t1b.t2b.x1f.x2g, z5.t1b.t2b.x1f.x2h,
z5.t1b.t2b.x1g.x2a, z5.t1b.t2b.x1g.x2b, z5.t1b.t2b.x1g.x2c, z5.t1b.t2b.x1g.x2d,
z5.t1b.t2b.x1g.x2e, z5.t1b.t2b.x1g.x2f, z5.t1b.t2b.x1g.x2g, z5.t1b.t2b.x1g.x2h,
z5.t1b.t2b.x1h.x2a, z5.t1b.t2b.x1h.x2b, z5.t1b.t2b.x1h.x2c, z5.t1b.t2b.x1h.x2d,
z5.t1b.t2b.x1h.x2e, z5.t1b.t2b.x1h.x2f, z5.t1b.t2b.x1h.x2g, z5.t1b.t2b.x1h.x2h,
z5.t1b.t2c.x1a.x2a, z5.t1b.t2c.x1a.x2b, z5.t1b.t2c.x1a.x2c, z5.t1b.t2c.x1a.x2d,
z5.t1b.t2c.x1a.x2e, z5.t1b.t2c.x1a.x2f, z5.t1b.t2c.x1a.x2g, z5.t1b.t2c.x1a.x2h,
z5.t1b.t2c.x1b.x2a, z5.t1b.t2c.x1b.x2b, z5.t1b.t2c.x1b.x2c, z5.t1b.t2c.x1b.x2d,
z5.t1b.t2c.x1b.x2e, z5.t1b.t2c.x1b.x2f, z5.t1b.t2c.x1b.x2g, z5.t1b.t2c.x1b.x2h,
z5.t1b.t2c.x1c.x2a, z5.t1b.t2c.x1c.x2b, z5.t1b.t2c.x1c.x2c, z5.t1b.t2c.x1c.x2d,
z5.t1b.t2c.x1c.x2e, z5.t1b.t2c.x1c.x2f, z5.t1b.t2c.x1c.x2g, z5.t1b.t2c.x1c.x2h,
z5.t1b.t2c.x1d.x2a, z5.t1b.t2c.x1d.x2b, z5.t1b.t2c.x1d.x2c, z5.t1b.t2c.x1d.x2d,
z5.t1b.t2c.x1d.x2e, z5.t1b.t2c.x1d.x2f, z5.t1b.t2c.x1d.x2g, z5.t1b.t2c.x1d.x2h,
z5.t1b.t2c.x1e.x2a, z5.t1b.t2c.x1e.x2b, z5.t1b.t2c.x1e.x2c, z5.t1b.t2c.x1e.x2d,
z5.t1b.t2c.x1e.x2e, z5.t1b.t2c.x1e.x2f, z5.t1b.t2c.x1e.x2g, z5.t1b.t2c.x1e.x2h,
z5.t1b.t2c.x1f.x2a, z5.t1b.t2c.x1f.x2b, z5.t1b.t2c.x1f.x2c, z5.t1b.t2c.x1f.x2d,
z5.t1b.t2c.x1f.x2e, z5.t1b.t2c.x1f.x2f, z5.t1b.t2c.x1f.x2g, z5.t1b.t2c.x1f.x2h,
z5.t1b.t2c.x1g.x2a, z5.t1b.t2c.x1g.x2b, z5.t1b.t2c.x1g.x2c, z5.t1b.t2c.x1g.x2d,
z5.t1b.t2c.x1g.x2e, z5.t1b.t2c.x1g.x2f, z5.t1b.t2c.x1g.x2g, z5.t1b.t2c.x1g.x2h,
z5.t1b.t2c.x1h.x2a, z5.t1b.t2c.x1h.x2b, z5.t1b.t2c.x1h.x2c, z5.t1b.t2c.x1h.x2d,
z5.t1b.t2c.x1h.x2e, z5.t1b.t2c.x1h.x2f, z5.t1b.t2c.x1h.x2g, z5.t1b.t2c.x1h.x2h,
z5.t1c.t2a.x1a.x2a, z5.t1c.t2a.x1a.x2b, z5.t1c.t2a.x1a.x2c, z5.t1c.t2a.x1a.x2d,
z5.t1c.t2a.x1a.x2e, z5.t1c.t2a.x1a.x2f, z5.t1c.t2a.x1a.x2g, z5.t1c.t2a.x1a.x2h,
z5.t1c.t2a.x1b.x2a, z5.t1c.t2a.x1b.x2b, z5.t1c.t2a.x1b.x2c, z5.t1c.t2a.x1b.x2d,
z5.t1c.t2a.x1b.x2e, z5.t1c.t2a.x1b.x2f, z5.t1c.t2a.x1b.x2g, z5.t1c.t2a.x1b.x2h,
z5.t1c.t2a.x1c.x2a, z5.t1c.t2a.x1c.x2b, z5.t1c.t2a.x1c.x2c, z5.t1c.t2a.x1c.x2d,
z5.t1c.t2a.x1c.x2e, z5.t1c.t2a.x1c.x2f, z5.t1c.t2a.x1c.x2g, z5.t1c.t2a.x1c.x2h,
z5.t1c.t2a.x1d.x2a, z5.t1c.t2a.x1d.x2b, z5.t1c.t2a.x1d.x2c, z5.t1c.t2a.x1d.x2d,
z5.t1c.t2a.x1d.x2e, z5.t1c.t2a.x1d.x2f, z5.t1c.t2a.x1c.x2g, z5.t1c.t2a.x1d.x2h,
z5.t1c.t2a.x1e.x2a, z5.t1c.t2a.x1e.x2b, z5.t1c.t2a.x1e.x2c, z5.t1c.t2a.x1e.x2d,
z5.t1c.t2a.x1e.x2e, z5.t1c.t2a.x1e.x2f, z5.t1c.t2a.x1e.x2g, z5.t1c.t2a.x1e.x2h,
z5.t1c.t2a.x1f.x2a, z5.t1c.t2a.x1f.x2b, z5.t1c.t2a.x1f.x2c, z5.t1c.t2a.x1f.x2d,
z5.t1c.t2a.x1f.x2e, z5.t1c.t2a.x1f.x2f, z5.t1c.t2a.x1f.x2g, z5.t1c.t2a.x1f.x2h,
z5.t1c.t2a.x1g.x2a, z5.t1c.t2a.x1g.x2b, z5.t1c.t2a.x1g.x2c, z5.t1c.t2a.x1g.x2d,
z5.t1c.t2a.x1g.x2e, z5.t1c.t2a.x1g.x2f, z5.t1c.t2a.x1g.x2g, z5.t1c.t2a.x1g.x2h,
z5.t1c.t2a.x1h.x2a, z5.t1c.t2a.x1h.x2b, z5.t1c.t2a.x1h.x2c, z5.t1c.t2a.x1h.x2d,
z5.t1c.t2a.x1h.x2e, z5.t1c.t2a.x1h.x2f, z5.t1c.t2a.x1h.x2g, z5.t1c.t2a.x1h.x2h,
z5.t1c.t2b.x1a.x2a, z5.t1c.t2b.x1a.x2b, z5.t1c.t2b.x1a.x2c, z5.t1c.t2b.x1a.x2d,
z5.t1c.t2b.x1a.x2e, z5.t1c.t2b.x1a.x2f, z5.t1c.t2b.x1a.x2g, z5.t1c.t2b.x1a.x2h,
z5.t1c.t2b.x1b.x2a, z5.t1c.t2b.x1b.x2b, z5.t1c.t2b.x1b.x2c, z5.t1c.t2b.x1b.x2d,
z5.t1c.t2b.x1b.x2e, z5.t1c.t2b.x1b.x2f, z5.t1c.t2b.x1b.x2g, z5.t1c.t2b.x1b.x2h,
z5.t1c.t2b.x1c.x2a, z5.t1c.t2b.x1c.x2b, z5.t1c.t2b.x1c.x2c, z5.t1c.t2b.x1c.x2d,
z5.t1c.t2b.x1c.x2e, z5.t1c.t2b.x1c.x2f, z5.t1c.t2b.x1c.x2g, z5.t1c.t2b.x1c.x2h,

TABLE 30.6-continued

List of Compound Structures of Formula III z5.t1c.t2b.x1d.x2a, z5.t1c.t2b.x1d.x2b, z5.t1c.t2b.x1d.x2c, z5.t1c.t2b.x1d.x2d,
z5.t1c.t2b.x1d.x2e, z5.t1c.t2b.x1d.x2f, z5.t1c.t2b.x1d.x2g, z5.t1c.t2b.x1d.x2h,
z5.t1c.t2b.x1e.x2a, z5.t1c.t2b.x1e.x2b, z5.t1c.t2b.x1e.x2c, z5.t1c.t2b.x1e.x2d,
z5.t1c.t2b.x1e.x2e, z5.t1c.t2b.x1e.x2f, z5.t1c.t2b.x1e.x2g, z5.t1c.t2b.x1e.x2h,
z5.t1c.t2b.x1f.x2a, z5.t1c.t2b.x1f.x2b, z5.t1c.t2b.x1f.x2c, z5.t1c.t2b.x1f.x2d,
z5.t1c.t2b.x1f.x2e, z5.t1c.t2b.x1f.x2f, z5.t1c.t2b.x1f.x2g, z5.t1c.t2b.x1f.x2h,
z5.t1c.t2b.x1g.x2a, z5.t1c.t2b.x1g.x2b, z5.t1c.t2b.x1g.x2c, z5.t1c.t2b.x1g.x2d,
z5.t1c.t2b.x1g.x2e, z5.t1c.t2b.x1g.x2f, z5.t1c.t2b.x1g.x2g, z5.t1c.t2b.x1g.x2h,
z5.t1c.t2b.x1h.x2a, z5.t1c.t2b.x1h.x2b, z5.t1c.t2b.x1h.x2c, z5.t1c.t2b.x1h.x2d,
z5.t1c.t2b.x1h.x2e, z5.t1c.t2b.x1h.x2f, z5.t1c.t2b.x1h.x2g, z5.t1c.t2b.x1h.x2h,
z5.t1c.t2c.x1a.x2a, z5.t1c.t2c.x1a.x2b, z5.t1c.t2c.x1a.x2c, z5.t1c.t2c.x1a.x2d,
z5.t1c.t2c.x1a.x2e, z5.t1c.t2c.x1a.x2f, z5.t1c.t2c.x1a.x2g, z5.t1c.t2c.x1a.x2h,
z5.t1c.t2c.x1b.x2a, z5.t1c.t2c.x1b.x2b, z5.t1c.t2c.x1b.x2c, z5.t1c.t2c.x1b.x2d,
z5.t1c.t2c.x1b.x2e, z5.t1c.t2c.x1b.x2f, z5.t1c.t2c.x1b.x2g, z5.t1c.t2c.x1b.x2h,
z5.t1c.t2c.x1c.x2a, z5.t1c.t2c.x1c.x2b, z5.t1c.t2c.x1c.x2c, z5.t1c.t2c.x1c.x2d,
z5.t1c.t2c.x1c.x2e, z5.t1c.t2c.x1c.x2f, z5.t1c.t2c.x1c.x2g, z5.t1c.t2c.x1c.x2h,
z5.t1c.t2c.x1d.x2a, z5.t1c.t2c.x1d.x2b, z5.t1c.t2c.x1d.x2c, z5.t1c.t2c.x1d.x2d,
z5.t1c.t2c.x1d.x2e, z5.t1c.t2c.x1d.x2f, z5.t1c.t2c.x1d.x2g, z5.t1c.t2c.x1d.x2h,
z5.t1c.t2c.x1e.x2a, z5.t1c.t2c.x1e.x2b, z5.t1c.t2c.x1e.x2c, z5.t1c.t2c.x1e.x2d,
z5.t1c.t2c.x1e.x2e, z5.t1c.t2c.x1e.x2f, z5.t1c.t2c.x1e.x2g, z5.t1c.t2c.x1e.x2h,
z5.t1c.t2c.x1f.x2a, z5.t1c.t2c.x1f.x2b, z5.t1c.t2c.x1f.x2c, z5.t1c.t2c.x1f.x2d,
z5.t1c.t2c.x1f.x2e, z5.t1c.t2c.x1f.x2f, z5.t1c.t2c.x1f.x2g, z5.t1c.t2c.x1f.x2h,
z5.t1c.t2c.x1g.x2a, z5.t1c.t2c.x1g.x2b, z5.t1c.t2c.x1g.x2c, z5.t1c.t2c.x1g.x2d,
z5.t1c.t2c.x1g.x2e, z5.t1c.t2c.x1g.x2f, z5.t1c.t2c.x1g.x2g, z5.t1c.t2c.x1g.x2h,
z5.t1c.t2c.x1h.x2a, z5.t1c.t2c.x1h.x2b, z5.t1c.t2c.x1h.x2c, z5.t1c.t2c.x1h.x2d,
z5.t1c.t2c.x1h.x2e, z5.t1c.t2c.x1h.x2f, z5.t1c.t2c.x1h.x2g, z5.t1c.t2c.x1h.x2h,
z5.t1d.t2a.x1a.x2a, z5.t1d.t2a.x1a.x2b, z5.t1d.t2a.x1a.x2c, z5.t1d.t2a.x1a.x2d,
z5.t1d.t2a.x1a.x2e, z5.t1d.t2a.x1a.x2f, z5.t1d.t2a.x1a.x2g, z5.t1d.t2a.x1a.x2h,
z5.t1d.t2a.x1b.x2a, z5.t1d.t2a.x1b.x2b, z5.t1d.t2a.x1b.x2c, z5.t1d.t2a.x1b.x2d,
z5.t1d.t2a.x1b.x2e, z5.t1d.t2a.x1b.x2f, z5.t1d.t2a.x1b.x2g, z5.t1d.t2a.x1b.x2h,
z5.t1d.t2a.x1c.x2a, z5.t1d.t2a.x1c.x2b, z5.t1d.t2a.x1c.x2c, z5.t1d.t2a.x1c.x2d,
z5.t1d.t2a.x1c.x2e, z5.t1d.t2a.x1c.x2f, z5.t1d.t2a.x1c.x2g, z5.t1d.t2a.x1c.x2h,
z5.t1d.t2a.x1d.x2a, z5.t1d.t2a.x1d.x2b, z5.t1d.t2a.x1d.x2c, z5.t1d.t2a.x1d.x2d,
z5.t1d.t2a.x1d.x2e, z5.t1d.t2a.x1d.x2f, z5.t1d.t2a.x1d.x2g, z5.t1d.t2a.x1d.x2h,
z5.t1d.t2a.x1e.x2a, z5.t1d.t2a.x1e.x2b, z5.t1d.t2a.x1e.x2c, z5.t1d.t2a.x1e.x2d,
z5.t1d.t2a.x1e.x2e, z5.t1d.t2a.x1e.x2f, z5.t1d.t2a.x1e.x2g, z5.t1d.t2a.x1e.x2h,
z5.t1d.t2a.x1f.x2a, z5.t1d.t2a.x1f.x2b, z5.t1d.t2a.x1f.x2c, z5.t1d.t2a.x1f.x2d,
z5.t1d.t2a.x1f.x2e, z5.t1d.t2a.x1f.x2f, z5.t1d.t2a.x1f.x2g, z5.t1d.t2a.x1f.x2h,
z5.t1d.t2a.x1g.x2a, z5.t1d.t2a.x1g.x2b, z5.t1d.t2a.x1g.x2c, z5.t1d.t2a.x1g.x2d,
z5.t1d.t2a.x1g.x2e, z5.t1d.t2a.x1g.x2f, z5.t1d.t2a.x1g.x2g, z5.t1d.t2a.x1g.x2h,
z5.t1d.t2a.x1h.x2a, z5.t1d.t2a.x1h.x2b, z5.t1d.t2a.x1h.x2c, z5.t1d.t2a.x1h.x2d,
z5.t1d.t2a.x1h.x2e, z5.t1d.t2a.x1h.x2f, z5.t1d.t2a.x1h.x2g, z5.t1d.t2a.x1h.x2h,
z5.t1d.t2b.x1a.x2a, z5.t1d.t2b.x1a.x2b, z5.t1d.t2b.x1a.x2c, z5.t1d.t2b.x1a.x2d,
z5.t1d.t2b.x1a.x2e, z5.t1d.t2b.x1a.x2f, z5.t1d.t2b.x1a.x2g, z5.t1d.t2b.x1a.x2h,
z5.t1d.t2b.x1b.x2a, z5.t1d.t2b.x1b.x2b, z5.t1d.t2b.x1b.x2c, z5.t1d.t2b.x1b.x2d,
z5.t1d.t2b.x1b.x2e, z5.t1d.t2b.x1b.x2f, z5.t1d.t2b.x1b.x2g, z5.t1d.t2b.x1b.x2h,
z5.t1d.t2b.x1c.x2a, z5.t1d.t2b.x1c.x2b, z5.t1d.t2b.x1c.x2c, z5.t1d.t2b.x1c.x2d,
z5.t1d.t2b.x1c.x2e, z5.t1d.t2b.x1c.x2f, z5.t1d.t2b.x1c.x2g, z5.t1d.t2b.x1c.x2h,
z5.t1d.t2b.x1d.x2a, z5.t1d.t2b.x1d.x2b, z5.t1d.t2b.x1d.x2c, z5.t1d.t2b.x1d.x2d,
z5.t1d.t2b.x1d.x2e, z5.t1d.t2b.x1d.x2f, z5.t1d.t2b.x1d.x2g, z5.t1d.t2b.x1d.x2h,
z5.t1d.t2b.x1e.x2a, z5.t1d.t2b.x1e.x2b, z5.t1d.t2b.x1e.x2c, z5.t1d.t2b.x1e.x2d,
z5.t1d.t2b.x1e.x2e, z5.t1d.t2b.x1e.x2f, z5.t1d.t2b.x1e.x2g, z5.t1d.t2b.x1e.x2h,
z5.t1d.t2b.x1f.x2a, z5.t1d.t2b.x1f.x2b, z5.t1d.t2b.x1f.x2c, z5.t1d.t2b.x1f.x2d,
z5.t1d.t2b.x1f.x2e, z5.t1d.t2b.x1f.x2f, z5.t1d.t2b.x1f.x2g, z5.t1d.t2b.x1f.x2h,
z5.t1d.t2b.x1g.x2a, z5.t1d.t2b.x1g.x2b, z5.t1d.t2b.x1g.x2c, z5.t1d.t2b.x1g.x2d,
z5.t1d.t2b.x1g.x2e, z5.t1d.t2b.x1g.x2f, z5.t1d.t2b.x1g.x2g, z5.t1d.t2b.x1g.x2h,
z5.t1d.t2b.x1h.x2a, z5.t1d.t2b.x1h.x2b, z5.t1d.t2b.x1h.x2c, z5.t1d.t2b.x1h.x2d,
z5.t1d.t2b.x1h.x2e, z5.t1d.t2b.x1h.x2f, z5.t1d.t2b.x1h.x2g, z5.t1d.t2b.x1h.x2h,
z5.t1d.t2c.x1a.x2a, z5.t1d.t2c.x1a.x2b, z5.t1d.t2c.x1a.x2c, z5.t1d.t2c.x1a.x2d,
z5.t1d.t2c.x1a.x2e, z5.t1d.t2c.x1a.x2f, z5.t1d.t2c.x1a.x2g, z5.t1d.t2c.x1a.x2h,
z5.t1d.t2c.x1b.x2a, z5.t1d.t2c.x1b.x2b, z5.t1d.t2c.x1b.x2c, z5.t1d.t2c.x1b.x2d,
z5.t1d.t2c.x1b.x2e, z5.t1d.t2c.x1b.x2f, z5.t1d.t2c.x1b.x2g, z5.t1d.t2c.x1b.x2h,
z5.t1d.t2c.x1c.x2a, z5.t1d.t2c.x1c.x2b, z5.t1d.t2c.x1c.x2c, z5.t1d.t2c.x1c.x2d,
z5.t1d.t2c.x1c.x2e, z5.t1d.t2c.x1c.x2f, z5.t1d.t2c.x1c.x2g, z5.t1d.t2c.x1c.x2h,
z5.t1d.t2c.x1d.x2a, z5.t1d.t2c.x1d.x2b, z5.t1d.t2c.x1d.x2c, z5.t1d.t2c.x1d.x2d,
z5.t1d.t2c.x1d.x2e, z5.t1d.t2c.x1d.x2f, z5.t1d.t2c.x1d.x2g, z5.t1d.t2c.x1d.x2h,
z5.t1d.t2c.x1e.x2a, z5.t1d.t2c.x1e.x2b, z5.t1d.t2c.x1e.x2c, z5.t1d.t2c.x1e.x2d,
z5.t1d.t2c.x1e.x2e, z5.t1d.t2c.x1e.x2f, z5.t1d.t2c.x1e.x2g, z5.t1d.t2c.x1e.x2h,
z5.t1d.t2c.x1f.x2a, z5.t1d.t2c.x1f.x2b, z5.t1d.t2c.x1f.x2c, z5.t1d.t2c.x1f.x2d,
z5.t1d.t2c.x1f.x2e, z5.t1d.t2c.x1f.x2f, z5.t1d.t2c.x1f.x2g, z5.t1d.t2c.x1f.x2h,
z5.t1d.t2c.x1g.x2a, z5.t1d.t2c.x1g.x2b, z5.t1d.t2c.x1g.x2c, z5.t1d.t2c.x1g.x2d,
z5.t1d.t2c.x1g.x2e, z5.t1d.t2c.x1g.x2f, z5.t1d.t2c.x1g.x2g, z5.t1d.t2c.x1g.x2h,
z5.t1d.t2c.x1h.x2a, z5.t1d.t2c.x1h.x2b, z5.t1d.t2c.x1h.x2c, z5.t1d.t2c.x1h.x2d,
z5.t1d.t2c.x1h.x2e, z5.t1d.t2c.x1h.x2f, z5.t1d.t2c.x1h.x2g, z5.t1d.t2c.x1h.x2h,
z5.t1e.t2a.x1a.x2a, z5.t1e.t2a.x1a.x2b, z5.t1e.t2a.x1a.x2c, z5.t1e.t2a.x1a.x2d,
z5.t1e.t2a.x1a.x2e, z5.t1e.t2a.x1a.x2f, z5.t1e.t2a.x1a.x2g, z5.t1e.t2a.x1a.x2h,
z5.t1e.t2a.x1b.x2a, z5.t1e.t2a.x1b.x2b, z5.t1e.t2a.x1b.x2c, z5.t1e.t2a.x1b.x2d,

TABLE 30.6-continued

List of Compound Structures of Formula III z5.t1e.t2a.x1b.x2e, z5.t1e.t2a.x1b.x2f, z5.t1e.t2a.x1b.x2g, z5.t1e.t2a.x1b.x2h,
z5.t1e.t2a.x1c.x2a, z5.t1e.t2a.x1c.x2b, z5.t1e.t2a.x1c.x2c, z5.t1e.t2a.x1c.x2d,
z5.t1e.t2a.x1c.x2e, z5.t1e.t2a.x1c.x2f, z5.t1e.t2a.x1c.x2g, z5.t1e.t2a.x1c.x2h,
z5.t1e.t2a.x1d.x2a, z5.t1e.t2a.x1d.x2b, z5.t1e.t2a.x1d.x2c, z5.t1e.t2a.x1d.x2d,
z5.t1e.t2a.x1d.x2e, z5.t1e.t2a.x1d.x2f, z5.t1e.t2a.x1d.x2g, z5.t1e.t2a.x1d.x2h,
z5.t1e.t2a.x1e.x2a, z5.t1e.t2a.x1e.x2b, z5.t1e.t2a.x1e.x2c, z5.t1e.t2a.x1e.x2d,
z5.t1e.t2a.x1e.x2e, z5.t1e.t2a.x1e.x2f, z5.t1e.t2a.x1e.x2g, z5.t1e.t2a.x1e.x2h,
z5.t1e.t2a.x1f.x2a, z5.t1e.t2a.x1f.x2b, z5.t1e.t2a.x1f.x2c, z5.t1e.t2a.x1f.x2d,
z5.t1e.t2a.x1f.x2e, z5.t1e.t2a.x1f.x2f, z5.t1e.t2a.x1f.x2g, z5.t1e.t2a.x1f.x2h,
z5.t1e.t2a.x1g.x2a, z5.t1e.t2a.x1g.x2b, z5.t1e.t2a.x1g.x2c, z5.t1e.t2a.x1g.x2d,
z5.t1e.t2a.x1g.x2e, z5.t1e.t2a.x1g.x2f, z5.t1e.t2a.x1g.x2g, z5.t1e.t2a.x1g.x2h,
z5.t1e.t2a.x1h.x2a, z5.t1e.t2a.x1h.x2b, z5.t1e.t2a.x1h.x2c, z5.t1e.t2a.x1h.x2d,
z5.t1e.t2a.x1h.x2e, z5.t1e.t2a.x1h.x2f, z5.t1e.t2a.x1h.x2g, z5.t1e.t2a.x1h.x2h,
z5.t1e.t2b.x1a.x2a, z5.t1e.t2b.x1a.x2b, z5.t1e.t2b.x1a.x2c, z5.t1e.t2b.x1a.x2d,
z5.t1e.t2b.x1a.x2e, z5.t1e.t2b.x1a.x2f, z5.t1e.t2b.x1a.x2g, z5.t1e.t2b.x1a.x2h,
z5.t1e.t2b.x1b.x2a, z5.t1e.t2b.x1b.x2b, z5.t1e.t2b.x1b.x2c, z5.t1e.t2b.x1b.x2d,
z5.t1e.t2b.x1b.x2e, z5.t1e.t2b.x1b.x2f, z5.t1e.t2b.x1b.x2g, z5.t1e.t2b.x1b.x2h,
z5.t1e.t2b.x1c.x2a, z5.t1e.t2b.x1c.x2b, z5.t1e.t2b.x1c.x2c, z5.t1e.t2b.x1c.x2d,
z5.t1e.t2b.x1c.x2e, z5.t1e.t2b.x1c.x2f, z5.t1e.t2b.x1c.x2g, z5.t1e.t2b.x1c.x2h,
z5.t1e.t2b.x1d.x2a, z5.t1e.t2b.x1d.x2b, z5.t1e.t2b.x1d.x2c, z5.t1e.t2b.x1d.x2d,
z5.t1e.t2b.x1d.x2e, z5.t1e.t2b.x1d.x2f, z5.t1e.t2b.x1d.x2g, z5.t1e.t2b.x1d.x2h,
z5.t1e.t2b.x1e.x2a, z5.t1e.t2b.x1e.x2b, z5.t1e.t2b.x1e.x2c, z5.t1e.t2b.x1e.x2d,
z5.t1e.t2b.x1e.x2e, z5.t1e.t2b.x1e.x2f, z5.t1e.t2b.x1e.x2g, z5.t1e.t2b.x1e.x2h,
z5.t1e.t2b.x1f.x2a, z5.t1e.t2b.x1f.x2b, z5.t1e.t2b.x1f.x2c, z5.t1e.t2b.x1f.x2d,
z5.t1e.t2b.x1f.x2e, z5.t1e.t2b.x1f.x2f, z5.t1e.t2b.x1f.x2g, z5.t1e.t2b.x1f.x2h,
z5.t1e.t2b.x1g.x2a, z5.t1e.t2b.x1g.x2b, z5.t1e.t2b.x1g.x2c, z5.t1e.t2b.x1g.x2d,
z5.t1e.t2b.x1g.x2e, z5.t1e.t2b.x1g.x2f, z5.t1e.t2b.x1g.x2g, z5.t1e.t2b.x1g.x2h,
z5.t1e.t2b.x1h.x2a, z5.t1e.t2b.x1h.x2b, z5.t1e.t2b.x1h.x2c, z5.t1e.t2b.x1h.x2d,
z5.t1e.t2b.x1h.x2e, z5.t1e.t2b.x1h.x2f, z5.t1e.t2b.x1h.x2g, z5.t1e.t2b.x1h.x2h,
z5.t1e.t2c.x1a.x2a, z5.t1e.t2c.x1a.x2b, z5.t1e.t2c.x1a.x2c, z5.t1e.t2c.x1a.x2d,
z5.t1e.t2c.x1a.x2e, z5.t1e.t2c.x1a.x2f, z5.t1e.t2c.x1a.x2g, z5.t1e.t2c.x1a.x2h,
z5.t1e.t2c.x1b.x2a, z5.t1e.t2c.x1b.x2b, z5.t1e.t2c.x1b.x2c, z5.t1e.t2c.x1b.x2d,
z5.t1e.t2c.x1b.x2e, z5.t1e.t2c.x1b.x2f, z5.t1e.t2c.x1b.x2g, z5.t1e.t2c.x1b.x2h,
z5.t1e.t2c.x1c.x2a, z5.t1e.t2c.x1c.x2b, z5.t1e.t2c.x1c.x2c, z5.t1e.t2c.x1c.x2d,
z5.t1e.t2c.x1c.x2e, z5.t1e.t2c.x1c.x2f, z5.t1e.t2c.x1c.x2g, z5.t1e.t2c.x1c.x2h,
z5.t1e.t2c.x1d.x2a, z5.t1e.t2c.x1d.x2b, z5.t1e.t2c.x1d.x2c, z5.t1e.t2c.x1d.x2d,
z5.t1e.t2c.x1d.x2e, z5.t1e.t2c.x1d.x2f, z5.t1e.t2c.x1d.x2g, z5.t1e.t2c.x1d.x2h,
z5.t1e.t2c.x1e.x2a, z5.t1e.t2c.x1e.x2b, z5.t1e.t2c.x1e.x2c, z5.t1e.t2c.x1e.x2d,
z5.t1e.t2c.x1e.x2e, z5.t1e.t2c.x1e.x2f, z5.t1e.t2c.x1e.x2g, z5.t1e.t2c.x1e.x2h,
z5.t1e.t2c.x1f.x2a, z5.t1e.t2c.x1f.x2b, z5.t1e.t2c.x1f.x2c, z5.t1e.t2c.x1f.x2d,
z5.t1e.t2c.x1f.x2e, z5.t1e.t2c.x1f.x2f, z5.t1e.t2c.x1f.x2g, z5.t1e.t2c.x1f.x2h,
z5.t1e.t2c.x1g.x2a, z5.t1e.t2c.x1g.x2b, z5.t1e.t2c.x1g.x2c, z5.t1e.t2c.x1g.x2d,
z5.t1e.t2c.x1g.x2e, z5.t1e.t2c.x1g.x2f, z5.t1e.t2c.x1g.x2g, z5.t1e.t2c.x1g.x2h,
z5.t1e.t2c.x1h.x2a, z5.t1e.t2c.x1h.x2b, z5.t1e.t2c.x1h.x2c, z5.t1e.t2c.x1h.x2d,
z5.t1e.t2c.x1h.x2e, z5.t1e.t2c.x1h.x2f, z5.t1e.t2c.x1h.x2g, z5.t1e.t2c.x1h.x2h.

Phosphonate Prodrug Compounds

The compounds of this invention can be phosphonate prodrug compounds (or conjugates) derived from the compounds of Formula I. For example, the compounds of Formula I can be associated, e.g., structurally linked directly or indirectly with one or more phosphonate groups, especially phosphonate groups capable of modifying bioavailability, efficacy, or targeting site(s) of the compounds. Usually the compounds of Formula I can be directly linked to one or more phosphonate groups through a covalent bond or through a linking group, e.g., a linker. The nature of the linker is not critical provided it does not interfere with the ability of the phosphonate containing compound to function as a therapeutic agent. In general, the phosphonate or the linker can be linked to the compound at any synthetically feasible position on the compound, e.g., any solvent accessible surface by removing a hydrogen or any portion of the compound to provide an open valence for attachment of the phosphonate or the linker.

The variables and definitions of these variables used in the present Phosphonate Prodrug Compound section of this application (e.g., $A^1$, $R^1$, etc.) pertain only to this section of the application, unless otherwise indicated.

In one embodiment, the linking group or linker (which can be designated "L") can include all or a portion of the group $A^0, A^1, A^2, A^3$, or $W^3$ described herein, such as for example, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

In another embodiment, the linking group or linker has a molecular weight of from about 20 daltons to about 400 daltons. In yet another embodiment, the linking group or linker has a length of about 5 angstroms to about 300 angstroms. In yet another embodiment, the linking group or linker separates the compound of this invention and the phosphorous of the phosphonate group by about 5 angstroms to about 200 angstroms, inclusive, in length.

In yet another embodiment, the linking group or linker is a divalent, branched or unbranched, saturated or unsaturated, hydrocarbon chain, having from 2 to 25 carbon atoms, wherein one or more (e.g. 1, 2, 3, or 4) of the carbon atoms is optionally replaced by (—O—), and wherein the chain is optionally substituted on carbon with one or more (e.g. 1, 2, 3, or 4) substituents selected from ($C_1$-$C_6$)alkoxy, ($C_3$-$C_6$)cycloalkyl, ($C_1$-$C_6$)alkanoyl, ($C_1$-$C_6$)alkanoyloxy, ($C_1$-$C_6$)alkoxycarbonyl, ($C_1$-$C_6$)alkylthio, azido, cyano, nitro, halo, hydroxy, oxo (=O), carboxy, aryl, aryloxy, heteroaryl, and heteroaryloxy.

In yet another embodiment, the linking group or linker is of the formula W-A wherein A is $(C_1-C_{24})$alkyl, $(C_2-C_{24})$alkenyl, $(C_2-C_{24})$alkynyl, $(C_3-C_8)$cycloalkyl, $(C_6-C_{10})$aryl or a combination thereof, wherein W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; wherein each R is independently H or $(C_1-C_6)$alkyl.

In yet another embodiment, the linking group or linker is a divalent radical formed from a peptide or amino acid. In yet another embodiment, the linking group or linker is a divalent radical formed from poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-lysine or poly-L-lysine-L-tyrosine.

In yet another embodiment, the linking group or linker is of the formula W—(CH$_2$)$_n$ wherein, n is between about 1 and about 10; and W is —N(R)C(=O)—, —C(=O)N(R)—, —OC(=O)—, —C(=O)O—, —O—, —S—, —S(O)—, —S(O)$_2$—, —C(=O)—, —N(R)—, or a direct bond; wherein each R is independently H or $(C_1-C_6)$alkyl. In yet another embodiment, the linking group or linker is methylene, ethylene, or propylene. In still another embodiment, the linking group or linker is attached to the phosphonate group through a carbon atom of the linker.

In one aspect, the compounds of this invention can be linked to one or more phosphonate groups capable of providing tissue or cell selection to the compounds, e.g., capable of directing the compounds to desired target tissue(s) or cell(s), especially tissues or cells associated with infections or inflammations including without any limitation white blood cells.

In another aspect, the compounds of this invention can be linked to one or more phosphonate groups capable of inducing or triggering an enzymatic activation, e.g., one or more in vivo enzymatic cleavages or modifications which could result in an intracellular accumulation of the cleaved or modified compounds. For example, the phosphonate group of the compounds of this invention may cleave in vivo in stages after they have reached the desired site of action, e.g., inside a cell. One mechanism of action inside a cell may entail a first cleavage, e.g., by esterase, to provide a negatively-charged "locked-in" intermediate. Cleavage of a terminal ester grouping in a compound of the invention thus affords an unstable intermediate which releases a negatively charged "locked in" intermediate. After passage inside a cell, intracellular enzymatic cleavage or modification of the phosphonate or prodrug compound may result in an intracellular accumulation of the cleaved or modified compound by a "trapping" mechanism. The cleaved or modified compound may then be "locked-in" the cell by a significant change in charge, polarity, or other physical property change which decreases the rate at which the cleaved or modified compound can exit the cell, relative to the rate at which it entered as the phosphonate prodrug. Other mechanisms by which a therapeutic effect is achieved may be operative as well. In general, enzymes capable of an enzymatic activation mechanism with the phosphonate prodrug compounds of the invention include, but are not limited to, amidases, esterases, microbial enzymes, phospholipases, cholinesterases, and phosphatases.

In one particular aspect, the compounds of this invention can be linked with one or more groups $A^0$; or a pharmaceutically acceptable salt thereof, wherein:

$A^0$ is $A^1$, $A^2$ or $W^3$;

$A^1$ is:

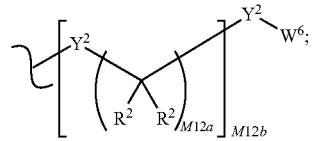

$A^2$ is:

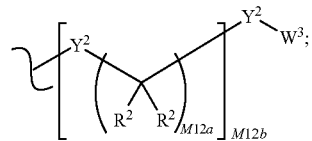

$A^3$ is:

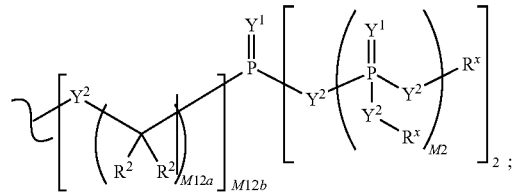

$Y^1$ is independently O, S, N(R$^x$), N(O)(R$^x$), N(OR$^x$), N(O)(OR$^x$), or N(N(R$^x$)(R$^x$));

$Y^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;

$R^x$ is independently H, $R^1$, $W^3$, a protecting group, or the formula:

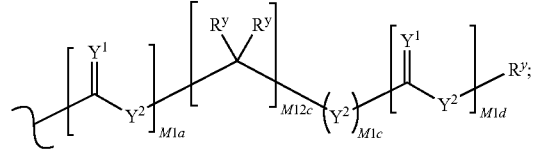

wherein:

$R^y$ is independently H, $W^3$, $R^2$ or a protecting group;

$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, N$_3$ or —NO$_2$;

$R^{3b}$ is $Y^1$;

$R^{3c}$ is —R$^x$, —N(R$^x$)(R$^x$), —SR$^x$, —S(O)R$^x$, —S(O)$_2$R$^x$, —S(O)(OR$^x$), —S(O)$_2$(OR$^x$), —OC(Y$^1$)R$^x$, —OC(Y$^1$)OR$^x$, —OC(Y$^1$)(N(R$^x$)(R$^x$)), —SC(Y$^1$)R$^x$, —SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$));

$R^{3d}$ is —C(Y$^1$)R$^x$, —C(Y$^1$)OR$^x$ or —C(Y$^1$)(N(R$^x$)(R$^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —$C(Y^1)R^5$, —$C(Y^1)W^5$, —$SO_2R^5$, or —$SO_2W^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1; and

M12c is 0, 1, 2, 3, 4, 5, 6, 7, 8, 9, 10, 11 or 12.

In one specific embodiment, $A^1$ is of the formula:

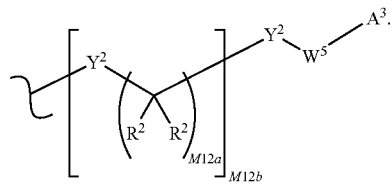

In another specific embodiment $A^1$ is of the formula:

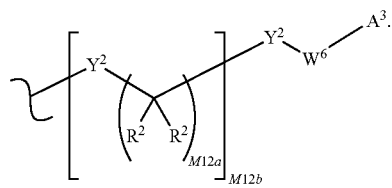

In another specific embodiment $A^1$ is of the formula:

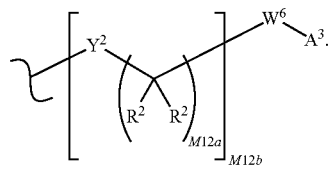

In another specific embodiment $A^1$ is of the formula:

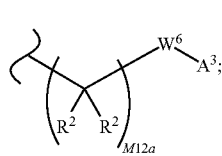

In another specific embodiment $A^1$ is of the formula:

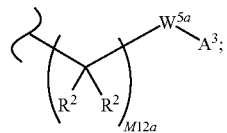

and $W^{5a}$ is a carbocycle or a heterocycle where $W^{5a}$ is independently substituted with 0 or 1 $R^2$ groups. A specific value for M12a is 1.

In another specific embodiment $A^1$ is of the formula:

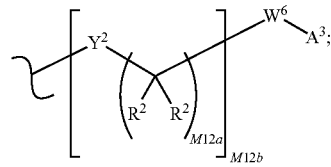

In another specific embodiment $A^1$ is of the formula:

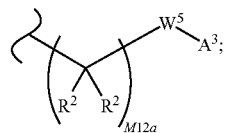

In another specific embodiment $A^1$ is of the formula:

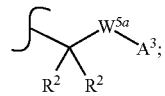

wherein $W^{5a}$ is a carbocycle independently substituted with 0 or 1 $R^2$ groups;

In another specific embodiment $A^1$ is of the formula:

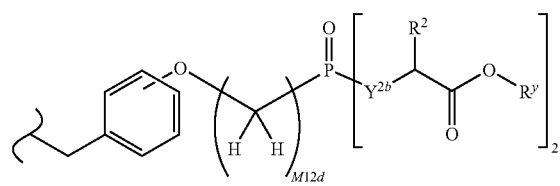

wherein $Y^{2b}$ is O or $N(R^2)$; and M12d is 1, 2, 3, 4, 5, 6, 7 or 8.

In another specific embodiment $A^1$ is of the formula:

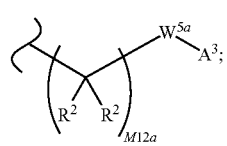

wherein $W^{5a}$ is a carbocycle independently substituted with 0 or 1 $R^2$ groups;

In another specific embodiment A¹ is of the formula:

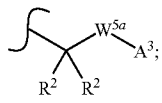

wherein $W^{5a}$ is a carbocycle or heterocycle where $W^{5a}$ is independently substituted with 0 or 1 $R^2$ groups.

In another specific embodiment A¹ is of the formula:

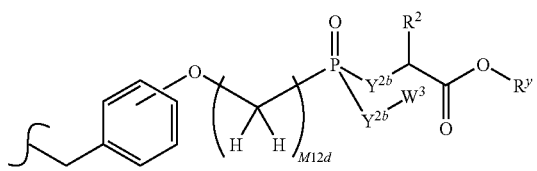

wherein $Y^{2b}$ is O or $N(R^2)$; and M12d is 1, 2, 3, 4, 5, 6, 7 or 8.

In yet another specific embodiment A² is of the formula:

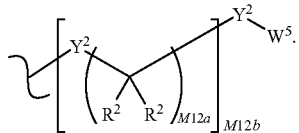

In another specific embodiment A² is of the formula:

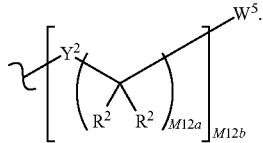

In another specific embodiment M12b is 1.

In another specific embodiment M12b is 0, $Y^2$ is a bond and $W^5$ is a carbocycle or heterocycle where $W^5$ is optionally and independently substituted with 1, 2, or 3 $R^2$ groups.

In another specific embodiment A² is of the formula:

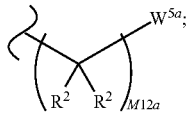

wherein $W^{5a}$ is a carbocycle or heterocycle where $W^{5a}$ is optionally and independently substituted with 1, 2, or 3 $R^2$ groups.

In another specific embodiment M12a is 1.

In another specific embodiment A² is selected from phenyl, substituted phenyl, benzyl, substituted benzyl, pyridyl and substituted pyridyl.

In another specific embodiment A² is of the formula:

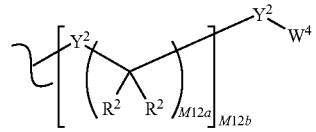

In another specific embodiment A² is of the formula:

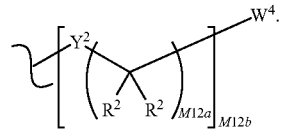

In another specific embodiment M12b is 1.

In yet another specific embodiment A³ is of the formula:

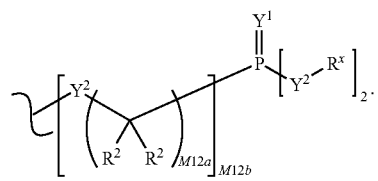

In another specific embodiment A³ is of the formula:

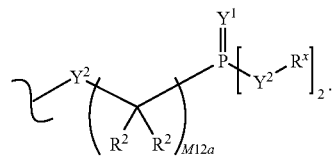

In another specific embodiment A³ is of the formula:

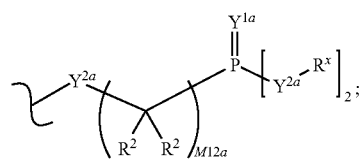

wherein $Y^{1a}$ is O or S; and $Y^{2}a$ is O, $N(R^x)$ or S.

In another specific embodiment A³ is of the formula:

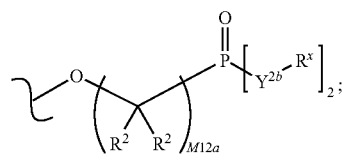

wherein $Y^{2b}$ is O or $N(R^x)$.

In another specific embodiment $A^3$ is of the formula:

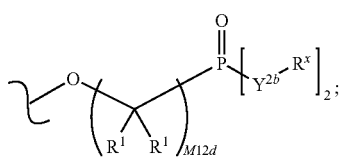

wherein $Y^{2b}$ is O or $N(R^x)$; and M12d is 1, 2, 3, 4, 5, 6, 7 or 8.

In another specific embodiment $A^3$ is of the formula:

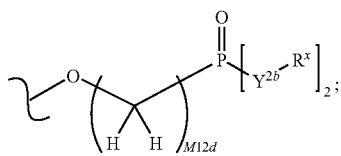

wherein $Y^{2b}$ bis O or $N(R^x)$; and M12d is 1, 2, 3, 4, 5, 6, 7 or 8.

In another specific embodiment M12d is 1.

In another specific embodiment $A^3$ is of the formula:

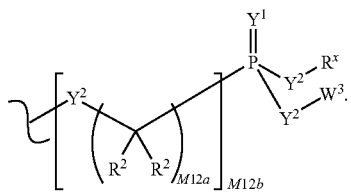

In another specific embodiment $A^3$ is of the formula:

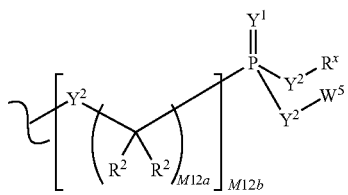

In another specific embodiment $W^5$ is a carbocycle.

In another specific embodiment $A^3$ is of the formula:

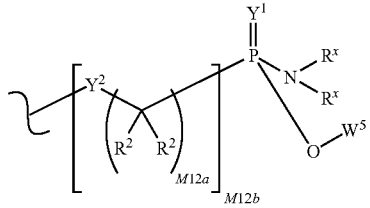

In another specific embodiment $W^5$ is phenyl.

In another specific embodiment $A^3$ is of the formula:

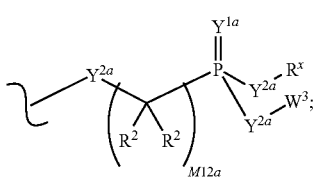

wherein $Y^{1a}$ is O or S; and $Y^{2a}$ is O, $N(R^x)$ or S.

In another specific embodiment $A^3$ is of the formula:

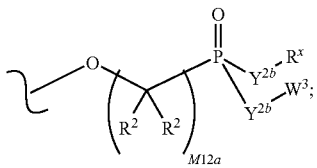

wherein $Y^{2b}$ is O or $N(R^x)$.

In another specific embodiment $A^3$ is of the formula:

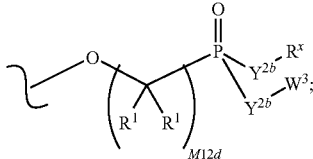

wherein $Y^{2b}$ is O or $N(R^x)$; and M12d is 1, 2, 3, 4, 5, 6, 7 or 8.

In another specific embodiment $R^1$ is H.

In another specific embodiment $A^3$ is of the formula:

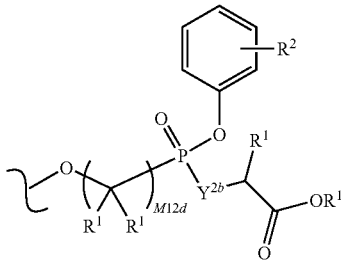

wherein the phenyl carbocycle is substituted with 0, 1, 2, or 3 $R^2$ groups.

In another specific embodiment $A^3$ is of the formula:

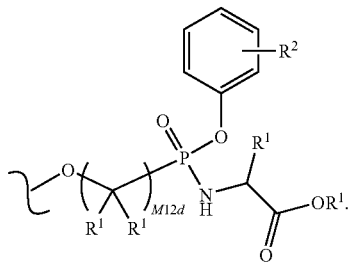

In another specific embodiment $A^3$ is of the formula:

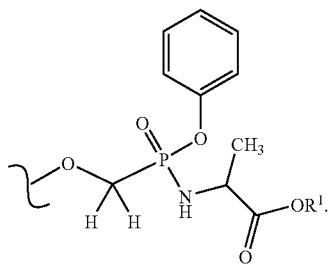

In another specific embodiment $A^3$ is of the formula:

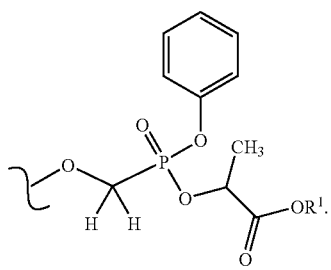

In another specific embodiment $A^3$ is of the formula:

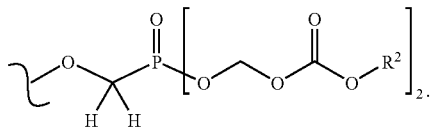

In another specific embodiment $A^3$ is of the formula:

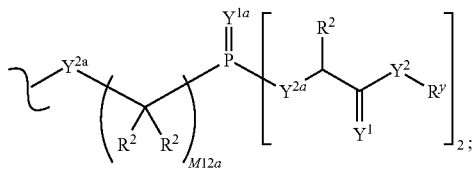

wherein $Y^{1a}$ is O or S; and $Y^1$ is O, $N(R^2)$ or S.

In another specific embodiment $A^3$ is of the formula:

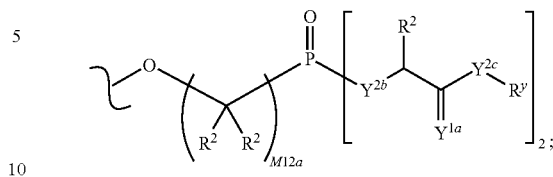

wherein $Y^{1a}$ is O or S; $Y^{2b}$ is O or $N(R^2)$; and $Y^{2c}$ is O, $N(R^Y)$ or S.

In another specific embodiment $A^3$ is of the formula:

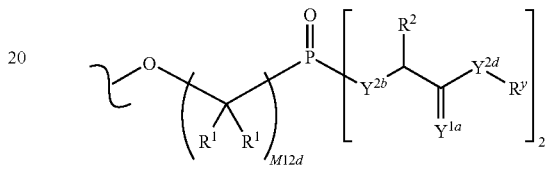

wherein $Y^{1a}$ is O or S; $Y^{2b}$ is O or $N(R^2)$; $Y^{2d}$ is O or $N(R^2)$; and M12d is 1, 2, 3, 4, 5, 6, 7 or 8.

In another specific embodiment $A^3$ is of the formula:

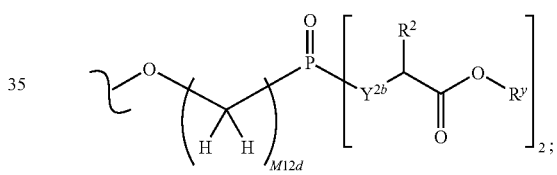

wherein $Y^{2b}$ is O or $N(R^2)$; and M12d is 1, 2, 3, 4, 5, 6, 7 or 8.

In another specific embodiment $A^3$ is of the formula:

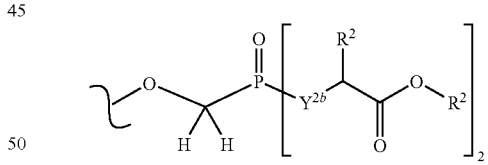

wherein $Y^{2b}$ is O or $N(R^2)$.

In another specific embodiment $A^3$ is of the formula:

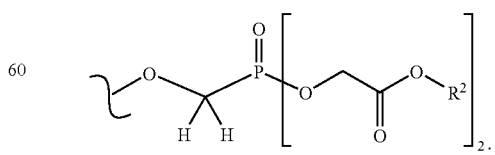

In another specific embodiment $A^3$ is of the formula:

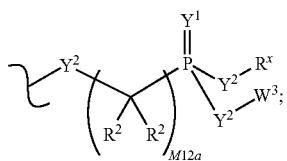

In another specific embodiment $A^3$ is of the formula:

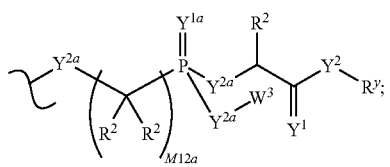

wherein $Y^{1a}$ is O or S; and $Y^{2a}$ is O, N($R^2$) or S.

In another specific embodiment $A^3$ is of the formula:

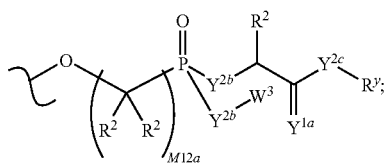

wherein $Y^{1a}$ is O or S; $Y^{2b}$ is O or N($R^2$); and $Y^{2c}$ is O, N($R^y$) or S.

In another specific embodiment $A^3$ is of the formula:

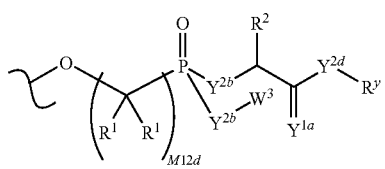

wherein $Y^{1a}$ is O or S; $Y^{2b}$ is O or N($R^2$); $Y^{2d}$ is O or N($R^y$); and M12d is 1, 2, 3, 4, 5, 6, 7 or 8.

In another specific embodiment $A^3$ is of the formula:

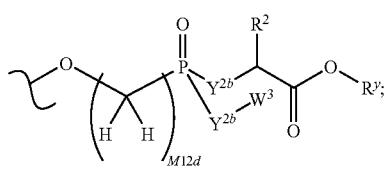

wherein $Y^{2b}$ is O or N($R^2$); and M12d is 1, 2, 3, 4, 5, 6, 7 or 8.

In another specific embodiment $A^3$ is of the formula:

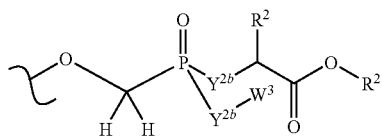

wherein $Y^{2b}$ is O or N($R^2$).

In another specific embodiment $A^3$ is of the formula:

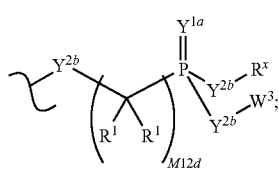

wherein: $Y^{2b}$ is O or N($R^x$); and M12d is 1, 2, 3, 4, 5, 6, 7 or 8.

In another specific embodiment $A^3$ is of the formula:

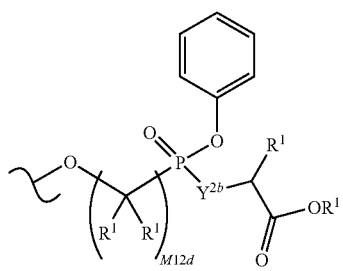

wherein the phenyl carbocycle is substituted with 0, 1, 2, or 3 $R^2$ groups.

In another specific embodiment $A^3$ is of the formula:

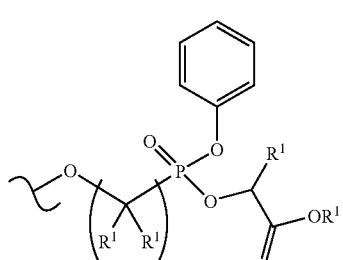

wherein the phenyl carbocycle is substituted with 0, 1, 2, or 3 $R^2$ groups.

In another specific embodiment $A^3$ is of the formula:

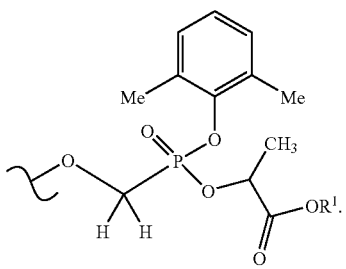

In yet another specific embodiment $A^0$ is of the formula:

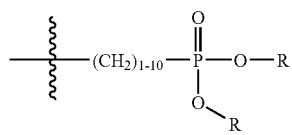

wherein each R is independently $(C_1-C_6)$alkyl.

In yet another specific embodiment $R^x$ is independently H, $R^1$, $W^3$, a protecting group, or the formula:

wherein:
$R^y$ is independently H, $W^3$, $R^2$ or a protecting group;
$R^1$ is independently H or alkyl of 1 to 18 carbon atoms;
$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

In yet another specific embodiment $R^x$ is of the formula:

wherein $Y^{1a}$ is O or S; and $Y^{2c}$ is O, $N(R^y)$ or S.

In yet another specific embodiment $R^x$ is of the formula:

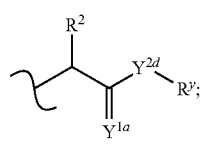

wherein $Y^{1a}$ is O or S; and $Y^{2d}$ is O or $N(R^y)$.

In yet another specific embodiment $R^x$ is of the formula:

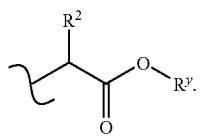

In yet another specific embodiment $R^y$ is hydrogen or alkyl of 1 to 10 carbons.

In yet another specific embodiment $R^x$ is of the formula:

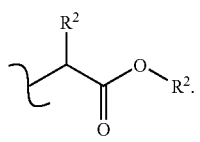

In yet another specific embodiment $R^x$ is of the formula:

In yet another specific embodiment $R^x$ is of the formula:

In yet another specific embodiment $Y^1$ is O or S
In yet another specific embodiment $Y^2$ is O, $N(R^y)$ or S.
In yet another specific embodiment $R^x$ is a group of the formula:

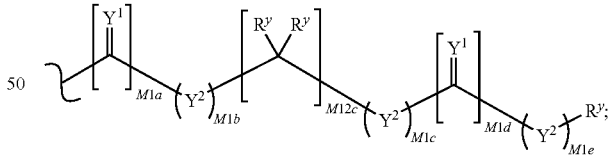

wherein:
m1a, m1b, m1c, m1d and m1e are independently 0 or 1;
m12c is 0, 1, 2, 3, 4, 5, 6, 7, 8, 9, 10, 11 or 12;
$R^y$ is H, $W^3$, $R^2$ or a protecting group;
provided that:
if m1a, m12c, and m1d are 0, then m1b, m1c and m1e are 0;
if m1a and m12c are 0 and m1d is not 0, then m1b and m1c are 0;
if m1a and m1d are 0 and m12c is not 0, then m1b and at least one of m1c and m1e are 0;
if m1a is 0 and m12c and m1d are not 0, then m1b is 0;

if m12c and m1d are 0 and m1a is not 0, then at least two of m1b, m1c and m1e are 0;

if m12c is 0 and m1a and m1d are not 0, then at least one of m1b and m1c are 0; and if m1d is 0 and m1a and m12c are not 0, then at least one of m1c and m1e are 0.

In yet another specific embodiment, the phosphonate prodrug compound of this invention has the formula:

[DRUG]-(A⁰)$_{nn}$ or a pharmaceutically acceptable salt thereof wherein,
DRUG is a compound of this invention
nn is 1, 2, or 3;
$A^0$ is $A^1$, $A^2$ or $W^3$ with the proviso that the compound includes at least one $A^1$;
$A^1$ is:

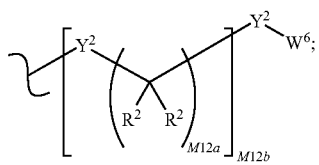

$A^2$ is:

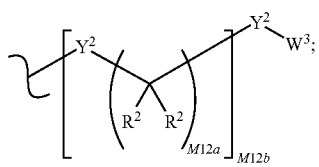

$A^3$ is:

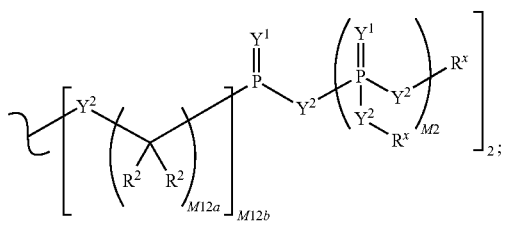

$Y^1$ is independently O, S, N(R$^x$), N(O)(R$^x$), N(OR$^x$), N(O)(OR$^x$), or N(N(R$^x$)(R$^x$));

$Y^2$ is independently a bond, O, N(R$^x$), N(O)(R$^x$), N(OR$^x$), N(O)(OR$^x$), N(N(R$^x$)(R$^x$)), —S(O)$_{M2}$, or —S(O)$_{M2}$—S(O)$_{M2}$—;

$R^x$ is independently H, $R^1$, $W^3$, a protecting group, or the formula:

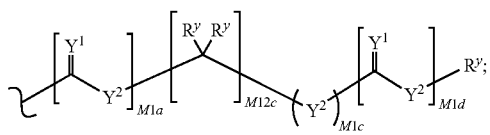

wherein:
$R^y$ is independently H, $W^3$, $R^2$ or a protecting group;
$R^1$ is independently H or alkyl of 1 to 18 carbon atoms;

$R^2$ is independently H, $R^1$, $R^3$ or $R^4$ wherein each $R^4$ is independently substituted with 0 to 3 $R^3$ groups or taken together at a carbon atom, two $R^2$ groups form a ring of 3 to 8 carbons and the ring may be substituted with 0 to 3 $R^3$ groups;

$R^3$ is $R^{3a}$, $R^{3b}$, $R^{3c}$ or $R^d$, provided that when $R^3$ is bound to a heteroatom, then $R^3$ is $R^{3c}$ or $R^{3d}$;

$R^{3a}$ is F, Cl, Br, I, —CN, N₃ or —NO₂;

$R^{3b}$ is $Y^1$;

$R^{3c}$ is —R$^x$, —N(R$^x$)(R$^x$), —SR$^x$, —S(O)R$^x$, —S(O)₂R$^x$, —S(O)(OR$^x$), —S(O)₂(OR$^x$), —OC(Y$^1$)R$^x$, —OC(Y$^1$)OR$^x$, —OC(Y$^1$)(N(R$^x$)(R$^x$)), SC(Y$^1$)R$^x$, SC(Y$^1$)OR$^x$, —SC(Y$^1$)(N(R$^x$)(R$^x$)), —N(R$^x$)C(Y$^1$)R$^x$, —N(R$^x$)C(Y$^1$)OR$^x$, or —N(R$^x$)C(Y$^1$)(N(R$^x$)(R$^x$));

$R^{3d}$ is C(Y$^1$)R$^x$, C(Y$^1$)OR$^x$ or —C(Y$^1$)(N(R$^x$)(R$^x$));

$R^4$ is an alkyl of 1 to 18 carbon atoms, alkenyl of 2 to 18 carbon atoms, or alkynyl of 2 to 18 carbon atoms;

$R^5$ is $R^4$ wherein each $R^4$ is substituted with 0 to 3 $R^3$ groups;

$R^{5a}$ is independently alkylene of 1 to 18 carbon atoms, alkenylene of 2 to 18 carbon atoms, or alkynylene of 2-18 carbon atoms any one of which alkylene, alkenylene or alkynylene is substituted with 0-3 $R^3$ groups;

$W^3$ is $W^4$ or $W^5$;

$W^4$ is $R^5$, —C(Y$^1$)R$^5$, —C(Y$^1$)W$^5$, —SO₂R$^5$, or —SO₂W$^5$;

$W^5$ is carbocycle or heterocycle wherein $W^5$ is independently substituted with 0 to 3 $R^2$ groups;

$W^6$ is $W^3$ independently substituted with 1, 2, or 3 $A^3$ groups;

M2 is 0, 1 or 2;
M12a is 1, 2, 3, 4, 5, 6, 7, 8, 9, 10, 11 or 12;
M12b is 0, 1, 2, 3, 4, 5, 6, 7, 8, 9, 10, 11 or 12;
M1a, M1c, and m1d are independently 0 or 1;
M12c is 0, 1, 2, 3, 4, 5, 6, 7, 8, 9, 10, 11 or 12;
$X^{66}$ is hydrogen or fluorine; and
$X^{67}$ is hydrogen, hydroxy, or acyloxy.

In yet another specific embodiment, the phosphonate prodrug compound of this invention has the formula:

[DRUG]-[L-P(=Y$^1$)—Y$^2$—R$^x$]$_{nn}$ or a pharmaceutically acceptable salt thereof wherein,
DRUG is a compound of this invention;
$Y^1$ is independently O, S, N(R$^x$), N(O)(R$^x$), N(OR$^x$), N(O)(OR$^x$), or N(N(R$^x$)(R$^x$));

$Y^2$ is independently a bond, O, N(R$^x$), N(O)(R$^x$), N(OR$^x$), N(O)(OR$^x$), N(N(R$^x$)(R$^x$)), —S(O)$_{M2}$— or —S(O)$_{M2}$—(O)$_{M2}$—;

$R^x$ is independently H, $W^3$, a protecting group, or the formula:

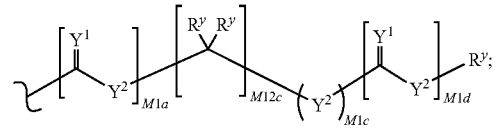

$R^y$ is independently H, $W^3$, $R^2$ or a protecting group;
$R^2$ is independently H, $R^3$ or $R^4$ wherein each $R^4$ is independently substituted with 0 to 3 $R^3$ groups;

$R^3$ is $R^{3a}$, $R^{3b}$, $R^{3c}$ or $R^{3d}$, provided that when $R^3$ is bound to a heteroatom, then $R^3$ is $R^{3c}$ or $R^{3d}$;

$R^{3a}$ is F, Cl, Br, I, —CN, N₃ or —NO₂;

$R^{3b}$ is $Y^1$;

$R^{3c}$ is R$^x$, N(R$^x$)(R$^x$), —SR$^x$, —S(O)R$^x$, —S(O)₂R$^x$, —S(O)(OR$^x$), —(S)₂(OR$^x$), —OC(Y$^1$)R$^x$, —OC(Y$^1$)OR$^x$,

—OC(Y$^1$)(N(R$^x$)(R$^x$)), SC(Y$^1$)R$^x$, —SC(Y$^1$)OR$^x$, —SC(Y$^1$)(N(R$^x$)(R$^x$)), N(R$^x$)C(Y$^1$)R$^x$, —N(R$^x$)C(Y$^1$)OR$^x$, or —N(R$^x$)C(Y$^1$)(N(R$^x$)(R$^x$));

R$^{3d}$ is C(Y$^1$)R$^x$, —C(Y$^1$)OR$^x$ or —C(Y$^1$)(N(R$^x$)(R$^x$));

R$^4$ is an alkyl of 1 to 18 carbon atoms, alkenyl of 2 to 18 carbon atoms, or alkynyl of 2 to 18 carbon atoms;

R$^5$ is R$^4$ wherein each R$^4$ is substituted with 0 to 3 R$^3$ groups;

W$^3$ is W$^4$ or W$^5$;

W$^4$ is R$^5$, —C(Y$^1$)R$^5$, —C(Y$^1$)W$^5$, —SO$_2$R$^5$, or —SO$_2$W$^5$;

W$^5$ is carbocycle or heterocycle wherein W$^5$ is independently substituted with 0 to 3 R$^2$ groups;

M2 is 1, 2, or 3;

M1a, M1c, and M1d are independently 0 or 1;

M12c is 0, 1, 2, 3, 4, 5, 6, 7, 8, 9, 10, 11 or 12;

X$^{66}$ is hydrogen or fluorine; and

X$^{67}$ is hydrogen, hydroxy, or acyloxy;

nn is 1, 2, or 3; and

L is a linking group.

In another specific embodiment, the phosphonate prodrug compound of this invention has the formula:

[DRUG]-(A$^0$)$_{nn}$ or a pharmaceutically acceptable salt thereof wherein,

DRUG is a compound of this invention;

nn is 1, 2, or 3;

A$^0$ is A$^1$, A$^2$, or W$^3$ with the proviso that the compound includes at least one A$^1$;

A$^1$ is:

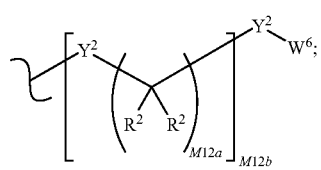

A$^2$ is:

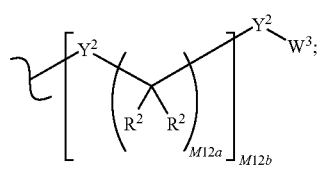

A$^3$ is:

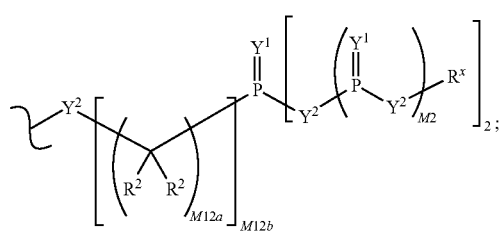

Y$^1$ is independently O, S, N(R$^x$), N(O)(R$^x$), N(OR$^x$), N(O)(OR$^x$), or N(N(R$^x$)(R$^x$));

Y$^2$ is independently a bond, O, N(R$^x$), N(O)(R$^x$), N(OR$^x$), N(O)(OR$^x$), N(N(R$^x$)(R$^x$)), —S(O)$_{M2}$—, or —S(O)$_{M2}$—S(O)$_{M2}$—;

R$^x$ is independently H, W$^3$, a protecting group, or the formula:

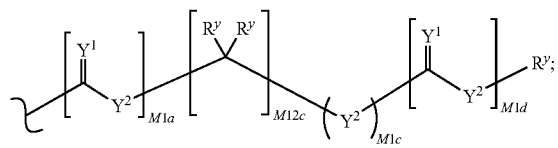

R$^y$ is independently H, W$^3$, R$^2$ or a protecting group;

R$^2$ is independently H, R$^3$ or R$^4$ wherein each R$^4$ is independently substituted with 0 to 3 R$^3$ groups;

R$^3$ is R$^{3a}$; R$^{3b}$, R$^{3c}$ or R$^{3d}$, provided that when R$^3$ is bound to a heteroatom, then R$^3$ is R$^{3c}$ or R$^{3d}$;

R$^{3b}$ is F, Cl, Br, I, —CN, N$_3$ or —NO$_2$;

R$^{3b}$ is Y$^1$;

R$^{3c}$ is —R$^x$, N(R$^x$)(R$^x$), —SR$^x$, —S(O)R$^x$, —S(O)$_2$R$^x$, —S(O)(OR$^x$), —S(O)$_2$(OR$^x$), —OC(Y$^1$)R$^x$, —OC(Y$^1$)OR$^x$, —OC(Y$^1$)(N(R$^x$)(R$^x$)), —SC(Y$^1$)R$^x$, —SC(Y$^1$)OR$^x$, SC(Y$^1$)(N(R$^x$)(R$^x$)), N(R$^x$)C(Y$^1$)R$^x$, —N(R$^x$)C(Y$^1$)OR$^x$, or —N(R$^x$)C(Y$^1$)(N(R$^x$)(R$^x$));

R$^{3d}$ is —C(Y$^1$)R$^x$, —C(Y$^1$)OR$^x$ or —C(Y$^1$)(N(R$^x$)(R$^x$));

R$^4$ is an alkyl of 1 to 18 carbon atoms, alkenyl of 2 to 18 carbon atoms, or alkynyl of 2 to 18 carbon atoms;

R$^5$ is R$^4$ wherein each R$^4$ is substituted with 0 to 3 R$^3$ groups;

W$^3$ is W$^4$ or W$^5$;

W$^4$ is R$^5$, —C(Y$^1$)R$^5$, —C(Y$^1$)W$^5$, —SO$_2$R$^5$, or —SO$_2$W$^5$;

W$^5$ is carbocycle or heterocycle wherein W$^5$ is independently substituted with 0 to 3 R$^2$ groups;

W$^6$ is W$^3$ independently substituted with 1, 2, or 3 A$^3$ groups;

M2 is 0, 1 or 2;

M12a is 1, 2, 3, 4, 5, 6, 7, 8, 9, 10, 11 or 12;

M12b is 0, 1, 2, 3, 4, 5, 6, 7, 8, 9, 10, 11 or 12;

M1a, M1c, and M1d are independently 0 or 1;

M12c is 0, 1, 2, 3, 4, 5, 6, 7, 8, 9, 10, 11 or 12;

X$^{66}$ is hydrogen or fluorine; and

X$^{67}$ is hydrogen, hydroxy, or acyloxy.

In one specific embodiment X$^{61}$ is methoxy, ethoxy, n-propoxy, difluoromethoxy, trifluoromethoxy, ethyl, methyl, propyl, or n-butyl)

In phosphonate prodrug compounds of this invention, W$^5$ carbocycles and W$^5$ heterocycles may be independently substituted with 0 to 3 R$^2$ groups. W$^5$ may be a saturated, unsaturated or aromatic ring comprising a mono- or bicyclic carbocycle or heterocycle. W$^5$ may have 3 to 10 ring atoms, e.g., 3 to 7 ring atoms. The W$^5$ rings are saturated when containing 3 ring atoms, saturated or mono-unsaturated when containing 4 ring atoms, saturated, or mono- or di-unsaturated when containing 5 ring atoms, and saturated, mono- or di-unsaturated, or aromatic when containing 6 ring atoms.

A W$^5$ heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). W$^5$ heterocyclic monocycles may have 3 to 6 ring atoms (2 to 5 carbon atoms and 1 to 2 heteroatoms selected from N, O, and S); or 5 or 6 ring atoms (3 to 5 carbon atoms and 1 to 2 heteroatoms selected from N and S). W$^5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6] system; or 9 to 10 ring atoms (8 to 9 carbon atoms and 1 to 2 hetero atoms selected from N and S) arranged as a bicyclo [5,6] or [6,6] system. The $W^5$ heterocycle may be bonded to $Y^2$ through a carbon, nitrogen, sulfur or other atom by a stable covalent bond.

$W^5$ heterocycles include for example, pyridyl, dihydropyridyl isomers, piperidine, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl. $W^5$ also includes, but is not limited to, examples such as:

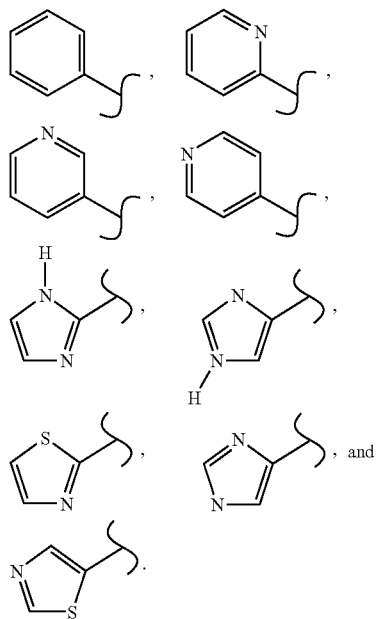

$W^5$ carbocycles and heterocycles may be independently substituted with 0 to 3 $R^2$ groups, as defined above. For example, substituted $W^5$ carbocycles include:

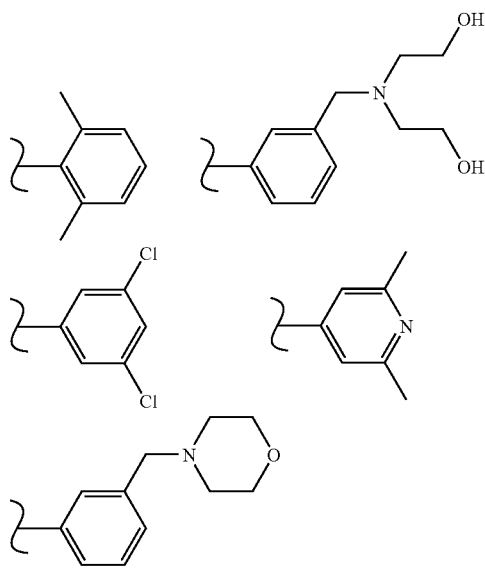

-continued

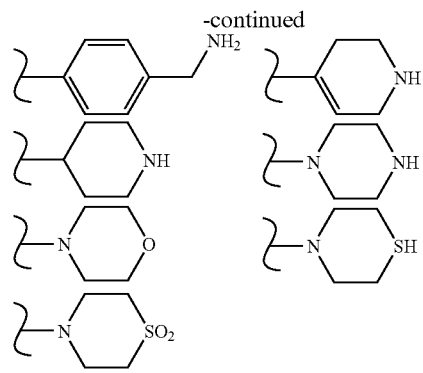

Examples of substituted phenyl carbocycles include:

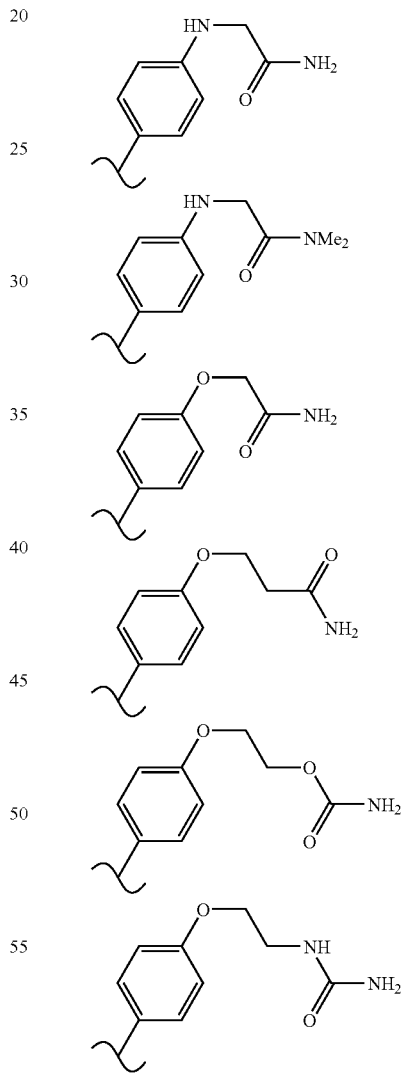

Additional phosphonate groups are disclosed in U.S. Publication No. 2004100960, the entirety of which is incorporated herein by reference. One skilled in the art will recognize that substituents and other moieties of the compounds under the present Phosphonate Prodrug Compound section of this application should be selected in order to provide a compound which is sufficiently stable, bioavailable, and suitable for providing a pharmaceutically useful compound which has a minimum level of biological activity and can be formulated into an acceptably stable and suitable pharmaceutical composition.

By way of example and not limitation, phosphonate prodrug embodiments of the invention are named below in tabular format (Table 7). These embodiments are of the general formula "MBF":

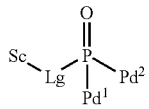

MBF

Each embodiment of MBF is depicted as a substituted nucleus (Sc). Sc is is described in formulae 1-14 of Table 1.1 herein, wherein Sc is a generic formula for a compound of Formula I, $A^0$ is the point of covalent attachment of Sc to Lg, nn designates the number of -Lg-P(O)Pd$^1$Pd$^2$ groups attached to Sc, and T1A, T2A, X$^1$A, X$^2$A, etc. and the terms "Alk", "Ar", and "Het" are as defined above (e.g., in Tables 1-5, and the text preceeding Tables 1-5).

For those embodiments described in Table 7, Sc is a nucleus designated by a number, and each substituent is designated in order by letter or number. Table 1.1 is a schedule of nuclei used in forming the embodiments of Table 7. Each nucleus (Sc) is given a number designation from Table 1.1, and this designation appears first in each embodiment name. Similarly, Tables 10.1 to 10.19 and 20.1 to 20.36 list the selected linking groups (Lg) and prodrug (Pd$^1$ and Pd$^2$) substituents, again by letter or number designation, respectively. Accordingly, a compound of the formula MBF includes compounds having Sc groups based on formula 1-14 herein as well as compounds according to Table 7 below. In all cases, compounds of the formula MBF have groups Lg, Pd$^1$ and Pd$^2$ set forth in the Tables below.

Accordingly, each named embodiment of Table 7 is depicted by a number designating the nucleus from Table 1.1, followed by a letter designating the linking group (Lg) from Table 10.1-10.19, and two numbers designating the two prodrug groups (Pd$^1$ and Pd$^2$) from Table 20.1-20.36. In graphical tabular form, each embodiment of Table 7 appears as a name having the syntax:

Sc.Lg.Pd$^1$.Pd$^2$

Q$^1$ and Q$^2$ of the linking groups (Lg), it should be understood, do not represent groups or atoms but are simply connectivity designations. Q$^1$ is the site of the covalent bond to the nucleus (Sc) and Q$^2$ is the site of the covalent bond to the phosphorous atom of formula MBF. Each prodrug group (Pd$^1$ and Pd$^2$) are covalently bonded to the phosphorous atom of MBF at the $A^0$ symbol. Some embodiments of Tables 10.1-10.19 and 20.1-20.36 may be designated as a combination of letters and numbers (Table 10.1-10.19) or number and letter (Table 20.1-20.36). For example there are Table 10 entries for BJ1 and BJ2. In any event, entries of Table 10.1-10.19 always begin with a letter and those of Table 20.1-20.36 always begin with a number. When a nucleus (Sc) is shown enclosed within square brackets ("[ ]") and a covalent bond extends outside the brackets, the point of covalent attachment of Sc to Lg may be at any substitutable site on Sc. Selection of the point of attachment is described herein. By way of example and not limitation, the point of attachment is selected from those depicted in the schemes and examples.

TABLE 1.1

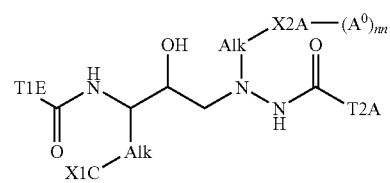

1

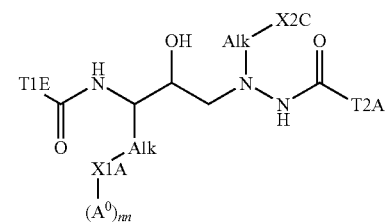

2

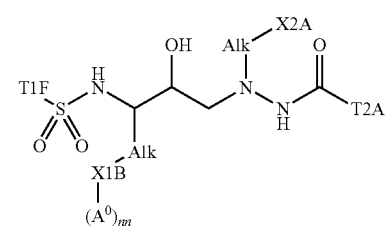

3

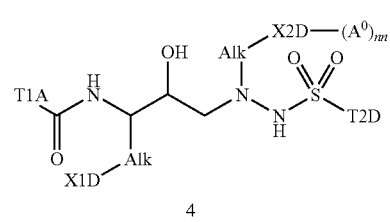

4

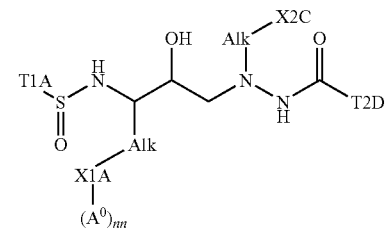

5

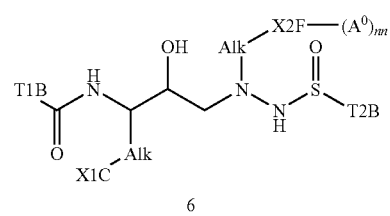

6

TABLE 1.1-continued
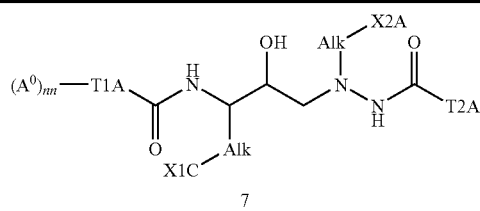
7
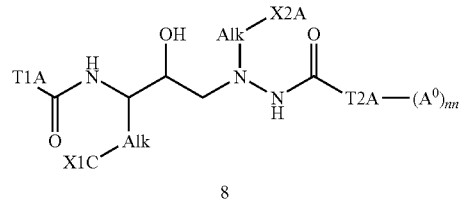
8
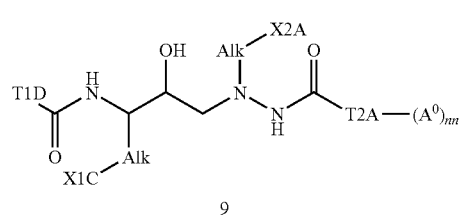
9
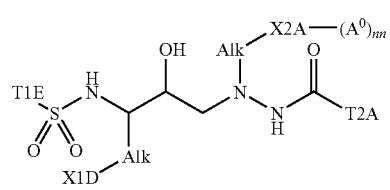
10
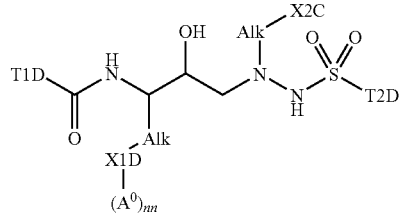
11
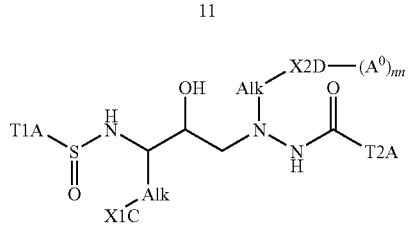
12
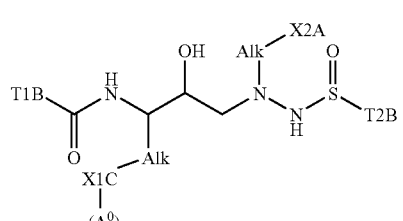
13
TABLE 1.1-continued
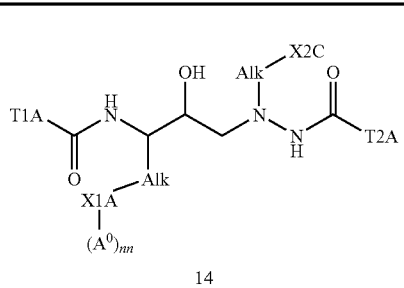
14
TABLE 10.1
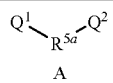
A
B
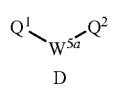
C
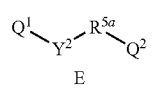
D
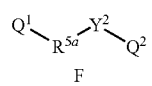
E
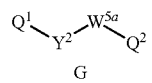
F
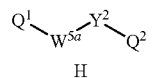
G
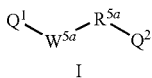
H
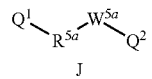
I
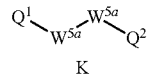
J
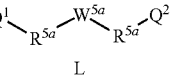
K
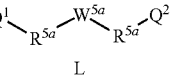
L
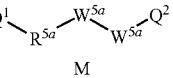
M TABLE 10.1-continued
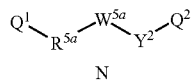
N
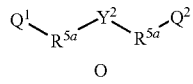
O
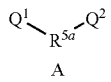
A
B
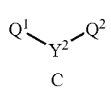
C
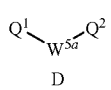
D
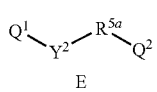
E
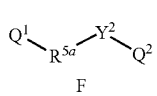
F
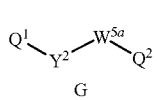
G
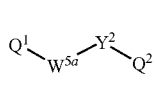
H
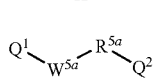
I
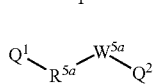
J
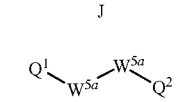
K
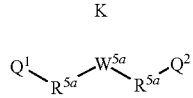
L
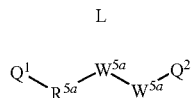
M
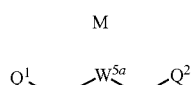
N
TABLE 10.1-continued
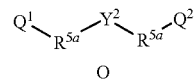
O
TABLE 10.2
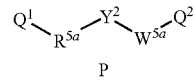
P
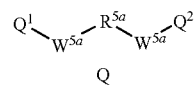
Q
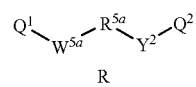
R
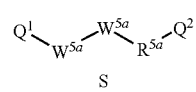
S
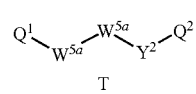
T
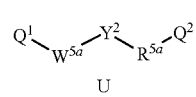
U
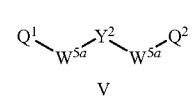
V
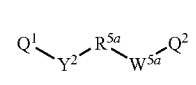
W
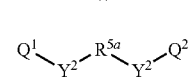
X
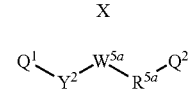
Y
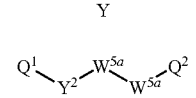
Z
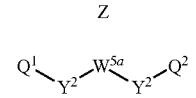
AA
TABLE 10.3
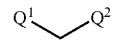
AB TABLE 10.3-continued
AC
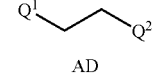
AD
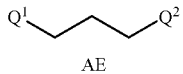
AE
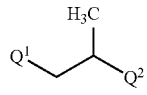
AF
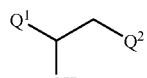
AG
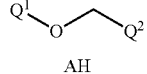
AH
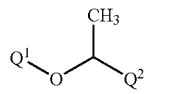
AI
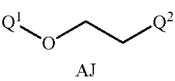
AJ
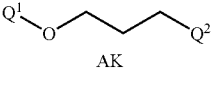
AK
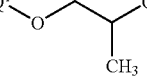
AL
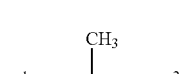
AM
TABLE 10.4
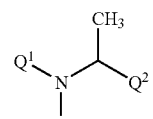
AN
TABLE 10.4-continued
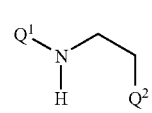
AO
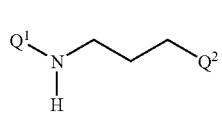
AP
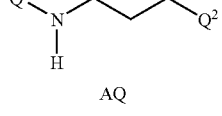
AQ
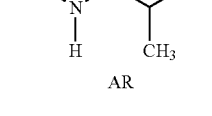
AR
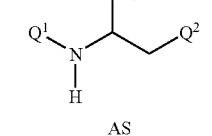
AS
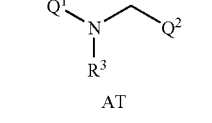
AT
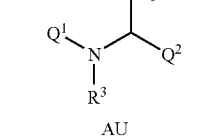
AU
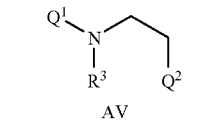
AV
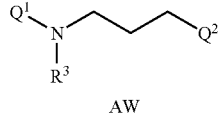
AW
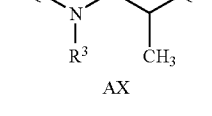
AX TABLE 10.4-continued
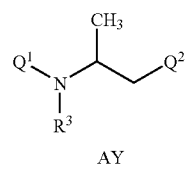
AY
TABLE 10.5
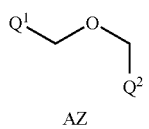
AZ
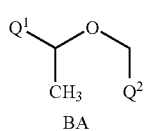
BA
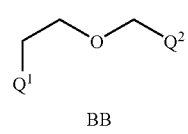
BB
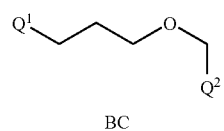
BC
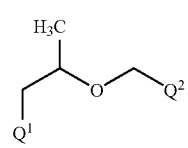
BD
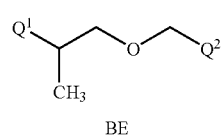
BE
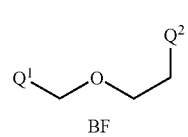
BF
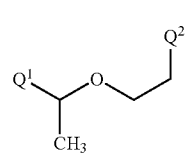
BG
TABLE 10.5-continued
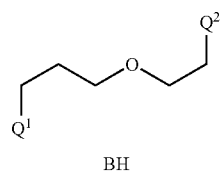
BH
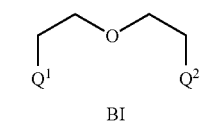
BI
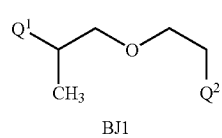
BJ1
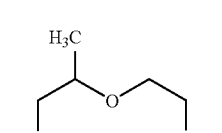
BJ2
TABLE 10.6
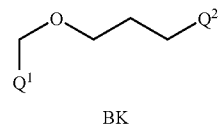
BK
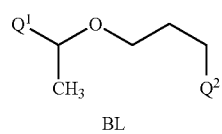
BL
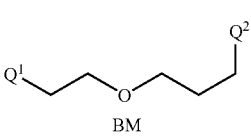
BM
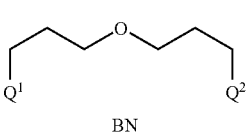
BN
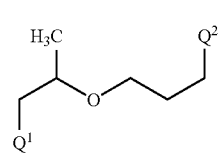
BO TABLE 10.6-continued
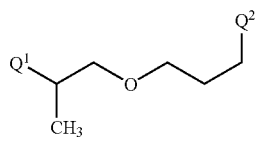
BP
TABLE 10.7
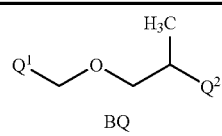
BQ
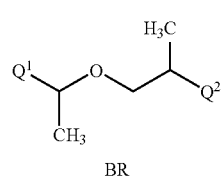
BR
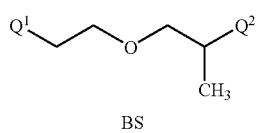
BS
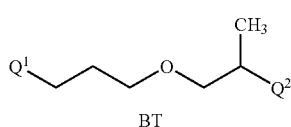
BT
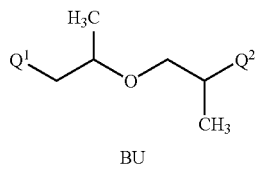
BU
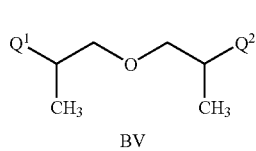
BV
TABLE 10.8
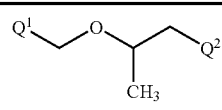
BW
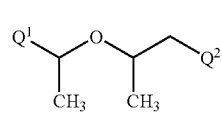
BX
TABLE 10.8-continued
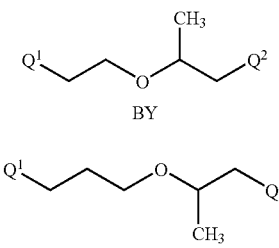
BY
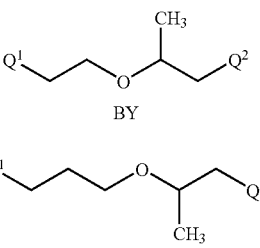
BZ
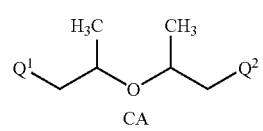
CA
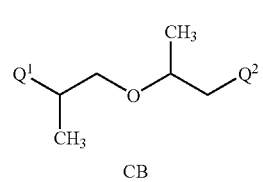
CB
TABLE 10.9
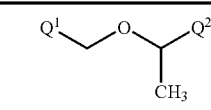
CC
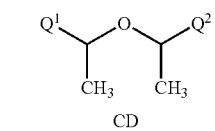
CD
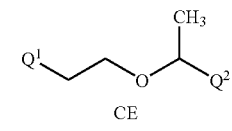
CE
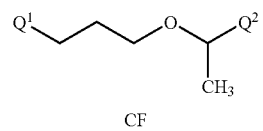
CF
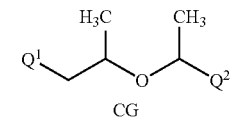
CG
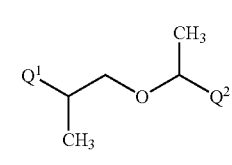
CH TABLE 10.10
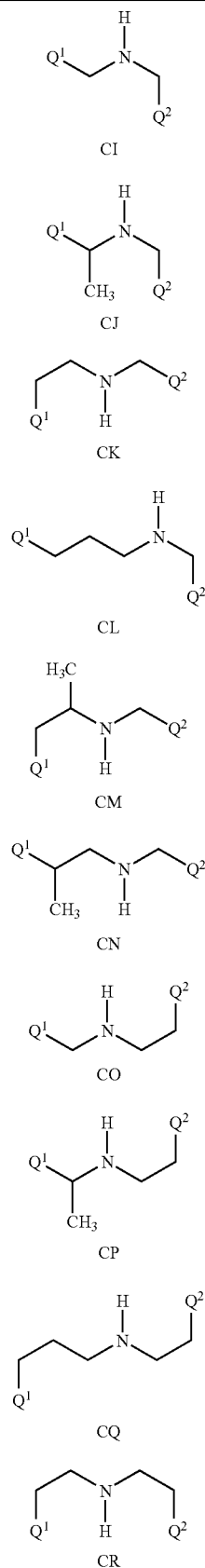
TABLE 10.10-continued
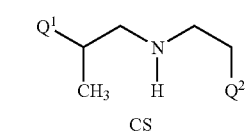
TABLE 10.11

TABLE 10.12
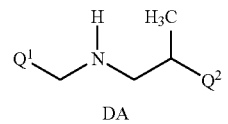
DA
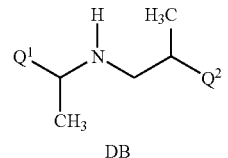
DB
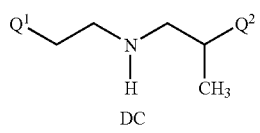
DC
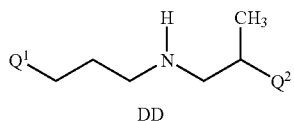
DD
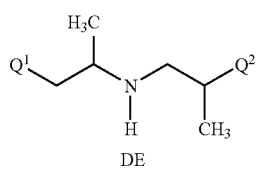
DE
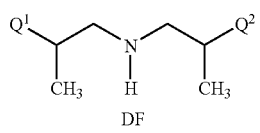
DF
TABLE 10.13
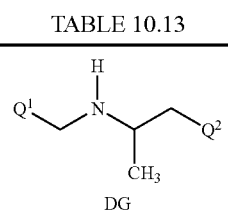
DG
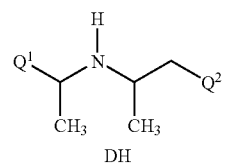
DH
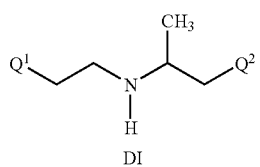
DI
TABLE 10.13-continued
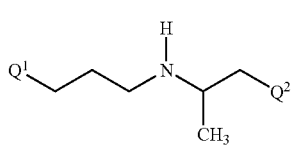
DJ
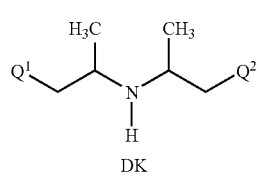
DK
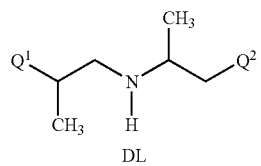
DL
TABLE 10.14
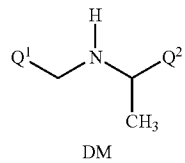
DM
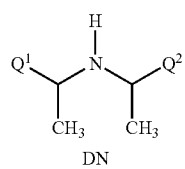
DN
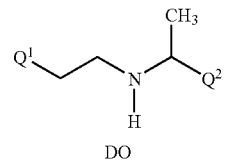
DO
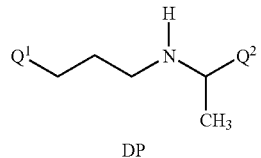
DP
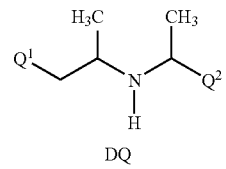
DQ TABLE 10.14-continued
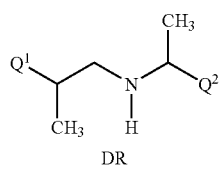
DR
TABLE 10.15
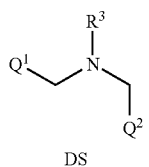
DS
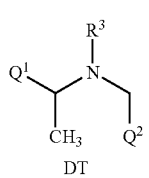
DT
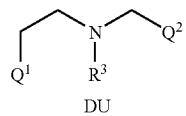
DU
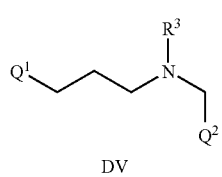
DV
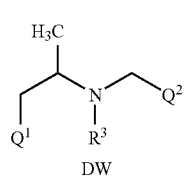
DW
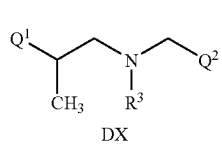
DX
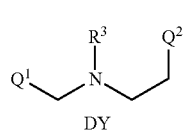
DY
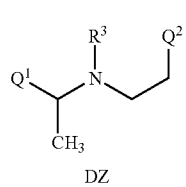
DZ
TABLE 10.15-continued
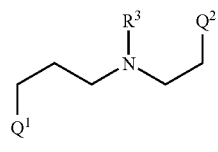
EA
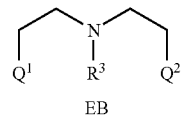
EB
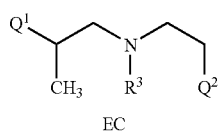
EC
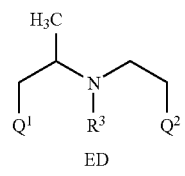
ED
TABLE 10.16
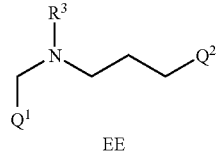
EE
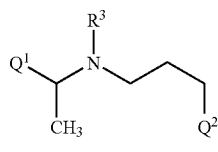
EF
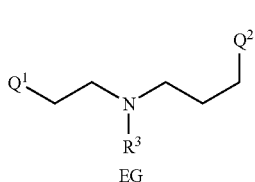
EG
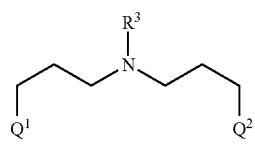
EH
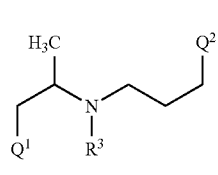
EI TABLE 10.16-continued
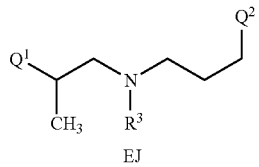
EJ
TABLE 10.17
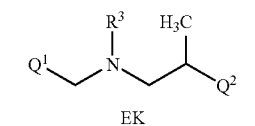
EK
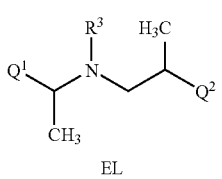
EL
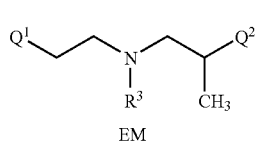
EM
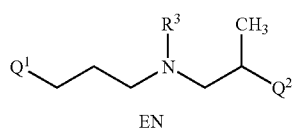
EN
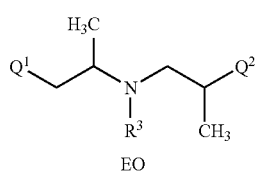
EO
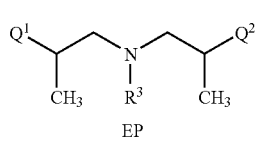
EP
TABLE 10.18
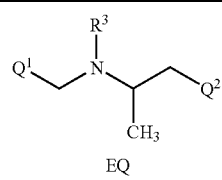
EQ
TABLE 10.18-continued
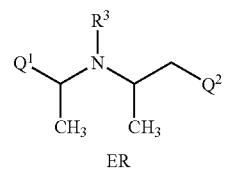
ER
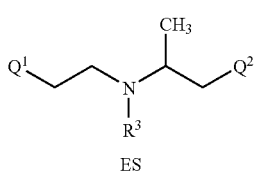
ES
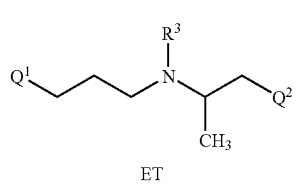
ET
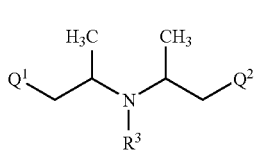
EU
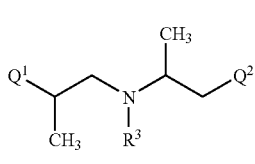
EV
TABLE 10.19
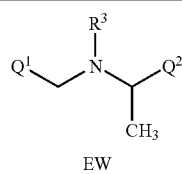
EW
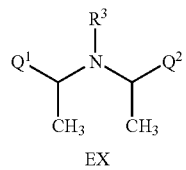
EX
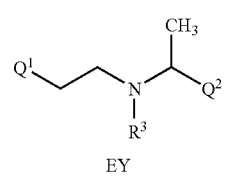
EY

TABLE 10.19-continued
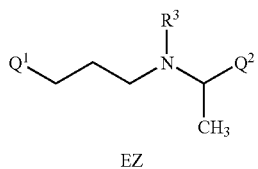
EZ
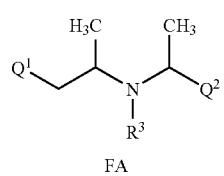
FA
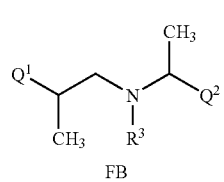
FB
TABLE 20.1
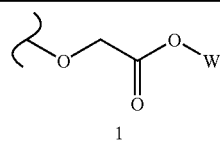
1
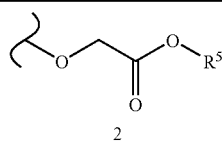
2
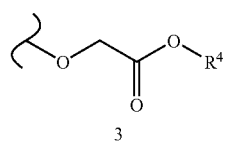
3
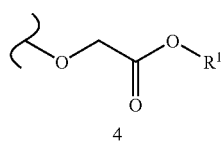
4
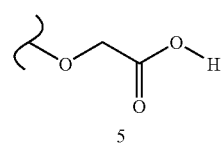
5
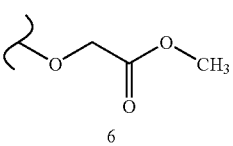
6
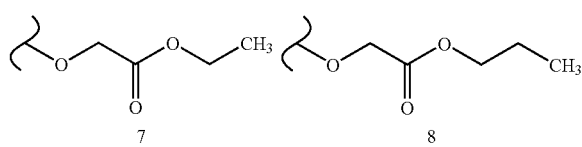
7      8
TABLE 20.2
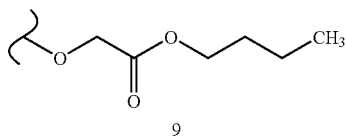
9
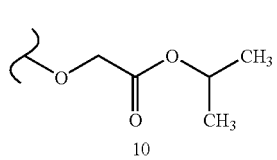
10
TABLE 20.2-continued
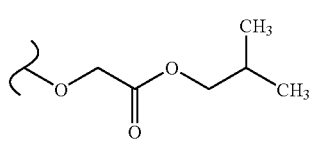
11
TABLE 20.3
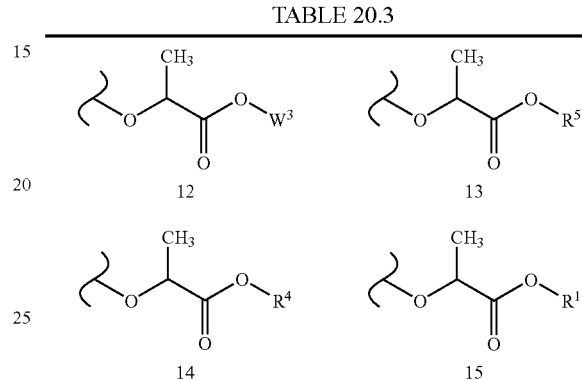
12      13
14      15
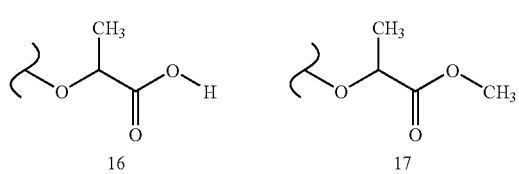
16      17
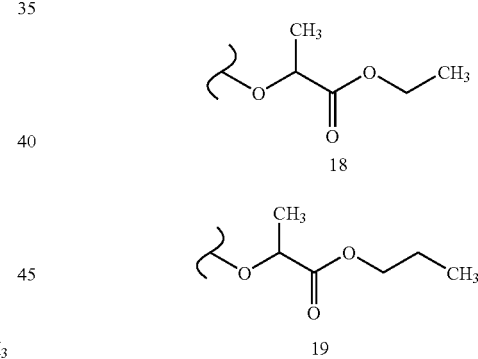
18
19
TABLE 20.4
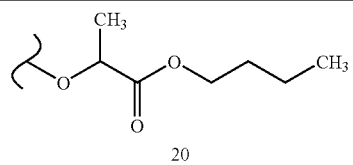
20
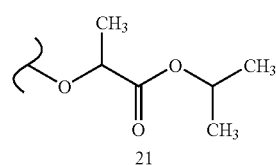
21

TABLE 20.4-continued
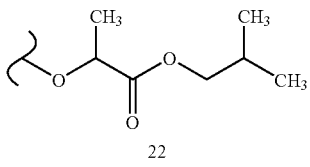
22
TABLE 20.5
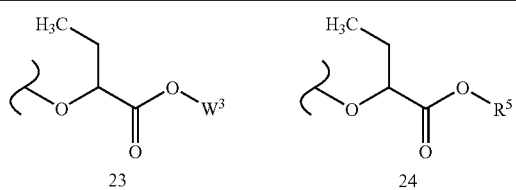
23   24
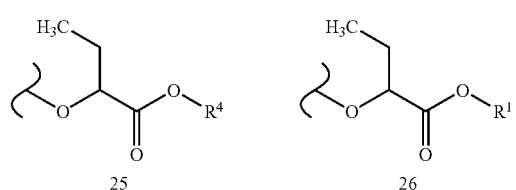
25   26
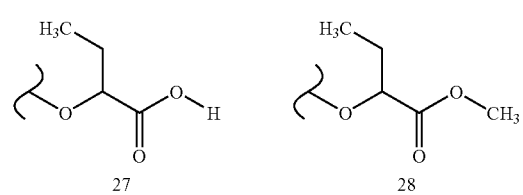
27   28
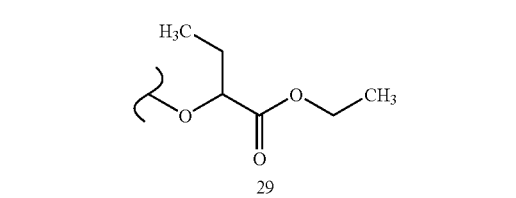
29
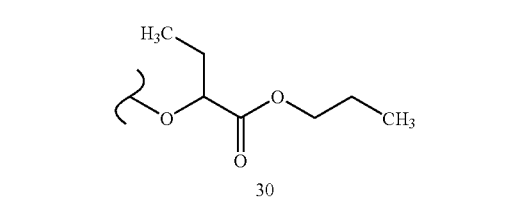
30
TABLE 20.6
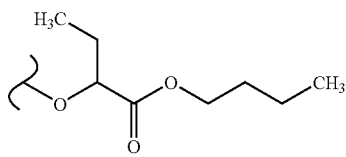
31
TABLE 20.6-continued
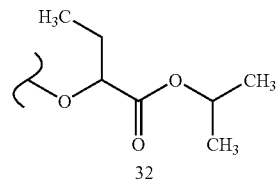
32
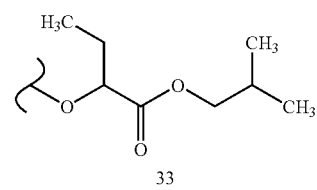
33
TABLE 20.7
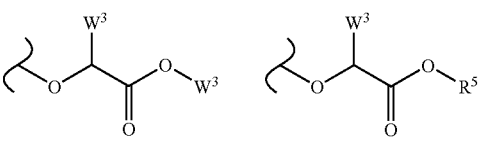
34   35
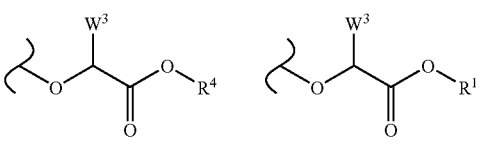
36   37
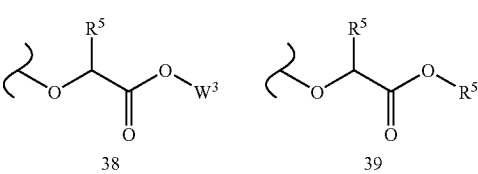
38   39
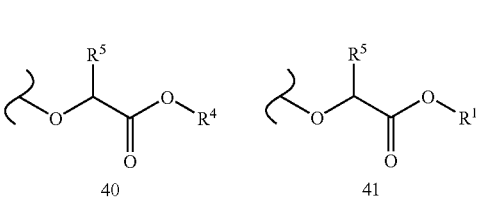
40   41
TABLE 20.8
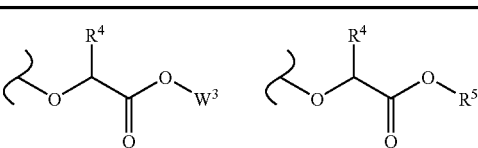
42   43

TABLE 20.8-continued 44, 45, 46, 47, 48, 49

TABLE 20.9

50, 51, 52, 53, 54, 55, 56, 57

TABLE 20.10

58

TABLE 20.10-continued 59, 60

TABLE 20.11

61, 62, 63, 64, 65, 66, 67, 68

TABLE 20.12

69, 70

TABLE 20.12-continued
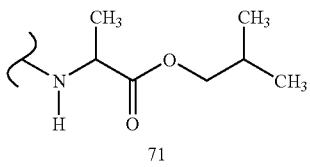
71
TABLE 20.13
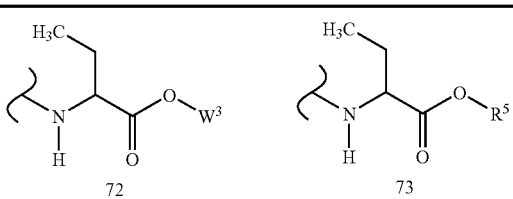
72    73
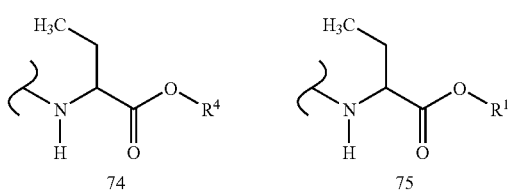
74    75
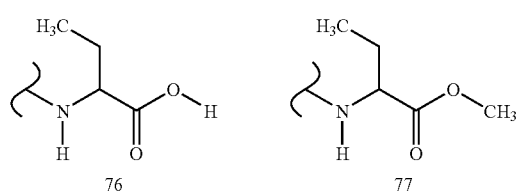
76    77
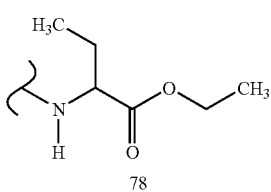
78
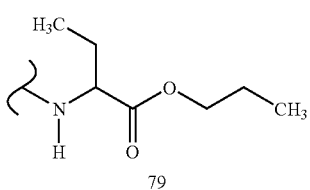
79
TABLE 20.14
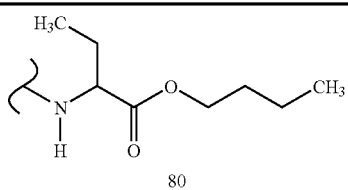
80
TABLE 20.14-continued
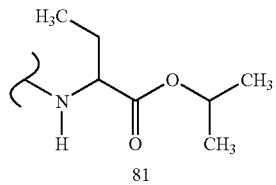
81
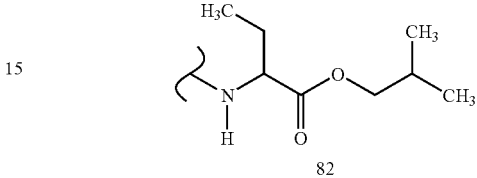
82
TABLE 20.15
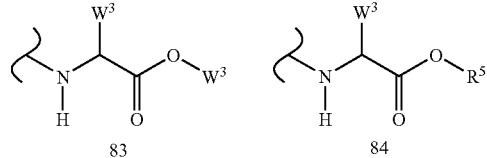
83    84
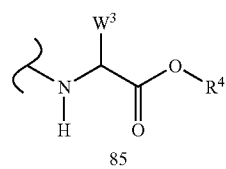
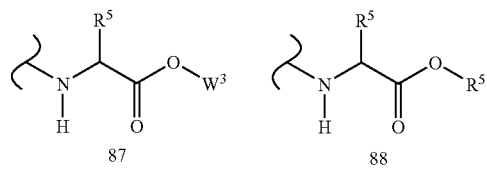
85    86
87    88
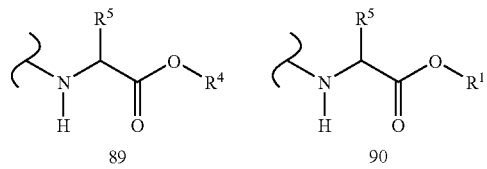
89    90
TABLE 20.16
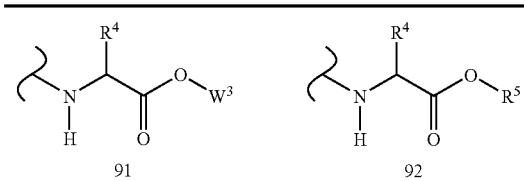
91    92

TABLE 20.16-continued 93, 94, 95, 96, 97, 98

TABLE 20.17

99, 100, 101, 102, 103, 104, 105, 106

TABLE 20.18

107, 108, 109

TABLE 20.19

110, 111, 112, 113, 114, 115, 116, 117

TABLE 20.20
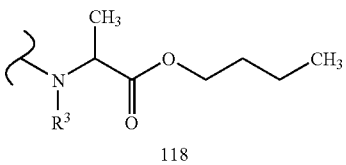
118
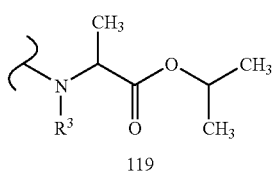
119
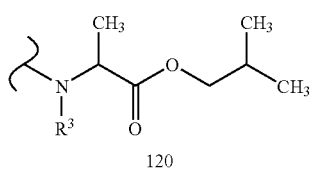
120
TABLE 20.21
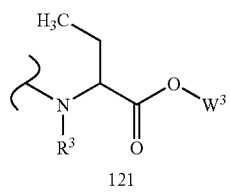
121
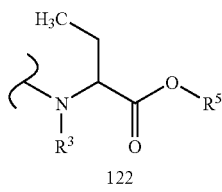
122
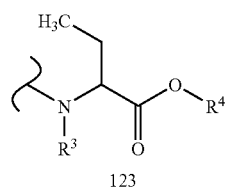
123
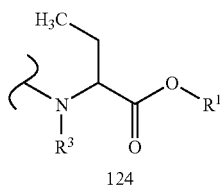
124
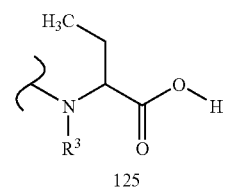
125
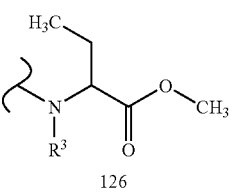
126
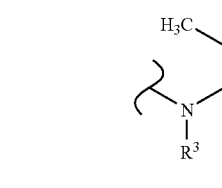
127
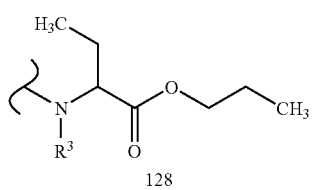
128
TABLE 20.22
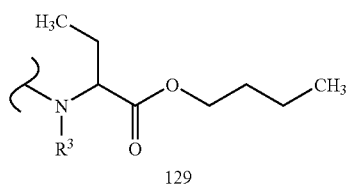
129
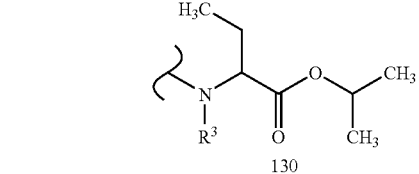
130
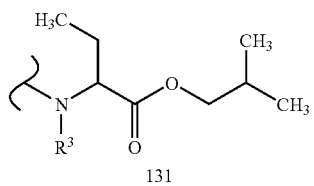
131
TABLE 20.23
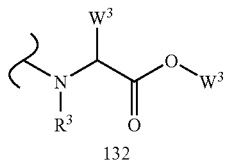
132
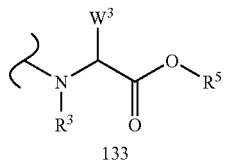
133
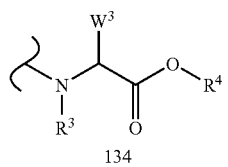
134
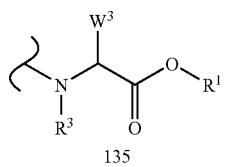
135
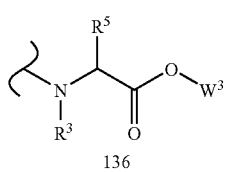
136
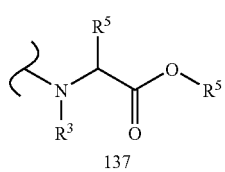
137
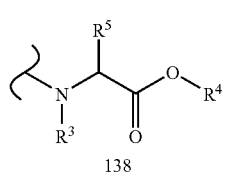
138
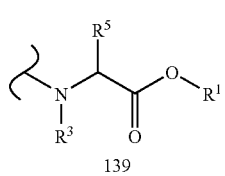
139

TABLE 20.24
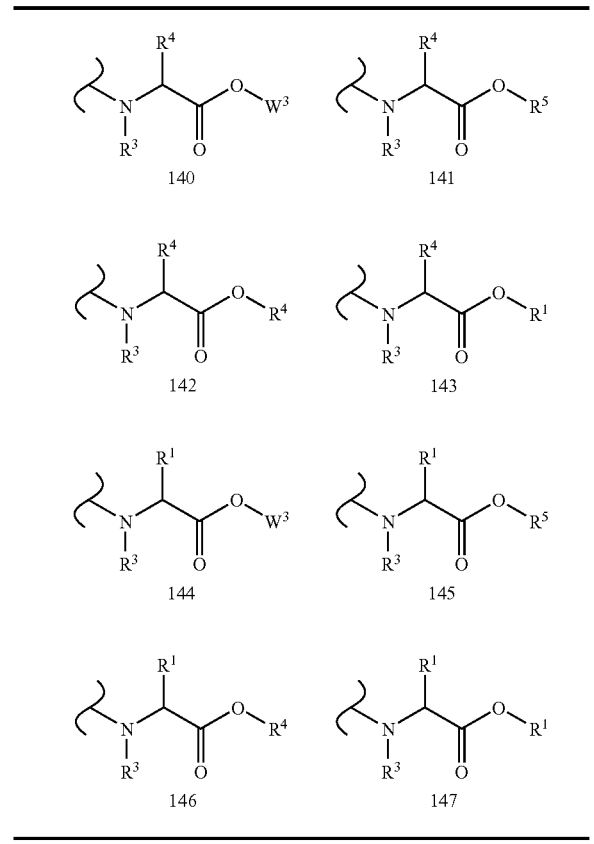
TABLE 20.25
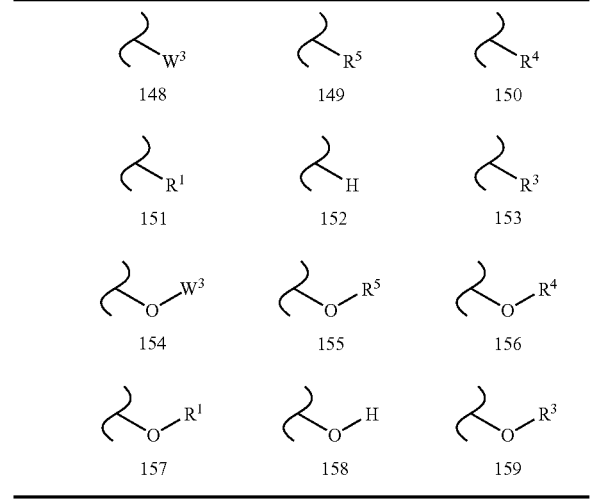
TABLE 20.26
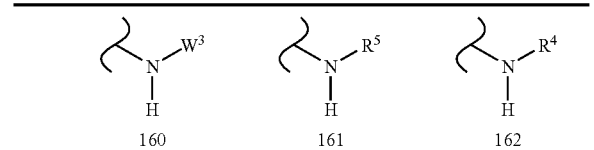
TABLE 20.26-continued
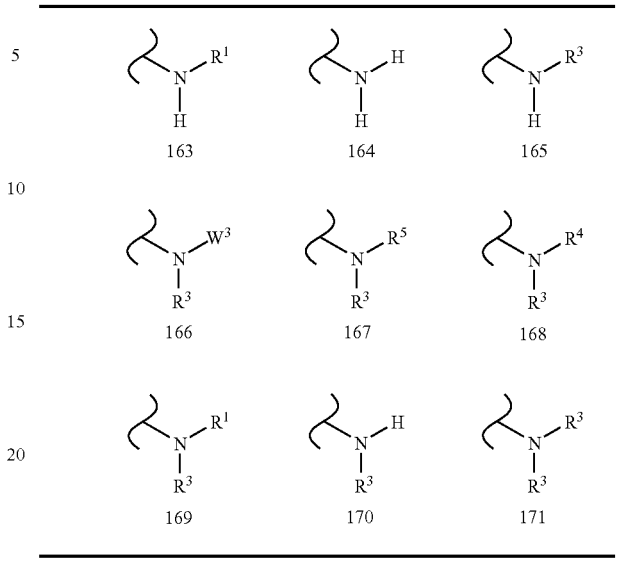
TABLE 20.27
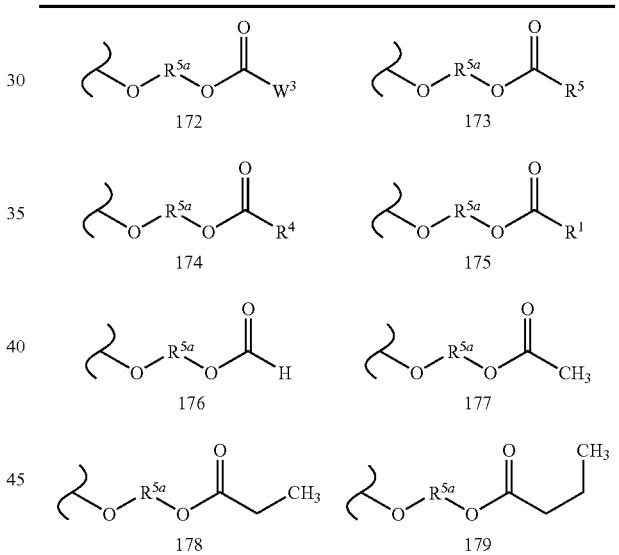
TABLE 20.28
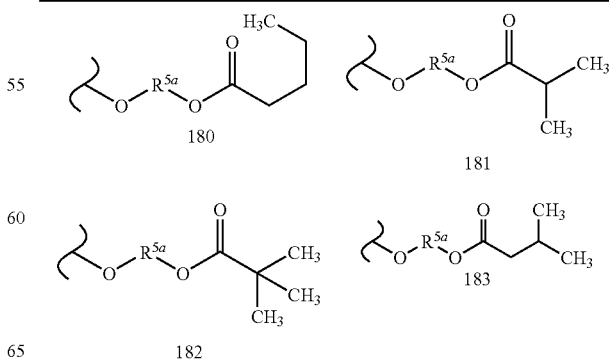

TABLE 20.28-continued
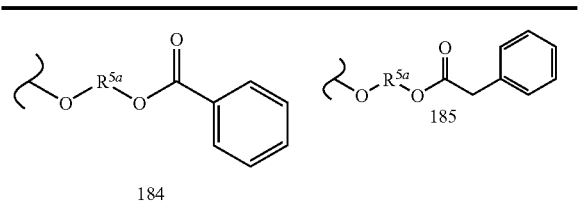
TABLE 20.29
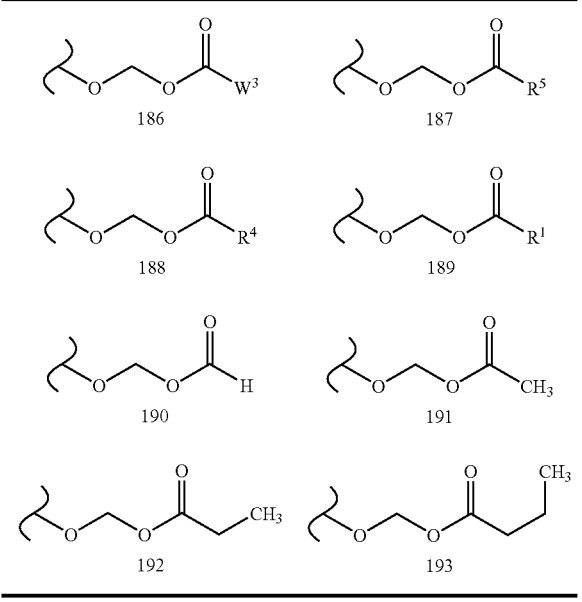
TABLE 20.30
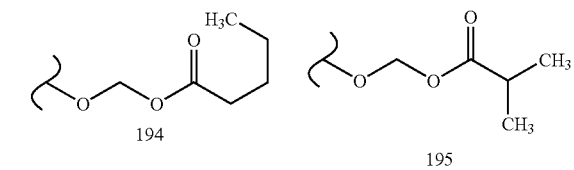
TABLE 20.30-continued
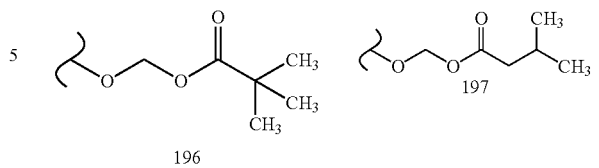
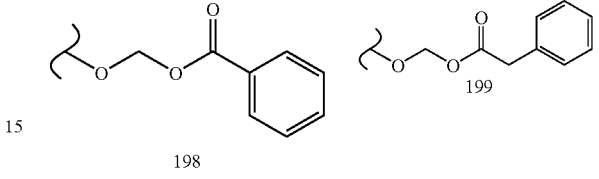
TABLE 20.31
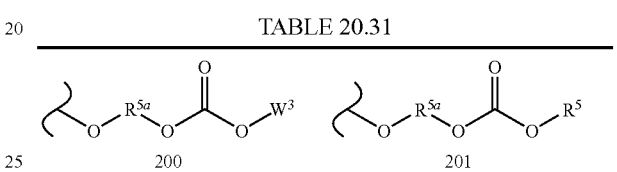
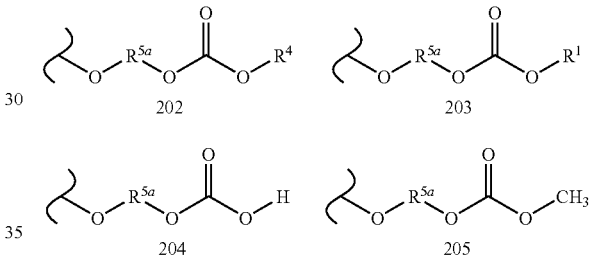
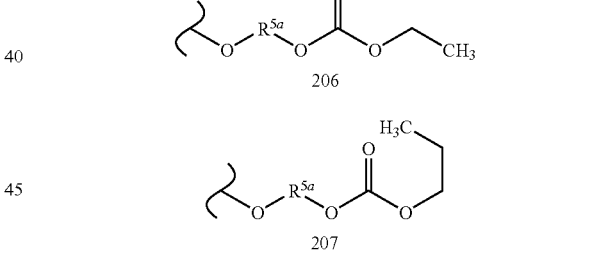
TABLE 20.32
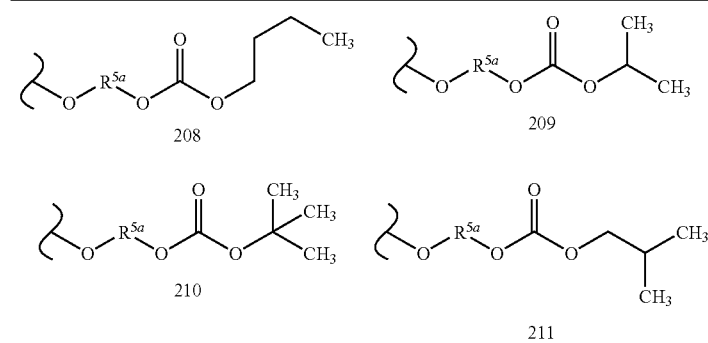

TABLE 20.32-continued
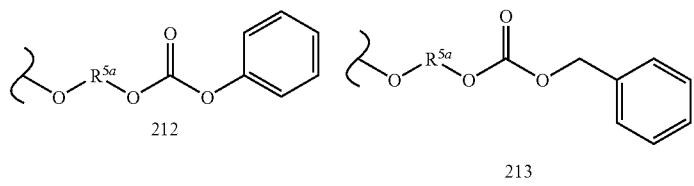
TABLE 20.33
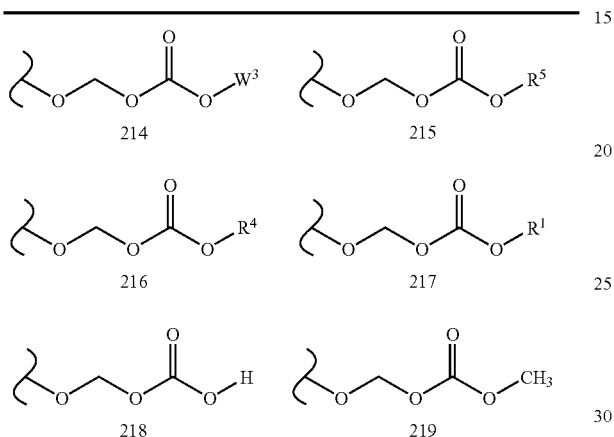
TABLE 20.33-continued
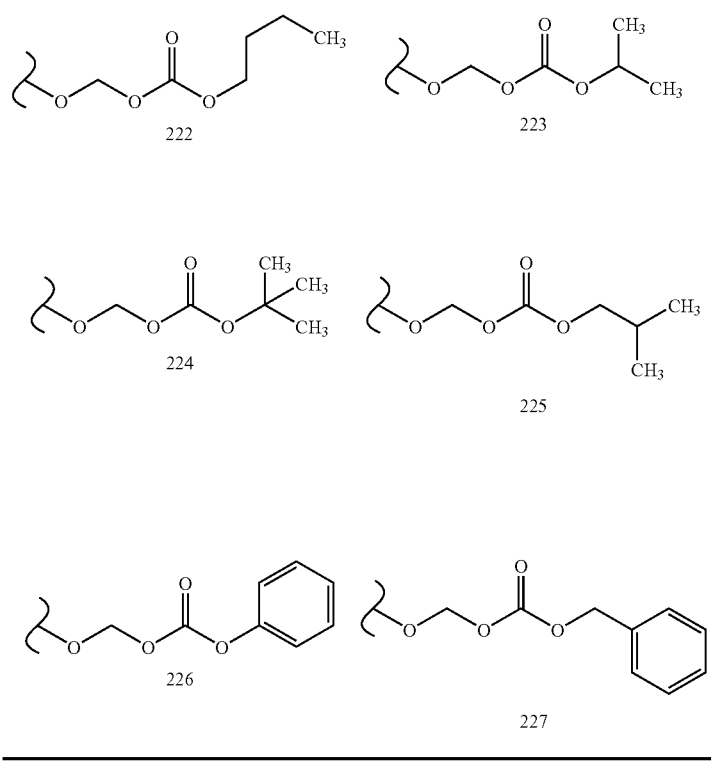
TABLE 20.34

TABLE 20.35

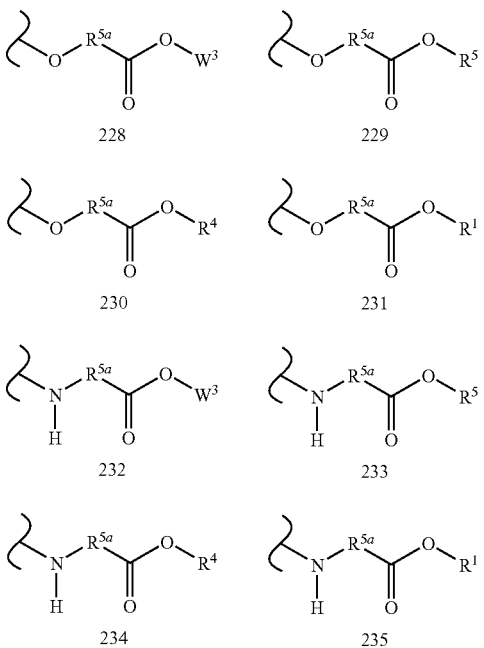

TABLE 20.36

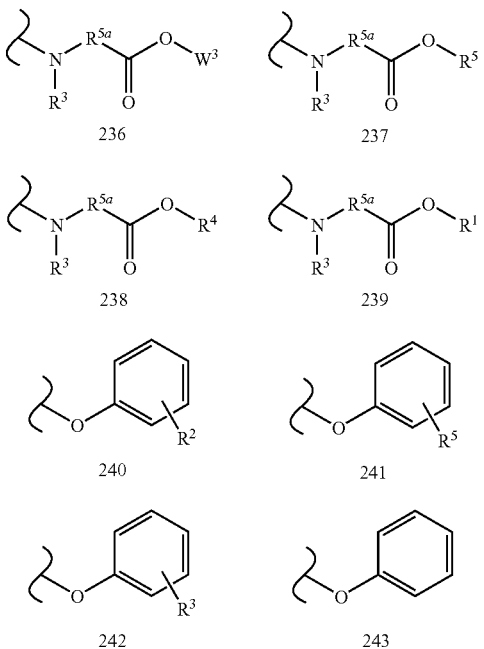

TABLE 20.37

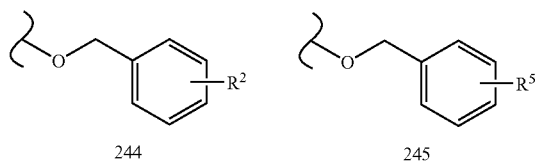

TABLE 20.37-continued

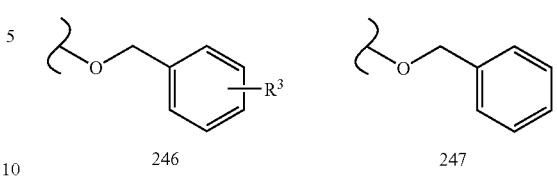

TABLE 7

Prodrugs of 1.B

1.B.228.228; 1.B.228.229; 1.B.228.230; 1.B.228.231; 1.B.228.236;
1.B.228.237; 1.B.228.238; 1.B.228.239; 1.B.228.154; 1.B.228.157;
1.B.228.166; 1.B.228.169; 1.B.228.172; 1.B.228.175; 1.B.228.240;
1.B.228.244; 1.B.229.228; 1.B.229.229; 1.B.229.230; 1.B.229.231;
1.B.229.236; 1.B.229.237; 1.B.229.238; 1.B.229.239; 1.B.229.154;
1.B.229.157; 1.B.229.166; 1.B.229.169; 1.B.229.172; 1.B.229.175;
1.B.229.240; 1.B.229.244; 1.B.230.228; 1.B.230.229; 1.B.230.230;
1.B.230.231; 1.B.230.236; 1.B.230.237; 1.B.230.238; 1.B.230.239;
1.B.230.154; 1.B.230.157; 1.B.230.166; 1.B.230.169; 1.B.230.172;
1.B.230.175; 1.B.230.240; 1.B.230.244; 1.B.231.228; 1.B.231.229;
1.B.231.230; 1.B.231.231; 1.B.231.236; 1.B.231.237; 1.B.231.238;
1.B.231.239; 1.B.231.154; 1.B.231.157; 1.B.231.166; 1.B.231.169;
1.B.231.172; 1.B.231.175; 1.B.231.240; 1.B.231.244; 1.B.236.228;
1.B.236.229; 1.B.236.230; 1.B.236.231; 1.B.236.236; 1.B.236.237;
1.B.236.238; 1.B.236.239; 1.B.236.154; 1.B.236.157; 1.B.236.166;
1.B.236.169; 1.B.236.172; 1.B.236.175; 1.B.236.240; 1.B.236.244;
1.B.237.228; 1.B.237.229; 1.B.237.230; 1.B.237.231; 1.B.237.236;
1.B.237.237; 1.B.237.238; 1.B.237.239; 1.B.237.154; 1.B.237.157;
1.B.237.166; 1.B.237.169; 1.B.237.172; 1.B.237.175; 1.B.237.240;
1.B.237.244; 1.B.238.228; 1.B.238.229; 1.B.238.230; 1.B.238.231;
1.B.238.236; 1.B.238.237; 1.B.238.238; 1.B.238.239; 1.B.238.154;
1.B.238.157; 1.B.238.166; 1.B.238.169; 1.B.238.172; 1.B.238.175;
1.B.238.240; 1.B.238.244; 1.B.239.228; 1.B.239.229; 1.B.239.230;
1.B.239.231; 1.B.239.236; 1.B.239.237; 1.B.239.238; 1.B.239.239;
1.B.239.154; 1.B.239.157; 1.B.239.166; 1.B.239.169; 1.B.239.172;
1.B.239.175; 1.B.239.240; 1.B.239.244; 1.B.154.228; 1.B.154.229;
1.B.154.230; 1.B.154.231; 1.B.154.236; 1.B.154.237; 1.B.154.238;
1.B.154.239; 1.B.154.154; 1.B.154.157; 1.B.154.166; 1.B.154.169;
1.B.154.172; 1.B.154.175; 1.B.154.240; 1.B.154.244; 1.B.157.228;
1.B.157.229; 1.B.157.230; 1.B.157.231; 1.B.157.236; 1.B.157.237;
1.B.157.238; 1.B.157.239; 1.B.157.154; 1.B.157.157; 1.B.157.166;
1.B.157.169; 1.B.157.172; 1.B.157.175; 1.B.157.240; 1.B.157.244;
1.B.166.228; 1.B.166.229; 1.B.166.230; 1.B.166.231; 1.B.166.236;
1.B.166.237; 1.B.166.238; 1.B.166.239; 1.B.166.154; 1.B.166.157;
1.B.166.166; 1.B.166.169; 1.B.166.172; 1.B.166.175; 1.B.166.240;
1.B.166.244; 1.B.169.228; 1.B.169.229; 1.B.169.230; 1.B.169.231;
1.B.169.236; 1.B.169.237; 1.B.169.238; 1.B.169.239; 1.B.169.154;
1.B.169.157; 1.B.169.166; 1.B.169.169; 1.B.169.172; 1.B.169.175;
1.B.169.240; 1.B.169.244; 1.B.172.228; 1.B.172.229; 1.B.172.230;
1.B.172.231; 1.B.172.236; 1.B.172.237; 1.B.172.238; 1.B.172.239;
1.B.172.154; 1.B.172.157; 1.B.172.166; 1.B.172.169; 1.B.172.172;
1.B.172.175; 1.B.172.240; 1.B.172.244; 1.B.175.228; 1.B.175.229;
1.B.175.230; 1.B.175.231; 1.B.175.236; 1.B.175.237; 1.B.175.238;
1.B.175.239; 1.B.175.154; 1.B.175.157; 1.B.175.166; 1.B.175.169;
1.B.175.172; 1.B.175.175; 1.B.175.240; 1.B.175.244; 1.B.240.228;
1.B.240.229; 1.B.240.230; 1.B.240.231; 1.B.240.236; 1.B.240.237;
1.B.240.238; 1.B.240.239; 1.B.240.154; 1.B.240.157; 1.B.240.166;
1.B.240.169; 1.B.240.172; 1.B.240.175; 1.B.240.240; 1.B.240.244;
1.B.244.228; 1.B.244.229; 1.B.244.230; 1.B.244.231; 1.B.244.236;
1.B.244.237; 1.B.244.238; 1.B.244.239; 1.B.244.154; 1.B.244.157;
1.B.244.166; 1.B.244.169; 1.B.244.172; 1.B.244.175; 1.B.244.240;
1.B.244.244;
Prodrugs of 1.D 1.D.228.228; 1.D.228.229; 1.D.228.230; 1.D.228.231; 1.D.228.236;
1.D.228.237; 1.D.228.238; 1.D.228.239; 1.D.228.154; 1.D.228.157;
1.D.228.166; 1.D.228.169; 1.D.228.172; 1.D.228.175; 1.D.228.240;
1.D.228.244; 1.D.229.228; 1.D.229.229; 1.D.229.230; 1.D.229.231;
1.D.229.236; 1.D.229.237; 1.D.229.238; 1.D.229.239; 1.D.229.154;
1.D.229.157; 1.D.229.166; 1.D.229.169; 1.D.229.172; 1.D.229.175;
1.D.229.240; 1.D.229.244; 1.D.230.228; 1.D.230.229; 1.D.230.230;
1.D.230.231; 1.D.230.236; 1.D.230.237; 1.D.230.238; 1.D.230.239;
1.D.230.154; 1.D.230.157; 1.D.230.166; 1.D.230.169; 1.D.230.172;

TABLE 7-continued

1.D.230.175; 1.D.230.240; 1.D.230.244; 1.D.231.228; 1.D.231.229;
1.D.231.230; 1.D.231.231; 1.D.231.236; 1.D.231.237; 1.D.231.238;
1.D.231.239; 1.D.231.154; 1.D.231.157; 1.D.231.166; 1.D.231.169;
1.D.231.172; 1.D.231.175; 1.D.231.240; 1.D.231.244; 1.D.236.228;
1.D.236.229; 1.D.236.230; 1.D.236.231; 1.D.236.236; 1.D.236.237;
1.D.236.238; 1.D.236.239; 1.D.236.154; 1.D.236.157; 1.D.236.166;
1.D.236.169; 1.D.236.172; 1.D.236.175; 1.D.236.240; 1.D.236.244;
1.D.237.228; 1.D.237.229; 1.D.237.230; 1.D.237.231; 1.D.237.236;
1.D.237.237; 1.D.237.238; 1.D.237.239; 1.D.237.154; 1.D.237.157;
1.D.237.166; 1.D.237.169; 1.D.237.172; 1.D.237.175; 1.D.237.240;
1.D.237.244; 1.D.238.228; 1.D.238.229; 1.D.238.230; 1.D.238.231;
1.D.238.236; 1.D.238.237; 1.D.238.238; 1.D.238.239; 1.D.238.154;
1.D.238.157; 1.D.238.166; 1.D.238.169; 1.D.238.172; 1.D.238.175;
1.D.238.240; 1.D.238.244; 1.D.239.228; 1.D.239.229; 1.D.239.230;
1.D.239.231; 1.D.239.236; 1.D.239.237; 1.D.239.238; 1.D.239.239;
1.D.239.154; 1.D.239.157; 1.D.239.166; 1.D.239.169; 1.D.239.172;
1.D.239.175; 1.D.239.240; 1.D.239.244; 1.D.154.228; 1.D.154.229;
1.D.154.230; 1.D.154.231; 1.D.154.236; 1.D.154.237; 1.D.154.238;
1.D.154.239; 1.D.154.154; 1.D.154.157; 1.D.154.166; 1.D.154.169;
1.D.154.172; 1.D.154.175; 1.D.154.240; 1.D.154.244; 1.D.157.228;
1.D.157.229; 1.D.157.230; 1.D.157.231; 1.D.157.236; 1.D.157.237;
1.D.157.238; 1.D.157.239; 1.D.157.154; 1.D.157.157; 1.D.157.166;
1.D.157.169; 1.D.157.172; 1.D.157.175; 1.D.157.240; 1.D.157.244;
1.D.166.228; 1.D.166.229; 1.D.166.230; 1.D.166.231; 1.D.166.236;
1.D.166.237; 1.D.166.238; 1.D.166.239; 1.D.166.154; 1.D.166.157;
1.D.166.166; 1.D.166.169; 1.D.166.172; 1.D.166.175; 1.D.166.240;
1.D.166.244; 1.D.169.228; 1.D.169.229; 1.D.169.230; 1.D.169.231;
1.D.169.236; 1.D.169.237; 1.D.169.238; 1.D.169.239; 1.D.169.154;
1.D.169.157; 1.D.169.166; 1.D.169.169; 1.D.169.172; 1.D.169.175;
1.D.169.240; 1.D.169.244; 1.D.172.228; 1.D.172.229; 1.D.172.230;
1.D.172.231; 1.D.172.236; 1.D.172.237; 1.D.172.238; 1.D.172.239;
1.D.172.154; 1.D.172.157; 1.D.172.166; 1.D.172.169; 1.D.172.172;
1.D.172.175; 1.D.172.240; 1.D.172.244; 1.D.175.228; 1.D.175.229;
1.D.175.230; 1.D.175.231; 1.D.175.236; 1.D.175.237; 1.D.175.238;
1.D.175.239; 1.D.175.154; 1.D.175.157; 1.D.175.166; 1.D.175.169;
1.D.175.172; 1.D.175.175; 1.D.175.240; 1.D.175.244; 1.D.240.228;
1.D.240.229; 1.D.240.230; 1.D.240.231; 1.D.240.236; 1.D.240.237;
1.D.240.238; 1.D.240.239; 1.D.240.154; 1.D.240.157; 1.D.240.166;
1.D.240.169; 1.D.240.172; 1.D.240.175; 1.D.240.240; 1.D.240.244;
1.D.244.228; 1.D.244.229; 1.D.244.230; 1.D.244.231; 1.D.244.236;
1.D.244.237; 1.D.244.238; 1.D.244.239; 1.D.244.154; 1.D.244.157;
1.D.244.166; 1.D.244.169; 1.D.244.172; 1.D.244.175; 1.D.244.240;
1.D.244.244;
Prodrugs of 1.E 1.E.228.228; 1.E.228.229; 1.E.228.230; 1.E.228.231; 1.E.228.236;
1.E.228.237; 1.E.228.238; 1.E.228.239; 1.E.228.154; 1.E.228.157;
1.E.228.166; 1.E.228.169; 1.E.228.172; 1.E.228.175; 1.E.228.240;
1.E.228.244; 1.E.229.228; 1.E.229.229; 1.E.229.230; 1.E.229.231;
1.E.229.236; 1.E.229.237; 1.E.229.238; 1.E.229.239; 1.E.229.154;
1.E.229.157; 1.E.229.166; 1.E.229.169; 1.E.229.172; 1.E.229.175;
1.E.229.240; 1.E.229.244; 1.E.230.228; 1.E.230.229; 1.E.230.230;
1.E.230.231; 1.E.230.236; 1.E.230.237; 1.E.230.238; 1.E.230.239;
1.E.230.154; 1.E.230.157; 1.E.230.166; 1.E.230.169; 1.E.230.172;
1.E.230.175; 1.E.230.240; 1.E.230.244; 1.E.231.228; 1.E.231.229;
1.E.231.230; 1.E.231.231; 1.E.231.236; 1.E.231.237; 1.E.231.238;
1.E.231.239; 1.E.231.154; 1.E.231.157; 1.E.231.166; 1.E.231.169;
1.E.231.172; 1.E.231.175; 1.E.231.240; 1.E.231.244; 1.E.236.228;
1.E.236.229; 1.E.236.230; 1.E.236.231; 1.E.236.236; 1.E.236.237;
1.E.236.238; 1.E.236.239; 1.E.236.154; 1.E.236.157; 1.E.236.166;
1.E.236.169; 1.E.236.172; 1.E.236.175; 1.E.236.240; 1.E.236.244;
1.E.237.228; 1.E.237.229; 1.E.237.230; 1.E.237.231; 1.E.237.236;
1.E.237.237; 1.E.237.238; 1.E.237.239; 1.E.237.154; 1.E.237.157;
1.E.237.166; 1.E.237.169; 1.E.237.172; 1.E.237.175; 1.E.237.240;
1.E.237.244; 1.E.238.228; 1.E.238.229; 1.E.238.230; 1.E.238.231;
1.E.238.236; 1.E.238.237; 1.E.238.238; 1.E.238.239; 1.E.238.154;
1.E.238.157; 1.E.238.166; 1.E.238.169; 1.E.238.172; 1.E.238.175;
1.E.238.240; 1.E.238.244; 1.E.239.228; 1.E.239.229; 1.E.239.230;
1.E.239.231; 1.E.239.236; 1.E.239.237; 1.E.239.238; 1.E.239.239;
1.E.239.154; 1.E.239.157; 1.E.239.166; 1.E.239.169; 1.E.239.172;
1.E.239.175; 1.E.239.240; 1.E.239.244; 1.E.154.228; 1.E.154.229;
1.E.154.230; 1.E.154.231; 1.E.154.236; 1.E.154.237; 1.E.154.238;
1.E.154.239; 1.E.154.154; 1.E.154.157; 1.E.154.166; 1.E.154.169;
1.E.154.172; 1.E.154.175; 1.E.154.240; 1.E.154.244; 1.E.157.228;
1.E.157.229; 1.E.157.230; 1.E.157.231; 1.E.157.236; 1.E.157.237;
1.E.157.238; 1.E.157.239; 1.E.157.154; 1.E.157.157; 1.E.157.166;
1.E.157.169; 1.E.157.172; 1.E.157.175; 1.E.157.240; 1.E.157.244;
1.E.166.228; 1.E.166.229; 1.E.166.230; 1.E.166.231; 1.E.166.236;
1.E.166.237; 1.E.166.238; 1.E.166.239; 1.E.166.154; 1.E.166.157;
1.E.166.166; 1.E.166.169; 1.E.166.172; 1.E.166.175; 1.E.166.240;
1.E.166.244; 1.E.169.228; 1.E.169.229; 1.E.169.230; 1.E.169.231;
1.E.169.236; 1.E.169.237; 1.E.169.238; 1.E.169.239; 1.E.169.154;
1.E.169.157; 1.E.169.166; 1.E.169.169; 1.E.169.172; 1.E.169.175;
1.E.169.240; 1.E.169.244; 1.E.172.228; 1.E.172.229; 1.E.172.230;
1.E.172.231; 1.E.172.236; 1.E.172.237; 1.E.172.238; 1.E.172.239;
1.E.172.154; 1.E.172.157; 1.E.172.166; 1.E.172.169; 1.E.172.172;
1.E.172.175; 1.E.172.240; 1.E.172.244; 1.E.175.228; 1.E.175.229;
1.E.175.230; 1.E.175.231; 1.E.175.236; 1.E.175.237; 1.E.175.238;
1.E.175.239; 1.E.175.154; 1.E.175.157; 1.E.175.166; 1.E.175.169;
1.E.175.172; 1.E.175.175; 1.E.175.240; 1.E.175.244; 1.E.240.228;
1.E.240.229; 1.E.240.230; 1.E.240.231; 1.E.240.236; 1.E.240.237;
1.E.240.238; 1.E.240.239; 1.E.240.154; 1.E.240.157; 1.E.240.166;
1.E.240.169; 1.E.240.172; 1.E.240.175; 1.E.240.240; 1.E.240.244;
1.E.244.228; 1.E.244.229; 1.E.244.230; 1.E.244.231; 1.E.244.236;
1.E.244.237; 1.E.244.238; 1.E.244.239; 1.E.244.154; 1.E.244.157;
1.E.244.166; 1.E.244.169; 1.E.244.172; 1.E.244.175; 1.E.244.240;
1.E.244.244;
Prodrugs of 1.G 1.G.228.228; 1.G.228.229; 1.G.228.230; 1.G.228.231; 1.G.228.236;
1.G.228.237; 1.G.228.238; 1.G.228.239; 1.G.228.154; 1.G.228.157;
1.G.228.166; 1.G.228.169; 1.G.228.172; 1.G.228.175; 1.G.228.240;
1.G.228.244; 1.G.229.228; 1.G.229.229; 1.G.229.230; 1.G.229.231;
1.G.229.236; 1.G.229.237; 1.G.229.238; 1.G.229.239; 1.G.229.154;
1.G.229.157; 1.G.229.166; 1.G.229.169; 1.G.229.172; 1.G.229.175;
1.G.229.240; 1.G.229.244; 1.G.230.228; 1.G.230.229; 1.G.230.230;
1.G.230.231; 1.G.230.236; 1.G.230.237; 1.G.230.238; 1.G.230.239;
1.G.230.154; 1.G.230.157; 1.G.230.166; 1.G.230.169; 1.G.230.172;
1.G.230.175; 1.G.230.240; 1.G.230.244; 1.G.231.228; 1.G.231.229;
1.G.231.230; 1.G.231.231; 1.G.231.236; 1.G.231.237; 1.G.231.238;
1.G.231.239; 1.G.231.154; 1.G.231.157; 1.G.231.166; 1.G.231.169;
1.G.231.172; 1.G.231.175; 1.G.231.240; 1.G.231.244; 1.G.236.228;
1.G.236.229; 1.G.236.230; 1.G.236.231; 1.G.236.236; 1.G.236.237;
1.G.236.238; 1.G.236.239; 1.G.236.154; 1.G.236.157; 1.G.236.166;
1.G.236.169; 1.G.236.172; 1.G.236.175; 1.G.236.240; 1.G.236.244;
1.G.237.228; 1.G.237.229; 1.G.237.230; 1.G.237.231; 1.G.237.236;
1.G.237.237; 1.G.237.238; 1.G.237;239; 1.G.237.154; 1.G.237.157;
1.G.237.166; 1.G.237.169; 1.G.237.172; 1.G.237.175; 1:G.237.240;
1.G.237.244; 1.G.238.228; 1.G.238.229; 1.G.238.230; 1.G.238.231;
1.G.238.236; 1.G.238.237; 1.G.238.238; 1.G.238.239; 1.G.238.154;
1.G.238.157; 1.G.238.166; 1.G.238.169; 1.G.238.172; 1.G.238.175;
1.G.238.240; 1.G.238.244; 1.G.239.228; 1.G.239.229; 1.G.239.230;
1.G.239.231; 1.G.239.236; 1.G.239.237; 1.G.239.238; 1.G.239.239;
1.G.239.154; 1.G.239.157; 1.G.239.166; 1.G.239.169; 1.G.239.172;
1.G.239.175; 1.G.239.240; 1.G.239.244; 1.G.154.228; 1.G.154.229;
1.G.154.230; 1.G.154.231; 1.G.154.236; 1.G.154.237; 1.G.154.238;
1.G.154.239; 1.G.154.154; 1.G.154.157; 1.G.154.166; 1.G.154.169;
1.G.154.172; 1.G.154.175; 1.G.154.240; 1.G.154.244; 1.G.157.228;
1.G.157.229; 1.G.157.230; 1.G.157.231; 1.G.157.236; 1.G.157.237;
1.G.157.238; 1.G.157.239; 1.G.157.154; 1.G.157.157; 1.G.157.166;
1.G.157.169; 1.G.157.172; 1.G.157.175; 1.G.157.240; 1.G.157.244;
1.G.166.228; 1.G.166.229; 1.G.166.230; 1.G.166.231; 1.G.166.236;
1.G.166.237; 1.G.166.238; 1.G.166.239; 1.G.166.154; 1.G.166.157;
1.G.166.166; 1.G.166.169; 1.G.166.172; 1.G.166.175; 1.G.166.240;
1.G.166.244; 1.G.169.228; 1.G.169.229; 1.G.169.230; 1.G.169.231;
1.G.169.236; 1.G.169.237; 1.G.169.238; 1.G.169.239; 1.G.169.154;
1.G.169.157; 1.G.169.166; 1.G.169.169; 1.G.169.172; 1.G.169.175;
1.G.169.240; 1.G.169.244; 1.G.172.228; 1.G.172.229; 1.G.172.230;
1.G.172.231; 1.G.172.236; 1.G.172.237; 1.G.172.238; 1.G.172.239;
1.G.172.154; 1.G.172.157; 1.G.172.166; 1.G.172.169; 1.G.172.172;
1.G.172.175; 1.G.172.240; 1.G.172.244; 1.G.175.228; 1.G.175.229;
1.G.175.230; 1.G.175.231; 1.G.175.236; 1.G.175.237; 1.G.175.238;
1.G.175.239; 1.G.175.154; 1.G.175.157; 1.G.175.166; 1.G.175.169;
1.G.175.172; 1.G.175.175; 1.G.175.240; 1.G.175.244; 1.G.240.228;
1.G.240.229; 1.G.240.230; 1.G.240.231; 1.G.240.236; 1.G.240.237;
1.G.240.238; 1.G.240.239; 1.G.240.154; 1.G.240.157; 1.G.240.166;
1.G.240.169; 1.G.240.172; 1.G.240.175; 1.G.240.240; 1.G.240.244;
1.G.244.228; 1.G.244.229; 1.G.244.230; 1.G.244.231; 1.G.244.236;
1.G.244.237; 1.G.244.238; 1.G.244.239; 1.G.244.154; 1.G.244.157;
1.G.244.166; 1.G.244.169; 1.G.244.172; 1.G.244.175; 1.G.244.240;
1.G.244.244;
Prodrugs of 1.I 1.I.228.228; 1.I.228.229; 1.I.228.230; 1.I.228.231; 1.I.228.236;
1.I.228.237; 1.I.228.238; 1.I.228.239; 1.I.228.154; 1.I.228.157;
1.I.228.166; 1.I.228.169; 1.I.228.172; 1.I.228.175; 1.I.228.240;
1.I.228.244; 1.I.229.228; 1.I.229.229; 1.I.229.230; 1.I.229.231;
1.I.229.236; 1.I.229.237; 1.I.229.238; 1.I.229.239; 1.I.229.154;

TABLE 7-continued

1.I.229.157; 1.I.229.166; 1.I.229.169; 1.I.229.172; 1.I.229.175; 1.I.229.240; 1.I.229.244; 1.I.230.228; 1.I.230.229; 1.I.230.230; 1.I.230.231; 1.I.230.236; 1.I.230.237; 1.I.230.238; 1.I.230.239; 1.I.230.154; 1.I.230.157; 1.I.230.166; 1.I.230.169; 1.I.230.172; 1.I.230.175; 1.I.230.240; 1.I.230.244; 1.I.231.228; 1.I.231.229; 1.I.231.230; 1.I.231.231; 1.I.231.236; 1.I.231.237; 1.I.231.238; 1.I.231.239; 1.I.231.154; 1.I.231.157; 1.I.231.166; 1.I.231.169; 1.I.231.172; 1.I.231.175; 1.I.231.240; 1.I.231.244; 1.I.236.228; 1.I.236.229; 1.I.236.230; 1.I.236.231; 1.I.236.236; 1.I.236.237; 1.I.236.238; 1.I.236.239; 1.I.236.154; 1.I.236.157; 1.I.236.166; 1.I.236.169; 1.I.236.172; 1.I.236.175; 1.I.236.240; 1.I.236.244; 1.I.237.228; 1.I.237.229; 1.I.237.230; 1.I.237.231; 1.I.237.236; 1.I.237.237; 1.I.237.238; 1.I.237.239; 1.I.237.154; 1.I.237.157; 1.I.237.166; 1.I.237.169; 1.I.237.172; 1.I.237.175; 1.I.237.240; 1.I.237.244; 1.I.238.228; 1.I.238.229; 1.I.238.230; 1.I.238.231; 1.I.238.236; 1.I.238.237; 1.I.238.238; 1.I.238.239; 1.I.238.154; 1.I.238.157; 1.I.238.166; 1.I.238.169; 1.I.238.172; 1.I.238.175; 1.I.238.240; 1.I.238.244; 1.I.239.228; 1.I.239.229; 1.I.239.230; 1.I.239.231; 1.I.239.236; 1.I.239.237; 1.I.239.238; 1.I.239.239; 1.I.239.154; 1.I.239.157; 1.I.239.166; 1.I.239.169; 1.I.239.172; 1.I.239.175; 1.I.239.240; 1.I.239.244; 1.I.154.228; 1.I.154.229; 1.I.154.230; 1.I.154.231; 1.I.154.236; 1.I.154.237; 1.I.154.238; 1.I.154.239; 1.I.154.154; 1.I.154.157; 1.I.154.166; 1.I.154.169; 1.I.154.172; 1.I.154.175; 1.I.154.240; 1.I.154.244; 1.I.157.228; 1.I.157.229; 1.I.157.230; 1.I.157.231; 1.I.157.236; 1.I.157.237; 1.I.157.238; 1.I.157.239; 1.I.157.154; 1.I.157.157; 1.I.157.166; 1.I.157.169; 1.I.157.172; 1.I.157.175; 1.I.157.240; 1.I.157.244; 1.I.166.228; 1.I.166.229; 1.I.166.230; 1.I.166.231; 1.I.166.236; 1.I.166.237; 1.I.166.238; 1.I.166.239; 1.I.166.154; 1.I.166.157; 1.I.166.166; 1.I.166.169; 1.I.166.172; 1.I.166.175; 1.I.166.240; 1.I.166.244; 1.I.169.228; 1.I.169.229; 1.I.169.230; 1.I.169.231; 1.I.169.236; 1.I.169.237; 1.I.169.238; 1.I.169.239; 1.I.169.154; 1.I.169.157; 1.I.169.166; 1.I.169.169; 1.I.169.172; 1.I.169.175; 1.I.169.240; 1.I.169.244; 1.I.172.228; 1.I.172.229; 1.I.172.230; 1.I.172.231; 1.I.172.236; 1.I.172.237; 1.I.172.238; 1.I.172.239; 1.I.172.154; 1.I.172.157; 1.I.172.166; 1.I.172.169; 1.I.172.172; 1.I.172.175; 1.I.172.240; 1.I.172.244; 1.I.175.228; 1.I.175.229; 1.I.175.230; 1.I.175.231; 1.I.175.236; 1.I.175.237; 1.I.175.238; 1.I.175.239; 1.I.175.154; 1.I.175.157; 1.I.175.166; 1.I.175.169; 1.I.175.172; 1.I.175.175; 1.I.175.240; 1.I.175.244; 1.I.240.228; 1.I.240.229; 1.I.240.230; 1.I.240.231; 1.I.240.236; 1.I.240.237; 1.I.240.238; 1.I.240.239; 1.I.240.154; 1.I.240.157; 1.I.240.166; 1.I.240.169; 1.I.240.172; 1.I.240.175; 1.I.240.240; 1.I.240.244; 1.I.244.228; 1.I.244.229; 1.I.244.230; 1.I.244.231; 1.I.244.236; 1.I.244.237; 1.I.244.238; 1.I.244.239; 1.I.244.154; 1.I.244.157; 1.I.244.166; 1.I.244.169; 1.I.244.172; 1.I.244.175; 1.I.244.240; 1.I.244.244;
Prodrugs of 1.J 1.J.228.228; 1.J.228.229; 1.J.228.230; 1.J.228.231; 1.J.228.236; 1.J.228.237; 1.J.228.238; 1.J.228.239; 1.J.228.154; 1.J.228.157; 1.J.228.166; 1.J.228.169; 1.J.228.172; 1.J.228.175; 1.J.228.240; 1.J.228.244; 1.J.229.228; 1.J.229.229; 1.J.229.230; 1.J.229.231; 1.J.229.236; 1.J.229.237; 1.J.229.238; 1.J.229.239; 1.J.229.154; 1.J.229.157; 1.J.229.166; 1.J.229.169; 1.J.229.172; 1.J.229.175; 1.J.229.240; 1.J.229.244; 1.J.230.228; 1.J.230.229; 1.J.230.230; 1.J.230.231; 1.J.230.236; 1.J.230.237; 1.J.230.238; 1.J.230.239; 1.J.230.154; 1.J.230.157; 1.J.230.166; 1.J.230.169; 1.J.230.172; 1.J.230.175; 1.J.230.240; 1.J.230.244; 1.J.231.228; 1.J.231.229; 1.J.231.230; 1.J.231.231; 1.J.231.236; 1.J.231.237; 1.J.231.238; 1.J.231.239; 1.J.231.154; 1.J.231.157; 1.J.231.166; 1.J.231.169; 1.J.231.172; 1.J.231.175; 1.J.231.240; 1.J.231.244; 1.J.236.228; 1.J.236.229; 1.J.236.230; 1.J.236.231; 1.J.236.236; 1.J.236.237; 1.J.236.238; 1.J.236.239; 1.J.236.154; 1.J.236.157; 1.J.236.166; 1.J.236.169; 1.J.236.172; 1.J.236.175; 1.J.236.240; 1.J.236.244; 1.J.237.228; 1.J.237.229; 1.J.237.230; 1.J.237.231; 1.J.237.236; 1.J.237.237; 1.J.237.238; 1.J.237.239; 1.J.237.154; 1.J.237.157; 1.J.237.166; 1.J.237.169; 1.J.237.172; 1.J.237.175; 1.J.237.240; 1.J.237.244; 1.J.238.228; 1.J.238.229; 1.J.238.230; 1.J.238.231; 1.J.238.236; 1.J.238.237; 1.J.238.238; 1.J.238.239; 1.J.238.154; 1.J.238.157; 1.J.238.166; 1.J.238.169; 1.J.238.172; 1.J.238.175; 1.J.238.240; 1.J.238.244; 1.J.239.228; 1.J.239.229; 1.J.239.230; 1.J.239.231; 1.J.239.236; 1.J.239.237; 1.J.239.238; 1.J.239.239; 1.J.239.154; 1.J.239.157; 1.J.239.166; 1.J.239.169; 1.J.239.172; 1.J.239.175; 1.J.239.240; 1.J.239.244; 1.J.154.228; 1.J.154.229; 1.J.154.230; 1.J.154.231; 1.J.154.236; 1.J.154.237; 1.J.154.238; 1.J.154.239; 1.J.154.154; 1.J.154.157; 1.J.154.166; 1.J.154.169; 1.J.154.172; 1.J.154.175; 1.J.154.240; 1.J.154.244; 1.J.157.228; 1.J.157.229; 1.J.157.230; 1.J.157.231; 1.J.157.236; 1.J.157.237; 1.J.157.238; 1.J.157.239; 1.J.157.154; 1.J.157.157; 1.J.157.166; 1.J.157.169; 1.J.157.172; 1.J.157.175; 1.J.157.240; 1.J.157.244; 1.J.166.228; 1.J.166.229; 1.J.166.230; 1.J.166.231; 1.J.166.236; 1.J.166.237; 1.J.166.238; 1.J.166.239; 1.J.166.154; 1.J.166.157; 1.J.166.166; 1.J.166.169; 1.J.166.172; 1.J.166.175; 1.J.166.240; 1.J.166.244; 1.J.169.228; 1.J.169.229; 1.J.169.230; 1.J.169.231; 1.J.169.236; 1.J.169.237; 1.J.169.238; 1.J.169.239; 1.J.169.154; 1.J.169.157; 1.J.169.166; 1.J.169.169; 1.J.169.172; 1.J.169.175; 1.J.169.240; 1.J.169.244; 1.J.172.228; 1.J.172.229; 1.J.172.230; 1.J.172.231; 1.J.172.236; 1.J.172.237; 1.J.172.238; 1.J.172.239; 1.J.172.154; 1.J.172.157; 1.J.172.166; 1.J.172.169; 1.J.172.172; 1.J.172.175; 1.J.172.240; 1.J.172.244; 1.J.175.228; 1.J.175.229; 1.J.175.230; 1.J.175.231; 1.J.175.236; 1.J.175.237; 1.J.175.238; 1.J.175.239; 1.J.175.154; 1.J.175.157; 1.J.175.166; 1.J.175.169; 1.J.175.172; 1.J.175.175; 1.J.175.240; 1.J.175.244; 1.J.240.228; 1.J.240.229; 1.J.240.230; 1.J.240.231; 1.J.240.236; 1.J.240.237; 1.J.240.238; 1.J.240.239; 1.J.240.154; 1.J.240.157; 1.J.240.166; 1.J.240.169; 1.J.240.172; 1.J.240.175; 1.J.240.240; 1.J.240.244; 1.J.244.228; 1.J.244.229; 1.J.244.230; 1.J.244.231; 1.J.244.236; 1.J.244.237; 1.J.244.238; 1.J.244.239; 1.J.244.154; 1.J.244.157; 1.J.244.166; 1.J.244.169; 1.J.244.172; 1.J.244.175; 1.J.244.240; 1.J.244.244;
Prodrugs of 1.L 1.L.228.228; 1.L.228.229; 1.L.228.230; 1.L.228.231; 1.L.228.236; 1.L.228.237; 1.L.228.238; 1.L.228.239; 1.L.228.154; 1.L.228.157; 1.L.228.166; 1.L.228.169; 1.L.228.172; 1.L.228.175; 1.L.228.240; 1.L.228.244; 1.L.229.228; 1.L.229.229; 1.L.229.230; 1.L.229.231; 1.L.229.236; 1.L.229.237; 1.L.229.238; 1.L.229.239; 1.L.229.154; 1.L.229.157; 1.L.229.166; 1.L.229.169; 1.L.229.172; 1.L.229.175; 1.L.229.240; 1.L.229.244; 1.L.230.228; 1.L.230.229; 1.L.230.230; 1.L.230.231; 1.L.230.236; 1.L.230.237; 1.L.230.238; 1.L.230.239; 1.L.230.154; 1.L.230.157; 1.L.230.166; 1.L.230.169; 1.L.230.172; 1.L.230.175; 1.L.230.240; 1.L.230.244; 1.L.231.228; 1.L.231.229; 1.L.231.230; 1.L.231.231; 1.L.231.236; 1.L.231.237; 1.L.231.238; 1.L.231.239; 1.L.231.154; 1.L.231.157; 1.L.231.166; 1.L.231.169; 1.L.231.172; 1.L.231.175; 1.L.231.240; 1.L.231.244; 1.L.236.228; 1.L.236.229; 1.L.236.230; 1.L.236.231; 1.L.236.236; 1.L.236.237; 1.L.236.238; 1.L.236.239; 1.L.236.154; 1.L.236.157; 1.L.236.166; 1.L.236.169; 1.L.236.172; 1.L.236.175; 1.L.236.240; 1.L.236.244; 1.L.237.228; 1.L.237.229; 1.L.237.230; 1.L.237.231; 1.L.237.236; 1.L.237.237; 1.L.237.238; 1.L.237.239; 1.L.237.154; 1.L.237.157; 1.L.237.166; 1.L.237.169; 1.L.237.172; 1.L.237.175; 1.L.237.240; 1.L.237.244; 1.L.238.228; 1.L.238.229; 1.L.238.230; 1.L.238.231; 1.L.238.236; 1.L.238.237; 1.L.238.238; 1.L.238.239; 1.L.238.154; 1.L.238.157; 1.L.238.166; 1.L.238.169; 1.L.238.172; 1.L.238.175; 1.L.238.240; 1.L.238.244; 1.L.239.228; 1.L.239.229; 1.L.239.230; 1.L.239.231; 1.L.239.236; 1.L.239.237; 1.L.239.238; 1.L.239.239; 1.L.239.154; 1.L.239.157; 1.L.239.166; 1.L.239.169; 1.L.239.172; 1.L.239.175; 1.L.239.240; 1.L.239.244; 1.L.154.228; 1.L.154.229; 1.L.154.230; 1.L.154.231; 1.L.154.236; 1.L.154.237; 1.L.154.238; 1.L.154.239; 1.L.154.154; 1.L.154.157; 1.L.154.166; 1.L.154.169; 1.L.154.172; 1.L.154.175; 1.L.154.240; 1.L.154.244; 1.L.157.228; 1.L.157.229; 1.L.157.230; 1.L.157.231; 1.L.157.236; 1.L.157.237; 1.L.157.238; 1.L.157.239; 1.L.157.154; 1.L.157.157; 1.L.157.166; 1.L.157.169; 1.L.157.172; 1.L.157.175; 1.L.157.240; 1.L.157.244; 1.L.166.228; 1.L.166.229; 1.L.166.230; 1.L.166.231; 1.L.166.236; 1.L.166.237; 1.L.166.238; 1.L.166.239; 1.L.166.154; 1.L.166.157; 1.L.166.166; 1.L.166.169; 1.L.166.172; 1.L.166.175; 1.L.166.240; 1.L.166.244; 1.L.169.228; 1.L.169.229; 1.L.169.230; 1.L.169.231; 1.L.169.236; 1.L.169.237; 1.L.169.238; 1.L.169.239; 1.L.169.154; 1.L.169.157; 1.L.169.166; 1.L.169.169; 1.L.169.172; 1.L.169.175; 1.L.169.240; 1.L.169.244; 1.L.172.228; 1.L.172.229; 1.L.172.230; 1.L.172.231; 1.L.172.236; 1.L.172.237; 1.L.172.238; 1.L.172.239; 1.L.172.154; 1.L.172.157; 1.L.172.166; 1.L.172.169; 1.L.172.172; 1.L.172.175; 1.L.172.240; 1.L.172.244; 1.L.175.228; 1.L.175.229; 1.L.175.230; 1.L.175.231; 1.L.175.236; 1.L.175.237; 1.L.175.238; 1.L.175.239; 1.L.175.154; 1.L.175.157; 1.L.175.166; 1.L.175.169; 1.L.175.172; 1.L.175.175; 1.L.175.240; 1.L.175.244; 1.L.240.228; 1.L.240.229; 1.L.240.230; 1.L.240.231; 1.L.240.236; 1.L.240.237; 1.L.240.238; 1.L.240.239; 1.L.240.154; 1.L.240.157; 1.L.240.166; 1.L.240.169; 1.L.240.172; 1.L.240.175; 1.L.240.240; 1.L.240.244; 1.L.244.228; 1.L.244.229; 1.L.244.230; 1.L.244.231; 1.L.244.236; 1.L.244.237; 1.L.244.238; 1.L.244.239; 1.L.244.154; 1.L.244.157; 1.L.244.166; 1.L.244.169; 1.L.244.172; 1.L.244.175; 1.L.244.240; 1.L.244.244;

TABLE 7-continued

Prodrugs of 1.O

1.O.228.228; 1.O.228.229; 1.O.228.230; 1.O.228.231; 1.O.228.236; 1.O.228.237; 1.O.228.238; 1.O.228.239; 1.O.228.154; 1.O.228.157; 1.O.228.166; 1.O.228.169; 1.O.228.172; 1.O.228.175; 1.O.228.240; 1.O.228.244; 1.O.229.228; 1.O.229.229; 1.O.229.230; 1.O.229.231; 1.O.229.236; 1.O.229.237; 1.O.229.238; 1.O.229.239; 1.O.229.154; 1.O.229.157; 1.O.229.166; 1.O.229.169; 1.O.229.172; 1.O.229.175; 1.O.229.240; 1.O.229.244; 1.O.230.228; 1.O.230.229; 1.O.230.230; 1.O.230.231; 1.O.230.236; 1.O.230.237; 1.O.230.238; 1.O.230.239; 1.O.230.154; 1.O.230.157; 1.O.230.166; 1.O.230.169; 1.O.230.172; 1.O.230.175; 1.O.230.240; 1.O.230.244; 1.O.231.228; 1.O.231.229; 1.O.231.230; 1.O.231.231; 1.O.231.236; 1.O.231.237; 1.O.231.238; 1.O.231.239; 1.O.231.154; 1.O.231.157; 1.O.231.166; 1.O.231.169; 1.O.231.172; 1.O.231.175; 1.O.231.240; 1.O.231.244; 1.O.236.228; 1.O.236.229; 1.O.236.230; 1.O.236.231; 1.O.236.236; 1.O.236.237; 1.O.236.238; 1.O.236.239; 1.O.236.154; 1.O.236.157; 1.O.236.166; 1.O.236.169; 1.O.236.172; 1.O.236.175; 1.O.236.240; 1.O.236.244; 1.O.237.228; 1.O.237.229; 1.O.237.230; 1.O.237.231; 1.O.237.236; 1.O.237.237; 1.O.237.238; 1.O.237.239; 1.O.237.154; 1.O.237.157; 1.O.237.166; 1.O.237.169; 1.O.237.172; 1.O.237.175; 1.O.237.240; 1.O.237.244; 1.O.238.228; 1.O.238.229; 1.O.238.230; 1.O.238.231; 1.O.238.236; 1.O.238.237; 1.O.238.238; 1.O.238.239; 1.O.238.154; 1.O.238.157; 1.O.238.166; 1.O.238.169; 1.O.238.172; 1.O.238.175; 1.O.238.240; 1.O.238.244; 1.O.239.228; 1.O.239.229; 1.O.239.230; 1.O.239.231; 1.O.239.236; 1.O.239.237; 1.O.239.238; 1.O.239.239; 1.O.239.154; 1.O.239.157; 1.O.239.166; 1.O.239.169; 1.O.239.172; 1.O.239.175; 1.O.239.240; 1.O.239.244; 1.O.154.228; 1.O.154.229; 1.O.154.230; 1.O.154.231; 1.O.154.236; 1.O.154.237; 1.O.154.238; 1.O.154.239; 1.O.154.154; 1.O.154.157; 1.O.154.166; 1.O.154.169; 1.O.154.172; 1.O.154.175; 1.O.154.240; 1.O.154.244; 1.O.157.228; 1.O.157.229; 1.O.157.230; 1.O.157.231; 1.O.157.236; 1.O.157.237; 1.O.157.238; 1.O.157.239; 1.O.157.154; 1.O.157.157; 1.O.157.166; 1.O.157.169; 1.O.157.172; 1.O.157.175; 1.O.157.240; 1.O.157.244; 1.O.166.228; 1.O.166.229; 1.O.166.230; 1.O.166.231; 1.O.166.236; 1.O.166.237; 1.O.166.238; 1.O.166.239; 1.O.166.154; 1.O.166.157; 1.O.166.166; 1.O.166.169; 1.O.166.172; 1.O.166.175; 1.O.166.240; 1.O.166.244; 1.O.169.228; 1.O.169.229; 1.O.169.230; 1.O.169.231; 1.O.169.236; 1.O.169.237; 1.O.169.238; 1.O.169.239; 1.O.169.154; 1.O.169.157; 1.O.169.166; 1.O.169.169; 1.O.169.172; 1.O.169.175; 1.O.169.240; 1.O.169.244; 1.O.172.228; 1.O.172.229; 1.O.172.230; 1.O.172.231; 1.O.172.236; 1.O.172.237; 1.O.172.238; 1.O.172.239; 1.O.172.154; 1.O.172.157; 1.O.172.166; 1.O.172.169; 1.O.172.172; 1.O.172.175; 1.O.172.240; 1.O.172.244; 1.O.175.228; 1.O.175.229; 1.O.175.230; 1.O.175.231; 1.O.175.236; 1.O.175.237; 1.O.175.238; 1.O.175.239; 1.O.175.154; 1.O.175.157; 1.O.175.166; 1.O.175.169; 1.O.175.172; 1.O.175.175; 1.O.175.240; 1.O.175.244; 1.O.240.228; 1.O.240.229; 1.O.240.230; 1.O.240.231; 1.O.240.236; 1.O.240.237; 1.O.240.238; 1.O.240.239; 1.O.240.154; 1.O.240.157; 1.O.240.166; 1.O.240.169; 1.O.240.172; 1.O.240.175; 1.O.240.240; 1.O.240.244; 1.O.244.228; 1.O.244.229; 1.O.244.230; 1.O.244.231; 1.O.244.236; 1.O.244.237; 1.O.244.238; 1.O.244.239; 1.O.244.154; 1.O.244.157; 1.O.244.166; 1.O.244.169; 1.O.244.172; 1.O.244.175; 1.O.244.240; 1.O.244.244;

Prodrugs of 1.P

1.P.228.228; 1.P.228.229; 1.P.228.230; 1.P.228.231; 1.P.228.236; 1.P.228.237; 1.P.228.238; 1.P.228.239; 1.P.228.154; 1.P.228.157; 1.P.228.166; 1.P.228.169; 1.P.228.172; 1.P.228.175; 1.P.228.240; 1.P.228.244; 1.P.229.228; 1.P.229.229; 1.P.229.230; 1.P.229.231; 1.P.229.236; 1.P.229.237; 1.P.229.238; 1.P.229.239; 1.P.229.154; 1.P.229.157; 1.P.229.166; 1.P.229.169; 1.P.229.172; 1.P.229.175; 1.P.229.240; 1.P.229.244; 1.P.230.228; 1.P.230.229; 1.P.230.230; 1.P.230.231; 1.P.230.236; 1.P.230.237; 1.P.230.238; 1.P.230.239; 1.P.230.154; 1.P.230.157; 1.P.230.166; 1.P.230.169; 1.P.230.172; 1.P.230.175; 1.P.230.240; 1.P.230.244; 1.P.231.228; 1.P.231.229; 1.P.231.230; 1.P.231.231; 1.P.231.236; 1.P.231.237; 1.P.231.238; 1.P.231.239; 1.P.231.154; 1.P.231.157; 1.P.231.166; 1.P.231.169; 1.P.231.172; 1.P.231.175; 1.P.231.240; 1.P.231.244; 1.P.236.228; 1.P.236.229; 1.P.236.230; 1.P.236.231; 1.P.236.236; 1.P.236.237; 1.P.236.238; 1.P.236.239; 1.P.236.154; 1.P.236.157; 1.P.236.166; 1.P.236.169; 1.P.236.172; 1.P.236.175; 1.P.236.240; 1.P.236.244; 1.P.237.228; 1.P.237.229; 1.P.237.230; 1.P.237.231; 1.P.237.236; 1.P.237.237; 1.P.237.238; 1.P.237.239; 1.P.237.154; 1.P.237.157; 1.P.237.166; 1.P.237.169; 1.P.237.172; 1.P.237.175; 1.P.237.240; 1.P.237.244; 1.P.238.228; 1.P.238.229; 1.P.238.230; 1.P.238.231; 1.P.238.236; 1.P.238.237; 1.P.238.238; 1.P.238.239; 1.P.238.154; 1.P.238.157; 1.P.238.166; 1.P.238.169; 1.P.238.172; 1.P.238.175; 1.P.238.240; 1.P.238.244; 1.P.239.228; 1.P.239.229; 1.P.239.230; 1.P.239.231; 1.P.239.236; 1.P.239.237; 1.P.239.238; 1.P.239.239; 1.P.239.154; 1.P.239.157; 1.P.239.166; 1.P.239.169; 1.P.239.172; 1.P.239.175; 1.P.239.240; 1.P.239.244; 1.P.154.228; 1.P.154.229; 1.P.154.230; 1.P.154.231; 1.P.154.236; 1.P.154.237; 1.P.154.238; 1.P.154.239; 1.P.154.154; 1.P.154.157; 1.P.154.166; 1.P.154.169; 1.P.154.172; 1.P.154.175; 1.P.154.240; 1.P.154.244; 1.P.157.228; 1.P.157.229; 1.P.157.230; 1.P.157.231; 1.P.157.236; 1.P.157.237; 1.P.157.238; 1.P.157.239; 1.P.157.154; 1.P.157.157; 1.P.157.166; 1.P.157.169; 1.P.157.172; 1.P.157.175; 1.P.157.240; 1.P.157.244; 1.P.166.228; 1.P.166.229; 1.P.166.230; 1.P.166.231; 1.P.166.236; 1.P.166.237; 1.P.166.238; 1.P.166.239; 1.P.166.154; 1.P.166.157; 1.P.166.166; 1.P.166.169; 1.P.166.172; 1.P.166.175; 1.P.166.240; 1.P.166.244; 1.P.169.228; 1.P.169.229; 1.P.169.230; 1.P.169.231; 1.P.169.236; 1.P.169.237; 1.P.169.238; 1.P.169.239; 1.P.169.154; 1.P.169.157; 1.P.169.166; 1.P.169.169; 1.P.169.172; 1.P.169.175; 1.P.169.240; 1.P.169.244; 1.P.172.228; 1.P.172.229; 1.P.172.230; 1.P.172.231; 1.P.172.236; 1.P.172.237; 1.P.172.238; 1.P.172.239; 1.P.172.154; 1.P.172.157; 1.P.172.166; 1.P.172.169; 1.P.172.172; 1.P.172.175; 1.P.172.240; 1.P.172.244; 1.P.175.228; 1.P.175.229; 1.P.175.230; 1.P.175.231; 1.P.175.236; 1.P.175.237; 1.P.175.238; 1.P.175.239; 1.P.175.154; 1.P.175.157; 1.P.175.166; 1.P.175.169; 1.P.175.172; 1.P.175.175; 1.P.175.240; 1.P.175.244; 1.P.240.228; 1.P.240.229; 1.P.240.230; 1.P.240.231; 1.P.240.236; 1.P.240.237; 1.P.240.238; 1.P.240.239; 1.P.240.154; 1.P.240.157; 1.P.240.166; 1.P.240.169; 1.P.240.172; 1.P.240.175; 1.P.240.240; 1.P.240.244; 1.P.244.228; 1.P.244.229; 1.P.244.230; 1.P.244.231; 1.P.244.236; 1.P.244.237; 1.P.244.238; 1.P.244.239; 1.P.244.154; 1.P.244.157; 1.P.244.166; 1.P.244.169; 1.P.244.172; 1.P.244.175; 1.P.244.240; 1.P.244.244;

Prodrugs of 1.U

1.U.228.228; 1.U.228.229; 1.U.228.230; 1.U.228.231; 1.U.228.236; 1.U.228.237; 1.U.228.238; 1.U.228.239; 1.U.228.154; 1.U.228.157; 1.U.228.166; 1.U.228.169; 1.U.228.172; 1.U.228.175; 1.U.228.240; 1.U.228.244; 1.U.229.228; 1.U.229.229; 1.U.229.230; 1.U.229.231; 1.U.229.236; 1.U.229.237; 1.U.229.238; 1.U.229.239; 1.U.229.154; 1.U.229.157; 1.U.229.166; 1.U.229.169; 1.U.229.172; 1.U.229.175; 1.U.229.240; 1.U.229.244; 1.U.230.228; 1.U.230.229; 1.U.230.230; 1.U.230.231; 1.U.230.236; 1.U.230.237; 1.U.230.238; 1.U.230.239; 1.U.230.154; 1.U.230.157; 1.U.230.166; 1.U.230.169; 1.U.230.172; 1.U.230.175; 1.U.230.240; 1.U.230.244; 1.U.231.228; 1.U.231.229; 1.U.231.230; 1.U.231.231; 1.U.231.236; 1.U.231.237; 1.U.231.238; 1.U.231.239; 1.U.231.154; 1.U.231.157; 1.U.231.166; 1.U.231.169; 1.U.231.172; 1.U.231.175; 1.U.231.240; 1.U.231.244; 1.U.236.228; 1.U.236.229; 1.U.236.230; 1.U.236.231; 1.U.236.236; 1.U.236.237; 1.U.236.238; 1.U.236.239; 1.U.236.154; 1.U.236.157; 1.U.236.166; 1.U.236.169; 1.U.236.172; 1.U.236.175; 1.U.236.240; 1.U.236.244; 1.U.237.228; 1.U.237.229; 1.U.237.230; 1.U.237.231; 1.U.237.236; 1.U.237.237; 1.U.237.238; 1.U.237.239; 1.U.237.154; 1.U.237.157; 1.U.237.166; 1.U.237.169; 1.U.237.172; 1.U.237.175; 1.U.237.240; 1.U.237.244; 1.U.238.228; 1.U.238.229; 1.U.238.230; 1.U.238.231; 1.U.238.236; 1.U.238.237; 1.U.238.238; 1.U.238.239; 1.U.238.154; 1.U.238.157; 1.U.238.166; 1.U.238.169; 1.U.238.172; 1.U.238.175; 1.U.238.240; 1.U.238.244; 1.U.239.228; 1.U.239.229; 1.U.239.230; 1.U.239.231; 1.U.239.236; 1.U.239.237; 1.U.239.238; 1.U.239.239; 1.U.239.154; 1.U.239.157; 1.U.239.166; 1.U.239.169; 1.U.239.172; 1.U.239.175; 1.U.239.240; 1.U.239.244; 1.U.154.228; 1.U.154.229; 1.U.154.230; 1.U.154.231; 1.U.154.236; 1.U.154.237; 1.U.154.238; 1.U.154.239; 1.U.154.154; 1.U.154.157; 1.U.154.166; 1.U.154.169; 1.U.154.172; 1.U.154.175; 1.U.154.240; 1.U.154.244; 1.U.157.228; 1.U.157.229; 1.U.157.230; 1.U.157.231; 1.U.157.236; 1.U.157.237; 1.U.157.238; 1.U.157.239; 1.U.157.154; 1.U.157.157; 1.U.157.166; 1.U.157.169; 1.U.157.172; 1.U.157.175; 1.U.157.240; 1.U.157.244; 1.U.166.228; 1.U.166.229; 1.U.166.230; 1.U.166.231; 1.U.166.236; 1.U.166.237; 1.U.166.238; 1.U.166.239; 1.U.166.154; 1.U.166.157; 1.U.166.166; 1.U.166.169; 1.U.166.172; 1.U.166.175; 1.U.166.240; 1.U.166.244; 1.U.169.228; 1.U.169.229; 1.U.169.230; 1.U.169.231; 1.U.169.236; 1.U.169.237; 1.U.169.238; 1.U.169.239; 1.U.169.154; 1.U.169.157; 1.U.169.166; 1.U.169.169; 1.U.169.172; 1.U.169.175; 1.U.169.240; 1.U.169.244; 1.U.172.228; 1.U.172.229; 1.U.172.230; 1.U.172.231; 1.U.172.236; 1.U.172.237; 1.U.172.238; 1.U.172.239; 1.U.172.154; 1.U.172.157; 1.U.172.166; 1.U.172.169; 1.U.172.172; 1.U.172.175; 1.U.172.240; 1.U.172.244; 1.U.175.228; 1.U.175.229; 1.U.175.230; 1.U.175.231; 1.U.175.236; 1.U.175.237; 1.U.175.238; 1.U.175.239; 1.U.175.154; 1.U.175.157; 1.U.175.166; 1.U.175.169; 1.U.175.172; 1.U.175.175; 1.U.175.240; 1.U.175.244; 1.U.240.228; 1.U.240.229; 1.U.240.230; 1.U.240.231; 1.U.240.236; 1.U.240.237; 1.U.240.238; 1.U.240.239; 1.U.240.154; 1.U.240.157; 1.U.240.166; 1.U.240.169; 1.U.240.172; 1.U.240.175; 1.U.240.240; 1.U.240.244;

TABLE 7-continued

1.U.244.228; 1.U.244.229; 1.U.244.230; 1.U.244.231; 1.U.244.236;
1.U.244.237; 1.U.244.238; 1.U.244.239; 1.U.244.154; 1.U.244.157;
1.U.244.166; 1.U.244.169; 1.U.244.172; 1.U.244.175; 1.U.244.240;
1.U.244.244;
Prodrugs of 1.W 1.W.228.228; 1.W.228.229; 1.W.228.230; 1.W.228.231; 1.W.228.236;
1.W.228.237; 1.W.228.238; 1.W.228.239; 1.W.228.154; 1.W.228.157;
1.W.228.166; 1.W.228.169; 1.W.228.172; 1.W.228.175; 1.W.228.240;
1.W.228.244; 1.W.229.228; 1.W.229.229; 1.W.229.230; 1.W.229.231;
1.W.229.236; 1.W.229.237; 1.W.229.238; 1.W.229.239; 1.W.229.154;
1.W.229.157; 1.W.229.166; 1.W.229.169; 1.W.229.172; 1.W.229.175;
1.W.229.240; 1.W.229.244; 1.W.230.228; 1.W.230.229; 1.W.230.230;
1.W.230.231; 1.W.230.236; 1.W.230.237; 1.W.230.238; 1.W.230.239;
1.W.230.154; 1.W.230.157; 1.W.230.166; 1.W.230.169; 1.W.230.172;
1.W.230.175; 1.W.230.240; 1.W.230.244; 1.W.231.228; 1.W.231.229;
1.W.231.230; 1.W.231.231; 1.W.231.236; 1.W.231.237; 1.W.231.238;
1.W.231.239; 1.W.231.154; 1.W.231.157; 1.W.231.166; 1.W.231.169;
1.W.231.172; 1.W.231.175; 1.W.231.240; 1.W.231.244; 1.W.236.228;
1.W.236.229; 1.W.236.230; 1.W.236.231; 1.W.236.236; 1.W.236.237;
1.W.236.238; 1.W.236.239; 1.W.236.154; 1.W.236.157; 1.W.236.166;
1.W.236.169; 1.W.236.172; 1.W.236.175; 1.W.236.240; 1.W.236.244;
1.W.237.228; 1.W.237.229; 1.W.237.230; 1.W.237.231; 1.W.237.236;
1.W.237.237; 1.W.237.238; 1.W.237.239; 1.W.237.154; 1.W.237.157;
1.W.237.166; 1.W.237.169; 1.W.237.172; 1.W.237.175; 1.W.237.240;
1.W.237.244; 1.W.238.228; 1.W.238.229; 1.W.238.230; 1.W.238.231;
1.W.238.236; 1.W.238.237; 1.W.238.238; 1.W.238.239; 1.W.238.154;
1.W.238.157; 1.W.238.166; 1.W.238.169; 1.W.238.172; 1.W.238.175;
1.W.238.240; 1.W.238.244; 1.W.239.228; 1.W.239.229; 1.W.239.230;
1.W.239.231; 1.W.239.236; 1.W.239.237; 1.W.239.238; 1.W.239.239;
1.W.239.154; 1.W.239.157; 1.W.239.166; 1.W.239.169; 1.W.239.172;
1.W.239.175; 1.W.239.240; 1.W.239.244; 1.W.154.228; 1.W.154.229;
1.W.154.230; 1.W.154.231; 1.W.154.236; 1.W.154.237; 1.W.154.238;
1.W.154.239; 1.W.154.154; 1.W.154.157; 1.W.154.166; 1.W.154.169;
1.W.154.172; 1.W.154.175; 1.W.154.240; 1.W.154.244; 1.W.157.228;
1.W.157.229; 1.W.157.230; 1.W.157.231; 1.W.157.236; 1.W.157.237;
1.W.157.238; 1.W.157.239; 1.W.157.154; 1.W.157.157; 1.W.157.166;
1.W.157.169; 1.W.157.172; 1.W.157.175; 1.W.157.240; 1.W.157.244;
1.W.166.228; 1.W.166.229; 1.W.166.230; 1.W.166.231; 1.W.166.236;
1.W.166.237; 1.W.166.238; 1.W.166.239; 1.W.166.154; 1.W.166.157;
1.W.166.166; 1.W.166.169; 1.W.166.172; 1.W.166.175; 1.W.166.240;
1.W.166.244; 1.W.169.228; 1.W.169.229; 1.W.169.230; 1.W.169.231;
1.W.169.236; 1.W.169.237; 1.W.169.238; 1.W.169.239; 1.W.169.154;
1.W.169.157; 1.W.169.166; 1.W.169.169; 1.W.169.172; 1.W.169.175;
1.W.169.240; 1.W.169.244; 1.W.172.228; 1.W.172.229; 1.W.172.230;
1.W.172.231; 1.W.172.236; 1.W.172.237; 1.W.172.238; 1.W.172.239;
1.W.172.154; 1.W.172.157; 1.W.172.166; 1.W.172.169; 1.W.172.172;
1.W.172.175; 1.W.172.240; 1.W.172.244; 1.W.175.228; 1.W.175.229;
1.W.175.230; 1.W.175.231; 1.W.175.236; 1.W.175.237; 1.W.175.238;
1.W.175.239; 1.W.175.154; 1.W.175.157; 1.W.175.166; 1.W.175.169;
1.W.175.172; 1.W.175.175; 1.W.175.240; 1.W.175.244; 1.W.240.228;
1.W.240.229; 1.W.240.230; 1.W.240.231; 1.W.240.236; 1.W.240.237;
1.W.240.238; 1.W.240.239; 1.W.240.154; 1.W.240.157; 1.W.240.166;
1.W.240.169; 1.W.240.172; 1.W.240.175; 1.W.240.240; 1.W.240.244;
1.W.244.228; 1.W.244.229; 1.W.244.230; 1.W.244.231; 1.W.244.236;
1.W.244.237; 1.W.244.238; 1.W.244.239; 1.W.244.154; 1.W.244.157;
1.W.244.166; 1.W.244.169; 1.W.244.172; 1.W.244.175; 1.W.244.240;
1.W.244.244;
Prodrugs of 1.Y 1.Y.228.228; 1.Y.228.229; 1.Y.228.230; 1.Y.228.231; 1.Y.228.236;
1.Y.228.237; 1.Y.228.238; 1.Y.228.239; 1.Y.228.154; 1.Y.228.157;
1.Y.228.166; 1.Y.228.169; 1.Y.228.172; 1.Y.228.175; 1.Y.228.240;
1.Y.228.244; 1.Y.229.228; 1.Y.229.229; 1.Y.229.230; 1.Y.229.231;
1.Y.229.236; 1.Y.229.237; 1.Y.229.238; 1.Y.229.239; 1.Y.229.154;
1.Y.229.157; 1.Y.229.166; 1.Y.229.169; 1.Y.229.172; 1.Y.229.175;
1.Y.229.240; 1.Y.229.244; 1.Y.230.228; 1.Y.230.229; 1.Y.230.230;
1.Y.230.231; 1.Y.230.236; 1.Y.230.237; 1.Y.230.238; 1.Y.230.239;
1.Y.230.154; 1.Y.230.157; 1.Y.230.166; 1.Y.230.169; 1.Y.230.172;
1.Y.230.175; 1.Y.230.240; 1.Y.230.244; 1.Y.231.228; 1.Y.231.229;
1.Y.231.230; 1.Y.231.231; 1.Y.231.236; 1.Y.231.237; 1.Y.231.238;
1.Y.231.239; 1.Y.231.154; 1.Y.231.157; 1.Y.231.166; 1.Y.231.169;
1.Y.231.172; 1.Y.231.175; 1.Y.231.240; 1.Y.231.244; 1.Y.236.228;
1.Y.236.229; 1.Y.236.230; 1.Y.236.231; 1.Y.236.236; 1.Y.236.237;
1.Y.236.238; 1.Y.236.239; 1.Y.236.154; 1.Y.236.157; 1.Y.236.166;
1.Y.236.169; 1.Y.236.172; 1.Y.236.175; 1.Y.236.240; 1.Y.236.244;
1.Y.237.228; 1.Y.237.229; 1.Y.237.230; 1.Y.237.231; 1.Y.237.236;
1.Y.237.237; 1.Y.237.238; 1.Y.237.239; 1.Y.237.154; 1.Y.237.157;
1.Y.237.166; 1.Y.237.169; 1.Y.237.172; 1.Y.237.175; 1.Y.237.240;
1.Y.237.244; 1.Y.238.228; 1.Y.238.229; 1.Y.238.230; 1.Y.238.231;
1.Y.238.236; 1.Y.238.237; 1.Y.238.238; 1.Y.238.239; 1.Y.238.154;
1.Y.238.157; 1.Y.238.166; 1.Y.238.169; 1.Y.238.172; 1.Y.238.175;
1.Y.238.240; 1.Y.238.244; 1.Y.239.228; 1.Y.239.229; 1.Y.239.230;
1.Y.239.231; 1.Y.239.236; 1.Y.239.237; 1.Y.239.238; 1.Y.239.239;
1.Y.239.154; 1.Y.239.157; 1.Y.239.166; 1.Y.239.169; 1.Y.239.172;
1.Y.239.175; 1.Y.239.240; 1.Y.239.244; 1.Y.154.228; 1.Y.154.229;
1.Y.154.230; 1.Y.154.231; 1.Y.154.236; 1.Y.154.237; 1.Y.154.238;
1.Y.154.239; 1.Y.154.154; 1.Y.154.157; 1.Y.154.166; 1.Y.154.169;
1.Y.154.172; 1.Y.154.175; 1.Y.154.240; 1.Y.154.244; 1.Y.157.228;
1.Y.157.229; 1.Y.157.230; 1.Y.157.231; 1.Y.157.236; 1.Y.157.237;
1.Y.157.238; 1.Y.157.239; 1.Y.157.154; 1.Y.157.157; 1.Y.157.166;
1.Y.157.169; 1.Y.157.172; 1.Y.157.175; 1.Y.157.240; 1.Y.157.244;
1.Y.166.228; 1.Y.166.229; 1.Y.166.230; 1.Y.166.231; 1.Y.166.236;
1.Y.166.237; 1.Y.166.238; 1.Y.166.239; 1.Y.166.154; 1.Y.166.157;
1.Y.166.166; 1.Y.166.169; 1.Y.166.172; 1.Y.166.175; 1.Y.166.240;
1.Y.166.244; 1.Y.169.228; 1.Y.169.229; 1.Y.169.230; 1.Y.169.231;
1.Y.169.236; 1.Y.169.237; 1.Y.169.238; 1.Y.169.239; 1.Y.169.154;
1.Y.169.157; 1.Y.169.166; 1.Y.169.169; 1.Y.169.172; 1.Y.169.175;
1.Y.169.240; 1.Y.169.244; 1.Y.172.228; 1.Y.172.229; 1.Y.172.230;
1.Y.172.231; 1.Y.172.236; 1.Y.172.237; 1.Y.172.238; 1.Y.172.239;
1.Y.172.154; 1.Y.172.157; 1.Y.172.166; 1.Y.172.169; 1.Y.172.172;
1.Y.172.175; 1.Y.172.240; 1.Y.172.244; 1.Y.175.228; 1.Y.175.229;
1.Y.175.230; 1.Y.175.231; 1.Y.175.236; 1.Y.175.237; 1.Y.175.238;
1.Y.175.239; 1.Y.175.154; 1.Y.175.157; 1.Y.175.166; 1.Y.175.169;
1.Y.175.172; 1.Y.175.175; 1.Y.175.240; 1.Y.175.244; 1.Y.240.228;
1.Y.240.229; 1.Y.240.230; 1.Y.240.231; 1.Y.240.236; 1.Y.240.237;
1.Y.240.238; 1.Y.240.239; 1.Y.240.154; 1.Y.240.157; 1.Y.240.166;
1.Y.240.169; 1.Y.240.172; 1.Y.240.175; 1.Y.240.240; 1.Y.240.244;
1.Y.244.228; 1.Y.244.229; 1.Y.244.230; 1.Y.244.231; 1.Y.244.236;
1.Y.244.237; 1.Y.244.238; 1.Y.244.239; 1.Y.244.154; 1.Y.244.157;
1.Y.244.166; 1.Y.244.169; 1.Y.244.172; 1.Y.244.175; 1.Y.244.240;
1.Y.244.244;
Prodrugs of 2.B 2.B.228.228; 2.B.228.229; 2.B.228.230; 2.B.228.231; 2.B.228.236;
2.B.228.237; 2.B.228.238; 2.B.228.239; 2.B.228.154; 2.B.228.157;
2.B.228.166; 2.B.228.169; 2.B.228.172; 2.B.228.175; 2.B.228.240;
2.B.228.244; 2.B.229.228; 2.B.229.229; 2.B.229.230; 2.B.229.231;
2.B.229.236; 2.B.229.237; 2.B.229.238; 2.B.229.239; 2.B.229.154;
2.B.229.157; 2.B.229.166; 2.B.229.169; 2.B.229.172; 2.B.229.175;
2.B.229.240; 2.B.229.244; 2.B.230.228; 2.B.230.229; 2.B.230.230;
2.B.230.231; 2.B.230.236; 2.B.230.237; 2.B.230.238; 2.B.230.239;
2.B.230.154; 2.B.230.157; 2.B.230.166; 2.B.230.169; 2.B.230.172;
2.B.230.175; 2.B.230.240; 2.B.230.244; 2.B.231.228; 2.B.231.229;
2.B.231.230; 2.B.231.231; 2.B.231.236; 2.B.231.237; 2.B.231.238;
2.B.231.239; 2.B.231.154; 2.B.231.157; 2.B.231.166; 2.B.231.169;
2.B.231.172; 2.B.231.175; 2.B.231.240; 2.B.231.244; 2.B.236.228;
2.B.236.229; 2.B.236.230; 2.B.236.231; 2.B.236.236; 2.B.236.237;
2.B.236.238; 2.B.236.239; 2.B.236.154; 2.B.236.157; 2.B.236.166;
2.B.236.169; 2.B.236.172; 2.B.236.175; 2.B.236.240; 2.B.236.244;
2.B.237.228; 2.B.237.229; 2.B.237.230; 2.B.237.231; 2.B.237.236;
2.B.237.237; 2.B.237.238; 2.B.237.239; 2.B.237.154; 2.B.237.157;
2.B.237.166; 2.B.237.169; 2.B.237.172; 2.B.237.175; 2.B.237.240;
2.B.237.244; 2.B.238.228; 2.B.238.229; 2.B.238.230; 2.B.238.231;
2.B.238.236; 2.B.238.237; 2.B.238.238; 2.B.238.239; 2.B.238.154;
2.B.238.157; 2.B.238.166; 2.B.238.169; 2.B.238.172; 2.B.238.175;
2.B.238.240; 2.B.238.244; 2.B.239.228; 2.B.239.229; 2.B.239.230;
2.B.239.231; 2.B.239.236; 2.B.239.237; 2.B.239.238; 2.B.239.239;
2.B.239.154; 2.B.239.157; 2.B.239.166; 2.B.239.169; 2.B.239.172;
2.B.239.175; 2.B.239.240; 2.B.239.244; 2.B.154.228; 2.B.154.229;
2.B.154.230; 2.B.154.231; 2.B.154.236; 2.B.154.237; 2.B.154.238;
2.B.154.239; 2.B.154.154; 2.B.154.157; 2.B.154.166; 2.B.154.169;
2.B.154.172; 2.B.154.175; 2.B.154.240; 2.B.154.244; 2.B.157.228;
2.B.157.229; 2.B.157.230; 2.B.157.231; 2.B.157.236; 2.B.157.237;
2.B.157.238; 2.B.157.239; 2.B.157.154; 2.B.157.157; 2.B.157.166;
2.B.157.169; 2.B.157.172; 2.B.157.175; 2.B.157.240; 2.B.157.244;
2.B.166.228; 2.B.166.229; 2.B.166.230; 2.B.166.231; 2.B.166.236;
2.B.166.237; 2.B.166.238; 2.B.166.239; 2.B.166.154; 2.B.166.157;
2.B.166.166; 2.B.166.169; 2.B.166.172; 2.B.166.175; 2.B.166.240;
2.B.166.244; 2.B.169.228; 2.B.169.229; 2.B.169.230; 2.B.169.231;
2.B.169.236; 2.B.169.237; 2.B.169.238; 2.B.169.239; 2.B.169.154;
2.B.169.157; 2.B.169.166; 2.B.169.169; 2.B.169.172; 2.B.169.175;
2.B.169.240; 2.B.169.244; 2.B.172.228; 2.B.172.229; 2.B.172.230;
2.B.172.231; 2.B.172.236; 2.B.172.237; 2.B.172.238; 2.B.172.239;
2.B.172.154; 2.B.172.157; 2.B.172.166; 2.B.172.169; 2.B.172.172;
2.B.172.175; 2.B.172.240; 2.B.172.244; 2.B.175.228; 2.B.175.229;
2.B.175.230; 2.B.175.231; 2.B.175.236; 2.B.175.237; 2.B.175.238;
2.B.175.239; 2.B.175.154; 2.B.175.157; 2.B.175.166; 2.B.175.169;

TABLE 7-continued

2.B.175.172; 2.B.175.175; 2.B.175.240; 2.B.175.244; 2.B.240.228;
2.B.240.229; 2.B.240.230; 2.B.240.231; 2.B.240.236; 2.B.240.237;
2.B.240.238; 2.B.240.239; 2.B.240.154; 2.B.240.157; 2.B.240.166;
2.B.240.169; 2.B.240.172; 2.B.240.175; 2.B.240.240; 2.B.240.244;
2.B.244.228; 2.B.244.229; 2.B.244.230; 2.B.244.231; 2.B.244.236;
2.B.244.237; 2.B.244.238; 2.B.244.239; 2.B.244.154; 2.B.244.157;
2.B.244.166; 2.B.244.169; 2.B.244.172; 2.B.244.175; 2.B.244.240;
2.B.244.244;
Prodrugs of 2.D 2.D.228.228; 2.D.228.229; 2.D.228.230; 2.D.228.231; 2.D.228.236;
2.D.228.237; 2.D.228.238; 2.D.228.239; 2.D.228.154; 2.D.228.157;
2.D.228.166; 2.D.228.169; 2.D.228.172; 2.D.228.175; 2.D.228.240;
2.D.228.244; 2.D.229.228; 2.D.229.229; 2.D.229.230; 2.D.229.231;
2.D.229.236; 2.D.229.237; 2.D.229.238; 2.D.229.239; 2.D.229.154;
2.D.229.157; 2.D.229.166; 2.D.229.169; 2.D.229.172; 2.D.229.175;
2.D.229.240; 2.D.229.244; 2.D.230.228; 2.D.230.229; 2.D.230.230;
2.D.230.231; 2.D.230.236; 2.D.230.237; 2.D.230.238; 2.D.230.239;
2.D.230.154; 2.D.230.157; 2.D.230.166; 2.D.230.169; 2.D.230.172;
2.D.230.175; 2.D.230.240; 2.D.230.244; 2.D.231.228; 2.D.231.229;
2.D.231.230; 2.D.231.231; 2.D.231.236; 2.D.231.237; 2.D.231.238;
2.D.231.239; 2.D.231.154; 2.D.231.157; 2.D.231.166; 2.D.231.169;
2.D.231.172; 2.D.231.175; 2.D.231.240; 2.D.231.244; 2.D.236.228;
2.D.236.229; 2.D.236.230; 2.D.236.231; 2.D.236.236; 2.D.236.237;
2.D.236.238; 2.D.236.239; 2.D.236.154; 2.D.236.157; 2.D.236.166;
2.D.236.169; 2.D.236.172; 2.D.236.175; 2.D.236.240; 2.D.236.244;
2.D.237.228; 2.D.237.229; 2.D.237.230; 2.D.237.231; 2.D.237.236;
2.D.237.237; 2.D.237.238; 2.D.237.239; 2.D.237.154; 2.D.237.157;
2.D.237.166; 2.D.237.169; 2.D.237.172; 2.D.237.175; 2.D.237.240;
2.D.237.244; 2.D.238.228; 2.D.238.229; 2.D.238.230; 2.D.238.231;
2.D.238.236; 2.D.238.237; 2.D.238.238; 2.D.238.239; 2.D.238.154;
2.D.238.157; 2.D.238.166; 2.D.238.169; 2.D.238.172; 2.D.238.175;
2.D.238.240; 2.D.238.244; 2.D.239.228; 2.D.239.229; 2.D.239.230;
2.D.239.231; 2.D.239.236; 2.D.239.237; 2.D.239.238; 2.D.239.239;
2.D.239.154; 2.D.239.157; 2.D.239.166; 2.D.239.169; 2.D.239.172;
2.D.239.175; 2.D.239.240; 2.D.239.244; 2.D.154.228; 2.D.154.229;
2.D.154.230; 2.D.154.231; 2.D.154.236; 2.D.154.237; 2.D.154.238;
2.D.154.239; 2.D.154.154; 2.D.154.157; 2.D.154.166; 2.D.154.169;
2.D.154.172; 2.D.154.175; 2.D.154.240; 2.D.154.244; 2.D.157.228;
2.D.157.229; 2.D.157.230; 2.D.157.231; 2.D.157.236; 2.D.157.237;
2.D.157.238; 2.D.157.239; 2.D.157.154; 2.D.157.157; 2.D.157.166;
2.D.157.169; 2.D.157.172; 2.D.157.175; 2.D.157.240; 2.D.157.244;
2.D.166.228; 2.D.166.229; 2.D.166.230; 2.D.166.231; 2.D.166.236;
2.D.166.237; 2.D.166.238; 2.D.166.239; 2.D.166.154; 2.D.166.157;
2.D.166.166; 2.D.166.169; 2.D.166.172; 2.D.166.175; 2.D.166.240;
2.D.166.244; 2.D.169.228; 2.D.169.229; 2.D.169.230; 2.D.169.231;
2.D.169.236; 2.D.169.237; 2.D.169.238; 2.D.169.239; 2.D.169.154;
2.D.169.157; 2.D.169.166; 2.D.169.169; 2.D.169.172; 2.D.169.175;
2.D.169.240; 2.D.169.244; 2.D.172.228; 2.D.172.229; 2.D.172.230;
2.D.172.231; 2.D.172.236; 2.D.172.237; 2.D.172.238; 2.D.172.239;
2.D.172.154; 2.D.172.157; 2.D.172.166; 2.D.172.169; 2.D.172.172;
2.D.172.175; 2.D.172.240; 2.D.172.244; 2.D.175.228; 2.D.175.229;
2.D.175.230; 2.D.175.231; 2.D.175.236; 2.D.175.237; 2.D.175.238;
2.D.175.239; 2.D.175.154; 2.D.175.157; 2.D.175.166; 2.D.175.169;
2.D.175.172; 2.D.175.175; 2.D.175.240; 2.D.175.244; 2.D.240.228;
2.D.240.229; 2.D.240.230; 2.D.240.231; 2.D.240.236; 2.D.240.237;
2.D.240.238; 2.D.240.239; 2.D.240.154; 2.D.240.157; 2.D.240.166;
2.D.240.169; 2.D.240.172; 2.D.240.175; 2.D.240.240; 2.D.240.244;
2.D.244.228; 2.D.244.229; 2.D.244.230; 2.D.244.231; 2.D.244.236;
2.D.244.237; 2.D.244.238; 2.D.244.239; 2.D.244.154; 2.D.244.157;
2.D.244.166; 2.D.244.169; 2.D.244.172; 2.D.244.175; 2.D.244.240;
2.D.244.244;
Prodrugs of 2.F 2.E.228.228; 2.E.228.229; 2.E.228.230; 2.E.228.231; 2.E.228.236;
2.E.228.237; 2.E.228.238; 2.E.228.239; 2.E.228.154; 2.E.228.157;
2.E.228.166; 2.E.228.169; 2.E.228.172; 2.E.228.175; 2.E.228.240;
2.E.228.244; 2.E.229.228; 2.E.229.229; 2.E.229.230; 2.E.229.231;
2.E.229.236; 2.E.229.237; 2.E.229.238; 2.E.229.239; 2.E.229.154;
2.E.229.157; 2.E.229.166; 2.E.229.169; 2.E.229.172; 2.E.229.175;
2.E.229.240; 2.E.229.244; 2.E.230.228; 2.E.230.229; 2.E.230.230;
2.E.230.231; 2.E.230.236; 2.E.230.237; 2.E.230.238; 2.E.230.239;
2.E.230.154; 2.E.230.157; 2.E.230.166; 2.E.230.169; 2.E.230.172;
2.E.230.175; 2.E.230.240; 2.E.230.244; 2.E.231.228; 2.E.231.229;
2.E.231.230; 2.E.231.231; 2.E.231.236; 2.E.231.237; 2.E.231.238;
2.E.231.239; 2.E.231.154; 2.E.231.157; 2.E.231.166; 2.E.231.169;
2.E.231.172; 2.E.231.175; 2.E.231.240; 2.E.231.244; 2.E.236.228;
2.E.236.229; 2.E.236.230; 2.E.236.231; 2.E.236.236; 2.E.236.237;
2.E.236.238; 2.E.236.239; 2.E.236.154; 2.E.236.157; 2.E.236.166;

TABLE 7-continued

2.E.236.169; 2.E.236.172; 2.E.236.175; 2.E.236.240; 2.E.236.244;
2.E.237.228; 2.E.237.229; 2.E.237.230; 2.E.237.231; 2.E.237.236;
2.E.237.237; 2.E.237.238; 2.E.237.239; 2.E.237.154; 2.E.237.157;
2.E.237.166; 2.E.237.169; 2.E.237.172; 2.E.237.175; 2.E.237.240;
2.E.237.244; 2.E.238.228; 2.E.238.229; 2.E.238.230; 2.E.238.231;
2.E.238.236; 2.E.238.237; 2.E.238.238; 2.E.238.239; 2.E.238.154;
2.E.238.157; 2.E.238.166; 2.E.238.169; 2.E.238.172; 2.E.238.175;
2.E.238.240; 2.E.238.244; 2.E.239.228; 2.E.239.229; 2.E.239.230;
2.E.239.231; 2.E.239.236; 2.E.239.237; 2.E.239.238; 2.E.239.239;
2.E.239.154; 2.E.239.157; 2.E.239.166; 2.E.239.169; 2.E.239.172;
2.E.239.175; 2.E.239.240; 2.E.239.244; 2.E.154.228; 2.E.154.229;
2.E.154.230; 2.E.154.231; 2.E.154.236; 2.E.154.237; 2.E.154.238;
2.E.154.239; 2.E.154.154; 2.E.154.157; 2.E.154.166; 2.E.154.169;
2.E.154.172; 2.E.154.175; 2.E.154.240; 2.E.154.244; 2.E.157.228;
2.E.157.229; 2.E.157.230; 2.E.157.231; 2.E.157.236; 2.E.157.237;
2.E.157.238; 2.E.157.239; 2.E.157.154; 2.E.157.157; 2.E.157.166;
2.E.157.169; 2.E.157.172; 2.E.157.175; 2.E.157.240; 2.E.157.244;
2.E.166.228; 2.E.166.229; 2.E.166.230; 2.E.166.231; 2.E.166.236;
2.E.166.237; 2.E.166.238; 2.E.166.239; 2.E.166.154; 2.E.166.157;
2.E.166.166; 2.E.166.169; 2.E.166.172; 2.E.166.175; 2.E.166.240;
2.E.166.244; 2.E.169.228; 2.E.169.229; 2.E.169.230; 2.E.169.231;
2.E.169.236; 2.E.169.237; 2.E.169.238; 2.E.169.239; 2.E.169.154;
2.E.169.157; 2.E.169.166; 2.E.169.169; 2.E.169.172; 2.E.169.175;
2.E.169.240; 2.E.169.244; 2.E.172.228; 2.E.172.229; 2.E.172.230;
2.E.172.231; 2.E.172.236; 2.E.172.237; 2.E.172.238; 2.E.172.239;
2.E.172.154; 2.E.172.157; 2.E.172.166; 2.E.172.169; 2.E.172.172;
2.E.172.175; 2.E.172.240; 2.E.172.244; 2.E.175.228; 2.E.175.229;
2.E.175.230; 2.E.175.231; 2.E.175.236; 2.E.175.237; 2.E.175.238;
2.E.175.239; 2.E.175.154; 2.E.175.157; 2.E.175.166; 2.E.175.169;
2.E.175.172; 2.E.175.175; 2.E.175.240; 2.E.175.244; 2.E.240.228;
2.E.240.229; 2.E.240.230; 2.E.240.231; 2.E.240.236; 2.E.240.237;
2.E.240.238; 2.E.240.239; 2.E.240.154; 2.E.240.157; 2.E.240.166;
2.E.240.169; 2.E.240.172; 2.E.240.175; 2.E.240.240; 2.E.240.244;
2.E.244.228; 2.E.244.229; 2.E.244.230; 2.E.244.231; 2.E.244.236;
2.E.244.237; 2.E.244.238; 2.E.244.239; 2.E.244.154; 2.E.244.157;
2.E.244.166; 2.E.244.169; 2.E.244.172; 2.E.244.175; 2.E.244.240;
2.E.244.244;
Prodrugs of 2.G 2.G.228.228; 2.G.228.229; 2.G.228.230; 2.G.228.231; 2.G.228.236;
2.G.228.237; 2.G.228.238; 2.G.228.239; 2.G.228.154; 2.G.228.157;
2.G.228.166; 2.G.228.169; 2.G.228.172; 2.G.228.175; 2.G.228.240;
2.G.228.244; 2.G.229.228; 2.G.229.229; 2.G.229.230; 2.G.229.231;
2.G.229.236; 2.G.229.237; 2.G.229.238; 2.G.229.239; 2.G.229.154;
2.G.229.157; 2.G.229.166; 2.G.229.169; 2.G.229.172; 2.G.229.175;
2.G.229.240; 2.G.229.244; 2.G.230.228; 2.G.230.229; 2.G.230.230;
2.G.230.231; 2.G.230.236; 2.G.230.237; 2.G.230.238; 2.G.230.239;
2.G.230.154; 2.G.230.157; 2.G.230.166; 2.G.230.169; 2.G.230.172;
2.G.230.175; 2.G.230.240; 2.G.230.244; 2.G.231.228; 2.G.231.229;
2.G.231.230; 2.G.231.231; 2.G.231.236; 2.G.231.237; 2.G.231.238;
2.G.231.239; 2.G.231.154; 2.G.231.157; 2.G.231.166; 2.G.231.169;
2.G.231.172; 2.G.231.175; 2.G.231.240; 2.G.231.244; 2.G.236.228;
2.G.236.229; 2.G.236.230; 2.G.236.231; 2.G.236.236; 2.G.236.237;
2.G.236.238; 2.G.236.239; 2.G.236.154; 2.G.236.157; 2.G.236.166;
2.G.236.169; 2.G.236.172; 2.G.236.175; 2.G.236.240; 2.G.236.244;
2.G.237.228; 2.G.237.229; 2.G.237.230; 2.G.237.231; 2.G.237.236;
2.G.237.237; 2.G.237.238; 2.G.237.239; 2.G.237.154; 2.G.237.157;
2.G.237.166; 2.G.237.169; 2.G.237.172; 2.G.237.175; 2.G.237.240;
2.G.237.244; 2.G.238.228; 2.G.238.229; 2.G.238.230; 2.G.238.231;
2.G.238.236; 2.G.238.237; 2.G.238.238; 2.G.238.239; 2.G.238.154;
2.G.238.157; 2.G.238.166; 2.G.238.169; 2.G.238.172; 2.G.238.175;
2.G.238.240; 2.G.238.244; 2.G.239.228; 2.G.239.229; 2.G.239.230;
2.G.239.231; 2.G.239.236; 2.G.239.237; 2.G.239.238; 2.G.239.239;
2.G.239.154; 2.G.239.157; 2.G.239.166; 2.G.239.169; 2.G.239.172;
2.G.239.175; 2.G.239.240; 2.G.239.244; 2.G.154.228; 2.G.154.229;
2.G.154.230; 2.G.154.231; 2.G.154.236; 2.G.154.237; 2.G.154.238;
2.G.154.239; 2.G.154.154; 2.G.154.157; 2.G.154.166; 2.G.154.169;
2.G.154.172; 2.G.154.175; 2.G.154.240; 2.G.154.244; 2.G.157.228;
2.G.157.229; 2.G.157.230; 2.G.157.231; 2.G.157.236; 2.G.157.237;
2.G.157.238; 2.G.157.239; 2.G.157.154; 2.G.157.157; 2.G.157.166;
2.G.157.169; 2.G.157.172; 2.G.157.175; 2.G.157.240; 2.G.157.244;
2.G.166.228; 2.G.166.229; 2.G.166.230; 2.G.166.231; 2.G.166.236;
2.G.166.237; 2.G.166.238; 2.G.166.239; 2.G.166.154; 2.G.166.157;
2.G.166.166; 2.G.166.169; 2.G.166.172; 2.G.166.175; 2.G.166.240;
2.G.166.244; 2.G.169.228; 2.G.169.229; 2.G.169.230; 2.G.169.231;
2.G.169.236; 2.G.169.237; 2.G.169.238; 2.G.169.239; 2.G.169.154;
2.G.169.157; 2.G.169.166; 2.G.169.169; 2.G.169.172; 2.G.169.175;
2.G.169.240; 2.G.169.244; 2.G.172.228; 2.G.172.229; 2.G.172.230;
2.G.172.231; 2.G.172.236; 2.G.172.237; 2.G.172.238; 2.G.172.239;

TABLE 7-continued

2.G.172.154; 2.G.172.157; 2.G.172.166; 2.G.172.169; 2.G.172.172; 2.G.172.175; 2.G.172.240; 2.G.172.244; 2.G.175.228; 2.G.175.229; 2.G.175.230; 2.G.175.231; 2.G.175.236; 2.G.175.237; 2.G.175.238; 2.G.175.239; 2.G.175.154; 2.G.175.157; 2.G.175.166; 2.G.175.169; 2.G.175.172; 2.G.175.175; 2.G.175.240; 2.G.175.244; 2.G.240.228; 2.G.240.229; 2.G.240.230; 2.G.240.231; 2.G.240.236; 2.G.240.237; 2.G.240238; 2.G.240.239; 2.G.240.154; 2.G.240.157; 2.G.240.166; 2.G.240.169; 2.G.240.172; 2.G.240.240; 2.G.240.244; 2.G.244.228; 2.G.244.229; 2.G.244.230; 2.G.244.231; 2.G.244.236; 2.G.244.237; 2.G.244.238; 2.G.244.239; 2.G.244.154; 2.G.244.157; 2.G.244.166; 2.G.244.169; 2.G.244.172; 2.G.244.175; 2.G.244.240; 2.G.244.244;

Prodrugs of 2.I

2.I.228.228; 2.I.228.229; 2.I.228.230; 2.I.228.231; 2.I.228.236; 2.I.228.237; 2.I.228.238; 2.I.228.239; 2.I.228.154; 2.I.228.157; 2.I.228.166; 2.I.228.169; 2.I.228.172; 2.I.228.175; 2.I.228.240; 2.I.228.244; 2.I.229.228; 2.I.229.229; 2.I.229.230; 2.I.229.231; 2.I.229.236; 2.I.229.237; 2.I.229.238; 2.I.229.239; 2.I.229.154; 2.I.229.157; 2.I.229.166; 2.I.229.169; 2.I.229.172; 2.I.229.175; 2.I.229.240; 2.I.229.244; 2.I.230.228; 2.I.230.229; 2.I.230.230; 2.I.230.231; 2.I.230.236; 2.I.230.237; 2.I.230.238; 2.I.230.239; 2.I.230.154; 2.I.230.157; 2.I.230.166; 2.I.230.169; 2.I.230.172; 2.I.230.175; 2.I.230.240; 2.I.230.244; 2.I.231.228; 2.I.231.229; 2.I.231.230; 2.I.231.231; 2.I.231.236; 2.I.231.237; 2.I.231.238; 2.I.231.239; 2.I.231.154; 2.I.231.157; 2.I.231.166; 2.I.231.169; 2.I.231.172; 2.I.231.175; 2.I.231.240; 2.I.231.244; 2.I.236.228; 2.I.236.229; 2.I.236.230; 2.I.236.231; 2.I.236.236; 2.I.236.237; 2.I.236.238; 2.I.236.239; 2.I.236.154; 2.I.236.157; 2.I.236.166; 2.I.236.169; 2.I.236.172; 2.I.236.175; 2.I.236.240; 2.I.236.244; 2.I.237.228; 2.I.237.229; 2.I.237.230; 2.I.237.231; 2.I.237.236; 2.I.237.237; 2.I.237.238; 2.I.237.239; 2.I.237.154; 2.I.237.157; 2.I.237.166; 2.I.237.169; 2.I.237.172; 2.I.237.175; 2.I.237.240; 2.I.237.244; 2.I.238.228; 2.I.238.229; 2.I.238.230; 2.I.238.231; 2.I.238.236; 2.I.238.237; 2.I.238.238; 2.I.238.239; 2.I.238.154; 2.I.238.157; 2.I.238.166; 2.I.238.169; 2.I.238.172; 2.I.238.175; 2.I.238.240; 2.I.238.244; 2.I.239.228; 2.I.239.229; 2.I.239.230; 2.I.239.231; 2.I.239.236; 2.I.239.237; 2.I.239.238; 2.I.239.239; 2.I.239.154; 2.I.239.157; 2.I.239.166; 2.I.239.169; 2.I.239.172; 2.I.239.175; 2.I.239.240; 2.I.239.244; 2.I.154.228; 2.I.154.229; 2.I.154.230; 2.I.154.231; 2.I.154.236; 2.I.154.237; 2.I.154.238; 2.I.154.239; 2.I.154.154; 2.I.154.157; 2.I.154.166; 2.I.154.169; 2.I.154.172; 2.I.154.175; 2.I.154.240; 2.I.154.244; 2.I.157.228; 2.I.157.229; 2.I.157.230; 2.I.157.231; 2.I.157.236; 2.I.157.237; 2.I.157.238; 2.I.157.239; 2.I.157.154; 2.I.157.157; 2.I.157.166; 2.I.157.169; 2.I.157.172; 2.I.157.175; 2.I.157.240; 2.I.157.244; 2.I.166.228; 2.I.166.229; 2.I.166.230; 2.I.166.231; 2.I.166.236; 2.I.166.237; 2.I.166.238; 2.I.166.239; 2.I.166.154; 2.I.166.157; 2.I.166.166; 2.I.166.169; 2.I.166.172; 2.I.166.175; 2.I.166.240; 2.I.166.244; 2.I.169.228; 2.I.169.229; 2.I.169.230; 2.I.169.231; 2.I.169.236; 2.I.169.237; 2.I.169.238; 2.I.169.239; 2.I.169.154; 2.I.169.157; 2.I.169.166; 2.I.169.169; 2.I.169.172; 2.I.169.175; 2.I.169.240; 2.I.169.244; 2.I.172.228; 2.I.172.229; 2.I.172.230; 2.I.172.231; 2.I.172.236; 2.I.172.237; 2.I.172.238; 2.I.172.239; 2.I.172.154; 2.I.172.157; 2.I.172.166; 2.I.172.169; 2.I.172.172; 2.I.172.175; 2.I.172.240; 2.I.172.244; 2.I.175.228; 2.I.175.229; 2.I.175.230; 2.I.175.231; 2.I.175.236; 2.I.175.237; 2.I.175.238; 2.I.175.239; 2.I.175.154; 2.I.175.157; 2.I.175.166; 2.I.175.169; 2.I.175.172; 2.I.175.175; 2.I.175.240; 2.I.175.244; 2.I.240.228; 2.I.240.229; 2.I.240.230; 2.I.240.231; 2.I.240.236; 2.I.240.237; 2.I.240.238; 2.I.240.239; 2.I.240.154; 2.I.240.157; 2.I.240.166; 2.I.240.169; 2.I.240.172; 2.I.240.175; 2.I.240.240; 2.I.240.244; 2.I.244.228; 2.I.244.229; 2.I.244.230; 2.I.244.231; 2.I.244.236; 2.I.244.237; 2.I.244.238; 2.I.244.239; 2.I.244.154; 2.I.244.157; 2.I.244.166; 2.I.244.169; 2.I.244.172; 2.I.244.175; 2.I.244.240; 2.I.244.244;

Prodrugs of 2.J

2.J.228.228; 2.J.228.229; 2.J.228.230; 2.J.228.231; 2.J.228.236; 2.J.228.237; 2.J.228.238; 2.J.228.239; 2.J.228.154; 2.J.228.157; 2.J.228.166; 2.J.228.169; 2.J.228.172; 2.J.228.175; 2.J.228.240; 2.J.228.244; 2.J.229.228; 2.J.229.229; 2.J.229.230; 2.J.229.231; 2.J.229.236; 2.J.229.237; 2.J.229.238; 2.J.229.239; 2.J.229.154; 2.J.229.157; 2.J.229.166; 2.J.229.169; 2.J.229.172; 2.J.229.175; 2.J.229.240; 2.J.229.244; 2.J.230.228; 2.J.230.229; 2.J.230.230; 2.J.230.231; 2.J.230.236; 2.J.230.237; 2.J.230.238; 2.J.230.239; 2.J.230.154; 2.J.230.157; 2.J.230.166; 2.J.230.169; 2.J.230.172; 2.J.230.175; 2.J.230.240; 2.J.230.244; 2.J.231.228; 2.J.231.229; 2.J.231.230; 2.J.231.231; 2.J.231.236; 2.J.231.237; 2.J.231.238; 2.J.231.239; 2.J.231.154; 2.J.231.157; 2.J.231.166; 2.J.231.169; 2.J.231.172; 2.J.231.175; 2.J.231.240; 2.J.231.244; 2.J.236.228; 2.J.236.229; 2.J.236.230; 2.J.236.231; 2.J.236.236; 2.J.236.237; 2.J.236.238; 2.J.236.239; 2.J.236.154; 2.J.236.157; 2.J.236.166; 2.J.236.169; 2.J.236.172; 2.J.236.175; 2.J.236.240; 2.J.236.244; 2.J.237.228; 2.J.237.229; 2.J.237.230; 2.J.237.231; 2.J.237.236; 2.J.237.237; 2.J.237.238; 2.J.237.239; 2.J.237.154; 2.J.237.157; 2.J.237.166; 2.J.237.169; 2.J.237.172; 2.J.237.175; 2.J.237.240; 2.J.237.244; 2.J.238.228; 2.J.238.229; 2.J.238.230; 2.J.238.231; 2.J.238.236; 2.J.238.237; 2.J.238.238; 2.J.238.239; 2.J.238.154; 2.J.238.157; 2.J.238.166; 2.J.238.169; 2.J.238.172; 2.J.238.175; 2.J.238.240; 2.J.238.244; 2.J.239.228; 2.J.239.229; 2.J.239.230; 2.J.239.231; 2.J.239.236; 2.J.239.237; 2.J.239.238; 2.J.239.239; 2.J.239.154; 2.J.239.157; 2.J.239.166; 2.J.239.169; 2.J.239.172; 2.J.239.175; 2.J.239.240; 2.J.239.244; 2.J.154.228; 2.J.154.229; 2.J.154.230; 2.J.154.231; 2.J.154.236; 2.J.154.237; 2.J.154.238; 2.J.154.239; 2.J.154.154; 2.J.154.157; 2.J.154.166; 2.J.154.169; 2.J.154.172; 2.J.154.175; 2.J.154.240; 2.J.154.244; 2.J.157.228; 2.J.157.229; 2.J.157.230; 2.J.157.231; 2.J.157.236; 2.J.157.237; 2.J.157.238; 2.J.157.239; 2.J.157.154; 2.J.157.157; 2.J.157.166; 2.J.157.169; 2.J.157.172; 2.J.157.175; 2.J.157.240; 2.J.157.244; 2.J.166.228; 2.J.166.229; 2.J.166.230; 2.J.166.231; 2.J.166.236; 2.J.166.237; 2.J.166.238; 2.J.166.239; 2.J.166.154; 2.J.166.157; 2.J.166.166; 2.J.166.169; 2.J.166.172; 2.J.166.175; 2.J.166.240; 2.J.166.244; 2.J.169.228; 2.J.169.229; 2.J.169.230; 2.J.169.231; 2.J.169.236; 2.J.169.237; 2.J.169.238; 2.J.169.239; 2.J.169.154; 2.J.169.157; 2.J.169.166; 2.J.169.169; 2.J.169.172; 2.J.169.175; 2.J.169.240; 2.J.169.244; 2.J.172.228; 2.J.172.229; 2.J.172.230; 2.J.172.231; 2.J.172.236; 2.J.172.237; 2.J.172.238; 2.J.172.239; 2.J.172.J54; 2.J.172.J57; 2.J.172.J66; 2.J.172.J69; 2.J.172.J72; 2.J.172.J75; 2.J.172.240; 2.J.172.244; 2.J.175.228; 2.J.175.229; 2.J.175.230; 2.J.175.231; 2.J.175.236; 2.J.175.237; 2.J.175.238; 2.J.175.239; 2.J.175.154; 2.J.175.157; 2.J.175.166; 2.J.175.169; 2.J.175.172; 2.J.175.175; 2.J.175.240; 2.J.175.244; 2.J.240.228; 2.J.240.229; 2.J.240.230; 2.J.240.231; 2.J.240.236; 2.J.240.237; 2.J.240.238; 2.J.240.239; 2.J.240.154; 2.J.240.157; 2.J.240.166; 2.J.240.169; 2.J.240.172; 2.J.240.175; 2.J.240.240; 2.J.240.244; 2.JJ.244.228; 2.J.244.229; 2.J.244.230; 2.J.244.231; 2.J.244.236; 2.J.244.237; 2.J.244.238; 2.J.244.239; 2.J.244.154; 2.J.244.157; 2.J.244.166; 2.J.244.169; 2.J.244.172; 2.J.244.175; 2.J.244.240; 2.J.244.244;

Prodrugs of 2.L

2.L.228.228; 2.L.228.229; 2.L.228.230; 2.L.228.231; 2.L.228.236; 2.L.228.237; 2.L.228.238; 2.L.228.239; 2.L.228.154; 2.L.228.157; 2.L.228.166; 2.L.228.169; 2.L.228.172; 2.L.228.175; 2.L.228.240; 2.L.228.244; 2.L.229.228; 2.L.229.229; 2.L.229.230; 2.L.229.231; 2.L.229.236; 2.L.229.237; 2.L.229.238; 2.L.229.239; 2.L.229.154; 2.L.229.157; 2.L.229.166; 2.L.229.169; 2.L.229.172; 2.L.229.175; 2.L.229.240; 2.L.229.244; 2.L.230.228; 2.L.230.229; 2.L.230.230; 2.L.230.231; 2.L.230.236; 2.L.230.237; 2.L.230.238; 2.L.230.239; 2.L.230.154; 2.L.230.157; 2.L.230.166; 2.L.230.169; 2.L.230.172; 2.L.230.175; 2.L.230.240; 2.L.230.244; 2.L.231.228; 2.L.231.229; 2.L.231.230; 2.L.231.231; 2.L.231.236; 2.L.231.237; 2.L.231.238; 2.L.231.239; 2.L.231.154; 2.L.231.157; 2.L.231.166; 2.L.231.169; 2.L.231.172; 2.L.231.175; 2.L.231.240; 2.L.231.244; 2.L.236.228; 2.L.236.229; 2.L.236.230; 2.L.236.231; 2.L.236.236; 2.L.236.237; 2.L.236.238; 2.L.236.239; 2.L.236.154; 2.L.236.157; 2.L.236.166; 2.L.236.169; 2.L.236.172; 2.L.236.175; 2.L.236.240; 2.L.236.244; 2.L.237.228; 2.L.237.229; 2.L.237.230; 2.L.237.231; 2.L.237.236; 2.L.237.237; 2.L.237.238; 2.L.237.239; 2.L.237.154; 2.L.237.157; 2.L.237.166; 2.L.237.169; 2.L.237.172; 2.L.237.175; 2.L.237.240; 2.L.237.244; 2.L.238.228; 2.L.238.229; 2.L.238.230; 2.L.238.231; 2.L.238.236; 2.L.238.237; 2.L.238.238; 2.L.238.239; 2.L.238.154; 2.L.238.157; 2.L.238.166; 2.L.238.169; 2.L.238.172; 2.L.238.175; 2.L.238.240; 2.L.238.244; 2.L.239.228; 2.L.239.229; 2.L.239.230; 2.L.239.231; 2.L.239.236; 2.L.239.237; 2.L.239.238; 2.L.239.239; 2.L.239.154; 2.L.239.157; 2.L.239.166; 2.L.239.169; 2.L.239.172; 2.L.239.175; 2.L.239.240; 2.L.239.244; 2.L.154.228; 2.L.154.229; 2.L.154.230; 2.L.154.231; 2.L.154.236; 2.L.154.237; 2.L.154.238; 2.L.154.239; 2.L.154.154; 2.L.154.157; 2.L.154.166; 2.L.154.169; 2.L.154.172; 2.L.154.175; 2.L.154.240; 2.L.154.244; 2.L.157.228; 2.L.157.229; 2.L.157.230; 2.L.157.231; 2.L.157.236; 2.L.157.237; 2.L.157.238; 2.L.157.239; 2.L.157.154; 2.L.157.157; 2.L.157.166; 2.L.157.169; 2.L.157.172; 2.L.157.175; 2.L.157.240; 2.L.157.244; 2.L.166.228; 2.L.166.229; 2.L.166.230; 2.L.166.231; 2.L.166.236; 2.L.166.237; 2.L.166.238; 2.L.166.239; 2.L.166.154; 2.L.166.157; 2.L.166.166; 2.L.166.169; 2.L.166.172; 2.L.166.175; 2.L.166.240; 2.L.166.244; 2.L.169.228; 2.L.169.229; 2.L.169.230; 2.L.169.231;

TABLE 7-continued

2.L.169.236; 2.L.169.237; 2.L.169.238; 2.L.169.239; 2.L.169.154;
2.L.169.157; 2.L.169.166; 2.L.169.169; 2.L.169.172; 2.L.169.175;
2.L.169.240; 2.L.169.244; 2.L.172.228; 2.L.172.229; 2.L.172.230;
2.L.172.231; 2.L.172.236; 2.L.172.237; 2.L.172.238; 2.L.172.239;
2.L.172.154; 2.L.172.157; 2.L.172.166; 2.L.172.169; 2.L.172.172;
2.L.172.175; 2.L.172.240; 2.L.172.244; 2.L.175.228; 2.L.175.229;
2.L.175.230; 2.L.175.231; 2.L.175.236; 2.L.175.237; 2.L.175.238;
2.L.175.239; 2.L.175.154; 2.L.175.157; 2.L.175.166; 2.L.175.169;
2.L.175.172; 2.L.175.175; 2.L.175.240; 2.L.175.244; 2.L.240.228;
2.L.240.229; 2.L.240.230; 2.L.240.231; 2.L.240.236; 2.L.240.237;
2.L.240.238; 2.L.240.239; 2.L.240.154; 2.L.240.157; 2.L.240.166;
2.L.240.169; 2.L.240.172; 2.L.240.175; 2.L.240.240; 2.L.240.244;
2.L.244.228; 2.L.244.229; 2.L.244.230; 2.L.244.231; 2.L.244.236;
2.L.244.237; 2.L.244.238; 2.L.244.239; 2.L.244.154; 2.L.244.157;
2.L.244.166; 2.L.244.169; 2.L.244.172; 2.L.244.175; 2.L.244.240;
2.L.244.244;
Prodrugs of 2.O 2.O.228.228; 2.O.228.229; 2.O.228.230; 2.O.228.231; 2.O.228.236;
2.O.228.237; 2.O.228.238; 2.O.228.239; 2.O.228.154; 2.O.228.157;
2.O.228.166; 2.O.228.169; 2.O.228.172; 2.O.228.175; 2.O.228.240;
2.O.228.244; 2.O.229.228; 2.O.229.229; 2.O.229.230; 2.O.229.231;
2.O.229.236; 2.O.229.237; 2.O.229.238; 2.O.229.239; 2.O.229.154;
2.O.229.157; 2.O.229.166; 2.O.229.169; 2.O.229.172; 2.O.229.175;
2.O.229.240; 2.O.229.244; 2.O.230.228; 2.O.230.229; 2.O.230.230;
2.O.230.231; 2.O.230.236; 2.O.230.237; 2.O.230.238; 2.O.230.239;
2.O.230.154; 2.O.230.157; 2.O.230.166; 2.O.230.169; 2.O.230.172;
2.O.230.175; 2.O.230.240; 2.O.230.244; 2.O.231.228; 2.O.231.229;
2.O.231.230; 2.O.231.231; 2.O.231.236; 2.O.231.237; 2.O.231.238;
2.O.231.239; 2.O.231.154; 2.O.231.157; 2.O.231.166; 2.O.231.169;
2.O.231.172; 2.O.231.175; 2.O.231.240; 2.O.231.244; 2.O.236.228;
2.O.236.229; 2.O.236.230; 2.O.236.231; 2.O.236.236; 2.O.236.237;
2.O.236.238; 2.O.236.239; 2.O.236.154; 2.O.236.157; 2.O.236.166;
2.O.236.169; 2.O.236.172; 2.O.236.175; 2.O.236.240; 2.O.236.244;
2.O.237.228; 2.O.237.229; 2.O.237.230; 2.O.237.231; 2.O.237.236;
2.O.237.237; 2.O.237.238; 2.O.237.239; 2.O.237.154; 2.O.237.157;
2.O.237.166; 2.O.237.169; 2.O.237.172; 2.O.237.175; 2.O.237.240;
2.O.237.244; 2.O.238.228; 2.O.238.229; 2.O.238.230; 2.O.238.231;
2.O.238.236; 2.O.238.237; 2.O.238.238; 2.O.238.239; 2.O.238.154;
2.O.238.157; 2.O.238.166; 2.O.238.169; 2.O.238.172; 2.O.238.175;
2.O.238.240; 2.O.238.244; 2.O.239.228; 2.O.239.229; 2.O.239.230;
2.O.239.231; 2.O.239.236; 2.O.239.237; 2.O.239.238; 2.O.239.239;
2.O.239.154; 2.O.239.157; 2.O.239.166; 2.O.239.169; 2.O.239.172;
2.O.239.175; 2.O.239.240; 2.O.239.244; 2.O.154.228; 2.O.154.229;
2.O.154.230; 2.O.154.231; 2.O.154.236; 2.O.154.237; 2.O.154.238;
2.O.154.239; 2.O.154.154; 2.O.154.157; 2.O.154.166; 2.O.154.169;
2.O.154.172; 2.O.154.175; 2.O.154.240; 2.O.154.244; 2.O.157.228;
2.O.157.229; 2.O.157.230; 2.O.157.231; 2.O.157.236; 2.O.157.237;
2.O.157.238; 2.O.157.239; 2.O.157.154; 2.O.157.157; 2.O.157.166;
2.O.157.169; 2.O.157.172; 2.O.157.175; 2.O.157.240; 2.O.157.244;
2.O.166.228; 2.O.166.229; 2.O.166.230; 2.O.166.231; 2.O.166.236;
2.O.166.237; 2.O.166.238; 2.O.166.239; 2.O.166.154; 2.O.166.157;
2.O.166.166; 2.O.166.169; 2.O.166.172; 2.O.166.175; 2.O.166.240;
2.O.166.244; 2.O.169.228; 2.O.169.229; 2.O.169.230; 2.O.169.231;
2.O.169.236; 2.O.169.237; 2.O.169.238; 2.O.169.239; 2.O.169.154;
2.O.169.157; 2.O.169.166; 2.O.169.169; 2.O.169.172; 2.O.169.175;
2.O.169.240; 2.O.169.244; 2.O.172.228; 2.O.172.229; 2.O.172.230;
2.O.172.231; 2.O.172.236; 2.O.172.237; 2.O.172.238; 2.O.172.239;
2.O.172.154; 2.O.172.157; 2.O.172.166; 2.O.172.169; 2.O.172.172;
2.O.172.175; 2.O.172.240; 2.O.172.244; 2.O.175.228; 2.O.175.229;
2.O.175.230; 2.O.175.231; 2.O.175.236; 2.O.175.237; 2.O.175.238;
2.O.175.239; 2.O.175.154; 2.O.175.157; 2.O.175.166; 2.O.175.169;
2.O.175.172; 2.O.175.175; 2.O.175.240; 2.O.175.244; 2.O.240.228;
2.O.240.229; 2.O.240.230; 2.O.240.231; 2.O.240.236; 2.O.240.237;
2.O.240.238; 2.O.240.239; 2.O.240.154; 2.O.240.157; 2.O.240.166;
2.O.240.169; 2.O.240.172; 2.O.240.175; 2.O.240.240; 2.O.240.244;
2.O.244.228; 2.O.244.229; 2.O.244.230; 2.O.244.231; 2.O.244.236;
2.O.244.237; 2.O.244.238; 2.O.244.239; 2.O.244.154; 2.O.244.157;
2.O.244.166; 2.O.244.169; 2.O.244.172; 2.O.244.175; 2.O.244.240;
2.O.244.244;
Prodrugs of 2.P 2.P.228.228; 2.P.228.229; 2.P.228.230; 2.P.228.231; 2.P.228.236;
2.P.228.237; 2.P.228.238; 2.P.228.239; 2.P.228.154; 2.P.228.157;
2.P.228.166; 2.P.228.169; 2.P.228.172; 2.P.228.175; 2.P.228.240;
2.P.228.244; 2.P.229.228; 2.P.229.229; 2.P.229.230; 2.P.229.231;
2.P.229.236; 2.P.229.237; 2.P.229.238; 2.P.229.239; 2.P.229.154;
2.P.229.157; 2.P.229.166; 2.P.229.169; 2.P.229.172; 2.P.229.175;
2.P.229.240; 2.P.229.244; 2.P.230.228; 2.P.230.229; 2.P.230.230;

TABLE 7-continued

2.P.230.231; 2.P.230.236; 2.P.230.237; 2.P.230.238; 2.P.230.239;
2.P.230.154; 2.P.230.157; 2.P.230.166; 2.P.230.169; 2.P.230.172;
2.P.230.175; 2.P.230.240; 2.P.230.244; 2.P.231.228; 2.P.231.229;
2.P.231.230; 2.P.231.231; 2.P.231.236; 2.P.231.237; 2.P.231.238;
2.P.231.239; 2.P.231.154; 2.P.231.157; 2.P.231.166; 2.P.231.169;
2.P.231.172; 2.P.231.175; 2.P.231.240; 2.P.231.244; 2.P.236.228;
2.P.236.229; 2.P.236.230; 2.P.236.231; 2.P.236.236; 2.P.236.237;
2.P.236.238; 2.P.236.239; 2.P.236.154; 2.P.236.157; 2.P.236.166;
2.P.236.169; 2.P.236.172; 2.P.236.175; 2.P.236.240; 2.P.236.244;
2.P.237.228; 2.P.237.229; 2.P.237.230; 2.P.237.231; 2.P.237.236;
2.P.237.237; 2.P.237.238; 2.P.237.239; 2.P.237.154; 2.P.237.157;
2.P.237.166; 2.P.237.169; 2.P.237.172; 2.P.237.175; 2.P.237.240;
2.P.237.244; 2.P.238.228; 2.P.238.229; 2.P.238.230; 2.P.238.231;
2.P.238.236; 2.P.238.237; 2.P.238.238; 2.P.238.239; 2.P.238.154;
2.P.238.157; 2.P.238.166; 2.P.238.169; 2.P.238.172; 2.P.238.175;
2.P.238.240; 2.P.238.244; 2.P.239.228; 2.P.239.229; 2.P.239.230;
2.P.239.231; 2.P.239.236; 2.P.239.237; 2.P.239.238; 2.P.239.239;
2.P.239.154; 2.P.239.157; 2.P.239.166; 2.P.239.169; 2.P.239.172;
2.P.239.175; 2.P.239.240; 2.P.239.244; 2.P.154.228; 2.P.154.229;
2.P.154.230; 2.P.154.231; 2.P.154.236; 2.P.154.237; 2.P.154.238;
2.P.154.239; 2.P.154.154; 2.P.154.157; 2.P.154.166; 2.P.154.169;
2.P.154.172; 2.P.154.175; 2.P.154.240; 2.P.154.244; 2.P.157.228;
2.P.157.229; 2.P.157.230; 2.P.157.231; 2.P.157.236; 2.P.157.237;
2.P.157.238; 2.P.157.239; 2.P.157.154; 2.P.157.157; 2.P.157.166;
2.P.157.169; 2.P.157.172; 2.P.157.175; 2.P.157.240; 2.P.157.244;
2.P.166.228; 2.P.166.229; 2.P.166.230; 2.P.166.231; 2.P.166.236;
2.P.166.237; 2.P.166.238; 2.P.166.239; 2.P.166.154; 2.P.166.157;
2.P.166.166; 2.P.166.169; 2.P.166.172; 2.P.166.175; 2.P.166.240;
2.P.166.244; 2.P.169.228; 2.P.169.229; 2.P.169.230; 2.P.169.231;
2.P.169.236; 2.P.169.237; 2.P.169.238; 2.P.169.239; 2.P.169.154;
2.P.169.157; 2.P.169.166; 2.P.169.169; 2.P.169.172; 2.P.169.175;
2.P.169.240; 2.P.169.244; 2.P.172.228; 2.P.172.229; 2.P.172.230;
2.P.172.231; 2.P.172.236; 2.P.172.237; 2.P.172.238; 2.P.172.239;
2.P.172.154; 2.P.172.157; 2.P.172.166; 2.P.172.169; 2.P.172.172;
2.P.172.175; 2.P.172.240; 2.P.172.244; 2.P.175.228; 2.P.175.229;
2.P.175.230; 2.P.175.231; 2.P.175.236; 2.P.175.237; 2.P.175.238;
2.P.175.239; 2.P.175.154; 2.P.175.157; 2.P.175.166; 2.P.175.169;
2.P.175.172; 2.P.175.175; 2.P.175.240; 2.P.175.244; 2.P.240.228;
2.P.240.229; 2.P.240.230; 2.P.240.231; 2.P.240.236; 2.P.240.237;
2.P.240.238; 2.P.240.239; 2.P.240.154; 2.P.240.157; 2.P.240.166;
2.P.240.169; 2.P.240.172; 2.P.240.175; 2.P.240.240; 2.P.240.244;
2.P.244.228; 2.P.244.229; 2.P.244.230; 2.P.244.231; 2.P.244.236;
2.P.244.237; 2.P.244.238; 2.P.244.239; 2.P.244.154; 2.P.244.157;
2.P.244.166; 2.P.244.169; 2.P.244.172; 2.P.244.175; 2.P.244.240;
2.P.244.244;
Prodrugs of 2.U 2.U.228.228; 2.U.228.229; 2.U.228.230; 2.U.228.231; 2.U.228.236;
2.U.228.237; 2.U.228.238; 2.U.228.239; 2.U.228.154; 2.U.228.157;
2.U.228.166; 2.U.228.169; 2.U.228.172; 2.U.228.175; 2.U.228.240;
2.U.228.244; 2.U.229.228; 2.U.229.229; 2.U.229.230; 2.U.229.231;
2.U.229.236; 2.U.229.237; 2.U.229.238; 2.U.229.239; 2.U.229.154;
2.U.229.157; 2.U.229.166; 2.U.229.169; 2.U.229.172; 2.U.229.175;
2.U.229.240; 2.U.229.244; 2.U.230.228; 2.U.230.229; 2.U.230.230;
2.U.230.231; 2.U.230.236; 2.U.230.237; 2.U.230.238; 2.U.230.239;
2.U.230.154; 2.U.230.157; 2.U.230.166; 2.U.230.169; 2.U.230.172;
2.U.230.175; 2.U.230.240; 2.U.230.244; 2.U.231.228; 2.U.231.229;
2.U.231.230; 2.U.231.231; 2.U.231.236; 2.U.231.237; 2.U.231.238;
2.U.231.239; 2.U.231.154; 2.U.231.157; 2.U.231.166; 2.U.231.169;
2.U.231.172; 2.U.231.175; 2.U.231.240; 2.U.231.244; 2.U.236.228;
2.U.236.229; 2.U.236.230; 2.U.236.231; 2.U.236.236; 2.U.236.237;
2.U.236.238; 2.U.236.239; 2.U.236.154; 2.U.236.157; 2.U.236.166;
2.U.236.169; 2.U.236.172; 2.U.236.175; 2.U.236.240; 2.U.236.244;
2.U.237.228; 2.U.237.229; 2.U.237.230; 2.U.237.231; 2.U.237.236;
2.U.237.237; 2.U.237.238; 2.U.237.239; 2.U.237.154; 2.U.237.157;
2.U.237.166; 2.U.237.169; 2.U.237.172; 2.U.237.175; 2.U.237.240;
2.U.237.244; 2.U.238.228; 2.U.238.229; 2.U.238.230; 2.U.238.231;
2.U.238.236; 2.U.238.237; 2.U.238.238; 2.U.238.239; 2.U.238.154;
2.U.238.157; 2.U.238.166; 2.U.238.169; 2.U.238.172; 2.U.238.175;
2.U.238.240; 2.U.238.244; 2.U.239.228; 2.U.239.229; 2.U.239.230;
2.U.239.231; 2.U.239.236; 2.U.239.237; 2.U.239.238; 2.U.239.239;
2.U.239.154; 2.U.239.157; 2.U.239.166; 2.U.239.169; 2.U.239.172;
2.U.239.175; 2.U.239.240; 2.U.239.244; 2.U.154.228; 2.U.154.229;
2.U.154.230; 2.U.154.231; 2.U.154.236; 2.U.154.237; 2.U.154.238;
2.U.154.239; 2.U.154.154; 2.U.154.157; 2.U.154.166; 2.U.154.169;
2.U.154.172; 2.U.154.175; 2.U.154.240; 2.U.154.244; 2.U.157.228;
2.U.157.229; 2.U.157.230; 2.U.157.231; 2.U.157.236; 2.U.157.237;
2.U.157.238; 2.U.157.239; 2.U.157.154; 2.U.157.157; 2.U.157.166;
2.U.157.169; 2.U.157.172; 2.U.157.175; 2.U.157.240; 2.U.157.244;

TABLE 7-continued

2.U.166.228; 2.U.166.229; 2.U.166.230; 2.U.166.231; 2.U.166.236; 2.U.166.237; 2.U.166.238; 2.U.166.239; 2.U.166.154; 2.U.166.157; 2.U.166.166; 2.U.166.169; 2.U.166.172; 2.U.166.175; 2.U.166.240; 2.U.166.244; 2.U.169.228; 2.U.169.229; 2.U.169.230; 2.U.169.231; 2.U.169.236; 2.U.169.237; 2.U.169.238; 2.U.169.239; 2.U.169.154; 2.U.169.157; 2.U.169.166; 2.U.169.169; 2.U.169.172; 2.U.169.175; 2.U.169.240; 2.U.169.244; 2.U.172.228; 2.U.172.229; 2.U.172.230; 2.U.172.231; 2.U.172.236; 2.U.172.237; 2.U.172.238; 2.U.172.239; 2.U.172.154; 2.U.172.157; 2.U.172.166; 2.U.172.169; 2.U.172.172; 2.U.172.175; 2.U.172.240; 2.U.172.244; 2.U.175.228; 2.U.175.229; 2.U.175.230; 2.U.175.231; 2.U.175.236; 2.U.175.237; 2.U.175.238; 2.U.175.239; 2.U.175.154; 2.U.175.157; 2.U.175.166; 2.U.175.169; 2.U.175.172; 2.U.175.175; 2.U.175.240; 2.U.175.244; 2.U.240.228; 2.U.240.229; 2.U.240.230; 2.U.240.231; 2.U.240.236; 2.U.240.237; 2.U.240.238; 2.U.240.239; 2.U.240.154; 2.U.240.157; 2.U.240.166; 2.U.240.169; 2.U.240.172; 2.U.240.175; 2.U.240.240; 2.U.240.244; 2.U.244.228; 2.U.244.229; 2.U.244.230; 2.U.244.231; 2.U.244.236; 2.U.244.237; 2.U.244.238; 2.U.244.239; 2.U.244.154; 2.U.244.157; 2.U.244.166; 2.U.244.169; 2.U.244.172; 2.U.244.175; 2.U.244.240; 2.U.244.244;
Prodrugs of 2.W 2.W.228.228; 2.W.228.229; 2.W.228.230; 2.W.228.231; 2.W.228.236; 2.W.228.237; 2.W.228.238; 2.W.228.239; 2.W.228.154; 2.W.228.157; 2.W.228.166; 2.W.228.169; 2.W.228.172; 2.W.228.175; 2.W.228.240; 2.W.228.244; 2.W.229.228; 2.W.229.229; 2.W.229.230; 2.W.229.231; 2.W.229.236; 2.W.229.237; 2.W.229.238; 2.W.229.239; 2.W.229.154; 2.W.229.157; 2.W.229.166; 2.W.229.169; 2.W.229.172; 2.W.229.175; 2.W.229.240; 2.W.229.244; 2.W.230.228; 2.W.230.229; 2.W.230.230; 2.W.230.231; 2.W.230.236; 2.W.230.237; 2.W.230.238; 2.W.230.239; 2.W.230.154; 2.W.230.157; 2.W.230.166; 2.W.230.169; 2.W.230.172; 2.W.230.175; 2.W.230.240; 2.W.230.244; 2.W.231.228; 2.W.231.229; 2.W.231.230; 2.W.231.231; 2.W.231.236; 2.W.231.237; 2.W.231.238; 2.W.231.239; 2.W.231.154; 2.W.231.157; 2.W.231.166; 2.W.231.169; 2.W.231.172; 2.W.231.175; 2.W.231.240; 2.W.231.244; 2.W.236.228; 2.W.236.229; 2.W.236.230; 2.W.236.231; 2.W.236.236; 2.W.236.237; 2.W.236.238; 2.W.236.239; 2.W.236.154; 2.W.236.157; 2.W.236.166; 2.W.236.169; 2.W.236.172; 2.W.236.175; 2.W.236.240; 2.W.236.244; 2.W.237.228; 2.W.237.229; 2.W.237.230; 2.W.237.231; 2.W.237.236; 2.W.237.237; 2.W.237.238; 2.W.237.239; 2.W.237.154; 2.W.237.157; 2.W.237.166; 2.W.237.169; 2.W.237.172; 2.W.237.175; 2.W.237.240; 2.W.237.244; 2.W.238.228; 2.W.238.229; 2.W.238.230; 2.W.238.231; 2.W.238.236; 2.W.238.237; 2.W.238.238; 2.W.238.239; 2.W.238.154; 2.W.238.157; 2.W.238.166; 2.W.238.169; 2.W.238.172; 2.W.238.175; 2.W.238.240; 2.W.238.244; 2.W.239.228; 2.W.239.229; 2.W.239.230; 2.W.239.231; 2.W.239.236; 2.W.239.237; 2.W.239.238; 2.W.239.239; 2.W.239.154; 2.W.239.157; 2.W.239.166; 2.W.239.169; 2.W.239.172; 2.W.239.175; 2.W.239.240; 2.W.239.244; 2.W.154.228; 2.W.154.229; 2.W.154.230; 2.W.154.231; 2.W.154.236; 2.W.154.237; 2.W.154.238; 2.W.154.239; 2.W.154.154; 2.W.154.157; 2.W.154.166; 2.W.154.169; 2.W.154.172; 2.W.154.175; 2.W.154.240; 2.W.154.244; 2.W.157.228; 2.W.157.229; 2.W.157.230; 2.W.157.231; 2.W.157.236; 2.W.157.237; 2.W.157.238; 2.W.157.239; 2.W.157.154; 2.W.157.157; 2.W.157.166; 2.W.157.169; 2.W.157.172; 2.W.157.175; 2.W.157.240; 2.W.157.244; 2.W.166.228; 2.W.166.229; 2.W.166.230; 2.W.166.231; 2.W.166.236; 2.W.166.237; 2.W.166.238; 2.W.166.239; 2.W.166.154; 2.W.166.157; 2.W.166.166; 2.W.166.169; 2.W.166.172; 2.W.166.175; 2.W.166.240; 2.W.166.244; 2.W.169.228; 2.W.169.229; 2.W.169.230; 2.W.169.231; 2.W.169.236; 2.W.169.237; 2.W.169.238; 2.W.169.239; 2.W.169.154; 2.W.169.157; 2.W.169.166; 2.W.169.169; 2.W.169.172; 2.W.169.175; 2.W.169.240; 2.W.169.244; 2.W.172.228; 2.W.172.229; 2.W.172.230; 2.W.172.231; 2.W.172.236; 2.W.172.237; 2.W.172.238; 2.W.172.239; 2.W.172.154; 2.W.172.157; 2.W.172.166; 2.W.172.169; 2.W.172.172; 2.W.172.175; 2.W.172.240; 2.W.172.244; 2.W.175.228; 2.W.175.229; 2.W.175.230; 2.W.175.231; 2.W.175.236; 2.W.175.237; 2.W.175.238; 2.W.175.239; 2.W.175.154; 2.W.175.157; 2.W.175.166; 2.W.175.169; 2.W.175.172; 2.W.175.175; 2.W.175.240; 2.W.175.244; 2.W.240.228; 2.W.240.229; 2.W.240.230; 2.W.240.231; 2.W.240.236; 2.W.240.237; 2.W.240.238; 2.W.240.239; 2.W.240.154; 2.W.240.157; 2.W.240.166; 2.W.240.169; 2.W.240.172; 2.W.240.175; 2.W.240.240; 2.W.240.244; 2.W.244.228; 2.W.244.229; 2.W.244.230; 2.W.244.231; 2.W.244.236; 2.W.244.237; 2.W.244.238; 2.W.244.239; 2.W.244.154; 2.W.244.157; 2.W.244.166; 2.W.244.169; 2.W.244.172; 2.W.244.175; 2.W.244.240; 2.W.244.244;
Prodrugs of 2.Y 2.Y.228.228; 2.Y.228.229; 2.Y.228.230; 2.Y.228.231; 2.Y.228.236; 2.Y.228.237; 2.Y.228.238; 2.Y.228.239; 2.Y.228.154; 2.Y.228.157; 2.Y.228.166; 2.Y.228.169; 2.Y.228.172; 2.Y.228.175; 2.Y.228.240; 2.Y.228.244; 2.Y.229.228; 2.Y.229.229; 2.Y.229.230; 2.Y.229.231; 2.Y.229.236; 2.Y.229.237; 2.Y.229.238; 2.Y.229.239; 2.Y.229.154; 2.Y.229.157; 2.Y.229.166; 2.Y.229.169; 2.Y.229.172; 2.Y.229.175; 2.Y.229.240; 2.Y.229.244; 2.Y.230.228; 2.Y.230.229; 2.Y.230.230; 2.Y.230.231; 2.Y.230.236; 2.Y.230.237; 2.Y.230.238; 2.Y.230.239; 2.Y.230.154; 2.Y.230.157; 2.Y.230.166; 2.Y.230.169; 2.Y.230.172; 2.Y.230.175; 2.Y.230.240; 2.Y.230.244; 2.Y.231.228; 2.Y.231.229; 2.Y.231.230; 2.Y.231.231; 2.Y.231.236; 2.Y.231.237; 2.Y.231.238; 2.Y.231.239; 2.Y.231.154; 2.Y.231.157; 2.Y.231.166; 2.Y.231.169; 2.Y.231.172; 2.Y.231.175; 2.Y.231.240; 2.Y.231.244; 2.Y.236.228; 2.Y.236.229; 2.Y.236.230; 2.Y.236.231; 2.Y.236.236; 2.Y.236.237; 2.Y.236.238; 2.Y.236.239; 2.Y.236.154; 2.Y.236.157; 2.Y.236.166; 2.Y.236.169; 2.Y.236.172; 2.Y.236.175; 2.Y.236.240; 2.Y.236.244; 2.Y.237.228; 2.Y.237.229; 2.Y.237.230; 2.Y.237.231; 2.Y.237.236; 2.Y.237.237; 2.Y.237.238; 2.Y.237.239; 2.Y.237.154; 2.Y.237.157; 2.Y.237.166; 2.Y.237.169; 2.Y.237.172; 2.Y.237.175; 2.Y.237.240; 2.Y.237;244; 2.Y.238.228; 2.Y.238.229; 2.Y.238.230; 2.Y.238.231; 2.Y.238.236; 2.Y.238.237; 2.Y.238.238; 2.Y.238.239; 2.Y.238.154; 2.Y.238.157; 2.Y.238.166; 2.Y.238.169; 2.Y.238.172; 2.Y.238.175; 2.Y.238.240; 2.Y.238.244; 2.Y.239.228; 2.Y.239.229; 2.Y.239.230; 2.Y.239.231; 2.Y.239.236; 2.Y.239.237; 2.Y.239.238; 2.Y.239.239; 2.Y.239.154; 2.Y.239.157; 2.Y.239.166; 2.Y.239.169; 2.Y.239.172; 2.Y.239.175; 2.Y.239.240; 2.Y.239.244; 2.Y.154.228; 2.Y.154.229; 2.Y.154.230; 2.Y.154.231; 2.Y.154.236; 2.Y.154.237; 2.Y.154.238; 2.Y.154.239; 2.Y.154.154; 2.Y.154.157; 2.Y.154.166; 2.Y.154.169; 2.Y.154.172; 2.Y.154.175; 2.Y.154.240; 2.Y.154.244; 2.Y.157.228; 2.Y.157.229; 2.Y.157.230; 2.Y.157.231; 2.Y.157.236; 2.Y.157.237; 2.Y.157.238; 2.Y.157.239; 2.Y.157.154; 2.Y.157.157; 2.Y.157.166; 2.Y.157.169; 2.Y.157.172; 2.Y.157.175; 2.Y.157.240; 2.Y.157.244; 2.Y.166.228; 2.Y.166.229; 2.Y.166.230; 2.Y.166.231; 2.Y.166.236; 2.Y.166.237; 2.Y.166.238; 2.Y.166.239; 2.Y.166.154; 2.Y.166.157; 2.Y.166.166; 2.Y.166.169; 2.Y.166.172; 2.Y.166.175; 2.Y.166.240; 2.Y.166.244; 2.Y.169.228; 2.Y.169.229; 2.Y.169.230; 2.Y.169.231; 2.Y.169.236; 2.Y.169.237; 2.Y.169.238; 2.Y.169.239; 2.Y.169.154; 2.Y.169.157; 2.Y.169.166; 2.Y.169.169; 2.Y.169.172; 2.Y.169.175; 2.Y.169.240; 2.Y.169.244; 2.Y.172.228; 2.Y.172.229; 2.Y.172.230; 2.Y.172.231; 2.Y.172.236; 2.Y.172.237; 2.Y.172.238; 2.Y.172.239; 2.Y.172.154; 2.Y.172.157; 2.Y.172.166; 2.Y.172.169; 2.Y.172.172; 2.Y.172.175; 2.Y.172.240; 2.Y.172.244; 2.Y.175.228; 2.Y.175.229; 2.Y.175.230; 2.Y.175.231; 2.Y.175.236; 2.Y.175.237; 2.Y.175.238; 2.Y.175.239; 2.Y.175.154; 2.Y.175.157; 2.Y.175.166; 2.Y.175.169; 2.Y.175.172; 2.Y.175.175; 2.Y.175.240; 2.Y.175.244; 2.Y.240.228; 2.Y.240.229; 2.Y.240.230; 2.Y.240.231; 2.Y.240.236; 2.Y.240.237; 2.Y.240.238; 2.Y.240.239; 2.Y.240.154; 2.Y.240.157; 2.Y.240.166; 2.Y.240.169; 2.Y.240.172; 2.Y.240.175; 2.Y.240.240; 2.Y.240.244; 2.Y.244.228; 2.Y.244.229; 2.Y.244.230; 2.Y.244.231; 2.Y.244.236; 2.Y.244.237; 2.Y.244.238; 2.Y.244.239; 2.Y.244.154; 2.Y.244.157; 2.Y.244.166; 2.Y.244.169; 2.Y.244.172; 2.Y.244.175; 2.Y.244.240; 2.Y.244.244;
Prodrugs of 3.B 3.B.228.228; 3.B.228.229; 3.B.228.230; 3.B.228.231; 3.B.228.236; 3.B.228.237; 3.B.228.238; 3.B.228.239; 3.B.228.154; 3.B.228.157; 3.B.228.166; 3.B.228.169; 3.B.228.172; 3.B.228.175; 3.B.228.240; 3.B.228.244; 3.B.229.228; 3.B.229.229; 3.B.229.230; 3.B.229.231; 3.B.229.236; 3.B.229.237; 3.B.229.238; 3.B.229.239; 3.B.229.154; 3.B.229.157; 3.B.229.166; 3.B.229.169; 3.B.229.172; 3.B.229.175; 3.B.229.240; 3.B.229.244; 3.B.230.228; 3.B.230.229; 3.B.230.230; 3.B.230.231; 3.B.230.236; 3.B.230.237; 3.B.230.238; 3.B.230.239; 3.B.230.154; 3.B.230.157; 3.B.230.166; 3.B.230.169; 3.B.230.172; 3.B.230.175; 3.B.230.240; 3.B.230.244; 3.B.231.228; 3.B.231.229; 3.B.231.230; 3.B.231.231; 3.B.231.236; 3.B.231.237; 3.B.231.238; 3.B.231.239; 3.B.231.154; 3.B.231.157; 3.B.231.166; 3.B.231.169; 3.B.231.172; 3.B.231.175; 3.B.231.240; 3.B.231.244; 3.B.236.228; 3.B.236.229; 3.B.236.230; 3.B.236.231; 3.B.236.236; 3.B.236.237; 3.B.236.238; 3.B.236.239; 3.B.236.154; 3.B.236.157; 3.B.236.166; 3.B.236.169; 3.B.236.172; 3.B.236.175; 3.B.236.240; 3.B.236.244; 3.B.237.228; 3.B.237.229; 3.B.237.230; 3.B.237.231; 3.B.237.236; 3.B.237.237; 3.B.237.238; 3.B.237.239; 3.B.237.154; 3.B.237.157; 3.B.237.166; 3.B.237.169; 3.B.237.172; 3.B.237.175; 3.B.237.240; 3.B.237.244; 3.B.238.228; 3.B.238.229; 3.B.238.230; 3.B.238.231; 3.B.238.236; 3.B.238.237; 3.B.238.238; 3.B.238.239; 3.B.238.154; 3.B.238.157; 3.B.238.166; 3.B.238.169; 3.B.238.172; 3.B.238.175; 3.B.238.240; 3.B.238.244; 3.B.239.228; 3.B.239.229; 3.B.239.230; 3.B.239.231; 3.B.239.236; 3.B.239.237; 3.B.239.238; 3.B.239.239; 3.B.239.154; 3.B.239.157; 3.B.239.166; 3.B.239.169; 3.B.239.172; 3.B.239.175; 3.B.239.240; 3.B.239.244; 3.B.154.228; 3.B.154.229; 3.B.154.230; 3.B.154.231; 3.B.154.236; 3.B.154.237; 3.B.154.238; 3.B.154.239; 3.B.154.154; 3.B.154.157; 3.B.154.166; 3.B.154.169;

TABLE 7-continued

3.B.154.172; 3.B.154.175; 3.B.154.240; 3.B.154.244; 3.B.157.228; 3.B.157.229; 3.B.157.230; 3.B.157.231; 3.B.157.236; 3.B.157.237; 3.B.157.238; 3.B.157.239; 3.B.157.154; 3.B.157.157; 3.B.157.166; 3.B.157.169; 3.B.157.172; 3.B.157.175; 3.B.157.240; 3.B.157.244; 3.B.166.228; 3.B.166.229; 3.B.166.230; 3.B.166.231; 3.B.166.236; 3.B.166.237; 3.B.166.238; 3.B.166.239; 3.B.166.240; 3.B.166.244; 3.B.169.228; 3.B.169.229; 3.B.169.230; 3.B.169.231; 3.B.169.236; 3.B.169.237; 3.B.169.238; 3.B.169.239; 3.B.169.154; 3.B.169.157; 3.B.169.166; 3.B.169.169; 3.B.169.172; 3.B.169.175; 3.B.169.240; 3.B.169.244; 3.B.172.228; 3.B.172.229; 3.B.172.230; 3.B.172.231; 3.B.172.236; 3.B.172.237; 3.B.172.238; 3.B.172.239; 3.B.172.154; 3.B.172.157; 3.B.172.166; 3.B.172.169; 3.B.172.172; 3.B.172.175; 3.B.172.240; 3.B.172.244; 3.B.175.228; 3.B.175.229; 3.B.175.230; 3.B.175.231; 3.B.175.236; 3.B.175.237; 3.B.175.238; 3.B.175.239; 3.B.175.154; 3.B.175.157; 3.B.175.166; 3.B.175.169; 3.B.175.172; 3.B.175.175; 3.B.175.240; 3.B.175.244; 3.B.240.228; 3.B.240.229; 3.B.240.230; 3.B.240.231; 3.B.240.236; 3.B.240.237; 3.B.240.238; 3.B.240.239; 3.B.240.154; 3.B.240.157; 3.B.240.166; 3.B.240.169; 3.B.240.172; 3.B.240.175; 3.B.240.240; 3.B.240.244; 3.B.244.228; 3.B.244.229; 3.B.244.230; 3.B.244.231; 3.B.244.236; 3.B.244.237; 3.B.244.238; 3.B.244.239; 3.B.244.154; 3.B.244.157; 3.B.244.166; 3.B.244.169; 3.B.244.172; 3.B.244.175; 3.B.244.240; 3.B.244.244;

Prodrugs of 3.D

3.D.228.228; 3.D.228.229; 3.D.228.230; 3.D.228.231; 3.D.228.236; 3.D.228.237; 3.D.228.238; 3.D.228.239; 3.D.228.154; 3.D.228.157; 3.D.228.166; 3.D.228.169; 3.D.228.172; 3.D.228.175; 3.D.228.240; 3.D.228.244; 3.D.229.228; 3.D.229.229; 3.D.229.230; 3.D.229.231; 3.D.229.236; 3.D.229.237; 3.D.229.238; 3.D.229.239; 3.D.229.154; 3.D.229.157; 3.D.229.166; 3.D.229.169; 3.D.229.172; 3.D.229.175; 3.D.229.240; 3.D.229.244; 3.D.230.228; 3.D.230.229; 3.D.230.230; 3.D.230.231; 3.D.230.236; 3.D.230.237; 3.D.230.238; 3.D.230.239; 3.D.230.154; 3.D.230.157; 3.D.230.166; 3.D.230.169; 3.D.230.172; 3.D.230.175; 3.D.230.240; 3.D.230.244; 3.D.231.228; 3.D.231.229; 3.D.231.230; 3.D.231.231; 3.D.231.236; 3.D.231.237; 3.D.231.238; 3.D.231.239; 3.D.231.154; 3.D.231.157; 3.D.231.166; 3.D.231.169; 3.D.231.172; 3.D.231.175; 3.D.231.240; 3.D.231.244; 3.D.236.228; 3.D.236.229; 3.D.236.230; 3.D.236.231; 3.D.236.236; 3.D.236.237; 3.D.236.238; 3.D.236.239; 3.D.236.154; 3.D.236.157; 3.D.236.166; 3.D.236.169; 3.D.236.172; 3.D.236.175; 3.D.236.240; 3.D.236.244; 3.D.237.228; 3.D.237.229; 3.D.237.230; 3.D.237.231; 3.D.237.236; 3.D.237.237; 3.D.237.238; 3.D.237.239; 3.D.237.154; 3.D.237.157; 3.D.237.166; 3.D.237.169; 3.D.237.172; 3.D.237.175; 3.D.237.240; 3.D.237.244; 3.D.238.228; 3.D.238.229; 3.D.238.230; 3.D.238.231; 3.D.238.236; 3.D.238.237; 3.D.238.238; 3.D.238.239; 3.D.238.154; 3.D.238.157; 3.D.238.166; 3.D.238.169; 3.D.238.172; 3.D.238.175; 3.D.238.240; 3.D.238.244; 3.D.239.228; 3.D.239.229; 3.D.239.230; 3.D.239.231; 3.D.239.236; 3.D.239.237; 3.D.239.238; 3.D.239.239; 3.D.239.154; 3.D.239.157; 3.D.239.166; 3.D.239.169; 3.D.239.172; 3.D.239.175; 3.D.239.240; 3.D.239.244; 3.D.154.228; 3.D.154.229; 3.D.154.230; 3.D.154.231; 3.D.154.236; 3.D.154.237; 3.D.154.238; 3.D.154.239; 3.D.154.154; 3.D.154.157; 3.D.154.166; 3.D.154.169; 3.D.154.172; 3.D.154.175; 3.D.154.240; 3.D.154.244; 3.D.157.228; 3.D.157.229; 3.D.157.230; 3.D.157.231; 3.D.157.236; 3.D.157.237; 3.D.157.238; 3.D.157.239; 3.D.157.154; 3.D.157.157; 3.D.157.166; 3.D.157.169; 3.D.157.172; 3.D.157.175; 3.D.157.240; 3.D.157.244; 3.D.166.228; 3.D.166.229; 3.D.166.230; 3.D.166.231; 3.D.166.236; 3.D.166.237; 3.D.166.238; 3.D.166.239; 3.D.166.154; 3.D.166.157; 3.D.166.166; 3.D.166.169; 3.D.166.172; 3.D.166.175; 3.D.166.240; 3.D.166.244; 3.D.169.228; 3.D.169.229; 3.D.169.230; 3.D.169.231; 3.D.169.236; 3.D.169.237; 3.D.169.238; 3.D.169.239; 3.D.169.154; 3.D.169.157; 3.D.169.166; 3.D.169.169; 3.D.169.172; 3.D.169.175; 3.D.169.240; 3.D.169.244; 3.D.172.228; 3.D.172.229; 3.D.172.230; 3.D.172.231; 3.D.172.236; 3.D.172.237; 3.D.172.238; 3.D.172.239; 3.D.172.154; 3.D.172.157; 3.D.172.166; 3.D.172.169; 3.D.172.172; 3.D.172.175; 3.D.172.240; 3.D.172.244; 3.D.175.228; 3.D.175.229; 3.D.175.230; 3.D.175.231; 3.D.175.236; 3.D.175.237; 3.D.175.238; 3.D.175.239; 3.D.175.154; 3.D.175.157; 3.D.175.166; 3.D.175.169; 3.D.175.172; 3.D.175.175; 3.D.175.240; 3.D.175.244; 3.D.240.228; 3.D.240.229; 3.D.240.230; 3.D.240.231; 3.D.240.236; 3.D.240.237; 3.D.240.238; 3.D.240.239; 3.D.240.154; 3.D.240.157; 3.D.240.166; 3.D.240.169; 3.D.240.172; 3.D.240.175; 3.D.240.240; 3.D.240.244; 3.D.244.228; 3.D.244.229; 3.D.244.230; 3.D.244.231; 3.D.244.236; 3.D.244.237; 3.D.244.238; 3.D.244.239; 3.D.244.154; 3.D.244.157; 3.D.244.166; 3.D.244.169; 3.D.244.172; 3.D.244.175; 3.D.244.240; 3.D.244.244;

Prodrugs of 3.E

3.E.228.228; 3.E.228.229; 3.E.228.230; 3.E.228.231; 3.E.228.236; 3.E.228.237; 3.E.228.238; 3.E.228.239; 3.E.228.154; 3.E.228.157; 3.E.228.166; 3.E.228.169; 3.E.228.172; 3.E.228.175; 3.E.228.240; 3.E.228.244; 3.E.229.228; 3.E.229.229; 3.E.229.230; 3.E.229.231; 3.E.229.236; 3.E.229.237; 3.E.229.238; 3.E.229.239; 3.E.229.154; 3.E.229.157; 3.E.229.166; 3.E.229.169; 3.E.229.172; 3.E.229.175; 3.E.229.240; 3.E.229.244; 3.E.230.228; 3.E.230.229; 3.E.230.230; 3.E.230.231; 3.E.230.236; 3.E.230.237; 3.E.230.238; 3.E.230.239; 3.E.230.154; 3.E.230.157; 3.E.230.166; 3.E.230.169; 3.E.230.172; 3.E.230.175; 3.E.230.240; 3.E.230.244; 3.E.231.228; 3.E.231.229; 3.E.231.230; 3.E.231.231; 3.E.231.236; 3.E.231.237; 3.E.231.238; 3.E.231.239; 3.E.231.154; 3.E.231.157; 3.E.231.166; 3.E.231.169; 3.E.231.172; 3.E.231.175; 3.E.231.240; 3.E.231.244; 3.E.236.228; 3.E.236.229; 3.E.236.230; 3.E.236.231; 3.E.236.236; 3.E.236.237; 3.E.236.238; 3.E.236.239; 3.E.236.154; 3.E.236.157; 3.E.236.166; 3.E.236.169; 3.E.236.172; 3.E.236.175; 3.E.236.240; 3.E.236.244; 3.E.237.228; 3.E.237.229; 3.E.237.230; 3.E.237.231; 3.E.237.236; 3.E.237.237; 3.E.237.238; 3.E.237.239; 3.E.237.154; 3.E.237.157; 3.E.237.166; 3.E.237.169; 3.E.237.172; 3.E.237.175; 3.E.237.240; 3.E.237.244; 3.E.238.228; 3.E.238.229; 3.E.238.230; 3.E.238.231; 3.E.238.236; 3.E.238.237; 3.E.238.238; 3.E.238.239; 3.E.238.154; 3.E.238.157; 3.E.238.166; 3.E.238.169; 3.E.238.172; 3.E.238.175; 3.E.238.240; 3.E.238.244; 3.E.239.228; 3.E.239.229; 3.E.239.230; 3.E.239.231; 3.E.239.236; 3.E.239.237; 3.E.239.238; 3.E.239.239; 3.E.239.154; 3.E.239.157; 3.E.239.166; 3.E.239.169; 3.E.239.172; 3.E.239.175; 3.E.239.240; 3.E.239.244; 3.E.154.228; 3.E.154.229; 3.E.154.230; 3.E.154.231; 3.E.154.236; 3.E.154.237; 3.E.154.238; 3.E.154.239; 3.E.154.154; 3.E.154.157; 3.E.154.166; 3.E.154.169; 3.E.154.172; 3.E.154.175; 3.E.154.240; 3.E.154.244; 3.E.157.228; 3.E.157.229; 3.E.157.230; 3.E.157.231; 3.E.157.236; 3.E.157.237; 3.E.157.238; 3.E.157.239; 3.E.157.154; 3.E.157.157; 3.E.157.166; 3.E.157.169; 3.E.157.172; 3.E.157.175; 3.E.157.240; 3.E.157.244; 3.E.166.228; 3.E.166.229; 3.E.166.230; 3.E.166.231; 3.E.166.236; 3.E.166.237; 3.E.166.238; 3.E.166.239; 3.E.166.154; 3.E.166.157; 3.E.166.166; 3.E.166.169; 3.E.166.172; 3.E.166.175; 3.E.166.240; 3.E.166.244; 3.E.169.228; 3.E.169.229; 3.E.169.230; 3.E.169.231; 3.E.169.236; 3.E.169.237; 3.E.169.238; 3.E.169.239; 3.E.169.154; 3.E.169.157; 3.E.169.166; 3.E.169.169; 3.E.169.172; 3.E.169.175; 3.E.169.240; 3.E.169.244; 3.E.172.228; 3.E.172.229; 3.E.172.230; 3.E.172.231; 3.E.172.236; 3.E.172.237; 3.E.172.238; 3.E.172.239; 3.E.172.154; 3.E.172.157; 3.E.172.166; 3.E.172.169; 3.E.172.172; 3.E.172.175; 3.E.172.240; 3.E.172.244; 3.E.175.228; 3.E.175.229; 3.E.175.230; 3.E.175.231; 3.E.175.236; 3.E.175.237; 3.E.175.238; 3.E.175.239; 3.E.175.154; 3.E.175.157; 3.E.175.166; 3.E.175.169; 3.E.175.172; 3.E.175.175; 3.E.175.240; 3.E.175.244; 3.E.240.228; 3.E.240.229; 3.E.240.230; 3.E.240.231; 3.E.240.236; 3.E.240.237; 3.E.240.238; 3.E.240.239; 3.E.240.154; 3.E.240.157; 3.E.240.166; 3.E.240.169; 3.E.240.172; 3.E.240.175; 3.E.240.240; 3.E.240.244; 3.E.244.228; 3.E.244.229; 3.E.244.230; 3.E.244.231; 3.E.244.236; 3.E.244.237; 3.E.244.238; 3.E.244.239; 3.E.244.154; 3.E.244.157; 3.E.244.166; 3.E.244.169; 3.E.244.172; 3.E.244.175; 3.E.244.240; 3.E.244.244;

Prodrugs of 3.G

3.G.228.228; 3.G.228.229; 3.G.228.230; 3.G.228.231; 3.G.228.236; 3.G.228.237; 3.G.228.238; 3.G.228.239; 3.G.228.154; 3.G.228.157; 3.G.228.166; 3.G.228.169; 3.G.228.172; 3.G.228.175; 3.G.228.240; 3.G.228.244; 3.G.229.228; 3.G.229.229; 3.G.229.230; 3.G.229.231; 3.G.229.236; 3.G.229.237; 3.G.229.238; 3.G.229.239; 3.G.229.154; 3.G.229.157; 3.G.229.166; 3.G.229.169; 3.G.229.172; 3.G.229.175; 3.G.229.240; 3.G.229.244; 3.G.230.228; 3.G.230.229; 3.G.230.230; 3.G.230.231; 3.G.230.236; 3.G.230.237; 3.G.230.238; 3.G.230.239; 3.G.230.154; 3.G.230.157; 3.G.230.166; 3.G.230.169; 3.G.230.172; 3.G.230.175; 3.G.230.240; 3.G.230.244; 3.G.231.228; 3.G.231.229; 3.G.231.230; 3.G.231.231; 3.G.231.236; 3.G.231.237; 3.G.231.238; 3.G.231.239; 3.G.231.154; 3.G.231.157; 3.G.231.166; 3.G.231.169; 3.G.231.172; 3.G.231.175; 3.G.231.240; 3.G.231.244; 3.G.236.228; 3.G.236.229; 3.G.236.230; 3.G.236.231; 3.G.236.236; 3.G.236.237; 3.G.236.238; 3.G.236.239; 3.G.236.154; 3.G.236.157; 3.G.236.166; 3.G.236.169; 3.G.236.172; 3.G.236.175; 3.G.236.240; 3.G.236.244; 3.G.237.228; 3.G.237.229; 3.G.237.230; 3.G.237.231; 3.G.237.236; 3.G.237.237; 3.G.237.238; 3.G.237.239; 3.G.237.154; 3.G.237.157; 3.G.237.166; 3.G.237.169; 3.G.237.172; 3.G.237.175; 3.G.237.240; 3.G.237.244; 3.G.238.228; 3.G.238.229; 3.G.238.230; 3.G.238.231; 3.G.238.236; 3.G.238.237; 3.G.238.238; 3.G.238.239; 3.G.238.154; 3.G.238.157; 3.G.238.166; 3.G.238.169; 3.G.238.172; 3.G.238.175; 3.G.238.240; 3.G.238.244; 3.G.239.228; 3.G.239.229; 3.G.239.230;

TABLE 7-continued

3.G.239.231; 3.G.239.236; 3.G.239.237; 3.G.239.238; 3.G.239.239;
3.G.239.154; 3.G.239.157; 3.G.239.166; 3.G.239.169; 3.G.239.172;
3.G.239.175; 3.G.239.240; 3.G.239.244; 3.G.154.228; 3.G.154.229;
3.G.154.230; 3.G.154.231; 3.G.154.236; 3.G.154.237; 3.G.154.238;
3.G.154.239; 3.G.154.154; 3.G.154.157; 3.G.154.166; 3.G.154.169;
3.G.154.172; 3.G.154.175; 3.G.154.240; 3.G.154.244; 3.G.157.228;
3.G.157.229; 3.G.157.230; 3.G.157.231; 3.G.157.236; 3.G.157.237;
3.G.157.238; 3.G.157.239; 3.G.157.154; 3.G.157.157; 3.G.157.166;
3.G.157.169; 3.G.157.172; 3.G.157.175; 3.G.157.240; 3.G.157.244;
3.G.166.228; 3.G.166.229; 3.G.166.230; 3.G.166.231; 3.G.166.236;
3.G.166.237; 3.G.166.238; 3.G.166.239; 3.G.166.154; 3.G.166.157;
3.G.166.166; 3.G.166.169; 3.G.166.172; 3.G.166.175; 3.G.166.240;
3.G.166.244; 3.G.169.228; 3.G.169.229; 3.G.169.230; 3.G.169.231;
3.G.169.236; 3.G.169.237; 3.G.169.238; 3.G.169.239; 3.G.169.154;
3.G.169.157; 3.G.169.166; 3.G.169.169; 3.G.169.172; 3.G.169.175;
3.G.169.240; 3.G.169.244; 3.G.172.228; 3.G.172.229; 3.G.172.230;
3.G.172.231; 3.G.172.236; 3.G.172.237; 3.G.172.238; 3.G.172.239;
3.G.172.154; 3.G.172.157; 3.G.172.166; 3.G.172.169; 3.G.172.172;
3.G.172.175; 3.G.172.240; 3.G.172.244; 3.G.175.228; 3.G.175.229;
3.G.175.230; 3.G.175.231; 3.G.175.236; 3.G.175.237; 3.G.175.238;
3.G.175.239; 3.G.175.154; 3.G.175.157; 3.G.175.166; 3.G.175.169;
3.G.175.172; 3.G.175.175; 3.G.175.240; 3.G.175.244; 3.G.240.228;
3.G.240.229; 3.G.240.230; 3.G.240.231; 3.G.240.236; 3.G.240.237;
3.G.240.238; 3.G.240.239; 3.G.240.154; 3.G.240.157; 3.G.240.166;
3.G.240.169; 3.G.240.172; 3.G.240.175; 3.G.240.240; 3.G.240.244;
3.G.244.228; 3.G.244.229; 3.G.244.230; 3.G.244.231; 3.G.244.236;
3.G.244.237; 3.G.244.238; 3.G.244.239; 3.G.244.154; 3.G.244.157;
3.G.244.166; 3.G.244.169; 3.G.244.172; 3.G.244.175; 3.G.244.240;
3.G.244.244;
Prodrugs of 3.I 3.I.228.228; 3.I.228.229; 3.I.228.230; 3.I.228.231; 3.I.228.236;
3.I.228.237; 3.I.228.238; 3.I.228.239; 3.I.228.154; 3.I.228.157;
3.I.228.166; 3.I.228.169; 3.I.228.172; 3.I.228.175; 3.I.228.240;
3.I.228.244; 3.I.229.228; 3.I.229.229; 3.I.229.230; 3.I.229.231;
3.I.229.236; 3.I.229.237; 3.I.229.238; 3.I.229.239; 3.I.229.154;
3.I.229.157; 3.I.229.166; 3.I.229.169; 3.I.229.172; 3.I.229.175;
3.I.229.240; 3.I.229.244; 3.I.230.228; 3.I.230.229; 3.I.230.230;
3.I.230.231; 3.I.230.236; 3.I.230.237; 3.I.230.238; 3.I.230.239;
3.I.230.154; 3.I.230.157; 3.I.230.166; 3.I.230.169; 3.I.230.172;
3.I.230.175; 3.I.230.240; 3.I.230.244; 3.I.231.228; 3.I.231.229;
3.I.231.230; 3.I.231.231; 3.I.231.236; 3.I.231.237; 3.I.231.238;
3.I.231.239; 3.I.231.154; 3.I.231.157; 3.I.231.166; 3.I.231.169;
3.I.231.172; 3.I.231.175; 3.I.231.240; 3.I.231.244; 3.I.236.228;
3.I.236.229; 3.I.236.230; 3.I.236.231; 3.I.236.236; 3.I.236.237;
3.I.236.238; 3.I.236.239; 3.I.236.154; 3.I.236.157; 3.I.236.166;
3.I.236.169; 3.I.236.172; 3.I.236.175; 3.I.236.240; 3.I.236.244;
3.I.237.228; 3.I.237.229; 3.I.237.230; 3.I.237.231; 3.I.237.236;
3.I.237.237; 3.I.237.238; 3.I.237.239; 3.I.237.154; 3.I.237.157;
3.I.237.166; 3.I.237.169; 3.I.237.172; 3.I.237.175; 3.I.237.240;
3.I.237.244; 3.I.238.228; 3.I.238.229; 3.I.238.230; 3.I.238.231;
3.I.238.236; 3.I.238.237; 3.I.238.238; 3.I.238.239; 3.I.238.154;
3.I.238.157; 3.I.238.166; 3.I.238.169; 3.I.238.172; 3.I.238.175;
3.I.238.240; 3.I.238.244; 3.I.239.228; 3.I.239.229; 3.I.239.230;
3.I.239.231; 3.I.239.236; 3.I.239.237; 3.I.239.238; 3.I.239.239;
3.I.239.154; 3.I.239.157; 3.I.239.166; 3.I.239.169; 3.I.239.172;
3.I.239.175; 3.I.239.240; 3.I.239.244; 3.I.154.228; 3.I.154.229;
3.I.154.230; 3.I.154.231; 3.I.154.236; 3.I.154.237; 3.I.154.238;
3.I.154.239; 3.I.154.154; 3.I.154.157; 3.I.154.166; 3.I.154.169;
3.I.154.172; 3.I.154.175; 3.I.154.240; 3.I.154.244; 3.I.157.228;
3.I.157.229; 3.I.157.230; 3.I.157.231; 3.I.157.236; 3.I.157.237;
3.I.157.238; 3.I.157.239; 3.I.157.154; 3.I.157.157; 3.I.157.166;
3.I.157.169; 3.I.157.172; 3.I.157.175; 3.I.157.240; 3.I.157.244;
3.I.166.228; 3.I.166.229; 3.I.166.230; 3.I.166.231; 3.I.166.236;
3.I.166.237; 3.I.166.238; 3.I.166.239; 3.I.166.154; 3.I.166.157;
3.I.166.166; 3.I.166.169; 3.I.166.172; 3.I.166.175; 3.I.166.240;
3.I.166.244; 3.I.169.228; 3.I.169.229; 3.I.169.230; 3.I.169.231;
3.I.169.236; 3.I.169.237; 3.I.169.238; 3.I.169.239; 3.I.169.154;
3.I.169.157; 3.I.169.166; 3.I.169.169; 3.I.169.172; 3.I.169.175;
3.I.169.240; 3.I.169.244; 3.I.172.228; 3.I.172.229; 3.I.172.230;
3.I.172.231; 3.I.172.236; 3.I.172.237; 3.I.172.238; 3.I.172.239;
3.I.172.154; 3.I.172.157; 3.I.172.166; 3.I.172.169; 3.I.172.172;
3.I.172.175; 3.I.172.240; 3.I.172.244; 3.I.175.228; 3.I.175.229;
3.I.175.230; 3.I.175.231; 3.I.175.236; 3.I.175.237; 3.I.175.238;
3.I.175.239; 3.I.175.154; 3.I.175.157; 3.I.175.166; 3.I.175.169;
3.I.175.172; 3.I.175.175; 3.I.175.240; 3.I.175.244; 3.I.240.228;
3.I.240.229; 3.I.240.230; 3.I.240.231; 3.I.240.236; 3.I.240.237;
3.I.240.238; 3.I.240.239; 3.I.240.154; 3.I.240.157; 3.I.240.166;
3.I.240.169; 3.I.240.172; 3.I.240.175; 3.I.240.240; 3.I.240.244;
3.I.244.228; 3.I.244.229; 3.I.244.230; 3.I.244.231; 3.I.244.236;
3.I.244.237; 3.I.244.238; 3.I.244.239; 3.I.244.154; 3.I.244.157;
3.I.244.166; 3.I.244.169; 3.I.244.172; 3.I.244.175; 3.I.244.240;
3.I.244.244;
Prodrugs of 3.J 3.J.228.228; 3.J.228.229; 3.J.228.230; 3.J.228.231; 3.J.228.236;
3.J.228.237; 3.J.228.238; 3.J.228.239; 3.J.228.154; 3.J.228.157;
3.J.228.166; 3.J.228.169; 3.J.228.172; 3.J.228.175; 3.J.228.240;
3.J.228.244; 3.J.229.228; 3.J.229.229; 3.J.229.230; 3.J.229.231;
3.J.229.236; 3.J.229.237; 3.J.229.238; 3.J.229.239; 3.J.229.154;
3.J.229.157; 3.J.229.166; 3.J.229.169; 3.J.229.172; 3.J.229.175;
3.J.229.240; 3.J.229.244; 3.J.230.228; 3.J.230.229; 3.J.230.230;
3.J.230.231; 3.J.230.236; 3.J.230.237; 3.J.230.238; 3.J.230.239;
3.J.230.154; 3.J.230.157; 3.J.230.166; 3.J.230.169; 3.J.230.172;
3.J.230.175; 3.J.230.240; 3.J.230.244; 3.J.231.228; 3.J.231.229;
3.J.231.230; 3.J.231.231; 3.J.231.236; 3.J.231.237; 3.J.231.238;
3.J.231.239; 3.J.231.154; 3.J.231.157; 3.J.231.166; 3.J.231.169;
3.J.231.172; 3.J.231.175; 3.J.231.240; 3.J.231.244; 3.J.236.228;
3.J.236.229; 3.J.236.230; 3.J.236.231; 3.J.236.236; 3.J.236.237;
3.J.236.238; 3.J.236.239; 3.J.236.154; 3.J.236.157; 3.J.236.166;
3.J.236.169; 3.J.236.172; 3.J.236.175; 3.J.236.240; 3.J.236.244;
3.J.237.228; 3.J.237.229; 3.J.237.230; 3.J.237.231; 3.J.237.236;
3.J.237.237; 3.J.237.238; 3.J.237.239; 3.J.237.154; 3.J.237.157;
3.J.237.166; 3.J.237.169; 3.J.237.172; 3.J.237.175; 3.J.237.240;
3.J.237.244; 3.J.238.228; 3.J.238.229; 3.J.238.230; 3.J.238.231;
3.J.238.236; 3.J.238.237; 3.J.238.238; 3.J.238.239; 3.J.238.154;
3.J.238.157; 3.J.238.166; 3.J.238.169; 3.J.238.172; 3.J.238.175;
3.J.238.240; 3.J.238.244; 3.J.239.228; 3.J.239.229; 3.J.239.230;
3.J.239.231; 3.J.239.236; 3.J.239.237; 3.J.239.238; 3.J.239.239;
3.J.239.154; 3.J.239.157; 3.J.239.166; 3.J.239.169; 3.J.239.172;
3.J.239.175; 3.J.239.240; 3.J.239.244; 3.1.154.228; 3.J.154.229;
3.J.154.230; 3.J.154.231; 3.J.154.236; 3.J.154.237; 3.J.154.238;
3.J.154.239; 3.J.154.154; 3.J.154.157; 3.J.154.166; 3.J.154.169;
3.J.154.172; 3.J.154.175; 3.J.154.240; 3.J.154.244; 3.J.157.228;
3.J.157.229; 3.J.157.230; 3.J.157.231; 3.J.157.236; 3.J.157.237;
3.J.157.238; 3.J.157.239; 3.J.157.154; 3.J.157.157; 3.J.157.166;
3.J.157.169; 3.J.157.172; 3.J.157.175; 3.J.157.240; 3.J.157.244;
3.J.166.228; 3.J.166.229; 3.J.166.230; 3.J.166.231; 3.J.166.236;
3.J.166.237; 3.J.166.238; 3.J.166.239; 3.J.166.154; 3.J.166.157;
3.J.166.166; 3.J.166.169; 3.J.166.172; 3.J.166.175; 3.J.166.240;
3.J.166.244; 3.J.169.228; 3.J.169.229; 3.J.169.230; 3.J.169.231;
3.1.169.236; 3.J.169.237; 3.J.169.238; 3.J.169.239; 3.J.169.154;
3.J.169.157; 3.J.169.166; 3.J.169.169; 3.J.169.172; 3.J.169.175;
3.J.169.240; 3.J.169.244; 3.J.172.228; 3.J.172.229; 3.J.172.230;
3.J.172.231; 3.J.172.236; 3.J.172.237; 3.J.172.238; 3.J.172.239;
3.J.172.154; 3.J.172.157; 3.J.172.166; 3.J.172.169; 3.J.172.172;
3.J.172.175; 3.J.172.240; 3.J.172.244; 3.J.175.228; 3.J.175.229;
3.J.175.230; 3.J.175.231; 3.J.175.236; 3.J.175.237; 3.J.175.238;
3.J.175.239; 3.J.175.154; 3.J.175.157; 3.1.175.166; 3.J.175.169;
3.J.175.172; 3.J.175.175; 3.1.175.240; 3.J.175.244; 3.J.240.228;
3.J.240.229; 3.J.240.230; 3.J.240.231; 3.J.240.236; 3.J.240.237;
3.J.240.238; 3.J.240.239; 3.J.240.154; 3.J.240.157; 3.J.240.166;
3.J.240.169; 3.J.240.172; 3.J.240.175; 3.J.240.240; 3.J.240.244;
3.J.244.228; 3.J.244.229; 3.J.244.230; 3.J.244.231; 3.J.244.236;
3.J.244.237; 3.J.244.238; 3.J.244.239; 3.J.244.154; 3.J.244.157;
3.J.244.166; 3.J.244.169; 3.J.244.172; 3.1.244.175; 3.J.244.240;
3.J.244.244;
Prodrugs of 3.L 3.L.228.228; 3.L.228.229; 3.L.228.230; 3.L.228.231; 3.L.228.236;
3.L.228.237; 3.L.228.238; 3.L.228.239; 3.L.228.154; 3.L.228.157;
3.L.228.166; 3.L.228.169; 3.L.228.172; 3.L.228.175; 3.L.228.240;
3.L.228.244; 3.L.229.228; 3.L.229.229; 3.L.229.230; 3.L.229.231;
3.L.229.236; 3.L.229.237; 3.L.229.238; 3.L.229.239; 3.L.229.154;
3.L.229.157; 3.L.229.166; 3.L.229.169; 3.L.229.172; 3.L.229.175;
3.L.229.240; 3.L.229.244; 3.L.230.228; 3.L.230.229; 3.L.230.230;
3.L.230.231; 3.L.230.236; 3.L.230.237; 3.L.230.238; 3.L.230.239;
3.L.230.154; 3.L.230.157; 3.L.230.166; 3.L.230.169; 3.L.230.172;
3.L.230.175; 3.L.230.240; 3.L.230.244; 3.L.231.228; 3.L.231.229;
3.L.231.230; 3.L.231.231; 3.L.231.236; 3.L.231.237; 3.L.231.238;
3.L.231.239; 3.L.231.154; 3.L.231.157; 3.L.231.166; 3.L.231.169;
3.L.231.172; 3.L.231.175; 3.L.231.240; 3.L.231.244; 3.L.236.228;
3.L.236.229; 3.L.236.230; 3.L.236.231; 3.L.236.236; 3.L.236.237;
3.L.236.238; 3.L.236.239; 3.L.236.154; 3.L.236.157; 3.L.236.166;
3.L.236.169; 3.L.236.172; 3.L.236.175; 3.L.236.240; 3.L.236.244;
3.L.237.228; 3.L.237.229; 3.L.237.230; 3.L.237.231; 3.L.237.236;
3.L.237.237; 3.L.237.238; 3.L.237.239; 3.L.237.154; 3.L.237.157;
3.L.237.166; 3.L.237.169; 3.L.237.172; 3.L.237.175; 3.L.237.240;

TABLE 7-continued

3.L.237.244; 3.L.238.228; 3.L.238.229; 3.L.238.230; 3.L.238.231; 3.L.238.236; 3.L.238.237; 3.L.238.238; 3.L.238.239; 3.L.238.154; 3.L.238.157; 3.L.238.166; 3.L.238.169; 3.L.238.172; 3.L.238.175; 3.L.238.240; 3.L.238.244; 3.L.239.228; 3.L.239.229; 3.L.239.230; 3.L.239.231; 3.L.239.236; 3.L.239.237; 3.L.239.238; 3.L.239.239; 3.L.239.154; 3.L.239.157; 3.L.239.166; 3.L.239.169; 3.L.239.172; 3.L.239.175; 3.L.239.240; 3.L.239.244; 3.L.154.228; 3.L.154.229; 3.L.154.230; 3.L.154.231; 3.L.154.236; 3.L.154.237; 3.L.154.238; 3.L.154.239; 3.L.154.154; 3.L.154.157; 3.L.154.166; 3.L.154.169; 3.L.154.172; 3.L.154.175; 3.L.154.240; 3.L.154.244; 3.L.157.228; 3.L.157.229; 3.L.157.230; 3.L.157.231; 3.L.157.236; 3.L.157.237; 3.L.157.238; 3.L.157.239; 3.L.157.154; 3.L.157.157; 3.L.157.166; 3.L.157.169; 3.L.157.172; 3.L.157.175; 3.L.157.240; 3.L.157.244; 3.L.166.228; 3.L.166.229; 3.L.166.230; 3.L.166.231; 3.L.166.236; 3.L.166.237; 3.L.166.238; 3.L.166.239; 3.L.166.154; 3.L.166.157; 3.L.166.166; 3.L.166.169; 3.L.166.172; 3.L.166.175; 3.L.166.240; 3.L.166.244; 3.L.169.228; 3.L.169.229; 3.L.169.230; 3.L.169.231; 3.L.169.236; 3.L.169.237; 3.L.169.238; 3.L.169.239; 3.L.169.154; 3.L.169.157; 3.L.169.166; 3.L.169.169; 3.L.169.172; 3.L.169.175; 3.L.169.240; 3.L.169.244; 3.L.172.228; 3.L.172.229; 3.L.172.230; 3.L.172.231; 3.L.172.236; 3.L.172.237; 3.L.172.238; 3.L.172.239; 3.L.172.154; 3.L.172.157; 3.L.172.166; 3.L.172.169; 3.L.172.172; 3.L.172.175; 3.L.172.240; 3.L.172.244; 3.L.175.228; 3.L.175.229; 3.L.175.230; 3.L.175.231; 3.L.175.236; 3.L.175.237; 3.L.175.238; 3.L.175.239; 3.L.175.154; 3.L.175.157; 3.L.175.166; 3.L.175.169; 3.L.175.172; 3.L.175.175; 3.L.175.240; 3.L.175.244; 3.L.240.228; 3.L.240.229; 3.L.240.230; 3.L.240.231; 3.L.240.236; 3.L.240.237; 3.L.240.238; 3.L.240.239; 3.L.240.154; 3.L.240.157; 3.L.240.166; 3.L.240.169; 3.L.240.172; 3.L.240.175; 3.L.240.240; 3.L.240.244; 3.L.244.228; 3.L.244.229; 3.L.244.230; 3.L.244.231; 3.L.244.236; 3.L.244.237; 3.L.244.238; 3.L.244.239; 3.L.244.154; 3.L.244.157; 3.L.244.166; 3.L.244.169; 3.L.244.172; 3.L.244.175; 3.L.244.240; 3.L.244.244;

Prodrugs of 3.O

3.O.228.228; 3.O.228.229; 3.O.228.230; 3.O.228.231; 3.O.228.236; 3.O.228.237; 3.O.228.238; 3.O.228.239; 3.O.228.154; 3.O.228.157; 3.O.228.166; 3.O.228.169; 3.O.228.172; 3.O.228.175; 3.O.228.240; 3.O.228.244; 3.O.229.228; 3.O.229.229; 3.O.229.230; 3.O.229.231; 3.O.229.236; 3.O.229.237; 3.O.229.238; 3.O.229.239; 3.O.229.154; 3.O.229.157; 3.O.229.166; 3.O.229.169; 3.O.229.172; 3.O.229.175; 3.O.229.240; 3.O.229.244; 3.O.230.228; 3.O.230.229; 3.O.230.230; 3.O.230.231; 3.O.230.236; 3.O.230.237; 3.O.230.238; 3.O.230.239; 3.O.230.154; 3.O.230.157; 3.O.230.166; 3.O.230.169; 3.O.230.172; 3.O.230.175; 3.O.230.240; 3.O.230.244; 3.O.231.228; 3.O.231.229; 3.O.231.230; 3.O.231.231; 3.O.231.236; 3.O.231.237; 3.O.231.238; 3.O.231.239; 3.O.231.154; 3.O.231.157; 3.O.231.166; 3.O.231.169; 3.O.231.172; 3.O.231.175; 3.O.231.240; 3.O.231.244; 3.O.236.228; 3.O.236.229; 3.O.236.230; 3.O.236.231; 3.O.236.236; 3.O.236.237; 3.O.236.238; 3.O.236.239; 3.O.236.154; 3.O.236.157; 3.O.236.166; 3.O.236.169; 3.O.236.172; 3.O.236.175; 3.O.236.240; 3.O.236.244; 3.O.237.228; 3.O.237.229; 3.O.237.230; 3.O.237.231; 3.O.237.236; 3.O.237.237; 3.O.237.238; 3.O.237.239; 3.O.237.154; 3.O.237.157; 3.O.237.166; 3.O.237.169; 3.O.237.172; 3.O.237.175; 3.O.237.240; 3.O.237.244; 3.O.238.228; 3.O.238.229; 3.O.238.230; 3.O.238.231; 3.O.238.236; 3.O.238.237; 3.O.238.238; 3.O.238.239; 3.O.238.154; 3.O.238.157; 3.O.238.166; 3.O.238.169; 3.O.238.172; 3.O.238.175; 3.O.238.240; 3.O.238.244; 3.O.239.228; 3.O.239.229; 3.O.239.230; 3.O.239.231; 3.O.239.236; 3.O.239.237; 3.O.239.238; 3.O.239.239; 3.O.239.154; 3.O.239.157; 3.O.239.166; 3.O.239.169; 3.O.239.172; 3.O.239.175; 3.O.239.240; 3.O.239.244; 3.O.154.228; 3.O.154.229; 3.O.154.230; 3.O.154.231; 3.O.154.236; 3.O.154.237; 3.O.154.238; 3.O.154.239; 3.O.154.154; 3.O.154.157; 3.O.154.166; 3.O.154.169; 3.O.154.172; 3.O.154.175; 3.O.154.240; 3.O.154.244; 3.O.157.228; 3.O.157.229; 3.O.157.230; 3.O.157.231; 3.O.157.236; 3.O.157.237; 3.O.157.238; 3.O.157.239; 3.O.157.154; 3.O.157.157; 3.O.157.166; 3.O.157.169; 3.O.157.172; 3.O.157.175; 3.O.157.240; 3.O.157.244; 3.O.166.228; 3.O.166.229; 3.O.166.230; 3.O.166.231; 3.O.166.236; 3.O.166.237; 3.O.166.238; 3.O.166.239; 3.O.166.154; 3.O.166.157; 3.O.166.166; 3.O.166.169; 3.O.166.172; 3.O.166.175; 3.O.166.240; 3.O.166.244; 3.O.169.228; 3.O.169.229; 3.O.169.230; 3.O.169.231; 3.O.169.236; 3.O.169.237; 3.O.169.238; 3.O.169.239; 3.O.169.154; 3.O.169.157; 3.O.169.166; 3.O.169.169; 3.O.169.172; 3.O.169.175; 3.O.169.240; 3.O.169.244; 3.O.172.228; 3.O.172.229; 3.O.172.230; 3.O.172.231; 3.O.172.236; 3.O.172.237; 3.O.172.238; 3.O.172.239; 3.O.172.154; 3.O.172.157; 3.O.172.166; 3.O.172.169; 3.O.172.172; 3.O.172.175; 3.O.172.240; 3.O.172.244; 3.O.175.228; 3.O.175.229; 3.O.175.230; 3.O.175.231; 3.O.175.236; 3.O.175.237; 3.O.175.238; 3.O.175.239; 3.O.175.154; 3.O.175.157; 3.O.175.166; 3.O.175.169; 3.O.175.172; 3.O.175.175; 3.O.175.240; 3.O.175.244; 3.O.240.228; 3.O.240.229; 3.O.240.230; 3.O.240.231; 3.O.240.236; 3.O.240.237; 3.O.240.238; 3.O.240.239; 3.O.240.154; 3.O.240.157; 3.O.240.166; 3.O.240.169; 3.O.240.172; 3.O.240.175; 3.O.240.240; 3.O.240.244; 3.O.244.228; 3.O.244.229; 3.O.244.230; 3.O.244.231; 3.O.244.236; 3.O.244.237; 3.O.244.238; 3.O.244.239; 3.O.244.154; 3.O.244.157; 3.O.244.166; 3.O.244.169; 3.O.244.172; 3.O.244.175; 3.O.244.240; 3.O.244.244;

Prodrugs of 3.P

3.P.228.228; 3.P.228.229; 3.P.228.230; 3.P.228.231; 3.P.228.236; 3.P.228.237; 3.P.228.238; 3.P.228.239; 3.P.228.154; 3.P.228.157; 3.P.228.166; 3.P.228.169; 3.P.228.172; 3.P.228.175; 3.P.228.240; 3.P.228.244; 3.P.229.228; 3.P.229.229; 3.P.229.230; 3.P.229.231; 3.P.229.236; 3.P.229.237; 3.P.229.238; 3.P.229.239; 3.P.229.154; 3.P.229.157; 3.P.229.166; 3.P.229.169; 3.P.229.172; 3.P.229.175; 3.P.229.240; 3.P.229.244; 3.P.230.228; 3.P.230.229; 3.P.230.230; 3.P.230.231; 3.P.230.236; 3.P.230.237; 3.P.230.238; 3.P.230.239; 3.P.230.154; 3.P.230.157; 3.P.230.166; 3.P.230.169; 3.P.230.172; 3.P.230.175; 3.P.230.240; 3.P.230.244; 3.P.231.228; 3.P.231.229; 3.P.231.230; 3.P.231.231; 3.P.231.236; 3.P.231.237; 3.P.231.238; 3.P.231.239; 3.P.231.154; 3.P.231.157; 3.P.231.166; 3.P.231.169; 3.P.231.172; 3.P.231.175; 3.P.231.240; 3.P.231.244; 3.P.236.228; 3.P.236.229; 3.P.236.230; 3.P.236.231; 3.P.236.236; 3.P.236.237; 3.P.236.238; 3.P.236.239; 3.P.236.154; 3.P.236.157; 3.P.236.166; 3.P.236.169; 3.P.236.172; 3.P.236.175; 3.P.236.240; 3.P.236.244; 3.P.237.228; 3.P.237.229; 3.P.237.230; 3.P.237.231; 3.P.237.236; 3.P.237.237; 3.P.237.238; 3.P.237.239; 3.P.237.154; 3.P.237.157; 3.P.237.166; 3.P.237.169; 3.P.237.172; 3.P.237.175; 3.P.237.240; 3.P.237.244; 3.P.238.228; 3.P.238.229; 3.P.238.230; 3.P.238.231; 3.P.238.236; 3.P.238.237; 3.P.238.238; 3.P.238.239; 3.P.238.154; 3.P.238.157; 3.P.238.166; 3.P.238.169; 3.P.238.172; 3.P.238.175; 3.P.238.240; 3.P.238.244; 3.P.239.228; 3.P.239.229; 3.P.239.230; 3.P.239.231; 3.P.239.236; 3.P.239.237; 3.P.239.238; 3.P.239.239; 3.P.239.154; 3.P.239.157; 3.P.239.166; 3.P.239.169; 3.P.239.172; 3.P.239.175; 3.P.239.240; 3.P.239.244; 3.P.154.228; 3.P.154.229; 3.P.154.230; 3.P.154.231; 3.P.154.236; 3.P.154.237; 3.P.154.238; 3.P.154.239; 3.P.154.154; 3.P.154.157; 3.P.154.166; 3.P.154.169; 3.P.154.172; 3.P.154.175; 3.P.154.240; 3.P.154.244; 3.P.157.228; 3.P.157.229; 3.P.157.230; 3.P.157.231; 3.P.157.236; 3.P.157.237; 3.P.157.238; 3.P.157.239; 3.P.157.154; 3.P.157.157; 3.P.157.166; 3.P.157.169; 3.P.157.172; 3.P.157.175; 3.P.157.240; 3.P.157.244; 3.P.166.228; 3.P.166.229; 3.P.166.230; 3.P.166.231; 3.P.166.236; 3.P.166.237; 3.P.166.238; 3.P.166.239; 3.P.166.154; 3.P.166.157; 3.P.166.166; 3.P.166.169; 3.P.166.172; 3.P.166.175; 3.P.166.240; 3.P.166.244; 3.P.169.228; 3.P.169.229; 3.P.169.230; 3.P.169.231; 3.P.169.236; 3.P.169.237; 3.P.169.238; 3.P.169.239; 3.P.169.154; 3.P.169.157; 3.P.169.166; 3.P.169.169; 3.P.169.172; 3.P.169.175; 3.P.169.240; 3.P.169.244; 3.P.172.228; 3.P.172.229; 3.P.172.230; 3.P.172.231; 3.P.172.236; 3.P.172.237; 3.P.172.238; 3.P.172.239; 3.P.172.154; 3.P.172.157; 3.P.172.166; 3.P.172.169; 3.P.172.172; 3.P.172.175; 3.P.172.240; 3.P.172.244; 3.P.175.228; 3.P.175.229; 3.P.175.230; 3.P.175.231; 3.P.175.236; 3.P.175.237; 3.P.175.238; 3.P.175.239; 3.P.175.154; 3.P.175.157; 3.P.175.166; 3.P.175.169; 3.P.175.172; 3.P.175.175; 3.P.175.240; 3.P.175.244; 3.P.240.228; 3.P.240.229; 3.P.240.230; 3.P.240.231; 3.P.240.236; 3.P.240.237; 3.P.240.238; 3.P.240.239; 3.P.240.154; 3.P.240.157; 3.P.240.166; 3.P.240.169; 3.P.240.172; 3.P.240.175; 3.P.240.240; 3.P.240.244; 3.P.244.228; 3.P.244.229; 3.P.244.230; 3.P.244.231; 3.P.244.236; 3.P.244.237; 3.P.244.238; 3.P.244.239; 3.P.244.154; 3.P.244.157; 3.P.244.166; 3.P.244.169; 3.P.244.172; 3.P.244.175; 3.P.244.240; 3.P.244.244;

Prodrugs of 3.U

3.U.228.228; 3.U.228.229; 3.U.228.230; 3.U.228.231; 3.U.228.236; 3.U.228.237; 3.U.228.238; 3.U.228.239; 3.U.228.154; 3.U.228.157; 3.U.228.166; 3.U.228.169; 3.U.228.172; 3.U.228.175; 3.U.228.240; 3.U.228.244; 3.U.229.228; 3.U.229.229; 3.U.229.230; 3.U.229.231; 3.U.229.236; 3.U.229.237; 3.U.229.238; 3.U.229.239; 3.U.229.154; 3.U.229.157; 3.U.229.166; 3.U.229.169; 3.U.229.172; 3.U.229.175; 3.U.229.240; 3.U.229.244; 3.U.230.228; 3.U.230.229; 3.U.230.230; 3.U.230.231; 3.U.230.236; 3.U.230.237; 3.U.230.238; 3.U.230.239; 3.U.230.154; 3.U.230.157; 3.U.230.166; 3.U.230.169; 3.U.230.172; 3.U.230.175; 3.U.230.240; 3.U.230.244; 3.U.231.228; 3.U.231.229; 3.U.231.230; 3.U.231.231; 3.U.231.236; 3.U.231.237; 3.U.231.238; 3.U.231.239; 3.U.231.154; 3.U.231.157; 3.U.231.166; 3.U.231.169; 3.U.231.172; 3.U.231.175; 3.U.231.240; 3.U.231.244; 3.U.236.228; 3.U.236.229; 3.U.236.230; 3.U.236.231; 3.U.236.236; 3.U.236.237; 3.U.236.238; 3.U.236.239; 3.U.236.154; 3.U.236.157; 3.U.236.166;

TABLE 7-continued

3.U.236.169; 3.U.236.172; 3.U.236.175; 3.U.236.240; 3.U.236.244; 3.U.237.228; 3.U.237.229; 3.U.237.230; 3.U.237.231; 3.U.237.236; 3.U.237.237; 3.U.237.238; 3.U.237.239; 3.U.237.154; 3.U.237.157; 3.U.237.166; 3.U.237.169; 3.U.237.172; 3.U.237.175; 3.U.237.240; 3.U.237.244; 3.U.238.228; 3.U.238.229; 3.U.238.230; 3.U.238.231; 3.U.238.236; 3.U.238.237; 3.U.238.238; 3.U.238.239; 3.U.238.154; 3.U.238.157; 3.U.238.166; 3.U.238.169; 3.U.238.172; 3.U.238.175; 3.U.238.240; 3.U.238.244; 3.U.239.228; 3.U.239.229; 3.U.239.230; 3.U.239.231; 3.U.239.236; 3.U.239.237; 3.U.239.238; 3.U.239.239; 3.U.239.154; 3.U.239.157; 3.U.239.166; 3.U.239.169; 3.U.239.172; 3.U.239.175; 3.U.239.240; 3.U.239.244; 3.U.154.228; 3.U.154.229; 3.U.154.230; 3.U.154.231; 3.U.154.236; 3.U.154.237; 3.U.154.238; 3.U.154.239; 3.U.154.154; 3.U.154.157; 3.U.154.166; 3.U.154.169; 3.U.154.172; 3.U.154.175; 3.U.154.240; 3.U.154.244; 3.U.157.228; 3.U.157.229; 3.U.157.230; 3.U.157.231; 3.U.157.236; 3.U.157.237; 3.U.157.238; 3.U.157.239; 3.U.157.154; 3.U.157.157; 3.U.157.166; 3.U.157.169; 3.U.157.172; 3.U.157.175; 3.U.157.240; 3.U.157.244; 3.U.166.228; 3.U.166.229; 3.U.166.230; 3.U.166.231; 3.U.166.236; 3.U.166.237; 3.U.166.238; 3.U.166.239; 3.U.166.154; 3.U.166.157; 3.U.166.166; 3.U.166.169; 3.U.166.172; 3.U.166.175; 3.U.166.240; 3.U.166.244; 3.U.169.228; 3.U.169.229; 3.U.169.230; 3.U.169.231; 3.U.169.236; 3.U.169.237; 3.U.169.238; 3.U.169.239; 3.U.169.154; 3.U.169.157; 3.U.169.166; 3.U.169.169; 3.U.169.172; 3.U.169.175; 3.U.169.240; 3.U.169.244; 3.U.172.228; 3.U.172.229; 3.U.172.230; 3.U.172.231; 3.U.172.236; 3.U.172.237; 3.U.172.238; 3.U.172.239; 3.U.172.154; 3.U.172.157; 3.U.172.166; 3.U.172.169; 3.U.172.172; 3.U.172.175; 3.U.172.240; 3.U.172.244; 3.U.175.228; 3.U.175.229; 3.U.175.230; 3.U.175.231; 3.U.175.236; 3.U.175.237; 3.U.175.238; 3.U.175.239; 3.U.175.154; 3.U.175.157; 3.U.175.166; 3.U.175.169; 3.U.175.172; 3.U.175.175; 3.U.175.240; 3.U.175.244; 3.U.240.228; 3.U.240.229; 3.U.240.230; 3.U.240.231; 3.U.240.236; 3.U.240.237; 3.U.240.238; 3.U.240.239; 3.U.240.154; 3.U.240.157; 3.U.240.166; 3.U.240.169; 3.U.240.172; 3.U.240.175; 3.U.240.240; 3.U.240.244; 3.U.244.228; 3.U.244.229; 3.U.244.230; 3.U.244.231; 3.U.244.236; 3.U.244.237; 3.U.244.238; 3.U.244.239; 3.U.244.154; 3.U.244.157; 3.U.244.166; 3.U.244.169; 3.U.244.172; 3.U.244.175; 3.U.244.240; 3.U.244.244;
Prodrugs of 3.W 3.W.228.228; 3.W.228.229; 3.W.228.230; 3.W.228.231; 3.W.228.236; 3.W.228.237; 3.W.228.238; 3.W.228.239; 3.W.228.154; 3.W.228.157; 3.W.228.166; 3.W.228.169; 3.W.228.172; 3.W.228.175; 3.W.228.240; 3.W.228.244; 3.W.229.228; 3.W.229.229; 3.W.229.230; 3.W.229.231; 3.W.229.236; 3.W.229.237; 3.W.229.238; 3.W.229.239; 3.W.229.154; 3.W.229.157; 3.W.229.166; 3.W.229.169; 3.W.229.172; 3.W.229.175; 3.W.229.240; 3.W.229.244; 3.W.230.228; 3.W.230.229; 3.W.230.230; 3.W.230.231; 3.W.230.236; 3.W.230.237; 3.W.230.238; 3.W.230.239; 3.W.230.154; 3.W.230.157; 3.W.230.166; 3.W.230.169; 3.W.230.172; 3.W.230.175; 3.W.230.240; 3.W.230.244; 3.W.231.228; 3.W.231.229; 3.W.231.230; 3.W.231.231; 3.W.231.236; 3.W.231.237; 3.W.231.238; 3.W.231.239; 3.W.231.154; 3.W.231.157; 3.W.231.166; 3.W.231.169; 3.W.231.172; 3.W.231.175; 3.W.231.240; 3.W.231.244; 3.W.236.228; 3.W.236.229; 3.W.236.230; 3.W.236.231; 3.W.236.236; 3.W.236.237; 3.W.236.238; 3.W.236.239; 3.W.236.154; 3.W.236.157; 3.W.236.166; 3.W.236.169; 3.W.236.172; 3.W.236.175; 3.W.236.240; 3.W.236.244; 3.W.237.228; 3.W.237.229; 3.W.237.230; 3.W.237.231; 3.W.237.236; 3.W.237.237; 3.W.237.238; 3.W.237.239; 3.W.237.154; 3.W.237.157; 3.W.237.166; 3.W.237.169; 3.W.237.172; 3.W.237.175; 3.W.237.240; 3.W.237.244; 3.W.238.228; 3.W.238.229; 3.W.238.230; 3.W.238.231; 3.W.238.236; 3.W.238.237; 3.W.238.238; 3.W.238.239; 3.W.238.154; 3.W.238.157; 3.W.238.166; 3.W.238.169; 3.W.238.172; 3.W.238.175; 3.W.238.240; 3.W.238.244; 3.W.239.228; 3.W.239.229; 3.W.239.230; 3.W.239.231; 3.W.239.236; 3.W.239.237; 3.W.239.238; 3.W.239.239; 3.W.239.154; 3.W.239.157; 3.W.239.166; 3.W.239.169; 3.W.239.172; 3.W.239.175; 3.W.239.240; 3.W.239.244; 3.W.154.228; 3.W.154.229; 3.W.154.230; 3.W.154.231; 3.W.154.236; 3.W.154.237; 3.W.154.238; 3.W.154.239; 3.W.154.154; 3.W.154.157; 3.W.154.166; 3.W.154.169; 3.W.154.172; 3.W.154.175; 3.W.154.240; 3.W.154.244; 3.W.157.228; 3.W.157.229; 3.W.157.230; 3.W.157.231; 3.W.157.236; 3.W.157.237; 3.W.157.238; 3.W.157.239; 3.W.157.154; 3.W.157.157; 3.W.157.166; 3.W.157.169; 3.W.157.172; 3.W.157.175; 3.W.157.240; 3.W.157.244; 3.W.166.228; 3.W.166.229; 3.W.166.230; 3.W.166.231; 3.W.166.236; 3.W.166.237; 3.W.166.238; 3.W.166.239; 3.W.166.154; 3.W.166.157; 3.W.166.166; 3.W.166.169; 3.W.166.172; 3.W.166.175; 3.W.166.240; 3.W.166.244; 3.W.169.228; 3.W.169.229; 3.W.169.230; 3.W.169.231; 3.W.169.236; 3.W.169.237; 3.W.169.238; 3.W.169.239; 3.W.169.154; 3.W.169.157; 3.W.169.166; 3.W.169.169; 3.W.169.172; 3.W.169.175; 3.W.169.240; 3.W.169.244; 3.W.172.228; 3.W.172.229; 3.W.172.230; 3.W.172.231; 3.W.172.236; 3.W.172.237; 3.W.172.238; 3.W.172.239; 3.W.172.154; 3.W.172.157; 3.W.172.166; 3.W.172.169; 3.W.172.172; 3.W.172.175; 3.W.172.240; 3.W.172.244; 3.W.175.228; 3.W.175.229; 3.W.175.230; 3.W.175.231; 3.W.175.236; 3.W.175.237; 3.W.175.238; 3.W.175.239; 3.W.175.154; 3.W.175.157; 3.W.175.166; 3.W.175.169; 3.W.175.172; 3.W.175.175; 3.W.175.240; 3.W.175.244; 3.W.240.228; 3.W.240.229; 3.W.240.230; 3.W.240.231; 3.W.240.236; 3.W.240.237; 3.W.240.238; 3.W.240.239; 3.W.240.154; 3.W.240.157; 3.W.240.166; 3.W.240.169; 3.W.240.172; 3.W.240.175; 3.W.240.240; 3.W.240.244; 3.W.244.228; 3.W.244.229; 3.W.244.230; 3.W.244.231; 3.W.244.236; 3.W.244.237; 3.W.244.238; 3.W.244.239; 3.W.244.154; 3.W.244.157; 3.W.244.166; 3.W.244.169; 3.W.244.172; 3.W.244.175; 3.W.244.240; 3.W.244.244;
Prodrugs of 3.Y 3.Y.228.228; 3.Y.228.229; 3.Y.228.230; 3.Y.228.231; 3.Y.228.236; 3.Y.228.237; 3.Y.228.238; 3.Y.228.239; 3.Y.228.154; 3.Y.228.157; 3.Y.228.166; 3.Y.228.169; 3.Y.228.172; 3.Y.228.175; 3.Y.228.240; 3.Y.228.244; 3.Y.229.228; 3.Y.229.229; 3.Y.229.230; 3.Y.229.231; 3.Y.229.236; 3.Y.229.237; 3.Y.229.238; 3.Y.229.239; 3.Y.229.154; 3.Y.229.157; 3.Y.229.166; 3.Y.229.169; 3.Y.229.172; 3.Y.229.175; 3.Y.229.240; 3.Y.229.244; 3.Y.230.228; 3.Y.230.229; 3.Y.230.230; 3.Y.230.231; 3.Y.230.236; 3.Y.230.237; 3.Y.230.238; 3.Y.230.239; 3.Y.230.154; 3.Y.230.157; 3.Y.230.166; 3.Y.230.169; 3.Y.230.172; 3.Y.230.175; 3.Y.230.240; 3.Y.230.244; 3.Y.231.228; 3.Y.231.229; 3.Y.231.230; 3.Y.231.231; 3.Y.231.236; 3.Y.231.237; 3.Y.231.238; 3.Y.231.239; 3.Y.231.154; 3.Y.231.157; 3.Y.231.166; 3.Y.231.169; 3.Y.231.172; 3.Y.231.175; 3.Y.231.240; 3.Y.231.244; 3.Y.236.228; 3.Y.236.229; 3.Y.236.230; 3.Y.236.231; 3.Y.236.236; 3.Y.236.237; 3.Y.236.238; 3.Y.236.239; 3.Y.236.154; 3.Y.236.157; 3.Y.236.166; 3.Y.236.169; 3.Y.236.172; 3.Y.236.175; 3.Y.236.240; 3.Y.236.244; 3.Y.237.228; 3.Y.237.229; 3.Y.237.230; 3.Y.237.231; 3.Y.237.236; 3.Y.237.237; 3.Y.237.238; 3.Y.237.239; 3.Y.237.154; 3.Y.237.157; 3.Y.237.166; 3.Y.237.169; 3.Y.237.172; 3.Y.237.175; 3.Y.237.240; 3.Y.237.244; 3.Y.238.228; 3.Y.238.229; 3.Y.238.230; 3.Y.238.231; 3.Y.238.236; 3.Y.238.237; 3.Y.238.238; 3.Y.238.239; 3.Y.238.154; 3.Y.238.157; 3.Y.238.166; 3.Y.238.169; 3.Y.238.172; 3.Y.238.175; 3.Y.238.240; 3.Y.238.244; 3.Y.239.228; 3.Y.239.229; 3.Y.239.230; 3.Y.239.231; 3.Y.239.236; 3.Y.239.237; 3.Y.239.238; 3.Y.239.239; 3.Y.239.154; 3.Y.239.157; 3.Y.239.166; 3.Y.239.169; 3.Y.239.172; 3.Y.239.175; 3.Y.239.240; 3.Y.239.244; 3.Y.154.228; 3.Y.154.229; 3.Y.154.230; 3.Y.154.231; 3.Y.154.236; 3.Y.154.237; 3.Y.154.238; 3.Y.154.239; 3.Y.154.154; 3.Y.154.157; 3.Y.154.166; 3.Y.154.169; 3.Y.154.172; 3.Y.154.175; 3.Y.154.240; 3.Y.154.244; 3.Y.157.228; 3.Y.157.229; 3.Y.157.230; 3.Y.157.231; 3.Y.157.236; 3.Y.157.237; 3.Y.157.238; 3.Y.157.239; 3.Y.157.154; 3.Y.157.157; 3.Y.157.166; 3.Y.157.169; 3.Y.157.172; 3.Y.157.175; 3.Y.157.240; 3.Y.157.244; 3.Y.166.228; 3.Y.166.229; 3.Y.166.230; 3.Y.166.231; 3.Y.166.236; 3.Y.166.237; 3.Y.166.238; 3.Y.166.239; 3.Y.166.154; 3.Y.166.157; 3.Y.166.166; 3.Y.166.169; 3.Y.166.172; 3.Y.166.175; 3.Y.166.240; 3.Y.166.244; 3.Y.169.228; 3.Y.169.229; 3.Y.169.230; 3.Y.169.231; 3.Y.169.236; 3.Y.169.237; 3.Y.169.238; 3.Y.169.239; 3.Y.169.154; 3.Y.169.157; 3.Y.169.166; 3.Y.169.169; 3.Y.169.172; 3.Y.169.175; 3.Y.169.240; 3.Y.169.244; 3.Y.172.228; 3.Y.172.229; 3.Y.172.230; 3.Y.172.231; 3.Y.172.236; 3.Y.172.237; 3.Y.172.238; 3.Y.172.239; 3.Y.172.154; 3.Y.172.157; 3.Y.172.166; 3.Y.172.169; 3.Y.172.172; 3.Y.172.175; 3.Y.172.240; 3.Y.172.244; 3.Y.175.228; 3.Y.175.229; 3.Y.175.230; 3.Y.175.231; 3.Y.175.236; 3.Y.175.237; 3.Y.175.238; 3.Y.175.239; 3.Y.175.154; 3.Y.175.157; 3.Y.175.166; 3.Y.175.169; 3.Y.175.172; 3.Y.175.175; 3.Y.175.240; 3.Y.175.244; 3.Y.240.228; 3.Y.240.229; 3.Y.240.230; 3.Y.240.231; 3.Y.240.236; 3.Y.240.237; 3.Y.240.238; 3.Y.240.239; 3.Y.240.154; 3.Y.240.157; 3.Y.240.166; 3.Y.240.169; 3.Y.240.172; 3.Y.240.175; 3.Y.240.240; 3.Y.240.244; 3.Y.244.228; 3.Y.244.229; 3.Y.244.230; 3.Y.244.231; 3.Y.244.236; 3.Y.244.237; 3.Y.244.238; 3.Y.244.239; 3.Y.244.154; 3.Y.244.157; 3.Y.244.166; 3.Y.244.169; 3.Y.244.172; 3.Y.244.175; 3.Y.244.240; 3.Y.244.244;
Prodrugs of 4.B 4.B.228.228; 4.B.228.229; 4.B.228.230; 4.B.228.231; 4.B.228.236; 4.B.228.237; 4.B.228.238; 4.B.228.239; 4.B.228.154; 4.B.228.157; 4.B.228.166; 4.B.228.169; 4.B.228.172; 4.B.228.175; 4.B.228.240; 4.B.228.244; 4.B.229.228; 4.B.229.229; 4.B.229.230; 4.B.229.231; 4.B.229.236; 4.B.229.237; 4.B.229.238; 4.B.229.239; 4.B.229.154; 4.B.229.157; 4.B.229.166; 4.B.229.169; 4.B.229.172; 4.B.229.175; 4.B.229.240; 4.B.229.244; 4.B.230.228; 4.B.230.229; 4.B.230.230; 4.B.230.231; 4.B.230.236; 4.B.230.237; 4.B.230.238; 4.B.230.239; 4.B.230.154; 4.B.230.157; 4.B.230.166; 4.B.230.169; 4.B.230.172; 4.B.230.175; 4.B.230.240; 4.B.230.244; 4.B.231.228; 4.B.231.229; 4.B.231.230; 4.B.231.231; 4.B.231.236; 4.B.231.237; 4.B.231.238;

TABLE 7-continued

4.B.231.239; 4.B.231.154; 4.B.231.157; 4.B.231.166; 4.B.231.169; 4.B.231.172; 4.B.231.175; 4.B.231.240; 4.B.231.244; 4.B.236.228; 4.B.236.229; 4.B.236.230; 4.B.236.231; 4.B.236.236; 4.B.236.237; 4.B.236.238; 4.B.236.239; 4.B.236.154; 4.B.236.157; 4.B.236.166; 4.B.236.169; 4.B.236.172; 4.B.236.175; 4.B.236.240; 4.B.236.244; 4.B.237.228; 4.B.237.229; 4.B.237.230; 4.B.237.231; 4.B.237.236; 4.B.237.237; 4.B.237.238; 4.B.237.239; 4.B.237.154; 4.B.237.157; 4.B.237.166; 4.B.237.169; 4.B.237.172; 4.B.237.175; 4.B.237.240; 4.B.237.244; 4.B.238.228; 4.B.238.229; 4.B.238.230; 4.B.238.231; 4.B.238.236; 4.B.238.237; 4.B.238.238; 4.B.238.239; 4.B.238.154; 4.B.238.157; 4.B.238.166; 4.B.238.169; 4.B.238.172; 4.B.238.175; 4.B.238.240; 4.B.238.244; 4.B.239.228; 4.B.239.229; 4.B.239.230; 4.B.239.231; 4.B.239.236; 4.B.239.237; 4.B.239.238; 4.B.239.239; 4.B.239.154; 4.B.239.157; 4.B.239.166; 4.B.239.169; 4.B.239.172; 4.B.239.175; 4.B.239.240; 4.B.239.244; 4.B.154.228; 4.B.154.229; 4.B.154.230; 4.B.154.231; 4.B.154.236; 4.B.154.237; 4.B.154.238; 4.B.154.239; 4.B.154.154; 4.B.154.157; 4.B.154.166; 4.B.154.169; 4.B.154.172; 4.B.154.175; 4.B.154.240; 4.B.154.244; 4.B.157.228; 4.B.157.229; 4.B.157.230; 4.B.157.231; 4.B.157.236; 4.B.157.237; 4.B.157.238; 4.B.157.239; 4.B.157.154; 4.B.157.157; 4.B.157.166; 4.B.157.169; 4.B.157.172; 4.B.157.175; 4.B.157.240; 4.B.157.244; 4.B.166.228; 4.B.166.229; 4.B.166.230; 4.B.166.231; 4.B.166.236; 4.B.166.237; 4.B.166.238; 4.B.166.239; 4.B.166.154; 4.B.166.157; 4.B.166.166; 4.B.166.169; 4.B.166.172; 4.B.166.175; 4.B.166.240; 4.B.166.244; 4.B.169.228; 4.B.169.229; 4.B.169.230; 4.B.169.231; 4.B.169.236; 4.B.169.237; 4.B.169.238; 4.B.169.239; 4.B.169.154; 4.B.169.157; 4.B.169.166; 4.B.169.169; 4.B.169.172; 4.B.169.175; 4.B.169.240; 4.B.169.244; 4.B.172.228; 4.B.172.229; 4.B.172.230; 4.B.172.231; 4.B.172.236; 4.B.172.237; 4.B.172.238; 4.B.172.239; 4.B.172.154; 4.B.172.157; 4.B.172.166; 4.B.172.169; 4.B.172.172; 4.B.172.175; 4.B.172.240; 4.B.172.244; 4.B.175.228; 4.B.175.229; 4.B.175.230; 4.B.175.231; 4.B.175.236; 4.B.175.237; 4.B.175.238; 4.B.175.239; 4.B.175.154; 4.B.175.157; 4.B.175.166; 4.B.175.169; 4.B.175.172; 4.B.175.175; 4.B.175.240; 4.B.175.244; 4.B.240.228; 4.B.240.229; 4.B.240.230; 4.B.240.231; 4.B.240.236; 4.B.240.237; 4.B.240.238; 4.B.240.239; 4.B.240.154; 4.B.240.157; 4.B.240.166; 4.B.240.169; 4.B.240.172; 4.B.240.175; 4.B.240.240; 4.B.240.244; 4.B.244.228; 4.B.244.229; 4.B.244.230; 4.B.244.231; 4.B.244.236; 4.B.244.237; 4.B.244.238; 4.B.244.239; 4.B.244.154; 4.B.244.157; 4.B.244.166; 4.B.244.169; 4.B.244.172; 4.B.244.175; 4.B.244.240; 4.B.244.244;

Prodrugs of 4.D

4.D.228.228; 4.D.228.229; 4.D.228.230; 4.D.228.231; 4.D.228.236; 4.D.228.237; 4.D.228.238; 4.D.228.239; 4.D.228.154; 4.D.228.157; 4.D.228.166; 4.D.228.169; 4.D.228.172; 4.D.228.175; 4.D.228.240; 4.D.228.244; 4.D.229.228; 4.D.229.229; 4.D.229.230; 4.D.229.231; 4.D.229.236; 4.D.229.237; 4.D.229.238; 4.D.229.239; 4.D.229.154; 4.D.229.157; 4.D.229.166; 4.D.229.169; 4.D.229.172; 4.D.229.175; 4.D.229.240; 4.D.229.244; 4.D.230.228; 4.D.230.229; 4.D.230.230; 4.D.230.231; 4.D.230.236; 4.D.230.237; 4.D.230.238; 4.D.230.239; 4.D.230.154; 4.D.230.157; 4.D.230.166; 4.D.230.169; 4.D.230.172; 4.D.230.175; 4.D.230.240; 4.D.230.244; 4.D.231.228; 4.D.231.229; 4.D.231.230; 4.D.231.231; 4.D.231.236; 4.D.231.237; 4.D.231.238; 4.D.231.239; 4.D.231.154; 4.D.231.157; 4.D.231.166; 4.D.231.169; 4.D.231.172; 4.D.231.175; 4.D.231.240; 4.D.231.244; 4.D.236.228; 4.D.236.229; 4.D.236.230; 4.D.236.231; 4.D.236.236; 4.D.236.237; 4.D.236.238; 4.D.236.239; 4.D.236.154; 4.D.236.157; 4.D.236.166; 4.D.236.169; 4.D.236.172; 4.D.236.175; 4.D.236.240; 4.D.236.244; 4.D.237.228; 4.D.237.229; 4.D.237.230; 4.D.237.231; 4.D.237.236; 4.D.237.237; 4.D.237.238; 4.D.237.239; 4.D.237.154; 4.D.237.157; 4.D.237.166; 4.D.237.169; 4.D.237.172; 4.D.237.175; 4.D.237.240; 4.D.237.244; 4.D.238.228; 4.D.238.229; 4.D.238.230; 4.D.238.231; 4.D.238.236; 4.D.238.237; 4.D.238.238; 4.D.238.239; 4.D.238.154; 4.D.238.157; 4.D.238.166; 4.D.238.169; 4.D.238.172; 4.D.238.175; 4.D.238.240; 4.D.238.244; 4.D.239.228; 4.D.239.229; 4.D.239.230; 4.D.239.231; 4.D.239.236; 4.D.239.237; 4.D.239.238; 4.D.239.239; 4.D.239.154; 4.D.239.157; 4.D.239.166; 4.D.239.169; 4.D.239.172; 4.D.239.175; 4.D.239.240; 4.D.239.244; 4.D.154.228; 4.D.154.229; 4.D.154.230; 4.D.154.231; 4.D.154.236; 4.D.154.237; 4.D.154.238; 4.D.154.239; 4.D.154.154; 4.D.154.157; 4.D.154.166; 4.D.154.169; 4.D.154.172; 4.D.154.175; 4.D.154.240; 4.D.154.244; 4.D.157.228; 4.D.157.229; 4.D.157.230; 4.D.157.231; 4.D.157.236; 4.D.157.237; 4.D.157.238; 4.D.157.239; 4.D.157.154; 4.D.157.157; 4.D.157.166; 4.D.157.169; 4.D.157.172; 4.D.157.175; 4.D.157.240; 4.D.157.244; 4.D.166.228; 4.D.166.229; 4.D.166.230; 4.D.166.231; 4.D.166.236; 4.D.166.237; 4.D.166.238; 4.D.166.239; 4.D.166.154; 4.D.166.157; 4.D.166.166; 4.D.166.169; 4.D.166.172; 4.D.166.175; 4.D.166.240; 4.D.166.244; 4.D.169.228; 4.D.169.229; 4.D.169.230; 4.D.169.231; 4.D.169.236; 4.D.169.237; 4.D.169.238; 4.D.169.239; 4.D.169.154; 4.D.169.157; 4.D.169.166; 4.D.169.169; 4.D.169.172; 4.D.169.175; 4.D.169.240; 4.D.169.244; 4.D.172.228; 4.D.172.229; 4.D.172.230; 4.D.172.231; 4.D.172.236; 4.D.172.237; 4.D.172.238; 4.D.172.239; 4.D.172.154; 4.D.172.157; 4.D.172.166; 4.D.172.169; 4.D.172.172; 4.D.172.175; 4.D.172.240; 4.D.172.244; 4.D.175.228; 4.D.175.229; 4.D.175.230; 4.D.175.231; 4.D.175.236; 4.D.175.237; 4.D.175.238; 4.D.175.239; 4.D.175.154; 4.D.175.157; 4.D.175.166; 4.D.175.169; 4.D.175.172; 4.D.175.175; 4.D.175.240; 4.D.175.244; 4.D.240.228; 4.D.240.229; 4.D.240.230; 4.D.240.231; 4.D.240.236; 4.D.240.237; 4.D.240.238; 4.D.240.239; 4.D.240.154; 4.D.240.157; 4.D.240.166; 4.D.240.169; 4.D.240.172; 4.D.240.175; 4.D.240.240; 4.D.240.244; 4.D.244.228; 4.D.244.229; 4.D.244.230; 4.D.244.231; 4.D.244.236; 4.D.244.237; 4.D.244.238; 4.D.244.239; 4.D.244.154; 4.D.244.157; 4.D.244.166; 4.D.244.169; 4.D.244.172; 4.D.244.175; 4.D.244.240; 4.D.244.244;

Prodrugs of 4.E

4.E.228.228; 4.E.228.229; 4.E.228.230; 4.E.228.231; 4.E.228.236; 4.E.228.237; 4.E.228.238; 4.E.228.239; 4.E.228.154; 4.E.228.157; 4.E.228.166; 4.E.228.169; 4.E.228.172; 4.E.228.175; 4.E.228.240; 4.E.228.244; 4.E.229.228; 4.E.229.229; 4.E.229.230; 4.E.229.231; 4.E.229.236; 4.E.229.237; 4.E.229.238; 4.E.229.239; 4.E.229.154; 4.E.229.157; 4.E.229.166; 4.E.229.169; 4.E.229.172; 4.E.229.175; 4.E.229.240; 4.E.229.244; 4.E.230.228; 4.E.230.229; 4.E.230.230; 4.E.230.231; 4.E.230.236; 4.E.230.237; 4.E.230.238; 4.E.230.239; 4.E.230.154; 4.E.230.157; 4.E.230.166; 4.E.230.169; 4.E.230.172; 4.E.230.175; 4.E.230.240; 4.E.230.244; 4.E.231.228; 4.E.231.229; 4.E.231.230; 4.E.231.231; 4.E.231.236; 4.E.231.237; 4.E.231.238; 4.E.231.239; 4.E.231.154; 4.E.231.157; 4.E.231.166; 4.E.231.169; 4.E.231.172; 4.E.231.175; 4.E.231.240; 4.E.231.244; 4.E.236.228; 4.E.236.229; 4.E.236.230; 4.E.236.231; 4.E.236.236; 4.E.236.237; 4.E.236.238; 4.E.236.239; 4.E.236.154; 4.E.236.157; 4.E.236.166; 4.E.236.169; 4.E.236.172; 4.E.236.175; 4.E.236.240; 4.E.236.244; 4.E.237.228; 4.E.237.229; 4.E.237.230; 4.E.237.231; 4.E.237.236; 4.E.237.237; 4.E.237.238; 4.E.237.239; 4.E.237.154; 4.E.237.157; 4.E.237.166; 4.E.237.169; 4.E.237.172; 4.E.237.175; 4.E.237.240; 4.E.237.244; 4.E.238.228; 4.E.238.229; 4.E.238.230; 4.E.238.231; 4.E.238.236; 4.E.238.237; 4.E.238.238; 4.E.238.239; 4.E.238.154; 4.E.238.157; 4.E.238.166; 4.E.238.169; 4.E.238.172; 4.E.238.175; 4.E.238.240; 4.E.238.244; 4.E.239.228; 4.E.239.229; 4.E.239.230; 4.E.239.231; 4.E.239.236; 4.E.239.237; 4.E.239.238; 4.E.239.239; 4.E.239.154; 4.E.239.157; 4.E.239.166; 4.E.239.169; 4.E.239.172; 4.E.239.175; 4.E.239.240; 4.E.239.244; 4.E.154.228; 4.E.154.229; 4.E.154.230; 4.E.154.231; 4.E.154.236; 4.E.154.237; 4.E.154.238; 4.E.154.239; 4.E.154.154; 4.E.154.157; 4.E.154.166; 4.E.154.169; 4.E.154.172; 4.E.154.175; 4.E.154.240; 4.E.154.244; 4.E.157.228; 4.E.157.229; 4.E.157.230; 4.E.157.231; 4.E.157.236; 4.E.157.237; 4.E.157.238; 4.E.157.239; 4.E.157.154; 4.E.157.157; 4.E.157.166; 4.E.157.169; 4.E.157.172; 4.E.157.175; 4.E.157.240; 4.E.157.244; 4.E.166.228; 4.E.166.229; 4.E.166.230; 4.E.166.231; 4.E.166.236; 4.E.166.237; 4.E.166.238; 4.E.166.239; 4.E.166.154; 4.E.166.157; 4.E.166.166; 4.E.166.169; 4.E.166.172; 4.E.166.175; 4.E.166.240; 4.E.166.244; 4.E.169.228; 4.E.169.229; 4.E.169.230; 4.E.169.231; 4.E.169.236; 4.E.169.237; 4.E.169.238; 4.E.169.239; 4.E.169.154; 4.E.169.157; 4.E.169.166; 4.E.169.169; 4.E.169.172; 4.E.169.175; 4.E.169.240; 4.E.169.244; 4.E.172.228; 4.E.172.229; 4.E.172.230; 4.E.172.231; 4.E.172.236; 4.E.172.237; 4.E.172.238; 4.E.172.239; 4.E.172.154; 4.E.172.157; 4.E.172.166; 4.E.172.169; 4.E.172.172; 4.E.172.175; 4.E.172.240; 4.E.172.244; 4.E.175.228; 4.E.175.229; 4.E.175.230; 4.E.175.231; 4.E.175.236; 4.E.175.237; 4.E.175.238; 4.E.175.239; 4.E.175.154; 4.E.175.157; 4.E.175.166; 4.E.175.169; 4.E.175.172; 4.E.175.175; 4.E.175.240; 4.E.175.244; 4.E.240.228; 4.E.240.229; 4.E.240.230; 4.E.240.231; 4.E.240.236; 4.E.240.237; 4.E.240.238; 4.E.240.239; 4.E.240.154; 4.E.240.157; 4.E.240.166; 4.E.240.169; 4.E.240.172; 4.E.240.175; 4.E.240.240; 4.E.240.244; 4.E.244.228; 4.E.244.229; 4.E.244.230; 4.E.244.231; 4.E.244.236; 4.E.244.237; 4.E.244.238; 4.E.244.239; 4.E.244.154; 4.E.244.157; 4.E.244.166; 4.E.244.169; 4.E.244.172; 4.E.244.175; 4.E.244.240; 4.E.244.244;

Prodrugs of 4.G

4.G.228.228; 4.G.228.229; 4.G.228.230; 4.G.228.231; 4.G.228.236; 4.G.228.237; 4.G.228.238; 4.G.228.239; 4.G.228.154; 4.G.228.157; 4.G.228.166; 4.G.228.169; 4.G.228.172; 4.G.228.175; 4.G.228.240; 4.G.228.244; 4.G.229.228; 4.G.229.229; 4.G.229.230; 4.G.229.231; 4.G.229.236; 4.G.229.237; 4.G.229.238; 4.G.229.239; 4.G.229.154; 4.G.229.157; 4.G.229.166; 4.G.229.169; 4.G.229.172; 4.G.229.175; 4.G.229.240; 4.G.229.244; 4.G.230.228; 4.G.230.229; 4.G.230.230;

TABLE 7-continued

4.G.230.231; 4.G.230.236; 4.G.230.237; 4.G.230.238; 4.G.230.239; 4.G.230.154; 4.G.230.157; 4.G.230.166; 4.G.230.169; 4.G.230.172; 4.G.230.175; 4.G.230.240; 4.G.230.244; 4.G.231.228; 4.G.231.229; 4.G.231.230; 4.G.231.231; 4.G.231.236; 4.G.231.237; 4.G.231.238; 4.G.231.239; 4.G.231.154; 4.G.231.157; 4.G.231.166; 4.G.231.169; 4.G.231.172; 4.G.231.175; 4.G.231.240; 4.G.231.244; 4.G.236.228; 4.G.236.229; 4.G.236.230; 4.G.236.231; 4.G.236.236; 4.G.236.237; 4.G.236.238; 4.G.236.239; 4.G.236.154; 4.G.236.157; 4.G.236.166; 4.G.236.169; 4.G.236.172; 4.G.236.175; 4.G.236.240; 4.G.236.244; 4.G.237.228; 4.G.237.229; 4.G.237.230; 4.G.237.231; 4.G.237.236; 4.G.237.237; 4.G.237.238; 4.G.237.239; 4.G.237.154; 4.G.237.157; 4.G.237.166; 4.G.237.169; 4.G.237.172; 4.G.237.175; 4.G.237.240; 4.G.237.244; 4.G.238.228; 4.G.238.229; 4.G.238.230; 4.G.238.231; 4.G.238.236; 4.G.238.237; 4.G.238.238; 4.G.238.239; 4.G.238.154; 4.G.238.157; 4.G.238.166; 4.G.238.169; 4.G.238.172; 4.G.238.175; 4.G.238.240; 4.G.238.244; 4.G.239.228; 4.G.239.229; 4.G.239.230; 4.G.239.231; 4.G.239.236; 4.G.239.237; 4.G.239.238; 4.G.239.239; 4.G.239.154; 4.G.239.157; 4.G.239.166; 4.G.239.169; 4.G.239.172; 4.G.239.175; 4.G.239.240; 4.G.239.244; 4.G.154.228; 4.G.154.229; 4.G.154.230; 4.G.154.231; 4.G.154.236; 4.G.154.237; 4.G.154.238; 4.G.154.239; 4.G.154.154; 4.G.154.157; 4.G.154.166; 4.G.154.169; 4.G.154.172; 4.G.154.175; 4.G.154.240; 4.G.154.244; 4.G.157.228; 4.G.157.229; 4.G.157.230; 4.G.157.231; 4.G.157.236; 4.G.157.237; 4.G.157.238; 4.G.157.239; 4.G.157.154; 4.G.157.157; 4.G.157.166; 4.G.157.169; 4.G.157.172; 4.G.157.175; 4.G.157.240; 4.G.157.244; 4.G.166.228; 4.G.166.229; 4.G.166.230; 4.G.166.231; 4.G.166.236; 4.G.166.237; 4.G.166.238; 4.G.166.239; 4.G.166.154; 4.G.166.157; 4.G.166.166; 4.G.166.169; 4.G.166.172; 4.G.166.175; 4.G.166.240; 4.G.166.244; 4.G.169.228; 4.G.169.229; 4.G.169.230; 4.G.169.231; 4.G.169.236; 4.G.169.237; 4.G.169.238; 4.G.169.239; 4.G.169.154; 4.G.169.157; 4.G.169.166; 4.G.169.169; 4.G.169.172; 4.G.169.175; 4.G.169.240; 4.G.169.244; 4.G.172.228; 4.G.172.229; 4.G.172.230; 4.G.172.231; 4.G.172.236; 4.G.172.237; 4.G.172.238; 4.G.172.239; 4.G.172.154; 4.G.172.157; 4.G.172.166; 4.G.172.169; 4.G.172.172; 4.G.172.175; 4.G.172.240; 4.G.172.244; 4.G.175.228; 4.G.175.229; 4.G.175.230; 4.G.175.231; 4.G.175.236; 4.G.175.237; 4.G.175.238; 4.G.175.239; 4.G.175.154; 4.G.175.157; 4.G.175.166; 4.G.175.169; 4.G.175.172; 4.G.175.175; 4.G.175.240; 4.G.175.244; 4.G.240.228; 4.G.240.229; 4.G.240.230; 4.G.240.231; 4.G.240.236; 4.G.240.237; 4.G.240.238; 4.G.240.239; 4.G.240.154; 4.G.240.157; 4.G.240.166; 4.G.240.169; 4.G.240.172; 4.G.240.175; 4.G.240.240; 4.G.240.244; 4.G.244.228; 4.G.244.229; 4.G.244.230; 4.G.244.231; 4.G.244.236; 4.G.244.237; 4.G.244.238; 4.G.244.239; 4.G.244.154; 4.G.244.157; 4.G.244.166; 4.G.244.169; 4.G.244.172; 4.G.244.175; 4.G.244.240; 4.G.244.244;
Prodrugs of 4.I 4.I.228.228; 4.I.228.229; 4.I.228.230; 4.I.228.231; 4.I.228.236; 4.I.228.237; 4.I.228.238; 4.I.228.239; 4.I.228.154; 4.I.228.157; 4.I.228.166; 4.I.228.169; 4.I.228.172; 4.I.228.175; 4.I.228.240; 4.I.228.244; 4.I.229.228; 4.I.229.229; 4.I.229.230; 4.I.229.231; 4.I.229.236; 4.I.229.237; 4.I.229.238; 4.I.229.239; 4.I.229.154; 4.I.229.157; 4.I.229.166; 4.I.229.169; 4.I.229.172; 4.I.229.175; 4.I.229.240; 4.I.229.244; 4.I.230.228; 4.I.230.229; 4.I.230.230; 4.I.230.231; 4.I.230.236; 4.I.230.237; 4.I.230.238; 4.I.230.239; 4.I.230.154; 4.I.230.157; 4.I.230.166; 4.I.230.169; 4.I.230.172; 4.I.230.175; 4.I.230.240; 4.I.230.244; 4.I.231.228; 4.I.231.229; 4.I.231.230; 4.I.231.231; 4.I.231.236; 4.I.231.237; 4.I.231.238; 4.I.231.239; 4.I.231.154; 4.I.231.157; 4.I.231.166; 4.I.231.169; 4.I.231.172; 4.I.231.175; 4.I.231.240; 4.I.231.244; 4.I.236.228; 4.I.236.229; 4.I.236.230; 4.I.236.231; 4.I.236.236; 4.I.236.237; 4.I.236.238; 4.I.236.239; 4.I.236.154; 4.I.236.157; 4.I.236.166; 4.I.236.169; 4.I.236.172; 4.I.236.175; 4.I.236.240; 4.I.236.244; 4.I.237.228; 4.I.237.229; 4.I.237.230; 4.I.237.231; 4.I.237.236; 4.I.237.237; 4.I.237.238; 4.I.237.239; 4.I.237.154; 4.I.237.157; 4.I.237.166; 4.I.237.169; 4.I.237.172; 4.I.237.175; 4.I.237.240; 4.I.237.244; 4.I.238.228; 4.I.238.229; 4.I.238.230; 4.I.238.231; 4.I.238.236; 4.I.238.237; 4.I.238.238; 4.I.238.239; 4.I.238.154; 4.I.238.157; 4.I.238.166; 4.I.238.169; 4.I.238.172; 4.I.238.175; 4.I.238.240; 4.I.238.244; 4.I.239.228; 4.I.239.229; 4.I.239.230; 4.I.239.231; 4.I.239.236; 4.I.239.237; 4.I.239.238; 4.I.239.239; 4.I.239.154; 4.I.239.157; 4.I.239.166; 4.I.239.169; 4.I.239.172; 4.I.239.175; 4.I.239.240; 4.I.239.244; 4.I.154.228; 4.I.154.229; 4.I.154.230; 4.I.154.231; 4.I.154.236; 4.I.154.237; 4.I.154.238; 4.I.154.239; 4.I.154.154; 4.I.154.157; 4.I.154.166; 4.I.154.169; 4.I.154.172; 4.I.154.175; 4.I.154.240; 4.I.154.244; 4.I.157.228; 4.I.157.229; 4.I.157.230; 4.I.157.231; 4.I.157.236; 4.I.157.237; 4.I.157.238; 4.I.157.239; 4.I.157.154; 4.I.157.157; 4.I.157.166; 4.I.157.169; 4.I.157.172; 4.I.157.175; 4.I.157.240; 4.I.157.244; 4.I.166.228; 4.I.166.229; 4.I.166.230; 4.I.166.231; 4.I.166.236; 4.I.166.237; 4.I.166.238; 4.I.166.239; 4.I.166.154; 4.I.166.157; 4.I.166.166; 4.I.166.169; 4.I.166.172; 4.I.166.175; 4.I.166.240; 4.I.166.244; 4.I.169.228; 4.I.169.229; 4.I.169.230; 4.I.169.231; 4.I.169.236; 4.I.169.237; 4.I.169.238; 4.I.169.239; 4.I.169.154; 4.I.169.157; 4.I.169.166; 4.I.169.169; 4.I.169.172; 4.I.169.175; 4.I.169.240; 4.I.169.244; 4.I.172.228; 4.I.172.229; 4.I.172.230; 4.I.172.231; 4.I.172.236; 4.I.172.237; 4.I.172.238; 4.I.172.239; 4.I.172.154; 4.I.172.157; 4.I.172.166; 4.I.172.169; 4.I.172.172; 4.I.172.175; 4.I.172.240; 4.I.172.244; 4.I.175.228; 4.I.175.229; 4.I.175.230; 4.I.175.231; 4.I.175.236; 4.I.175.237; 4.I.175.238; 4.I.175.239; 4.I.175.154; 4.I.175.157; 4.I.175.166; 4.I.175.169; 4.I.175.172; 4.I.175.175; 4.I.175.240; 4.I.175.244; 4.I.240.228; 4.I.240.229; 4.I.240.230; 4.I.240.231; 4.I.240.236; 4.I.240.237; 4.I.240.238; 4.I.240.239; 4.I.240.154; 4.I.240.157; 4.I.240.166; 4.I.240.169; 4.I.240.172; 4.I.240.175; 4.I.240.240; 4.I.240.244; 4.I.244.228; 4.I.244.229; 4.I.244.230; 4.I.244.231; 4.I.244.236; 4.I.244.237; 4.I.244.238; 4.I.244.239; 4.I.244.154; 4.I.244.157; 4.I.244.166; 4.I.244.169; 4.I.244.172; 4.I.244.175; 4.I.244.240; 4.I.244.244;
Prodrugs of 4.J 4.J.228.228; 4.J.228.229; 4.J.228.230; 4.J.228.231; 4.J.228.236; 4.J.228.237; 4.J.228.238; 4.J.228.239; 4.J.228.154; 4.J.228.157; 4.J.228.166; 4.J.228.169; 4.J.228.172; 4.J.228.175; 4.J.228.240; 4.J.228.244; 4.J.229.228; 4.J.229.229; 4.J.229.230; 4.J.229.231; 4.J.229.236; 4.J.229.237; 4.J.229.238; 4.J.229.239; 4.J.229.154; 4.J.229.157; 4.J.229.166; 4.J.229.169; 4.J.229.172; 4.J.229.175; 4.J.229.240; 4.J.229.244; 4.J.230.228; 4.J.230.229; 4.J.230.230; 4.J.230.231; 4.J.230.236; 4.J.230.237; 4.J.230.238; 4.J.230.239; 4.J.230.154; 4.J.230.157; 4.J.230.166; 4.J.230.169; 4.J.230.172; 4.J.230.175; 4.J.230.240; 4.J.230.244; 4.J.231.228; 4.J.231.229; 4.J.231.230; 4.J.231.231; 4.J.231.236; 4.J.231.237; 4.J.231.238; 4.J.231.239; 4.J.231.154; 4.J.231.157; 4.J.231.166; 4.J.231.169; 4.J.231.172; 4.J.231.175; 4.J.231.240; 4.J.231.244; 4.J.236.228; 4.J.236.229; 4.J.236.230; 4.J.236.231; 4.J.236.236; 4.J.236.237; 4.J.236.238; 4.J.236.239; 4.J.236.154; 4.J.236.157; 4.J.236.166; 4.J.236.169; 4.J.236.172; 4.J.236.175; 4.J.236.240; 4.J.236.244; 4.J.237.228; 4.J.237.229; 4.J.237.230; 4.J.237.231; 4.J.237.236; 4.J.237.237; 4.J.237.238; 4.J.237.239; 4.J.237.154; 4.J.237.157; 4.J.237.166; 4.J.237.169; 4.J.237.172; 4.J.237.175; 4.J.237.240; 4.J.237.244; 4.J.238.228; 4.J.238.229; 4.J.238.230; 4.J.238.231; 4.J.238.236; 4.J.238.237; 4.J.238.238; 4.J.238.239; 4.J.238.154; 4.J.238.157; 4.J.238.166; 4.J.238.169; 4.J.238.172; 4.J.238.175; 4.J.238.240; 4.J.238.244; 4.J.239.228; 4.J.239.229; 4.J.239.230; 4.J.239.231; 4.J.239.236; 4.J.239.237; 4.J.239.238; 4.J.239.239; 4.J.239.154; 4.J.239.157; 4.J.239.166; 4.J.239.169; 4.J.239.172; 4.J.239.175; 4.J.239.240; 4.J.239.244; 4.J.154.228; 4.J.154.229; 4.J.154.230; 4.J.154.231; 4.J.154.236; 4.J.154.237; 4.J.154.238; 4.J.154.239; 4.J.154.154; 4.J.154.157; 4.J.154.166; 4.J.154.169; 4.J.154.172; 4.J.154.175; 4.J.154.240; 4.J.154.244; 4.J.157.228; 4.J.157.229; 4.J.157.230; 4.J.157.231; 4.J.157.236; 4.J.157.237; 4.J.157.238; 4.J.157.239; 4.J.157.154; 4.J.157.157; 4.J.157.166; 4.J.157.169; 4.J.157.172; 4.J.157.175; 4.J.157.240; 4.J.157.244; 4.J.166.228; 4.J.166.229; 4.J.166.230; 4.J.166.231; 4.J.166.236; 4.J.166.237; 4.J.166.238; 4.J.166.239; 4.J.166.154; 4.J.166.157; 4.J.166.166; 4.J.166.169; 4.J.166.172; 4.J.166.175; 4.J.166.240; 4.J.166.244; 4.J.169.228; 4.J.169.229; 4.J.169.230; 4.J.169.231; 4.J.169.236; 4.J.169.237; 4.J.169.238; 4.J.169.239; 4.J.169.154; 4.J.169.157; 4.J.169.166; 4.J.169.169; 4.J.169.172; 4.J.169.175; 4.J.169.240; 4.J.169.244; 4.J.172.228; 4.J.172.229; 4.J.172.230; 4.J.172.231; 4.J.172.236; 4.J.172.237; 4.J.172.238; 4.J.172.239; 4.J.172.154; 4.J.172.157; 4.J.172.166; 4.J.172.169; 4.J.172.172; 4.J.172.175; 4.J.172.240; 4.J.172.244; 4.J.175.228; 4.J.175.229; 4.J.175.230; 4.J.175.231; 4.J.175.236; 4.J.175.237; 4.J.175.238; 4.J.175.239; 4.J.175.154; 4.J.175.157; 4.J.175.166; 4.J.175.169; 4.J.175.172; 4.J.175.175; 4.J.175.240; 4.J.175.244; 4.J.240.228; 4.J.240.229; 4.J.240.230; 4.J.240.231; 4.J.240.236; 4.J.240.237; 4.J.240.238; 4.J.240.239; 4.J.240.154; 4.J.240.157; 4.J.240.166; 4.J.240.169; 4.J.240.172; 4.J.240.175; 4.J.240.240; 4.J.240.244; 4.J.244.228; 4.J.244.229; 4.J.244.230; 4.J.244.231; 4.J.244.236; 4.J.244.237; 4.J.244.238; 4.J.244.239; 4.J.244.154; 4.J.244.157; 4.J.244.166; 4.J.244.169; 4.J.244.172; 4.J.244.175; 4.J.244.240; 4.J.244.244;
Prodrugs of 4.L 4.L.228.228; 4.L.228.229; 4.L.228.230; 4.L.228.231; 4.L.228.236; 4.L.228.237; 4.L.228.238; 4.L.228.239; 4.L.228.154; 4.L.228.157; 4.L.228.166; 4.L.228.169; 4.L.228.172; 4.L.228.175; 4.L.228.240;

TABLE 7-continued

4.L.228.244; 4.L.229.228; 4.L.229.229; 4.L.229.230; 4.L.229.231; 4.L.229.236; 4.L.229.237; 4.L.229.238; 4.L.229.239; 4.L.229.154; 4.L.229.157; 4.L.229.166; 4.L.229.169; 4.L.229.172; 4.L.229.175; 4.L.229.240; 4.L.229.244; 4.L.230.228; 4.L.230.229; 4.L.230.230; 4.L.230.231; 4.L.230.236; 4.L.230.237; 4.L.230.238; 4.L.230.239; 4.L.230.154; 4.L.230.157; 4.L.230.166; 4.L.230.169; 4.L.230.172; 4.L.230.175; 4.L.230.240; 4.L.230.244; 4.L.231.228; 4.L.231.229; 4.L.231.230; 4.L.231.231; 4.L.231.236; 4.L.231.237; 4.L.231.238; 4.L.231.239; 4.L.231.154; 4.L.231.157; 4.L.231.166; 4.L.231.169; 4.L.231.172; 4.L.231.175; 4.L.231.240; 4.L.231.244; 4.L.236.228; 4.L.236.229; 4.L.236.230; 4.L.236.231; 4.L.236.236; 4.L.236.237; 4.L.236.238; 4.L.236.239; 4.L.236.154; 4.L.236.157; 4.L.236.166; 4.L.236.169; 4.L.236.172; 4.L.236.175; 4.L.236.240; 4.L.236.244; 4.L.237.228; 4.L.237.229; 4.L.237.230; 4.L.237.231; 4.L.237.236; 4.L.237.237; 4.L.237.238; 4.L.237.239; 4.L.237.154; 4.L.237.157; 4.L.237.166; 4.L.237.169; 4.L.237.172; 4.L.237.175; 4.L.237.240; 4.L.237.244; 4.L.238.228; 4.L.238.229; 4.L.238.230; 4.L.238.231; 4.L.238.236; 4.L.238.237; 4.L.238.238; 4.L.238.239; 4.L.238.154; 4.L.238.157; 4.L.238.166; 4.L.238.169; 4.L.238.172; 4.L.238.175; 4.L.238.240; 4.L.238.244; 4.L.239.228; 4.L.239.229; 4.L.239.230; 4.L.239.231; 4.L.239.236; 4.L.239.237; 4.L.239.238; 4.L.239.239; 4.L.239.154; 4.L.239.157; 4.L.239.166; 4.L.239.169; 4.L.239.172; 4.L.239.175; 4.L.239.240; 4.L.239.244; 4.L.154.228; 4.L.154.229; 4.L.154.230; 4.L.154.231; 4.L.154.236; 4.L.154.237; 4.L.154.238; 4.L.154.239; 4.L.154.154; 4.L.154.157; 4.L.154.166; 4.L.154.169; 4.L.154.172; 4.L.154.175; 4.L.154.240; 4.L.154.244; 4.L.157.228; 4.L.157.229; 4.L.157.230; 4.L.157.231; 4.L.157.236; 4.L.157.237; 4.L.157.238; 4.L.157.239; 4.L.157.154; 4.L.157.157; 4.L.157.166; 4.L.157.169; 4.L.157.172; 4.L.157.175; 4.L.157.240; 4.L.157.244; 4.L.166.228; 4.L.166.229; 4.L.166.230; 4.L.166.231; 4.L.166.236; 4.L.166.237; 4.L.166.238; 4.L.166.239; 4.L.166.154; 4.L.166.157; 4.L.166.166; 4.L.166.169; 4.L.166.172; 4.L.166.175; 4.L.166.240; 4.L.166.244; 4.L.169.228; 4.L.169.229; 4.L.169.230; 4.L.169.231; 4.L.169.236; 4.L.169.237; 4.L.169.238; 4.L.169.239; 4.L.169.154; 4.L.169.157; 4.L.169.166; 4.L.169.169; 4.L.169.172; 4.L.169.175; 4.L.169.240; 4.L.169.244; 4.L.172.228; 4.L.172.229; 4.L.172.230; 4.L.172.231; 4.L.172.236; 4.L.172.237; 4.L.172.238; 4.L.172.239; 4.L.172.154; 4.L.172.157; 4.L.172.166; 4.L.172.169; 4.L.172.172; 4.L.172.175; 4.L.172.240; 4.L.172.244; 4.L.175.228; 4.L.175.229; 4.L.175.230; 4.L.175.231; 4.L.175.236; 4.L.175.237; 4.L.175.238; 4.L.175.239; 4.L.175.154; 4.L.175.157; 4.L.175.166; 4.L.175.169; 4.L.175.172; 4.L.175.175; 4.L.175.240; 4.L.175.244; 4.L.240.228; 4.L.240.229; 4.L.240.230; 4.L.240.231; 4.L.240.236; 4.L.240.237; 4.L.240.238; 4.L.240.239; 4.L.240.154; 4.L.240.157; 4.L.240.166; 4.L.240.169; 4.L.240.172; 4.L.240.175; 4.L.240.240; 4.L.240.244; 4.L.244.228; 4.L.244.229; 4.L.244.230; 4.L.244.231; 4.L.244.236; 4.L.244.237; 4.L.244.238; 4.L.244.239; 4.L.244.154; 4.L.244.157; 4.L.244.166; 4.L.244.169; 4.L.244.172; 4.L.244.175; 4.L.244.240; 4.L.244.244;
Prodrugs of 4.O 4.O.228.228; 4.O.228.229; 4.O.228.230; 4.O.228.231; 4.O.228.236; 4.O.228.237; 4.O.228.238; 4.O.228.239; 4.O.228.154; 4.O.228.157; 4.O.228.166; 4.O.228.169; 4.O.228.172; 4.O.228.175; 4.O.228.240; 4.O.228.244; 4.O.229.228; 4.O.229.229; 4.O.229.230; 4.O.229.231; 4.O.229.236; 4.O.229.237; 4.O.229.238; 4.O.229.239; 4.O.229.154; 4.O.229.157; 4.O.229.166; 4.O.229.169; 4.O.229.172; 4.O.229.175; 4.O.229.240; 4.O.229.244; 4.O.230.228; 4.O.230.229; 4.O.230.230; 4.O.230.231; 4.O.230.236; 4.O.230.237; 4.O.230.238; 4.O.230.239; 4.O.230.154; 4.O.230.157; 4.O.230.166; 4.O.230.169; 4.O.230.172; 4.O.230.175; 4.O.230.240; 4.O.230.244; 4.O.231.228; 4.O.231.229; 4.O.231.230; 4.O.231.231; 4.O.231.236; 4.O.231.237; 4.O.231.238; 4.O.231.239; 4.O.231.154; 4.O.231.157; 4.O.231.166; 4.O.231.169; 4.O.231.172; 4.O.231.175; 4.O.231.240; 4.O.231.244; 4.O.236.228; 4.O.236.229; 4.O.236.230; 4.O.236.231; 4.O.236.236; 4.O.236.237; 4.O.236.238; 4.O.236.239; 4.O.236.154; 4.O.236.157; 4.O.236.166; 4.O.236.169; 4.O.236.172; 4.O.236.175; 4.O.236.240; 4.O.236.244; 4.O.237.228; 4.O.237.229; 4.O.237.230; 4.O.237.231; 4.O.237.236; 4.O.237.237; 4.O.237.238; 4.O.237.239; 4.O.237.154; 4.O.237.157; 4.O.237.166; 4.O.237.169; 4.O.237.172; 4.O.237.175; 4.O.237.240; 4.O.237.244; 4.O.238.228; 4.O.238.229; 4.O.238.230; 4.O.238.231; 4.O.238.236; 4.O.238.237; 4.O.238.238; 4.O.238.239; 4.O.238.154; 4.O.238.157; 4.O.238.166; 4.O.238.169; 4.O.238.172; 4.O.238.175; 4.O.238.240; 4.O.238.244; 4.O.239.228; 4.O.239.229; 4.O.239.230; 4.O.239.231; 4.O.239.236; 4.O.239.237; 4.O.239.238; 4.O.239.239; 4.O.239.154; 4.O.239.157; 4.O.239.166; 4.O.239.169; 4.O.239.172; 4.O.239.175; 4.O.239.240; 4.O.239.244; 4.O.154.228; 4.O.154.229; 4.O.154.230; 4.O.154.231; 4.O.154.236; 4.O.154.237; 4.O.154.238; 4.O.154.239; 4.O.154.154; 4.O.154.157; 4.O.154.166; 4.O.154.169; 4.O.154.172; 4.O.154.175; 4.O.154.240; 4.O.154.244; 4.O.157.228; 4.O.157.229; 4.O.157.230; 4.O.157.231; 4.O.157.236; 4.O.157.237; 4.O.157.238; 4.O.157.239; 4.O.157.154; 4.O.157.157; 4.O.157.166; 4.O.157.169; 4.O.157.172; 4.O.157.175; 4.O.157.240; 4.O.157.244; 4.O.166.228; 4.O.166.229; 4.O.166.230; 4.O.166.231; 4.O.166.236; 4.O.166.237; 4.O.166.238; 4.O.166.239; 4.O.166.154; 4.O.166.157; 4.O.166.166; 4.O.166.169; 4.O.166.172; 4.O.166.175; 4.O.166.240; 4.O.166.244; 4.O.169.228; 4.O.169.229; 4.O.169.230; 4.O.169.231; 4.O.169.236; 4.O.169.237; 4.O.169.238; 4.O.169.239; 4.O.169.154; 4.O.169.157; 4.O.169.166; 4.O.169.169; 4.O.169.172; 4.O.169.175; 4.O.169.240; 4.O.169.244; 4.O.172.228; 4.O.172.229; 4.O.172.230; 4.O.172.231; 4.O.172.236; 4.O.172.237; 4.O.172.238; 4.O.172.239; 4.O.172.154; 4.O.172.157; 4.O.172.166; 4.O.172.169; 4.O.172.172; 4.O.172.175; 4.O.172.240; 4.O.172.244; 4.O.175.228; 4.O.175.229; 4.O.175.230; 4.O.175.231; 4.O.175.236; 4.O.175.237; 4.O.175.238; 4.O.175.239; 4.O.175.154; 4.O.175.157; 4.O.175.166; 4.O.175.169; 4.O.175.172; 4.O.175.175; 4.O.175.240; 4.O.175.244; 4.O.240.228; 4.O.240.229; 4.O.240.230; 4.O.240.231; 4.O.240.236; 4.O.240.237; 4.O.240.238; 4.O.240.239; 4.O.240.154; 4.O.240.157; 4.O.240.166; 4.O.240.169; 4.O.240.172; 4.O.240.175; 4.O.240.240; 4.O.240.244; 4.O.244.228; 4.O.244.229; 4.O.244.230; 4.O.244.231; 4.O.244.236; 4.O.244.237; 4.O.244.238; 4.O.244.239; 4.O.244.154; 4.O.244.157; 4.O.244.166; 4.O.244.169; 4.O.244.172; 4.O.244.175; 4.O.244.240; 4.O.244.244;
Prodrugs of 4.P 4.P.228.228; 4.P.228.229; 4.P.228.230; 4.P.228.231; 4.P.228.236; 4.P.228.237; 4.P.228.238; 4.P.228.239; 4.P.228.154; 4.P.228.157; 4.P.228.166; 4.P.228.169; 4.P.228.172; 4.P.228.175; 4.P.228.240; 4.P.228.244; 4.P.229.228; 4.P.229.229; 4.P.229.230; 4.P.229.231; 4.P.229.236; 4.P.229.237; 4.P.229.238; 4.P.229.239; 4.P.229.154; 4.P.229.157; 4.P.229.166; 4.P.229.169; 4.P.229.172; 4.P.229.175; 4.P.229.240; 4.P.229.244; 4.P.230.228; 4.P.230.229; 4.P.230.230; 4.P.230.231; 4.P.230.236; 4.P.230.237; 4.P.230.238; 4.P.230.239; 4.P.230.154; 4.P.230.157; 4.P.230.166; 4.P.230.169; 4.P.230.172; 4.P.230.175; 4.P.230.240; 4.P.230.244; 4.P.231.228; 4.P.231.229; 4.P.231.230; 4.P.231.231; 4.P.231.236; 4.P.231.237; 4.P.231.238; 4.P.231.239; 4.P.231.154; 4.P.231.157; 4.P.231.166; 4.P.231.169; 4.P.231.172; 4.P.231.175; 4.P.231.240; 4.P.231.244; 4.P.236.228; 4.P.236.229; 4.P.236.230; 4.P.236.231; 4.P.236.236; 4.P.236.237; 4.P.236.238; 4.P.236.239; 4.P.236.154; 4.P.236.157; 4.P.236.166; 4.P.236.169; 4.P.236.172; 4.P.236.175; 4.P.236.240; 4.P.236.244; 4.P.237.228; 4.P.237.229; 4.P.237.230; 4.P.237.231; 4.P.237.236; 4.P.237.237; 4.P.237.238; 4.P.237.239; 4.P.237.154; 4.P.237.157; 4.P.237.166; 4.P.237.169; 4.P.237.172; 4.P.237.175; 4.P.237.240; 4.P.237.244; 4.P.238.228; 4.P.238.229; 4.P.238.230; 4.P.238.231; 4.P.238.236; 4.P.238.237; 4.P.238.238; 4.P.238.239; 4.P.238.154; 4.P.238.157; 4.P.238.166; 4.P.238.169; 4.P.238.172; 4.P.238.175; 4.P.238.240; 4.P.238.244; 4.P.239.228; 4.P.239.229; 4.P.239.230; 4.P.239.231; 4.P.239.236; 4.P.239.237; 4.P.239.238; 4.P.239.239; 4.P.239.154; 4.P.239.157; 4.P.239.166; 4.P.239.169; 4.P.239.172; 4.P.239.175; 4.P.239.240; 4.P.239.244; 4.P.154.228; 4.P.154.229; 4.P.154.230; 4.P.154.231; 4.P.154.236; 4.P.154.237; 4.P.154.238; 4.P.154.239; 4.P.154.154; 4.P.154.157; 4.P.154.166; 4.P.154.169; 4.P.154.172; 4.P.154.175; 4.P.154.240; 4.P.154.244; 4.P.157.228; 4.P.157.229; 4.P.157.230; 4.P.157.231; 4.P.157.236; 4.P.157.237; 4.P.157.238; 4.P.157.239; 4.P.157.154; 4.P.157.157; 4.P.157.166; 4.P.157.169; 4.P.157.172; 4.P.157.175; 4.P.157.240; 4.P.157.244; 4.P.166.228; 4.P.166.229; 4.P.166.230; 4.P.166.231; 4.P.166.236; 4.P.166.237; 4.P.166.238; 4.P.166.239; 4.P.166.154; 4.P.166.157; 4.P.166.166; 4.P.166.169; 4.P.166.172; 4.P.166.175; 4.P.166.240; 4.P.166.244; 4.P.169.228; 4.P.169.229; 4.P.169.230; 4.P.169.231; 4.P.169.236; 4.P.169.237; 4.P.169.238; 4.P.169.239; 4.P.169.154; 4.P.169.157; 4.P.169.166; 4.P.169.169; 4.P.169.172; 4.P.169.175; 4.P.169.240; 4.P.169.244; 4.P.172.228; 4.P.172.229; 4.P.172.230; 4.P.172.231; 4.P.172.236; 4.P.172.237; 4.P.172.238; 4.P.172.239; 4.P.172.154; 4.P.172.157; 4.P.172.166; 4.P.172.169; 4.P.172.172; 4.P.172.175; 4.P.172.240; 4.P.172.244; 4.P.175.228; 4.P.175.229; 4.P.175.230; 4.P.175.231; 4.P.175.236; 4.P.175.237; 4.P.175.238; 4.P.175.239; 4.P.175.154; 4.P.175.157; 4.P.175.166; 4.P.175.169; 4.P.175.172; 4.P.175.175; 4.P.175.240; 4.P.175.244; 4.P.240.228; 4.P.240.229; 4.P.240.230; 4.P.240.231; 4.P.240.236; 4.P.240.237; 4.P.240.238; 4.P.240.239; 4.P.240.154; 4.P.240.157; 4.P.240.166; 4.P.240.169; 4.P.240.172; 4.P.240.175; 4.P.240.240; 4.P.240.244; 4.P.244.228; 4.P.244.229; 4.P.244.230; 4.P.244.231; 4.P.244.236; 4.P.244.237; 4.P.244.238; 4.P.244.239; 4.P.244.154; 4.P.244.157; 4.P.244.166; 4.P.244.169; 4.P.244.172; 4.P.244.175; 4.P.244.240; 4.P.244.244;

TABLE 7-continued

Prodrugs of 4.U

4.U.228.228; 4.U.228.229; 4.U.228.230; 4.U.228.231; 4.U.228.236; 4.U.228.237; 4.U.228.238; 4.U.228.239; 4.U.228.154; 4.U.228.157; 4.U.228.166; 4.U.228.169; 4.U.228.172; 4.U.228.175; 4.U.228.240; 4.U.228.244; 4.U.229.228; 4.U.229.229; 4.U.229.230; 4.U.229.231; 4.U.229.236; 4.U.229.237; 4.U.229.238; 4.U.229.239; 4.U.229.154; 4.U.229.157; 4.U.229.166; 4.U.229.169; 4.U.229.172; 4.U.229.175; 4.U.229.240; 4.U.229.244; 4.U.230.228; 4.U.230.229; 4.U.230.230; 4.U.230.231; 4.U.230.236; 4.U.230.237; 4.U.230.238; 4.U.230.239; 4.U.230.154; 4.U.230.157; 4.U.230.166; 4.U.230.169; 4.U.230.172; 4.U.230.175; 4.U.230.240; 4.U.230.244; 4.U.231.228; 4.U.231.229; 4.U.231.230; 4.U.231.231; 4.U.231.236; 4.U.231.237; 4.U.231.238; 4.U.231.239; 4.U.231.154; 4.U.231.157; 4.U.231.166; 4.U.231.169; 4.U.231.172; 4.U.231.175; 4.U.231.240; 4.U.231.244; 4.U.236.228; 4.U.236.229; 4.U.236.230; 4.U.236.231; 4.U.236.236; 4.U.236.237; 4.U.236.238; 4.U.236.239; 4.U.236.154; 4.U.236.157; 4.U.236.166; 4.U.236.169; 4.U.236.172; 4.U.236.175; 4.U.236.240; 4.U.236.244; 4.U.237.228; 4.U.237.229; 4.U.237.230; 4.U.237.231; 4.U.237.236; 4.U.237.237; 4.U.237.238; 4.U.237.239; 4.U.237.154; 4.U.237.157; 4.U.237.166; 4.U.237.169; 4.U.237.172; 4.U.237.175; 4.U.237.240; 4.U.237.244; 4.U.238.228; 4.U.238.229; 4.U.238.230; 4.U.238.231; 4.U.238.236; 4.U.238.237; 4.U.238.238; 4.U.238.239; 4.U.238.154; 4.U.238.157; 4.U.238.166; 4.U.238.169; 4.U.238.172; 4.U.238.175; 4.U.238.240; 4.U.238.244; 4.U.239.228; 4.U.239.229; 4.U.239.230; 4.U.239.231; 4.U.239.236; 4.U.239.237; 4.U.239.238; 4.U.239.239; 4.U.239.154; 4.U.239.157; 4.U.239.166; 4.U.239.169; 4.U.239.172; 4.U.239.175; 4.U.239.240; 4.U.239.244; 4.U.154.228; 4.U.154.229; 4.U.154.230; 4.U.154.231; 4.U.154.236; 4.U.154.237; 4.U.154.238; 4.U.154.239; 4.U.154.154; 4.U.154.157; 4.U.154.166; 4.U.154.169; 4.U.154.172; 4.U.154.175; 4.U.154.240; 4.U.154.244; 4.U.157.228; 4.U.157.229; 4.U.157.230; 4.U.157.231; 4.U.157.236; 4.U.157.237; 4.U.157.238; 4.U.157.239; 4.U.157.154; 4.U.157.157; 4.U.157.166; 4.U.157.169; 4.U.157.172; 4.U.157.175; 4.U.157.240; 4.U.157.244; 4.U.166.228; 4.U.166.229; 4.U.166.230; 4.U.166.231; 4.U.166.236; 4.U.166.237; 4.U.166.238; 4.U.166.239; 4.U.166.154; 4.U.166.157; 4.U.166.166; 4.U.166.169; 4.U.166.172; 4.U.166.175; 4.U.166.240; 4.U.166.244; 4.U.169.228; 4.U.169.229; 4.U.169.230; 4.U.169.231; 4.U.169.236; 4.U.169.237; 4.U.169.238; 4.U.169.239; 4.U.169.154; 4.U.169.157; 4.U.169.166; 4.U.169.169; 4.U.169.172; 4.U.169.175; 4.U.169.240; 4.U.169.244; 4.U.172.228; 4.U.172.229; 4.U.172.230; 4.U.172.231; 4.U.172.236; 4.U.172.237; 4.U.172.238; 4.U.172.239; 4.U.172.154; 4.U.172.157; 4.U.172.166; 4.U.172.169; 4.U.172.172; 4.U.172.175; 4.U.172.240; 4.U.172.244; 4.U.175.228; 4.U.175.229; 4.U.175.230; 4.U.175.231; 4.U.175.236; 4.U.175.237; 4.U.175.238; 4.U.175.239; 4.U.175.154; 4.U.175.157; 4.U.175.166; 4.U.175.169; 4.U.175.172; 4.U.175.175; 4.U.175.240; 4.U.175.244; 4.U.240.228; 4.U.240.229; 4.U.240.230; 4.U.240.231; 4.U.240.236; 4.U.240.237; 4.U.240.238; 4.U.240.239; 4.U.240.154; 4.U.240.157; 4.U.240.166; 4.U.240.169; 4.U.240.172; 4.U.240.175; 4.U.240.240; 4.U.240.244; 4.U.244.228; 4.U.244.229; 4.U.244.230; 4.U.244.231; 4.U.244.236; 4.U.244.237; 4.U.244.238; 4.U.244.239; 4.U.244.154; 4.U.244.157; 4.U.244.166; 4.U.244.169; 4.U.244.172; 4.U.244.175; 4.U.244.240; 4.U.244.244;

Prodrugs of 4.W

4.W.228.228; 4.W.228.229; 4.W.228.230; 4.W.228.231; 4.W.228.236; 4.W.228.237; 4.W.228.238; 4.W.228.239; 4.W.228.154; 4.W.228.157; 4.W.228.166; 4.W.228.169; 4.W.228.172; 4.W.228.175; 4.W.228.240; 4.W.228.244; 4.W.229.228; 4.W.229.229; 4.W.229.230; 4.W.229.231; 4.W.229.236; 4.W.229.237; 4.W.229.238; 4.W.229.239; 4.W.229.154; 4.W.229.157; 4.W.229.166; 4.W.229.169; 4.W.229.172; 4.W.229.175; 4.W.229.240; 4.W.229.244; 4.W.230.228; 4.W.230.229; 4.W.230.230; 4.W.230.231; 4.W.230.236; 4.W.230.237; 4.W.230.238; 4.W.230.239; 4.W.230.154; 4.W.230.157; 4.W.230.166; 4.W.230.169; 4.W.230.172; 4.W.230.175; 4.W.230.240; 4.W.230.244; 4.W.231.228; 4.W.231.229; 4.W.231.230; 4.W.231.231; 4.W.231.236; 4.W.231.237; 4.W.231.238; 4.W.231.239; 4.W.231.154; 4.W.231.157; 4.W.231.166; 4.W.231.169; 4.W.231.172; 4.W.231.175; 4.W.231.240; 4.W.231.244; 4.W.236.228; 4.W.236.229; 4.W.236.230; 4.W.236.231; 4.W.236.236; 4.W.236.237; 4.W.236.238; 4.W.236.239; 4.W.236.154; 4.W.236.157; 4.W.236.166; 4.W.236.169; 4.W.236.172; 4.W.236.175; 4.W.236.240; 4.W.236.244; 4.W.237.228; 4.W.237.229; 4.W.237.230; 4.W.237.231; 4.W.237.236; 4.W.237.237; 4.W.237.238; 4.W.237.239; 4.W.237.154; 4.W.237.157; 4.W.237.166; 4.W.237.169; 4.W.237.172; 4.W.237.175; 4.W.237.240; 4.W.237.244; 4.W.238.228; 4.W.238.229; 4.W.238.230; 4.W.238.231; 4.W.238.236; 4.W.238.237; 4.W.238.238; 4.W.238.239; 4.W.238.154; 4.W.238.157; 4.W.238.166; 4.W.238.169; 4.W.238.172; 4.W.238.175; 4.W.238.240; 4.W.238.244; 4.W.239.228; 4.W.239.229; 4.W.239.230; 4.W.239.231; 4.W.239.236; 4.W.239.237; 4.W.239.238; 4.W.239.239; 4.W.239.154; 4.W.239.157; 4.W.239.166; 4.W.239.169; 4.W.239.172; 4.W.239.175; 4.W.239.240; 4.W.239.244; 4.W.154.228; 4.W.154.229; 4.W.154.230; 4.W.154.231; 4.W.154.236; 4.W.154.237; 4.W.154.238; 4.W.154.239; 4.W.154.154; 4.W.154.157; 4.W.154.166; 4.W.154.169; 4.W.154.172; 4.W.154.175; 4.W.154.240; 4.W.154.244; 4.W.157.228; 4.W.157.229; 4.W.157.230; 4.W.157.231; 4.W.157.236; 4.W.157.237; 4.W.157.238; 4.W.157.239; 4.W.157.154; 4.W.157.157; 4.W.157.166; 4.W.157.169; 4.W.157.172; 4.W.157.175; 4.W.157.240; 4.W.157.244; 4.W.166.228; 4.W.166.229; 4.W.166.230; 4.W.166.231; 4.W.166.236; 4.W.166.237; 4.W.166.238; 4.W.166.239; 4.W.166.154; 4.W.166.157; 4.W.166.166; 4.W.166.169; 4.W.166.172; 4.W.166.175; 4.W.166.240; 4.W.166.244; 4.W.169.228; 4.W.169.229; 4.W.169.230; 4.W.169.231; 4.W.169.236; 4.W.169.237; 4.W.169.238; 4.W.169.239; 4.W.169.154; 4.W.169.157; 4.W.169.166; 4.W.169.169; 4.W.169.172; 4.W.169.175; 4.W.169.240; 4.W.169.244; 4.W.172.228; 4.W.172.229; 4.W.172.230; 4.W.172.231; 4.W.172.236; 4.W.172.237; 4.W.172.238; 4.W.172.239; 4.W.172.154; 4.W.172.157; 4.W.172.166; 4.W.172.169; 4.W.172.172; 4.W.172.175; 4.W.172.240; 4.W.172.244; 4.W.175.228; 4.W.175.229; 4.W.175.230; 4.W.175.231; 4.W.175.236; 4.W.175.237; 4.W.175.238; 4.W.175.239; 4.W.175.154; 4.W.175.157; 4.W.175.166; 4.W.175.169; 4.W.175.172; 4.W.175.175; 4.W.175.240; 4.W.175.244; 4.W.240.228; 4.W.240.229; 4.W.240.230; 4.W.240.231; 4.W.240.236; 4.W.240.237; 4.W.240.238; 4.W.240.239; 4.W.240.154; 4.W.240.157; 4.W.240.166; 4.W.240.169; 4.W.240.172; 4.W.240.175; 4.W.240.240; 4.W.240.244; 4.W.244.228; 4.W.244.229; 4.W.244.230; 4.W.244.231; 4.W.244.236; 4.W.244.237; 4.W.244.238; 4.W.244.239; 4.W.244.154; 4.W.244.157; 4.W.244.166; 4.W.244.169; 4.W.244.172; 4.W.244.175; 4.W.244.240; 4.W.244.244;

Prodrugs of 4.Y

4.Y.228.228; 4.Y.228.229; 4.Y.228.230; 4.Y.228.231; 4.Y.228.236; 4.Y.228.237; 4.Y.228.238; 4.Y.228.239; 4.Y.228.154; 4.Y.228.157; 4.Y.228.166; 4.Y.228.169; 4.Y.228.172; 4.Y.228.175; 4.Y.228.240; 4.Y.228.244; 4.Y.229.228; 4.Y.229.229; 4.Y.229.230; 4.Y.229.231; 4.Y.229.236; 4.Y.229.237; 4.Y.229.238; 4.Y.229.239; 4.Y.229.154; 4.Y.229.157; 4.Y.229.166; 4.Y.229.169; 4.Y.229.172; 4.Y.229.175; 4.Y.229.240; 4.Y.229.244; 4.Y.230.228; 4.Y.230.229; 4.Y.230.230; 4.Y.230.231; 4.Y.230.236; 4.Y.230.237; 4.Y.230.238; 4.Y.230.239; 4.Y.230.154; 4.Y.230.157; 4.Y.230.166; 4.Y.230.169; 4.Y.230.172; 4.Y.230.175; 4.Y.230.240; 4.Y.230.244; 4.Y.231.228; 4.Y.231.229; 4.Y.231.230; 4.Y.231.231; 4.Y.231.236; 4.Y.231.237; 4.Y.231.238; 4.Y.231.239; 4.Y.231.154; 4.Y.231.157; 4.Y.231.166; 4.Y.231.169; 4.Y.231.172; 4.Y.231.175; 4.Y.231.240; 4.Y.231.244; 4.Y.236.228; 4.Y.236.229; 4.Y.236.230; 4.Y.236.231; 4.Y.236.236; 4.Y.236.237; 4.Y.236.238; 4.Y.236.239; 4.Y.236.154; 4.Y.236.157; 4.Y.236.166; 4.Y.236.169; 4.Y.236.172; 4.Y.236.175; 4.Y.236.240; 4.Y.236.244; 4.Y.237.228; 4.Y.237.229; 4.Y.237.230; 4.Y.237.231; 4.Y.237.236; 4.Y.237.237; 4.Y.237.238; 4.Y.237.239; 4.Y.237.154; 4.Y.237.157; 4.Y.237.166; 4.Y.237.169; 4.Y.237.172; 4.Y.237.175; 4.Y.237.240; 4.Y.237.244; 4.Y.238.228; 4.Y.238.229; 4.Y.238.230; 4.Y.238.231; 4.Y.238.236; 4.Y.238.237; 4.Y.238.238; 4.Y.238.239; 4.Y.238.154; 4.Y.238.157; 4.Y.238.166; 4.Y.238.169; 4.Y.238.172; 4.Y.238.175; 4.Y.238.240; 4.Y.238.244; 4.Y.239.228; 4.Y.239.229; 4.Y.239.230; 4.Y.239.231; 4.Y.239.236; 4.Y.239.237; 4.Y.239.238; 4.Y.239.239; 4.Y.239.154; 4.Y.239.157; 4.Y.239.166; 4.Y.239.169; 4.Y.239.172; 4.Y.239.175; 4.Y.239.240; 4.Y.239.244; 4.Y.154.228; 4.Y.154.229; 4.Y.154.230; 4.Y.154.231; 4.Y.154.236; 4.Y.154.237; 4.Y.154.238; 4.Y.154.239; 4.Y.154.154; 4.Y.154.157; 4.Y.154.166; 4.Y.154.169; 4.Y.154.172; 4.Y.154.175; 4.Y.154.240; 4.Y.154.244; 4.Y.157.228; 4.Y.157.229; 4.Y.157.230; 4.Y.157.231; 4.Y.157.236; 4.Y.157.237; 4.Y.157.238; 4.Y.157.239; 4.Y.157.154; 4.Y.157.157; 4.Y.157.166; 4.Y.157.169; 4.Y.157.172; 4.Y.157.175; 4.Y.157.240; 4.Y.157.244; 4.Y.166.228; 4.Y.166.229; 4.Y.166.230; 4.Y.166.231; 4.Y.166.236; 4.Y.166.237; 4.Y.166.238; 4.Y.166.239; 4.Y.166.154; 4.Y.166.157; 4.Y.166.166; 4.Y.166.169; 4.Y.166.172; 4.Y.166.175; 4.Y.166.240; 4.Y.166.244; 4.Y.169.228; 4.Y.169.229; 4.Y.169.230; 4.Y.169.231; 4.Y.169.236; 4.Y.169.237; 4.Y.169.238; 4.Y.169.239; 4.Y.169.154; 4.Y.169.157; 4.Y.169.166; 4.Y.169.169; 4.Y.169.172; 4.Y.169.175; 4.Y.169.240; 4.Y.169.244; 4.Y.172.228; 4.Y.172.229; 4.Y.172.230; 4.Y.172.231; 4.Y.172.236; 4.Y.172.237; 4.Y.172.238; 4.Y.172.239; 4.Y.172.154; 4.Y.172.157; 4.Y.172.166; 4.Y.172.169; 4.Y.172.172; 4.Y.172.175; 4.Y.172.240; 4.Y.172.244; 4.Y.175.228; 4.Y.175.229; 4.Y.175.230; 4.Y.175.231; 4.Y.175.236; 4.Y.175.237; 4.Y.175.238; 4.Y.175.239; 4.Y.175.154; 4.Y.175.157; 4.Y.175.166; 4.Y.175.169; 4.Y.175.172; 4.Y.175.175; 4.Y.175.240; 4.Y.175.244; 4.Y.240.228; 4.Y.240.229; 4.Y.240.230; 4.Y.240.231; 4.Y.240.236; 4.Y.240.237; 4.Y.240.238; 4.Y.240.239; 4.Y.240.154; 4.Y.240.157; 4.Y.240.166; 4.Y.240.169; 4.Y.240.172; 4.Y.240.175; 4.Y.240.240; 4.Y.240.244;

TABLE 7-continued

4.Y.244.228; 4.Y.244.229; 4.Y.244.230; 4.Y.244.231; 4.Y.244.236; 4.Y.244.237; 4.Y.244.238; 4.Y.244.239; 4.Y.244.154; 4.Y.244.157; 4.Y.244.166; 4.Y.244.169; 4.Y.244.172; 4.Y.244.175; 4.Y.244.240; 4.Y.244.244;
Prodrugs of 5.B 5.B.228.228; 5.B.228.229; 5.B.228.230; 5.B.228.231; 5.B.228.236; 5.B.228.237; 5.B.228.238; 5.B.228.239; 5.B.228.154; 5.B.228.157; 5.B.228.166; 5.B.228.169; 5.B.228.172; 5.B.228.175; 5.B.228.240; 5.B.228.244; 5.B.229.228; 5.B.229.229; 5.B.229.230; 5.B.229.231; 5.B.229.236; 5.B.229.237; 5.B.229.238; 5.B.229.239; 5.B.229.154; 5.B.229.157; 5.B.229.166; 5.B.229.169; 5.B.229.172; 5.B.229.175; 5.B.229.240; 5.B.229.244; 5.B.230.228; 5.B.230.229; 5.B.230.230; 5.B.230.231; 5.B.230.236; 5.B.230.237; 5.B.230.238; 5.B.230.239; 5.B.230.154; 5.B.230.157; 5.B.230.166; 5.B.230.169; 5.B.230.172; 5.B.230.175; 5.B.230.240; 5.B.230.244; 5.B.231.228; 5.B.231.229; 5.B.231.230; 5.B.231.231; 5.B.231.236; 5.B.231.237; 5.B.231.238; 5.B.231.239; 5.B.231.154; 5.B.231.157; 5.B.231.166; 5.B.231.169; 5.B.231.172; 5.B.231.175; 5.B.231.240; 5.B.231.244; 5.B.236.228; 5.B.236.229; 5.B.236.230; 5.B.236.231; 5.B.236.236; 5.B.236.237; 5.B.236.238; 5.B.236.239; 5.B.236.154; 5.B.236.157; 5.B.236.166; 5.B.236.169; 5.B.236.172; 5.B.236.175; 5.B.236.240; 5.B.236.244; 5.B.237.228; 5.B.237.229; 5.B.237.230; 5.B.237.231; 5.B.237.236; 5.B.237.237; 5.B.237.238; 5.B.237.239; 5.B.237.154; 5.B.237.157; 5.B.237.166; 5.B.237.169; 5.B.237.172; 5.B.237.175; 5.B.237.240; 5.B.237.244; 5.B.238.228; 5.B.238.229; 5.B.238.230; 5.B.238.231; 5.B.238.236; 5.B.238.237; 5.B.238.238; 5.B.238.239; 5.B.238.154; 5.B.238.157; 5.B.238.166; 5.B.238.169; 5.B.238.172; 5.B.238.175; 5.B.238.240; 5.B.238.244; 5.B.239.228; 5.B.239.229; 5.B.239.230; 5.B.239.231; 5.B.239.236; 5.B.239.237; 5.B.239.238; 5.B.239.239; 5.B.239.154; 5.B.239.157; 5.B.239.166; 5.B.239.169; 5.B.239.172; 5.B.239.175; 5.B.239.240; 5.B.239.244; 5.B.154.228; 5.B.154.229; 5.B.154.230; 5.B.154.231; 5.B.154.236; 5.B.154.237; 5.B.154.238; 5.B.154.239; 5.B.154.154; 5.B.154.157; 5.B.154.166; 5.B.154.169; 5.B.154.172; 5.B.154.175; 5.B.154.240; 5.B.154.244; 5.B.157.228; 5.B.157.229; 5.B.157.230; 5.B.157.231; 5.B.157.236; 5.B.157.237; 5.B.157.238; 5.B.157.239; 5.B.157.154; 5.B.157.157; 5.B.157.166; 5.B.157.169; 5.B.157.172; 5.B.157.175; 5.B.157.240; 5.B.157.244; 5.B.166.228; 5.B.166.229; 5.B.166.230; 5.B.166.231; 5.B.166.236; 5.B.166.237; 5.B.166.238; 5.B.166.239; 5.B.166.154; 5.B.166.157; 5.B.166.166; 5.B.166.169; 5.B.166.172; 5.B.166.175; 5.B.166.240; 5.B.166.244; 5.B.169.228; 5.B.169.229; 5.B.169.230; 5.B.169.231; 5.B.169.236; 5.B.169.237; 5.B.169.238; 5.B.169.239; 5.B.169.154; 5.B.169.157; 5.B.169.166; 5.B.169.169; 5.B.169.172; 5.B.169.175; 5.B.169.240; 5.B.169.244; 5.B.172.228; 5.B.172.229; 5.B.172.230; 5.B.172.231; 5.B.172.236; 5.B.172.237; 5.B.172.238; 5.B.172.239; 5.B.172.154; 5.B.172.157; 5.B.172.166; 5.B.172.169; 5.B.172.172; 5.B.172.175; 5.B.172.240; 5.B.172.244; 5.B.175.228; 5.B.175.229; 5.B.175.230; 5.B.175.231; 5.B.175.236; 5.B.175.237; 5.B.175.238; 5.B.175.239; 5.B.175.154; 5.B.175.157; 5.B.175.166; 5.B.175.169; 5.B.175.172; 5.B.175.175; 5.B.175.240; 5.B.175.244; 5.B.240.228; 5.B.240.229; 5.B.240.230; 5.B.240.231; 5.B.240.236; 5.B.240.237; 5.B.240.238; 5.B.240.239; 5.B.240.154; 5.B.240.157; 5.B.240.166; 5.B.240.169; 5.B.240.172; 5.B.240.175; 5.B.240.240; 5.B.240.244; 5.B.244.228; 5.B.244.229; 5.B.244.230; 5.B.244.231; 5.B.244.236; 5.B.244.237; 5.B.244.238; 5.B.244.239; 5.B.244.154; 5.B.244.157; 5.B.244.166; 5.B.244.169; 5.B.244.172; 5.B.244.175; 5.B.244.240; 5.B.244.244;
Prodrugs of 5.D 5.D.228.228; 5.D.228.229; 5.D.228.230; 5.D.228.231; 5.D.228.236; 5.D.228.237; 5.D.228.238; 5.D.228.239; 5.D.228.154; 5.D.228.157; 5.D.228.166; 5.D.228.169; 5.D.228.172; 5.D.228.175; 5.D.228.240; 5.D.228.244; 5.D.229.228; 5.D.229.229; 5.D.229.230; 5.D.229.231; 5.D.229.236; 5.D.229.237; 5.D.229.238; 5.D.229.239; 5.D.229.154; 5.D.229.157; 5.D.229.231; 5.D.229.166; 5.D.229.169; 5.D.229.172; 5.D.229.175; 5.D.229.240; 5.D.229.244; 5.D.230.228; 5.D.230.229; 5.D.230.230; 5.D.230.231; 5.D.230.236; 5.D.230.237; 5.D.230.238; 5.D.230.239; 5.D.230.154; 5.D.230.157; 5.D.230.166; 5.D.230.169; 5.D.230.172; 5.D.230.175; 5.D.230.240; 5.D.230.244; 5.D.231.228; 5.D.231.229; 5.D.231.230; 5.D.231.231; 5.D.231.236; 5.D.231.237; 5.D.231.238; 5.D.231.239; 5.D.231.154; 5.D.231.157; 5.D.231.166; 5.D.231.169; 5.D.231.172; 5.D.231.175; 5.D.231.240; 5.D.231.244; 5.D.236.228; 5.D.236.229; 5.D.236.230; 5.D.236.231; 5.D.236.236; 5.D.236.237; 5.D.236.238; 5.D.236.239; 5.D.236.154; 5.D.236.157; 5.D.236.166; 5.D.236.169; 5.D.236.172; 5.D.236.175; 5.D.236.240; 5.D.236.244; 5.D.237.228; 5.D.237.229; 5.D.237.230; 5.D.237.231; 5.D.237.236; 5.D.237.237; 5.D.237.238; 5.D.237.239; 5.D.237.154; 5.D.237.157; 5.D.237.166; 5.D.237.169; 5.D.237.172; 5.D.237.175; 5.D.237.240; 5.D.237.244; 5.D.238.228; 5.D.238.229; 5.D.238.230; 5.D.238.231; 5.D.238.236; 5.D.238.237; 5.D.238.238; 5.D.238.239; 5.D.238.154; 5.D.238.157; 5.D.238.166; 5.D.238.169; 5.D.238.172; 5.D.238.175; 5.D.238.240; 5.D.238.244; 5.D.239.228; 5.D.239.229; 5.D.239.230; 5.D.239.231; 5.D.239.236; 5.D.239.237; 5.D.239.238; 5.D.239.239; 5.D.239.154; 5.D.239.157; 5.D.239.166; 5.D.239.169; 5.D.239.172; 5.D.239.175; 5.D.239.240; 5.D.239.244; 5.D.154.228; 5.D.154.229; 5.D.154.230; 5.D.154.231; 5.D.154.236; 5.D.154.237; 5.D.154.238; 5.D.154.239; 5.D.154.154; 5.D.154.157; 5.D.154.166; 5.D.154.169; 5.D.154.172; 5.D.154.175; 5.D.154.240; 5.D.154.244; 5.D.157.228; 5.D.157.229; 5.D.157.230; 5.D.157.231; 5.D.157.236; 5.D.157.237; 5.D.157.238; 5.D.157.239; 5.D.157.1S4; 5.D.157.1S7; 5.D.157.166; 5.D.157.169; 5.D.157.172; 5.D.157.175; 5.D.157.240; 5.D.157.244; 5.D.166.228; 5.D.166.229; 5.D.166.230; 5.D.166.231; 5.D.166.236; 5.D.166.237; 5.D.166.238; 5.D.166.239; 5.D.166.154; 5.D.166.157; 5.D.166.166; 5.D.166.169; 5.D.166.172; 5.D.166.175; 5.D.166.240; 5.D.166.244; 5.D.169.228; 5.D.169.229; 5.D.169.230; 5.D.169.231; 5.D.169.236; 5.D.169.237; 5.D.169.238; 5.D.169.239; 5.D.169.154; 5.D.169.157; 5.D.169.166; 5.D.169.169; 5.D.169.172; 5.D.169.175; 5.D.169.240; 5.D.169.244; 5.D.172.228; 5.D.172.229; 5.D.172.230; 5.D.172.231; 5.D.172.236; 5.D.172.237; 5.D.172.238; 5.D.172.239; 5.D.172.154; 5.D.172.157; 5.D.172.166; 5.D.172.169; 5.D.172.172; 5.D.172.175; 5.D.172.240; 5.D.172.244; 5.D.175.228; 5.D.17S.229; 5.D.175.230; 5.D.175.231; 5.D.175.236; 5.D.175.237; 5.D.175.238; 5.D.175.239; 5.D.175.154; 5.D.175.157; 5.D.175.166; 5.D.175.169; 5.D.175.172; 5.D.175.175; 5.D.175.240; 5.D.175.244; 5.D.240.228; 5.D.240.229; 5.D.240.230; 5.D.240.231; 5.D.240.236; 5.D.240.237; 5.D.240.238; 5.D.240.239; 5.D.240.154; 5.D.240.157; 5.D.240.166; 5.D.240.169; 5.D.240.172; 5.D.240.175; 5.D.240.240; 5.D.240.244; 5.D.244.228; 5.D.244.229; 5.D.244.230; 5.D.244.231; 5.D.244.236; 5.D.244.237; 5.D.244.238; 5.D.244.239; 5.D.244.154; 5.D.244.157; 5.D.244.166; 5.D.244.169; 5.D.244.172; 5.D.244.175; 5.D.244.240; 5.D.244.244;
Prodrugs of 5.E 5.E.228.228; 5.E228.229; 5.E228.230; 5.E228.231; 5.E228.236; 5.E228.237; 5.E.228.238; 5.E228.239; 5.E.228.154; 5.E.228.157; 5.E.228.166; 5.E.228.169; 5.E.228.172; 5.E.228.175; 5.E.228.240; 5.E.228.244; 5.E.229.228; 5.E.229.229; 5.E.229.230; 5.E.229.231; 5.E.229.236; 5.E.229.237; 5.E.229.238; 5.E.229.239; 5.E.229.154; 5.E.229.157; 5.E.229.166; 5.E.229.169; 5.E.229.172; 5.E.229.175; 5.E.229.240; 5.E.229.244; 5.E.230.228; 5.E.230.229; 5.E.230.230; 5.E.230.231; 5.E.230.236; 5.E.230.237; 5.E.230.238; 5.E.230.239; 5.E.230.154; 5.E.230.157; 5.E.230.166; 5.E.230.169; 5.E.230.172; 5.E.230.175; 5.E.230.240; 5.E.230.244; 5.E.231.228; 5.E.231.229; 5.E.231.230; 5.E.231.231; 5.E.231.236; 5.E.231.237; 5.E.231.238; 5.E.231.239; 5.E.231.154; 5.E.231.157; 5.E.231.166; 5.E.231.169; 5.E.231.172; 5.E.231.175; 5.E.231.240; 5.E.231.244; 5.E.236.228; 5.E.236.229; 5.E.236.230; 5.E.236.231; 5.E.236.236; 5.E.236.237; 5.E.236.238; 5.E.236.239; 5.E.236.154; 5.E.236.157; 5.E.236.166; 5.E.236.169; 5.E.236.172; 5.E.236.175; 5.E.236.240; 5.E.236.244; 5.E.237.228; 5.E.237.229; 5.E.237.230; 5.E.237.231; 5.E.237.236; 5.E.237.237; 5.E.237.238; 5.E.237.239; 5.E.237.154; 5.E.237.157; 5.E.237.166; 5.E.237.169; 5.E.237.172; 5.E.237.175; 5.E.237.240; 5.E.237.244; 5.E.238.228; 5.E.238.229; 5.E.238.230; 5.E.238.231; 5.E.238.236; 5.E.238.237; 5.E.238.238; 5.E.238.239; 5.E.238.154; 5.E.238.157; 5.E.238.166; 5.E.238.169; 5.E.238.172; 5.E.238.175; 5.E.238.240; 5.E.238.244; 5.E.239.228; 5.E.239.229; 5.E.239.230; 5.E.239.231; 5.E.239.236; 5.E.239.237; 5.E.239.238; 5.E.239.239; 5.E.239.154; 5.E.239.157; 5.E.239.166; 5.E.239.169; 5.E.239.172; 5.E.239.175; 5.E.239.240; 5.E.239.244; 5.E.154.228; 5.E.154.229; 5.E.154.230; 5.E.154.231; 5.E.154.236; 5.E.154.237; 5.E.154.238; 5.E.154.239; 5.E.154.154; 5.E.154.157; 5.E.154.166; 5.E.154.169; 5.E.154.172; 5.E.154.175; 5.E.154.240; 5.E.154.244; 5.E.157.228; 5.E.157.229; 5.E.157.230; 5.E.157.231; 5.E.157.236; 5.E.157.237; 5.E.157.238; 5.E.157.239; 5.E.157.154; 5.E.157.157; 5.E.157.166; 5.E.157.169; 5.E.157.172; 5.E.157.175; 5.E.157.240; 5.E.157.244; 5.E.166.228; 5.E.166.229; 5.E.166.230; 5.E.166.231; 5.E.166.236; 5.E.166.237; 5.E.166.238; 5.E.166.239; 5.E.166.154; 5.E.166.157; 5.E.166.166; 5.E.166.169; 5.E.166.172; 5.E.166.175; 5.E.166.240; 5.E.166.244; 5.E.169.228; 5.E.169.229; 5.E.169.230; 5.E.169.231; 5.E.169.236; 5.E.169.237; 5.E.169.238; 5.E.169.239; 5.E.169.154; 5.E.169.157; 5.E.169.166; 5.E.169.169; 5.E.169.172; 5.E.169.175; 5.E.169.240; 5.E.169.244; 5.E.172.228; 5.E.172.229; 5.E.172.230; 5.E.172.231; 5.E.172.236; 5.E.172.237; 5.E.172.238; 5.E.172.239; 5.E.172.154; 5.E.172.157; 5.E.172.166; 5.E.172.169; 5.E.172.172; 5.E.172.175; 5.E.172.240; 5.E.172.244; 5.E.175.228; 5.E.175.229; 5.E.175.230; 5.E.175.231; 5.E.175.236; 5.E.175.237; 5.E.175.238; 5.E.175.239; 5.E.175.154; 5.E.175.157; 5.E.175.166; 5.E.175.169;

TABLE 7-continued

5.E.175.172; 5.E.175.175; 5.E.175.240; 5.E.175.244; 5.E.240.228; 5.E.240.229; 5.E.240.230; 5.E.240.231; 5.E.240.236; 5.E.240.237; 5.E.240.238; 5.E.240.239; 5.E.240.154; 5.E.240.157; 5.E.240.166; 5.E.240.169; 5.E.240.172; 5.E.240.175; 5.E.240.240; 5.E.240.244; 5.E.244.228; 5.E.244.229; 5.E.244.230; 5.E.244.231; 5.E.244.236; 5.E.244.237; 5.E.244.238; 5.E.244.239; 5.E.244.154; 5.E.244.157; 5.E.244.166; 5.E.244.169; 5.E.244.172; 5.E.244.175; 5.E.244.240; 5.E.244.244;

Prodrugs of 5.G

5.G.228.228; 5.G.228.229; 5.G.228.230; 5.G.228.231; 5.G.228.236; 5.G.228.237; 5.G.228.238; 5.G.228.239; 5.G.228.154; 5.G.228.157; 5.G.228.166; 5.G.228.169; 5.G.228.172; 5.G.228.175; 5.G.228.240; 5.G.228.244; 5.G.229.228; 5.G.229.229; 5.G.229.230; 5.G.229.231; 5.G.229.236; 5.G.229.237; 5.G.229.238; 5.G.229.239; 5.G.229.154; 5.G.229.157; 5.G.229.166; 5.G.229.169; 5.G.229.172; 5.G.229.175; 5.G.229.240; 5.G.229.244; 5.G.230.228; 5.G.230.229; 5.G.230.230; 5.G.230.231; 5.G.230.236; 5.G.230.237; 5.G.230.238; 5.G.230.239; 5.G.230.154; 5.G.230.157; 5.G.230.166; 5.G.230.169; 5.G.230.172; 5.G.230.175; 5.G.230.240; 5.G.230.244; 5.G.231.228; 5.G.231.229; 5.G.231.230; 5.G.231.231; 5.G.231.236; 5.G.231.237; 5.G.231.238; 5.G.231.239; 5.G.231.154; 5.G.231.157; 5.G.231.166; 5.G.231.169; 5.G.231.172; 5.G.231.175; 5.G.231.240; 5.G.231.244; 5.G.236.228; 5.G.236.229; 5.G.236.230; 5.G.236.231; 5.G.236.236; 5.G.236.237; 5.G.236.238; 5.G.236.239; 5.G.236.154; 5.G.236.157; 5.G.236.166; 5.G.236.169; 5.G.236.172; 5.G.236.175; 5.G.236.240; 5.G.236.244; 5.G.237.228; 5.G.237.229; 5.G.237.230; 5.G.237.231; 5.G.237.236; 5.G.237.237; 5.G.237.238; 5.G.237.239; 5.G.237.154; 5.G.237.157; 5.G.237.166; 5.G.237.169; 5.G.237.172; 5.G.237.175; 5.G.237.240; 5.G.237.244; 5.G.238.228; 5.G.238.229; 5.G.238.230; 5.G.238.231; 5.G.238.236; 5.G.238.237; 5.G.238.238; 5.G.238.239; 5.G.238.154; 5.G.238.157; 5.G.238.166; 5.G.238.169; 5.G.238.172; 5.G.238.175; 5.G.238.240; 5.G.238.244; 5.G.239.228; 5.G.239.229; 5.G.239.230; 5.G.239.231; 5.G.239.236; 5.G.239.237; 5.G.239.238; 5.G.239.239; 5.G.239.154; 5.G.239.157; 5.G.239.166; 5.G.239.169; 5.G.239.172; 5.G.239.175; 5.G.239.240; 5.G.239.244; 5.G.154.228; 5.G.154.229; 5.G.154.230; 5.G.154.231; 5.G.154.236; 5.G.154.237; 5.G.154.238; 5.G.154.239; S.C.154.154; 5.G.154.157; 5.G.154.166; 5.G.154.169; 5.G.154.172; 5.G.154.175; 5.G.154.240; 5.G.154.244; 5.G.157.228; 5.G.157.229; 5.G.157.230; 5.G.157.231; 5.G.157.236; 5.G.157.237; 5.G.157.238; 5.G.157.239; 5.G.157.154; 5.G.157.157; 5.G.157.166; 5.G.157.169; 5.G.157.172; 5.G.157.175; 5.G.157.240; 5.G.157.244; 5.G.166.228; 5.G.166.229; 5.G.166.230; 5.G.166.231; 5.G.166.236; 5.G.166.237; 5.G.166.238; 5.G.166.239; 5.G.166.154; 5.G.166.157; 5.G.166.166; 5.G.166.169; 5.G.166.172; 5.G.166.175; 5.G.166.240; 5.G.166.244; 5.G.169.228; 5.G.169.229; 5.G.169.230; 5.G.169.231; 5.G.169.236; 5.G.169.237; 5.G.169.238; 5.G.169.239; 5.G.169.154; 5.G.169.157; 5.G.169.166; 5.G.169.169; 5.G.169.172; 5.G.169.175; 5.G.169.240; 5.G.169.244; 5.G.172.228; 5.G.172.229; 5.G.172.230; 5.G.172.231; 5.G.172.236; 5.G.172.237; 5.G.172.238; 5.G.172.239; 5.G.172.154; 5.G.172.157; 5.G.172.166; 5.G.172.169; 5.G.172.172; 5.G.172.175; 5.G.172.240; 5.G.172.244; 5.G.175.228; 5.G.175.229; 5.G.175.230; 5.G.175.231; 5.G.175.236; 5.G.175.237; 5.G.175.238; 5.G.175.239; 5.G.175.154; 5.G.175.157; 5.G.175.166; 5.G.175.169; 5.G.175.172; 5.G.175.175; 5.G.175.240; 5.G.175.244; 5.G.240.228; 5.G.240.229; 5.G.240.230; 5.G.240.231; 5.G.240.236; 5.G.240.237; 5.G.240.238; 5.G.240.239; 5.G.240.154; 5.G.240.157; 5.G.240.166; 5.G.240.169; 5.G.240.172; 5.G.240.175; 5.G.240.240; 5.G.240.244; 5.G.244.228; 5.G.244.229; 5.G.244.230; 5.G.244.231; 5.G.244.236; 5.G.244.237; 5.G.244.238; 5.G.244.239; 5.G.244.154; 5.G.244.157; 5.G.244.166; 5.G.244.169; 5.G.244.172; 5.G.244.175; 5.G.244.240; 5.G.244.244;

Prodrugs of 5.I

5.I.228.228; 5.I.228.229; 5.I.228.230; 5.I.228.231; 5.I.228.236; 5.I.228.237; 5.I.228.238; 5.I.228.239; 5.I.228.154; 5.I.228.157; 5.I.228.166; 5.I.228.169; 5.I.228.172; 5.I.228.175; 5.I.228.240; 5.I.228.244; 5.I.229.228; 5.I.229.229; 5.I.229.230; 5.I.229.231; 5.I.229.236; 5.I.229.237; 5.I.229.238; 5.I.229.239; 5.I.229.154; 5.I.229.157; 5.I.229.166; 5.I.229.169; 5.I.229.172; 5.I.229.175; 5.I.229.240; 5.I.229.244; 5.I.230.228; 5.I.230.229; 5.I.230.230; 5.I.230.231; 5.I.230.236; 5.I.230.237; 5.I.230.238; 5.I.230.239; 5.I.230.154; 5.I.230.157; 5.I.230.166; 5.I.230.169; 5.I.230.172; 5.I.230.175; 5.I.230.240; 5.I.230.244; 5.I.231.228; 5.I.231.229; 5.I.231.230; 5.I.231.231; 5.I.231.236; 5.I.231.237; 5.I.231.238; 5.I.231.239; 5.I.231.154; 5.I.231.157; 5.I.231.166; 5.I.231.169; 5.I.231.172; 5.I.231.175; 5.I.231.240; 5.I.231.244; 5.I.236.228; 5.I.236.229; 5.I.236.230; 5.I.236.231; 5.I.236.236; 5.I.236.237; 5.I.236.238; 5.I.236.239; 5.I.236.154; 5.I.236.157; 5.I.236.166; 5.I.236.169; 5.I.236.172; 5.I.236.175; 5.I.236.240; 5.I.236.244; 5.I.237.228; 5.I.237.229; 5.I.237.230; 5.I.237.231; 5.I.237.236; 5.I.237.237; 5.I.237.238; 5.I.237.239; 5.I.237.154; 5.I.237.157; 5.I.237.166; 5.I.237.172; 5.I.237.175; 5.I.237.240; 5.I.237.244; 5.I.238.228; 5.I.238.229; 5.I.238.230; 5.I.238.231; 5.I.238.236; 5.I.238.237; 5.I.238.238; 5.I.238.239; 5.I.238.154; 5.I.238.157; 5.I.238.166; 5.I.238.169; 5.I.238.172; 5.I.238.175; 5.I.238.240; 5.I.238.244; 5.I.239.228; 5.I.239.229; 5.I.239.230; 5.I.239.231; 5.I.239.236; 5.I.239.237; 5.I.239.238; 5.I.239.239; 5.I.239.154; 5.I.239.157; 5.I.239.166; 5.I.239.169; 5.I.239.172; 5.I.239.175; 5.I.239.240; 5.I.239.244; 5.I.154.228; 5.I.154.229; 5.I.154.230; 5.I.154.231; 5.I.154.236; 5.I.154.237; 5.I.154.238; 5.I.154.239; 5.I.154.154; 5.I.154.157; 5.I.154.166; 5.I.154.169; 5.I.154.172; 5.I.154.175; 5.I.154.240; 5.I.154.244; 5.I.157.228; 5.I.157.229; 5.I.157.230; 5.I.157.231; 5.I.157.236; 5.I.157.237; 5.I.157.238; 5.I.157.239; 5.I.157.154; 5.I.157.157; 5.I.157.166; 5.I.157.169; 5.I.157.172; 5.I.157.175; 5.I.157.240; 5.I.157.244; 5.I.166.228; 5.I.166.229; 5.I.166.230; 5.I.166.231; 5.I.166.236; 5.I.166.237; 5.I.166.238; 5.I.166.239; 5.I.166.154; 5.I.166.157; 5.I.166.166; 5.I.166.169; 5.I.166.172; 5.I.166.175; 5.I.166.240; 5.I.166.244; 5.I.169.228; 5.I.169.229; 5.I.169.230; 5.I.169.231; 5.I.169.236; 5.I.169.237; 5.I.169.238; 5.I.169.239; 5.I.169.154; 5.I.169.157; 5.I.169.166; 5.I.169.169; 5.I.169.172; 5.I.169.175; 5.I.169.240; 5.I.169.244; 5.I.172.228; 5.I.172.229; 5.I.172.230; 5.I.172.231; 5.I.172.236; 5.I.172.237; 5.I.172.238; 5.I.172.239; 5.I.172.154; 5.I.172.157; 5.I.172.166; 5.I.172.169; 5.I.172.172; 5.I.172.175; 5.I.172.240; 5.I.172.244; 5.I.175.228; 5.I.175.229; 5.I.175.230; 5.I.175.231; 5.I.175.236; 5.I.175.237; 5.I.175.238; 5.I.175.239; 5.I.175.154; 5.I.175.157; 5.I.175.166; 5.I.175.169; 5.I.175.172; 5.I.175.175; 5.I.175.240; 5.I.175.244; 5.I.240.228; 5.I.240.229; 5.I.240.230; 5.I.240.231; 5.I.240.236; 5.I.240.237; 5.I.240.238; 5.I.240.239; 5.I.240.154; 5.I.240.157; 5.I.240.166; 5.I.240.169; 5.I.240.172; 5.I.240.175; 5.I.240.240; 5.I.240.244; 5.I.244.228; 5.I.244.229; 5.I.244.230; 5.I.244.231; 5.I.244.236; 5.I.244.237; 5.I.244.238; 5.I.244.239; 5.I.244.154; 5.I.244.157; 5.I.244.166; 5.I.244.169; 5.I.244.172; 5.I.244.175; 5.I.244.240; 5.I.244.244;

Prodrugs of 5.J

5.J.228.228; 5.J.228.229; 5.J.228.230; 5.J.228.231; 5.J.228.236; 5.J.228.237; 5.J.228.238; 5.J.228.239; 5.J.228.154; 5.J.228.157; 5.J.228.166; 5.J.228.169; 5.J.228.172; 5.J.228.175; 5.J.228.240; 5.J.228.244; 5.J.229.228; 5.J.229.229; 5.J.229.230; 5.J.229.231; 5.J.229.236; 5.J.229.237; 5.J.229.238; 5.J.229.239; 5.J.229.154; 5.J.229.157; 5.J.229.166; 5.J.229.169; 5.J.229.172; 5.J.229.175; 5.J.229.240; 5.J.229.244; 5.J.230.228; 5.J.230.229; 5.J.230.230; 5.J.230.231; 5.J.230.236; 5.J.230.237; 5.J.230.238; 5.J.230.239; 5.J.230.154; 5.J.230.157; 5.J.230.166; 5.J.230.169; 5.J.230.172; 5.J.230.175; 5.J.230.240; 5.J.230.244; 5.J.231.228; 5.J.231.229; 5.J.231.230; 5.J.231.231; 5.J.231.236; 5.J.231.237; 5.J.231.238; 5.J.231.239; 5.J.231.154; 5.J.231.157; 5.J.231.166; 5.J.231.169; 5.J.231.172; 5.J.231.175; 5.J.231.240; 5.J.231.244; 5.J.236.228; 5.J.236.229; 5.J.236.230; 5.J.236.231; 5.J.236.236; 5.J.236.237; 5.J.236.238; 5.J.236.239; 5.J.236.154; 5.J.236.157; 5.J.236.166; 5.J.236.169; 5.J.236.172; 5.J.236.175; 5.J.236.240; 5.J.236.244; 5.J.237.228; 5.J.237.229; 5.J.237.230; 5.J.237.231; 5.J.237.236; 5.J.237.237; 5.J.237.238; 5.J.237.239; 5.J.237.154; 5.J.237.157; 5.J.237.166; 5.J.237.169; 5.J.237.172; 5.J.237.175; 5.J.237.240; 5.J.237.244; 5.J.238.228; 5.J.238.229; 5.J.238.230; 5.J.238.231; 5.J.238.236; 5.J.238.237; 5.J.238.238; 5.J.238.239; 5.J.238.154; 5.J.238.157; 5.J.238.166; 5.J.238.169; 5.J.238.172; 5.J.238.175; 5.J.238.240; 5.J.238.244; 5.J.239.228; 5.J.239.229; 5.J.239.230; 5.J.239.231; 5.J.239.236; 5.J.239.237; 5.J.239.238; 5.J.239.239; 5.J.239.154; 5.J.239.157; 5.J.239.166; 5.J.239.169; 5.J.239.172; 5.J.239.175; 5.J.239.240; 5.J.239.244; 5.J.154.228; 5.J.154.229; 5.J.154.230; 5.J.154.231; 5.J.154.236; 5.J.154.237; 5.J.154.238; 5.J.154.239; 5.J.154.154; 5.J.154.157; 5.J.154.166; 5.J.154.169; 5.J.154.172; 5.J.154.175; 5.J.154.240; 5.J.154.244; 5.J.157.228; 5.J.157.229; 5.J.157.230; 5.J.157.231; 5.J.157.236; 5.J.157.237; 5.J.157.238; 5.J.157.239; 5.J.157.154; 5.J.157.157; 5.J.157.166; 5.J.157.169; 5.J.157.172; 5.J.157.175; 5.J.157.240; 5.J.157.244; 5.J.166.228; 5.J.166.229; 5.J.166.230; 5.J.166.231; 5.J.166.236; 5.J.166.237; 5.J.166.238; 5.J.166.239; 5.J.166.154; 5.J.166.157; 5.J.166.166; 5.J.166.169; 5.J.166.172; 5.J.166.175; 5.J.166.240; 5.J.166.244; 5.J.169.228; 5.J.169.229; 5.J.169.230; 5.J.169.231; 5.J.169.236; 5.J.169.237; 5.J.169.238; 5.J.169.239; 5.J.169.154; 5.J.169.157; 5.J.169.166; 5.J.169.169; 5.J.169.172; 5.J.169.175; 5.J.169.240; 5.J.169.244; 5.J.172.228; 5.J.172.229; 5.J.172.230; 5.J.172.231; 5.J.172.236; 5.J.172.237; 5.J.172.238; 5.J.172.239;

TABLE 7-continued

5.J.172.154; 5.J.172.157; 5.J.172.166; 5.J.172.169; 5.J.172.172;
5.J.172.175; 5.J.172.240; 5.J.172.244; 5.J.175.228; 5.J.175.229;
5.J.175.230; 5.J.175.231; 5.J.175.236; 5.J.175.237; 5.J.175.238;
5.J.175.239; 5.J.175.154; 5.J.175.157; 5.J.175.166; 5.J.175.169;
5.J.175.172; 5.J.175.175; 5.J.175.240; 5.J.175.244; 5.J.240.228;
5.J.240.229; 5.J.240.230; 5.J.240.231; 5.J.240.236; 5.J.240.237;
5.J.240.238; 5.J.240.239; 5.J.240.154; 5.J.240.157; 5.J.240.166;
5.J.240.169; 5.J.240.172; 5.J.240.175; 5.J.240.240; 5.J.240.244;
5.J.244.228; 5.J.244.229; 5.J.244.230; 5.J.244.231; 5.J.244.236;
5.J.244.237; 5.J.244.238; 5.J.244.239; 5.J.244.154; 5.J.244.157;
5.J.244.166; 5.J.244.169; 5.J.244.172; 5.J.244.175; 5.J.244.240;
5.J.244.244;
Prodrugs of 5.L 5.L.228.228; 5.L.228.229; 5.L.228.230; 5.L.228.231; 5.L.228.236;
5.L.228.237; 5.L.228.238; 5.L.228.239; 5.L.228.154; 5.L.228.157;
5.L.228.166; 5.L.228.169; 5.L.228.172; 5.L.228.175; 5.L.228.240;
5.L.228.244; 5.L.229.228; 5.L.229.229; 5.L.229.230; 5.L.229.231;
5.L.229.236; 5.L.229.237; 5.L.229.238; 5.L.229.239; 5.L.229.154;
5.L.229.157; 5.L.229.166; 5.L.229.169; 5.L.229.172; 5.L.229.175;
5.L.229.240; 5.L.229.244; 5.L.230.228; 5.L.230.229; 5.L.230.230;
5.L.230.231; 5.L.230.236; 5.L.230.237; 5.L.230.238; 5.L.230.239;
5.L.230.154; 5.L.230.157; 5.L.230.166; 5.L.230.169; 5.L.230.172;
5.L.230.175; 5.L.230.240; 5.L.230.244; 5.L.231.228; 5.L.231.229;
5.L.231.230; 5.L.231.231; 5.L.231.236; 5.L.231.237; 5.L.231.238;
5.L.231.239; 5.L.231.154; 5.L.231.157; 5.L.231.166; 5.L.231.169;
5.L.231.172; 5.L.231.175; 5.L.231.240; 5.L.231.244; 5.L.236.228;
5.L.236.229; 5.L.236.230; 5.L.236.231; 5.L.236.236; 5.L.236.237;
5.L.236.238; 5.L.236.239; 5.L.236.154; 5.L.236.157; 5.L.236.166;
5.L.236.169; 5.L.236.172; 5.L.236.175; 5.L.236.240; 5.L.236.244;
5.L.237.228; 5.L.237.229; 5.L.237.230; 5.L.237.231; 5.L.237.236;
5.L.237.237; 5.L.237.238; 5.L.237.239; 5.L.237.154; 5.L.237.157;
5.L.237.166; 5.L.237.169; 5.L.237.172; 5.L.237.175; 5.L.237.240;
5.L.237.244; 5.L.238.228; 5.L.238.229; 5.L.238.230; 5.L.238.231;
5.L.238.236; 5.L.238.237; 5.L.238.238; 5.L.238.239; 5.L.238.154;
5.L.238.157; 5.L.238.166; 5.L.238.169; 5.L.238.172; 5.L.238.175;
5.L.238.240; 5.L.238.244; 5.L.239.228; 5.L.239.229; 5.L.239.230;
5.L.239.231; 5.L.239.236; 5.L.239.237; 5.L.239.238; 5.L.239.239;
5.L.239.154; 5.L.239.157; 5.L.239.166; 5.L.239.169; 5.L.239.172;
5.L.239.175; 5.L.239.240; 5.L.239.244; 5.L.154.228; 5.L.154.229;
5.L.154.230; 5.L.154.231; 5.L.154.236; 5.L.154.237; 5.L.154.238;
5.L.154.239; 5.L.154.154; 5.L.154.157; 5.L.154.166; 5.L.154.169;
5.L.154.172; 5.L.154.175; 5.L.154.240; 5.L.154.244; 5.L.157.228;
5.L.157.229; 5.L.157.230; 5.L.157.231; 5.L.157.236; 5.L.157.237;
5.L.157.238; 5.L.157.239; 5.L.157.154; 5.L.157.157; 5.L.157.166;
5.L.157.169; 5.L.157.172; 5.L.157.175; 5.L.157.240; 5.L.157.244;
5.L.166.228; 5.L.166.229; 5.L.166.230; 5.L.166.231; 5.L.166.236;
5.L.166.237; 5.L.166.238; 5.L.166.239; 5.L.166.154; 5.L.166.157;
5.L.166.166; 5.L.166.169; 5.L.166.172; 5.L.166.175; 5.L.166.240;
5.L.166.244; 5.L.169.228; 5.L.169.229; 5.L.169.230; 5.L.169.231;
5.L.169.236; 5.L.169.237; 5.L.169.238; 5.L.169.239; 5.L.169.154;
5.L.169.157; 5.L.169.166; 5.L.169.169; 5.L.169.172; 5.L.169.175;
5.L.169.240; 5.L.169.244; 5.L.172.228; 5.L.172.229; 5.L.172.230;
5.L.172.231; 5.L.172.236; 5.L.172.237; 5.L.172.238; 5.L.172.239;
5.L.172.154; 5.L.172.157; 5.L.172.166; 5.L.172.169; 5.L.172.172;
5.L.172.175; 5.L.172.240; 5.L.172.244; 5.L.175.228; 5.L.175.229;
5.L.175.230; 5.L.175.231; 5.L.175.236; 5.L.175.237; 5.L.175.238;
5.L.175.239; 5.L.175.154; 5.L.175.157; 5.L.175.166; 5.L.175.169;
5.L.175.172; 5.L.175.175; 5.L.175.240; 5.L.175.244; 5.L.240.228;
5.L.240.229; 5.L.240.230; 5.L.240.231; 5.L.240.236; 5.L.240.237;
5.L.240.238; 5.L.240.239; 5.L.240.154; 5.L.240.157; 5.L.240.166;
5.L.240.169; 5.L.240.172; 5.L.240.175; 5.L.240.240; 5.L.240.244;
5.L.244.228; 5.L.244.229; 5.L.244.230; 5.L.244.231; 5.L.244.236;
5.L.244.237; 5.L.244.238; 5.L.244.239; 5.L.244.154; 5.L.244.157;
5.L.244.166; 5.L.244.169; 5.L.244.172; 5.L.244.175; 5.L.244.240;
5.L.244.244;
Prodrugs of 5.O 5.O.228.228; 5.O.228.229; 5.O.228.230; 5.O.228.231; 5.O.228.236;
5.O.228.237; 5.O.228.238; 5.O.228.239; 5.O.228.154; 5.O.228.157;
5.O.228.166; 5.O.228.169; 5.O.228.172; 5.O.228.175; 5.O.228.240;
5.O.228.244; 5.O.229.228; 5.O.229.229; 5.O.229.230; 5.O.229.231;
5.O.229.236; 5.O.229.237; 5.O.229.238; 5.O.229.239; 5.O.229.154;
5.O.229.157; 5.O.229.166; 5.O.229.169; 5.O.229.172; 5.O.229.175;
5.O.229.240; 5.O.229.244; 5.O.230.228; 5.O.230.229; 5.O.230.230;
5.O.230.231; 5.O.230.236; 5.O.230.237; 5.O.230.238; 5.O.230.239;
5.O.230.154; 5.O.230.157; 5.O.230.166; 5.O.230.169; 5.O.230.172;
5.O.230.175; 5.O.230.240; 5.O.230.244; 5.O.231.228; 5.O.231.229;
5.O.231.230; 5.O.231.231; 5.O.231.236; 5.O.231.237; 5.O.231.238;
5.O.231.239; 5.O.231.154; 5.O.231.157; 5.O.231.166; 5.O.231.169;
5.O.231.172; 5.O.231.175; 5.O.231.240; 5.O.231.244; 5.O.236.228;
5.O.236.229; 5.O.236.230; 5.O.236.231; 5.O.236.236; 5.O.236.237;
5.O.236.238; 5.O.236.239; 5.O.236.154; 5.O.236.157; 5.O.236.166;
5.O.236.169; 5.O.236.172; 5.O.236.175; 5.O.236.240; 5.O.236.244;
5.O.237.228; 5.O.237.229; 5.O.237.230; 5.O.237.231; 5.O.237.236;
5.O.237.237; 5.O.237.238; 5.O.237.239; 5.O.237.154; 5.O.237.157;
5.O.237.166; 5.O.237.169; 5.O.237.172; 5.O.237.175; 5.O.237.240;
5.O.237.244; 5.O.238.228; 5.O.238.229; 5.O.238.230; 5.O.238.231;
5.O.238.236; 5.O.238.237; 5.O.238.238; 5.O.238.239; 5.O.238.154;
5.O.238.157; 5.O.238.166; 5.O.238.169; 5.O.238.172; 5.O.238.175;
5.O.238.240; 5.O.238.244; 5.O.239.228; 5.O.239.229; 5.O.239.230;
5.O.239.231; 5.O.239.236; 5.O.239.237; 5.O.239.238; 5.O.239.239;
5.O.239.154; 5.O.239.157; 5.O.239.166; 5.O.239.169; 5.O.239.172;
5.O.239.175; 5.O.239.240; 5.O.239.244; 5.O.154.228; 5.O.154.229;
5.O.154.230; 5.O.154.231; 5.O.154.236; 5.O.154.237; 5.O.154.238;
5.O.154.239; 5.O.154.154; 5.O.154.157; 5.O.154.166; 5.O.154.169;
5.O.154.172; 5.O.154.175; 5.O.154.240; 5.O.154.244; 5.O.157.228;
5.O.157.229; 5.O.157.230; 5.O.157.231; 5.O.157.236; 5.O.157.237;
5.O.157.238; 5.O.157.239; 5.O.157.154; 5.O.157.157; 5.O.157.166;
5.O.157.169; 5.O.157.172; 5.O.157.175; 5.O.157.240; 5.O.157.244;
5.O.166.228; 5.O.166.229; 5.O.166.230; 5.O.166.231; 5.O.166.236;
5.O.166.237; 5.O.166.238; 5.O.166.239; 5.O.166.154; 5.O.166.157;
5.O.166.166; 5.O.166.169; 5.O.166.172; 5.O.166.175; 5.O.166.240;
5.O.166.244; 5.O.169.228; 5.O.169.229; 5.O.169.230; 5.O.169.231;
5.O.169.236; 5.O.169.237; 5.O.169.238; 5.O.169.239; 5.O.169.154;
5.O.169.157; 5.O.169.166; 5.O.169.169; 5.O.169.172; 5.O.169.175;
5.O.169.240; 5.O.169.244; 5.O.172.228; 5.O.172.229; 5.O.172.230;
5.O.172.231; 5.O.172.236; 5.O.172.237; 5.O.172.238; 5.O.172.239;
5.O.172.154; 5.O.172.157; 5.O.172.166; 5.O.172.169; 5.O.172.172;
5.O.172.175; 5.O.172.240; 5.O.172.244; 5.O.175.228; 5.O.175.229;
5.O.175.230; 5.O.175.231; 5.O.175.236; 5.O.175.237; 5.O.175.238;
5.O.175.239; 5.O.175.154; 5.O.175.157; 5.O.175.166; 5.O.175.169;
5.O.175.172; 5.O.175.175; 5.O.175.240; 5.O.175.244; 5.O.240.228;
5.O.240.229; 5.O.240.230; 5.O.240.231; 5.O.240.236; 5.O.240.237;
5.O.240.238; 5.O.240.239; 5.O.240.154; 5.O.240.157; 5.O.240.166;
5.O.240.169; 5.O.240.172; 5.O.240.175; 5.O.240.240; 5.O.240.244;
5.O.244.228; 5.O.244.229; 5.O.244.230; 5.O.244.231; 5.O.244.236;
5.O.244.237; 5.O.244.238; 5.O.244.239; 5.O.244.154; 5.O.244.157;
5.O.244.166; 5.O.244.169; 5.O.244.172; 5.O.244.175; 5.O.244.240;
5.O.244.244;
Prodrugs of 5.P 5.P.228.228; 5.P.228.229; 5.P.228.230; 5.P.228.231; 5.P.228.236;
5.P.228.237; 5.P.228.238; 5.P.228.239; 5.P.228.154; 5.P.228.157;
5.P.228.166; 5.P.228.169; 5.P.228.172; 5.P.228.175; 5.P.228.240;
5.P.228.244; 5.P.229.228; 5.P.229.229; 5.P.229.230; 5.P.229.231;
5.P.229.236; 5.P.229.237; 5.P.229.238; 5.P.229.239; 5.P.229.154;
5.P.229.157; 5.P.229.166; 5.P.229.169; 5.P.229.172; 5.P.229.175;
5.P.229.240; 5.P.229.244; 5.P.230.228; 5.P.230.229; 5.P.230.230;
5.P.230.231; 5.P.230.236; 5.P.230.237; 5.P.230.238; 5.P.230.239;
5.P.230.154; 5.P.230.157; 5.P.230.166; 5.P.230.169; 5.P.230.172;
5.P.230.175; 5.P.230.240; 5.P.230.244; 5.P.231.228; 5.P.231.229;
5.P.231.230; 5.P.231.231; 5.P.231.236; 5.P.231.237; 5.P.231.238;
5.P.231.239; 5.P.231.154; 5.P.231.157; 5.P.231.166; 5.P.231.169;
5.P.231.172; 5.P.231.175; 5.P.231.240; 5.P.231.244; 5.P.236.228;
5.P.236.229; 5.P.236.230; 5.P.236.231; 5.P.236.236; 5.P.236.237;
5.P.236.238; 5.P.236.239; 5.P.236.154; 5.P.236.157; 5.P.236.166;
5.P.236.169; 5.P.236.172; 5.P.236.175; 5.P.236.240; 5.P.236.244;
5.P.237.228; 5.P.237.229; 5.P.237.230; 5.P.237.231; 5.P.237.236;
5.P.237.237; 5.P.237.238; 5.P.237.239; 5.P.237.154; 5.P.237.157;
5.P.237.166; 5.P.237.169; 5.P.237.172; 5.P.237.175; 5.P.237.240;
5.P.237.244; 5.P.238.228; 5.P.238.229; 5.P.238.230; 5.P.238.231;
5.P.238.236; 5.P.238.237; 5.P.238.238; 5.P.238.239; 5.P.238.154;
5.P.238.157; 5.P.238.166; 5.P.238.169; 5.P.238.172; 5.P.238.175;
5.P.238.240; 5.P.238.244; 5.P.239.228; 5.P.239.229; 5.P.239.230;
5.P.239.231; 5.P.239.236; 5.P.239.237; 5.P.239.238; 5.P.239.239;
5.P.239.154; 5.P.239.157; 5.P.239.166; 5.P.239.169; 5.P.239.172;
5.P.239.175; 5.P.239.240; 5.P.239.244; 5.P.154.228; 5.P.154.229;
5.P.154.230; 5.P.154.231; 5.P.154.236; 5.P.154.237; 5.P.154.238;
5.P.154.239; 5.P.154.154; 5.P.154.157; 5.P.154.166; 5.P.154.169;
5.P.154.172; 5.P.154.175; 5.P.154.240; 5.P.154.244; 5.P.157.228;
5.P.157.229; 5.P.157.230; 5.P.157.231; 5.P.157.236; 5.P.157.237;
5.P.157.238; 5.P.157.239; 5.P.157.154; 5.P.157.157; 5.P.157.166;
5.P.157.169; 5.P.157.172; 5.P.157.175; 5.P.157.240; 5.P.157.244;
5.P.166.228; 5.P.166.229; 5.P.166.230; 5.P.166.231; 5.P.166.236;
5.P.166.237; 5.P.166.238; 5.P.166.239; 5.P.166.154; 5.P.166.157;
5.P.166.166; 5.P.166.169; 5.P.166.172; 5.P.166.175; 5.P.166.240;
5.P.166.244; 5.P.169.228; 5.P.169.229; 5.P.169.230; 5.P.169.231;

TABLE 7-continued

5.P.169.236; 5.P.169.237; 5.P.169.238; 5.P.169.239; 5.P.169.154;
5.P.169.157; 5.P.169.166; 5.P.169.169; 5.P.169.172; 5.P.169.175;
5.P.169.240; 5.P.169.244; 5.P.172.228; 5.P.172.229; 5.P.172.230;
5.P.172.231; 5.P.172.236; 5.P.172.237; 5.P.172.238; 5.P.172.239;
5.P.172.154; 5.P.172.157; 5.P.172.166; 5.P.172.169; 5.P.172.172;
5.P.172.175; 5.P.172.240; 5.P.172.244; 5.P.175.228; 5.P.175.229;
5.P.175.230; 5.P.175.231; 5.P.175.236; 5.P.175.237; 5.P.175.238;
5.P.175.239; 5.P.175.154; 5.P.175.157; 5.P.175.166; 5.P.175.169;
5.P.175.172; 5.P.175.175; 5.P.175.240; 5.P.175.244; 5.P.240.228;
5.P.240.229; 5.P.240.230; 5.P.240.231; 5.P.240.236; 5.P.240.237;
5.P.240.238; 5.P.240.239; 5.P.240.154; 5.P.240.157; 5.P.240.166;
5.P.240.169; 5.P.240.172; 5.P.240.175; 5.P.240.240; 5.P.240.244;
5.P.244.228; 5.P.244.229; 5.P.244.230; 5.P.244.231; 5.P.244.236;
5.P.244.237; 5.P.244.238; 5.P.244.239; 5.P.244.154; 5.P.244.157;
5.P.244.166; 5.P.244.169; 5.P.244.172; 5.P.244.175; 5.P.244.240;
5.P.244.244;
Prodrugs of 5.U 5.U.228.228; 5.U.228.229; 5.U.228.230; 5.U.228.231; 5.U.228.236;
5.U.228.237; 5.U.228.238; 5.U.228.239; 5.U.228.154; 5.U.228.157;
5.U.228.166; 5.U.228.169; 5.U.228.172; 5.U.228.175; 5.U.228.240;
5.U.228.244; 5.U.229.228; 5.U.229.229; 5.U.229.230; 5.U.229.231;
5.U.229.236; 5.U.229.237; 5.U.229.238; 5.U.229.239; 5.U.229.154;
5.U.229.157; 5.U.229.166; 5.U.229.169; 5.U.229.172; 5.U.229.175;
5.U.229.240; 5.U.229.244; 5.U.230.228; 5.U.230.229; 5.U.230.230;
5.U.230.231; 5.U.230.236; 5.U.230.237; 5.U.230.238; 5.U.230.239;
5.U.230.154; 5.U.230.157; 5.U.230.166; 5.U.230.169; 5.U.230.172;
5.U.230.175; 5.U.230.240; 5.U.230.244; 5.U.231.228; 5.U.231.229;
5.U.231.230; 5.U.231.231; 5.U.231.236; 5.U.231.237; 5.U.231.238;
5.U.231.239; 5.U.231.154; 5.U.231.157; 5.U.231.166; 5.U.231.169;
5.U.231.172; 5.U.231.175; 5.U.231.240; 5.U.231.244; 5.U.236.228;
5.U.236.229; 5.U.236.230; 5.U.236.231; 5.U.236.236; 5.U.236.237;
5.U.236.238; 5.U.236.239; 5.U.236.154; 5.U.236.157; 5.U.236.166;
5.U.236.169; 5.U.236.172; 5.U.236.175; 5.U.236.240; 5.U.236.244;
5.U.237.228; 5.U.237.229; 5.U.237.230; 5.U.237.231; 5.U.237.236;
5.U.237.237; 5.U.237.238; 5.U.237.239; 5.U.237.154; 5.U.237.157;
5.U.237.166; 5.U.237.169; 5.U.237.172; 5.U.237.175; 5.U.237.240;
5.U.237.244; 5.U.238.228; 5.U.238.229; 5.U.238.230; 5.U.238.231;
5.U.238.236; 5.U.238.237; 5.U.238.238; 5.U.238.239; 5.U.238.154;
5.U.238.157; 5.U.238.166; 5.U.238.169; 5.U.238.172; 5.U.238.175;
5.U.238.240; 5.U.238.244; 5.U.239.228; 5.U.239.229; 5.U.239.230;
5.U.239.231; 5.U.239.236; 5.U.239.237; 5.U.239.238; 5.U.239.239;
5.U.239.154; 5.U.239.157; 5.U.239.166; 5.U.239.169; 5.U.239.172;
5.U.239.175; 5.U.239.240; 5.U.239.244; 5.U.154.228; 5.U.154.229;
5.U.154.230; 5.U.154.231; 5.U.154.236; 5.U.154.237; 5.U.154.238;
5.U.154.239; 5.U.154.154; 5.U.154.157; 5.U.154.166; 5.U.154.169;
5.U.154.172; 5.U.154.175; 5.U.154.240; 5.U.154.244; 5.U.157.228;
5.U.157.229; 5.U.157.230; 5.U.157.231; 5.U.157.236; 5.U.157.237;
5.U.157.238; 5.U.157.239; 5.U.157.154; 5.U.157.157; 5.U.157.166;
5.U.157.169; 5.U.157.172; 5.U.157.175; 5.U.157.240; 5.U.157.244;
5.U.166.228; 5.U.166.229; 5.U.166.230; 5.U.166.231; 5.U.166.236;
5.U.166.237; 5.U.166.238; 5.U.166.239; 5.U.166.154; 5.U.166.157;
5.U.166.166; 5.U.166.169; 5.U.166.172; 5.U.166.175; 5.U.166.240;
5.U.166.244; 5.U.169.228; 5.U.169.229; 5.U.169.230; 5.U.169.231;
5.U.169.236; 5.U.169.237; 5.U.169.238; 5.U.169.239; 5.U.169.154;
5.U.169.157; 5.U.169.166; 5.U.169.169; 5.U.169.172; 5.U.169.175;
5.U.169.240; 5.U.169.244; 5.U.172.228; 5.U.172.229; 5.U.172.230;
5.U.172.231; 5.U.172.236; 5.U.172.237; 5.U.172.238; 5.U.172.239;
5.U.172.154; 5.U.172.157; 5.U.172.166; 5.U.172.169; 5.U.172.172;
5.U.172.175; 5.U.172.240; 5.U.172.244; 5.U.175.228; 5.U.175.229;
5.U.175.230; 5.U.175.231; 5.U.175.236; 5.U.175.237; 5.U.175.238;
5.U.175.239; 5.U.175.154; 5.U.175.157; 5.U.175.166; 5.U.175.169;
5.U.175.172; 5.U.175.175; 5.U.175.240; 5.U.175.244; 5.U.240.228;
5.U.240.229; 5.U.240.230; 5.U.240.231; 5.U.240.236; 5.U.240.237;
5.U.240.238; 5.U.240.239; 5.U.240.154; 5.U.240.157; 5.U.240.166;
5.U.240.169; 5.U.240.172; 5.U.240.175; 5.U.240.240; 5.U.240.244;
5.U.244.228; 5.U.244.229; 5.U.244.230; 5.U.244.231; 5.U.244.236;
5.U.244.237; 5.U.244.238; 5.U.244.239; 5.U.244.154; 5.U.244.157;
5.U.244.166; 5.U.244.169; 5.U.244.172; 5.U.244.175; 5.U.244.240;
5.U.244.244;
Prodrugs of 5.W 5.W.228.228; 5.W.228.229; 5.W.228.230; 5.W.228.231; 5.W.228.236;
5.W.228.237; 5.W.228.238; 5.W.228.239; 5.W.228.154; 5.W.228.157;
5.W.228.166; 5.W.228.169; 5.W.228.172; 5.W.228.175; 5.W.228.240;
5.W.228.244; 5.W.229.228; 5.W.229.229; 5.W.229.230; 5.W.229.231;
5.W.229.236; 5.W.229.237; 5.W.229.238; 5.W.229.239; 5.W.229.154;
5.W.229.157; 5.W.229.166; 5.W.229.169; 5.W.229.172; 5.W.229.175;
5.W.229.240; 5.W.229.244; 5.W.230.228; 5.W.230.229; 5.W.230.230;
5.W.230.231; 5.W.230.236; 5.W.230.237; 5.W.230.238; 5.W.230.239;
5.W.230.154; 5.W.230.157; 5.W.230.166; 5.W.230.169; 5.W.230.172;
5.W.230.175; 5.W.230.240; 5.W.230.244; 5.W.231.228; 5.W.231.229;
5.W.231.230; 5.W.231.231; 5.W.231.236; 5.W.231.237; 5.W.231.238;
5.W.231.239; 5.W.231.154; 5.W.231.157; 5.W.231.166; 5.W.231.169;
5.W.231.172; 5.W.231.175; 5.W.231.240; 5.W.231.244; 5.W.236.228;
5.W.236.229; 5.W.236.230; 5.W.236.231; 5.W.236.236; 5.W.236.237;
5.W.236.238; 5.W.236.239; 5.W.236.154; 5.W.236.157; 5.W.236.166;
5.W.236.169; 5.W.236.172; 5.W.236.175; 5.W.236.240; 5.W.236.244;
5.W.237.228; 5.W.237.229; 5.W.237.230; 5.W.237.231; 5.W.237.236;
5.W.237.237; 5.W.237.238; 5.W.237.239; 5.W.237.154; 5.W.237.157;
5.W.237.166; 5.W.237.169; 5.W.237.172; 5.W.237.175; 5.W.237.240;
5.W.237.244; 5.W.238.228; 5.W.238.229; 5.W.238.230; 5.W.238.231;
5.W.238.236; 5.W.238.237; 5.W.238.238; 5.W.238.239; 5.W.238.154;
5.W.238.157; 5.W.238.166; 5.W.238.169; 5.W.238.172; 5.W.238.175;
5.W.238.240; 5.W.238.244; 5.W.239.228; 5.W.239.229; 5.W.239.230;
5.W.239.231; 5.W.239.236; 5.W.239.237; 5.W.239.238; 5.W.239.239;
5.W.239.154; 5.W.239.157; 5.W.239.166; 5.W.239.169; 5.W.239.172;
5.W.239.175; 5.W.239.240; 5.W.239.244; 5.W.154.228; 5.W.154.229;
5.W.154.230; 5.W.154.231; 5.W.154.236; 5.W.154.237; 5.W.154.238;
5.W.154.239; 5.W.154.154; 5.W.154.157; 5.W.154.166; 5.W.154.169;
5.W.154.172; 5.W.154.175; 5.W.154.240; 5.W.154.244; 5.W.157.228;
5.W.157.229; 5.W.157.230; 5.W.157.231; 5.W.157.236; 5.W.157.237;
5.W.157.238; 5.W.157.239; 5.W.157.154; 5.W.157.157; 5.W.157.166;
5.W.157.169; 5.W.157.172; 5.W.157.175; 5.W.157.240; 5.W.157.244;
5.W.166.228; 5.W.166.229; 5.W.166.230; 5.W.166.231; 5.W.166.236;
5.W.166.237; 5.W.166.238; 5.W.166.239; 5.W.166.154; 5.W.166.157;
5.W.166.166; 5.W.166.169; 5.W.166.172; 5.W.166.175; 5.W.166.240;
5.W.166.244; 5.W.169.228; 5.W.169.229; 5.W.169.230; 5.W.169.231;
5.W.169.236; 5.W.169.237; 5.W.169.238; 5.W.169.239; 5.W.169.154;
5.W.169.157; 5.W.169.166; 5.W.169.169; 5.W.169.172; 5.W.169.175;
5.W.169.240; 5.W.169.244; 5.W.172.228; 5.W.172.229; 5.W.172.230;
5.W.172.231; 5.W.172.236; 5.W.172.237; 5.W.172.238; 5.W.172.239;
5.W.172.154; 5.W.172.157; 5.W.172.166; 5.W.172.169; 5.W.172.172;
5.W.172.175; 5.W.172.240; 5.W.172.244; 5.W.175.228; 5.W.175.229;
5.W.175.230; 5.W.175.231; 5.W.175.236; 5.W.175.237; 5.W.175.238;
5.W.175.239; 5.W.175.154; 5.W.175.157; 5.W.175.166; 5.W.175.169;
5.W.175.172; 5.W.175.175; 5.W.175.240; 5.W.175.244; 5.W.240.228;
5.W.240.229; 5.W.240.230; 5.W.240.231; 5.W.240.236; 5.W.240.237;
5.W.240.238; 5.W.240.239; 5.W.240.154; 5.W.240.157; 5.W.240.166;
5.W.240.169; 5.W.240.172; 5.W.240.175; 5.W.240.240; 5.W.240.244;
5.W.244.228; 5.W.244.229; 5.W.244.230; 5.W.244.231; 5.W.244.236;
5.W.244.237; 5.W.244.238; 5.W.244.239; 5.W.244.154; 5.W.244.157;
5.W.244.166; 5.W.244.169; 5.W.244.172; 5.W.244.175; 5.W.244.240;
5.W.244.244;
Prodrugs of 5.Y 5.Y.228.228; 5.Y.228.229; 5.Y.228.230; 5.Y.228.231; 5.Y.228.236;
5.Y.228.237; 5.Y.228.238; 5.Y.228.239; 5.Y.228.154; 5.Y.228.157;
5.Y.228.166; 5.Y.228.169; 5.Y.228.172; 5.Y.228.175; 5.Y.228.240;
5.Y.228.244; 5.Y.229.228; 5.Y.229.229; 5.Y.229.230; 5.Y.229.231;
5.Y.229.236; 5.Y.229.237; 5.Y.229.238; 5.Y.229.239; 5.Y.229.154;
5.Y.229.157; 5.Y.229.166; 5.Y.229.169; 5.Y.229.172; 5.Y.229.175;
5.Y.229.240; 5.Y.229.244; 5.Y.230.228; 5.Y.230.229; 5.Y.230.230;
5.Y.230.231; 5.Y.230.236; 5.Y.230.237; 5.Y.230.238; 5.Y.230.239;
5.Y.230.154; 5.Y.230.157; 5.Y.230.166; 5.Y.230.169; 5.Y.230.172;
5.Y.230.175; 5.Y.230.240; 5.Y.230.244; 5.Y.231.228; 5.Y.231.229;
5.Y.231.230; 5.Y.231.231; 5.Y.231.236; 5.Y.231.237; 5.Y.231.238;
5.Y.231.239; 5.Y.231.154; 5.Y.231.157; 5.Y.231.166; 5.Y.231.169;
5.Y.231.172; 5.Y.231.175; 5.Y.231.240; 5.Y.231.244; 5.Y.236.228;
5.Y.236.229; 5.Y.236.230; 5.Y.236.231; 5.Y.236.236; 5.Y.236.237;
5.Y.236.238; 5.Y.236.239; 5.Y.236.154; 5.Y.236.157; 5.Y.236.166;
5.Y.236.169; 5.Y.236.172; 5.Y.236.175; 5.Y.236.240; 5.Y.236.244;
5.Y.237.228; 5.Y.237.229; 5.Y.237.230; 5.Y.237.231; 5.Y.237.236;
5.Y.237.237; 5.Y.237.238; 5.Y.237.239; 5.Y.237.154; 5.Y.237.157;
5.Y.237.166; 5.Y.237.169; 5.Y.237.172; 5.Y.237.175; 5.Y.237.240;
5.Y.237.244; 5.Y.238.228; 5.Y.238.229; 5.Y.238.230; 5.Y.238.231;
5.Y.238.236; 5.Y.238.237; 5.Y.238.238; 5.Y.238.239; 5.Y.238.154;
5.Y.238.157; 5.Y.238.166; 5.Y.238.169; 5.Y.238.172; 5.Y.238.175;
5.Y.238.240; 5.Y.238.244; 5.Y.239.228; 5.Y.239.229; 5.Y.239.230;
5.Y.239.231; 5.Y.239.236; 5.Y.239.237; 5.Y.239.238; 5.Y.239.239;
5.Y.239.154; 5.Y.239.157; 5.Y.239.166; 5.Y.239.169; 5.Y.239.172;
5.Y.239.175; 5.Y.239.240; 5.Y.239.244; 5.Y.154.228; 5.Y.154.229;
5.Y.154.230; 5.Y.154.231; 5.Y.154.236; 5.Y.154.237; 5.Y.154.238;
5.Y.154.239; 5.Y.154.154; 5.Y.154.157; 5.Y.154.166; 5.Y.154.169;
5.Y.154.172; 5.Y.154.175; 5.Y.154.240; 5.Y.154.244; 5.Y.157.228;
5.Y.157.229; 5.Y.157.230; 5.Y.157.231; 5.Y.157.236; 5.Y.157.237;
5.Y.157.238; 5.Y.157.239; 5.Y.157.154; 5.Y.157.157; 5.Y.157.166;
5.Y.157.169; 5.Y.157.172; 5.Y.157.175; 5.Y.157.240; 5.Y.157.244;

TABLE 7-continued

5.Y.166.228; 5.Y.166.229; 5.Y.166.230; 5.Y.166.231; 5.Y.166.236; 5.Y.166.237; 5.Y.166.238; 5.Y.166.239; 5.Y.166.154; 5.Y.166.157; 5.Y.166.166; 5.Y.166.169; 5.Y.166.172; 5.Y.166.175; 5.Y.166.240; 5.Y.166.244; 5.Y.169.228; 5.Y.169.229; 5.Y.169.230; 5.Y.169.231; 5.Y.169.236; 5.Y.169.237; 5.Y.169.238; 5.Y.169.239; 5.Y.169.154; 5.Y.169.157; 5.Y.169.166; 5.Y.169.169; 5.Y.169.172; 5.Y.169.175; 5.Y.169.240; 5.Y.169.244; 5.Y.172.228; 5.Y.172.229; 5.Y.172.230; 5.Y.172.231; 5.Y.172.236; 5.Y.172.237; 5.Y.172.238; 5.Y.172.239; 5.Y.172.154; 5.Y.172.157; 5.Y.172.166; 5.Y.172.169; 5.Y.172.172; 5.Y.172.175; 5.Y.172.240; 5.Y.172.244; 5.Y.175.228; 5.Y.175.229; 5.Y.175.230; 5.Y.175.231; 5.Y.175.236; 5.Y.175.237; 5.Y.175.238; 5.Y.175.239; 5.Y.175.154; 5.Y.175.157; 5.Y.175.166; 5.Y.175.169; 5.Y.175.172; 5.Y.175.175; 5.Y.175.240; 5.Y.175.244; 5.Y.240.228; 5.Y.240.229; 5.Y.240.230; 5.Y.240.231; 5.Y.240.236; 5.Y.240.237; 5.Y.240.238; 5.Y.240.239; 5.Y.240.154; 5.Y.240.157; 5.Y.240.166; 5.Y.240.169; 5.Y.240.172; 5.Y.240.175; 5.Y.240.240; 5.Y.240.244; 5.Y.244.228; 5.Y.244.229; 5.Y.244.230; 5.Y.244.231; 5.Y.244.236; 5.Y.244.237; 5.Y.244.238; 5.Y.244.239; 5.Y.244.154; 5.Y.244.157; 5.Y.244.166; 5.Y.244.169; 5.Y.244.172; 5.Y.244.175; 5.Y.244.240; 5.Y.244.244;

Prodrugs of 6.B

6.B.228.228; 6.B.228.229; 6.B.228.230; 6.B.228.231; 6.B.228.236; 6.B.228.237; 6.B.228.238; 6.B.228.239; 6.B.228.154; 6.B.228.157; 6.B.228.166; 6.B.228.169; 6.B.228.172; 6.B.228.175; 6.B.228.240; 6.B.228.244; 6.B.229.228; 6.B.229.229; 6.B.229.230; 6.B.229.231; 6.B.229.236; 6.B.229.237; 6.B.229.238; 6.B.229.239; 6.B.229.154; 6.B.229.157; 6.B.229.166; 6.B.229.169; 6.B.229.172; 6.B.229.175; 6.B.229.240; 6.B.229.244; 6.B.230.228; 6.B.230.229; 6.B.230.230; 6.B.230.231; 6.B.230.236; 6.B.230.237; 6.B.230.238; 6.B.230.239; 6.B.230.154; 6.B.230.157; 6.B.230.166; 6.B.230.169; 6.B.230.172; 6.B.230.175; 6.B.230.240; 6.B.230.244; 6.B.231.228; 6.B.231.229; 6.B.231.230; 6.B.231.231; 6.B.231.236; 6.B.231.237; 6.B.231.238; 6.B.231.239; 6.B.231.154; 6.B.231.157; 6.B.231.166; 6.B.231.169; 6.B.231.172; 6.B.231.175; 6.B.231.240; 6.B.231.244; 6.B.236.228; 6.B.236.229; 6.B.236.230; 6.B.236.231; 6.B.236.236; 6.B.236.237; 6.B.236.238; 6.B.236.239; 6.B.236.154; 6.B.236.157; 6.B.236.166; 6.B.236.169; 6.B.236.172; 6.B.236.175; 6.B.236.240; 6.B.236.244; 6.B.237.228; 6.B.237.229; 6.B.237.230; 6.B.237.231; 6.B.237.236; 6.B.237.237; 6.B.237.238; 6.B.237.239; 6.B.237.154; 6.B.237.157; 6.B.237.166; 6.B.237.169; 6.B.237.172; 6.B.237.175; 6.B.237.240; 6.B.237.244; 6.B.238.228; 6.B.238.229; 6.B.238.230; 6.B.238.231; 6.B.238.236; 6.B.238.237; 6.B.238.238; 6.B.238.239; 6.B.238.154; 6.B.238.157; 6.B.238.166; 6.B.238.169; 6.B.238.172; 6.B.238.175; 6.B.238.240; 6.B.238.244; 6.B.239.228; 6.B.239.229; 6.B.239.230; 6.B.239.231; 6.B.239.236; 6.B.239.237; 6.B.239.238; 6.B.239.239; 6.B.239.154; 6.B.239.157; 6.B.239.166; 6.B.239.169; 6.B.239.172; 6.B.239.175; 6.B.239.240; 6.B.239.244; 6.B.154.228; 6.B.154.229; 6.B.154.230; 6.B.154.231; 6.B.154.236; 6.B.154.237; 6.B.154.238; 6.B.154.239; 6.B.154.154; 6.B.154.157; 6.B.154.166; 6.B.154.169; 6.B.154.172; 6.B.154.175; 6.B.154.240; 6.B.154.244; 6.B.157.228; 6.B.157.229; 6.B.157.230; 6.B.157.231; 6.B.157.236; 6.B.157.237; 6.B.157.238; 6.B.157.239; 6.B.157.154; 6.B.157.157; 6.B.157.166; 6.B.157.169; 6.B.157.172; 6.B.157.175; 6.B.157.240; 6.B.157.244; 6.B.166.228; 6.B.166.229; 6.B.166.230; 6.B.166.231; 6.B.166.236; 6.B.166.237; 6.B.166.238; 6.B.166.239; 6.B.166.154; 6.B.166.157; 6.B.166.166; 6.B.166.169; 6.B.166.172; 6.B.166.175; 6.B.166.240; 6.B.166.244; 6.B.169.228; 6.B.169.229; 6.B.169.230; 6.B.169.231; 6.B.169.236; 6.B.169.237; 6.B.169.238; 6.B.169.239; 6.B.169.154; 6.B.169.157; 6.B.169.166; 6.B.169.169; 6.B.169.172; 6.B.169.175; 6.B.169.240; 6.B.169.244; 6.B.172.228; 6.B.172.229; 6.B.172.230; 6.B.172.231; 6.B.172.236; 6.B.172.237; 6.B.172.238; 6.B.172.239; 6.B.172.154; 6.B.172.157; 6.B.172.166; 6.B.172.169; 6.B.172.172; 6.B.172.175; 6.B.172.240; 6.B.172.244; 6.B.175.228; 6.B.175.229; 6.B.175.230; 6.B.175.231; 6.B.175.236; 6.B.175.237; 6.B.175.238; 6.B.175.239; 6.B.175.154; 6.B.175.157; 6.B.175.166; 6.B.175.169; 6.B.175.172; 6.B.175.175; 6.B.175.240; 6.B.175.244; 6.B.240.228; 6.B.240.229; 6.B.240.230; 6.B.240.231; 6.B.240.236; 6.B.240.237; 6.B.240.238; 6.B.240.239; 6.B.240.154; 6.B.240.157; 6.B.240.166; 6.B.240.169; 6.B.240.172; 6.B.240.175; 6.B.240.240; 6.B.240.244; 6.B.244.228; 6.B.244.229; 6.B.244.230; 6.B.244.231; 6.B.244.236; 6.B.244.237; 6.B.244.238; 6.B.244.239; 6.B.244.154; 6.B.244.157; 6.B.244.166; 6.B.244.169; 6.B.244.172; 6.B.244.175; 6.B.244.240; 6.B.244.244;

Prodrugs of 6.D

6.D.228.228; 6.D.228.229; 6.D.228.230; 6.D.228.231; 6.D.228.236; 6.D.228.237; 6.D.228.238; 6.D.228.239; 6.D.228.154; 6.D.228.157; 6.D.228.166; 6.D.228.169; 6.D.228.172; 6.D.228.175; 6.D.228.240; 6.D.228.244; 6.D.229.228; 6.D.229.229; 6.D.229.230; 6.D.229.231; 6.D.229.236; 6.D.229.237; 6.D.229.238; 6.D.229.239; 6.D.229.154; 6.D.229.157; 6.D.229.166; 6.D.229.169; 6.D.229.172; 6.D.229.175; 6.D.229.240; 6.D.229.244; 6.D.230.228; 6.D.230.229; 6.D.230.230; 6.D.230.231; 6.D.230.236; 6.D.230.237; 6.D.230.238; 6.D.230.239; 6.D.230.154; 6.D.230.157; 6.D.230.166; 6.D.230.169; 6.D.230.172; 6.D.230.175; 6.D.230.240; 6.D.230.244; 6.D.231.228; 6.D.231.229; 6.D.231.230; 6.D.231.231; 6.D.231.236; 6.D.231.237; 6.D.231.238; 6.D.231.239; 6.D.231.154; 6.D.231.157; 6.D.231.166; 6.D.231.169; 6.D.231.172; 6.D.231.175; 6.D.231.240; 6.D.231.244; 6.D.236.228; 6.D.236.229; 6.D.236.230; 6.D.236.231; 6.D.236.236; 6.D.236.237; 6.D.236.238; 6.D.236.239; 6.D.236.154; 6.D.236.157; 6.D.236.166; 6.D.236.169; 6.D.236.172; 6.D.236.175; 6.D.236.240; 6.D.236.244; 6.D.237.228; 6.D.237.229; 6.D.237.230; 6.D.237.231; 6.D.237.236; 6.D.237.237; 6.D.237.238; 6.D.237.239; 6.D.237.154; 6.D.237.157; 6.D.237.166; 6.D.237.169; 6.D.237.172; 6.D.237.175; 6.D.237.240; 6.D.237.244; 6.D.238.228; 6.D.238.229; 6.D.238.230; 6.D.238.231; 6.D.238.236; 6.D.238.237; 6.D.238.238; 6.D.238.239; 6.D.238.154; 6.D.238.157; 6.D.238.166; 6.D.238.169; 6.D.238.172; 6.D.238.175; 6.D.238.240; 6.D.238.244; 6.D.239.228; 6.D.239.229; 6.D.239.230; 6.D.239.231; 6.D.239.236; 6.D.239.237; 6.D.239.238; 6.D.239.239; 6.D.239.154; 6.D.239.157; 6.D.239.166; 6.D.239.169; 6.D.239.172; 6.D.239.175; 6.D.239.240; 6.D.239.244; 6.D.154.228; 6.D.154.229; 6.D.154.230; 6.D.154.231; 6.D.154.236; 6.D.154.237; 6.D.154.238; 6.D.154.239; 6.D.154.154; 6.D.154.157; 6.D.154.166; 6.D.154.169; 6.D.154.172; 6.D.154.175; 6.D.154.240; 6.D.154.244; 6.D.157.228; 6.D.157.229; 6.D.157.230; 6.D.157.231; 6.D.157.236; 6.D.157.237; 6.D.157.238; 6.D.157.239; 6.D.157.154; 6.D.157.157; 6.D.157.166; 6.D.157.169; 6.D.157.172; 6.D.157.175; 6.D.157.240; 6.D.157.244; 6.D.166.228; 6.D.166.229; 6.D.166.230; 6.D.166.231; 6.D.166.236; 6.D.166.237; 6.D.166.238; 6.D.166.239; 6.D.166.154; 6.D.166.157; 6.D.166.166; 6.D.166.169; 6.D.166.172; 6.D.166.175; 6.D.166.240; 6.D.166.244; 6.D.169.228; 6.D.169.229; 6.D.169.230; 6.D.169.231; 6.D.169.236; 6.D.169.237; 6.D.169.238; 6.D.169.239; 6.D.169.154; 6.D.169.157; 6.D.169.166; 6.D.169.169; 6.D.169.172; 6.D.169.175; 6.D.169.240; 6.D.169.244; 6.D.172.228; 6.D.172.229; 6.D.172.230; 6.D.172.231; 6.D.172.236; 6.D.172.237; 6.D.172.238; 6.D.172.239; 6.D.172.154; 6.D.172.157; 6.D.172.166; 6.D.172.169; 6.D.172.172; 6.D.172.175; 6.D.172.240; 6.D.172.244; 6.D.175.228; 6.D.175.229; 6.D.175.230; 6.D.175.231; 6.D.175.236; 6.D.175.237; 6.D.175.238; 6.D.175.239; 6.D.175.154; 6.D.175.157; 6.D.175.166; 6.D.175.169; 6.D.175.172; 6.D.175.175; 6.D.175.240; 6.D.175.244; 6.D.240.228; 6.D.240.229; 6.D.240.230; 6.D.240.231; 6.D.240.236; 6.D.240.237; 6.D.240.238; 6.D.240.239; 6.D.240.154; 6.D.240.157; 6.D.240.166; 6.D.240.169; 6.D.240.172; 6.D.240.175; 6.D.240.240; 6.D.240.244; 6.D.244.228; 6.D.244.229; 6.D.244.230; 6.D.244.231; 6.D.244.236; 6.D.244.237; 6.D.244.238; 6.D.244.239; 6.D.244.154; 6.D.244.157; 6.D.244.166; 6.D.244.169; 6.D.244.172; 6.D.244.175; 6.D.244.240; 6.D.244.244;

Prodrugs of 6.E

6.E.228.228; 6.E.228.229; 6.E.228.230; 6.E.228.231; 6.E.228.236; 6.E.228.237; 6.E.228.238; 6.E.228.239; 6.E.228.154; 6.E.228.157; 6.E.228.166; 6.E.228.169; 6.E.228.172; 6.E.228.175; 6.E.228.240; 6.E.228.244; 6.E.229.228; 6.E.229.229; 6.E.229.230; 6.E.229.231; 6.E.229.236; 6.E.229.237; 6.E.229.238; 6.E.229.239; 6.E.229.154; 6.E.229.157; 6.E.229.166; 6.E.229.169; 6.E.229.172; 6.E.229.175; 6.E.229.240; 6.E.229.244; 6.E.230.228; 6.E.230.229; 6.E.230.230; 6.E.230.231; 6.E.230.236; 6.E.230.237; 6.E.230.238; 6.E.230.239; 6.E.230.154; 6.E.230.157; 6.E.230.166; 6.E.230.169; 6.E.230.172; 6.E.230.175; 6.E.230.240; 6.E.230.244; 6.E.231.228; 6.F.231.229; 6.E.231.230; 6.E.231.231; 6.E.231.236; 6.E.231.237; 6.E.231.238; 6.E.231.239; 6.E.231.154; 6.E.231.157; 6.E.231.166; 6.E.231.169; 6.E.231.172; 6.E.231.175; 6.E.231.240; 6.E.231.244; 6.E.236.228; 6.E.236.229; 6.E.236.230; 6.E.236.231; 6.E.236.236; 6.E.236.237; 6.E.236.238; 6.E.236.239; 6.E.236.154; 6.E.236.157; 6.E.236.166; 6.E.236.169; 6.E.236.172; 6.E.236.175; 6.E.236.240; 6.E.236.244; 6.F.237.228; 6.E.237.229; 6.E.237.230; 6.E.237.231; 6.E.237.236; 6.E.237.237; 6.E.237.238; 6.E.237.239; 6.E.237.154; 6.E.237.157; 6.E.237.166; 6.E.237.169; 6.E.237.172; 6.E.237.175; 6.E.237.240; 6.E.237.244; 6.E.238.228; 6.E.238.229; 6.E.238.230; 6.E.238.231; 6.E.238.236; 6.E.238.237; 6.E.238.238; 6.E.238.239; 6.E.238.154; 6.E.238.157; 6.E.238.166; 6.E.238.169; 6.E.238.172; 6.E.238.175; 6.E.238.240; 6.E.238.244; 6.E.239.228; 6.E.239.229; 6.E.239.230; 6.E.239.231; 6.E.239.236; 6.E.239.237; 6.E.239.238; 6.E.239.239; 6.E.239.154; 6.E.239.157; 6.E.239.166; 6.E.239.169; 6.E.239.172; 6.E.239.175; 6.E.239.240; 6.E.239.244; 6.E.154.228; 6.E.154.229; 6.E.154.230; 6.E.154.231; 6.E.154.236; 6.E.154.237; 6.E.154.238; 6.E.154.239; 6.E.154.154; 6.E.154.157; 6.E.154.166; 6.E.154.169;

TABLE 7-continued

6.E.154.172; 6.E.154.175; 6.E.154.240; 6.E.154.244; 6.E.157.228;
6.E.157.229; 6.E.157.230; 6.E.157.231; 6.E.157.236; 6.E.157.237;
6.E.157.238; 6.E.157.239; 6.E.157.154; 6.E.157.157; 6.E.157.166;
6.E.157.169; 6.E.157.172; 6.E.157.175; 6.E.157.240; 6.E.157.244;
6.E.166.228; 6.E.166.229; 6.E.166.230; 6.E.166.231; 6.E.166.236;
6.E.166.237; 6.E.166.238; 6.E.166.239; 6.E.166.154; 6.E.166.157;
6.E.166.166; 6.E.166.169; 6.E.166.172; 6.E.166.175; 6.E.166.240;
6.E.166.244; 6.E.169.228; 6.E.169.229; 6.E.169.230; 6.E.169.231;
6.E.169.236; 6.E.169.237; 6.E.169.238; 6.E.169.239; 6.E.169.154;
6.E.169.157; 6.E.169.166; 6.E.169.169; 6.E.169.172; 6.E.169.175;
6.E.169.240; 6.E.169.244; 6.E.172.228; 6.E.172.229; 6.E.172.230;
6.E.172.231; 6.E.172.236; 6.E.172.237; 6.E.172.238; 6.E.172.239;
6.E.172.154; 6.E.172.157; 6.E.172.166; 6.E.172.169; 6.E.172.172;
6.E.172.175; 6.E.172.240; 6.E.172.244; 6.E.175.228; 6.E.175.229;
6.E.175.230; 6.E.175.231; 6.E.175.236; 6.E.175.237; 6.E.175.238;
6.E.175.239; 6.E.175.154; 6.E.175.157; 6.E.175.166; 6.E.175.169;
6.E.175.172; 6.E.175.175; 6.E.175.240; 6.E.175.244; 6.E.240.228;
6.E.240.229; 6.E.240.230; 6.E.240.231; 6.E.240.236; 6.E.240.237;
6.E.240.238; 6.E.240.239; 6.E.240.154; 6.E.240.157; 6.E.240.166;
6.E.240.169; 6.E.240.172; 6.E.240.175; 6.E.240.240; 6.E.240.244;
6.E.244.228; 6.E.244.229; 6.E.244.230; 6.E.244.231; 6.E.244.236;
6.E.244.237; 6.E.244.238; 6.E.244.239; 6.E.244.154; 6.E.244.157;
6.E.244.166; 6.E.244.169; 6.E.244.172; 6.E.244.175; 6.E.244.240;
6.E.244.244;
Prodrugs of 6.G 6.G.228.228; 6.G.228.229; 6.G.228.230; 6.G.228.231; 6.G.228.236;
6.G.228.237; 6.G.228.238; 6.G.228.239; 6.G.228.154; 6.G.228.157;
6.G.228.166; 6.G.228.169; 6.G.228.172; 6.G.228.175; 6.G.228.240;
6.G.228.244; 6.G.229.228; 6.G.229.229; 6.G.229.230; 6.G.229.231;
6.G.229.236; 6.G.229.237; 6.G.229.238; 6.G.229.239; 6.G.229.154;
6.G.229.157; 6.G.229.166; 6.G.229.169; 6.G.229.172; 6.G.229.175;
6.G.229.240; 6.G.229.244; 6.G.230.228; 6.G.230.229; 6.G.230.230;
6.G.230.231; 6.G.230.236; 6.G.230.237; 6.G.230.238; 6.G.230.239;
6.G.230.154; 6.G.230.157; 6.G.230.166; 6.G.230.169; 6.G.230.172;
6.G.230.175; 6.G.230.240; 6.G.230.244; 6.G.231.228; 6.G.231.229;
6.G.231.230; 6.G.231.231; 6.G.231.236; 6.G.231.237; 6.G.231.238;
6.G.231.239; 6.G.231.154; 6.G.231.157; 6.G.231.166; 6.G.231.169;
6.G.231.172; 6.G.231.175; 6.G.231.240; 6.G.231.244; 6.G.236.228;
6.G.236.229; 6.G.236.230; 6.G.236.231; 6.G.236.236; 6.G.236.237;
6.G.236.238; 6.G.236.239; 6.G.236.154; 6.G.236.157; 6.G.236.166;
6.G.236.169; 6.G.236.172; 6.G.236.175; 6.G.236.240; 6.G.236.244;
6.G.237.228; 6.G.237.229; 6.G.237.230; 6.G.237.231; 6.G.237.236;
6.G.237.237; 6.G.237.238; 6.G.237.239; 6.G.237.154; 6.G.237.157;
6.G.237.166; 6.G.237.169; 6.G.237.172; 6.G.237.175; 6.G.237.240;
6.G.237.244; 6.G.238.228; 6.G.238.229; 6.G.238.230; 6.G.238.231;
6.G.238.236; 6.G.238.237; 6.G.238.238; 6.G.238.239; 6.G.238.154;
6.G.238.157; 6.G.238.166; 6.G.238.169; 6.G.238.172; 6.G.238.175;
6.G.238.240; 6.G.238.244; 6.G.239.228; 6.G.239.229; 6.G.239.230;
6.G.239.231; 6.G.239.236; 6.G.239.237; 6.G.239.238; 6.G.239.239;
6.G.239.154; 6.G.239.157; 6.G.239.166; 6.G.239.169; 6.G.239.172;
6.G.239.175; 6.G.239.240; 6.G.239.244; 6.G.154.228; 6.G.154.229;
6.G.154.230; 6.G.154.231; 6.G.154.236; 6.G.154.237; 6.G.154.238;
6.G.154.239; 6.G.154.154; 6.G.154.157; 6.G.154.166; 6.G.154.169;
6.G.154.172; 6.G.154.175; 6.G.154.240; 6.G.154.244; 6.G.157.228;
6.G.157.229; 6.G.157.230; 6.G.157.231; 6.G.157.236; 6.G.157.237;
6.G.157.238; 6.G.157.239; 6.G.157.154; 6.G.157.157; 6.G.157.166;
6.G.157.169; 6.G.157.172; 6.G.157.175; 6.G.157.240; 6.G.157.244;
6.G.166.228; 6.G.166.229; 6.G.166.230; 6.G.166.231; 6.G.166.236;
6.G.166.237; 6.G.166.238; 6.G.166.239; 6.G.166.154; 6.G.166.157;
6.G.166.166; 6.G.166.169; 6.G.166.172; 6.G.166.175; 6.G.166.240;
6.G.166.244; 6.G.169.228; 6.G.169.229; 6.G.169.230; 6.G.169.231;
6.G.169.236; 6.G.169.237; 6.G.169.238; 6.G.169.239; 6.G.169.154;
6.G.169.157; 6.G.169.166; 6.G.169.169; 6.G.169.172; 6.G.169.175;
6.G.169.240; 6.G.169.244; 6.G.172.228; 6.G.172.229; 6.G.172.230;
6.G.172.231; 6.G.172.236; 6.G.172.237; 6.G.172.238; 6.G.172.239;
6.G.172.154; 6.G.172.157; 6.G.172.166; 6.G.172.169; 6.G.172.172;
6.G.172.175; 6.G.172.240; 6.G.172.244; 6.G.175.228; 6.G.175.229;
6.G.175.230; 6.G.175.231; 6.G.175.236; 6.G.175.237; 6.G.175.238;
6.G.175.239; 6.G.175.154; 6.G.175.157; 6.G.175.166; 6.G.175.169;
6.G.175.172; 6.G.175.175; 6.G.175.240; 6.G.175.244; 6.G.240.228;
6.G.240.229; 6.G.240.230; 6.G.240.231; 6.G.240.236; 6.G.240.237;
6.G.240.238; 6.G.240.239; 6.G.240.154; 6.G.240.157; 6.G.240.166;
6.G.240.169; 6.G.240.172; 6.G.240.175; 6.G.240.240; 6.G.240.244;
6.G.244.228; 6.G.244.229; 6.G.244.230; 6.G.244.231; 6.G.244.236;
6.G.244.237; 6.G.244.238; 6.G.244.239; 6.G.244.154; 6.G.244.157;
6.G.244.166; 6.G.244.169; 6.G.244.172; 6.G.244.175; 6.G.244.240;
6.G.244.244;
Prodrugs of 6.I 6.I.228.228; 6.I.228.229; 6.I.228.230; 6.I.228.231; 6.I.228.236;
6.I.228.237; 6.I.228.238; 6.I.228.239; 6.I.228.154; 6.I.228.157;
6.I.228.166; 6.I.228.169; 6.I.228.172; 6.I.228.175; 6.I.228.240;
6.I.228.244; 6.I.229.228; 6.I.229.229; 6.I.229.230; 6.I.229.231;
6.I.229.236; 6.I.229.237; 6.I.229.238; 6.I.229.239; 6.I.229.154;
6.I.229.157; 6.I.229.166; 6.I.229.169; 6.I.229.172; 6.I.229.175;
6.I.229.240; 6.I.229.244; 6.I.230.228; 6.I.230.229; 6.I.230.230;
6.I.230.231; 6.I.230.236; 6.I.230.237; 6.I.230.238; 6.I.230.239;
6.I.230.154; 6.I.230.157; 6.I.230.166; 6.I.230.169; 6.I.230.172;
6.I.230.175; 6.I.230.240; 6.I.230.244; 6.I.231.228; 6.I.231.229;
6.I.231.230; 6.I.231.231; 6.I.231.236; 6.I.231.237; 6.I.231.238;
6.I.231.239; 6.I.231.154; 6.I.231.157; 6.I.231.166; 6.I.231.169;
6.I.231.172; 6.I.231.175; 6.I.231.240; 6.I.231.244; 6.I.236.228;
6.I.236.229; 6.I.236.230; 6.I.236.231; 6.I.236.236; 6.I.236.237;
6.I.236.238; 6.I.236.239; 6.I.236.154; 6.I.236.157; 6.I.236.166;
6.I.236.169; 6.I.236.172; 6.I.236.175; 6.I.236.240; 6.I.236.244;
6.I.237.228; 6.I.237.229; 6.I.237.230; 6.I.237.231; 6.I.237.236;
6.I.237.237; 6.I.237.238; 6.I.237.239; 6.I.237.154; 6.I.237.157;
6.I.237.166; 6.I.237.169; 6.I.237.172; 6.I.237.175; 6.I.237.240;
6.I.237.244; 6.I.238.228; 6.I.238.229; 6.I.238.230; 6.I.238.231;
6.I.238.236; 6.I.238.237; 6.I.238.238; 6.I.238.239; 6.I.238.154;
6.I.238.157; 6.I.238.166; 6.I.238.169; 6.I.238.172; 6.I.238.175;
6.I.238.240; 6.I.238.244; 6.I.239.228; 6.I.239.229; 6.I.239.230;
6.I.239.231; 6.I.239.236; 6.I.239.237; 6.I.239.238; 6.I.239.239;
6.I.239.154; 6.I.239.157; 6.I.239.166; 6.I.239.169; 6.I.239.172;
6.I.239.175; 6.I.239.240; 6.I.239.244; 6.I.154.228; 6.I.154.229;
6.I.154.230; 6.I.154.231; 6.I.154.236; 6.I.154.237; 6.I.154.238;
6.I.154.239; 6.I.154.154; 6.I.154.157; 6.I.154.166; 6.I.154.169;
6.I.154.172; 6.I.154.175; 6.I.154.240; 6.I.154.244; 6.I.157.228;
6.I.157.229; 6.I.157.230; 6.I.157.231; 6.I.157.236; 6.I.157.237;
6.I.157.238; 6.I.157.239; 6.I.157.154; 6.I.157.157; 6.I.157.166;
6.I.157.169; 6.I.157.172; 6.I.157.175; 6.I.157.240; 6.I.157.244;
6.I.166.228; 6.I.166.229; 6.I.166.230; 6.I.166.231; 6.I.166.236;
6.I.166.237; 6.I.166.238; 6.I.166.239; 6.I.166.154; 6.I.166.157;
6.I.166.166; 6.I.166.169; 6.I.166.172; 6.I.166.175; 6.I.166.240;
6.I.166.244; 6.I.169.228; 6.I.169.229; 6.I.169.230; 6.I.169.231;
6.I.169.236; 6.I.169.237; 6.I.169.238; 6.I.169.239; 6.I.169.154;
6.I.169.157; 6.I.169.166; 6.I.169.169; 6.I.169.172; 6.I.169.175;
6.I.169.240; 6.I.169.244; 6.I.172.228; 6.I.172.229; 6.I.172.230;
6.I.172.231; 6.I.172.236; 6.I.172.237; 6.I.172.238; 6.I.172.239;
6.I.172.154; 6.I.172.157; 6.I.172.166; 6.I.172.169; 6.I.172.172;
6.I.172.175; 6.I.172.240; 6.I.172.244; 6.I.175.228; 6.I.175.229;
6.I.175.230; 6.I.175.231; 6.I.175.236; 6.I.175.237; 6.I.175.238;
6.I.175.239; 6.I.175.154; 6.I.175.157; 6.I.175.166; 6.I.175.169;
6.I.175.172; 6.I.175.175; 6.I.175.240; 6.I.175.244; 6.I.240.228;
6.I.240.229; 6.I.240.230; 6.I.240.231; 6.I.240.236; 6.I.240.237;
6.I.240.238; 6.I.240.239; 6.I.240.154; 6.I.240.157; 6.I.240.166;
6.I.240.169; 6.I.240.172; 6.I.240.175; 6.I.240.240; 6.I.240.244;
6.I.244.228; 6.I.244.229; 6.I.244.230; 6.I.244.231; 6.I.244.236;
6.I.244.237; 6.I.244.238; 6.I.244.239; 6.I.244.154; 6.I.244.157;
6.I.244.166; 6.I.244.169; 6.I.244.172; 6.I.244.175; 6.I.244.240;
6.I.244.244;
Prodrugs of 6.J 6.J.228.228; 6.J.228.229; 6.J.228.230; 6.J.228.231; 6.J.228.236;
6.J.228.237; 6.J.228.238; 6.J.228.239; 6.J.228.154; 6.J.228.157;
6.J.228.166; 6.J.228.169; 6.J.228.172; 6.J.228.175; 6.J.228.240;
6.J.228.244; 6.J.229.228; 6.J.229.229; 6.J.229.230; 6.J.229.231;
6.J.229.236; 6.J.229.237; 6.J.229.238; 6.J.229.239; 6.J.229.154;
6.J.229.157; 6.J.229.166; 6.J.229.169; 6.J.229.172; 6.J.229.175;
6.J.229.240; 6.J.229.244; 6.J.230.228; 6.J.230.229; 6.J.230.230;
6.J.230.231; 6.J.230.236; 6.J.230.237; 6.J.230.238; 6.J.230.239;
6.J.230.154; 6.J.230.157; 6.J.230.166; 6.J.230.169; 6.J.230.172;
6.J.230.175; 6.J.230.240; 6.J.230.244; 6.J.231.228; 6.J.231.229;
6.J.231.230; 6.J.231.231; 6.J.231.236; 6.J.231.237; 6.J.231.238;
6.J.231.239; 6.J.231.154; 6.J.231.157; 6.J.231.166; 6.J.231.169;
6.J.231.172; 6.J.231.175; 6.J.231.240; 6.J.231.244; 6.J.236.228;
6.J.236.229; 6.J.236.230; 6.J.236.231; 6.J.236.236; 6.J.236.237;
6.J.236.238; 6.J.236.239; 6.J.236.154; 6.J.236.157; 6.J.236.166;
6.J.236.169; 6.J.236.172; 6.J.236.175; 6.J.236.240; 6.J.236.244;
6.J.237.228; 6.J.237.229; 6.J.237.230; 6.J.237.231; 6.J.237.236;
6.J.237.237; 6.J.237.238; 6.J.237.239; 6.J.237.154; 6.J.237.157;
6.J.237.166; 6.J.237.169; 6.J.237.172; 6.J.237.175; 6.J.237.240;
6.J.237.244; 6.J.238.228; 6.J.238.229; 6.J.238.230; 6.J.238.231;
6.J.238.236; 6.J.238.237; 6.J.238.238; 6.J.238.239; 6.J.238.154;
6.J.238.157; 6.J.238.166; 6.J.238.169; 6.J.238.172; 6.J.238.175;
6.J.238.240; 6.J.238.244; 6.J.239.228; 6.J.239.229; 6.J.239.230;

TABLE 7-continued

6.J.239.231; 6.J.239.236; 6.J.239.237; 6.J.239.238; 6.J.239.239;
6.J.239.154; 6.J.239.157; 6.J.239.166; 6.J.239.169; 6.J.239.172;
6.J.239.175; 6.J.239.240; 6.J.239.244; 6.J.154.228; 6.J.154.229;
6.J.154.230; 6.J.154.231; 6.J.154.236; 6.J.154.237; 6.J.154.238;
6.J.154.239; 6.J.154.154; 6.J.154.157; 6.J.154.166; 6.J.154.169;
6.J.154.172; 6.J.154.175; 6.J.154.240; 6.J.154.244; 6.J.157.228;
6.J.157.229; 6.J.157.230; 6.J.157.231; 6.J.157.236; 6.J.157.237;
6.J.157.238; 6.J.157.239; 6.J.157.154; 6.J.157.157; 6.J.157.166;
6.J.157.169; 6.J.157.172; 6.J.157.175; 6.J.157.240; 6.J.157.244;
6.J.166.228; 6.J.166.229; 6.J.166.230; 6.J.166.231; 6.J.166.236;
6.J.166.237; 6.J.166.238; 6.J.166.239; 6.J.166.154; 6.J.166.157;
6.J.166.166; 6.J.166.169; 6.J.166.172; 6.J.166.175; 6.J.166.240;
6.J.166.244; 6.J.169.228; 6.J.169.229; 6.J.169.230; 6.J.169.231;
6.J.169.236; 6.J.169.237; 6.J.169.238; 6.J.169.239; 6.J.169.154;
6.J.169.157; 6.J.169.166; 6.J.169.169; 6.J.169.172; 6.J.169.175;
6.J.169.240; 6.J.169.244; 6.J.172.228; 6.J.172.229; 6.J.172.230;
6.J.172.231; 6.J.172.236; 6.J.172.237; 6.J.172.238; 6.J.172.239;
6.J.172.154; 6.J.172.157; 6.J.172.166; 6.J.172.169; 6.J.172.172;
6.J.172.175; 6.J.172.240; 6.J.172.244; 6.J.175.228; 6.J.175.229;
6.J.175.230; 6.J.175.231; 6.J.175.236; 6.J.175.237; 6.J.175.238;
6.J.175.239; 6.J.175.154; 6.J.175.157; 6.J.175.166; 6.J.175.169;
6.J.175.172; 6.J.175.175; 6.J.175.240; 6.J.175.244; 6.J.240.228;
6.J.240.229; 6.I.240.230; 6.J.240.231; 6.J.240.236; 6.J.240.237;
6.J.240.238; 6.J.240.239; 6.J.240.154; 6.J.240.157; 6.J.240.166;
6.J.240.169; 6.J.240.172; 6.J.240.175; 6.J.240.240; 6.J.240.244;
6.J.244.228; 6.J.244.229; 6.J.244.230; 6.J.244.231; 6.J.244.236;
6.J.244.237; 6.J.244.238; 6.J.244.239; 6.J.244.154; 6.J.244.157;
6.J.244.166; 6.J.244.169; 6.J.244.172; 6.J.244.175; 6.J.244.240;
6.J.244.244;
Prodrugs of 6.L 6.L.228.228; 6.L.228.229; 6.L.228.230; 6.L.228.231; 6.L.228.236;
6.L.228.237; 6.L.228.238; 6.L.228.239; 6.L.228.154; 6.L.228.157;
6.L.228.166; 6.L.228.169; 6.L.228.172; 6.L.228.175; 6.L.228.240;
6.L.228.244; 6.L.229.228; 6.L.229.229; 6.L.229.230; 6.L.229.231;
6.L.229.236; 6.L.229.237; 6.L.229.238; 6.L.229.239; 6.L.229.154;
6.L.229.157; 6.L.229.166; 6.L.229.169; 6.L.229.172; 6.L.229.175;
6.L.229.240; 6.L.229.244; 6.L.230.228; 6.L.230.229; 6.L.230.230;
6.L.230.231; 6.L.230.236; 6.L.230.237; 6.L.230.238; 6.L.230.239;
6.L.230.154; 6.L.230.157; 6.L.230.166; 6.L.230.169; 6.L.230.172;
6.L.230.175; 6.L.230.240; 6.L.230.244; 6.L.231.228; 6.L.231.229;
6.L.231.230; 6.L.231.231; 6.L.231.236; 6.L.231.237; 6.L.231.238;
6.L.231.239; 6.L.231.154; 6.L.231.157; 6.L.231.166; 6.L.231.169;
6.L.231.172; 6.L.231.175; 6.L.231.240; 6.L.231.244; 6.L.236.228;
6.L.236.229; 6.L.236.230; 6.L.236.231; 6.L.236.236; 6.L.236.237;
6.L.236.238; 6.L.236.239; 6.L.236.154; 6.L.236.157; 6.L.236.166;
6.L.236.169; 6.L.236.172; 6.L.236.175; 6.L.236.240; 6.L.236.244;
6.L.237.228; 6.L.237.229; 6.L.237.230; 6.L.237.231; 6.L.237.236;
6.L.237.237; 6.L.237.238; 6.L.237.239; 6.L.237.154; 6.L.237.157;
6.L.237.166; 6.L.237.169; 6.L.237.172; 6.L.237.175; 6.L.237.240;
6.L.237.244; 6.L.238.228; 6.L.238.229; 6.L.238.230; 6.L.238.231;
6.L.238.236; 6.L.238.237; 6.L.238.238; 6.L.238.239; 6.L.238.154;
6.L.238.157; 6.L.238.166; 6.L.238.169; 6.L.238.172; 6.L.238.175;
6.L.238.240; 6.L.238.244; 6.L.239.228; 6.L.239.229; 6.L.239.230;
6.L.239.231; 6.L.239.236; 6.L.239.237; 6.L.239.238; 6.L.239.239;
6.L.239.154; 6.L.239.157; 6.L.239.166; 6.L.239.169; 6.L.239.172;
6.L.239.175; 6.L.239.240; 6.L.239.244; 6.L.154.228; 6.L.154.229;
6.L.154.230; 6.L.154.231; 6.L.154.236; 6.L.154.237; 6.L.154.238;
6.L.154.239; 6.L.154.154; 6.L.154.157; 6.L.154.166; 6.L.154.169;
6.L.154.172; 6.L.154.175; 6.L.154.240; 6.L.154.244; 6.L.157.228;
6.L.157.229; 6.L.157.230; 6.L.157.231; 6.L.157.236; 6.L.157.237;
6.L.157.238; 6.L.157.239; 6.L.157.154; 6.L.157.157; 6.L.157.166;
6.L.157.169; 6.L.157.172; 6.L.157.175; 6.L.157.240; 6.L.157.244;
6.L.166.228; 6.L.166.229; 6.L.166.230; 6.L.166.231; 6.L.166.236;
6.L.166.237; 6.L.166.238; 6.L.166.239; 6.L.166.154; 6.L.166.157;
6.L.166.166; 6.L.166.169; 6.L.166.172; 6.L.166.175; 6.L.166.240;
6.L.166.244; 6.L.169.228; 6.L.169.229; 6.L.169.230; 6.L.169.231;
6.L.169.236; 6.L.169.237; 6.L.169.238; 6.L.169.239; 6.L.169.154;
6.L.169.157; 6.L.169.166; 6.L.169.169; 6.L.169.172; 6.L.169.175;
6.L.169.240; 6.L.169.244; 6.L.172.228; 6.L.172.229; 6.L.172.230;
6.L.172.231; 6.L.172.236; 6.L.172.237; 6.L.172.238; 6.L.172.239;
6.L.172.154; 6.L.172.157; 6.L.172.166; 6.L.172.169; 6.L.172.172;
6.L.172.175; 6.L.172.240; 6.L.172.244; 6.L.175.228; 6.L.175.229;
6.L.175.230; 6.L.175.231; 6.L.175.236; 6.L.175.237; 6.L.175.238;
6.L.175.239; 6.L.175.154; 6.L.175.157; 6.L.175.166; 6.L.175.169;
6.L.175.172; 6.L.175.175; 6.L.175.240; 6.L.175.244; 6.L.240.228;
6.L.240.229; 6.L.240.230; 6.L.240.231; 6.L.240.236; 6.L.240.237;
6.L.240.238; 6.L.240.239; 6.L.240.154; 6.L.240.157; 6.L.240.166;
6.L.240.169; 6.L.240.172; 6.L.240.175; 6.L.240.240; 6.L.240.244;
6.L.244.228; 6.L.244.229; 6.L.244.230; 6.L.244.231; 6.L.244.236;
6.L.244.237; 6.L.244.238; 6.L.244.239; 6.L.244.154; 6.L.244.157;
6.L.244.166; 6.L.244.169; 6.L.244.172; 6.L.244.175; 6.L.244.240;
6.L.244.244;
Prodrugs of 6.O 6.O.228.228; 6.O.228.229; 6.O.228.230; 6.O.228.231; 6.O.228.236;
6.O.228.237; 6.O.228.238; 6.O.228.239; 6.O.228.154; 6.O.228.157;
6.O.228.166; 6.O.228.169; 6.O.228.172; 6.O.228.175; 6.O.228.240;
6.O.228.244; 6.O.229.228; 6.O.229.229; 6.O.229.230; 6.O.229.231;
6.O.229.236; 6.O.229.237; 6.O.229.238; 6.O.229.239; 6.O.229.154;
6.O.229.157; 6.O.229.166; 6.O.229.169; 6.O.229.172; 6.O.229.175;
6.O.229.240; 6.O.229.244; 6.O.230.228; 6.O.230.229; 6.O.230.230;
6.O.230.231; 6.O.230.236; 6.O.230.237; 6.O.230.238; 6.O.230.239;
6.O.230.154; 6.O.230.157; 6.O.230.166; 6.O.230.169; 6.O.230.172;
6.O.230.175; 6.O.230.240; 6.O.230.244; 6.O.231.228; 6.O.231.229;
6.O.231.230; 6.O.231.231; 6.O.231.236; 6.O.231.237; 6.O.231.238;
6.O.231.239; 6.O.231.154; 6.O.231.157; 6.O.231.166; 6.O.231.169;
6.O.231.172; 6.O.231.175; 6.O.231.240; 6.O.231.244; 6.O.236.228;
6.O.236.229; 6.O.236.230; 6.O.236.231; 6.O.236.236; 6.O.236.237;
6.O.236.238; 6.O.236.239; 6.O.236.154; 6.O.236.157; 6.O.236.166;
6.O.236.169; 6.O.236.172; 6.O.236.175; 6.O.236.240; 6.O.236.244;
6.O.237.228; 6.O.237.229; 6.O.237.230; 6.O.237.231; 6.O.237.236;
6.O.237.237; 6.O.237.238; 6.O.237.239; 6.O.237.154; 6.O.237.157;
6.O.237.166; 6.O.237.169; 6.O.237.172; 6.O.237.175; 6.O.237.240;
6.O.237.244; 6.O.238.228; 6.O.238.229; 6.O.238.230; 6.O.238.231;
6.O.238.236; 6.O.238.237; 6.O.238.238; 6.O.238.239; 6.O.238.154;
6.O.238.157; 6.O.238.166; 6.O.238.169; 6.O.238.172; 6.O.238.175;
6.O.238.240; 6.O.238.244; 6.O.239.228; 6.O.239.229; 6.O.239.230;
6.O.239.231; 6.O.239.236; 6.O.239.237; 6.O.239.238; 6.O.239.239;
6.O.239.154; 6.O.239.157; 6.O.239.166; 6.O.239.169; 6.O.239.172;
6.O.239.175; 6.O.239.240; 6.O.239.244; 6.O.154.228; 6.O.154.229;
6.O.154.230; 6.O.154.231; 6.O.154.236; 6.O.154.237; 6.O.154.238;
6.O.154.239; 6.O.154.154; 6.O.154.157; 6.O.154.166; 6.O.154.169;
6.O.154.172; 6.O.154.175; 6.O.154.240; 6.O.154.244; 6.O.157.228;
6.O.157.229; 6.O.157.230; 6.O.157.231; 6.O.157.236; 6.O.157.237;
6.O.157.238; 6.O.157.239; 6.O.157.154; 6.O.157.157; 6.O.157.166;
6.O.157.169; 6.O.157.172; 6.O.157.175; 6.O.157.240; 6.O.157.244;
6.O.166.228; 6.O.166.229; 6.O.166.230; 6.O.166.231; 6.O.166.236;
6.O.166.237; 6.O.166.238; 6.O.166.239; 6.O.166.154; 6.O.166.157;
6.O.166.166; 6.O.166.169; 6.O.166.172; 6.O.166.175; 6.O.166.240;
6.O.166.244; 6.O.169.228; 6.O.169.229; 6.O.169.230; 6.O.169.231;
6.O.169.236; 6.O.169.237; 6.O.169.238; 6.O.169.239; 6.O.169.154;
6.O.169.157; 6.O.169.166; 6.O.169.169; 6.O.169.172; 6.O.169.175;
6.O.169.240; 6.O.169.244; 6.O.172.228; 6.O.172.229; 6.O.172.230;
6.O.172.231; 6.O.172.236; 6.O.172.237; 6.O.172.238; 6.O.172.239;
6.O.172.154; 6.O.172.157; 6.O.172.166; 6.O.172.169; 6.O.172.172;
6.O.172.175; 6.O.172.240; 6.O.172.244; 6.O.175.228; 6.O.175.229;
6.O.175.230; 6.O.175.231; 6.O.175.236; 6.O.175.237; 6.O.175.238;
6.O.175.239; 6.O.175.154; 6.O.175.157; 6.O.175.166; 6.O.175.169;
6.O.175.172; 6.O.175.175; 6.O.175.240; 6.O.175.244; 6.O.240.228;
6.O.240.229; 6.O.240.230; 6.O.240.231; 6.O.240.236; 6.O.240.237;
6.O.240.238; 6.O.240.239; 6.O.240.154; 6.O.240.157; 6.O.240.166;
6.O.240.169; 6.O.240.172; 6.O.240.175; 6.O.240.240; 6.O.240.244;
6.O.244.228; 6.O.244.229; 6.O.244.230; 6.O.244.231; 6.O.244.236;
6.O.244.237; 6.O.244.238; 6.O.244.239; 6.O.244.154; 6.O.244.157;
6.O.244.166; 6.O.244.169; 6.O.244.172; 6.O.244.175; 6.O.244.240;
6.O.244.244;
Prodrugs of 6.P 6.P.228.228; 6.P.228.229; 6.P.228.230; 6.P.228.231; 6.P.228.236;
6.P.228.237; 6.P.228.238; 6.P.228.239; 6.P.228.154; 6.P.228.157;
6.P.228.166; 6.P.228.169; 6.P.228.172; 6.P.228.175; 6.P.228.240;
6.P.228.244; 6.P.229.228; 6.P.229.229; 6.P.229.230; 6.P.229.231;
6.P.229.236; 6.P.229.237; 6.P.229.238; 6.P.229.239; 6.P.229.154;
6.P.229.157; 6.P.229.166; 6.P.229.169; 6.P.229.172; 6.P.229.175;
6.P.229.240; 6.P.229.244; 6.P.230.228; 6.P.230.229; 6.P.230.230;
6.P.230.231; 6.P.230.236; 6.P.230.237; 6.P.230.238; 6.P.230.239;
6.P.230.154; 6.P.230.157; 6.P.230.166; 6.P.230.169; 6.P.230.172;
6.P.230.175; 6.P.230.240; 6.P.230.244; 6.P.231.228; 6.P.231.229;
6.P.231.230; 6.P.231.231; 6.P.231.236; 6.P.231.237; 6.P.231.238;
6.P.231.239; 6.P.231.154; 6.P.231.157; 6.P.231.166; 6.P.231.169;
6.P.231.172; 6.P.231.175; 6.P.231.240; 6.P.231.244; 6.P.236.228;
6.P.236.229; 6.P.236.230; 6.P.236.231; 6.P.236.236; 6.P.236.237;
6.P.236.238; 6.P.236.239; 6.P.236.154; 6.P.236.157; 6.P.236.166;
6.P.236.169; 6.P.236.172; 6.P.236.175; 6.P.236.240; 6.P.236.244;
6.P.237.228; 6.P.237.229; 6.P.237.230; 6.P.237.231; 6.P.237.236;
6.P.237.237; 6.P.237.238; 6.P.237.239; 6.P.237.154; 6.P.237.157;
6.P.237.166; 6.P.237.169; 6.P.237.172; 6.P.237.175; 6.P.237.240;

TABLE 7-continued

6.P.237.244; 6.P.238.228; 6.P.238.229; 6.P.238.230; 6.P.238.231;
6.P.238.236; 6.P.238.237; 6.P.238.238; 6.P.238.239; 6.P.238.154;
6.P.238.157; 6.P.238.166; 6.P.238.169; 6.P.238.172; 6.P.238.175;
6.P.238.240; 6.P.238.244; 6.P.239.228; 6.P.239.229; 6.P.239.230;
6.P.239.231; 6.P.239.236; 6.P.239.237; 6.P.239.238; 6.P.239.239;
6.P.239.154; 6.P.239.157; 6.P.239.166; 6.P.239.169; 6.P.239.172;
6.P.239.175; 6.P.239.240; 6.P.239.244; 6.P.154.228; 6.P.154.229;
6.P.154.230; 6.P.154.231; 6.P.154.236; 6.P.154.237; 6.P.154.238;
6.P.154.239; 6.P.154.154; 6.P.154.157; 6.P.154.166; 6.P.154.169;
6.P.154.172; 6.P.154.175; 6.P.154.240; 6.P.154.244; 6.P.157.228;
6.P.157.229; 6.P.157.230; 6.P.157.231; 6.P.157.236; 6.P.157.237;
6.P.157.238; 6.P.157.239; 6.P.157.154; 6.P.157.157; 6.P.157.166;
6.P.157.169; 6.P.157.172; 6.P.157.175; 6.P.157.240; 6.P.157.244;
6.P.166.228; 6.P.166.229; 6.P.166.230; 6.P.166.231; 6.P.166.236;
6.P.166.237; 6.P.166.238; 6.P.166.239; 6.P.166.154; 6.P.166.157;
6.P.166.166; 6.P.166.169; 6.P.166.172; 6.P.166.175; 6.P.166.240;
6.P.166.244; 6.P.169.228; 6.P.169.229; 6.P.169.230; 6.P.169.231;
6.P.169.236; 6.P.169.237; 6.P.169.238; 6.P.169.239; 6.P.169.154;
6.P.169.157; 6.P.169.166; 6.P.169.169; 6.P.169.172; 6.P.169.175;
6.P.169.240; 6.P.169.244; 6.P.172.228; 6.P.172.229; 6.P.172.230;
6.P.172.231; 6.P.172.236; 6.P.172.237; 6.P.172.238; 6.P.172.239;
6.P.172.154; 6.P.172.157; 6.P.172.166; 6.P.172.169; 6.P.172.172;
6.P.172.175; 6.P.172.240; 6.P.172.244; 6.P.175.228; 6.P.175.229;
6.P.175.230; 6.P.175.231; 6.P.175.236; 6.P.175.237; 6.P.175.238;
6.P.175.239; 6.P.175.154; 6.P.175.157; 6.P.175.166; 6.P.175.169;
6.P.175.172; 6.P.175.175; 6.P.175.240; 6.P.175.244; 6.P.240.228;
6.P.240.229; 6.P.240.230; 6.P.240.231; 6.P.240.236; 6.P.240.237;
6.P.240.238; 6.P.240.239; 6.P.240.154; 6.P.240.157; 6.P.240.166;
6.P.240.169; 6.P.240.172; 6.P.240.175; 6.P.240.240; 6.P.240.244;
6.P.244.228; 6.P.244.229; 6.P.244.230; 6.P.244.231; 6.P.244.236;
6.P.244.237; 6.P.244.238; 6.P.244.239; 6.P.244.154; 6.P.244.157;
6.P.244.166; 6.P.244.169; 6.P.244.172; 6.P.244.175; 6.P.244.240;
6.P.244.244;
Prodrugs of 6.U 6.U.228.228; 6.U.228.229; 6.U.228.230; 6.U.228.231; 6.U.228.236;
6.U.228.237; 6.U.228.238; 6.U.228.239; 6.U.228.154; 6.U.228.157;
6.U.228.166; 6.U.228.169; 6.U.228.172; 6.U.228.175; 6.U.228.240;
6.U.228.244; 6.U.229.228; 6.U.229.229; 6.U.229.230; 6.U.229.231;
6.U.229.236; 6.U.229.237; 6.U.229.238; 6.U.229.239; 6.U.229.154;
6.U.229.157; 6.U.229.166; 6.U.229.169; 6.U.229.172; 6.U.229.175;
6.U.229.240; 6.U.229.244; 6.U.230.228; 6.U.230.229; 6.U.230.230;
6.U.230.231; 6.U.230.236; 6.U.230.237; 6.U.230.238; 6.U.230.239;
6.U.230.154; 6.U.230.157; 6.U.230.166; 6.U.230.169; 6.U.230.172;
6.U.230.175; 6.U.230.240; 6.U.230.244; 6.U.231.228; 6.U.231.229;
6.U.231.230; 6.U.231.231; 6.U.231.236; 6.U.231.237; 6.U.231.238;
6.U.231.239; 6.U.231.154; 6.U.231.157; 6.U.231.166; 6.U.231.169;
6.U.231.172; 6.U.231.175; 6.U.231.240; 6.U.231.244; 6.U.236.228;
6.U.236.229; 6.U.236.230; 6.U.236.231; 6.U.236.236; 6.U.236.237;
6.U.236.238; 6.U.236.239; 6.U.236.154; 6.U.236.157; 6.U.236.166;
6.U.236.169; 6.U.236.172; 6.U.236.175; 6.U.236.240; 6.U.236.244;
6.U.237.228; 6.U.237.229; 6.U.237.230; 6.U.237.231; 6.U.237.236;
6.U.237.237; 6.U.237.238; 6.U.237.239; 6.U.237.154; 6.U.237.157;
6.U.237.166; 6.U.237.169; 6.U.237.172; 6.U.237.175; 6.U.237.240;
6.U.237.244; 6.U.238.228; 6.U.238.229; 6.U.238.230; 6.U.238.231;
6.U.238.236; 6.U.238.237; 6.U.238.238; 6.U.238.239; 6.U.238.154;
6.U.238.157; 6.U.238.166; 6.U.238.169; 6.U.238.172; 6.U.238.175;
6.U.238.240; 6.U.238.244; 6.U.239.228; 6.U.239.229; 6.U.239.230;
6.U.239.231; 6.U.239.236; 6.U.239.237; 6.U.239.238; 6.U.239.239;
6.U.239.154; 6.U.239.157; 6.U.239.166; 6.U.239.169; 6.U.239.172;
6.U.239.175; 6.U.239.240; 6.U.239.244; 6.U.154.228; 6.U.154.229;
6.U.154.230; 6.U.154.231; 6.U.154.236; 6.U.154.237; 6.U.154.238;
6.U.154.239; 6.U.154.154; 6.U.154.157; 6.U.154.166; 6.U.154.169;
6.U.154.172; 6.U.154.175; 6.U.154.240; 6.U.154.244; 6.U.157.228;
6.U.157.229; 6.U.157.230; 6.U.157.231; 6.U.157.236; 6.U.157.237;
6.U.157.238; 6.U.157.239; 6.U.157.154; 6.U.157.157; 6.U.157.166;
6.U.157.169; 6.U.157.172; 6.U.157.175; 6.U.157.240; 6.U.157.244;
6.U.166.228; 6.U.166.229; 6.U.166.230; 6.U.166.231; 6.U.166.236;
6.U.166.237; 6.U.166.238; 6.U.166.239; 6.U.166.154; 6.U.166.157;
6.U.166.166; 6.U.166.169; 6.U.166.172; 6.U.166.175; 6.U.166.240;
6.U.166.244; 6.U.169.228; 6.U.169.229; 6.U.169.230; 6.U.169.231;
6.U.169.236; 6.U.169.237; 6.U.169.238; 6.U.169.239; 6.U.169.154;
6.U.169.157; 6.U.169.166; 6.U.169.169; 6.U.169.172; 6.U.169.175;
6.U.169.240; 6.U.169.244; 6.U.172.228; 6.U.172.229; 6.U.172.230;
6.U.172.231; 6.U.172.236; 6.U.172.237; 6.U.172.238; 6.U.172.239;
6.U.172.154; 6.U.172.157; 6.U.172.166; 6.U.172.169; 6.U.172.172;
6.U.172.175; 6.U.172.240; 6.U.172.244; 6.U.175.228; 6.U.175.229;
6.U.175.230; 6.U.175.231; 6.U.175.236; 6.U.175.237; 6.U.175.238;
6.U.175.239; 6.U.175.154; 6.U.175.157; 6.U.175.166; 6.U.175.169;
6.U.175.172; 6.U.175.175; 6.U.175.240; 6.U.175.244; 6.U.240.228;
6.U.240.229; 6.U.240.230; 6.U.240.231; 6.U.240.236; 6.U.240.237;
6.U.240.238; 6.U.240.239; 6.U.240.154; 6.U.240.157; 6.U.240.166;
6.U.240.169; 6.U.240.172; 6.U.240.175; 6.U.240.240; 6.U.240.244;
6.U.244.228; 6.U.244.229; 6.U.244.230; 6.U.244.231; 6.U.244.236;
6.U.244.237; 6.U.244.238; 6.U.244.239; 6.U.244.154; 6.U.244.157;
6.U.244.166; 6.U.244.169; 6.U.244.172; 6.U.244.175; 6.U.244.240;
6.U.244.244;
Prodrugs of 6.W 6.W.228.228; 6.W.228.229; 6.W.228.230; 6.W.228.231; 6.W.228.236;
6.W.228.237; 6.W.228.238; 6.W.228.239; 6.W.228.154; 6.W.228.157;
6.W.228.166; 6.W.228.169; 6.W.228.172; 6.W.228.175; 6.W.228.240;
6.W.228.244; 6.W.229.228; 6.W.229.229; 6.W.229.230; 6.W.229.231;
6.W.229.236; 6.W.229.237; 6.W.229.238; 6.W.229.239; 6.W.229.154;
6.W.229.157; 6.W.229.166; 6.W.229.169; 6.W.229.172; 6.W.229.175;
6.W.229.240; 6.W.229.244; 6.W.230.228; 6.W.230.229; 6.W.230.230;
6.W.230.231; 6.W.230.236; 6.W.230.237; 6.W.230.238; 6.W.230.239;
6.W.230.154; 6.W.230.157; 6.W.230.166; 6.W.230.169; 6.W.230.172;
6.W.230.175; 6.W.230.240; 6.W.230.244; 6.W.231.228; 6.W.231.229;
6.W.231.230; 6.W.231.231; 6.W.231.236; 6.W.231.237; 6.W.231.238;
6.W.231.239; 6.W.231.154; 6.W.231.157; 6.W.231.166; 6.W.231.169;
6.W.231.172; 6.W.231.175; 6.W.231.240; 6.W.231.244; 6.W.236.228;
6.W.236.229; 6.W.236.230; 6.W.236.231; 6.W.236.236; 6.W.236.237;
6.W.236.238; 6.W.236.239; 6.W.236.154; 6.W.236.157; 6.W.236.166;
6.W.236.169; 6.W.236.172; 6.W.236.175; 6.W.236.240; 6.W.236.244;
6.W.237.228; 6.W.237.229; 6.W.237.230; 6.W.237.231; 6.W.237.236;
6.W.237.237; 6.W.237.238; 6.W.237.239; 6.W.237.154; 6.W.237.157;
6.W.237.166; 6.W.237.169; 6.W.237.172; 6.W.237.175; 6.W.237.240;
6.W.237.244; 6.W.238.228; 6.W.238.229; 6.W.238.230; 6.W.238.231;
6.W.238.236; 6.W.238.237; 6.W.238.238; 6.W.238.239; 6.W.238.154;
6.W.238.157; 6.W.238.166; 6.W.238.169; 6.W.238.172; 6.W.238.175;
6.W.238.240; 6.W.238.244; 6.W.239.228; 6.W.239.229; 6.W.239.230;
6.W.239.231; 6.W.239.236; 6.W.239.237; 6.W.239.238; 6.W.239.239;
6.W.239.154; 6.W.239.157; 6.W.239.166; 6.W.239.169; 6.W.239.172;
6.W.239.175; 6.W.239.240; 6.W.239.244; 6.W.154.228; 6.W.154.229;
6.W.154.230; 6.W.154.231; 6.W.154.236; 6.W.154.237; 6.W.154.238;
6.W.154.239; 6.W.154.154; 6.W.154.157; 6.W.154.166; 6.W.154.169;
6.W.154.172; 6.W.154.175; 6.W.154.240; 6.W.154.244; 6.W.157.228;
6.W.157.229; 6.W.157.230; 6.W.157.231; 6.W.157.236; 6.W.157.237;
6.W.157.238; 6.W.157.239; 6.W.157.154; 6.W.157.157; 6.W.157.166;
6.W.157.169; 6.W.157.172; 6.W.157.175; 6.W.157.240; 6.W.157.244;
6.W.166.228; 6.W.166.229; 6.W.166.230; 6.W.166.231; 6.W.166.236;
6.W.166.237; 6.W.166.238; 6.W.166.239; 6.W.166.154; 6.W.166.157;
6.W.166.166; 6.W.166.169; 6.W.166.172; 6.W.166.175; 6.W.166.240;
6.W.166.244; 6.W.169.228; 6.W.169.229; 6.W.169.230; 6.W.169.231;
6.W.169.236; 6.W.169.237; 6.W.169.238; 6.W.169.239; 6.W.169.154;
6.W.169.157; 6.W.169.166; 6.W.169.169; 6.W.169.172; 6.W.169.175;
6.W.169.240; 6.W.169.244; 6.W.172.228; 6.W.172.229; 6.W.172.230;
6.W.172.231; 6.W.172.236; 6.W.172.237; 6.W.172.238; 6.W.172.239;
6.W.172.154; 6.W.172.157; 6.W.172.166; 6.W.172.169; 6.W.172.172;
6.W.172.175; 6.W.172.240; 6.W.172.244; 6.W.175.228; 6.W.175.229;
6.W.175.230; 6.W.175.231; 6.W.175.236; 6.W.175.237; 6.W.175.238;
6.W.175.239; 6.W.175.154; 6.W.175.157; 6.W.175.166; 6.W.175.169;
6.W.175.172; 6.W.175.175; 6.W.175.240; 6.W.175.244; 6.W.240.228;
6.W.240.229; 6.W.240.230; 6.W.240.231; 6.W.240.236; 6.W.240.237;
6.W.240.238; 6.W.240.239; 6.W.240.154; 6.W.240.157; 6.W.240.166;
6.W.240.169; 6.W.240.172; 6.W.240.175; 6.W.240.240; 6.W.240.244;
6.W.244.228; 6.W.244.229; 6.W.244.230; 6.W.244.231; 6.W.244.236;
6.W.244.237; 6.W.244.238; 6.W.244.239; 6.W.244.154; 6.W.244.157;
6.W.244.166; 6.W.244.169; 6.W.244.172; 6.W.244.175; 6.W.244.240;
6.W.244.244;
Prodrugs of 6.Y 6.Y.228.228; 6.Y.228.229; 6.Y.228.230; 6.Y.228.231; 6.Y.228.236;
6.Y.228.237; 6.Y.228.238; 6.Y.228.239; 6.Y.228.154; 6.Y.228.157;
6.Y.228.166; 6.Y.228.169; 6.Y.228.172; 6.Y.228.175; 6.Y.228.240;
6.Y.228.244; 6.Y.229.228; 6.Y.229.229; 6.Y.229.230; 6.Y.229.231;
6.Y.229.236; 6.Y.229.237; 6.Y.229.238; 6.Y.229.239; 6.Y.229.154;
6.Y.229.157; 6.Y.229.166; 6.Y.229.169; 6.Y.229.172; 6.Y.229.175;
6.Y.229.240; 6.Y.229.244; 6.Y.230.228; 6.Y.230.229; 6.Y.230.230;
6.Y.230.231; 6.Y.230.236; 6.Y.230.237; 6.Y.230.238; 6.Y.230.239;
6.Y.230.154; 6.Y.230.157; 6.Y.230.166; 6.Y.230.169; 6.Y.230.172;
6.Y.230.175; 6.Y.230.240; 6.Y.230.244; 6.Y.231.228; 6.Y.231.229;
6.Y.231.230; 6.Y.231.231; 6.Y.231.236; 6.Y.231.237; 6.Y.231.238;
6.Y.231.239; 6.Y.231.154; 6.Y.231.157; 6.Y.231.166; 6.Y.231.169;
6.Y.231.172; 6.Y.231.175; 6.Y.231.240; 6.Y.231.244; 6.Y.236.228;
6.Y.236.229; 6.Y.236.230; 6.Y.236.231; 6.Y.236.236; 6.Y.236.237;
6.Y.236.238; 6.Y.236.239; 6.Y.236.154; 6.Y.236.157; 6.Y.236.166;

TABLE 7-continued

6.Y.236.169; 6.Y.236.172; 6.Y.236.175; 6.Y.236.240; 6.Y.236.244;
6.Y.237.228; 6.Y.237.229; 6.Y.237.230; 6.Y.237.231; 6.Y.237.236;
6.Y.237.237; 6.Y.237.238; 6.Y.237.239; 6.Y.237.154; 6.Y.237.157;
6.Y.237.166; 6.Y.237.169; 6.Y.237.172; 6.Y.237.175; 6.Y.237.240;
6.Y.237.244; 6.Y.238.228; 6.Y.238.229; 6.Y.238.230; 6.Y.238.231;
6.Y.238.236; 6.Y.238.237; 6.Y.238.238; 6.Y.238.239; 6.Y.238.154;
6.Y.238.157; 6.Y.238.166; 6.Y.238.169; 6.Y.238.172; 6.Y.238.175;
6.Y.238.240; 6.Y.238.244; 6.Y.239.228; 6.Y.239.229; 6.Y.239.230;
6.Y.239.231; 6.Y.239.236; 6.Y.239.237; 6.Y.239.238; 6.Y.239.239;
6.Y.239.154; 6.Y.239.157; 6.Y.239.166; 6.Y.239.169; 6.Y.239.172;
6.Y.239.175; 6.Y.239.240; 6.Y.239.244; 6.Y.154.228; 6.Y.154.229;
6.Y.154.230; 6.Y.154.231; 6.Y.154.236; 6.Y.154.237; 6.Y.154.238;
6.Y.154.239; 6.Y.154.154; 6.Y.154.157; 6.Y.154.166; 6.Y.154.169;
6.Y.154.172; 6.Y.154.175; 6.Y.154.240; 6.Y.154.244; 6.Y.157.228;
6.Y.157.229; 6.Y.157.230; 6.Y.157.231; 6.Y.157.236; 6.Y.157.237;
6.Y.157.238; 6.Y.157.239; 6.Y.157.154; 6.Y.157.157; 6.Y.157.166;
6.Y.157.169; 6.Y.157.172; 6.Y.157.175; 6.Y.157.240; 6.Y.157.244;
6.Y.166.228; 6.Y.166.229; 6.Y.166.230; 6.Y.166.231; 6.Y.166.236;
6.Y.166.237; 6.Y.166.238; 6.Y.166.239; 6.Y.166.154; 6.Y.166.157;
6.Y.166.166; 6.Y.166.169; 6.Y.166.172; 6.Y.166.175; 6.Y.166.240;
6.Y.166.244; 6.Y.169.228; 6.Y.169.229; 6.Y.169.230; 6.Y.169.231;
6.Y.169.236; 6.Y.169.237; 6.Y.169.238; 6.Y.169.239; 6.Y.169.154;
6.Y.169.157; 6.Y.169.166; 6.Y.169.169; 6.Y.169.172; 6.Y.169.175;
6.Y.169.240; 6.Y.169.244; 6.Y.172.228; 6.Y.172.229; 6.Y.172.230;
6.Y.172.231; 6.Y.172.236; 6.Y.172.237; 6.Y.172.238; 6.Y.172.239;
6.Y.172.154; 6.Y.172.157; 6.Y.172.166; 6.Y.172.169; 6.Y.172.172;
6.Y.172.175; 6.Y.172.240; 6.Y.172.244; 6.Y.175.228; 6.Y.175.229;
6.Y.175.230; 6.Y.175.231; 6.Y.175.236; 6.Y.175.237; 6.Y.175.238;
6.Y.175.239; 6.Y.175.154; 6.Y.175.157; 6.Y.175.166; 6.Y.175.169;
6.Y.175.172; 6.Y.175.175; 6.Y.175.240; 6.Y.175.244; 6.Y.240.228;
6.Y.240.229; 6.Y.240.230; 6.Y.240.231; 6.Y.240.236; 6.Y.240.237;
6.Y.240.238; 6.Y.240.239; 6.Y.240.154; 6.Y.240.157; 6.Y.240.166;
6.Y.240.169; 6.Y.240.172; 6.Y.240.175; 6.Y.240.240; 6.Y.240.244;
6.Y.244.228; 6.Y.244.229; 6.Y.244.230; 6.Y.244.231; 6.Y.244.236;
6.Y.244.237; 6.Y.244.238; 6.Y.244.239; 6.Y.244.154; 6.Y.244.157;
6.Y.244.166; 6.Y.244.169; 6.Y.244.172; 6.Y.244.175; 6.Y.244.240;
6.Y.244.244;

Prodrugs of 7.AH

7.AH.4.157; 7.AH.4.158; 7.AH.4.196; 7.AH.4.223; 7.AH.4.240;
7.AH.4.244; 7.AH.4.243; 7.AH.4.247; 7.AH.5.157; 7.AH.5.158;
7.AH.5.196; 7.AH.5.223; 7.AH.5.240; 7.AH.5.244; 7.AH.5.243;
7.AH.5.247; 7.AH.7.157; 7.AH.7.158; 7.AH.7.196; 7.AH.7.223;
7.AH.7.240; 7.AH.7.244; 7.AH.7.243; 7.AH.7.247; 7.AH.15.157;
7.AH.15.158; 7.AH.15.196; 7.AH.15.223; 7.AH.15.240; 7.AH.15.244;
7.AH.15.243; 7.AH.15.247; 7.AH.16.157; 7.AH.16.158; 7.AH.16.196;
7.AH.16.223; 7.AH.16.240; 7.AH.16.244; 7.AH.16.243; 7.AH.16.247;
7.AH.18.157; 7.AH.18.158; 7.AH.18.196; 7.AH.18.223; 7.AH.18.240;
7.AH.18.244; 7.AH.18.243; 7.AH.18.247; 7.AH.26.157; 7.AH.26.158;
7.AH.26.196; 7.AH.26.223; 7.AH.26.240; 7.AH.26.244; 7.AH.26.243;
7.AH.26.247; 7.AH.27.157; 7.AH.27.158; 7.AH.27.196; 7.AH.27.223;
7.AH.27.240; 7.AH.27.244; 7.AH.27.243; 7.AH.27.247; 7.AH.29.157;
7.AH.29.158; 7.AH.29.196; 7.AH.29.223; 7.AH.29.240; 7.AH.29.244;
7.AH.29.243; 7.AH.29.247; 7.AH.54.157; 7.AH.54.158; 7.AH.54.196;
7.AH.54.223; 7.AH.54.240; 7.AH.54.244; 7.AH.54.243; 7.AH.54.247;
7.AH.55.157; 7.AH.55.158; 7.AH.55.196; 7.AH.55.223; 7.AH.55.240;
7.AH.55.244; 7.AH.55.243; 7.AH.55.247; 7.AH.56.157; 7.AH.56.158;
7.AH.56.196; 7.AH.56.223; 7.AH.56.240; 7.AH.56.244; 7.AH.56.243;
7.AH.56.247; 7.AH.157.157; 7.AH.157.158; 7.AH.157.196; 7.AH.157.223;
7.AH.157.240; 7.AH.157.244; 7.AH.157.243; 7.AH.157.247; 7.AH.196.157;
7.AH.196.158; 7.AH.196.196; 7.AH.196.223; 7.AH.196.240; 7.AH.196.244;
7.AH.196.243; 7.AH.196.247; 7.AH.223.157; 7.AH.223.158; 7.AH.223.196;
7.AH.223.223; 7.AH.223.240; 7.AH.223.244; 7.AH.223.243; 7.AH.223.247;
7.AH.240.157; 7.AH.240.158; 7.AH.240.196; 7.AH.240.223; 7.AH.240.240;
7.AH.240.244; 7.AH.240.243; 7.AH.240.247; 7.AH.244.157; 7.AH.244.158;
7.AH.244.196; 7.AH.244.223; 7.AH.244.240; 7.AH.244.244; 7.AH.244.243;
7.AH.244.247; 7.AH.247.157; 7.AH.247.158; 7.AH.247.196; 7.AH.247.223;
7.AH.247.240; 7.AH.247.244; 7.AH.247.243; 7.AH.247.247;

Prodrugs of 7.AJ

7.AJ.4.157; 7.AJ.4.158; 7.AJ.4.196; 7.AJ.4.223; 7.AJ.4.240;
7.AJ.4.244; 7.AJ.4.243; 7.AJ.4.247; 7.AJ.5.157; 7.AJ.5.158;
7.AJ.5.196; 7.AJ.5.223; 7.AJ.5.240; 7.AJ.5.244; 7.AJ.5.243;
7.AJ.5.247; 7.AJ.7.157; 7.AJ.7.158; 7.AJ.7.196; 7.AJ.7.223;
7.AJ.7.240; 7.AJ.7.244; 7.AJ.7.243; 7.AJ.7.247; 7.AJ.15.157;
7.AJ.15.158; 7.AJ.15.196; 7.AJ.15.223; 7.AJ.15.240; 7.AJ.15.244;
7.AJ.15.243; 7.AJ.15.247; 7.AJ.16.157; 7.AJ.16.158; 7.AJ.16.196;
7.AJ.16.223; 7.AJ.16.240; 7.AJ.16.244; 7.AJ.16.243; 7.AJ.16.247;
7.AJ.18.157; 7.AJ.18.158; 7.AJ.18.196; 7.AJ.18.223; 7.AJ.18.240;

7.AJ.18.244; 7.AJ.18.243; 7.AJ.18.247; 7.AJ.26.157; 7.AJ.26.158;
7.AJ.26.196; 7.AJ.26.223; 7.AJ.26.240; 7.AJ.26.244; 7.AJ.26.243;
7.AJ.26.247; 7.AJ.27.157; 7.AJ.27.158; 7.AJ.27.196; 7.AJ.27.223;
7.AJ.27.240; 7.AJ.27.244; 7.AJ.27.243; 7.AJ.27.247; 7.AJ.29.157;
7.AJ.29.158; 7.AJ.29.196; 7.AJ.29.223; 7.AJ.29.240; 7.AJ.29.244;
7.AJ.29.243; 7.AJ.29.247; 7.AJ.54.157; 7.AJ.54.158; 7.AJ.54.196;
7.AJ.54.223; 7.AJ.54.240; 7.AJ.54.244; 7.AJ.54.243; 7.AJ.54.247;
7.AJ.55.157; 7.AJ.55.158; 7.AJ.55.196; 7.AJ.55.223; 7.AJ.55.240;
7.AJ.55.244; 7.AJ.55.243; 7.AJ.55.247; 7.AJ.56.157; 7.AJ.56.158;
7.AJ.56.196; 7.AJ.56.223; 7.AJ.56.240; 7.AJ.56.244; 7.AJ.56.243;
7.AJ.56.247; 7.AJ.157.157; 7.AJ.157.158; 7.AJ.157.196; 7.AJ.157.223;
7.AJ.157.240; 7.AJ.157.244; 7.AJ.157.243; 7.AJ.157.247; 7.AJ.196.157;
7.AJ.196.158; 7.AJ.196.196; 7.AJ.196.223; 7.AJ.196.240; 7.AJ.196.244;
7.AJ.196.243; 7.AJ.196.247; 7.AJ.223.157; 7.AJ.223.158; 7.AJ.223.196;
7.AJ.223.223; 7.AJ.223.240; 7.AJ.223.244; 7.AJ.223.243; 7.AJ.223.247;
7.AJ.240.157; 7.AJ.240.158; 7.AJ.240.196; 7.AJ.240.223; 7.AJ.240.240;
7.AJ.240.244; 7.AJ.240.243; 7.AJ.240.247; 7.AJ.244.157; 7.AJ.244.158;
7.AJ.244.196; 7.AJ.244.223; 7.AJ.244.240; 7.AJ.244.244; 7.AJ.244.243;
7.AJ.244.247; 7.AJ.247.157; 7.AJ.247.158; 7.AJ.247.196; 7.AJ.247.223;
7.AJ.247.240; 7.AJ.247.244; 7.AJ.247.243; 7.AJ.247.247;

Prodrugs of 7.AN

7.AN.4.157; 7.AN.4.158; 7.AN.4.196; 7.AN.4.223; 7.AN.4.240;
7.AN.4.244; 7.AN.4.243; 7.AN.4.247; 7.AN.5.157; 7.AN.5.158;
7.AN.5.196; 7.AN.5.223; 7.AN.5.240; 7.AN.5.244; 7.AN.5.243;
7.AN.5.247; 7.AN.7.157; 7.AN.7.158; 7.AN.7.196; 7.AN.7.223;
7.AN.7.240; 7.AN.7.244; 7.AN.7.243; 7.AN.7.247; 7.AN.15.157;
7.AN.15.158; 7.AN.15.196; 7.AN.15.223; 7.AN.15.240; 7.AN.15.244;
7.AN.15.243; 7.AN.15.247; 7.AN.16.157; 7.AN.16.158; 7.AN.16.196;
7.AN.16.223; 7.AN.16.240; 7.AN.16.244; 7.AN.16.243; 7.AN.16.247;
7.AN.18.157; 7.AN.18.158; 7.AN.18.196; 7.AN.18.223; 7.AN.18.240;
7.AN.18.244; 7.AN.18.243; 7.AN.18.247; 7.AN.26.157; 7.AN.26.158;
7.AN.26.196; 7.AN.26.223; 7.AN.26.240; 7.AN.26.244; 7.AN.26.243;
7.AN.26.247; 7.AN.27.157; 7.AN.27.158; 7.AN.27.196; 7.AN.27.223;
7.AN.27.240; 7.AN.27.244; 7.AN.27.243; 7.AN.27.247; 7.AN.29.157;
7.AN.29.158; 7.AN.29.196; 7.AN.29.223; 7.AN.29.240; 7.AN.29.244;
7.AN.29.243; 7.AN.29.247; 7.AN.54.157; 7.AN.54.158; 7.AN.54.196;
7.AN.54.223; 7.AN.54.240; 7.AN.54.244; 7.AN.54.243; 7.AN.54.247;
7.AN.55.157; 7.AN.55.158; 7.AN.55.196; 7.AN.55.223; 7.AN.55.240;
7.AN.55.244; 7.AN.55.243; 7.AN.55.247; 7.AN.56.157; 7.AN.56.158;
7.AN.56.196; 7.AN.56.223; 7.AN.56.240; 7.AN.56.244; 7.AN.56.243;
7.AN.56.247; 7.AN.157.157; 7.AN.157.158; 7.AN.157.196; 7.AN.157.223;
7.AN.157.240; 7.AN.157.244; 7.AN.157.243; 7.AN.157.247; 7.AN.196.157;
7.AN.196.158; 7.AN.196.196; 7.AN.196.223; 7.AN.196.240; 7.AN.196.244;
7.AN.196.243; 7.AN.196.247; 7.AN.223.157; 7.AN.223.158; 7.AN.223.196;
7.AN.223.223; 7.AN.223.240; 7.AN.223.244; 7.AN.223.243; 7.AN.223.247;
7.AN.240.157; 7.AN.240.158; 7.AN.240.196; 7.AN.240.223; 7.AN.240.240;
7.AN.240.244; 7.AN.240.243; 7.AN.240.247; 7.AN.244.157; 7.AN.244.158;
7.AN.244.196; 7.AN.244.223; 7.AN.244.240; 7.AN.244.244; 7.AN.244.243;
7.AN.244.247; 7.AN.247.157; 7.AN.247.158; 7.AN.247.196; 7.AN.247.223;
7.AN.247.240; 7.AN.247.244; 7.AN.247.243; 7.AN.247.247;

Prodrugs of 7.AP

7.AP.4.157; 7.AP.4.158; 7.AP.4.196; 7.AP.4.223; 7.AP.4.240; 7.AP.4.244;
7.AP.4.243; 7.AP.4.247; 7.AP.5.157; 7.AP.5.158; 7.AP.5.196; 7.AP.5.223;
7.AP.5.240; 7.AP.5.244; 7.AP.5.243; 7.AP.5.247; 7.AP.7.157; 7.AP.7.158;
7.AP.7.196; 7.AP.7.223; 7.AP.7.240; 7.AP.7.244; 7.AP.7.243;
7.AP.7.247; 7.AP.15.157; 7.AP.15.158; 7.AP.15.196; 7.AP.15.223;
7.AP.15.240; 7.AP.15.244; 7.AP.15.243; 7.AP.15.247; 7.AP.16.157;
7.AP.16.158; 7.AP.16.196; 7.AP.16.223; 7.AP.16.240; 7.AP.16.244;
7.AP.16.243; 7.AP.16.247; 7.AP.18.157; 7.AP.18.158; 7.AP.18.196;
7.AP.18.223; 7.AP.18.240; 7.AP.18.244; 7.AP.18.243; 7.AP.18.247;
7.AP.26.157; 7.AP.26.158; 7.AP.26.196; 7.AP.26.223; 7.AP.26.240;
7.AP.26.244; 7.AP.26.243; 7.AP.26.247; 7.AP.27.157; 7.AP.27.158;
7.AP.27.196; 7.AP.27.223; 7.AP.27.240; 7.AP.27.244; 7.AP.27.243;
7.AP.27.247; 7.AP.29.157; 7.AP.29.158; 7.AP.29.196; 7.AP.29.223;
7.AP.29.240; 7.AP.29.244; 7.AP.29.243; 7.AP.29.247; 7.AP.54.157;
7.AP.54.158; 7.AP.54.196; 7.AP.54.223; 7.AP.54.240; 7.AP.54.244;
7.AP.54.243; 7.AP.54.247; 7.AP.55.157; 7.AP.55.158; 7.AP.55.196;
7.AP.55.223; 7.AP.55.240; 7.AP.55.244; 7.AP.55.243; 7.AP.55.247;
7.AP.56.157; 7.AP.56.158; 7.AP.56.196; 7.AP.56.223; 7.AP.56.240;
7.AP.56.244; 7.AP.56.243; 7.AP.56.247; 7.AP.157.157; 7.AP.157.158;
7.AP.157.196; 7.AP.157.223; 7.AP.157.240; 7.AP.157.244; 7.AP.157.243;
7.AP.157.247; 7.AP.196.157; 7.AP.196.158; 7.AP.196.196; 7.AP.196.223;
7.AP.196.240; 7.AP.196.244; 7.AP.196.243; 7.AP.196.247; 7.AP.223.157;
7.AP.223.158; 7.AP.223.196; 7.AP.223.223; 7.AP.223.240; 7.AP.223.244;
7.AP.223.243; 7.AP.223.247; 7.AP.240.157; 7.AP.240.158; 7.AP.240.196;
7.AP.240.223; 7.AP.240.240; 7.AP.240.244; 7.AP.240.243; 7.AP.240.247;
7.AP.244.157; 7.AP.244.158; 7.AP.244.196; 7.AP.244.223; 7.AP.244.240;

TABLE 7-continued

7.AP.244.244; 7.AP.244.243; 7.AP.244.247; 7.AP.247.157; 7.AP.247.158; 7.AP.247.196; 7.AP.247.223; 7.AP.247.240; 7.AP.247.244; 7.AP.247.243; 7.AP.247.247;

Prodrugs of 7.AZ

7.AZ.4.157; 7.AZ.4.158; 7.AZ.4.196; 7.AZ.4.223; 7.AZ.4.240; 7.AZ.4.244; 7.AZ.4.243; 7.AZ.4.247; 7.AZ.5.157; 7.AZ.5.158; 7.AZ.5.196; 7.AZ.5.223; 7.AZ.5.240; 7.AZ.5.244; 7.AZ.5.243; 7.AZ.5.247; 7.AZ.7.157; 7.AZ.7.158; 7.AZ.7.196; 7.AZ.7.223; 7.AZ.7.240; 7.AZ.7.244; 7.AZ.7.243; 7.AZ.7.247; 7.AZ.15.157; 7.AZ.15.158; 7.AZ.15.196; 7.AZ.15.223; 7.AZ.15.240; 7.AZ.15.244; 7.AZ.15.243; 7.AZ.15.247; 7.AZ.16.157; 7.AZ.16.158; 7.AZ.16.196; 7.AZ.16.223; 7.AZ.16.240; 7.AZ.16.244; 7.AZ.16.243; 7.AZ.16.247; 7.AZ.18.157; 7.AZ.18.158; 7.AZ.18.196; 7.AZ.18.223; 7.AZ.18.240; 7.AZ.18.244; 7.AZ.18.243; 7.AZ.18.247; 7.AZ.26.157; 7.AZ.26.158; 7.AZ.26.196; 7.AZ.26.223; 7.AZ.26.240; 7.AZ.26.244; 7.AZ.26.243; 7.AZ.26.247; 7.AZ.27.157; 7.AZ.27.158; 7.AZ.27.196; 7.AZ.27.223; 7.AZ.27.240; 7.AZ.27.244; 7.AZ.27.243; 7.AZ.27.247; 7.AZ.29.157; 7.AZ.29.158; 7.AZ.29.196; 7.AZ.29.223; 7.AZ.29.240; 7.AZ.29.244; 7.AZ.29.243; 7.AZ.29.247; 7.AZ.54.157; 7.AZ.54.158; 7.AZ.54.196; 7.AZ.54.223; 7.AZ.54.240; 7.AZ.54.244; 7.AZ.54.243; 7.AZ.54.247; 7.AZ.55.157; 7.AZ.55.158; 7.AZ.55.196; 7.AZ.55.223; 7.AZ.55.240; 7.AZ.55.244; 7.AZ.55.243; 7.AZ.55.247; 7.AZ.56.157; 7.AZ.56.158; 7.AZ.56.196; 7.AZ.56.223; 7.AZ.56.240; 7.AZ.56.244; 7.AZ.56.243; 7.AZ.56.247; 7.AZ.157.157; 7.AZ.157.158; 7.AZ.157.196; 7.AZ.157.223; 7.AZ.157.240; 7.AZ.157.244; 7.AZ.157.243; 7.AZ.157.247; 7.AZ.196.157; 7.AZ.196.158; 7.AZ.196.196; 7.AZ.196.223; 7.AZ.196.240; 7.AZ.196.244; 7.AZ.196.243; 7.AZ.196.247; 7.AZ.223.157; 7.AZ.223.158; 7.AZ.223.196; 7.AZ.223.223; 7.AZ.223.240; 7.AZ.223.244; 7.AZ.223.243; 7.AZ.223.247; 7.AZ.240.157; 7.AZ.240.158; 7.AZ.240.196; 7.AZ.240.223; 7.AZ.240.240; 7.AZ.240.244; 7.AZ.240.243; 7.AZ.240.247; 7.AZ.244.157; 7.AZ.244.158; 7.AZ.244.196; 7.AZ.244.223; 7.AZ.244.240; 7.AZ.244.244; 7.AZ.244.243; 7.AZ.244.247; 7.AZ.247.157; 7.AZ.247.158; 7.AZ.247.196; 7.AZ.247.223; 7.AZ.247.240; 7.AZ.247.244; 7.AZ.247.243; 7.AZ.247.247;

Prodrugs of 7.BF

7.BF.4.157; 7.BF.4.158; 7.BF.4.196; 7.BF.4.223; 7.BF.4.240; 7.BF.4.244; 7.BF.4.243; 7.BF.4.247; 7.BF.5.157; 7.BF.5.158; 7.BF.5.196; 7.BF.5.223; 7.BF.5.240; 7.BF.5.244; 7.BF.5.243; 7.BF.5.247; 7.BF.7.157; 7.BF.7.158; 7.BF.7.196; 7.BF.7.223; 7.BF.7.240; 7.BF.7.244; 7.BF.7.243; 7.BF.7.247; 7.BF.15.157; 7.BF.15.158; 7.BF.15.196; 7.BF.15.223; 7.BF.15.240; 7.BF.15.244; 7.BF.15.243; 7.BF.15.247; 7.BF.16.157; 7.BF.16.158; 7.BF.16.196; 7.BF.16.223; 7.BF.16.240; 7.BF.16.244; 7.BF.16.243; 7.BF.16.247; 7.BF.18.157; 7.BF.18.158; 7.BF.18.196; 7.BF.18.223; 7.BF.18.240; 7.BF.18.244; 7.BF.18.243; 7.BF.18.247; 7.BF.26.157; 7.BF.26.158; 7.BF.26.196; 7.BF.26.223; 7.BF.26.240; 7.BF.26.244; 7.BF.26.243; 7.BF.26.247; 7.BF.27.157; 7.BF.27.158; 7.BF.27.196; 7.BF.27.223; 7.BF.27.240; 7.BF.27.244; 7.BF.27.243; 7.BF.27.247; 7.BF.29.157; 7.BF.29.158; 7.BF.29.196; 7.BF.29.223; 7.BF.29.240; 7.BF.29.244; 7.BF.29.243; 7.BF.29.247; 7.BF.54.157; 7.BF.54.158; 7.BF.54.196; 7.BF.54.223; 7.BF.54.240; 7.BF.54.244; 7.BF.54.243; 7.BF.54.247; 7.BF.55.157; 7.BF.55.158; 7.BF.55.196; 7.BF.55.223; 7.BF.55.240; 7.BF.55.244; 7.BF.55.243; 7.BF.55.247; 7.BF.56.157; 7.BF.56.158; 7.BF.56.196; 7.BF.56.223; 7.BF.56.240; 7.BF.56.244; 7.BF.56.243; 7.BF.56.247; 7.BF.157.157; 7.BF.157.158; 7.BF.157.196; 7.BF.157.223; 7.BF.157.240; 7.BF.157.244; 7.BF.157.243; 7.BF.157.247; 7.BF.196.157; 7.BF.196.158; 7.BF.196.196; 7.BF.196.223; 7.BF.196.240; 7.BF.196.244; 7.BF.196.243; 7.BF.196.247; 7.BF.223.157; 7.BF.223.158; 7.BF.223.196; 7.BF.223.223; 7.BF.223.240; 7.BF.223.244; 7.BF.223.243; 7.BF.223.247; 7.BF.240.157; 7.BF.240.158; 7.BF.240.196; 7.BF.240.223; 7.BF.240.240; 7.BF.240.244; 7.BF.240.243; 7.BF.240.247; 7.BF.244.157; 7.BF.244.158; 7.BF.244.196; 7.BF.244.223; 7.BF.244.240; 7.BF.244.244; 7.BF.244.243; 7.BF.244.247; 7.BF.247.157; 7.BF.247.158; 7.BF.247.196; 7.BF.247.223; 7.BF.247.240; 7.BF.247.244; 7.BF.247.243; 7.BF.247.247;

Prodrugs of 7.CI

7.CI.4.157; 7.CI.4.158; 7.CI.4.196; 7.CI.4.223; 7.CI.4.240; 7.CI.4.244; 7.CI.4.243; 7.CI.4.247; 7.CI.5.157; 7.CI.5.158; 7.CI.5.196; 7.CI.5.223; 7.CI.5.240; 7.CI.5.244; 7.CI.5.243; 7.CI.5.247; 7.CI.7.157; 7.CI.7.158; 7.CI.7.196; 7.CI.7.223; 7.CI.7.240; 7.CI.7.244; 7.CI.7.243; 7.CI.7.247; 7.CI.15.157; 7.CI.15.158; 7.CI.15.196; 7.CI.15.223; 7.CI.15.240; 7.CI.15.244; 7.CI.15.243; 7.CI.15.247; 7.CI.16.157; 7.CI.16.158; 7.CI.16.196; 7.CI.16.223; 7.CI.16.240; 7.CI.16.244; 7.CI.16.243; 7.CI.16.247; 7.CI.18.157; 7.CI.18.158; 7.CI.18.196; 7.CI.18.223; 7.CI.18.240; 7.CI.18.244; 7.CI.18.243; 7.CI.18.247; 7.CI.26.157; 7.CI.26.158; 7.CI.26.196; 7.CI.26.223; 7.CI.26.240; 7.CI.26.244; 7.CI.26.243; 7.CI.26.247; 7.CI.27.157; 7.CI.27.158; 7.CI.27.196; 7.CI.27.223; 7.CI.27.240; 7.CI.27.244; 7.CI.27.243; 7.CI.27.247; 7.CI.29.157; 7.CI.29.158; 7.CI.29.196; 7.CI.29.223; 7.CI.29.240; 7.CI.29.244; 7.CI.29.243; 7.CI.29.247; 7.CI.54.157; 7.CI.54.158; 7.CI.54.196; 7.CI.54.223; 7.CI.54.240; 7.CI.54.244; 7.CI.54.243; 7.CI.54.247; 7.CI.55.157; 7.CI.55.158; 7.CI.55.196; 7.CI.55.223; 7.CI.55.240; 7.CI.55.244; 7.CI.55.243; 7.CI.55.247; 7.CI.56.157; 7.CI.56.158; 7.CI.56.196; 7.CI.56.223; 7.CI.56.240; 7.CI.56.244; 7.CI.56.243; 7.CI.56.247; 7.CI.157.157; 7.CI.157.158; 7.CI.157.196; 7.CI.157.223; 7.CI.157.240; 7.CI.157.244; 7.CI.157.243; 7.CI.157.247; 7.CI.196.157; 7.CI.196.158; 7.CI.196.196; 7.CI.196.223; 7.CI.196.240; 7.CI.196.244; 7.CI.196.243; 7.CI.196.247; 7.CI.223.157; 7.CI.223.158; 7.CI.223.196; 7.CI.223.223; 7.CI.223.240; 7.CI.223.244; 7.CI.223.243; 7.CI.223.247; 7.CI.240.157; 7.CI.240.158; 7.CI.240.196; 7.CI.240.223; 7.CI.240.240; 7.CI.240.244; 7.CI.240.243; 7.CI.240.247; 7.CI.244.157; 7.CI.244.158; 7.CI.244.196; 7.CI.244.223; 7.CI.244.240; 7.CI.244.244; 7.CI.244.243; 7.CI.244.247; 7.CI.247.157; 7.CI.247.158; 7.CI.247.196; 7.CI.247.223; 7.CI.247.240; 7.CI.247.244; 7.CI.247.243; 7.CI.247.247;

Prodrugs of 7.CO

7.CO.4.157; 7.CO.4.158; 7.CO.4.196; 7.CO.4.223; 7.CO.4.240; 7.CO.4.244; 7.CO.4.243; 7.CO.4.247; 7.CO.5.157; 7.CO.5.158; 7.CO.5.196; 7.CO.5.223; 7.CO.5.240; 7.CO.5.244; 7.CO.5.243; 7.CO.5.247; 7.CO.7.157; 7.CO.7.158; 7.CO.7.196; 7.CO.7.223; 7.CO.7.240; 7.CO.7.244; 7.CO.7.243; 7.CO.7.247; 7.CO.15.157; 7.CO.15.158; 7.CO.15.196; 7.CO.15.223; 7.CO.15.240; 7.CO.15.244; 7.CO.15.243; 7.CO.15.247; 7.CO.16.157; 7.CO.16.158; 7.CO.16.196; 7.CO.16.223; 7.CO.16.240; 7.CO.16.244; 7.CO.16.243; 7.CO.16.247; 7.CO.18.157; 7.CO.18.158; 7.CO.18.196; 7.CO.18.223; 7.CO.18.240; 7.CO.18.244; 7.CO.18.243; 7.CO.18.247; 7.CO.26.157; 7.CO.26.158; 7.CO.26.196; 7.CO.26.223; 7.CO.26.240; 7.CO.26.244; 7.CO.26.243; 7.CO.26.247; 7.CO.27.157; 7.CO.27.158; 7.CO.27.196; 7.CO.27.223; 7.CO.27.240; 7.CO.27.244; 7.CO.27.243; 7.CO.27.247; 7.CO.29.157; 7.CO.29.158; 7.CO.29.196; 7.CO.29.223; 7.CO.29.240; 7.CO.29.244; 7.CO.29.243; 7.CO.29.247; 7.CO.54.157; 7.CO.54.158; 7.CO.54.196; 7.CO.54.223; 7.CO.54.240; 7.CO.54.244; 7.CO.54.243; 7.CO.54.247; 7.CO.55.157; 7.CO.55.158; 7.CO.55.196; 7.CO.55.223; 7.CO.55.240; 7.CO.55.244; 7.CO.55.243; 7.CO.55.247; 7.CO.56.157; 7.CO.56.158; 7.CO.56.196; 7.CO.56.223; 7.CO.56.240; 7.CO.56.244; 7.CO.56.243; 7.CO.56.247; 7.CO.157.157; 7.CO.157.158; 7.CO.157.196; 7.CO.157.223; 7.CO.157.240; 7.CO.157.244; 7.CO.157.243; 7.CO.157.247; 7.CO.196.157; 7.CO.196.158; 7.CO.196.196; 7.CO.196.223; 7.CO.196.240; 7.CO.196.244; 7.CO.196.243; 7.CO.196.247; 7.CO.223.157; 7.CO.223.158; 7.CO.223.196; 7.CO.223.223; 7.CO.223.240; 7.CO.223.244; 7.CO.223.243; 7.CO.223.247; 7.CO.240.157; 7.CO.240.158; 7.CO.240.196; 7.CO.240.223; 7.CO.240.240; 7.CO.240.244; 7.CO.240.243; 7.CO.240.247; 7.CO.244.157; 7.CO.244.158; 7.CO.244.196; 7.CO.244.223; 7.CO.244.240; 7.CO.244.244; 7.CO.244.243; 7.CO.244.247; 7.CO.4.157; 7.CO.4.158; 7.CO.4.196; 7.CO.4.223; 7.CO.4.240; 7.CO.4.244; 7.CO.4.243; 7.CO.4.247;

Prodrugs of 8.AH

8.AH.4.157; 8.AH.4.158; 8.AH.4.196; 8.AH.4.223; 8.AH.4.240; 8.AH.4.244; 8.AH.4.243; 8.AH.4.247; 8.AH.5.157; 8.AH.5.158; 8.AH.5.196; 8.AH.5.223; 8.AH.5.240; 8.AH.5.244; 8.AH.5.243; 8.AH.5.247; 8.AH.7.157; 8.AH.7.158; 8.AH.7.196; 8.AH.7.223; 8.AH.7.240; 8.AH.7.244; 8.AH.7.243; 8.AH.7.247; 8.AH.15.157; 8.AH.15.158; 8.AH.15.196; 8.AH.15.223; 8.AH.15.240; 8.AH.15.244; 8.AH.15.243; 8.AH.15.247; 8.AH.16.157; 8.AH.16.158; 8.AH.16.196; 8.AH.16.223; 8.AH.16.240; 8.AH.16.244; 8.AH.16.243; 8.AH.16.247; 8.AH.18.157; 8.AH.18.158; 8.AH.18.196; 8.AH.18.223; 8.AH.18.240; 8.AH.18.244; 8.AH.18.243; 8.AH.18.247; 8.AH.26.157; 8.AH.26.158; 8.AH.26.196; 8.AH.26.223; 8.AH.26.240; 8.AH.26.244; 8.AH.26.243; 8.AH.26.247; 8.AH.27.157; 8.AH.27.158; 8.AH.27.196; 8.AH.27.223; 8.AH.27.240; 8.AH.27.244; 8.AH.27.243; 8.AH.27.247; 8.AH.29.157; 8.AH.29.158; 8.AH.29.196; 8.AH.29.223; 8.AH.29.240; 8.AH.29.244; 8.AH.29.243; 8.AH.29.247; 8.AH.54.157; 8.AH.54.158; 8.AH.54.196; 8.AH.54.223; 8.AH.54.240; 8.AH.54.244; 8.AH.54.243; 8.AH.54.247; 8.AH.55.157; 8.AH.55.158; 8.AH.55.196; 8.AH.55.223; 8.AH.55.240; 8.AH.55.244; 8.AH.55.243; 8.AH.55.247; 8.AH.56.157; 8.AH.56.158; 8.AH.56.196; 8.AH.56.223; 8.AH.56.240; 8.AH.56.244; 8.AH.56.243; 8.AH.56.247; 8.AH.157.157; 8.AH.157.158; 8.AH.157.196; 8.AH.157.223; 8.AH.157.240; 8.AH.157.244; 8.AH.157.243; 8.AH.157.247; 8.AH.196.157; 8.AH.196.158; 8.AH.196.196; 8.AH.196.223; 8.AH.196.240; 8.AH.196.244; 8.AH.196.243; 8.AH.196.247; 8.AH.223.157; 8.AH.223.158; 8.AH.223.196; 8.AH.223.223; 8.AH.223.240; 8.AH.223.244; 8.AH.223.243; 8.AH.223.247; 8.AH.240.157; 8.AH.240.158; 8.AH.240.196; 8.AH.240.223; 8.AH.240.240; 8.AH.240.244; 8.AH.240.243; 8.AH.240.247; 8.AH.244.157; 8.AH.244.158; 8.AH.244.196; 8.AH.244.223; 8.AH.244.240; 8.AH.244.244; 8.AH.244.243; 8.AH.244.247; 8.AH.247.157; 8.AH.247.158; 8.AH.247.196; 8.AH.247.223; 8.AH.247.240; 8.AH.247.244; 8.AH.247.243; 8.AH.247.247;

TABLE 7-continued

Prodrugs of 8.AJ

8.AJ.4.157; 8.AJ.4.158; 8.AJ.4.196; 8.AJ.4.223; 8.AJ.4.240; 8.AJ.4.244; 8.AJ.4.243; 8.AJ.4.247; 8.AJ.5.157; 8.AJ.5.158; 8.AJ.5.196; 8.AJ.5.223; 8.AJ.5.240; 8.AJ.5.244; 8.AJ.5.243; 8.AJ.5.247; 8.AJ.7.157; 8.AJ.7.158; 8.AJ.7.196; 8.AJ.7.223; 8.AJ.7.240; 8.AJ.7.244; 8.AJ.7.243; 8.AJ.7.247; 8.AJ.15.157; 8.AJ.15.158; 8.AJ.15.196; 8.AJ.15.223; 8.AJ.15.240; 8.AJ.15.244; 8.AJ.15.243; 8.AJ.15.247; 8.AJ.16.157; 8.AJ.16.158; 8.AJ.16.196; 8.AJ.16.223; 8.AJ.16.240; 8.AJ.16.244; 8.AJ.16.243; 8.AJ.16.247; 8.AJ.18.157; 8.AJ.18.158; 8.AJ.18.196; 8.AJ.18.223; 8.AJ.18.240; 8.AJ.18.244; 8.AJ.18.243; 8.AJ.18.247; 8.AJ.26.157; 8.AJ.26.158; 8.AJ.26.196; 8.AJ.26.223; 8.AJ.26.240; 8.AJ.26.244; 8.AJ.26.243; 8.AJ.26.247; 8.AJ.27.157; 8.AJ.27.158; 8.AJ.27.196; 8.AJ.27.223; 8.AJ.27.240; 8.AJ.27.244; 8.AJ.27.243; 8.AJ.27.247; 8.AJ.29.157; 8.AJ.29.158; 8.AJ.29.196; 8.AJ.29.223; 8.AJ.29.240; 8.AJ.29.244; 8.AJ.29.243; 8.AJ.29.247; 8.AJ.54.157; 8.AJ.54.158; 8.AJ.54.196; 8.AJ.54.223; 8.AJ.54.240; 8.AJ.54.244; 8.AJ.54.243; 8.AJ.54.247; 8.AJ.55.157; 8.AJ.55.158; 8.AJ.55.196; 8.AJ.55.223; 8.AJ.55.240; 8.AJ.55.244; 8.AJ.55.243; 8.AJ.55.247; 8.AJ.56.157; 8.AJ.56.158; 8.AJ.56.196; 8.AJ.56.223; 8.AJ.56.240; 8.AJ.56.244; 8.AJ.56.243; 8.AJ.56.247; 8.AJ.157.157; 8.AJ.157.158; 8.AJ.157.196; 8.AJ.157.223; 8.AJ.157.240; 8.AJ.157.244; 8.AJ.157.243; 8.AJ.157.247; 8.AJ.196.157; 8.AJ.196.158; 8.AJ.196.196; 8.AJ.196.223; 8.AJ.196.240; 8.AJ.196.244; 8.AJ.196.243; 8.AJ.196.247; 8.AJ.223.157; 8.AJ.223.158; 8.AJ.223.196; 8.AJ.223.223; 8.AJ.223.240; 8.AJ.223.244; 8.AJ.223.243; 8.AJ.223.247; 8.AJ.240.157; 8.AJ.240.158; 8.AJ.240.196; 8.AJ.240.223; 8.AJ.240.240; 8.AJ.240.244; 8.AJ.240.243; 8.AJ.240.247; 8.AJ.244.157; 8.AJ.244.158; 8.AJ.244.196; 8.AJ.244.223; 8.AJ.244.240; 8.AJ.244.244; 8.AJ.244.243; 8.AJ.244.247; 8.AJ.247.157; 8.AJ.247.158; 8.AJ.247.196; 8.AJ.247.223; 8.AJ.247.240; 8.AJ.247.244; 8.AJ.247.243; 8.AJ.247.247;

Prodrugs of 8.AN

8.AN.4.157; 8.AN.4.158; 8.AN.4.196; 8.AN.4.223; 8.AN.4.240; 8.AN.4.244; 8.AN.4.243; 8.AN.4.247; 8.AN.5.157; 8.AN.5.158; 8.AN.5.196; 8.AN.5.223; 8.AN.5.240; 8.AN.5.244; 8.AN.5.243; 8.AN.5.247; 8.AN.7.157; 8.AN.7.158; 8.AN.7.196; 8.AN.7.223; 8.AN.7.240; 8.AN.7.244; 8.AN.7.243; 8.AN.7.247; 8.AN.15.157; 8.AN.15.158; 8.AN.15.196; 8.AN.15.223; 8.AN.15.240; 8.AN.15.244; 8.AN.15.243; 8.AN.15.247; 8.AN.16.157; 8.AN.16.158; 8.AN.16.196; 8.AN.16.223; 8.AN.16.240; 8.AN.16.244; 8.AN.16.243; 8.AN.16.247; 8.AN.18.157; 8.AN.18.158; 8.AN.18.196; 8.AN.18.223; 8.AN.18.240; 8.AN.18.244; 8.AN.18.243; 8.AN.18.247; 8.AN.26.157; 8.AN.26.158; 8.AN.26.196; 8.AN.26.223; 8.AN.26.240; 8.AN.26.244; 8.AN.26.243; 8.AN.26.247; 8.AN.27.157; 8.AN.27.158; 8.AN.27.196; 8.AN.27.223; 8.AN.27.240; 8.AN.27.244; 8.AN.27.243; 8.AN.27.247; 8.AN.29.157; 8.AN.29.158; 8.AN.29.196; 8.AN.29.223; 8.AN.29.240; 8.AN.29.244; 8.AN.29.243; 8.AN.29.247; 8.AN.54.157; 8.AN.54.158; 8.AN.54.196; 8.AN.54.223; 8.AN.54.240; 8.AN.54.244; 8.AN.54.243; 8.AN.54.247; 8.AN.55.157; 8.AN.55.158; 8.AN.55.196; 8.AN.55.223; 8.AN.55.240; 8.AN.55.244; 8.AN.55.243; 8.AN.55.247; 8.AN.56.157; 8.AN.56.158; 8.AN.56.196; 8.AN.56.223; 8.AN.56.240; 8.AN.56.244; 8.AN.56.243; 8.AN.56.247; 8.AN.157.157; 8.AN.157.158; 8.AN.157.196; 8.AN.157.223; 8.AN.157.240; 8.AN.157.244; 8.AN.157.243; 8.AN.157.247; 8.AN.196.157; 8.AN.196.158; 8.AN.196.196; 8.AN.196.223; 8.AN.196.240; 8.AN.196.244; 8.AN.196.243; 8.AN.196.247; 8.AN.223.157; 8.AN.223.158; 8.AN.223.196; 8.AN.223.223; 8.AN.223.240; 8.AN.223.244; 8.AN.223.243; 8.AN.223.247; 8.AN.240.157; 8.AN.240.158; 8.AN.240.196; 8.AN.240.223; 8.AN.240.240; 8.AN.240.244; 8.AN.240.243; 8.AN.240.247; 8.AN.244.157; 8.AN.244.158; 8.AN.244.196; 8.AN.244.223; 8.AN.244.240; 8.AN.244.244; 8.AN.244.243; 8.AN.244.247; 8.AN.247.157; 8.AN.247.158; 8.AN.247.196; 8.AN.247.223; 8.AN.247.240; 8.AN.247.243; 8.AN.247.247;

Prodrugs of 8.AP

8.AP.4.157; 8.AP.4.158; 8.AP.4.196; 8.AP.4.223; 8.AP.4.240; 8.AP.4.244; 8.AP.4.243; 8.AP.4.247; 8.AP.5.157; 8.AP.5.158; 8.AP.5.196; 8.AP.5.223; 8.AP.5.240; 8.AP.5.244; 8.AP.5.243; 8.AP.5.247; 8.AP.7.157; 8.AP.7.158; 8.AP.7.196; 8.AP.7.223; 8.AP.7.240; 8.AP.7.244; 8.AP.7.243; 8.AP.7.247; 8.AP.15.157; 8.AP.15.158; 8.AP.15.196; 8.AP.15.223; 8.AP.15.240; 8.AP.15.244; 8.AP.15.243; 8.AP.15.247; 8.AP.16.157; 8.AP.16.158; 8.AP.16.196; 8.AP.16.223; 8.AP.16.240; 8.AP.16.244; 8.AP.16.243; 8.AP.16.247; 8.AP.18.157; 8.AP.18.158; 8.AP.18.196; 8.AP.18.223; 8.AP.18.240; 8.AP.18.244; 8.AP.18.243; 8.AP.18.247; 8.AP.26.157; 8.AP.26.158; 8.AP.26.196; 8.AP.26.223; 8.AP.26.240; 8.AP.26.244; 8.AP.26.243; 8.AP.26.247; 8.AP.27.157; 8.AP.27.158; 8.AP.27.196; 8.AP.27.223; 8.AP.27.240; 8.AP.27.244; 8.AP.27.243; 8.AP.27.247; 8.AP.29.157; 8.AP.29.158; 8.AP.29.196; 8.AP.29.223; 8.AP.29.240; 8.AP.29.244; 8.AP.29.243; 8.AP.29.247; 8.AP.54.157; 8.AP.54.158; 8.AP.54.196; 8.AP.54.223; 8.AP.54.240; 8.AP.54.244; 8.AP.54.243; 8.AP.54.247; 8.AP.55.157; 8.AP.55.158; 8.AP.55.196; 8.AP.55.223; 8.AP.55.240; 8.AP.55.244; 8.AP.55.243; 8.AP.55.247; 8.AP.56.157; 8.AP.56.158; 8.AP.56.196; 8.AP.56.223; 8.AP.56.240; 8.AP.56.244; 8.AP.56.243; 8.AP.56.247; 8.AP.157.157; 8.AP.157.158; 8.AP.157.196; 8.AP.157.223; 8.AP.157.240; 8.AP.157.244; 8.AP.157.243; 8.AP.157.247; 8.AP.196.157; 8.AP.196.158; 8.AP.196.196; 8.AP.196.223; 8.AP.196.240; 8.AP.196.244; 8.AP.196.243; 8.AP.196.247; 8.AP.223.157; 8.AP.223.158; 8.AP.223.196; 8.AP.223.223; 8.AP.223.240; 8.AP.223.244; 8.AP.223.243; 8.AP.223.247; 8.AP.240.157; 8.AP.240.158; 8.AP.240.196; 8.AP.240.223; 8.AP.240.240; 8.AP.240.244; 8.AP.240.243; 8.AP.240.247; 8.AP.244.157; 8.AP.244.158; 8.AP.244.196; 8.AP.244.223; 8.AP.244.240; 8.AP.244.244; 8.AP.244.243; 8.AP.244.247; 8.AP.247.157; 8.AP.247.158; 8.AP.247.196; 8.AP.247.223; 8.AP.247.240; 8.AP.247.244; 8.AP.247.243; 8.AP.247.247;

Prodrugs of 8.AZ

8.AZ.4.157; 8.AZ.4.158; 8.AZ.4.196; 8.AZ.4.223; 8.AZ.4.240; 8.AZ.4.244; 8.AZ.4.243; 8.AZ.4.247; 8.AZ.5.157; 8.AZ.5.158; 8.AZ.5.196; 8.AZ.5.223; 8.AZ.5.240; 8.AZ.5.244; 8.AZ.5.243; 8.AZ.5.247; 8.AZ.7.157; 8.AZ.7.158; 8.AZ.7.196; 8.AZ.7.223; 8.AZ.7.240; 8.AZ.7.244; 8.AZ.7.243; 8.AZ.7.247; 8.AZ.15.157; 8.AZ.15.158; 8.AZ.15.196; 8.AZ.15.223; 8.AZ.15.240; 8.AZ.15.244; 8.AZ.15.243; 8.AZ.15.247; 8.AZ.16.157; 8.AZ.16.158; 8.AZ.16.196; 8.AZ.16.223; 8.AZ.16.240; 8.AZ.16.244; 8.AZ.16.243; 8.AZ.16.247; 8.AZ.18.157; 8.AZ.18.158; 8.AZ.18.196; 8.AZ.18.223; 8.AZ.18.240; 8.AZ.18.244; 8.AZ.18.243; 8.AZ.18.247; 8.AZ.26.157; 8.AZ.26.158; 8.AZ.26.196; 8.AZ.26.223; 8.AZ.26.240; 8.AZ.26.244; 8.AZ.26.243; 8.AZ.26.247; 8.AZ.27.157; 8.AZ.27.158; 8.AZ.27.196; 8.AZ.27.223; 8.AZ.27.240; 8.AZ.27.244; 8.AZ.27.243; 8.AZ.27.247; 8.AZ.29.157; 8.AZ.29.158; 8.AZ.29.196; 8.AZ.29.223; 8.AZ.29.240; 8.AZ.29.244; 8.AZ.29.243; 8.AZ.29.247; 8.AZ.54.157; 8.AZ.54.158; 8.AZ.54.196; 8.AZ.54.223; 8.AZ.54.240; 8.AZ.54.244; 8.AZ.54.243; 8.AZ.54.247; 8.AZ.55.157; 8.AZ.55.158; 8.AZ.55.196; 8.AZ.55.223; 8.AZ.55.240; 8.AZ.55.244; 8.AZ.55.243; 8.AZ.55.247; 8.AZ.56.157; 8.AZ.56.158; 8.AZ.56.196; 8.AZ.56.223; 8.AZ.56.240; 8.AZ.56.244; 8.AZ.56.243; 8.AZ.56.247; 8.AZ.157.157; 8.AZ.157.158; 8.AZ.157.196; 8.AZ.157.223; 8.AZ.157.240; 8.AZ.157.244; 8.AZ.157.243; 8.AZ.157.247; 8.AZ.196.157; 8.AZ.196.158; 8.AZ.196.196; 8.AZ.196.223; 8.AZ.196.240; 8.AZ.196.244; 8.AZ.196.243; 8.AZ.196.247; 8.AZ.223.157; 8.AZ.223.158; 8.AZ.223.196; 8.AZ.223.223; 8.AZ.223.240; 8.AZ.223.244; 8.AZ.223.243; 8.AZ.223.247; 8.AZ.240.157; 8.AZ.240.158; 8.AZ.240.196; 8.AZ.240.223; 8.AZ.240.240; 8.AZ.240.244; 8.AZ.240.243; 8.AZ.240.247; 8.AZ.244.157; 8.AZ.244.158; 8.AZ.244.196; 8.AZ.244.223; 8.AZ.244.240; 8.AZ.244.244; 8.AZ.244.243; 8.AZ.244.247; 8.AZ.247.157; 8.AZ.247.158; 8.AZ.247.196; 8.AZ.247.223; 8.AZ.247.240; 8.AZ.247.244; 8.AZ.247.243; 8.AZ.247.247;

Prodrugs of 8.BF

8.BF.4.157; 8.BF.4.158; 8.BF.4.196; 8.BF.4.223; 8.BF.4.240; 8.BF.4.244; 8.BF.4.243; 8.BF.4.247; 8.BF.5.157; 8.BF.5.158; 8.BF.5.196; 8.BF.5.223; 8.BF.5.240; 8.BF.5.244; 8.BF.5.243; 8.BF.5.247; 8.BF.7.157; 8.BF.7.158; 8.BF.7.196; 8.BF.7.223; 8.BF.7.240; 8.BF.7.244; 8.BF.7.243; 8.BF.7.247; 8.BF.15.157; 8.BF.15.158; 8.BF.15.196; 8.BF.15.223; 8.BF.15.240; 8.BF.15.244; 8.BF.15.243; 8.BF.15.247; 8.BF.16.157; 8.BF.16.158; 8.BF.16.196; 8.BF.16.223; 8.BF.16.240; 8.BF.16.244; 8.BF.16.243; 8.BF.16.247; 8.BF.18.157; 8.BF.18.158; 8.BF.18.196; 8.BF.18.223; 8.BF.18.240; 8.BF.18.244; 8.BF.18.243; 8.BF.18.247; 8.BF.26.157; 8.BF.26.158; 8.BF.26.196; 8.BF.26.223; 8.BF.26.240; 8.BF.26.244; 8.BF.26.243; 8.BF.26.247; 8.BF.27.157; 8.BF.27.158; 8.BE.27.196; 8.BF.27.223; 8.BF.27.240; 8.BF.27.244; 8.BF.27.243; 8.BF.27.247; 8.BF.29.157; 8.BF.29.158; 8.BF.29.196; 8.BF.29.223; 8.BF.29.240; 8.BF.29.244; 8.BF.29.243; 8.BF.29.247; 8.BF.54.157; 8.BF.54.158; 8.BF.54.196; 8.BF.54.223; 8.BF.54.240; 8.BF.54.244; 8.BF.54.243; 8.BF.54.247; 8.BF.55.157; 8.BF.55.158; 8.BF.55.196; 8.BF.55.223; 8.BF.55.240; 8.BF.55.244; 8.BF.55.243; 8.BF.55.247; 8.BF.56.157; 8.BF.56.158; 8.BF.56.196; 8.BF.56.223; 8.BF.56.240; 8.BF.56.244; 8.BF.56.243; 8.BF.56.247; 8.BF.157.157; 8.BF.157.158; 8.BF.157.196; 8.BF.157.223; 8.BF.157.240; 8.BF.157.244; 8.BF.157.243; 8.BF.157.247; 8.BF.196.157; 8.BF.196.158; 8.BF.196.196; 8.BF.196.223; 8.BF.196.240; 8.BF.196.244; 8.BF.196.243; 8.BF.196.247; 8.BF.223.157; 8.BF.223.158; 8.BF.223.196; 8.BF.223.223; 8.BF.223.240; 8.BF.223.244; 8.BF.223.243; 8.BF.223.247; 8.BF.240.157; 8.BF.240.158; 8.BF.240.196; 8.BF.240.223; 8.BF.240.240; 8.BF.240.244; 8.BF.240.243; 8.BF.240.247; 8.BF.244.157; 8.BF.244.158; 8.BF.244.196; 8.BF.244.223; 8.BF.244.240; 8.BF.244.244; 8.BF.244.243; 8.BF.244.247; 8.BF.247.157; 8.BF.247.158; 8.BF.247.196;

TABLE 7-continued

8.BF.247.223; 8.BF.247.240; 8.BF.247.244; 8.BF.247.243; 8.BF.247.247;
Prodrugs of 8.CI 8.CI.4.157; 8.CI.4.158; 8.CI.4.196; 8.CI.4.223; 8.CI.4.240; 8.CI.4.244;
8.CI.4.243; 8.CI.4.247; 8.CI.5.157; 8.CI.5.158; 8.CI.5.196; 8.CI.5.223;
8.CI.5.240; 8.CI.5.244; 8.CI.5.243; 8.CI.5.247; 8.CI.7.157; 8.CI.7.158;
8.CI.7.196; 8.CI.7.223; 8.CI.7.240; 8.CI.7.244; 8.CI.7.243; 8.CI.7.247;
8.CI.15.157; 8.CI.15.158; 8.CI.15.196; 8.CI.15.223; 8.CI.15.240;
8.CI.15.244; 8.CI.15.243; 8.CI.15.247; 8.CI.16.157; 8.CI.16.158;
8.CI.16.196; 8.CI.16.223; 8.CI.16.240; 8.CI.16.244; 8.CI.16.243;
8.CI.16.247; 8.CI.18.157; 8.CI.18.158; 8.CI.18.196; 8.CI.18.223;
8.CI.18.240; 8.CI.18.244; 8.CI.18.243; 8.CI.18.247; 8.CI.26.157;
8.CI.26.158; 8.CI.26.196; 8.CI.26.223; 8.CI.26.240; 8.CI.26.244;
8.CI.26.243; 8.CI.26.247; 8.CI.27.157; 8.CI.27.158; 8.CI.27.196;
8.CI.27.223; 8.CI.27.240; 8.CI.27.244; 8.CI.27.243; 8.CI.27.247;
8.CI.29.157; 8.CI.29.158; 8.CI.29.196; 8.CI.29.223; 8.CI.29.240;
8.CI.29.244; 8.CI.29.243; 8.CI.29.247; 8.CI.54.157; 8.CI.54.158;
8.CI.54.196; 8.CI.54.223; 8.CI.54.240; 8.CI.54.244; 8.CI.54.243;
8.CI.54.247; 8.CI.55.157; 8.CI.55.158; 8.CI.55.196; 8.CI.55.223;
8.CI.55.240; 8.CI.55.244; 8.CI.55.243; 8.CI.55.247; 8.CI.56.157;
8.CI.56.158; 8.CI.56.196; 8.CI.56.223; 8.CI.56.240; 8.CI.56.244;
8.CI.56.243; 8.CI.56.247; 8.CI.157.157; 8.CI.157.158; 8.CI.157.196;
8.CI.157.223; 8.CI.157.240; 8.CI.157.244; 8.CI.157.243; 8.CI.157.247;
8.CI.196.157; 8.CI.196.158; 8.CI.196.196; 8.CI.196.223; 8.CI.196.240;
8.CI.196.244; 8.CI.196.243; 8.CI.196.247; 8.CI.223.157; 8.CI.223.158;
8.CI.223.196; 8.CI.223.223; 8.CI.223.240; 8.CI.223.244; 8.CI.223.243;
8.CI.223.247; 8.CI.240.157; 8.CI.240.158; 8.CI.240.196; 8.CI.240.223;
8.CI.240.240; 8.CI.240.244; 8.CI.240.243; 8.CI.240.247; 8.CI.244.157;
8.CI.244.158; 8.CI.244.196; 8.CI.244.223; 8.CI.244.240; 8.CI.244.244;
8.CI.244.243; 8.CI.244.247; 8.CI.247.157; 8.CI.247.158; 8.CI.247.196;
8.CI.247.223; 8.CI.247.240; 8.CI.247.244; 8.CI.247.243; 8.CI.247.247;
Prodrugs of 8.CO 8.CO.4.157; 8.CO.4.158; 8.CO.4.196; 8.CO.4.223; 8.CO.4.240;
8.CO.4.244; 8.CO.4.243; 8.CO.4.247; 8.CO.5.157; 8.CO.5.158;
8.CO.5.196; 8.CO.5.223; 8.CO.5.240; 8.CO.5.244; 8.CO.5.243;
8.CO.5.247; 8.CO.7.157; 8.CO.7.158; 8.CO.7.196; 8.CO.7.223;
8.CO.7.240; 8.CO.7.244; 8.CO.7.243; 8.CO.7.247; 8.CO.15.157;
8.CO.15.158; 8.CO.15.196; 8.CO.15.223; 8.CO.15.240; 8.CO.15.244;
8.CO.15.243; 8.CO.15.247; 8.CO.16.157; 8.CO.16.158; 8.CO.16.196;
8.CO.16.223; 8.CO.16.240; 8.CO.16.244; 8.CO.16.243; 8.CO.16.247;
8.CO.18.157; 8.CO.18.158; 8.CO.18.196; 8.CO.18.223; 8.CO.18.240;
8.CO.18.244; 8.CO.18.243; 8.CO.18.247; 8.CO.26.157; 8.CO.26.158;
8.CO.26.196; 8.CO.26.223; 8.CO.26.240; 8.CO.26.244; 8.CO.26.243;
8.CO.26.247; 8.CO.27.157; 8.CO.27.158; 8.CO.27.196; 8.CO.27.223;
8.CO.27.240; 8.CO.27.244; 8.CO.27.243; 8.CO.27.247; 8.CO.29.157;
8.CO.29.158; 8.CO.29.196; 8.CO.29.223; 8.CO.29.240; 8.CO.29.244;
8.CO.29.243; 8.CO.29.247; 8.CO.54.157; 8.CO.54.158; 8.CO.54.196;
8.CO.54.223; 8.CO.54.240; 8.CO.54.244; 8.CO.54.243; 8.CO.54.247;
8.CO.55.157; 8.CO.55.158; 8.CO.55.196; 8.CO.55.223; 8.CO.55.240;
8.CO.55.244; 8.CO.55.243; 8.CO.55.247; 8.CO.56.157; 8.CO.56.158;
8.CO.56.196; 8.CO.56.223; 8.CO.56.240; 8.CO.56.244; 8.CO.56.243;
8.CO.56.247; 8.CO.157.157; 8.CO.157.158; 8.CO.157.196;
8.CO.157.223; 8.CO.157.240; 8.CO.157.244; 8.CO.157.243;
8.CO.157.247; 8.CO.196.157; 8.CO.196.158; 8.CO.196.196;
8.CO.196.223; 8.CO.196.240; 8.CO.196.244; 8.CO.196.243;
8.CO.196.247; 8.CO.223.157; 8.CO.223.158; 8.CO.223.196;
8.CO.223.223; 8.CO.223.240; 8.CO.223.244; 8.CO.223.243;
8.CO.223.247; 8.CO.240.157; 8.CO.240.158; 8.CO.240.196;
8.CO.240.223; 8.CO.240.240; 8.CO.240.244; 8.CO.240.243;
8.CO.240.247; 8.CO.244.157; 8.CO.244.158; 8.CO.244.196;
8.CO.244.223; 8.CO.244.240; 8.CO.244.244; 8.CO.244.243;
8.CO.244.247; 8.CO.247.157; 8.CO.247.158; 8.CO.247.196;
8.CO.247.223; 8.CO.247.240; 8.CO.247.244; 8.CO.247.243;
8.CO.247.247;
Prodrugs of 9.AH 9.AH.4.157; 9.AH.4.158; 9.AH.4.196; 9.AH.4.223; 9.AH.4.240;
9.AH.4.244; 9.AH.4.243; 9.AH.4.247; 9.AH.5.157; 9.AH.5.158;
9.AH.5.196; 9.AH.5.223; 9.AH.5.240; 9.AH.5.244; 9.AH.5.243;
9.AH.5.247; 9.AH.7.157; 9.AH.7.158; 9.AH.7.196; 9.AH.7.223;
9.AH.7.240; 9.AH.7.244; 9.AH.7.243; 9.AH.7.247; 9.AH.15.157;
9.AH.15.158; 9.AH.15.196; 9.AH.15.223; 9.AH.15.240; 9.AH.15.244;
9.AH.15.243; 9.AH.15.247; 9.AH.16.157; 9.AH.16.158; 9.AH.16.196;
9.AH.16.223; 9.AH.16.240; 9.AH.16.244; 9.AH.16.243; 9.AH.16.247;
9.AH.18.157; 9.AH.18.158; 9.AH.18.196; 9.AH.18.223; 9.AH.18.240;
9.AH.18.244; 9.AH.18.243; 9.AH.18.247; 9.AH.26.157; 9.AH.26.158;
9.AH.26.196; 9.AH.26.223; 9.AH.26.240; 9.AH.26.244; 9.AH.26.243;
9.AH.26.247; 9.AH.27.157; 9.AH.27.158; 9.AH.27.196; 9.AH.27.223;
9.AH.27.240; 9.AH.27.244; 9.AH.27.243; 9.AH.27.247; 9.AH.29.157;
9.AH.29.158; 9.AH.29.196; 9.AH.29.223; 9.AH.29.240; 9.AH.29.244;
9.AH.29.243; 9.AH.29.247; 9.AH.54.157; 9.AH.54.158; 9.AH.54.196;
9.AH.54.223; 9.AH.54.240; 9.AH.54.244; 9.AH.54.243; 9.AH.54.247;
9.AH.55.157; 9.AH.55.158; 9.AH.55.196; 9.AH.55.223; 9.AH.55.240;
9.AH.55.244; 9.AH.55.243; 9.AH.55.247; 9.AH.56.157; 9.AH.56.158;
9.AH.56.196; 9.AH.56.223; 9.AH.56.240; 9.AH.56.244; 9.AH.56.243;
9.AH.56.247; 9.AH.157.157; 9.AH.157.158; 9.AH.157.196;
9.AH.157.223; 9.AH.157.240; 9.AH.157.244; 9.AH.157.243;
9.AH.157.247; 9.AH.196.157; 9.AH.196.158; 9.AH.196.196;
9.AH.196.223; 9.AH.196.240; 9.AH.196.244; 9.AH.196.243;
9.AH.196.247; 9.AH.223.157; 9.AH.223.158; 9.AH.223.196;
9.AH.223.223; 9.AH.223.240; 9.AH.223.244; 9.AH.223.243;
9.AH.223.247; 9.AH.240.157; 9.AH.240.158; 9.AH.240.196;
9.AH.240.223; 9.AH.240.240; 9.AH.240.244; 9.AH.240.243;
9.AH.240.247; 9.AH.244.157; 9.AH.244.158; 9.AH.244.196;
9.AH.244.223; 9.AH.244.240; 9.AH.244.244; 9.AH.244.243;
9.AH.244.247; 9.AH.247.157; 9.AH.247.158; 9.AH.247.196;
9.AH.247.223; 9.AH.247.240; 9.AH.247.244; 9.AH.247.243;
9.AH.247.247;
Prodrugs of 9.AJ 9.AJ.4.157; 9.AJ.4.158; 9.AJ.4.196; 9.AJ.4.223; 9.AJ.4.240; 9.AJ.4.244;
9.AJ.4.243; 9.AJ.4.247; 9.AJ.5.157; 9.AJ.5.158; 9.AJ.5.196; 9.AJ.5.223;
9.AJ.5.240; 9.AJ.5.244; 9.AJ.5.243; 9.AJ.5.247; 9.AJ.7.157; 9.AJ.7.158;
9.AJ.7.196; 9.AJ.7.223; 9.AJ.7.240; 9.AJ.7.244; 9.AJ.7.243; 9.AJ.7.247;
9.AJ.15.157; 9.AJ.15.158; 9.AJ.15.196; 9.AJ.15.223; 9.AJ.15.240;
9.AJ.15.244; 9.AJ.15.243; 9.AJ.15.247; 9.AJ.16.157; 9.AJ.16.158;
9.AJ.16.196; 9.AJ.16.223; 9.AJ.16.240; 9.AJ.16.244; 9.AJ.16.243;
9.AJ.16.247; 9.AJ.18.157; 9.AJ.18.158; 9.AJ.18.196; 9.AJ.18.223;
9.AJ.18.240; 9.AJ.18.244; 9.AJ.18.243; 9.AJ.18.247; 9.AJ.26.157;
9.AJ.26.158; 9.AJ.26.196; 9.AJ.26.223; 9.AJ.26.240; 9.AJ.26.244;
9.AJ.26.243; 9.AJ.26.247; 9.AJ.27.157; 9.AJ.27.158; 9.AJ.27.196;
9.AJ.27.223; 9.AJ.27.240; 9.AJ.27.244; 9.AJ.27.243; 9.AJ.27.247;
9.AJ.29.157; 9.AJ.29.158; 9.AJ.29.196; 9.AJ.29.223; 9.AJ.29.240;
9.AJ.29.244; 9.AJ.29.243; 9.AJ.29.247; 9.AJ.54.157; 9.AJ.54.158;
9.AJ.54.196; 9.AJ.54.223; 9.AJ.54.240; 9.AJ.54.244; 9.AJ.54.243;
9.AJ.54.247; 9.AJ.55.157; 9.AJ.55.158; 9.AJ.55.196; 9.AJ.55.223;
9.AJ.55.240; 9.AJ.55.244; 9.AJ.55.243; 9.AJ.55.247; 9.AJ.56.157;
9.AJ.56.158; 9.AJ.56.196; 9.AJ.56.223; 9.AJ.56.240; 9.AJ.56.244;
9.AJ.56.243; 9.AJ.56.247; 9.AJ.157.157; 9.AJ.157.158; 9.AJ.157.196;
9.AJ.157.223; 9.AJ.157.240; 9.AJ.157.244; 9.AJ.157.243; 9.AJ.157.247;
9.AJ.196.157; 9.AJ.196.158; 9.AJ.196.196; 9.AJ.196.223; 9.AJ.196.240;
9.AJ.196.244; 9.AJ.196.243; 9.AJ.196.247; 9.AJ.223.157; 9.AJ.223.158;
9.AJ.223.196; 9.AJ.223.223; 9.AJ.223.240; 9.AJ.223.244; 9.AJ.223.243;
9.AJ.223.247; 9.AJ.240.157; 9.AJ.240.158; 9.AJ.240.196; 9.AJ.240.223;
9.AJ.240.240; 9.AJ.240.244; 9.AJ.240.243; 9.AJ.240.247; 9.AJ.244.157;
9.AJ.244.158; 9.AJ.244.196; 9.AJ.244.223; 9.AJ.244.240; 9.AJ.244.244;
9.AJ.244.243; 9.AJ.244.247; 9.AJ.247.157; 9.AJ.247.158; 9.AJ.247.196;
9.AJ.247.223; 9.AJ.247.240; 9.AJ.247.244; 9.AJ.247.243; 9.AJ.247.247;
Prodrugs of 9.AN 9.AN.4.157; 9.AN.4.158; 9.AN.4.196; 9.AN.4.223; 9.AN.4.240;
9.AN.4.244; 9.AN.4.243; 9.AN.4.247; 9.AN.5.157; 9.AN.5.158;
9.AN.5.196; 9.AN.5.223; 9.AN.5.240; 9.AN.5.244; 9.AN.5.243;
9.AN.5.247; 9.AN.7.157; 9.AN.7.158; 9.AN.7.196; 9.AN.7.223;
9.AN.7.240; 9.AN.7.244; 9.AN.7.243; 9.AN.7.247; 9.AN.15.157;
9.AN.15.158; 9.AN.15.196; 9.AN.15.223; 9.AN.15.240; 9.AN.15.244;
9.AN.15.243; 9.AN.15.247; 9.AN.16.157; 9.AN.16.158; 9.AN.16.196;
9.AN.16.223; 9.AN.16.240; 9.AN.16.244; 9.AN.16.243; 9.AN.16.247;
9.AN.18.157; 9.AN.18.158; 9.AN.18.196; 9.AN.18.223; 9.AN.18.240;
9.AN.18.244; 9.AN.18.243; 9.AN.18.247; 9.AN.26.157; 9.AN.26.158;
9.AN.26.196; 9.AN.26.223; 9.AN.26.240; 9.AN.26.244; 9.AN.26.243;
9.AN.26.247; 9.AN.27.157; 9.AN.27.158; 9.AN.27.196; 9.AN.27.223;
9.AN.27.240; 9.AN.27.244; 9.AN.27.243; 9.AN.27.247; 9.AN.29.157;
9.AN.29.158; 9.AN.29.196; 9.AN.29.223; 9.AN.29.240; 9.AN.29.244;
9.AN.29.243; 9.AN.29.247; 9.AN.54.157; 9.AN.54.158; 9.AN.54.196;
9.AN.54.223; 9.AN.54.240; 9.AN.54.244; 9.AN.54.243; 9.AN.54.247;
9.AN.55.157; 9.AN.55.158; 9.AN.55.196; 9.AN.55.223; 9.AN.55.240;
9.AN.55.244; 9.AN.55.243; 9.AN.55.247; 9.AN.56.157; 9.AN.56.158;
9.AN.56.196; 9.AN.56.223; 9.AN.56.240; 9.AN.56.244; 9.AN.56.243;
9.AN.56.247; 9.AN.157.157; 9.AN.157.158; 9.AN.157.196;
9.AN.157.223; 9.AN.157.240; 9.AN.157.244; 9.AN.157.243;
9.AN.157.247; 9.AN.196.157; 9.AN.196.158; 9.AN.196.196;
9.AN.196.223; 9.AN.196.240; 9.AN.196.244; 9.AN.196.243;
9.AN.196.247; 9.AN.223.157; 9.AN.223.158; 9.AN.223.196;
9.AN.223.223; 9.AN.223.240; 9.AN.223.244; 9.AN.223.243;
9.AN.223.247; 9.AN.240.157; 9.AN.240.158; 9.AN.240.196;
9.AN.240.223; 9.AN.240.240; 9.AN.240.244; 9.AN.240.243;

TABLE 7-continued

9.AN.240.247; 9.AN.244.157; 9.AN.244.158; 9.AN.244.196;
9.AN.244.223; 9.AN.244.240; 9.AN.244.244; 9.AN.244.243;
9.AN.244.247; 9.AN.247.157; 9.AN.247.158; 9.AN.247.196;
9.AN.247.223; 9.AN.247.240; 9.AN.247.244; 9.AN.247.243;
9.AN.247.247;
Prodrugs of 9.AP 9.AP.4.157; 9.AP.4.158; 9.AP.4.196; 9.AP.4.223; 9.AP.4.240;
9.AP.4.244; 9.AP.4.243; 9.AP.4.247; 9.AP.5.157; 9.AP.5.158;
9.AP.5.196; 9.AP.5.223; 9.AP.5.240; 9.AP.5.244; 9.AP.5.243;
9.AP.5.247; 9.AP.7.157; 9.AP.7.158; 9.AP.7.196; 9.AP.7.223;
9.AP.7.240; 9.AP.7.244; 9.AP.7.243; 9.AP.7.247; 9.AP.15.157;
9.AP.15.158; 9.AP.15.196; 9.AP.15.223; 9.AP.15.240; 9.AP.15.244;
9.AP.15.243; 9.AP.15.247; 9.AP.16.157; 9.AP.16.158; 9.AP.16.196;
9.AP.16.223; 9.AP.16.240; 9.AP.16.244; 9.AP.16.243; 9.AP.16.247;
9.AP.18.157; 9.AP.18.158; 9.AP.18.196; 9.AP.18.223; 9.AP.18.240;
9.AP.18.244; 9.AP.18.243; 9.AP.18.247; 9.AP.26.157; 9.AP.26.158;
9.AP.26.196; 9.AP.26.223; 9.AP.26.240; 9.AP.26.244; 9.AP.26.243;
9.AP.26.247; 9.AP.27.157; 9.AP.27.158; 9.AP.27.196; 9.AP.27.223;
9.AP.27.240; 9.AP.27.244; 9.AP.27.243; 9.AP.27.247; 9.AP.29.157;
9.AP.29.158; 9.AP.29.196; 9.AP.29.223; 9.AP.29.240; 9.AP.29.244;
9.AP.29.243; 9.AP.29.247; 9.AP.54.157; 9.AP.54.158; 9.AP.54.196;
9.AP.54.223; 9.AP.54.240; 9.AP.54.244; 9.AP.54.243; 9.AP.54.247;
9.AP.55.157; 9.AP.55.158; 9.AP.55.196; 9.AP.55.223; 9.AP.55.240;
9.AP.55.244; 9.AP.55.243; 9.AP.55.247; 9.AP.56.157; 9.AP.56.158;
9.AP.56.196; 9.AP.56.223; 9.AP.56.240; 9.AP.56.244; 9.AP.56.243;
9.AP.56.247; 9.AP.157.157; 9.AP.157.158; 9.AP.157.196; 9.AP.157.223;
9.AP.157.240; 9.AP.157.244; 9.AP.157.243; 9.AP.157.247;
9.AP.196.157; 9.AP.196.158; 9.AP.196.196; 9.AP.196.223;
9.AP.196.240; 9.AP.196.244; 9.AP.196.243; 9.AP.196.247;
9.AP.223.157; 9.AP.223.158; 9.AP.223.196; 9.AP.223.223;
9.AP.223.240; 9.AP.223.244; 9.AP.223.243; 9.AP.223.247;
9.AP.240.157; 9.AP.240.158; 9.AP.240.196; 9.AP.240.223;
9.AP.240.240; 9.AP.240.244; 9.AP.240.243; 9.AP.240.247;
9.AP.244.157; 9.AP.244.158; 9.AP.244.196; 9.AP.244.223;
9.AP.244.240; 9.AP.244.244; 9.AP.244.243; 9.AP.244.247;
9.AP.247.157; 9.AP.247.158; 9.AP.247.196; 9.AP.247.223;
9.AP.247.240; 9:AP.247.244; 9.AP.247.243; 9.AP.247.247;
Prodrugs of 9.AZ 9.AZ.4.157; 9.AZ.4.158; 9.AZ.4.196; 9.AZ.4.223; 9.AZ.4.240;
9.AZ.4.244; 9.AZ.4.243; 9.AZ.4.247; 9.AZ.5.157; 9.AZ.5.158;
9.AZ.5.196; 9.AZ.5.223; 9.AZ.5.240; 9.AZ.5.244; 9.AZ.5.243;
9.AZ.5.247; 9.AZ.7.157; 9.AZ.7.158; 9.AZ.7.196; 9.AZ.7.223;
9.AZ.7.240; 9.AZ.7.244; 9.AZ.7.243; 9.AZ.7.247; 9.AZ.15.157;
9.AZ.15.158; 9.AZ.15.196; 9.AZ.15.223; 9.AZ.15.240; 9.AZ.15.244;
9.AZ.15.243; 9.AZ.15.247; 9.AZ.16.157; 9.AZ.16.158; 9.AZ.16.196;
9.AZ.16.223; 9.AZ.16.240; 9.AZ.16.244; 9.AZ.16.243; 9.AZ.16.247;
9.AZ.18.157; 9.AZ.18.158; 9.AZ.18.196; 9.AZ.18.223; 9.AZ.18.240;
9.AZ.18.244; 9.AZ.18.243; 9.AZ.18.247; 9.AZ.26.157; 9.AZ.26.158;
9.AZ.26.196; 9.AZ.26.223; 9.AZ.26.240; 9.AZ.26.244; 9.AZ.26.243;
9.AZ.26.247; 9.AZ.27.157; 9.AZ.27.158; 9.AZ.27.196; 9.AZ.27.223;
9.AZ.27.240; 9.AZ.27.244; 9.AZ.27.243; 9.AZ.27.247; 9.AZ.29.157;
9.AZ.29.158; 9.AZ.29.196; 9.AZ.29.223; 9.AZ.29.240; 9.AZ.29.244;
9.AZ.29.243; 9.AZ.29.247; 9.AZ.54.157; 9.AZ.54.158; 9.AZ.54.196;
9.AZ.54.223; 9.AZ.54.240; 9.AZ.54.244; 9.AZ.54.243; 9.AZ.54.247;
9.AZ.55.157; 9.AZ.55.158; 9.AZ.55.196; 9.AZ.55.223; 9.AZ.55.240;
9.AZ.55.244; 9.AZ.55.243; 9.AZ.55.247; 9.AZ.56.157; 9.AZ.56.158;
9.AZ.56.196; 9.AZ.56.223; 9.AZ.56.240; 9.AZ.56.244; 9.AZ.56.243;
9.AZ.56.247; 9.AZ.157.157; 9.AZ.157.158; 9.AZ.157.196; 9.AZ.157.223;
9.AZ.157.240; 9.AZ.157.244; 9.AZ.157.243; 9.AZ.157.247;
9.AZ.196.157; 9.AZ.196.158; 9.AZ.196.196; 9.AZ.196.223;
9.AZ.196.240; 9.AZ.196.244; 9.AZ.196.243; 9.AZ.196.247;
9.AZ.223.157; 9.AZ.223.158; 9.AZ.223.196; 9.AZ.223.223;
9.AZ.223.240; 9.AZ.223.244; 9.AZ.223.243; 9.AZ.223.247;
9.AZ.240.157; 9.AZ.240.158; 9.AZ.240.196; 9.AZ.240.223;
9.AZ.240.240; 9.AZ.240.244; 9.AZ.240.243; 9.AZ.240.247;
9.AZ.244.157; 9.AZ.244.158; 9.AZ.244.196; 9.AZ.244.223;
9.AZ.244.240; 9.AZ.244.244; 9.AZ.244.243; 9.AZ.244.247;
9.AZ.247.157; 9.AZ.247.158; 9.AZ.247.196; 9.AZ.247.223;
9.AZ.247.240; 9.AZ.247.244; 9.AZ.247.243; 9.AZ.247.247;
Prodrugs of 9.BF 9.BF.4.157; 9.BF.4.158; 9.BF.4.196; 9.BF.4.223; 9.BF.4.240; 9.BF.4.244;
9.BF.4.243; 9.BF.4.247; 9.BF.5.157; 9.BF.5.158; 9.BF.5.196; 9.BF.5.223;
9.BF.5.240; 9.BF.5.244; 9.BF.5.243; 9.BF.5.247; 9.BF.7.157; 9.BF.7.158;
9.BF.7.196; 9.BF.7.223; 9.BF.7.240; 9.BF.7.244; 9.BF.7.243; 9.BF.7.247;
9.BF.15.157; 9.BF.15.158; 9.BF.15.196; 9.BF.15.223; 9.BF.15.240;
9.BF.15.244; 9.BF.15.243; 9.BF.15.247; 9.BF.16.157; 9.BF.16.158;
9.BF.16.196; 9.BF.16.223; 9.BF.16.240; 9.BF.16.244; 9.BF.16.243;
9.BF.16.247; 9.BF.18.157; 9.BF.18.158; 9.BF.18.196; 9.BF.18.223;
9.BF.18.240; 9.BF.18.244; 9.BF.18.243; 9.BF.18.247; 9.BF.26.157;
9.BF.26.158; 9.BF.26.196; 9.BF.26.223; 9.BF.26.240; 9.BF.26.244;
9.BF.26.243; 9.BF.26.247; 9.BF.27.157; 9.BF.27.158; 9.BF.27.196;
9.BF.27.223; 9.BF.27.240; 9.BF.27.244; 9.BF.27.243; 9.BF.27.247;
9.BF.29.157; 9.BF.29.158; 9.BF.29.196; 9.BF.29.223; 9.BF.29.240;
9.BF.29.244; 9.BF.29.243; 9.BF.29.247; 9.BF.54.157; 9.BF.54.158;
9.BF.54.196; 9.BF.54.223; 9.BF.54.240; 9.BF.54.244; 9.BF.54.243;
9.BF.54.247; 9.BF.55.157; 9.BF.55.158; 9.BF.55.196; 9.BF.55.223;
9.BF.55.240; 9.BF.55.244; 9.BF.55.243; 9.BF.55.247; 9.BF.56.157;
9.BF.56.158; 9.BF.56.196; 9.BF.56.223; 9.BF.56.240; 9.BF.56.244;
9.BF.56.243; 9.BF.56.247; 9.BF.157.157; 9.BF.157.158; 9.BF.157.196;
9.BF.157.223; 9.BF.157.240; 9.BF.157.244; 9.BF.157.243; 9.BF.157.247;
9.BF.196.157; 9.BF.196.158; 9.BF.196.196; 9.BF.196.223; 9.BF.196.240;
9.BF.196.244; 9.BF.196.243; 9.BF.196.247; 9.BF.223.157; 9.BF.223.158;
9.BF.223.196; 9.BF.223.223; 9.BF.223.240; 9.BF.223.244; 9.BF.223.243;
9.BF.223.247; 9.BF.240.157; 9.BF.240.158; 9.BF.240.196; 9.BF.240.223;
9.BF.240.240; 9.BF.240.244; 9.BF.240.243; 9.BF.240.247; 9.BF.244.157;
9.BF.244.158; 9.BF.244.196; 9.BF.244.223; 9.BF.244.240; 9.BF.244.244;
9.BF.244.243; 9.BF.244.247; 9.BF.247.157; 9.BF.247.158; 9.BF.247.196;
9.BF.247.223; 9.BF.247.240; 9.BF.247.244; 9.BF.247.243; 9.BF.247.247;
Prodrugs of 9.CI 9.CI.4.157; 9.CI.4.158; 9.CI.4.196; 9.CI.4.223; 9.CI.4.240; 9.CI.4.244;
9.CI.4.243; 9.CI.4.247; 9.CI.5.157; 9.CI.5.158; 9.CI.5.196; 9.CI.5.223;
9.CI.5.240; 9.CI.5.244; 9.CI.5.243; 9.CI.5.247; 9.CI.7.157; 9.CI.7.158;
9.CI.7.196; 9.CI.7.223; 9.CI.7.240; 9.CI.7.244; 9.CI.7.243; 9.CI.7.247;
9.CI.15.157; 9.CI.15.158; 9.CI.15.196; 9.CI.15.223; 9.CI.15.240;
9.CI.15.244; 9.CI.15.243; 9.CI.15.247; 9.CI.16.157; 9.CI.16.158;
9.CI.16.196; 9.CI.16.223; 9.CI.16.240; 9.CI.16.244; 9.CI.16.243;
9.CI.16.247; 9.CI.18.157; 9.CI.18.158; 9.CI.18.196; 9.CI.18.223;
9.CI.18.240; 9.CI.18.244; 9.CI.18.243; 9.CI.18.247; 9.CI.26.157;
9.CI.26.158; 9.CI.26.196; 9.CI.26.223; 9.CI.26.240; 9.CI.26.244;
9.CI.26.243; 9.CI.26.247; 9.CI.27.157; 9.CI.27.158; 9.CI.27.196;
9.CI.27.223; 9.CI.27.240; 9.CI.27.244; 9.CI.27.243; 9.CI.27.247;
9.CI.29.157; 9.CI.29.158; 9.CI.29.196; 9.CI.29.223; 9.CI.29.240;
9.CI.29.244; 9.CI.29.243; 9.CI.29.247; 9.CI.54.157; 9.CI.54.158;
9.CI.54.196; 9.CI.54.223; 9.CI.54.240; 9.CI.54.244; 9.CI.54.243;
9.CI.54.247; 9.CI.55.157; 9.CI.55.158; 9.CI.55.196; 9.CI.55.223;
9.CI.55.240; 9.CI.55.244; 9.CI.55.243; 9.CI.55.247; 9.CI.56.157;
9.CI.56.158; 9.CI.56.196; 9.CI.56.223; 9.CI.56.240; 9.CI.56.244;
9.CI.56.243; 9.CI.56.247; 9.CI.157.157; 9.CI.157.158; 9.CI.157.196;
9.CI.157.223; 9.CI.157.240; 9.CI.157.244; 9.CI.157.243; 9.CI.157.247;
9.CI.196.157; 9.CI.196.158; 9.CI.196.196; 9.CI.196.223; 9.CI.196.240;
9.CI.196.244; 9.CI.196.243; 9.CI.196.247; 9.CI.223.157; 9.CI.223.158;
9.CI.223.196; 9.CI.223.223; 9.CI.223.240; 9.CI.223.244; 9.CI.223.243;
9.CI.223.247; 9.CI.240.157; 9.CI.240.158; 9.CI.240.196; 9.CI.240.223;
9.CI.240.240; 9.CI.240.244; 9.CI.240.243; 9.CI.240.247; 9.CI.244.157;
9.CI.244.158; 9.CI.244.196; 9.CI.244.223; 9.CI.244.240; 9.CI.244.244;
9.CI.244.243; 9.CI.244.247; 9.CI.247.157; 9.CI.247.158; 9.CI.247.196;
9.CI.247.223; 9.CI.247.240; 9.CI.247.244; 9.CI.247.243; 9.CI.247.247;
Prodrugs of 9.CO 9.CO.4.157; 9.CO.4.158; 9.CO.4.196; 9.CO.4.223; 9.CO.4.240;
9.CO.4.244; 9.CO.4.243; 9.CO.4.247; 9.CO.5.157; 9.CO.5.158;
9.CO.5.196; 9.CO.5.223; 9.CO.5.240; 9.CO.5.244; 9.CO.5.243;
9.CO.5.247; 9.CO.7.157; 9.CO.7.158; 9.CO.7.196; 9.CO.7.223;
9.CO.7.240; 9.CO.7.244; 9.CO.7.243; 9.CO.7.247; 9.CO.15.157;
9.CO.15.158; 9.CO.15.196; 9.CO.15.223; 9.CO.15.240; 9.CO.15.244;
9.CO.15.243; 9.CO.15.247; 9.CO.16.157; 9.CO.16.158; 9.CO.16.196;
9.CO.16.223; 9.CO.16.240; 9.CO.16.244; 9.CO.16.243; 9.CO.16.247;
9.CO.18.157; 9.CO.18.158; 9.CO.18.196; 9.CO.18.223; 9.CO.18.240;
9.CO.18.244; 9.CO.18.243; 9.CO.18.247; 9.CO.26.157; 9.CO.26.158;
9.CO.26.196; 9.CO.26.223; 9.CO.26.240; 9.CO.26.244; 9.CO.26.243;
9.CO.26.247; 9.CO.27.157; 9.CO.27.158; 9.CO.27.196; 9.CO.27.223;
9.CO.27.240; 9.CO.27.244; 9.CO.27.243; 9.CO.27.247; 9.CO.29.157;
9.CO.29.158; 9.CO.29.196; 9.CO.29.223; 9.CO.29.240; 9.CO.29.244;
9.CO.29.243; 9.CO.29.247; 9.CO.54.157; 9.CO.54.158; 9.CO.54.196;
9.CO.54.223; 9.CO.54.240; 9.CO.54.244; 9.CO.54.243; 9.CO.54.247;
9.CO.55.157; 9.CO.55.158; 9.CO.55.196; 9.CO.55.223; 9.CO.55.240;
9.CO.55.244; 9.CO.55.243; 9.CO.55.247; 9.CO.56.157; 9.CO.56.158;
9.CO.56.196; 9.CO.56.223; 9.CO.56.240; 9.CO.56.244; 9.CO.56.243;
9.CO.56.247; 9.CO.157.157; 9.CO.157.158; 9.CO.157.196;
9.CO.157.223; 9.CO.157.240; 9.CO.157.244; 9.CO.157.243;
9.CO.157.247; 9.CO.196.157; 9.CO.196.158; 9.CO.196.196;
9.CO.196.223; 9.CO.196.240; 9.CO.196.244; 9.CO.196.243;
9.CO.196.247; 9.CO.223.157; 9.CO.223.158; 9.CO.223.196;
9.CO.223.223; 9.CO.223.240; 9.CO.223.244; 9.CO.223.243;

TABLE 7-continued

9.CO.223.247; 9.CO.240.157; 9.CO.240.158; 9.CO.240.196;
9.CO.240.223; 9.CO.240.240; 9.CO.240.244; 9.CO.240.243;
9.CO.240.247; 9.CO.244.157; 9.CO.244.158; 9.CO.244.196;
9.CO.244.223; 9.CO.244.240; 9.CO.244.244; 9.CO.244.243;
9.CO.244.247; 9.CO.247.157; 9.CO.247.158; 9.CO.247.196;
9.CO.247.223; 9.CO.247.240; 9.CO.247.244; 9.CO.247.243;
9.CO.247.247;

Prodrugs of 10.AH

10.AH.4.157; 10.AH.4.158; 10.AH.4.196; 10.AH.4.223; 10.AH.4.240;
10.AH.4.244; 10.AH.4.243; 10.AH.4.247; 10.AH.5.157; 10.AH.5.158;
10.AH.5.196; 10.AH.5.223; 10.AH.5.240; 10.AH.5.244; 10.AH.5.243;
10.AH.5.247; 10.AH.7.157; 10.AH.7.158; 10.AH.7.196; 10.AH.7.223;
10.AH.7.240; 10.AH.7.244; 10.AH.7.243; 10.AH.7.247; 10.AH.15.157;
10.AH.15.158; 10.AH.15.196; 10.AH.15.223; 10.AH.15.240;
10.AH.15.244; 10.AH.15.243; 10.AH.15.247; 10.AH.16.157;
10.AH.16.158; 10.AH.16.196; 10.AH.16.223; 10.AH.16.240;
10.AH.16.244; 10.AH.16.243; 10.AH.16.247; 10.AH.18.157;
10.AH.18.158; 10.AH.18.196; 10.AH.18.223; 10.AH.18.240;
10.AH.18.244; 10.AH.18.243; 10.AH.18.247; 10.AH.26.157;
10.AH.26.158; 10.AH.26.196; 10.AH.26.223; 10.AH.26.240;
10.AH.26.244; 10.AH.26.243; 10.AH.26.247; 10.AH.27.157;
10.AH.27.158; 10.AH.27.196; 10.AH.27.223; 10.AH.27.240;
10.AH.27.244; 10.AH.27.243; 10.AH.27.247; 10.AH.29.157;
10.AH.29.158; 10.AH.29.196; 10.AH.29.223; 10.AH.29.240;
10.AH.29.244; 10.AH.29.243; 10.AH.29.247; 10.AH.54.157;
10.AH.54.158; 10.AH.54.196; 10.AH.54.223; 10.AH.54.240;
10.AH.54.244; 10.AH.54.243; 10.AH.54.247; 10.AH.55.157;
10.AH.55.158; 10.AH.55.196; 10.AH.55.223; 10.AH.55.240;
10.AH.55.244; 10.AH.55.243; 10.AH.55.247; 10.AH.56.157;
10.AH.56.158; 10.AH.56.196; 10.AH.56.223; 10.AH.56.240;
10.AH.56.244; 10.AH.56.243; 10.AH.56.247; 10.AH.157.157;
10.AH.157.158; 10.AH.157.196; 10.AH.157.223; 10.AH.157.240;
10.AH.157.244; 10.AH.157.243; 10.AH.157.247; 10.AH.196.157;
10.AH.196.158; 10.AH.196.196; 10.AH.196.223; 10.AH.196.240;
10.AH.196.244; 10.AH.196.243; 10.AH.196.247; 10.AH.223.157;
10.AH.223.158; 10.AH.223.196; 10.AH.223.223; 10.AH.223.240;
10.AH.223.244; 10.AH.223.243; 10.AH.223.247; 10.AH.240.157;
10.AH.240.158; 10.AH.240.196; 10.AH.240.223; 10.AH.240.240;
10.AH.240.244; 10.AH.240.243; 10.AH.240.247; 10.AH.244.157;
10.AH.244.158; 10.AH.244.196; 10.AH.244.223; 10.AH.244.240;
10.AH.244.244; 10.AH.244.243; 10.AH.244.247; 10.AH.247.157;
10.AH.247.158; 10.AH.247.196; 10.AH.247.223; 10.AH.247.240;
10.AH.247.244; 10.AH.247.243; 10.AH.247.247;

Prodrugs of 10.AJ

10.AJ.4.157; 10.AJ.4.158; 10.AJ.4.196; 10.AJ.4.223; 10.AJ.4.240;
10.AJ.4.244; 10.AJ.4.243; 10.AJ.4.247; 10.AJ.5.157; 10.AJ.5.158;
10.AJ.5.196; 10.AJ.5.223; 10.AJ.5.240; 10.AJ.5.244; 10.AJ.5.243;
10.AJ.5.247; 10.AJ.7.157; 10.AJ.7.158; 10.AJ.7.196; 10.AJ.7.223;
10.AJ.7.240; 10.AJ.7.244; 10.AJ.7.243; 10.AJ.7.247; 10.AJ.15.157;
10.AJ.15.158; 10.AJ.15.196; 10.AJ.15.223; 10.AJ.15.240; 10.AJ.15.244;
10.AJ.15.243; 10.AJ.15.247; 10.AJ.16.157; 10.AJ.16.158; 10.AJ.16.196;
10.AJ.16.223; 10.AJ.16.240; 10.AJ.16.244; 10.AJ.16.243; 10.AJ.16.247;
10.AJ.18.157; 10.AJ.18.158; 10.AJ.18.196; 10.AJ.18.223; 10.AJ.18.240;
10.AJ.18.244; 10.AJ.18.243; 10.AJ.18.247; 10.AJ.26.157; 10.AJ.26.158;
10.AJ.26.196; 10.AJ.26.223; 10.AJ.26.240; 10.AJ.26.244; 10.AJ.26.243;
10.AJ.26.247; 10.AJ.27.157; 10.AJ.27.158; 10.AJ.27.196; 10.AJ.27.223;
10.AJ.27.240; 10.AJ.27.244; 10.AJ.27.243; 10.AJ.27.247; 10.AJ.29.157;
10.AJ.29.158; 10.AJ.29.196; 10.AJ.29.223; 10.AJ.29.240; 10.AJ.29.244;
10.AJ.29.243; 10.AJ.29.247; 10.AJ.54.157; 10.AJ.54.158; 10.AJ.54.196;
10.AJ.54.223; 10.AJ.54.240; 10.AJ.54.244; 10.AJ.54.243; 10.AJ.54.247;
10.AJ.55.157; 10.AJ.55.158; 10.AJ.55.196; 10.AJ.55.223; 10.AJ.55.240;
10.AJ.55.244; 10.AJ.55.243; 10.AJ.55.247; 10.AJ.56.157; 10.AJ.56.158;
10.AJ.56.196; 10.AJ.56.223; 10.AJ.56.240; 10.AJ.56.244; 10.AJ.56.243;
10.AJ.56.247; 10.AJ.157.157; 10.AJ.157.158; 10.AJ.157.196;
10.AJ.157.223; 10.AJ.157.240; 10.AJ.157.244; 10.AJ.157.243;
10.AJ.157.247; 10.AJ.196.157; 10.AJ.196.158; 10.AJ.196.196;
10.AJ.196.223; 10.AJ.196.240; 10.AJ.196.244; 10.AJ.196.243;
10.AJ.196.247; 10.AJ.223.157; 10.AJ.223.158; 10.AJ.223.196;
10.AJ.223.223; 10.AJ.223.240; 10.AJ.223.244; 10.AJ.223.243;
10.AJ.223.247; 10.AJ.240.157; 10.AJ.240.158; 10.AJ.240.196;
10.AJ.240.223; 10.AJ.240.240; 10.AJ.240.244; 10.AJ.240.243;
10.AJ.240.247; 10.AJ.244.157; 10.AJ.244.158; 10.AJ.244.196;
10.AJ.244.223; 10.AJ.244.240; 10.AJ.244.244; 10.AJ.244.243;
10.AJ.244.247; 10.AJ.247.157; 10.AJ.247.158; 10.AJ.247.196;
10.AJ.247.223; 10.AJ.247.240; 10.AJ.247.244; 10.AJ.247.243;
10.AJ.247.247;

Prodrugs of 10.AN

10.AN.4.157; 10.AN.4.158; 10.AN.4.196; 10.AN.4.223; 10.AN.4.240;
10.AN.4.244; 10.AN.4.243; 10.AN.4.247; 10.AN.5.157; 10.AN.5.158;
10.AN.5.196; 10.AN.5.223; 10.AN.5.240; 10.AN.5.244; 10.AN.5.243;
10.AN.5.247; 10.AN.7.157; 10.AN.7.158; 10.AN.7.196; 10.AN.7.223;
10.AN.7.240; 10.AN.7.244; 10.AN.7.243; 10.AN.7.247; 10.AN.15.157;
10.AN.15.158; 10.AN.15.196; 10.AN.15.223; 10.AN.15.240;
10.AN.15.244; 10.AN.15.243; 10.AN.15.247; 10.AN.16.157;
10.AN.16.158; 10.AN.16.196; 10.AN.16.223; 10.AN.16.240;
10.AN.16.244; 10.AN.16.243; 10.AN.16.247; 10.AN.18.157;
10.AN.18.158; 10.AN.18.196; 10.AN.18.223; 10.AN.18.240;
10.AN.18.244; 10.AN.18.243; 10.AN.18.247; 10.AN.26.157;
10.AN.26.158; 10.AN.26.196; 10.AN.26.223; 10.AN.26.240;
10.AN.26.244; 10.AN.26.243; 10.AN.26.247; 10.AN.27.157;
10.AN.27.158; 10.AN.27.196; 10.AN.27.223; 10.AN.27.240;
10.AN.27.244; 10.AN.27.243; 10.AN.27.247; 10.AN.29.157;
10.AN.29.158; 10.AN.29.196; 10.AN.29.223; 10.AN.29.240;
10.AN.29.244; 10.AN.29.243; 10.AN.29.247; 10.AN.54.157;
10.AN.54.158; 10.AN.54.196; 10.AN.54.223; 10.AN.54.240;
10.AN.54.244; 10.AN.54.243; 10.AN.54.247; 10.AN.55.157;
10.AN.55.158; 10.AN.55.196; 10.AN.55.223; 10.AN.55.240;
10.AN.55.244; 10.AN.55.243; 10.AN.55.247; 10.AN.56.157;
10.AN.56.158; 10.AN.56.196; 10.AN.56.223; 10.AN.56.240;
10.AN.56.244; 10.AN.56.243; 10.AN.56.247; 10.AN.157.157;
10.AN.157.158; 10.AN.157.196; 10.AN.157.223; 10.AN.157.240;
10.AN.157.244; 10.AN.157.243; 10.AN.157.247; 10.AN.196.157;
10.AN.196.158; 10.AN.196.196; 10.AN.196.223; 10.AN.196.240;
10.AN.196.244; 10.AN.196.243; 10.AN.196.247; 10.AN.223.157;
10.AN.223.158; 10.AN.223.196; 10.AN.223.223; 10.AN.223.240;
10.AN.223.244; 10.AN.223.243; 10.AN.223.247; 10.AN.240.157;
10.AN.240.158; 10.AN.240.196; 10.AN.240.223; 10.AN.240.240;
10.AN.240.244; 10.AN.240.243; 10.AN.240.247; 10.AN.244.157;
10.AN.244.158; 10.AN.244.196; 10.AN.244.223; 10.AN.244.240;
10.AN.244.244; 10.AN.244.243; 10.AN.244.247; 10.AN.247.157;
10.AN.247.158; 10.AN.247.196; 10.AN.247.223; 10.AN.247.240;
10.AN.247.244; 10.AN.247.243; 10.AN.247.247;

Prodrugs of 10.AP

10.AP.4.157; 10.AP.4.158; 10.AP.4.196; 10.AP.4.223; 10.AP.4.240;
10.AP.4.244; 10.AP.4.243; 10.AP.4.247; 10.AP.5.157; 10.AP.5.158;
10.AP.5.196; 10.AP.5.223; 10.AP.5.240; 10.AP.5.244; 10.AP.5.243;
10.AP.5.247; 10.AP.7.157; 10.AP.7.158; 10.AP.7.196; 10.AP.7.223;
10.AP.7.240; 10.AP.7.244; 10.AP.7.243; 10.AP.7.247; 10.AP.15.157;
10.AP.15.158; 10.AP.15.196; 10.AP.15.223; 10.AP.15.240;
10.AP.15.244; 10.AP.15.243; 10.AP.15.247; 10.AP.16.157;
10.AP.16.158; 10.AP.16.196; 10.AP.16.223; 10.AP.16.240;
10.AP.16.244; 10.AP.16.243; 10.AP.16.247; 10.AP.18.157;
10.AP.18.158; 10.AP.18.196; 10.AP.18.223; 10.AP.18.240;
10.AP.18.244; 10.AP.18.243; 10.AP.18.247; 10.AP.26.157;
10.AP.26.158; 10.AP.26.196; 10.AP.26.223; 10.AP.26.240;
10.AP.26.244; 10.AP.26.243; 10.AP.26.247; 10.AP.27.157;
10.AP.27.158; 10.AP.27.196; 10.AP.27.223; 10.AP.27.240;
10.AP.27.244; 10.AP.27.243; 10.AP.27.247; 10.AP.29.157;
10.AP.29.158; 10.AP.29.196; 10.AP.29.223; 10.AP.29.240;
10.AP.29.244; 10.AP.29.243; 10.AP.29.247; 10.AP.54.157;
10.AP.54.158; 10.AP.54.196; 10.AP.54.223; 10.AP.54.240;
10.AP.54.244; 10.AP.54.243; 10.AP.54.247; 10.AP.55.157;
10.AP.55.158; 10.AP.55.196; 10.AP.55.223; 10.AP.55.240;
10.AP.55.244; 10.AP.55.243; 10.AP.55.247; 10.AP.56.157;
10.AP.56.158; 10.AP.56.196; 10.AP.56.223; 10.AP.56.240;
10.AP.56.244; 10.AP.56.243; 10.AP.56.247; 10.AP.157.157;
10.AP.157.158; 10.AP.157.196; 10.AP.157.223; 10.AP.157.240;
10.AP.157.244; 10.AP.157.243; 10.AP.157.247; 10.AP.196.157;
10.AP.196.158; 10.AP.196.196; 10.AP.196.223; 10.AP.196.240;
10.AP.196.244; 10.AP.196.243; 10.AP.196.247; 10.AP.223.157;
10.AP.223.158; 10.AP.223.196; 10.AP.223.223; 10.AP.223.240;
10.AP.223.244; 10.AP.223.243; 10.AP.223.247; 10.AP.240.157;
10.AP.240.158; 10.AP.240.196; 10.AP.240.223; 10.AP.240.240;
10.AP.240.244; 10.AP.240.243; 10.AP.240.247; 10.AP.244.157;
10.AP.244.158; 10.AP.244.196; 10.AP.244.223; 10.AP.244.240;
10.AP.244.244; 10.AP.244.243; 10.AP.244.247; 10.AP.247.157;
10.AP.247.158; 10.AP.247.196; 10.AP.247.223; 10.AP.247.240;
10.AP.247.244; 10.AP.247.243; 10.AP.247.247;

Prodrugs of 10.AZ

10.AZ.4.157; 10.AZ.4.158; 10.AZ.4.196; 10.AZ.4.223; 10.AZ.4.240;
10.AZ.4.244; 10.AZ.4.243; 10.AZ.4.247; 10.AZ.5.157; 10.AZ.5.158;
10.AZ.5.196; 10.AZ.5.223; 10.AZ.5.240; 10.AZ.5.244; 10.AZ.5.243;

TABLE 7-continued

10.AZ.5.247; 10.AZ.7.157; 10.AZ.7.158; 10.AZ.7.196; 10.AZ.7.223; 10.AZ.7.240; 10.AZ.7.244; 10.AZ.7.243; 10.AZ.7.247; 10.AZ.15.157; 10.AZ.15.158; 10.AZ.15.196; 10.AZ.15.223; 10.AZ.15.240; 10.AZ.15.244; 10.AZ.15.243; 10.AZ.15.247; 10.AZ.16.157; 10.AZ.16.158; 10.AZ.16.196; 10.AZ.16.223; 10.AZ.16.240; 10.AZ.16.244; 10.AZ.16.243; 10.AZ.16.247; 10.AZ.18.157; 10.AZ.18.158; 10.AZ.18.196; 10.AZ.18.223; 10.AZ.18.240; 10.AZ.18.244; 10.AZ.18.243; 10.AZ.18.247; 10.AZ.26.157; 10.AZ.26.158; 10.AZ.26.196; 10.AZ.26.223; 10.AZ.26.240; 10.AZ.26.244; 10.AZ.26.243; 10.AZ.26.247; 10.AZ.27.157; 10.AZ.27.158; 10.AZ.27.196; 10.AZ.27.223; 10.AZ.27.240; 10.AZ.27.244; 10.AZ.27.243; 10.AZ.27.247; 10.AZ.29.157; 10.AZ.29.158; 10.AZ.29.196; 10.AZ.29.223; 10.AZ.29.240; 10.AZ.29.244; 10.AZ.29.243; 10.AZ.29.247; 10.AZ.54.157; 10.AZ.54.158; 10.AZ.54.196; 10.AZ.54.223; 10.AZ.54.240; 10.AZ.54.244; 10.AZ.54.243; 10.AZ.54.247; 10.AZ.55.157; 10.AZ.55.158; 10.AZ.55.196; 10.AZ.55.223; 10.AZ.55.240; 10.AZ.55.244; 10.AZ.55.243; 10.AZ.55.247; 10.AZ.56.157; 10.AZ.56.158; 10.AZ.56.196; 10.AZ.56.223; 10.AZ.56.240; 10.AZ.56.244; 10.AZ.56.243; 10.AZ.56.247; 10.AZ.157.157; 10.AZ.157.158; 10.AZ.157.196; 10.AZ.157.223; 10.AZ.157.240; 10.AZ.157.244; 10.AZ.157.243; 10.AZ.157.247; 10.AZ.196.157; 10.AZ.196.158; 10.AZ.196.196; 10.AZ.196.223; 10.AZ.196.240; 10.AZ.196.244; 10.AZ.196.243; 10.AZ.196.247; 10.AZ.223.157; 10.AZ.223.158; 10.AZ.223.196; 10.AZ.223.223; 10.AZ.223.240; 10.AZ.223.244; 10.AZ.223.243; 10.AZ.223.247; 10.AZ.240.157; 10.AZ.240.158; 10.AZ.240.196; 10.AZ.240.223; 10.AZ.240.240; 10.AZ.240.244; 10.AZ.240.243; 10.AZ.240.247; 10.AZ.244.157; 10.AZ.244.158; 10.AZ.244.196; 10.AZ.244.223; 10.AZ.244.240; 10.AZ.244.244; 10.AZ.244.243; 10.AZ.244.247; 10.AZ.247.157; 10.AZ.247.158; 10.AZ.247.196; 10.AZ.247.223; 10.AZ.247.240; 10.AZ.247.244; 10.AZ.247.243; 10.AZ.247.247;
Prodrugs of 10.BF 10.BF.4.157; 10.BF.4.158; 10.BF.4.196; 10.BF.4.223; 10.BF.4.240; 10.BF.4.244; 10.BF.4.243; 10.BF.4.247; 10.BF.5.157; 10.BF.5.158; 10.BF.5.196; 10.BF.5.223; 10.BF.5.240; 10.BF.5.244; 10.BF.5.243; 10.BF.5.247; 10.BF.7.157; 10.BF.7.158; 10.BF.7.196; 10.BF.7.223; 10.BF.7.240; 10.BF.7.244; 10.BF.7.243; 10.BF.7.247; 10.BF.15.157; 10.BF.15.158; 10.BF.15.196; 10.BF.15.223; 10.BF.15.240; 10.BF.15.244; 10.BF.15.243; 10.BF.15.247; 10.BF.16.157; 10.BF.16.158; 10.BF.16.196; 10.BF.16.223; 10.BF.16.240; 10.BF.16.244; 10.BF.16.243; 10.BF.16.247; 10.BF.18.157; 10.BF.18.158; 10.BF.18.196; 10.BF.18.223; 10.BF.18.240; 10.BF.18.244; 10.BF.18.243; 10.BF.18.247; 10.BF.26.157; 10.BF.26.158; 10.BF.26.196; 10.BF.26.223; 10.BF.26.240; 10.BF.26.244; 10.BF.26.243; 10.BF.26.247; 10.BF.27.157; 10.BF.27.158; 10.BF.27.196; 10.BF.27.223; 10.BF.27.240; 10.BF.27.244; 10.BF.27.243; 10.BF.27.247; 10.BF.29.157; 10.BF.29.158; 10.BF.29.196; 10.BF.29.223; 10.BF.29.240; 10.BF.29.244; 10.BF.29.243; 10.BF.29.247; 10.BF.54.157; 10.BF.54.158; 10.BF.54.196; 10.BF.54.223; 10.BF.54.240; 10.BF.54.244; 10.BF.54.243; 10.BF.54.247; 10.BF.55.157; 10.BF.55.158; 10.BF.55.196; 10.BF.55.223; 10.BF.55.240; 10.BF.55.244; 10.BF.55.243; 10.BF.55.247; 10.BF.56.157; 10.BF.56.158; 10.BF.56.196; 10.BF.56.223; 10.BF.56.240; 10.BF.56.244; 10.BF.56.243; 10.BF.56.247; 10.BF.157.157; 10.BF.157.158; 10.BF.157.196; 10.BF.157.223; 10.BF.157.240; 10.BF.157.244; 10.BF.157.243; 10.BF.157.247; 10.BF.196.157; 10.BF.196.158; 10.BF.196.196; 10.BF.196.223; 10.BF.196.240; 10.BF.196.244; 10.BF.196.243; 10.BF.196.247; 10.BF.223.157; 10.BF.223.158; 10.BF.223.196; 10.BF.223.223; 10.BF.223.240; 10.BF.223.244; 10.BF.223.243; 10.BF.223.247; 10.BF.240.157; 10.BF.240.158; 10.BF.240.196; 10.BF.240.223; 10.BF.240.240; 10.BF.240.244; 10.BF.240.243; 10.BF.240.247; 10.BF.244.157; 10.BF.244.158; 10.BF.244.196; 10.BF.244.223; 10.BF.244.240; 10.BF.244.244; 10.BF.244.243; 10.BF.244.247; 10.BF.247.157; 10.BF.247.158; 10.BF.247.196; 10.BF.247.223; 10.BF.247.240; 10.BF.247.244; 10.BF.247.243; 10.BF.247.247;
Prodrugs of 10.CI 10.CI.4.157; 10.CI.4.158; 10.CI.4.196; 10.CI.4.223; 10.CI.4.240; 10.CI.4.244; 10.CI.4.243; 10.CI.4.247; 10.CI.5.157; 10.CI.5.158; 10.CI.5.196; 10.CI.5.223; 10.CI.5.240; 10.CI.5.244; 10.CI.5.243; 10.CI.5.247; 10.CI.7.157; 10.CI.7.158; 10.CI.7.196; 10.CI.7.223; 10.CI.7.240; 10.CI.7.244; 10.CI.7.243; 10.CI.7.247; 10.CI.15.157; 10.CI.15.158; 10.CI.15.196; 10.CI.15.223; 10.CI.15.240; 10.CI.15.244; 10.CI.15.243; 10.CI.15.247; 10.CI.16.157; 10.CI.16.158; 10.CI.16.196; 10.CI.16.223; 10.CI.16.240; 10.CI.16.244; 10.CI.16.243; 10.CI.16.247; 10.CI.18.157; 10.CI.18.158; 10.CI.18.196; 10.CI.18.223; 10.CI.18.240; 10.CI.18.244; 10.CI.18.243; 10.CI.18.247; 10.CI.26.157; 10.CI.26.158; 10.CI.26.196; 10.CI.26.223; 10.CI.26.240; 10.CI.26.244; 10.CI.26.243; 10.CI.26.247; 10.CI.27.157; 10.CI.27.158; 10.CI.27.196; 10.CI.27.223; 10.CI.27.240; 10.CI.27.244; 10.CI.27.243; 10.CL.27.247; 10.CI.29.157; 10.CI.29.158; 10.CL.29.196; 10.CI.29.223; 10.CI.29.240; 10.CI.29.244; 10.CI.29.243; 10.CI.29.247; 10.CI.54.157; 10.CI.54.158; 10.CI.54.196; 10.CI.54.223; 10.CI.54.240; 10.CI.54.244; 10.CI.54.243; 10.CI.54.247; 10.CI.55.157; 10.CI.55.158; 10.CI.55.196; 10.CI.55.223; 10.CI.55.240; 10.CI.55.244; 10.CI.55.243; 10.CI.55.247; 10.CI.56.157; 10.CI.56.158; 10.CI.56.196; 10.CI.56.223; 10.CI.56.240; 10.CI.56.244; 10.CI.56.243; 10.CI.56.247; 10.CI.157.157; 10.CI.157.158; 10.CI.157.196; 10.CI.157.223; 10.CI.157.240; 10.CI.157.244; 10.CI.157.243; 10.CI.157.247; 10.CI.196.157; 10.CI.196.158; 10.CI.196.196; 10.CI.196.223; 10.CI.196.240; 10.CI.196.244; 10.CI.196.243; 10.CI.196.247; 10.CI.223.157; 10.CI.223.158; 10.CI.223.196; 10.CI.223.223; 10.CI.223.240; 10.CI.223.244; 10.CI.223.243; 10.CI.223.247; 10.CI.240.157; 10.CI.240.158; 10.CI.240.196; 10.CI.240.223; 10.CI.240.240; 10.CI.240.244; 10.CI.240.243; 10.CI.240.247; 10.CI.244.157; 10.CI.244.158; 10.CI.244.196; 10.CI.244.223; 10.CI.244.240; 10.CI.244.244; 10.CI.244.243; 10.CI.244.247; 10.CI.247.157; 10.CI.247.158; 10.CI.247.196; 10.CI.247.223; 10.CI.247.240; 10.CI.247.244; 10.CI.247.243; 10.CI.247.247;
Prodrugs of 10.CO 10.CO.4.157; 10.CO.4.158; 10.CO.4.196; 10.CO.4.223; 10.CO.4.240; 10.CO.4.244; 10.CO.4.243; 10.CO.4.247; 10.CO.5.157; 10.CO.5.158; 10.CO.5.196; 10.CO.5.223; 10.CO.5.240; 10.CO.5.244; 10.CO.5.243; 10.CO.5.247; 10.CO.7.157; 10.CO.7.158; 10.CO.7.196; 10.CO.7.223; 10.CO.7.240; 10.CO.7.244; 10.CO.7.243; 10.CO.7.247; 10.CO.15.157; 10.CO.15.158; 10.CO.15.196; 10.CO.15.223; 10.CO.15.240; 10.CO.15.244; 10.CO.15.243; 10.CO.15.247; 10.CO.16.157; 10.CO.16.158; 10.CO.16.196; 10.CO.16.223; 10.CO.16.240; 10.CO.16.244; 10.CO.16.243; 10.CO.16.247; 10.CO.18.157; 10.CO.18.158; 10.CO.18.196; 10.CO.18.223; 10.CO.18.240; 10.CO.18.244; 10.CO.18.243; 10.CO.18.247; 10.CO.26.157; 10.CO.26.158; 10.CO.26.196; 10.CO.26.223; 10.CO.26.240; 10.CO.26.244; 10.CO.26.243; 10.CO.26.247; 10.CO.27.157; 10.CO.27.158; 10.CO.27.196; 10.CO.27.223; 10.CO.27.240; 10.CO.27.244; 10.CO.27.243; 10.CO.27.247; 10.CO.29.157; 10.CO.29.158; 10.CO.29.196; 10.CO.29.223; 10.CO.29.240; 10.CO.29.244; 10.CO.29.243; 10.CO.29.247; 10.CO.54.157; 10.CO.54.158; 10.CO.54.196; 10.CO.54.223; 10.CO.54.240; 10.CO.54.244; 10.CO.54.243; 10.CO.54.247; 10.CO.55.157; 10.CO.55.158; 10.CO.55.196; 10.CO.55.223; 10.CO.55.240; 10.CO.55.244; 10.CO.55.243; 10.CO.55.247; 10.CO.56.157; 10.CO.56.158; 10.CO.56.196; 10.CO.56.223; 10.CO.56.240; 10.CO.56.244; 10.CO.56.243; 10.CO.56.247; 10.CO.157.157; 10.CO.157.158; 10.CO.157.196; 10.CO.157.223; 10.CO.157.240; 10.CO.157.244; 10.CO.157.243; 10.CO.157.247; 10.CO.196.157; 10.CO.196.158; 10.CO.196.196; 10.CO.196.223; 10.CO.196.240; 10.CO.196.244; 10.CO.196.243; 10.CO.196.247; 10.CO.223.157; 10.CO.223.158; 10.CO.223.196; 10.CO.223.223; 10.CO.223.240; 10.CO.223.244; 10.CO.223.243; 10.CO.223.247; 10.CO.240.157; 10.CO.240.158; 10.CO.240.196; 10.CO.240.223; 10.CO.240.240; 10.CO.240.244; 10.CO.240.243; 10.CO.240.247; 10.CO.244.157; 10.CO.244.158; 10.CO.244.196; 10.CO.244.223; 10.CO.244.240; 10.CO.244.244; 10.CO.244.243; 10.CO.244.247; 10.CO.247.157; 10.CO.247.158; 10.CO.247.196; 10.CO.247.223; 10.CO.247.240; 10.CO.247.244; 10.CO.247.243; 10.CO.247.247;
Prodrugs of 11.AH 11.AH.4.157; 11.AH.4.158; 11.AH.4.196; 11.AH.4.223; 11.AH.4.240; 11.AH.4.244; 11.AH.4.243; 11.AH.4.247; 11.AH.5.157; 11.AH.5.158; 11.AH.5.196; 11.AH.5.223; 11.AH.5.240; 11.AH.5.244; 11.AH.5.243; 11.AH.5.247; 11.AH.7.157; 11.AH.7.158; 11.AH.7.196; 11.AH.7.223; 11.AH.7.240; 11.AH.7.244; 11.AH.7.243; 11.AH.7.247; 11.AH.15.157; 11.AH.15.158; 11.AH.15.196; 11.AH.15.223; 11.AH.15.240; 11.AH.15.244; 11.AH.15.243; 11.AH.15.247; 11.AH.16.157; 11.AH.16.158; 11.AH.16.196; 11.AH.16.223; 11.AH.16.240; 11.AH.16.244; 11.AH.16.243; 11.AH.16.247; 11.AH.18.157; 11.AH.18.158; 11.AH.18.196; 11.AH.18.223; 11.AH.18.240; 11.AH.18.244; 11.AH.18.243; 11.AH.18.247; 11.AH.26.157; 11.AH.26.158; 11.AH.26.196; 11.AH.26.223; 11.AH.26.240; 11.AH.26.244; 11.AH.26.243; 11.AH.26.247; 11.AH.27.157; 11.AH.27.158; 11.AH.27.196; 11.AH.27.223; 11.AH.27.240; 11.AH.27.244; 11.AH.27.243; 11.AH.27.247; 11.AH.29.157; 11.AH.29.158; 11.AH.29.196; 11.AH.29.223; 11.AH.29.240; 11.AH.29.244; 11.AH.29.243; 11.AH.29.247; 11.AH.54.157; 11.AH.54.158; 11.AH.54.196; 11.AH.54.223; 11.AH.54.240; 11.AH.54.244; 11.AH.54.243; 11.AH.55.157;

TABLE 7-continued

11.AH.55.158; 11.AH.55.196; 11.AH.55.223; 11.AH.55.240;
11.AH.55.244; 11.AH.55.243; 11.AH.55.247; 11.AH.56.157;
11.AH.56.158; 11.AH.56.196; 11.AH.56.223; 11.AH.56.240;
11.AH.56.244; 11.AH.56.243; 11.AH.56.247; 11.AH.157.157;
11.AH.157.158; 11.AH.157.196; 11.AH.157.223; 11.AH.157.240;
11.AH.157.244; 11.AH.157.243; 11.AH.157.247; 11.AH.196.157;
11.AH.196.158; 11.AH.196.196; 11.AH.196.223; 11.AH.196.240;
11.AH.196.244; 11.AH.196.243; 11.AH.196.247; 11.AH.223.157;
11.AH.223.158; 11.AH.223.196; 11.AH.223.223; 11.AH.223.240;
11.AH.223.244; 11.AH.223.243; 11.AH.223.247; 11.AH.240.157;
11.AH.240.158; 11.AH.240.196; 11.AH.240.223; 11.AH.240.240;
11.AH.240.244; 11.AH.240.243; 11.AH.240.247; 11.AH.244.157;
11.AH.244.158; 11.AH.244.196; 11.AH.244.223; 11.AH.244.240;
11.AH.244.244; 11.AH.244.243; 11.AH.244.247; 11.AH.247.157;
11.AH.247.158; 11.AH.247.196; 11.AH.247.223; 11.AH.247.240;
11.AH.247.244; 11.AH.247.243; 11.AH.247.247;
Prodrugs of 11.AJ 11.AJ.4.157; 11.AJ.4.158; 11.AJ.4.196; 11.AJ.4.223; 11.AJ.4.240;
11.AJ.4.244; 11.AJ.4.243; 11.AJ.4.247; 11.AJ.5.157; 11.AJ.5.158;
11.AJ.5.196; 11.AJ.5.223; 11.AJ.5.240; 11.AJ.5.244; 11.AJ.5.243;
11.AJ.5.247; 11.AJ.7.157; 11.AJ.7.158; 11.AJ.7.196; 11.AJ.7.223;
11.AJ.7.240; 11.AJ.7.244; 11.AJ.7.243; 11.AJ.7.247; 11.AJ.15.157;
11.AJ.15.158; 11.AJ.15.196; 11.AJ.15.223; 11.AJ.15.240; 11.AJ.15.244;
11.AJ.15.243; 11.AJ.15.247; 11.AJ.16.157; 11.AJ.16.158; 11.AJ.16.196;
11.AJ.16.223; 11.AJ.16.240; 11.AJ.16.244; 11.AJ.16.243; 11.AJ.16.247;
11.AJ.18.157; 11.AJ.18.158; 11.AJ.18.196; 11.AJ.18.223; 11.AJ.18.240;
11.AJ.18.244; 11.AJ.18.243; 11.AJ.18.247; 11.AJ.26.157; 11.AJ.26.158;
11.AJ.26.196; 11.AJ.26.223; 11.AJ.26.240; 11.AJ.26.244; 11.AJ.26.243;
11.AJ.26.247; 11.AJ.27.157; 11.AJ.27.158; 11.AJ.27.196; 11.AJ.27.223;
11.AJ.27.240; 11.AJ.27.244; 11.AJ.27.243; 11.AJ.27.247; 11.AJ.29.157;
11.AJ.29.158; 11.AJ.29.196; 11.AJ.29.223; 11.AJ.29.240; 11.AJ.29.244;
11.AJ.29.243; 11.AJ.29.247; 11.AJ.54.157; 11.AJ.54.158; 11.AJ.54.196;
11.AJ.54.223; 11.AJ.54.240; 11.AJ.54.244; 11.AJ.54.243; 11.AJ.54.247;
11.AJ.55.157; 11.AJ.55.158; 11.AJ.55.196; 11.AJ.55.223; 11.AJ.55.240;
11.AJ.55.244; 11.AJ.55.243; 11.AJ.55.247; 11.AJ.56.157; 11.AJ.56.158;
11.AJ.56.196; 11.AJ.56.223; 11.AJ.56.240; 11.AJ.56.244; 11.AJ.56.243;
11.AJ.56.247; 11.AJ.157.157; 11.AJ.157.158; 11.AJ.157.196;
11.AJ.157.223; 11.AJ.157.240; 11.AJ.157.244; 11.AJ.157.243;
11.AJ.157.247; 11.AJ.196.157; 11.AJ.196.158; 11.AJ.196.196;
11.AJ.196.223; 11.AJ.196.240; 11.AJ.196.244; 11.AJ.196.243;
11.AJ.196.247; 11.AJ.223.157; 11.AJ.223.158; 11.AJ.223.196;
11.AJ.223.223; 11.AJ.223.240; 11.AJ.223.244; 11.AJ.223.243;
11.AJ.223.247; 11.AJ.240.157; 11.AJ.240.158; 11.AJ.240.196;
11.AJ.240.223; 11.AJ.240.240; 11.AJ.240.244; 11.AJ.240.243;
11.AJ.240.247; 11.AJ.244.157; 11.AJ.244.158; 11.AJ.244.196;
11.AJ.244.223; 11.AJ.244.240; 11.AJ.244.244; 11.AJ.244.243;
11.AJ.244.247; 11.AJ.247.157; 11.AJ.247.158; 11.AJ.247.196;
11.AJ.247.223; 11.AJ.247.240; 11.AJ.247.244; 11.AJ.247.243;
11.AJ.247.247;
Prodrugs of 11.AN 11.AN.4.157; 11.AN.4.158; 11.AN.4.196; 11.AN.4.223; 11.AN.4.240;
11.AN.4.244; 11.AN.4.243; 11.AN.4.247; 11.AN.5.157; 11.AN.5.158;
11.AN.5.196; 11.AN.5.223; 11.AN.5.240; 11.AN.5.244; 11.AN.5.243;
11.AN.5.247; 11.AN.7.157; 11.AN.7.158; 11.AN.7.196; 11.AN.7.223;
11.AN.7.240; 11.AN.7.244; 11.AN.7.243; 11.AN.7.247; 11.AN.15.157;
11.AN.15.158; 11.AN.15.196; 11.AN.15.223; 11.AN.15.240; 11.AN.15.244;
11.AN.15.243; 11.AN.15.247; 11.AN.16.157; 11.AN.16.158; 11.AN.16.196;
11.AN.16.223; 11.AN.16.240; 11.AN.16.244; 11.AN.16.243; 11.AN.16.247;
11.AN.18.157; 11.AN.18.158; 11.AN.18.196; 11.AN.18.223; 11.AN.18.240;
11.AN.18.244; 11.AN.18.243; 11.AN.18.247; 11.AN.26.157; 11.AN.26.158;
11.AN.26.196; 11.AN.26.223; 11.AN.26.240; 11.AN.26.244; 11.AN.26.243;
11.AN.26.247; 11.AN.27.157; 11.AN.27.158; 11.AN.27.196; 11.AN.27.223;
11.AN.27.240; 11.AN.27.244; 11.AN.27.243; 11.AN.27.247; 11.AN.29.157;
11.AN.29.158; 11.AN.29.196; 11.AN.29.223; 11.AN.29.240; 11.AN.29.244;
11.AN.29.243; 11.AN.29.247; 11.AN.54.157; 11.AN.54.158; 11.AN.54.196;
11.AN.54.223; 11.AN.54.240; 11.AN.54.244; 11.AN.54.243; 11.AN.54.247;
11.AN.55.157; 11.AN.55.158; 11.AN.55.196; 11.AN.55.223; 11.AN.55.240;
11.AN.55.244; 11.AN.55.243; 11.AN.55.247; 11.AN.56.157; 11.AN.56.158;
11.AN.56.196; 11.AN.56.223; 11.AN.56.240; 11.AN.56.244; 11.AN.56.243;
11.AN.56.247; 11.AN.157.157; 11.AN.157.158; 11.AN.157.196;
11.AN.157.223; 11.AN.157.240; 11.AN.157.244; 11.AN.157.243;
11.AN.157.247; 11.AN.196.157; 11.AN.196.158; 11.AN.196.196;
11.AN.196.223; 11.AN.196.240; 11.AN.196.244; 11.AN.196.243;
11.AN.196.247; 11.AN.223.157; 11.AN.223.158; 11.AN.223.196;
11.AN.223.223; 11.AN.223.240; 11.AN.223.244; 11.AN.223.243;
11.AN.223.247; 11.AN.240.157; 11.AN.240.158; 11.AN.240.196;
11.AN.240.223; 11.AN.240.240; 11.AN.240.244; 11.AN.240.243;
11.AN.240.247; 11.AN.244.157; 11.AN.244.158; 11.AN.244.196;
11.AN.244.223; 11.AN.244.240; 11.AN.244.244; 11.AN.244.243;
11.AN.244.247; 11.AN.247.157; 11.AN.247.158; 11.AN.247.196;
11.AN.247.223; 11.AN.247.240; 11.AN.247.244; 11.AN.247.243;
11.AN.247.247;
Prodrugs of 11.AP 11.AP.4.157; 11.AP.4.158; 11.AP.4.196; 11.AP.4.223; 11.AP.4.240;
11.AP.4.244; 11.AP.4.243; 11.AP.4.247; 11.AP.5.157; 11.AP.5.158;
11.AP.5.196; 11.AP.5.223; 11.AP.5.240; 11.AP.5.244; 11.AP.5.243;
11.AP.5.247; 11.AP.7.157; 11.AP.7.158; 11.AP.7.196; 11.AP.7.223;
11.AP.7.240; 11.AP.7.244; 11.AP.7.243; 11.AP.7.247; 11.AP.15.157;
11.AP.15.158; 11.AP.15.196; 11.AP.15.223; 11.AP.15.240;
11.AP.15.244; 11.AP.15.243; 11.AP.15.247; 11.AP.16.157;
11.AP.16.158; 11.AP.16.196; 11.AP.16.223; 11.AP.16.240;
11.AP.16.244; 11.AP.16.243; 11.AP.16.247; 11.AP.18.157;
11.AP.18.158; 11.AP.18.196; 11.AP.18.223; 11.AP.18.240;
11.AP.18.244; 11.AP.18.243; 11.AP.18.247; 11.AP.26.157;
11.AP.26.158; 11.AP.26.196; 11.AP.26.223; 11.AP.26.240;
11.AP.26.244; 11.AP.26.243; 11.AP.26.247; 11.AP.27.157;
11.AP.27.158; 11.AP.27.196; 11.AP.27.223; 11.AP.27.240;
11.AP.27.244; 11.AP.27.243; 11.AP.27.247; 11.AP.29.157;
11.AP.29.158; 11.AP.29.196; 11.AP.29.223; 11.AP.29.240;
11.AP.29.244; 11.AP.29.243; 11.AP.29.247; 11.AP.54.157;
11.AP.54.158; 11.AP.54.196; 11.AP.54.223; 11.AP.54.240;
11.AP.54.244; 11.AP.54.243; 11.AP.54.247; 11.AP.55.157;
11.AP.55.158; 11.AP.55.196; 11.AP.55.223; 11.AP.55.240;
11.AP.55.244; 11.AP.55.243; 11.AP.55.247; 11.AP.56.157;
11.AP.56.158; 11.AP.56.196; 11.AP.56.223; 11.AP.56.240;
11.AP.56.244; 11.AP.56.243; 11.AP.56.247; 11.AP.157.157;
11.AP.157.158; 11.AP.157.196; 11.AP.157.223; 11.AP.157.240;
11.AP.157.244; 11.AP.157.243; 11.AP.157.247; 11.AP.196.157;
11.AP.196.158; 11.AP.196.196; 11.AP.196.223; 11.AP.196.240;
11.AP.196.244; 11.AP.196.243; 11.AP.196.247; 11.AP.223.157;
11.AP.223.158; 11.AP.223.196; 11.AP.223.223; 11.AP.223.240;
11.AP.223.244; 11.AP.223.243; 11.AP.223.247; 11.AP.240.157;
11.AP.240.158; 11.AP.240.196; 11.AP.240.223; 11.AP.240.240;
11.AP.240.244; 11.AP.240.243; 11.AP.240.247; 11.AP.244.157;
11.AP.244.158; 11.AP.244.196; 11.AP.244.223; 11.AP.244.240;
11.AP.244.244; 11.AP.244.243; 11.AP.244.247; 11.AP.247.157;
11.AP.247.158; 11.AP.247.196; 11.AP.247.223; 11.AP.247.240;
11.AP.247.244; 11.AP.247.243; 11.AP.247.247;
Prodrugs of 11.AZ 11.AZ.4.157; 11.AZ.4.158; 11.AZ.4.196; 11.AZ.4.223; 11.AZ.4.240;
11.AZ.4.244; 11.AZ.4.243; 11.AZ.4.247; 11.AZ.5.157; 11.AZ.5.158;
11.AZ.5.196; 11.AZ.5.223; 11.AZ.5.240; 11.AZ.5.244; 11.AZ.5.243;
11.AZ.5.247; 11.AZ.7.157; 11.AZ.7.158; 11.AZ.7.196; 11.AZ.7.223;
11.AZ.7.240; 11.AZ.7.244; 11.AZ.7.243; 11.AZ.7.247; 11.AZ.15.157;
11.AZ.15.158; 11.AZ.15.196; 11.AZ.15.223; 11.AZ.15.240;
11.AZ.15.244; 11.AZ.15.243; 11.AZ.15.247; 11.AZ.16.157;
11.AZ.16.158; 11.AZ.16.196; 11.AZ.16.223; 11.AZ.16.240;
11.AZ.16.244; 11.AZ.16.243; 11.AZ.16.247; 11.AZ.18.157;
11.AZ.18.158; 11.AZ.18.196; 11.AZ.18.223; 11.AZ.18.240;
11.AZ.18.244; 11.AZ.18.243; 11.AZ.18.247; 11.AZ.26.157;
11.AZ.26.158; 11.AZ.26.196; 11.AZ.26.223; 11.AZ.26.240;
11.AZ.26.244; 11.AZ.26.243; 11.AZ.26.247; 11.AZ.27.157;
11.AZ.27.158; 11.AZ.27.196; 11.AZ.27.223; 11.AZ.27.240;
11.AZ.27.244; 11.AZ.27.243; 11.AZ.27.247; 11.AZ.29.157;
11.AZ.29.158; 11.AZ.29.196; 11.AZ.29.223; 11.AZ.29.240;
11.AZ.29.244; 11.AZ.29.243; 11.AZ.29.247; 11.AZ.54.157;
11.AZ.54.158; 11.AZ.54.196; 11.AZ.54.223; 11.AZ.54.240;
11.AZ.54.244; 11.AZ.54.243; 11.AZ.54.247; 11.AZ.55.157;
11.AZ.55.158; 11.AZ.55.196; 11.AZ.55.223; 11.AZ.55.240;
11.AZ.55.244; 11.AZ.55.243; 11.AZ.55.247; 11.AZ.56.157;
11.AZ.56.158; 11.AZ.56.196; 11.AZ.56.223; 11.AZ.56.240;
11.AZ.56.244; 11.AZ.56.243; 11.AZ.56.247; 11.AZ.157.157;
11.AZ.157.158; 11.AZ.157.196; 11.AZ.157.223; 11.AZ.157.240;
11.AZ.157.244; 11.AZ.157.243; 11.AZ.157.247; 11.AZ.196.157;
11.AZ.196.158; 11.AZ.196.196; 11.AZ.196.223; 11.AZ.196.240;
11.AZ.196.244; 11.AZ.196.243; 11.AZ.196.247; 11.AZ.223.157;
11.AZ.223.158; 11.AZ.223.196; 11.AZ.223.223; 11.AZ.223.240;
11.AZ.223.244; 11.AZ.223.243; 11.AZ.223.247; 11.AZ.240.157;
11.AZ.240.158; 11.AZ.240.196; 11 AZ.240.223; 11 AZ.240.240;
11.AZ.240.244; 11.AZ.240.243; 11.AZ.240.247; 11.AZ.244.157;
11.AZ.244.158; 11.AZ.244.196; 11.AZ.244.223; 11.AZ.244.240;
11.AZ.244.244; 11.AZ.244.243; 11.AZ.244.247; 11.AZ.247.157;
11.AZ.247.158; 11.AZ.247.196; 11.AZ.247.223; 11.AZ.247.240;
11.AZ.247.244; 11.AZ.247.243; 11.AZ.247.247;

TABLE 7-continued

Prodrugs of 11.BF

11.BF.4.157; 11.BF.4.158; 11.BF.4.196; 11.BF.4.223; 11.BF.4.240;
11.BF.4.244; 11.BF.4.243; 11.BF.4.247; 11.BF.5.157; 11.BF.5.158;
11.BF.5.196; 11.BF.5.223; 11.BF.5.240; 11.BF.5.244; 11.BF.5.243;
11.BF.5.247; 11.BF.7.157; 11.BF.7.158; 11.BF.7.196; 11.BF.7.223;
11.BF.7.240; 11.BF.7.244; 11.BF.7.243; 11.BF.7.247; 11.BF.15.157;
11.BF.15.158; 11.BF.15.196; 11.BF.15.223; 11.BF.15.240; 11.BF.15.244;
11.BF.15.243; 11.BF.15.247; 11.BF.16.157; 11.BF.16.158; 11.BF.16.196;
11.BF.16.223; 11.BF.16.240; 11.BF.16.244; 11.BF.16.243; 11.BF.16.247;
11.BF.18.157; 11.BF.18.158; 11.BF.18.196; 11.BF.18.223; 11.BF.18.240;
11.BF.18.244; 11.BF.18.243; 11.BF.18.247; 11.BF.26.157; 11.BF.26.158;
11.BF.26.196; 11.BF.26.223; 11.BF.26.240; 11.BF.26.244; 11.BF.26.243;
11.BF.26.247; 11.BF.27.157; 11.BF.27.158; 11.BF.27.196; 11.BF.27.223;
11.BF.27.240; 11.BF.27.244; 11.BF.27.243; 11.BF.27;247; 11.BF.29.157;
11.BF.29.158; 11.BF.29.196; 11.BF.29.223; 11.BF.29.240; 11.BF.29.244;
11.BF.29.243; 11.BF.29.247; 11.BF.54.157; 11.BF.54.158; 11.BF.54.196;
11.BF.54.223; 11.BF.554.240; 11.BF.54.244; 11.BF.54.243; 11.BF.54.247;
11.BF.55.157; 11.BF.55.158; 11.BF.55.196; 11.BF.55.223; 11.BF.55.240;
11.BF.55.244; 11.BF.55.243; 11.BF.55.247; 11.BF.56.157; 11.BF.56.158;
11.BF.56.196; 11.BF.56.223; 11.BF.56.240; 11.BF.56.244; 11.BF.56.243;
11.BF.56.247; 11.BF.157.157; 11.BF.157.158; 11.BF.157.196;
11.BF.157.223; 11.BF.157.240; 11.BF.157.244; 11.BF.157.243;
11.BF.157.147; 11.BF.196.157; 11.BF.196.158; 11.BF.196.196;
11.BF.196.223; 11.BF.196.240; 11.BF.196.244; 11.BF.196.243;
11.BF.196.247; 11.BF.223.157; 11.BF.223.158; 11.BF.223.196;
11.BF.223.223; 11.BF.223.240; 11.BF.223.244; 11.BF.223.243;
11.BF.223.247; 11.BF.240.157; 11.BF.240.158; 11.BF.240.196;
11.BF.240.247; 11.BF.240.240; 11.BF.240.244; 11.BF.240.243;
11.BF.240.247; 11.BF.244.157; 11.BF.244.158; 11.BF.244.196;
11.BF.244.223; 11.BF.244.240; 11.BF.244.244; 11.BF.244.243;
11.BF.244.247; 11.BF.247.157; 11.BF.247.158; 11.BF.247.196;
11.BF.247.223; 11.BF.247.240; 11.BF.247.244; 11.BF.247.243;
11.BF.247.247;

Prodrugs of 11.CI

11.CI.4.157; 11.CI.4.158; 11.CI.4.196; 11.CI.4.223; 11.CI.4.240;
11.CI.4.244; 11.CI.4.243; 11.CI.4.247; 11.CI.5.157; 11.CI.5.158;
11.CI.5.196; 11.CI.5.223; 11.CI.5.240; 11.CI.5.244; 11.CI.5.243;
11.CI.5.247; 11.CI.7.157; 11.CI.7.158; 11.CI.7.196; 11.CI.7.223;
11.CI.7.240; 11.CI.7.244; 11.CL.7.243; 11.CI.7.247; 11.CI.15.157;
11.CI.15.158; 11.CI.15.196; 11.CI.15.223; 11.CI.15.240; 11.CI.15.244;
11.CI.15.243; 11.CI.15.247; 11.CI.16.157; 11.CI.16.158; 11.CI.16.196;
11.CI.16.223; 11.CI.16.240; 11.CI.16.244; 11.CI.16.243; 11.CI.16.247;
11.CI.18.157; 11.CI.18.196; 11.CI.18.223; 11.CI.18.240;
11.CI.18.244; 11.CI.18.243; 11.CI.18.247; 11.CL.26.157; 11.CI.26.158;
11.CI.26.196; 11.CI.26.223; 11.CI.26.240; 11.CI.26.244; 11.CI.26.243;
11.CI.26.247; 11.CI.27.157; 11.CI.27.158; 11.CI.27.196; 11.CI.27.223;
11.CI.27.240; 11.CI.27.244; 11.CI.27.243; 11.CI.27.247; 11.CI.29.157;
11.CI.29.158; 11.CI.29.196; 11.CI.29.223; 11.CI.29.240; 11.CI.29.244;
11.CI.29.243; 11.CI.29.247; 11.CL.54.157; 11.CI.54.158; 11.CI.54.196;
11.CI.54.223; 11.CI.54.240; 11.CI.54.244; 11.CI.54.243; 11.CI.54.247;
11.CI.55.157; 11.CI.55.158; 11.CI.55.196; 11.CI.55.223; 11.CI.55.240;
11.CI.55.244; 11.CI.55.243; 11.CI.55.247; 11.CI.56.157; 11.CI.56.158;
11.CI.56.196; 11.CI.56.223; 11.CI.56.240; 11.CI.56.244; 11.CI.56.243;
11.CI.56.247; 11.CI.157.157; 11.CI.157.158; 11.CI.157.196;
11.CI.157.223; 11.CL.157.240; 11.CI.157.244; 11.CI.157.243;
11.CI.157.247; 11.CI.196.157; 11.CI.196.158; 11.CI.196.196;
11.CI.196.323; 11.CI.196.240; 11.CI.196.244; 11.CI.196.243;
11.CI.196.247; 11.CI.223.157; 11.CI.223.158; 11.CL.223.196;
11.CI.223.223; 11.CI.223.240; 11.CI.223.244; 11.CI.223.243;
11.CI.223.247; 11.CI.240.157; 11.CI.240.158; 11.CI.240.196;
11.CI.240.223; 11.CI.240.240; 11.CI.240.244; 11.CI.240.243;
11.CI.240.247; 11.CI.244.157; 11.CI.244.158; 11.CL.244.196;
11.CI.244.223; 11.CI.244.240; 11.CI.244.244; 11.CI.244.243;
11.CL.244.247; 11.CI.247.157; 11.CL.247.158; 11.CL.247.196;
11.CI.247.223; 11.CI.247.240; 11.CI.247.244; 11.CI.247.243;
11.CI.247.247;

Prodrugs of 11.CO

11.CO.4.157; 11.CO.4.158; 11.CO.4.196; 11.CO.4.223; 11.CO.4.240;
11.CO.4.244; 11.CO.4.243; 11.CO.4.247; 11.CO.5.157; 11.CO.5.158;
11.CO.5.196; 11.CO.5.223; 11.CO.5.240; 11.CO.5.244; 11.CO.5.243;
11.CO.5.247; 11.CO.7.157; 11.CO.7.158; 11.CO.7.196; 11.CO.7.223;
11.CO.7.240; 11.CO.7.244; 11.CO.7.243; 11.CO.7.247; 11.CO.15.157;
11.CO.15.158; 11.CO.15.196; 11.CO.15.223; 11.CO.15.240;
11.CO.15.244; 11.CO.15.243; 11.CO.15.247; 11.CO.16.157;
11.CO.16.158; 11.CO.16.196; 11.CO.16.223; 11.CO.16.240;
11.CO.16.244; 11.CO.16.243; 11.CO.16.247; 11.CO.18.157;
11.CO.18.158; 11.CO.18.196; 11.CO.18.223; 11.CO.18.240;
11.CO.18.244; 11.CO.18.243; 11.CO.18.247; 11.CO.26.157;
11.CO.26.158; 11.CO.26.196; 11.CO.26.223; 11.CO.26.240;
11.CO.26.244; 11.CO.26.243; 11.CO.26.247; 11.CO.27.157;
11.CO.27.158; 11.CO.27.196; 11.CO.27.223; 11.CO.27.240;
11.CO.27.244; 11.CO.27.243; 11.CO.27.247; 11.CO.29.157;
11.CO.29.158; 11.CO.29.196; 11.CO.29.223; 11.CO.29.240;
11.CO.29.244; 11.CO.29.243; 11.CO.29.247; 11.CO.54.157;
11.CO.54.158; 11.CO.54.196; 11.CO.54.223; 11.CO.54.240;
11.CO.54.244; 11.CO.54.243; 11.CO.54.247; 11.CO.55.157;
11.CO.55.158; 11.CO.55.196; 11.CO.55.223; 11.CO.55.240;
11.CO.55.244; 11.CO.55.243; 11.CO.55.247; 11.CO.56.157;
11.CO.56.158; 11.CO.56.196; 11.CO.56.223; 11.CO.56.240;
11.CO.56.244; 11.CO.56.243; 11.CO.56.247; 11.CO.157.157;
11.CO.157.158; 11.CO.157.196; 11.CO.157.223; 11.CO.157.240;
11.CO.157.244; 11.CO.157.243; 11.CO.157.247; 11.CO.196.157;
11.CO.196.158; 11.CO.196.196; 11.CO.196.223; 11.CO.196.240;
11.CO.196.244; 11.CO.196.243; 11.CO.196.247; 11.CO.223.157;
11.CO.223.158; 11.CO.223.196; 11.CO.223.223; 11.CO.223.240;
11.CO.223.244; 11.CO.223.243; 11.CO.223.247; 11.CO.240.157;
11.CO.240.158; 11.CO.240.196; 11.CO.240.223; 11.CO.240.240;
11.CO.240.244; 11.CO.240.243; 11.CO.240.247; 11.CO.244.157;
11.CO.244.158; 11.CO.244.196; 11.CO.244.223; 11.CO.244.240;
11.CO.244.244; 11.CO.244.243; 11.CO.244.247; 11.CO.247.157;
11.CO.247.158; 11.CO.247.196; 11.CO.247.223; 11.CO.247.240;
11.CO.247.244; 11.CO.247.243; 11.CO.247.247;

Prodrugs of 12.AH

12.AH.4.157; 12.AH.4.158; 12.AH.4.196; 12.AH.4.223; 12.AH.4.240;
12.AH.4.244; 12.AH.4.243; 12.AH.4.247; 12.AH.5.157; 12.AH.5.158;
12.AH.5.196; 12.AH.5.223; 12.AH.5.240; 12.AH.5.244; 12.AH.5.243;
12.AH.5.247; 12.AH.7.157; 12.AH.7.158; 12.AH.7.196; 12.AH.7.223;
12.AH.7.240; 12.AH.7.244; 12.AH.7.243; 12.AH.7.247; 12.AH.15.157;
12.AH.15.158; 12.AH.15.196; 12.AH.15.223; 12.AH.15.240;
12.AH.15.244; 12.AH.15.243; 12.AH.15.247; 12.AH.16.157;
12.AH.16.158; 12.AH.16.196; 12.AH.16.223; 12.AH.16.240;
12.AH.16.244; 12.AH.16.243; 12.AH.16.247; 12.AH.18.157;
12.AH.18.158; 12.AH.18.196; 12.AH.18.223; 12.AH.18.240;
12.AH.18.244; 12.AH.18.243; 12.AH.18.247; 12.AH.26.157;
12.AH.26.158; 12.AH.26.196; 12.AH.26.223; 12.AH.26.240;
12.AH.26.244; 12.AH.26.243; 12.AH.26.247; 12.AH.27.157;
12.AH.27.158; 12.AH.27.196; 12.AH.27.223; 12.AH.27.240;
12.AH.27.244; 12.AH.27.243; 12.AH.27.247; 12.AH.29.157;
12.AH.29.158; 12.AH.29.196; 12.AH.29.223; 12.AH.29.240;
12.AH.29.244; 12.AH.29.243; 12.AH.29.247; 12.AH.54.157;
12.AH.54.158; 12.AH.54.196; 12.AH.54.223; 12.AH.54.240;
12.AH.54.244; 12.AH.54.243; 12.AH.54.247; 12.AH.55.157;
12.AH.55.158; 12.AH.55.196; 12.AH.55.223; 12.AH.55.240;
12.AH.55.244; 12.AH.55.243; 12.AH.55.247; 12.AH.56.157;
12.AH.56.158; 12.AH.56.196; 12.AH.56.223; 12.AH.56.240;
12.AH.56.244; 12.AH.56.243; 12.AH.56.247; 12.AH.157.157;
12.AH.157.158; 12.AH.157.196; 12.AH.157.223; 12.AH.157.240;
12.AH.157.244; 12.AH.157.243; 12.AH.157.247; 12.AH.196.157;
12.AH.196.158; 12.AH.196.196; 12.AH.196.223; 12.AH.196.240;
12.AH.196.244; 12.AH.196.243; 12.AH.196.247; 12.AH.223.157;
12.AH.223.158; 12.AH.223.196; 12.AH.223.223; 12.AH.223.240;
12.AH.223.244; 12.AH.223.243; 12.AH.223.247; 12.AH.240.157;
12.AH.240.158; 12.AH.240.196; 12.AH.240.223; 12.AH.240.240;
12.AH.240.244; 12.AH.240.243; 12.AH.240.247; 12.AH.244.157;
12.AH.244.158; 12.AH.244.196; 12.AH.244.223; 12.AH.244.240;
12.AH.244.244; 12.AH.244.243; 12.AH.244.247; 12.AH.247.157;
12.AH.247.158; 12.AH.247.196; 12.AH.247.223; 12.AH.247.240;
12.AH.247.244; 12.AH.247.243; 12.AH.247.247;

Prodrugs of 12.AJ

12.AJ.4.157; 12.AJ.4.158; 12.AJ.4.196; 12.AJ.4.223; 12.AJ.4.240;
12.AJ.4.244; 12.AJ.4.243; 12.AJ.4.247; 12.AJ.5.157; 12.AJ.5.158;
12.AJ.5.196; 12.AJ.5.223; 12.AJ.5.240; 12.AJ.5.244; 12.AJ.5.243;
12.AJ.5.247; 12.AJ.7.157; 12.AJ.7.158; 12.AJ.7.196; 12.AJ.7.223;
12.AJ.7.240; 12.AJ.7.244; 12.AJ.7.243; 12.AJ.7.247; 12.AJ.15.157;
12.AJ.15.158; 12.AJ.15.196; 12.AJ.15.223; 12.AJ.15.240; 12.AJ.15.244;
12.AJ.15.243; 12.AJ.15.247; 12.AJ.16.157; 12.AJ.16.158; 12.AJ.16.196;
12.AJ.16.223; 12.AJ.16.240; 12.AJ.16.244; 12.AJ.16.243; 12.AJ.16.247;
12.AJ.18.157; 12.AJ.18.158; 12.AJ.18.196; 12.AJ.18.223; 12.AJ.18.240;
12.AJ.18.244; 12.AJ.18.243; 12.AJ.18.247; 12.AJ.26.157; 12.AJ.26.158;
12.AJ.26.196; 12.AJ.26.223; 12.AJ.26.240; 12.AJ.26.244; 12.AJ.26.243;
12.AJ.26.247; 12.AJ.27.157; 12.AJ.27.158; 12.AJ.27.196; 12.AJ.27.223;
12.AJ.27.240; 12.AJ.27.244; 12.AJ.27.243; 12.AJ.27.247; 12.AJ.29.157;
12.AJ.29.158; 12.AJ.29.196; 12.AJ.29.223; 12.AJ.29.240; 12.AJ.29.244;

TABLE 7-continued

12.AJ.29.243; 12.AJ.29.247; 12.AJ.54.157; 12.AJ.54.158; 12.AJ.54.196;
12.AJ.54.223; 12.AJ.54.240; 12.AJ.54.244; 12.AJ.54.243; 12.AJ.54.247;
12.AJ.55.157; 12.AJ.55.158; 12.AJ.55.196; 12.AJ.55.223; 12.AJ.55.240;
12.AJ.55.244; 12.AJ.55.243; 12.AJ.55.247; 12.AJ.56.157; 12.AJ.56.158;
12.AJ.56.196; 12.AJ.56.223; 12.AJ.56.240; 12.AJ.56.244; 12.AJ.56.243;
12.AJ.56.247; 12.AJ.157.157; 12.AJ.157.158; 12.AJ.157.196;
12.AJ.157.223; 12.AJ.157.240; 12.AJ.157.244; 12.AJ.157.243;
12.AJ.157.247; 12.AJ.196.157; 12.AJ.196.158; 12.AJ.196.196;
12.AJ.196.223; 12.AJ.196.240; 12.AJ.196.244; 12.AJ.196.243;
12.AJ.196.247; 12.AJ.223.157; 12.AJ.223.158; 12.AJ.223.196;
12.AJ.223.223; 12.AJ.223.240; 12.AJ.223.244; 12.AJ.223.243;
12.AJ.223.247; 12.AJ.240.157; 12.AJ.240.158; 12.AJ.240.196;
12.AJ.240.223; 12.AJ.240.240; 12.AJ.240.244; 12.AJ.240.243;
12.AJ.240.247; 12.AJ.244.157; 12.AJ.244.158; 12.AJ.244.196;
12.AJ.244.223; 12.AJ.244.240; 12.AJ.244.244; 12.AJ.244.243;
12.AJ.244.247; 12.AJ.247.157; 12.AJ.247.158; 12.AJ.247.196;
12.AJ.247.223; 12.AJ.247.240; 12.AJ.247.244; 12.AJ.247.243;
12.AJ.247.247;
Prodrugs of 12.AN 12.AN.4.157; 12.AN.4.158; 12.AN.4.196; 12.AN.4.223; 12.AN.4.240;
12.AN.4.244; 12.AN.4.243; 12.AN.4.247; 12.AN.5.157; 12.AN.5.158;
12.AN.5.196; 12.AN.5.223; 12.AN.5.240; 12.AN.5.244; 12.AN.5.243;
12.AN.5.247; 12.AN.7.157; 12.AN.7.158; 12.AN.7.196; 12.AN.7.223;
12.AN.7.240; 12.AN.7.244; 12.AN.7.243; 12.AN.7.247; 12.AN.15.157;
12.AN.15.158; 12.AN.15.196; 12.AN.15.223; 12.AN.15.240;
12.AN.15.244; 12.AN.15.243; 12.AN.15.247; 12.AN.16.157;
12.AN.16.158; 12.AN.16.196; 12.AN.16.223; 12.AN.16.240;
12.AN.16.244; 12.AN.16.243; 12.AN.16.247; 12.AN.18.157;
12.AN.18.158; 12.AN.18.196; 12.AN.18.223; 12.AN.18.240;
12.AN.18.244; 12.AN.18.243; 12.AN.18.247; 12.AN.26.157;
12.AN.26.158; 12.AN.26.196; 12.AN.26.223; 12.AN.26.240;
12.AN.26.244; 12.AN.26.243; 12.AN.26.247; 12.AN.27.157;
12.AN.27.158; 12.AN.27.196; 12.AN.27.223; 12.AN.27.240;
12.AN.27.244; 12.AN.27.243; 12.AN.27.247; 12.AN.29.157;
12.AN.29.158; 12.AN.29.196; 12.AN.29.223; 12.AN.29.240;
12.AN.29.244; 12.AN.29.243; 12.AN.29.247; 12.AN.54.157;
12.AN.54.158; 12.AN.54.196; 12.AN.54.223; 12.AN.54.240;
12.AN.54.244; 12.AN.54.243; 12.AN.54.247; 12.AN.55.157;
12.AN.55.158; 12.AN.55.196; 12.AN.55.223; 12.AN.55.240;
12.AN.55.244; 12.AN.55.243; 12.AN.55.247; 12.AN.56.157;
12.AN.56.158; 12.AN.56.196; 12.AN.56.223; 12.AN.56.240;
12.AN.56.244; 12.AN.56.243; 12.AN.56.247; 12.AN.157.157;
12.AN.157.158; 12.AN.157.196; 12;AN.157.223; 12.AN.157.240;
12.AN.157.244; 12.AN.157.243; 12.AN.157.247; 12.AN.196.157;
12.AN.196.158; 12.AN.196.196; 12.AN.196.223; 12.AN.196.240;
12.AN.196.244; 12.AN.196.243; 12.AN.196.247; 12.AN.223.157;
12.AN.223.158; 12.AN.223.196; 12.AN.223.223; 12.AN.223.240;
12.AN.223.244; 12.AN.223.243; 12.AN.223.247; 12.AN.240.157;
12.AN.240.158; 12.AN.240.196; 12.AN.240.223; 12.AN.240.240;
12.AN.240.244; 12.AN.240.243; 12.AN.240.247; 12.AN.244.157;
12.AN.244.158; 12.AN.244.196; 12.AN.244.223; 12.AN.244.240;
12.AN.244.244; 12.AN.244.243; 12.AN.244.247; 12.AN.247.157;
12.AN.247.158; 12.AN.247.196; 12.AN.247.223; 12.AN.247.240;
12.AN.247.244; 12.AN.247.243; 12.AN.247.247;
Prodrugs of 12.AP 12.AP.4.157; 12.AP.4.158; 12.AP.4.196; 12.AP.4.223; 12.AP.4.240;
12.AP.4.244; 12.AP.4.243; 12.AP.4.247; 12.AP.5.157; 12.AP.5.158;
12.AP.5.196; 12.AP.5.223; 12.AP.5.240; 12.AP.5.244; 12.AP.5.243;
12.AP.5.247; 12.AP.7.157; 12.AP.7.158; 12.AP.7.196; 12.AP.7.223;
12.AP.7.240; 12.AP.7.244; 12.AP.7.243; 12.AP.7.247; 12.AP.15.157;
12.AP.15.158; 12.AP.15.196; 12.AP.15.223; 12.AP.15.240;
12.AP.15.244; 12.AP.15.243; 12.AP.15.247; 12.AP.16.157;
12.AP.16.158; 12.AP.16.196; 12.AP.16.223; 12.AP.16.240;
12.AP.16.244; 12.AP.16.243; 12.AP.16.247; 12.AP.18.157;
12.AP.18.158; 12.AP.18.196; 12.AP.18.223; 12.AP.18.240;
12.AP.18.244; 12.AP.18.243; 12.AP.18.247; 12.AP.26.157;
12.AP.26.158; 12.AP.26.196; 12.AP.26.223; 12.AP.26.240;
12.AP.26.244; 12.AP.26.243; 12.AP.26.247; 12.AP.27.157;
12.AP.27.158; 12.AP.27.196; 12.AP.27.223; 12.AP.27.240;
12.AP.27.244; 12.AP.27.243; 12.AP.27.247; 12.AP.29.157;
12.AP.29.158; 12.AP.29.196; 12.AP.29.223; 12.AP.29.240;
12.AP.29.244; 12.AP.29.243; 12.AP.29.247; 12.AP.54.157;
12.AP.54.158; 12.AP.54.196; 12.AP.54.223; 12.AP.54.240;
12.AP.54.244; 12.AP.54.243; 12.AP.54.247; 12.AP.55.157;
12.AP.55.158; 12.AP.55.196; 12.AP.55.223; 12.AP.55.240;
12.AP.55.244; 12.AP.55.243; 12.AP.55.247; 12.AP.56.157;
12.AP.56.158; 12.AP.56.196; 12.AP.56.223; 12.AP.56.240;
12.AP.56.244; 12.AP.56.243; 12.AP.56.247; 12.AP.157.157;
12.AP.157.158; 12.AP.157.196; 12.AP.157.223; 12.AP.157.240;
12.AP.157.244; 12.AP.157.243; 12.AP.157.247; 12.AP.196.157;
12.AP.196.158; 12.AP.196.196; 12.AP.196.223; 12.AP.196.240;
12.AP.196.244; 12.AP.196.243; 12.AP.196.247; 12.AP.223.157;
12.AP.223.158; 12.AP.223.196; 12.AP.223.223; 12.AP.223.240;
12.AP.223.244; 12.AP.223.243; 12.AP.223.247; 12.AP.240.157;
12.AP.240.158; 12.AP.240.196; 12.AP.240.223; 12.AP.240.240;
12.AP.240.244; 12.AP.240.243; 12.AP.240.247; 12.AP.244.157;
12.AP.244.158; 12.AP.244.196; 12.AP.244.223; 12.AP.244.240;
12.AP.244.244; 12.AP.244.243; 12.AP.244.247; 12.AP.247.157;
12.AP.247.158; 12.AP.247.196; 12.AP.247.223; 12.AP.247.240;
12.AP.247.244; 12.AP.247.243; 12.AP.247.247;
Prodrugs of 12.AZ 12.AZ.4.157; 12.AZ.4.158; 12.AZ.4.196; 12.AZ.4.223; 12.AZ.4.240;
12.AZ.4.244; 12.AZ.4.243; 12.AZ.4.247; 12.AZ.5.157; 12.AZ.5.158;
12.AZ.5.196; 12.AZ.5.223; 12.AZ.5.240; 12.AZ.5.244; 12.AZ.5.243;
12.AZ.5.247; 12.AZ.7.157; 12.AZ.7.158; 12.AZ.7.196; 12.AZ.7.223;
12.AZ.7.240; 12.AZ.7.244; 12.AZ.7.243; 12.AZ.7.247; 12.AZ.15.157;
12.AZ.15.158; 12.AZ.15.196; 12.AZ.15.223; 12.AZ.15.240;
12.AZ.15.244; 12.AZ.15.243; 12.AZ.15.247; 12.AZ.16.157;
12.AZ.16.158; 12.AZ.16.196; 12.AZ.16.223; 12.AZ.16.240;
12.AZ.16.244; 12.AZ.16.243; 12.AZ.16.247; 12.AZ.18.157;
12.AZ.18.158; 12.AZ.18.196; 12.AZ.18.223; 12.AZ.18.240;
12.AZ.18.244; 12.AZ.18.243; 12.AZ.18.247; 12.AZ.26.157;
12.AZ.26.158; 12.AZ.26.196; 12.AZ.26.223; 12.AZ.26.240;
12.AZ.26.244; 12.AZ.26.243; 12.AZ.26.247; 12.AZ.27.157;
12.AZ.27.158; 12.AZ.27.196; 12.AZ.27.223; 12.AZ.27.240;
12.AZ.27.244; 12.AZ.27.243; 12.AZ.27.247; 12.AZ.29.157;
12.AZ.29.158; 12.AZ.29.196; 12.AZ.29.223; 12.AZ.29.240;
12.AZ.29.244; 12.AZ.29.243; 12.AZ.29.247; 12.AZ.54.157;
12.AZ.54.158; 12.AZ.54.196; 12.AZ.54.223; 12.AZ.54.240;
12.AZ.54.244; 12.AZ.54.243; 12.AZ.54.247; 12.AZ.55.157;
12.AZ.55.158; 12.AZ.55.196; 12.AZ.55.223; 12.AZ.55.240;
12.AZ.55.244; 12.AZ.55.243; 12.AZ.55.247; 12.AZ.56.157;
12.AZ.56.158; 12.AZ.56.196; 12.AZ.56.223; 12.AZ.56.240;
12.AZ.56.244; 12.AZ.56.243; 12.AZ.56.247; 12.AZ.157.157;
12.AZ.157.158; 12.AZ.157.196; 12.AZ.157.223; 12.AZ.157.240;
12.AZ.157.244; 12.AZ.157.243; 12.AZ.157.247; 12.AZ.196.157;
12.AZ.196.158; 12.AZ.196.196; 12.AZ.196.223; 12.AZ.196.240;
12.AZ.196.244; 12.AZ.196.243; 12.AZ.196.247; 12.AZ.223.157;
12.AZ.223.158; 12.AZ.223.196; 12.AZ.223.223; 12.AZ.223.240;
12.AZ.223.244; 12.AZ.223.243; 12.AZ.223.247; 12.AZ.240.157;
12.AZ.240.158; 12.AZ.240.196; 12.AZ.240.223; 12.AZ.240.240;
12.AZ.240.244; 12.AZ.240.243; 12.AZ.240.247; 12.AZ.244.157;
12.AZ.244.158; 12.AZ.244.196; 12.AZ.244.223; 12.AZ.244.240;
12.AZ.244.244; 12.AZ.244.243; 12.AZ.244.247; 12.AZ.247.157;
12.AZ.247.158; 12.AZ.247.196; 12.AZ.247.223; 12.AZ.247.240;
12.AZ.247.244; 12.AZ.247.243; 12.AZ.247.247;
Prodrugs of 12.BF 12.BF.4.157; 12.BF.4.158; 12.BF.4.196; 12.BF.4.223; 12.BF.4.240;
12.BF.4.244; 12.BF.4.243; 12.BF.4.247; 12.BF.5.157; 12.BF.5.158;
12.BF.5.196; 12.BF.5.223; 12.BF.5.240; 12.BF.5.244; 12.BF.5.243;
12.BF.5.247; 12.BF.7.157; 12.BF.7.158; 12.BF.7.196; 12.BF.7.223;
12.BF.7.240; 12.BF.7.244; 12.BF.7.243; 12.BF.7.247; 12.BF.15.157;
12.BF.15.158; 12.BF.15.196; 12.BF.15.223; 12.BF.15.240; 12.BF.15.244;
12.BF.15.243; 12.BF.15.247; 12.BF.16.157; 12.BF.16.158; 12.BF.16.196;
12.BF.16.223; 12.BF.16.240; 12.BF.16.244; 12.BF.16.243; 12.BF.16.247;
12.BF.18.157; 12.BF.18.158; 12.BF.18.196; 12.BF.18.223; 12.BF.18.240;
12.BF.18.244; 12.BF.18.243; 12.BF.18.247; 12.BF.26.157; 12.BF.26.158;
12.BF.26.196; 12.BF.26.223; 12.BF.26.240; 12.BF.26.244; 12.BF.26.243;
12.BF.26.247; 12.BF.27.157; 12.BF.27.158; 12.BF.27.196; 12.BF.27.223;
12.BF.27.240; 12.BF.27.244; 12.BF.27.243; 12.BF.27.247; 12.BF.29.157;
12.BF.29.158; 12.BF.29.196; 12.BF.29.223; 12.BF.29.240; 12.BF.29.244;
12.BF.29.243; 12.BF.29.247; 12.BF.54.157; 12.BF.54.158; 12.BF.54.196;
12.BF.54.223; 12.BF.54.240; 12.BF.54.244; 12.BF.54.243; 12.BF.54.247;
12.BF.55.157; 12.BF.55.158; 12.BF.55.196; 12.BF.55.223; 12.BF.55.240;
12.BF.55.244; 12.BF.55.243; 12.BF.55.247; 12.BF.56.157; 12.BF.56.158;
12.BF.56.196; 12.BF.56.223; 12.BF.56.240; 12.BF.56.244; 12.BF.56.243;
12.BF.56.247; 12.BF.157.157; 12.BF.157.158; 12.BF.157.196;
12.BF.157.223; 12.BF.157.240; 12.BF.157.244; 12.BF.157.243;
12.BF.157.247; 12.BF.196.157; 12.BF.196.158; 12.BF.196.196;
12.BF.196.223; 12.BF.196.240; 12.BF.196.244; 12.BF.196.243;
12.BF.196.247; 12.BF.223.157; 12.BF.223.158; 12.BF.223.196;
12.BF.223.223; 12.BF.223.240; 12.BF.223.244; 12.BF.223.243;
12.BF.223.247; 12.BF.240.157; 12.BF.240.158; 12.BF.240.196;
12.BF.240.223; 12.BF.240.240; 12.BF.240.244; 12.BF.240.243;

TABLE 7-continued

12.BF.240.247; 12.BF.244.157; 12.BF.244.158; 12.BF.244.196; 12.BF.244.223; 12.BF.244.240; 12.BF.244.244; 12.BF.244.243; 12.BF.244.247; 12.BF.247.157; 12.BF.247.158; 12.BF.247.196; 12.BF.247.223; 12.BF.247.240; 12.BF.247.244; 12.BF.247.243; 12.BF.247.247;

Prodrugs of 12.CI

12.CI.4.157; 12.CI.4.158; 12.CI.4.196; 12.CI.4.223; 12.CI.4.240; 12.CI.4.244; 12.CI.4.243; 12.CI.4.247; 12.CI.5.157; 12.CI.5.158; 12.CI.5.196; 12.CI.5.223; 12.CI.5.240; 12.CI.5.244; 12.CI.5.243; 12.CI.5.247; 12.CI.7.157; 12.CI.7.158; 12.CI.7.196; 12.CI.7.223; 12.CI.7.240; 12.CI.7.244; 12.CI.7.243; 12.CI.7.247; 12.CI.15.157; 12.CI.15.158; 12.CI.15.196; 12.CI.15.223; 12.CL.15.240; 12.CI.15.244; 12.CI.15.243; 12.CI.15.247; 12.CI.16.157; 12.CI.16.158; 12.CI.16.196; 12.CI.16.223; 12.CI.16.240; 12.CI.16.244; 12.CI.16.243; 12.CI.16.247; 12.CI.18.157; 12.CI.18.158; 12.CI.18.196; 12.CI.18.223; 12.CI.18.240; 12.CI.18.244; 12.CI.18.243; 12.CI.18.247; 12.CI.26.157; 12.CI.26.158; 12.CI.26.196; 12.CI.26.223; 12.CI.26.240; 12.CI.26.244; 12.CI.26.243; 12.CL.26.247; 12.CI.27.157; 12.CI.27.158; 12.CI.27.196; 12.CI.27.223; 12.CI.27.240; 12.CI.27.244; 12.CI.27.243; 12.CI.27.247; 12.CI.29.157; 12.CI.29.158; 12.CI.29.196; 12.CL.29.223; 12.CI.29.240; 12.CI.29.244; 12.CI.29.243; 12.CI.29.247; 12.CI.54.157; 12.CL.54.158; 12.CL.54.196; 12.CI.54.223; 12.CI.54.240; 12.CI.54.244; 12.CI.54.243; 12.CI.54.247; 12.CI.55.157; 12.CI.55.158; 12.CI.55.196; 12.CI.55.223; 12.CI.55.240; 12.CL.55.244; 12.CI.55.243; 12.CI.55.247; 12.CI.56.157; 12.CI.56.158; 12.CL.56.196; 12.CL.56.223; 12.CL.56.240; 12.CI.56.244; 12.CI.56.243; 12.CI.56.247; 12.CI.157.157; 12.CL.157.158; 12.CI.157.196; 12.CI.157.223; 12.CI.157.240; 12.CI.157.244; 12.CL.157.243; 12.CI.157.247; 12.CI.196.157; 12.CI.196.158; 12.CI.196.196; 12.CI.196.223; 12.CL.196.240; 12.CI.196.244; 12.CI.196.243; 12.CI.196.247; 12.CI.223.157; 12.CI.223.158; 12.CI.223.196; 12.CI.223.223; 12.CI.223.240; 12.CI.223.244; 12.CI.223.243; 12.CI.223.247; 12.CI.240.157; 12.CI.240.158; 12.CI.240.196; 12.CI.240.223; 12.CI.240.240; 12.CI.240.244; 12.CL.240.243; 12.CI.240.247; 12.CI.244.157; 12.CI.244.158; 12.CI.244.196; 12.CI.244.223; 12.CI.244.240; 12.CI.244.244; 12.CI.244.243; 12.CI.244.247; 12.CI.247.157; 12.CI.247.158; 12.CI.247.196; 12.CI.247.223; 12.CI.247.240; 12.CI.247.244; 12.CI.247.243; 12.CI.247.247;

Prodrugs of 12.CO

12.CO.4.157; 12.CO.4.158; 12.CO.4.196; 12.CO.4.223; 12.CO.4.240; 12.CO.4.244; 12.CO.4.243; 12.CO.4.247; 12.CO.5.157; 12.CO.5.158; 12.CO.5.196; 12.CO.5.223; 12.CO.5.240; 12.CO.5.244; 12.CO.5.243; 12.CO.5.247; 12.CO.7.157; 12.CO.7.158; 12.CO.7.196; 12.CO.7.223; 12.CO.7.240; 12.CO.7.244; 12.CO.7.243; 12.CO.7.247; 12.CO.15.157; 12.CO.15.158; 12.CO.15.196; 12.CO.15.223; 12.CO.15.240; 12.CO.15.244; 12.CO.15.243; 12.CO.15.247; 12.CO.16.157; 12.CO.16.158; 12.CO.16.196; 12.CO.16.223; 12.CO.16.240; 12.CO.16.244; 12.CO.16.243; 12.CO.16.247; 12.CO.18.157; 12.CO.18.158; 12.CO.18.196; 12.CO.18.223; 12.CO.18.240; 12.CO.18.244; 12.CO.18.243; 12.CO.18.247; 12.CO.26.157; 12.CO.26.158; 12.CO.26.196; 12.CO.26.223; 12.CO.26.240; 12.CO.26.244; 12.CO.26.243; 12.CO.26.247; 12.CO.27.157; 12.CO.27.158; 12.CO.27.196; 12.CO.27.223; 12.CO.27.240; 12.CO.27.244; 12.CO.27.243; 12.CO.27.247; 12.CO.29.157; 12.CO.29.158; 12.CO.29.196; 12.CO.29.223; 12.CO.29.240; 12.CO.29.244; 12.CO.29.243; 12.CO.29.247; 12.CO.54.157; 12.CO.54.158; 12.CO.54.196; 12.CO.54.223; 12.CO.54.240; 12.CO.54.244; 12.CO.54.243; 12.CO.54.244; 12.CO.54.247; 12.CO.55.157; 12.CO.55.158; 12.CO.55.196; 12.CO.55.223; 12.CO.55.240; 12.CO.55.244; 12.CO.55.243; 12.CO.55.247; 12.CO.56.157; 12.CO.56.158; 12.CO.56.196; 12.CO.56.223; 12.CO.56.240; 12.CO.56.244; 12.CO.56.243; 12.CO.56.247; 12.CO.157.157; 12.CO.157.158; 12.CO.157.196; 12.CO.157.223; 12.CO.157.240; 12.CO.157.244; 12.CO.157.243; 12.CO.157.247; 12.CO.196.157; 12.CO.196.158; 12.CO.196.196; 12.CO.196.223; 12.CO.196.240; 12.CO.196.244; 12.CO.196.243; 12.CO.196.247; 12.CO.223.157; 12.CO.223.158; 12.CO.223.196; 12.CO.223.223; 12.CO.223.240; 12.CO.223.244; 12.CO.223.243; 12.CO.223.247; 12.CO.240.157; 12.CO.240.158; 12.CO.240.196; 12.CO.240.223; 12.CO.240.240; 12.CO.240.244; 12.CO.240.243; 12.CO.240.247; 12.CO.244.157; 12.CO.244.158; 12.CO.244.196; 12.CO.244.223; 12.CO.244.240; 12.CO.244.244; 12.CO.244.243; 12.CO.244.247; 12.CO.247.157; 12.CO.247.158; 12.CO.247.196; 12.CO.247.223; 12.CO.247.240; 12.CO.247.244; 12.CO.247.243; 12.CO.247.247.

Prodrugs of 13.B

13.B.228.228; 13.B.228.229; 13.B.228.230; 13.B.228.231; 13.B.228.236; 13.B.228.237; 13.B.228.238; 13.B.228.239; 13.B.228.154; 13.B.228.157; 13.B.228.166; 13.B.228.169; 13.B.228.172; 13.B.228.175; 13.B.228.240; 13.B.228.244; 13.B.229.228; 13.B.229.229; 13.B.229.230; 13.B.229.231; 13.B.229.236; 13.B.229.237; 13.B.229.238; 13.B.229.239; 13.B.229.154; 13.B.229.157; 13.B.229.166; 13.B.229.169; 13.B.229.172; 13.B.229.175; 13.B.229.240; 13.B.229.244; 13.B.230.228; 13.B.230.229; 13.B.230.230; 13.B.230.231; 13.B.230.236; 13.B.230.237; 13.B.230.238; 13.B.230.239; 13.B.230.154; 13.B.230.157; 13.B.230.166; 13.B.230.169; 13.B.230.172; 13.B.230.175; 13.B.230.240; 13.B.230.244; 13.B.231.228; 13.B.231.229; 13.B.231.230; 13.B.231.231; 13.B.231.236; 13.B.231.237; 13.B.231.238; 13.B.231.239; 13.B.231.154; 13.B.231.157; 13.B.231.166; 13.B.231.169; 13.B.231.172; 13.B.231.175; 13.B.231.240; 13.B.231.244; 13.B.236.228; 13.B.236.229; 13.B.236.230; 13.B.236.231; 13.B.236.236; 13.B.236.237; 13.B.236.238; 13.B.236.239; 13.B.236.154; 13.B.236.157; 13.B.236.166; 13.B.236.169; 13.B.236.172; 13.B.236.175; 13.B.236.240; 13.B.236.244; 13.B.237.228; 13.B.237.229; 13.B.237.230; 13.B.237.231; 13.B.237.236; 13.B.237.237; 13.B.237.238; 13.B.237.239; 13.B.237.154; 13.B.237.157; 13.B.237.166; 13.B.237.169; 13.B.237.172; 13.B.237.175; 13.B.237.240; 13.B.237.244; 13.B.238.228; 13.B.238.229; 13.B.238.230; 13.B.238.231; 13.B.238.236; 13.B.238.237; 13.B.238.238; 13.B.238.239; 13.B.238.154; 13.B.238.157; 13.B.238.166; 13.B.238.169; 13.B.238.172; 13.B.238.175; 13.B.238.240; 13.B.238.244; 13.B.239.228; 13.B.239.229; 13.B.239.230; 13.B.239.231; 13.B.239.236; 13.B.239.237; 13.B.239.238; 13.B.239.239; 13.B.239.154; 13.B.239.157; 13.B.239.166; 13.B.239.169; 13.B.239.172; 13.B.239.175; 13.B.239.240; 13.B.239.244; 13.B.154.228; 13.B.154.229; 13.B.154.230; 13.B.154.231; 13.B.154.236; 13.B.154.237; 13.B.154.238; 13.B.154.239; 13.B.154.154; 13.B.154.157; 13.B.154.166; 13.B.154.169; 13.B.154.172; 13.B.154.175; 13.B.154.240; 13.B.154.244; 13.B.157.228; 13.B.157.229; 13.B.157.230; 13.B.157.231; 13.B.157.236; 13.B.157.237; 13.B.157.238; 13.B.157.239; 13.B.157.154; 13.B.157.157; 13.B.157.166; 13.B.157.169; 13.B.157.172; 13.B.157.175; 13.B.157.240; 13.B.157.244; 13.B.166.228; 13.B.166.229; 13.B.166.230; 13.B.166.231; 13.B.166.236; 13.B.166.237; 13.B.166.238; 13.B.166.239; 13.B.166.154; 13.B.166.157; 13.B.166.166; 13.B.166.169; 13.B.166.172; 13.B.166.175; 13.B.166.240; 13.B.166.244; 13.B.169.228; 13.B.169.229; 13.B.169.230; 13.B.169.231; 13.B.169.236; 13.B.169.237; 13.B.169.238; 13.B.169.239; 13.B.169.154; 13.B.169.157; 13.B.169.166; 13.B.169.169; 13.B.169.172; 13.B.169.175; 13.B.169.240; 13.B.169.244; 13.B.172.228; 13.B.172.229; 13.B.172.230; 13.B.172.231; 13.B.172.236; 13.B.172.237; 13.B.172.238; 13.B.172.239; 13.B.172.154; 13.B.172.157; 13.B.172.166; 13.B.172.169; 13.B.172.172; 13.B.172.175; 13.B.172.240; 13.B.172.244; 13.B.175.228; 13.B.175.229; 13.B.175.230; 13.B.175.231; 13.B.175.236; 13.B.175.237; 13.B.175.238; 13.B.175.239; 13.B.175.154; 13.B.175.157; 13.B.175.166; 13.B.175.169; 13.B.175.172; 13.B.175.175; 13.B.175.240; 13.B.175.244; 13.B.240.228; 13.B.240.229; 13.B.240.230; 13.B.240.231; 13.B.240.236; 13.B.240.237; 13.B.240.238; 13.B.240.239; 13.B.240.154; 13.B.240.157; 13.B.240.166; 13.B.240.169; 13.B.240.172; 13.B.240.175; 13.B.240.240; 13.B.240.244; 13.B.244.228; 13.B.244.229; 13.B.244.230; 13.B.244.231; 13.B.244.236; 13.B.244.237; 13.B.244.238; 13.B.244.239; 13.B.244.154; 13.B.244.157; 13.B.244.166; 13.B.244.169; 13.B.244.172; 13.B.244.175; 13.B.244.240; 13.B.244.244;

Prodrugs of 13.D

13.D.228.228; 13.D.228.229; 13.D.228.230; 13.D.228.231; 13.D.228.236; 13.D.228.237; 13.D.228.238; 13.D.228.239; 13.D.228.154; 13.D.228.157; 13.D.228.166; 13.D.228.169; 13.D.228.172; 13.D.228.175; 13.D.228.240; 13.D.228.244; 13.D.229.228; 13.D.229.229; 13.D.229.230; 13.D.229.231; 13.D.229.236; 13.D.229.237; 13.D.229.238; 13.D.229.239; 13.D.229.154; 13.D.229.157; 13.D.229.166; 13.D.229.169; 13.D.229.172; 13.D.229.175; 13.D.229.240; 13.D.229.244; 13.D.230.228; 13.D.230.229; 13.D.230.230; 13.D.230.231; 13.D.230.236; 13.D.230.237; 13.D.230.238; 13.D.230.239; 13.D.230.154; 13.D.230.157; 13.D.230.166; 13.D.230.169; 13.D.230.172; 13.D.230.175; 13.D.230.240; 13.D.230.244; 13.D.231.228; 13.D.231.229; 13.D.231.230; 13.D.231.231; 13.D.231.236; 13.D.231.237; 13.D.231.238; 13.D.231.239; 13.D.231.154; 13.D.231.157; 13.D.231.166; 13.D.231.169; 13.D.231.172; 13.D.231.175; 13.D.231.240; 13.D.231.244; 13.D.236.228; 13.D.236.229; 13.D.236.230; 13.D.236.231; 13.D.236.236; 13.D.236.237; 13.D.236.238; 13.D.236.239; 13.D.236.154; 13.D.236.157; 13.D.236.166; 13.D.236.169; 13.D.236.172; 13.D.236.175; 13.D.236.240; 13.D.236.244; 13.D.237.228; 13.D.237.229; 13.D.237.230; 13.D.237.231; 13.D.237.236; 13.D.237.237; 13.D.237.238; 13.D.237.239; 13.D.237.154; 13.D.237.157; 13.D.237.166; 13.D.237.169; 13.D.237.172; 13.D.237.175; 13.D.237.240; 13.D.237.244; 13.D.238.228; 13.D.238.229; 13.D.238.230; 13.D.238.231; 13.D.238.236; 13.D.238.237; 13.D.238.238; 13.D.238.239; 13.D.238.154; 13.D.238.157; 13.D.238.166; 13.D.238.169; 13.D.238.172; 13.D.238.175; 13.D.238.240; 13.D.238.244; 13.D.239.228; 13.D.239.229; 13.D.239.230;

TABLE 7-continued

13.D.239.231; 13.D.239.236; 13.D.239.237; 13.D.239.238; 13.D.239.239;
13.D.239.154; 13.D.239.157; 13.D.239.166; 13.D.239.169; 13.D.239.172;
13.D.239.175; 13.D.239.240; 13.D.239.244; 13.D.154.228; 13.D.154.229;
13.D.154.230; 13.D.154.231; 13.D.154.236; 13.D.154.237; 13.D.154.238;
13.D.154.239; 13.D.154.154; 13.D.154.157; 13.D.154.166; 13.D.154.169;
13.D.154.172; 13.D.154.175; 13.D.154.240; 13.D.154.244; 13.D.157.228;
13.D.157.229; 13.D.157.230; 13.D.157.231; 13.D.157.236; 13.D.157.237;
13.D.157.238; 13.D.157.239; 13.D.157.154; 13.D.157.157; 13.D.157.166;
13.D.157.169; 13.D.157.172; 13.D.157.175; 13.D.157.240; 13.D.157.244;
13.D.166.228; 13.D.166.229; 13.D.166.230; 13.D.166.231; 13.D.166.236;
13.D.166.237; 13.D.166.238; 13.D.166.239; 13.D.166.154; 13.D.166.157;
13.D.166.166; 13.D.166.169; 13.D.166.172; 13.D.166.175; 13.D.166.240;
13.D.166.244; 13.D.169.228; 13.D.169.229; 13.D.169.230; 13.D.169.231;
13.D.169.236; 13.D.169.237; 13.D.169.238; 13.D.169.239; 13.D.169.154;
13.D.169.157; 13.D.169.166; 13.D.169.169; 13.D.169.172; 13.D.169.175;
13.D.169.240; 13.D.169.244; 13.D.172.228; 13.D.172.229; 13.D.172.230;
13.D.172.231; 13.D.172.236; 13.D.172.237; 13.D.172.238; 13.D.172.239;
13.D.172.154; 13.D.172.157; 13.D.172.166; 13.D.172.169; 13.D.172.172;
13.D.172.175; 13.D.172.240; 13.D.172.244; 13.D.175.228; 13.D.175.229;
13.D.175.230; 13.D.175.231; 13.D.175.236; 13.D.175.237; 13.D.175.238;
13.D.175.239; 13.D.175.154; 13.D.175.157; 13.D.175.166; 13.D.175.169;
13.D.175.172; 13.D.175.175; 13.D.175.240; 13.D.175.244; 13.D.240.228;
13.D.240.229; 13.D.240.230; 13.D.240.231; 13.D.240.236; 13.D.240.237;
13.D.240.238; 13.D.240.239; 13.D.240.154; 13.D.240.157; 13.D.240.166;
13.D.240.169; 13.D.240.172; 13.D.240.175; 13.D.240.240; 13.D.240.244;
13.D.244.228; 13.D.244.229; 13.D.244.230; 13.D.244.231; 13.D.244.236;
13.D.244.237; 13.D.244.238; 13.D.244.239; 13.D.244.154; 13.D.244.157;
13.D.244.166; 13.D.244.169; 13.D.244.172; 13.D.244.175; 13.D.244.240;
13.D.244.244;
Prodrugs of 13.E 13.E.228.228; 13.E.228.229; 13.E.228.230; 13.E.228.231; 13.E.228.236;
13.E.228.237; 13.E.228.238; 13.E.228.239; 13.E.228.154; 13.E.228.157;
13.E.228.166; 13.E.228.169; 13.E.228.172; 13.E.228.175; 13.E.228.240;
13.E.228.244; 13.E.229.228; 13.E.229.229; 13.E.229.230; 13.E.229.231;
13.E.229.236; 13.E.229.237; 13.E.229.238; 13.E.229.239; 13.E.229.154;
13.E.229.157; 13.E.229.166; 13.E.229.169; 13.E.229.172; 13.E.229.175;
13.E.229.240; 13.E.229.244; 13.E.230.228; 13.E.230.229; 13.E.230.230;
13.E.230.231; 13.E.230.236; 13.E.230.237; 13.E.230.238; 13.E.230.239;
13.E.230.154; 13.E.230.157; 13.E.230.166; 13.E.230.169; 13.E.230.172;
13.E.230.175; 13.E.230.240; 13.E.230.244; 13.E.231.228; 13.E.231.229;
13.E.231.230; 13.E.231.231; 13.E.231.236; 13.E.231.237; 13.E.231.238;
13.E.231.239; 13.F.231.154; 13.E.231.157; 13.E.231.166; 13.E.231.169;
13.E.231.172; 13.E.231.175; 13.E.231.240; 13.E.231.244; 13.E.236.228;
13.E.236.229; 13.E.236.230; 13.E.236.231; 13.E.236.236; 13.E.236.237;
13.E.236.238; 13.E.236.239; 13.E.236.154; 13.E.236.157; 13.E.236.166;
13.E.236.169; 13.E.236.172; 13.E.236.175; 13.F.236.240; 13.E.236.244;
13.E.237.228; 13.F.237.229; 13.E.237.230; 13.E.237.231; 13.E.237.236;
13.E.237.237; 13.E.237.238; 13.E.237.239; 13.E.237.154; 13.E.237.157;
13.E.237.166; 13.E.237.169; 13.E.237.172; 13.E.237.175; 13.E.237.240;
13.E.237.244; 13.E.238.228; 13.E.238.229; 13.E.238.230; 13.E.238.231;
13.F.238.236; 13.E.238.237; 13.E.238.238; 13.E.238.239; 13.E.238.154;
13.E.238.157; 13.E.238.166; 13.E.238.169; 13.E.238.172; 13.E.238.175;
13.E.238.240; 13.E.238.244; 13.E.239.228; 13.E.239.229; 13.E.239.230;
13.E.239.231; 13.E.239.236; 13.E.239.237; 13.E.239.238; 13.E.239.239;
13.E.239.154; 13.E.239.157; 13.E.239.166; 13.E.239.169; 13.E.239.172;
13.E.239.175; 13.E.239.240; 13.E.239.244; 13.E.154.228; 13.E.154.229;
13.E.154.230; 13.E.154.231; 13.E.154.236; 13.E.154.237; 13.E.154.238;
13.E.154.239; 13.E.154.154; 13.E.154.157; 13.F.154.166; 13.E.154.169;
13.E.154.172; 13.E.154.175; 13.E.154.240; 13.E.154.244; 13.E.157.228;
13.F.157.229; 13.E.157.230; 13.E.157.231; 13.E.157.236; 13.E.157.237;
13.E.157.238; 13.E.157.239; 13.E.157.154; 13.E.157.157; 13.E.157.166;
13.E.157.169; 13.E.157.172; 13.E.157.175; 13.E.157.240; 13.E.157.244;
13.E.166.228; 13.E.166.229; 13.E.166.230; 13.E.166.231; 13.E.166.236;
13.E.166.237; 13.E.166.238; 13.E.166.239; 13.F.166.154; 13.E.166.157;
13.E.166.166; 13.E.166.169; 13.E.166.172; 13.E.166.175; 13.E.166.240;
13.E.166.244; 13.E.169.228; 13.E.169.229; 13.E.169.230; 13.E.169.231;
13.E.169.236; 13.E.169.237; 13.E.169.238; 13.E.169.239; 13.E.169.154;
13.E.169.157; 13.E.169.166; 13.E.169.169; 13.E.169.172; 13.E.169.175;
13.E.169.240; 13.E.169.244; 13.E.172.228; 13.E.172.229; 13.E.172.230;
13.E.172.231; 13.E.172.236; 13.E.172.237; 13.E.172.238; 13.E.172.239;
13.E.172.154; 13.E.172.157; 13.E.172.166; 13.E.172.169; 13.F.172.172;
13.E.172.175; 13.E.172.240; 13.E.172.244; 13.E.175.228; 13.E.175.229;
13.E.175.230; 13.E.175.231; 13.E.175.236; 13.E.175.237; 13.E.175.238;
13.E.175.239; 13.E.175.154; 13.E.175.157; 13.E.175.166; 13.E.175.169;
13.E.175.172; 13.E.175.175; 13.E.175.240; 13.E.175.244; 13.E.240.228;
13.E.240.229; 13.E.240.230; 13.E.240.231; 13.E.240.236; 13.E.240.237;
13.E.240.238; 13.E.240.239; 13.E.240.154; 13.E.240.157; 13.E.240.166;
13.E.240.169; 13.E.240.172; 13.E.240.175; 13.E.240.240; 13.E.240.244;

TABLE 7-continued

13.E.244.228; 13.E.244.229; 13.E.244.230; 13.E.244.231; 13.E.244.236;
13.E.244.237; 13.E.244.238; 13.E.244.239; 13.E.244.154; 13.E.244.157;
13.E.244.166; 13.E.244.169; 13.E.244.172; 13.E.244.175; 13.E.244.240;
13.E.244.244;
Prodrugs of 13.G 13.G.228.228; 13.G.228.229; 13.G.228.230; 13.G.228.231; 13.G.228.236;
13.G.228.237; 13.G.228.238; 13.G.228.239; 13.G.228.154; 13.G.228.157;
13.G.228.166; 13.G.228.169; 13.G.228.172; 13.G.228.175; 13.G.228.240;
13.G.228.244; 13.G.229.228; 13.G.229.229; 13.G.229.230; 13.G.229.231;
13.G.229.236; 13.G.229.237; 13.G.229.238; 13.G.229.239; 13.G.229.154;
13.G.229.157; 13.G.229.166; 13.G.229.169; 13.G.229.172; 13.G.229.175;
13.G.229.240; 13.G.229.244; 13.G.230.228; 13.G.230.229; 13.G.230.230;
13.G.230.231; 13.G.230.236; 13.G.230.237; 13.G.230.238; 13.G.230.239;
13.G.230.154; 13.G.230.157; 13.G.230.166; 13.G.230.169; 13.G.230.172;
13.G.230.175; 13.G.230.240; 13.G.230.244; 13.G.231.228; 13.G.231.229;
13.G.231.230; 13.G.231.231; 13.G.231.236; 13.G.231.237; 13.G.231.238;
13.G.231.239; 13.G.231.154; 13.G.231.157; 13.G.231.166; 13.G.231.169;
13.G.231.172; 13.G.231.175; 13.G.231.240; 13.G.231.244; 13.G.236.228;
13.G.236.229; 13.G.236.230; 13.G.236.231; 13.G.236.236; 13.G.236.237;
13.G.236.238; 13.G.236.239; 13.G.236.154; 13.G.236.157; 13.G.236.166;
13.G.236.169; 13.G.236.172; 13.G.236.175; 13.G.236.240; 13.G.236.244;
13.G.237.228; 13.G.237.229; 13.G.237.230; 13.G.237.231; 13.G.237.236;
13.G.237.237; 13.G.237.238; 13.G.237.239; 13.G.237.154; 13.G.237.157;
13.G.237.166; 13.G.237.169; 13.G.237.172; 13.G.237.175; 13.G.237.240;
13.G.237.244; 13.G.238.228; 13.G.238.229; 13.G.238.230; 13.G.238.231;
13.G.238.236; 13.G.238.237; 13.G.238.238; 13.G.238.239; 13.G.238.154;
13.G.238.157; 13.G.238.166; 13.G.238.169; 13.G.238.172; 13.G.238.175;
13.G.238.240; 13.G.238.244; 13.G.239.228; 13.G.239.229; 13.G.239.230;
13.G.239.231; 13.G.239.236; 13.G.239.237; 13.G.239.238; 13.G.239.239;
13.G.239.154; 13.G.239.157; 13.G.239.166; 13.G.239.169; 13.G.239.172;
13.G.239.175; 13.G.239.240; 13.G.239.244; 13.G.154.228; 13.G.154.229;
13.G.154.230; 13.G.154.231; 13.G.154.236; 13.G.154.237; 13.G.154.238;
13.G.154.239; 13.G.154.154; 13.G.154.157; 13.G.154.166; 13.G.154.169;
13.G.154.172; 13.G.154.175; 13.G.154.240; 13.G.154.244; 13.G.157.228;
13.G.157.229; 13.G.157.230; 13.G.157.231; 13.G.157.236; 13.G.157.237;
13.G.157.238; 13.G.157.239; 13.G.157.154; 13.G.157.157; 13.G.157.166;
13.G.157.169; 13.G.157.172; 13.G.157.175; 13.G.157.240; 13.G.157.244;
13.G.166.228; 13.G.166.229; 13.G.166.230; 13.G.166.231; 13.G.166.236;
13.G.166.237; 13.G.166.238; 13.G.166.239; 13.G.166.154; 13.G.166.157;
13.G.166.166; 13.G.166.169; 13.G.166.172; 13.G.166.175; 13.G.166.240;
13.G.166.244; 13.G.169.228; 13.G.169.229; 13.G.169.230; 13.G.169.231;
13.G.169.236; 13.G.169.237; 13.G.169.238; 13.G.169.239; 13.G.169.154;
13.G.169.157; 13.G.169.166; 13.G.169.169; 13.G.169.172; 13.G.169.175;
13.G.169.240; 13.G.169.244; 13.G.172.228; 13.G.172.229; 13.G.172.230;
13.G.172.231; 13.G.172.236; 13.G.172.237; 13.G.172.238; 13.G.172.239;
13.G.172.154; 13.G.172.157; 13.G.172.166; 13.G.172.169; 13.G.172.172;
13.G.172.175; 13.G.172.240; 13.G.172.244; 13.G.175.228; 13.G.175.229;
13.G.175.230; 13.G.175.231; 13.G.175.236; 13.G.175.237; 13.G.175.238;
13.G.175.239; 13.G.175.154; 13.G.175.157; 13.G.175.166; 13.G.175.169;
13.G.175.172; 13.G.175.175; 13.G.175.240; 13.G.175.244; 13.G.240.228;
13.G.240.229; 13.G.240.230; 13.G.240.231; 13.G.240.236; 13.G.240.237;
13.G.240.238; 13.G.240.239; 13.G.240.154; 13.G.240.157; 13.G.240.166;
13.G.240.169; 13.G.240.172; 13.G.240.175; 13.G.240.240; 13.G.240.244;
13.G.244.228; 13.G.244.229; 13.G.244.230; 13.G.244.231; 13.G.244.236;
13.G.244.237; 13.G.244.238; 13.G.244.239; 13.G.244.154; 13.G.244.157;
13.G.244.166; 13.G.244.169; 13.G.244.172; 13.G.244.175; 13.G.244.240;
13.G.244.244;
Prodrugs of 13.I 13.I.228.228; 13.I.228.229; 13.I.228.230; 13.I.228.231; 13.I.228.236;
13.I.228.237; 13.I.228.238; 13.I.228.239; 13.I.228.154; 13.I.228.157;
13.I.228.166; 13.I.228.169; 13.I.228.172; 13.I.228.175; 13.I.228.240;
13.I.228.244; 13.I.229.228; 13.I.229.229; 13.I.229.230; 13.I.229.231;
13.I.229.236; 13.I.229.237; 13.I.229.238; 13.I.229.239; 13.I.229.154;
13.I.229.157; 13.I.229.166; 13.I.229.169; 13.I.229.172; 13.I.229.175;
13.I.229.240; 13.I.229.244; 13.I.230.228; 13.I.230.229; 13.I.230.230;
13.I.230.231; 13.I.230.236; 13.I.230.237; 13.I.230.238; 13.I.230.239;
13.I.230.154; 13.I.230.157; 13.I.230.166; 13.I.230.169; 13.I.230.172;
13.I.230.175; 13.I.230.240; 13.I.230.244; 13.I.231.228; 13.I.231.229;
13.I.231.230; 13.I.231.231; 13.I.231.236; 13.I.231.237; 13.I.231.238;
13.I.231.239; 13.I.231.154; 13.I.231.157; 13.I.231.166; 13.I.231.169;
13.I.231.172; 13.I.231.175; 13.I.231.240; 13.I.231.244; 13.I.236.228;
13.I.236.229; 13.I.236.230; 13.I.236.231; 13.I.236.236; 13.I.236.237;
13.I.236.238; 13.I.236.239; 13.I.236.154; 13.I.236.157; 13.I.236.166;
13.I.236.169; 13.I.236.172; 13.I.236.175; 13.I.236.240; 13.I.236.244;
13.I.237.228; 13.I.237.229; 13.I.237.230; 13.I.237.231; 13.I.237.236;
13.I.237.237; 13.I.237.238; 13.I.237.239; 13.I.237.154; 13.I.237.157;
13.I.237.166; 13.I.237.169; 13.I.237.172; 13.I.237.175; 13.I.237.240;

TABLE 7-continued

13.I.237.244; 13.I.238.228; 13.I.238.229; 13.I.238.230; 13.I.238.231;
13.I.238.236; 13.I.238.237; 13.I.238.238; 13.I.238.239; 13.I.238.154;
13.I.238.157; 13.I.238.166; 13.I.238.169; 13.I.238.172; 13.I.238.175;
13.I.238.240; 13.I.238.244; 13.I.239.228; 13.I.239.229; 13.I.239.230;
13.I.239.231; 13.I.239.236; 13.I.239.237; 13.I.239.238; 13.I.239.239;
13.I.239.154; 13.I.239.157; 13.I.239.166; 13.I.239.169; 13.I.239.172;
13.I.239.175; 13.I.239.240; 13.I.239.244; 13.I.154.228; 13.I.154.229;
13.I.154.230; 13.I.154.231; 13.I.154.236; 13.I.154.237; 13.I.154.238;
13.I.154.239; 13.I.154.154; 13.I.154.157; 13.I.154.166; 13.I.154.169;
13.I.154.172; 13.I.154.175; 13.I.154.240; 13.I.154.244; 13.I.157.228;
13.I.157.229; 13.I.157.230; 13.I.157.231; 13.I.157.236; 13.I.157.237;
13.I.157.238; 13.I.157.239; 13.I.157.154; 13.I.157.157; 13.I.157.166;
13.I.157.169; 13.I.157.172; 13.I.157.175; 13.I.157.240; 13.I.157.244;
13.I.166.228; 13.I.166.229; 13.I.166.230; 13.I.166.231; 13.I.166.236;
13.I.166.237; 13.I.166.238; 13.I.166.239; 13.I.166.154; 13.I.166.157;
13.I.166.166; 13.I.166.169; 13.I.166.172; 13.I.166.175; 13.I.166.240;
13.I.166.244; 13.I.169.228; 13.I.169.229; 13.I.169.230; 13.I.169.231;
13.I.169.236; 13.I.169.237; 13.I.169.238; 13.I.169.239; 13.I.169.154;
13.I.169.157; 13.I.169.166; 13.I.169.169; 13.I.169.172; 13.I.169.175;
13.I.169.240; 13.I.169.244; 13.I.172.228; 13.I.172.229; 13.I.172.230;
13.I.172.231; 13.I.172.236; 13.I.172.237; 13.I.172.238; 13.I.172.239;
13.I.172.154; 13.I.172.157; 13.I.172.166; 13.I.172.169; 13.I.172.172;
13.I.172.175; 13.I.172.240; 13.I.172.244; 13.I.175.228; 13.I.175.229;
13.I.175.230; 13.I.175.231; 13.I.175.236; 13.I.175.237; 13.I.175.238;
13.I.175.239; 13.I.175.154; 13.I.175.157; 13.I.175.166; 13.I.175.169;
13.I.175.172; 13.I.175.175; 13.I.175.240; 13.I.175.244; 13.I.240.228;
13.I.240.229; 13.I.240.230; 13.I.240.231; 13.I.240.236; 13.I.240.237;
13.I.240.238; 13.I.240.239; 13.I.240.154; 13.I.240.157; 13.I.240.166;
13.I.240.169; 13.I.240.172; 13.I.240.175; 13.I.240.240; 13.I.240.244;
13.I.244.228; 13.I.244.229; 13.I.244.230; 13.I.244.231; 13.I.244.236;
13.I.244.237; 13.I.244.238; 13.I.244.239; 13.I.244.154; 13.I.244.157;
13.I.244.166; 13.I.244.169; 13.I.244.172; 13.I.244.175; 13.I.244.240;
13.I.244.244;

Prodrugs of 13.J

13.J.228.228; 13.J.228.229; 13.J.228.230; 13.J.228.231; 13.J.228.236;
13.J.228.237; 13.J.228.238; 13.J.228.239; 13.J.228.154; 13.J.228.157;
13.J.228.166; 13.J.228.169; 13.J.228.172; 13.J.228.175; 13.J.228.240;
13.J.228.244; 13.J.229.228; 13.J.229.229; 13.J.229.230; 13.J.229.231;
13.J.229.236; 13.J.229.237; 13.J.229.238; 13.J.229.239; 13.J.229.154;
13.J.229.157; 13.J.229.166; 13.J.229.169; 13.J.229.172; 13.J.229.175;
13.J.229.240; 13.J.229.244; 13.J.230.228; 13.J.230.229; 13.J.230.230;
13.J.230.231; 13.J.230.236; 13.J.230.237; 13.J.230.238; 13.J.230.239;
13.J.230.154; 13.J.230.157; 13.J.230.166; 13.J.230.169; 13.J.230.172;
13.J.230.175; 13.J.230.240; 13.J.230.244; 13.J.231.228; 13.J.231.229;
13.J.231.230; 13.J.231.231; 13.J.231.236; 13.J.231.237; 13.J.231.238;
13.J.231.239; 13.J.231.154; 13.J.231.157; 13.J.231.166; 13.J.231.169;
13.J.231.172; 13.J.231.175; 13.J.231.240; 13.J.231.244; 13.J.236.228;
13.J.236.229; 13.J.236.230; 13.J.236.231; 13.J.236.236; 13.J.236.237;
13.J.236.238; 13.J.236.239; 13.J.236.154; 13.J.236.157; 13.J.236.166;
13.J.236.169; 13.J.236.172; 13.J.236.175; 13.J.236.240; 13.J.236.244;
13.J.237.228; 13.J.237.229; 13.J.237.230; 13.J.237.231; 13.J.237.236;
13.J.237.237; 13.J.237.238; 13.J.237.239; 13.J.237.154; 13.J.237.157;
13.J.237.166; 13.J.237.169; 13.J.237.172; 13.J.237.175; 13.J.237.240;
13.J.237.244; 13.J.238.228; 13.J.238.229; 13.J.238.230; 13.J.238.231;
13.J.238.236; 13.J.238.237; 13.J.238.238; 13.J.238.239; 13.J.238.154;
13.J.238.157; 13.J.238.166; 13.J.238.169; 13.J.238.172; 13.J.238.175;
13.J.238.240; 13.J.238.244; 13.J.239.228; 13.J.239.229; 13.J.239.230;
13.J.239.231; 13.J.239.236; 13.J.239.237; 13.J.239.238; 13.J.239.239;
13.J.239.154; 13.J.239.157; 13.J.239.166; 13.J.239.169; 13.J.239.172;
13.J.239.175; 13.J.239.240; 13.J.239.244; 13.J.154.228; 13.J.154.229;
13.J.154.230; 13.J.154.231; 13.J.154.236; 13.J.154.237; 13.J.154.238;
13.J.154.239; 13.J.154.154; 13.J.154.157; 13.J.154.166; 13.J.154.169;
13.J.154.172; 13.J.154.175; 13.J.154.240; 13.J.154.244; 13.J.157.228;
13.J.157.229; 13.J.157.230; 13.J.157.231; 13.J.157.236; 13.J.157.237;
13.J.157.238; 13.J.157.239; 13.J.157.154; 13.J.157.157; 13.J.157.166;
13.J.157.169; 13.J.157.172; 13.J.157.175; 13.J.157.240; 13.J.157.244;
13.J.166.228; 13.J.166.229; 13.J.166.230; 13.J.166.231; 13.J.166.236;
13.J.166.237; 13.J.166.238; 13.J.166.239; 13.J.166.154; 13.J.166.157;
13.J.166.166; 13.J.166.169; 13.J.166.172; 13.J.166.175; 13.J.166.240;
13.J.166.244; 13.J.169.228; 13.J.169.229; 13.J.169.230; 13.J.169.231;
13.J.169.236; 13.J.169.237; 13.J.169.238; 13.J.169.239; 13.J.169.154;
13.J.169.157; 13.J.169.166; 13.J.169.169; 13.J.169.172; 13.J.169.175;
13.J.169.240; 13.J.169.244; 13.J.172.228; 13.J.172.229; 13.J.172.230;
13.J.172.231; 13.J.172.236; 13.J.172.237; 13.J.172.238; 13.J.172.239;
13.J.172.154; 13.J.172.157; 13.J.172.166; 13.J.172.169; 13.J.172.172;
13.J.172.175; 13.J.172.240; 13.J.172.244; 13.J.175.228; 13.J.175.229;
13.J.175.230; 13.J.175.231; 13.J.175.236; 13.J.175.237; 13.J.175.238;
13.J.175.239; 13.J.175.154; 13.J.175.157; 13.J.175.166; 13.J.175.169;
13.J.175.172; 13.J.175.175; 13.J.175.240; 13.J.175.244; 13.J.240.228;
13.J.240.229; 13.J.240.230; 13.J.240.231; 13.J.240.236; 13.J.240.237;
13.J.240.238; 13.J.240.239; 13.J.240.154; 13.J.240.157; 13.J.240.166;
13.J.240.169; 13.J.240.172; 13.J.240.175; 13.J.240.240; 13.J.240.244;
13.J.244.228; 13.J.244.229; 13.J.244.230; 13.J.244.231; 13.J.244.236;
13.J.244.237; 13.J.244.238; 13.J.244.239; 13.J.244.154; 13.J.244.157;
13.J.244.166; 13.J.244.169; 13.J.244.172; 13.J.244.175; 13.J.244.240;
13.J.244.244;

Prodrugs of 13.L

13.L.228.228; 13.L.228.229; 13.L.228.230; 13.L.228.231; 13.L.228.236;
13.L.228.237; 13.L.228.238; 13.L.228.239; 13.L.228.154; 13.L.228.157;
13.L.228.166; 13.L.228.169; 13.L.228.172; 13.L.228.175; 13.L.228.240;
13.L.228.244; 13.L.229.228; 13.L.229.229; 13.L.229.230; 13.L.229.231;
13.L.229.236; 13.L.229.237; 13.L.229.238; 13.L.229.239; 13.L.229.154;
13.L.229.157; 13.L.229.166; 13.L.229.169; 13.L.229.172; 13.L.229.175;
13.L.229.240; 13.L.229.244; 13.L.230.228; 13.L.230.229; 13.L.230.230;
13.L.230.231; 13.L.230.236; 13.L.230.237; 13.L.230.238; 13.L.230.239;
13.L.230.154; 13.L.230.157; 13.L.230.166; 13.L.230.169; 13.L.230.172;
13.L.230.175; 13.L.230.240; 13.L.230.244; 13.L.231.228; 13.L.231.229;
13.L.231.230; 13.L.231.231; 13.L.231.236; 13.L.231.237; 13.L.231.238;
13.L.231.239; 13.L.231.154; 13.L.231.157; 13.L.231.166; 13.L.231.169;
13.L.231.172; 13.L.231.175; 13.L.231.240; 13.L.231.244; 13.L.236.228;
13.L.236.229; 13.L.236.230; 13.L.236.231; 13.L.236.236; 13.L.236.237;
13.L.236.238; 13.L.236.239; 13.L.236.154; 13.L.236.157; 13.L.236.166;
13.L.236.169; 13.L.236.172; 13.L.236.175; 13.L.236.240; 13.L.236.244;
13.L.237.228; 13.L.237.229; 13.L.237.230; 13.L.237.231; 13.L.237.236;
13.L.237.237; 13.L.237.238; 13.L.237.239; 13.L.237.154; 13.L.237.157;
13.L.237.166; 13.L.237.169; 13.L.237.172; 13.L.237.175; 13.L.237.240;
13.L.237.244; 13.L.238.228; 13.L.238.229; 13.L.238.230; 13.L.238.231;
13.L.238.236; 13.L.238.237; 13.L.238.238; 13.L.238.239; 13.L.238.154;
13.L.238.157; 13.L.238.166; 13.L.238.169; 13.L.238.172; 13.L.238.175;
13.L.238.240; 13.L.238.244; 13.L.239.228; 13.L.239.229; 13.L.239.230;
13.L.239.231; 13.L.239.236; 13.L.239.237; 13.L.239.238; 13.L.239.239;
13.L.239.154; 13.L.239.157; 13.L.239.166; 13.L.239.169; 13.L.239.172;
13.L.239.175; 13.L.239.240; 13.L.239.244; 13.L.154.228; 13.L.154.229;
13.L.154.230; 13.L.154.231; 13.L.154.236; 13.L.154.237; 13.L.154.238;
13.L.154.239; 13.L.154.154; 13.L.154.157; 13.L.154.166; 13.L.154.169;
13.L.154.172; 13.L.154.175; 13.L.154.240; 13.L.154.244; 13.L.157.228;
13.L.157.229; 13.L.157.230; 13.L.157.231; 13.L.157.236; 13.L.157.237;
13.L.157.238; 13.L.157.239; 13.L.157.154; 13.L.157.157; 13.L.157.166;
13.L.157.169; 13.L.157.172; 13.L.157.175; 13.L.157.240; 13.L.157.244;
13.L.166.228; 13.L.166.229; 13.L.166.230; 13.L.166.231; 13.L.166.236;
13.L.166.237; 13.L.166.238; 13.L.166.239; 13.L.166.154; 13.L.166.157;
13.L.166.166; 13.L.166.169; 13.L.166.172; 13.L.166.175; 13.L.166.240;
13.L.166.244; 13.L.169.228; 13.L.169.229; 13.L.169.230; 13.L.169.231;
13.L.169.236; 13.L.169.237; 13.L.169.238; 13.L.169.239; 13.L.169.154;
13.L.169.157; 13.L.169.166; 13.L.169.169; 13.L.169.172; 13.L.169.175;
13.L.169.240; 13.L.169.244; 13.L.172.228; 13.L.172.229; 13.L.172.230;
13.L.172.231; 13.L.172.236; 13.L.172.237; 13.L.172.238; 13.L.172.239;
13.L.172.154; 13.L.172.157; 13.L.172.166; 13.L.172.169; 13.L.172.172;
13.L.172.175; 13.L.172.240; 13.L.172.244; 13.L.175.228; 13.L.175.229;
13.L.175.230; 13.L.175.231; 13.L.175.236; 13.L.175.237; 13.L.175.238;
13.L.175.239; 13.L.175.154; 13.L.175.157; 13.L.175.166; 13.L.175.169;
13.L.175.172; 13.L.175.175; 13.L.175.240; 13.L.175.244; 13.L.240.228;
13.L.240.229; 13.L.240.230; 13.L.240.231; 13.L.240.236; 13.L.240.237;
13.L.240.238; 13.L.240.239; 13.L.240.154; 13.L.240.157; 13.L.240.166;
13.L.240.169; 13.L.240.172; 13.L.240.175; 13.L.240.240; 13.L.240.244;
13.L.244.228; 13.L.244.229; 13.L.244.230; 13.L.244.231; 13.L.244.236;
13.L.244.237; 13.L.244.238; 13.L.244.239; 13.L.244.154; 13.L.244.157;
13.L.244.166; 13.L.244.169; 13.L.244.172; 13.L.244.175; 13.L.244.240;
13.L.244.244;

Prodrugs of 13.O

13.O.228.228; 13.O.228.229; 13.O.228.230; 13.O.228.231; 13.O.228.236;
13.O.228.237; 13.O.228.238; 13.O.228.239; 13.O.228.154; 13.O.228.157;
13.O.228.166; 13.O.228.169; 13.O.228.172; 13.O.228.175; 13.O.228.240;
13.O.228.244; 13.O.229.228; 13.O.229.229; 13.O.229.230; 13.O.229.231;
13.O.229.236; 13.O.229.237; 13.O.229.238; 13.O.229.239; 13.O.229.154;
13.O.229.157; 13.O.229.166; 13.O.229.169; 13.O.229.172; 13.O.229.175;
13.O.229.240; 13.O.229.244; 13.O.230.228; 13.O.230.229; 13.O.230.230;
13.O.230.231; 13.O.230.236; 13.O.230.237; 13.O.230.238; 13.O.230.239;
13.O.230.154; 13.O.230.157; 13.O.230.166; 13.O.230.169; 13.O.230.172;
13.O.230.175; 13.O.230.240; 13.O.230.244; 13.O.231.228; 13.O.231.229;
13.O.231.230; 13.O.231.231; 13.O.231.236; 13.O.231.237; 13.O.231.238;
13.O.231.239; 13.O.231.154; 13.O.231.157; 13.O.231.166; 13.O.231.169;
13.O.231.172; 13.O.231.175; 13.O.231.240; 13.O.231.244; 13.O.236.228;
13.O.236.229; 13.O.236.230; 13.O.236.231; 13.O.236.236; 13.O.236.237;
13.O.236.238; 13.O.236.239; 13.O.236.154; 13.O.236.157; 13.O.236.166;

TABLE 7-continued

13.O.236.169; 13.O.236.172; 13.O.236.175; 13.O.236.240; 13.O.236.244;
13.O.237.228; 13.O.237.229; 13.O.237.230; 13.O.237.231; 13.O.237.236;
13.O.237.237; 13.O.237.238; 13.O.237.239; 13.O.237.154; 13.O.237.157;
13.O.237.166; 13.O.237.169; 13.O.237.172; 13.O.237.175; 13.O.237.240;
13.O.237.244; 13.O.238.228; 13.O.238.229; 13.O.238.230; 13.O.238.231;
13.O.238.236; 13.O.238.237; 13.O.238.238; 13.O.238.239; 13.O.238.154;
13.O.238.157; 13.O.238.166; 13.O.238.169; 13.O.238.172; 13.O.238.175;
13.O.238.240; 13.O.238.244; 13.O.239.228; 13.O.239.229; 13.O.239.230;
13.O.239.231; 13.O.239.236; 13.O.239.237; 13.O.239.238; 13.O.239.239;
13.O.239.154; 13.O.239.157; 13.O.239.166; 13.O.239.169; 13.O.239.172;
13.O.239.175; 13.O.239.240; 13.O.239.244; 13.O.154.228; 13.O.154.229;
13.O.154.230; 13.O.154.231; 13.O.154.236; 13.O.154.237; 13.O.154.238;
13.O.154.239; 13.O.154.154; 13.O.154.157; 13.O.154.166; 13.O.154.169;
13.O.154.172; 13.O.154.175; 13.O.154.240; 13.O.154.244; 13.O.157.228;
13.O.157.229; 13.O.157.230; 13.O.157.231; 13.O.157.236; 13.O.157.237;
13.O.157.238; 13.O.157.239; 13.O.157.154; 13.O.157.157; 13.O.157.166;
13.O.157.169; 13.O.157.172; 13.O.157.175; 13.O.157.240; 13.O.157.244;
13.O.166.228; 13.O.166.229; 13.O.166.230; 13.O.166.231; 13.O.166.236;
13.O.166.237; 13.O.166.238; 13.O.166.239; 13.O.166.154; 13.O.166.157;
13.O.166.166; 13.O.166.169; 13.O.166.172; 13.O.166.175; 13.O.166.240;
13.O.166.244; 13.O.169.228; 13.O.169.229; 13.O.169.230; 13.O.169.231;
13.O.169.236; 13.O.169.237; 13.O.169.238; 13.O.169.239; 13.O.169.154;
13.O.169.157; 13.O.169.166; 13.O.169.169; 13.O.169.172; 13.O.169.175;
13.O.169.240; 13.O.169.244; 13.O.172.228; 13.O.172.229; 13.O.172.230;
13.O.172.231; 13.O.172.236; 13.O.172.237; 13.O.172.238; 13.O.172.239;
13.O.172.154; 13.O.172.157; 13.O.172.166; 13.O.172.169; 13.O.172.172;
13.O.172.175; 13.O.172.240; 13.O.172.244; 13.O.175.228; 13.O.175.229;
13.O.175.230; 13.O.175.231; 13.O.175.236; 13.O.175.237; 13.O.175.238;
13.O.175.239; 13.O.175.154; 13.O.175.157; 13.O.175.166; 13.O.175.169;
13.O.175.172; 13.O.175.175; 13.O.175.240; 13.O.175.244; 13.O.240.228;
13.O.240.229; 13.O.240.230; 13.O.240.231; 13.O.240.236; 13.O.240.237;
13.O.240.238; 13.O.240.239; 13.O.240.154; 13.O.240.157; 13.O.240.166;
13.O.240.169; 13.O.240.172; 13.O.240.175; 13.O.240.240; 13.O.240.244;
13.O.244.228; 13.O.244.229; 13.O.244.230; 13.O.244.231; 13.O.244.236;
13.O.244.237; 13.O.244.238; 13.O.244.239; 13.O.244.154; 13.O.244.157;
13.O.244.166; 13.O.244.169; 13.O.244.172; 13.O.244.175; 13.O.244.240;
13.O.244.244;
Prodrugs of 13.P 13.P.228.228; 13.P.228.229; 13.P.228.230; 13.P.228.231; 13.P.228.236;
13.P.228.237; 13.P.228.238; 13.P.228.239; 13.P.228.154; 13.P.228.157;
13.P.228.166; 13.P.228.169; 13.P.228.172; 13.P.228.175; 13.P.228.240;
13.P.228.244; 13.P.229.228; 13.P.229.229; 13.P.229.230; 13.P.229.231;
13.P.229.236; 13.P.229.237; 13.P.229.238; 13.P.229.239; 13.P.229.154;
13.P.229.157; 13.P.229.166; 13.P.229.169; 13.P.229.172; 13.P.229.175;
13.P.229.240; 13.P.229.244; 13.P.230.228; 13.P.230.229; 13.P.230.230;
13.P.230.231; 13.P.230.236; 13.P.230.237; 13.P.230.238; 13.P.230.239;
13.P.230.154; 13.P.230.157; 13.P.230.166; 13.P.230.169; 13.P.230.172;
13.P.230.175; 13.P.230.240; 13.P.230.244; 13.P.231.228; 13.P.231.229;
13.P.231.230; 13.P.231.231; 13.P.231.236; 13.P.231.237; 13.P.231.238;
13.P.231.239; 13.P.231.154; 13.P.231.157; 13.P.231.166; 13.P.231.169;
13.P.231.172; 13.P.231.175; 13.P.231.240; 13.P.231.244; 13.P.236.228;
13.P.236.229; 13.P.236.230; 13.P.236.231; 13.P.236.236; 13.P.236.237;
13.P.236.238; 13.P.236.239; 13.P.236.154; 13.P.236.157; 13.P.236.166;
13.P.236.169; 13.P.236.172; 13.P.236.175; 13.P.236.240; 13.P.236.244;
13.P.237.228; 13.P.237.229; 13.P.237.230; 13.P.237.231; 13.P.237.236;
13.P.237.237; 13.P.237.238; 13.P.237.239; 13.P.237.154; 13.P.237.157;
13.P.237.166; 13.P.237.169; 13.P.237.172; 13.P.237.175; 13.P.237.240;
13.P.237.244; 13.P.238.228; 13.P.238.229; 13.P.238.230; 13.P.238.231;
13.P.238.236; 13.P.238.237; 13.P.238.238; 13.P.238.239; 13.P.238.154;
13.P.238.157; 13.P.238.166; 13.P.238.169; 13.P.238.172; 13.P.238.175;
13.P.238.240; 13.P.238.244; 13.P.239.228; 13.P.239.229; 13.P.239.230;
13.P.239.231; 13.P.239.236; 13.P.239.237; 13.P.239.238; 13.P.239.239;
13.P.239.154; 13.P.239.157; 13.P.239.166; 13.P.239.169; 13.P.239.172;
13.P.239.175; 13.P.239.240; 13.P.239.244; 13.P.154.228; 13.P.154.229;
13.P.154.230; 13.P.154.231; 13.P.154.236; 13.P.154.237; 13.P.154.238;
13.P.154.239; 13.P.154.154; 13.P.154.157; 13.P.154.166; 13.P.154.169;
13.P.154.172; 13.P.154.175; 13.P.154.240; 13.P.154.244; 13.P.157.228;
13.P.157.229; 13.P.157.230; 13.P.157.231; 13.P.157.236; 13.P.157.237;
13.P.157.238; 13.P.157.239; 13.P.157.154; 13.P.157.157; 13.P.157.166;
13.P.157.169; 13.P.157.172; 13.P.157.175; 13.P.157.240; 13.P.157.244;
13.P.166.228; 13.P.166.229; 13.P.166.230; 13.P.166.231; 13.P.166.236;
13.P.166.237; 13.P.166.238; 13.P.166.239; 13.P.166.154; 13.P.166.157;
13.P.166.166; 13.P.166.169; 13.P.166.172; 13.P.166.175; 13.P.166.240;
13.P.166.244; 13.P.169.228; 13.P.169.229; 13.P.169.230; 13.P.169.231;
13.P.169.236; 13.P.169.237; 13.P.169.238; 13.P.169.239; 13.P.169.154;
13.P.169.157; 13.P.169.166; 13.P.169.169; 13.P.169.172; 13.P.169.175;
13.P.169.240; 13.P.169.244; 13.P.172.228; 13.P.172.229; 13.P.172.230;
13.P.172.231; 13.P.172.236; 13.P.172.237; 13.P.172.238; 13.P.172.239;
13.P.172.154; 13.P.172.157; 13.P.172.166; 13.P.172.169; 13.P.172.172;
13.P.172.175; 13.P.172.240; 13.P.172.244; 13.P.175.228; 13.P.175.229;
13.P.175.230; 13.P.175.231; 13.P.175.236; 13.P.175.237; 13.P.175.238;
13.P.175.239; 13.P.175.154; 13.P.175.157; 13.P.175.166; 13.P.175.169;
13.P.175.172; 13.P.175.175; 13.P.175.240; 13.P.175.244; 13.P.240.228;
13.P.240.229; 13.P.240.230; 13.P.240.231; 13.P.240.236; 13.P.240.237;
13.P.240.238; 13.P.240.239; 13.P.240.154; 13.P.240.157; 13.P.240.166;
13.P.240.169; 13.P.240.172; 13.P.240.175; 13.P.240.240; 13.P.240.244;
13.P.244.228; 13.P.244.229; 13.P.244.230; 13.P.244.231; 13.P.244.236;
13.P.244.237; 13.P.244.238; 13.P.244.239; 13.P.244.154; 13.P.244.157;
13.P.244.166; 13.P.244.169; 13.P.244.172; 13.P.244.175; 13.P.244.240;
13.P.244.244;
Prodrugs of 13.U 13.U.228.228; 13.U.228.229; 13.U.228.230; 13.U.228.231; 13.U.228.236;
13.U.228.237; 13.U.228.238; 13.U.228.239; 13.U.228.154; 13.U.228.157;
13.U.228.166; 13.U.228.169; 13.U.228.172; 13.U.228.175; 13.U.228.240;
13.U.228.244; 13.U.229.228; 13.U.229.229; 13.U.229.230; 13.U.229.231;
13.U.229.236; 13.U.229.237; 13.U.229.238; 13.U.229.239; 13.U.229.154;
13.U.229.157; 13.U.229.166; 13.U.229.169; 13.U.229.172; 13.U.229.175;
13.U.229.240; 13.U.229.244; 13.U.230.228; 13.U.230.229; 13.U.230.230;
13.U.230.231; 13.U.230.236; 13.U.230.237; 13.U.230.238; 13.U.230.239;
13.U.230.154; 13.U.230.157; 13.U.230.166; 13.U.230.169; 13.U.230.172;
13.U.230.175; 13.U.230.240; 13.U.230.244; 13.U.231.228; 13.U.231.229;
13.U.231.230; 13.U.231.231; 13.U.231.236; 13.U.231.237; 13.U.231.238;
13.U.231.239; 13.U.231.154; 13.U.231.157; 13.U.231.166; 13.U.231.169;
13.U.231.172; 13.U.231.175; 13.U.231.240; 13.U.231.244; 13.U.236.228;
13.U.236.229; 13.U.236.230; 13.U.236.231; 13.U.236.236; 13.U.236.237;
13.U.236.238; 13.U.236.239; 13.U.236.154; 13.U.236.157; 13.U.236.166;
13.U.236.169; 13.U.236.172; 13.U.236.175; 13.U.236.240; 13.U.236.244;
13.U.237.228; 13.U.237.229; 13.U.237.230; 13.U.237.231; 13.U.237.236;
13.U.237.237; 13.U.237.238; 13.U.237.239; 13.U.237.154; 13.U.237.157;
13.U.237.166; 13.U.237.169; 13.U.237.172; 13.U.237.175; 13.U.237.240;
13.U.237.244; 13.U.238.228; 13.U.238.229; 13.U.238.230; 13.U.238.231;
13.U.238.236; 13.U.238.237; 13.U.238.238; 13.U.238.239; 13.U.238.154;
13.U.238.157; 13.U.238.166; 13.U.238.169; 13.U.238.172; 13.U.238.175;
13.U.238.240; 13.U.238.244; 13.U.239.228; 13.U.239.229; 13.U.239.230;
13.U.239.231; 13.U.239.236; 13.U.239.237; 13.U.239.238; 13.U.239.239;
13.U.239.154; 13.U.239.157; 13.U.239.166; 13.U.239.169; 13.U.239.172;
13.U.239.175; 13.U.239.240; 13.U.239.244; 13.U.154.228; 13.U.154.229;
13.U.154.230; 13.U.154.231; 13.U.154.236; 13.U.154.237; 13.U.154.238;
13.U.154.239; 13.U.154.154; 13.U.154.157; 13.U.154.166; 13.U.154.169;
13.U.154.172; 13.U.154.175; 13.U.154.240; 13.U.154.244; 13.U.157.228;
13.U.157.229; 13.U.157.230; 13.U.157.231; 13.U.157.236; 13.U.157.237;
13.U.157.238; 13.U.157.239; 13.U.157.154; 13.U.157.157; 13.U.157.166;
13.U.157.169; 13.U.157.172; 13.U.157.175; 13.U.157.240; 13.U.157.244;
13.U.166.228; 13.U.166.229; 13.U.166.230; 13.U.166.231; 13.U.166.236;
13.U.166.237; 13.U.166.238; 13.U.166.239; 13.U.166.154; 13.U.166.157;
13.U.166.166; 13.U.166.169; 13.U.166.172; 13.U.166.175; 13.U.166.240;
13.U.166.244; 13.U.169.228; 13.U.169.229; 13:U.169.230; 13.U.169.231;
13.U.169.236; 13.U.169.237; 13.U.169.238; 13:U.169.239; 13.U.169.154;
13.U.169.157; 13.U.169.166; 13.U.169.169; 13.U.169.172; 13.U.169.175;
13.U.169.240; 13.U.169.244; 13.U.172.228; 13.U.172.229; 13.U.172.230;
13.U.172.231; 13.U.172.236; 13.U.172.237; 13.U.172.238; 13.U.172.239;
13.U.172.154; 13.U.172.157; 13.U.172.166; 13.U.172.169; 13.U.172.172;
13.U.172.175; 13.U.172.240; 13.U.172.244; 13.U.175.228; 13.U.175.229;
13.U.175.230; 13.U.175.231; 13.U.175.236; 13.U.175.237; 13.U.175.238;
13.U.175.239; 13.U.175.154; 13.U.175.157; 13.U.175.166; 13.U.175.169;
13.U.175.172; 13.U.175.175; 13.U.175.240; 13.U.175.244; 13.U.240.228;
13.U.240.229; 13.U.240.230; 13.U.240.231; 13.U.240.236; 13.U.240.237;
13.U.240.238; 13.U.240.239; 13.U.240.154; 13.U.240.157; 13.U.240.166;
13.U.240.169; 13.U.240.172; 13.U.240.175; 13.U.240.240; 13.U.240.244;
13.U.244.228; 13.U.244.229; 13.U.244.230; 13.U.244.231; 13.U.244.236;
13.U.244.237; 13.U.244.238; 13.U.244.239; 13.U.244.154; 13.U.244.157;
13.U.244.166; 13.U.244.169; 13.U.244.172; 13.U.244.175; 13.U.244.240;
13.U.244.244;
Prodrugs of 13.W 13.W.228.228; 13.W.228.229; 13.W.228.230; 13.W.228.231;
13.W.228.236; 13.W.228.237; 13.W.228.238; 13.W.228.239;
13.W.228.154; 13.W.228.157; 13.W.228.166; 13.W.228.169;
13.W.228.172; 13.W.228.175; 13.W.228.240; 13.W.228.244;
13.W.229.228; 13.W.229.229; 13.W.229.230; 13.W.229.231;
13.W.229.236; 13.W.229.237; 13.W.229.238; 13.W.229.239;
13.W.229.154; 13.W.229.157; 13.W.229.166; 13.W.229.169;
13.W.229.172; 13.W.229.175; 13.W.229.240; 13.W.229.244;
13.W.230.228; 13.W.230.229; 13.W.230.230; 13.W.230.231;
13.W.230.236; 13.W.230.237; 13.W.230.238; 13.W.230.239;
13.W.230.154; 13.W.230.157; 13.W.230.166; 13.W.230.169;

TABLE 7-continued

13.W.230.172; 13.W.230.175; 13.W.230.240; 13.W.230.244;
13.W.231.228; 13.W.231.229; 13.W.231.230; 13.W.231.231;
13.W.231.236; 13.W.231.237; 13.W.231.238; 13.W.231.239;
13.W.231.154; 13.W.231.157; 13.W.231.166; 13.W.231.169;
13.W.231.172; 13.W.231.175; 13.W.231.240; 13.W.231.244;
13.W.236.228; 13.W.236.229; 13.W.236.230; 13.W.236.231;
13.W.236.236; 13.W.236.237; 13.W.236.238; 13.W.236.239;
13.W.236.154; 13.W.236.157; 13.W.236.166; 13.W.236.169;
13.W.236.172; 13.W.236.175; 13.W.236.240; 13.W.236.244;
13.W.237.228; 13.W.237.229; 13.W.237.230; 13.W.237.231;
13.W.237.236; 13.W.237.237; 13.W.237.238; 13.W.237.239;
13.W.237.154; 13.W.237.157; 13.W.237.166; 13.W.237.169;
13.W.237.172; 13.W.237.175; 13.W.237.240; 13.W.237.244;
13.W.238.228; 13.W.238.229; 13.W.238.230; 13.W.238.231;
13.W.238.236; 13.W.238.237; 13.W.238.238; 13.W.238.239;
13.W.238.154; 13.W.238.157; 13.W.238.166; 13.W.238.169;
13.W.238.172; 13.W.238.175; 13.W.238.240; 13.W.238.244;
13.W.239.228; 13.W.239.229; 13.W.239.230; 13.W.239.231;
13.W.239.236; 13.W.239.237; 13.W.239.238; 13.W.239.239;
13.W.239.154; 13.W.239.157; 13.W.239.166; 13.W.239.169;
13.W.239.172; 13.W.239.175; 13.W.239.240; 13.W.239.244;
13.W.154.228; 13.W.154.229; 13.W.154.230; 13.W.154.231;
13.W.154.236; 13.W.154.237; 13.W.154.238; 13.W.154.239;
13.W.154.154; 13.W.154.157; 13.W.154.166; 13.W.154.169;
13.W.154.172; 13.W.154.175; 13.W.154.240; 13.W.154.244;
13.W.157.228; 13.W.157.229; 13.W.157.230; 13.W.157.231;
13.W.157.236; 13.W.157.237; 13.W.157.238; 13.W.157.239;
13.W.157.154; 13.W.157.157; 13.W.157.166; 13.W.157.169;
13.W.157.172; 13.W.157.175; 13.W.157.240; 13.W.157.244;
13.W.166.228; 13.W.166.229; 13.W.166.230; 13.W.166.231;
13.W.166.236; 13.W.166.237; 13.W.166.238; 13.W.166.239;
13.W.166.154; 13.W.166.157; 13.W.166.166; 13.W.166.169;
13.W.166.172; 13.W.166.175; 13.W.166.240; 13.W.166.244;
13.W.169.228; 13.W.169.229; 13.W.169.230; 13.W.169.231;
13.W.169.236; 13.W.169.237; 13.W.169.238; 13.W.169.239;
13.W.169.154; 13.W.169.157; 13.W.169.166; 13.W.169.169;
13.W.169.172; 13.W.169.175; 13.W.169.240; 13.W.169.244;
13.W.172.228; 13.W.172.229; 13.W.172.230; 13.W.172.231;
13.W.172.236; 13.W.172.237; 13.W.172.238; 13.W.172.239;
13.W.172.154; 13.W.172.157; 13.W.172.166; 13.W.172.169;
13.W.172.172; 13.W.172.175; 13.W.172.240; 13.W.172.244;
13.W.175.228; 13.W.175.229; 13.W.175.230; 13.W.175.231;
13.W.175.236; 13.W.175.237; 13.W.175.238; 13.W.175.239;
13.W.175.154; 13.W.175.157; 13.W.175.166; 13.W.175.169;
13.W.175.172; 13.W.175.175; 13.W.175.240; 13.W.175.244;
13.W.240.228; 13.W.240.229; 13.W.240.230; 13.W.240.231;
13.W.240.236; 13.W.240.237; 13.W.240.238; 13.W.240.239;
13.W.240.154; 13.W.240.157; 13.W.240.166; 13.W.240.169;
13.W.240.172; 13.W.240.175; 13.W.240.240; 13.W.240.244;
13.W.244.228; 13.W.244.229; 13.W.244.230; 13.W.244.231;
13.W.244.236; 13.W.244.237; 13.W.244.238; 13.W.244.239;
13.W.244.154; 13.W.244.157; 13.W.244.166; 13.W.244.169;
13.W.244.172; 13.W.244.175; 13.W.244.240; 13.W.244.244;
Prodrugs of 13.Y 13.Y.228.228; 13.Y.228.229; 13.Y.228.230; 13.Y.228.231; 13.Y.228.236;
13.Y.228.237; 13.Y.228.238; 13.Y.228.239; 13.Y.228.154; 13.Y.228.157;
13.Y.228.166; 13.Y.228.169; 13.Y.228.172; 13.Y.228.175; 13.Y.228.240;
13.Y.228.244; 13.Y.229.228; 13.Y.229.229; 13.Y.229.230; 13.Y.229.231;
13.Y.229.236; 13.Y.229.237; 13.Y.229.238; 13.Y.229.239; 13.Y.229.154;
13.Y.229.157; 13.Y.229.166; 13.Y.229.169; 13.Y.229.172; 13.Y.229.175;
13.Y.229.240; 13.Y.229.244; 13.Y.230.228; 13.Y.230.229; 13.Y.230.230;
13.Y.230.231; 13.Y.230.236; 13.Y.230.237; 13.Y.230.238; 13.Y.230.239;
13.Y.230.154; 13.Y.230.157; 13.Y.230.166; 13.Y.230.169; 13.Y.230.172;
13.Y.230.175; 13.Y.230.240; 13.Y.230.244; 13.Y.231.228; 13.Y.231.229;
13.Y.231.230; 13.Y.231.231; 13.Y.231.236; 13.Y.231.237; 13.Y.231.238;
13.Y.231.239; 13.Y.231.154; 13.Y.231.157; 13.Y.231.166; 13.Y.231.169;
13.Y.231.172; 13.Y.231.175; 13.Y.231.240; 13.Y.231.244; 13.Y.236.228;
13.Y.236.229; 13.Y.236.230; 13.Y.236.231; 13.Y.236.236; 13.Y.236.237;
13.Y.236.238; 13.Y.236.239; 13.Y.236.154; 13.Y.236.157; 13.Y.236.166;
13.Y.236.169; 13.Y.236.172; 13.Y.236.175; 13.Y.236.240; 13.Y.236.244;
13.Y.237.228; 13.Y.237.229; 13.Y.237.230; 13.Y.237.231; 13.Y.237.236;
13.Y.237.237; 13.Y.237.238; 13.Y.237.239; 13.Y.237.154; 13.Y.237.157;
13.Y.237.166; 13.Y.237.169; 13.Y.237.172; 13.Y.237.175; 13.Y.237.240;
13.Y.237.244; 13.Y.238.228; 13.Y.238.229; 13.Y.238.230; 13.Y.238.231;
13.Y.238.236; 13.Y.238.237; 13.Y.238.238; 13.Y.238.239; 13.Y.238.154;
13.Y.238.157; 13.Y.238.166; 13.Y.238.169; 13.Y.238.172; 13.Y.238.175;
13.Y.238.240; 13.Y.238.244; 13.Y.239.228; 13.Y.239.229; 13.Y.239.230;
13.Y.239.231; 13.Y.239.236; 13.Y.239.237; 13.Y.239.238; 13.Y.239.239;
13.Y.239.154; 13.Y.239.157; 13.Y.239.166; 13.Y.239.169; 13.Y.239.172;
13.Y.239.175; 13.Y.239.240; 13.Y.239.244; 13.Y.154.228; 13.Y.154.229;
13.Y.154.230; 13.Y.154.231; 13.Y.154.236; 13.Y.154.237; 13.Y.154.238;
13.Y.154.239; 13.Y.154.154; 13.Y.154.157; 13.Y.154.166; 13.Y.154.169;
13.Y.154.172; 13.Y.154.175; 13.Y.154.240; 13.Y.154.244; 13.Y.157.228;
13.Y.157.229; 13.Y.157.230; 13.Y.157.231; 13.Y.157.236; 13.Y.157.237;
13.Y.157.238; 13.Y.157.239; 13.Y.157.154; 13.Y.157.157; 13.Y.157.166;
13.Y.157.169; 13.Y.157.172; 13.Y.157.175; 13.Y.157.240; 13.Y.157.244;
13.Y.166.228; 13.Y.166.229; 13.Y.166.230; 13.Y.166.231; 13.Y.166.236;
13.Y.166.237; 13.Y.166.238; 13.Y.166.239; 13.Y.166.154; 13.Y.166.157;
13.Y.166.166; 13.Y.166.169; 13.Y.166.172; 13.Y.166.175; 13.Y.166.240;
13.Y.166.244; 13.Y.169.228; 13.Y.169.229; 13.Y.169.230; 13.Y.169.231;
13.Y.169.236; 13.Y.169.237; 13.Y.169.238; 13.Y.169.239; 13.Y.169.154;
13.Y.169.157; 13.Y.169.166; 13.Y.169.169; 13.Y.169.172; 13.Y.169.175;
13.Y.169.240; 13.Y.169.244; 13.Y.172.228; 13.Y.172.229; 13.Y.172.230;
13.Y.172.231; 13.Y.172.236; 13.Y.172.237; 13.Y.172.238; 13.Y.172.239;
13.Y.172.154; 13.Y.172.157; 13.Y.172.166; 13.Y.172.169; 13.Y.172.172;
13.Y.172.175; 13.Y.172.240; 13.Y.172.244; 13.Y.175.228; 13.Y.175.229;
13.Y.175.230; 13.Y.175.231; 13.Y.175.236; 13.Y.175.237; 13.Y.175.238;
13.Y.175.239; 13.Y.175.154; 13.Y.175.157; 13.Y.175.166; 13.Y.175.169;
13.Y.175.172; 13.Y.175.175; 13.Y.175.240; 13.Y.175.244; 13.Y.240.228;
13.Y.240.229; 13.Y.240.230; 13.Y.240.231; 13.Y.240.236; 13.Y.240.237;
13.Y.240.238; 13.Y.240.239; 13.Y.240.154; 13.Y.240.157; 13.Y.240.166;
13.Y.240.169; 13.Y.240.172; 13.Y.240.175; 13.Y.240.240; 13.Y.240.244;
13.Y.244.228; 13.Y.244.229; 13.Y.244.230; 13.Y.244.231; 13.Y.244.236;
13.Y.244.237; 13.Y.244.238; 13.Y.244.239; 13.Y.244.154; 13.Y.244.157;
13.Y.244.166; 13.Y.244.169; 13.Y.244.172; 13.Y.244.175; 13.Y.244.240;
13.Y.244.244;
Prodrugs of 14.AH 14.AH.4.157; 14.AH.4.158; 14.AH.4.196; 14.AH.4.223; 14.AH.4.240;
14.AH.4.244; 14.AH.4.243; 14.AH.4.247; 14.AH.5.157; 14.AH.5.158;
14.AH.5.196; 14.AH.5.223; 14.AH.5.240; 14.AH.5.244; 14.AH.5.243;
14.AH.5.247; 14.AH.7.157; 14.AH.7.158; 14.AH.7.196; 14.AH.7.223;
14.AH.7.240; 14.AH.7.244; 14.AH.7.243; 14.AH.7.247; 14.AH.15.157;
14.AH.15.158; 14.AH.15.196; 14.AH.15.223; 14.AH.15.240;
14.AH.15.244; 14.AH.15.243; 14.AH.15.247; 14.AH.16.157;
14.AH.16.158; 14.AH.16.196; 14.AH.16.223; 14.AH.16.240;
14.AH.16.244; 14.AH.16.243; 14.AH.16.247; 14.AH.18.157;
14.AH.18.158; 14.AH.18.196; 14.AH.18.223; 14.AH.18.240;
14.AH.18.244; 14.AH.18.243; 14.AH.18.247; 14.AH.26.157;
14.AH.26.158; 14.AH.26.196; 14.AH.26.223; 14.AH.26.240;
14.AH.26.244; 14.AH.26.243; 14.AH.26.247; 14.AH.27.157;
14.AH.27.158; 14.AH.27.196; 14.AH.27.223; 14.AH.27.240;
14.AH.27.244; 14.AH.27.243; 14.AH.27.247; 14.AH.29.157;
14.AH.29.158; 14.AH.29.196; 14.AH.29.223; 14.AH.29.240;
14.AH.29.244; 14.AH.29.243; 14.AH.29.247; 14.AH.54.157;
14.AH.54.158; 14.AH.54.196; 14.AH.54.223; 14.AH.54.240;
14.AH.54.244; 14.AH.54.243; 14.AH.54.247; 14.AH.55.157;
14.AH.55.158; 14.AH.55.196; 14.AH.55.223; 14.AH.55.240;
14.AH.55.244; 14.AH.55.243; 14.AH.55.247; 14.AH.56.157;
14.AH.56.158; 14.AH.56.196; 14.AH.56.223; 14.AH.56.240;
14.AH.56.244; 14.AH.56.243; 14.AH.56.247; 14.AH.157.157;
14.AH.157.158; 14.AH.157.196; 14.AH.157.223; 14.AH.157.240;
14.AH.157.244; 14.AH.157.243; 14.AH.157.247; 14.AH.196.157;
14.AH.196.158; 14.AH.196.196; 14.AH.196.223; 14.AH.196.240;
14.AH.196.244; 14.AH.196.243; 14.AH.196.247; 14.AH.223.157;
14.AH.223.158; 14.AH.223.196; 14.AH.223.223; 14.AH.223.240;
14.AH.223.244; 14.AH.223.243; 14.AH.223.247; 14.AH.240.157;
14.AH.240.158; 14.AH.240.196; 14.AH.240.223; 14.AH.240.240;
14.AH.240.244; 14.AH.240.243; 14.AH.240.247; 14.AH.244.157;
14.AH.244.158; 14.AH.244.196; 14.AH.244.223; 14.AH.244.240;
14.AH.244.244; 14.AH.244.243; 14.AH.244.247; 14.AH.247.157;
14.AH.247.158; 14.AH.247.196; 14.AH.247.223; 14.AH.247.240;
14.AH.247.244; 14.AH.247.243; 14.AH.247.247;
Prodrugs of 14.AJ 14.AJ.4.157; 14.AJ.4.158; 14.AJ.4.196; 14.AJ.4.223; 14.AJ.4.240;
14.AJ.4.244; 14.AJ.4.243; 14.AJ.4.247; 14.AJ.5.157; 14.AJ.5.158;
14.AJ.5.196; 14.AJ.5.223; 14.AJ.5.240; 14.AJ.5.244; 14.AJ.5.243;
14.AJ.5.247; 14.AJ.7.157; 14.AJ.7.158; 14.AJ.7.196; 14.AJ.7.223;
14.AJ.7.240; 14.AJ.7.244; 14.AJ.7.243; 14.AJ.7.247; 14.AJ.15.157;
14.AJ.15.158; 14.AJ.15.196; 14.AJ.15.223; 14.AJ.15.240; 14.AJ.15.244;
14.AJ.15.243; 14.AJ.15.247; 14.AJ.16.157; 14.AJ.16.158; 14.AJ.16.196;
14.AJ.16.223; 14.AJ.16.240; 14.AJ.16.244; 14.AJ.16.243; 14.AJ.16.247;
14.AJ.18.157; 14.AJ.18.158; 14.AJ.18.196; 14.AJ.18.223; 14.AJ.18.240;
14.AJ.18.244; 14.AJ.18.243; 14.AJ.18.247; 14.AJ.26.157; 14.AJ.26.158;
14.AJ.26.196; 14.AJ.26.223; 14.AJ.26.240; 14.AJ.26.244; 14.AJ.26.243;
14.AJ.26.247; 14.AJ.27.157; 14.AJ.27.158; 14.AJ.27.196; 14.AJ.27.223;

TABLE 7-continued

14.AJ.27.240; 14.AJ.27.244; 14.AJ.27.243; 14.AJ.27.247; 14.AJ.29.157;
14.AJ.29.158; 14.AJ.29.196; 14.AJ.29.223; 14.AJ.29.240; 14.AJ.29.244;
14.AJ.29.243; 14.AJ.29.247; 14.AJ.54.157; 14.AJ.54.158; 14.AJ.54.196;
14.AJ.54.223; 14.AJ.54.240; 14.AJ.54.244; 14.AJ.54.243; 14.AJ.54.247;
14.AJ.55.157; 14.AJ.55.158; 14.AJ.55.196; 14.AJ.55.223; 14.AJ.55.240;
14.AJ.55.244; 14.AJ.55.243; 14.AJ.55.247; 14.AJ.56.157; 14.AJ.56.158;
14.AJ.56.196; 14.AJ.56.223; 14.AJ.56.240; 14.AJ.56.244; 14.AJ.56.243;
14.AJ.56.247; 14.AJ.157.157; 14.AJ.157.158; 14.AJ.157.196;
14.AJ.157.223; 14.AJ.157.240; 14.AJ.157.244; 14.AJ.157.243;
14.AJ.157.247; 14.AJ.196.157; 14.AJ.196.158; 14.AJ.196.196;
14.AJ.196.223; 14.AJ.196.240; 14.AJ.196.244; 14.AJ.196.243;
14.AJ.196.247; 14.AJ.223.157; 14.AJ.223.158; 14.AJ.223.196;
14.AJ.223.223; 14.AJ.223.240; 14.AJ.223.244; 14.AJ.223.243;
14.AJ.223.247; 14.AJ.240.157; 14.AJ.240.158; 14.AJ.240.196;
14.AJ.240.223; 14.AJ.240.240; 14.AJ.240.244; 14.AJ.240.243;
14.AJ.240.247; 14.AJ.244.157; 14.AJ.244.158; 14.AJ.244.196;
14.AJ.244.223; 14.AJ.244.240; 14.AJ.244.244; 14.AJ.244.243;
14.AJ.244.247; 14.AJ.247.157; 14.AJ.247.158; 14.AJ.247.196;
14.AJ.247.223; 14.AJ.247.240; 14.AJ.247.244; 14.AJ.247.243;
14.AJ.247.247;
Prodrugs of 14.AN 14.AN.4.157; 14.AN.4.158; 14.AN.4.196; 14.AN.4.223; 14.AN.4.240;
14.AN.4.244; 14.AN.4.243; 14.AN.4.247; 14.AN.5.157; 14.AN.5.158;
14.AN.5.196; 14.AN.5.223; 14.AN.5.240; 14.AN.5.244; 14.AN.5.243;
14.AN.5.247; 14.AN.7.157; 14.AN.7.158; 14.AN.7.196; 14.AN.7.223;
14.AN.7.240; 14.AN.7.244; 14.AN.7.243; 14.AN.7.247; 14.AN.15.157;
14.AN.15.158; 14.AN.15.196; 14.AN.15.223; 14.AN.15.240;
14.AN.15.244; 14.AN.15.243; 14.AN.15.247; 14.AN.16.157;
14.AN.16.158; 14.AN.16.196; 14.AN.16.223; 14.AN.16.240;
14.AN.16.244; 14.AN.16.243; 14.AN.16.247; 14.AN.18.157;
14.AN.18.158; 14.AN.18.196; 14.AN.18.223; 14.AN.18.240;
14.AN.18.244; 14.AN.18.243; 14.AN.18.247; 14.AN.26.157;
14.AN.26.158; 14.AN.26.196; 14.AN.26.223; 14.AN.26.240;
14.AN.26.244; 14.AN.26.243; 14.AN.26.247; 14.AN.27.157;
14.AN.27.158; 14.AN.27.196; 14.AN.27.223; 14.AN.27.240;
14.AN.27.244; 14.AN.27.243; 14.AN.27.247; 14.AN.29.157;
14.AN.29.158; 14.AN.29.196; 14.AN.29.223; 14.AN.29.240;
14.AN.29.244; 14.AN.29.243; 14.AN.29.247; 14.AN.54.157;
14.AN.54.158; 14.AN.54.196; 14.AN.54.223; 14.AN.54.240;
14.AN.54.244; 14.AN.54.243; 14.AN.54.247; 14.AN.55.157;
14.AN.55.158; 14.AN.55.196; 14.AN.55.223; 14.AN.55.240;
14.AN.55.244; 14.AN.55.243; 14.AN.55.247; 14.AN.56.157;
14.AN.56.158; 14.AN.56.196; 14.AN.56.223; 14.AN.56.240;
14.AN.56.244; 14.AN.56.243; 14.AN.56.247; 14.AN.157.157;
14.AN.157.158; 14.AN.157.196; 14.AN.157.223; 14.AN.157.240;
14.AN.157.244; 14.AN.157.243; 14.AN.157.247; 14.AN.196.157;
14.AN.196.158; 14.AN.196.196; 14.AN.196.223; 14.AN.196.240;
14.AN.196.244; 14.AN.196.243; 14.AN.196.247; 14.AN.223.157;
14.AN.223.158; 14.AN.223.196; 14.AN.223.223; 14.AN.223.240;
14.AN.223.244; 14.AN.223.243; 14.AN.223.247; 14.AN.240.157;
14.AN.240.158; 14.AN.240.196; 14.AN.240.223; 14.AN.240.240;
14.AN.240.244; 14.AN.240.243; 14.AN.240.247; 14.AN.244.157;
14.AN.244.158; 14.AN.244.196; 14.AN.244.223; 14.AN.244.240;
14.AN.244.244; 14.AN.244.243; 14.AN.244.247; 14.AN.247.157;
14.AN.247.158; 14.AN.247.196; 14.AN.247.223; 14.AN.247.240;
14.AN.247.244; 14.AN.247.243; 14.AN.247.247;
Prodrugs of 14.AP 14.AP.4.157; 14.AP.4.158; 14.AP.4.196; 14.AP.4.223; 14.AP.4.240;
14.AP.4.244; 14.AP.4.243; 14.AP.4.247; 14.AP.5.157; 14.AP.5.158;
14.AP.5.196; 14.AP.5.223; 14.AP.5.240; 14.AP.5.244; 14.AP.5.243;
14.AP.5.247; 14.AP.7.157; 14.AP.7.158; 14.AP.7.196; 14.AP.7.223;
14.AP.7.240; 14.AP.7.244; 14.AP.7.243; 14.AP.7.247; 14.AP.15.157;
14.AP.15.158; 14.AP.15.196; 14.AP.15.223; 14.AP.15.240;
14.AP.15.244; 14.AP.15.243; 14.AP.15.247; 14.AP.16.157;
14.AP.16.158; 14.AP.16.196; 14.AP.16.223; 14.AP.16.240;
14.AP.16.244; 14.AP.16.243; 14.AP.16.247; 14.AP.18.157;
14.AP.18.158; 14.AP.18.196; 14.AP.18.223; 14.AP.18.240;
14.AP.18.244; 14.AP.18.243; 14.AP.18.247; 14.AP.26.157;
14.AP.26.158; 14.AP.26.196; 14.AP.26.223; 14.AP.26.240;
14.AP.26.244; 14.AP.26.243; 14.AP.26.247; 14.AP.27.157;
14.AP.27.158; 14.AP.27.196; 14.AP.27.223; 14.AP.27.240;
14.AP.27.244; 14.AP.27.243; 14.AP.27.247; 14.AP.29.157;
14.AP.29.158; 14.AP.29.196; 14.AP.29.223; 14.AP.29.240;
14.AP.29.244; 14.AP.29.243; 14.AP.29.247; 14.AP.54.157;
14.AP.54.158; 14.AP.54.196; 14.AP.54.223; 14.AP.54.240;
14.AP.54.244; 14.AP.54.243; 14.AP.54.247; 14.AP.55.157;
14.AP.55.158; 14.AP.55.196; 14.AP.55.223; 14.AP.55.240;
14.AP.55.244; 14.AP.55.243; 14.AP.55.247; 14.AP.56.157;
14.AP.56.158; 14.AP.56.196; 14.AP.56.223; 14.AP.56.240;
14.AP.56.244; 14.AP.56.243; 14.AP.56.247; 14.AP.157.157;
14.AP.157.158; 14.AP.157.196; 14.AP.157.223; 14.AP.157.240;
14.AP.157.244; 14.AP.157.243; 14.AP.157.247; 14.AP.196.157;
14.AP.196.158; 14.AP.196.196; 14.AP.196.223; 14.AP.196.240;
14.AP.196.244; 14.AP.196.243; 14.AP.196.247; 14.AP.223.157;
14.AP.223.158; 14.AP.223.196; 14.AP.223.223; 14.AP.223.240;
14.AP.223.244; 14.AP.223.243; 14.AP.223.247; 14.AP.240.157;
14.AP.240.158; 14.AP.240.196; 14.AP.240.223; 14.AP.240.240;
14.AP.240.244; 14.AP.240.243; 14.AP.240.247; 14.AP.244.157;
14.AP.244.158; 14.AP.244.196; 14.AP.244.223; 14.AP.244.240;
14.AP.244.244; 14.AP.244.243; 14.AP.244.247; 14.AP.247.157;
14.AP.247.158; 14.AP.247.196; 14.AP.247.223; 14.AP.247.240;
14.AP.247.244; 14.AP.247.243; 14.AP.247.247;
Prodrugs of 14.AZ 14.AZ.4.157; 14.AZ.4.158; 14.AZ.4.196; 14.AZ.4.223; 14.AZ.4.240;
14.AZ.4.244; 14.AZ.4.243; 14.AZ.4.247; 14.AZ.5.157; 14.AZ.5.158;
14.AZ.5.196; 14.AZ.5.223; 14.AZ.5.240; 14.AZ.5.244; 14.AZ.5.243;
14.AZ.5.247; 14.AZ.7.157; 14.AZ.7.158; 14.AZ.7.196; 14.AZ.7.223;
14.AZ.7.240; 14.AZ.7.244; 14.AZ.7.243; 14.AZ.7.247; 14.AZ.15.157;
14.AZ.15.158; 14.AZ.15.196; 14.AZ.15.223; 14.AZ.15.240;
14.AZ.15.244; 14.AZ.15.243; 14.AZ.15.247; 14.AZ.16.157;
14.AZ.16.158; 14.AZ.16.196; 14.AZ.16.223; 14.AZ.16.240;
14.AZ.16.244; 14.AZ.16.243; 14.AZ.16.247; 14.AZ.18.157;
14.AZ.18.158; 14.AZ.18.196; 14.AZ.18.223; 14.AZ.18.240;
14.AZ.18.244; 14.AZ.18.243; 14.AZ.18.247; 14.AZ.26.157;
14.AZ.26.158; 14.AZ.26.196; 14.AZ.26.223; 14.AZ.26.240;
14.AZ.26.244; 14.AZ.26.243; 14.AZ.26.247; 14.AZ.27.157;
14.AZ.27.158; 14.AZ.27.196; 14.AZ.27.223; 14.AZ.27.240;
14.AZ.27.244; 14.AZ.27.243; 14.AZ.27.247; 14.AZ.29.157;
14.AZ.29.158; 14.AZ.29.196; 14.AZ.29.223; 14.AZ.29.240;
14.AZ.29.244; 14.AZ.29.243; 14.AZ.29.247; 14.AZ.54.157;
14.AZ.54.158; 14.AZ.54.196; 14.AZ.54.223; 14.AZ.54.240;
14.AZ.54.244; 14.AZ.54.243; 14.AZ.54.247; 14.AZ.55.157;
14.AZ.55.158; 14.AZ.55.196; 14.AZ.55.223; 14.AZ.55.240;
14.AZ.55.244; 14.AZ.55.243; 14.AZ.55.247; 14.AZ.56.157;
14.AZ.56.158; 14.AZ.56.196; 14.AZ.56.223; 14.AZ.56.240;
14.AZ.56.244; 14.AZ.56.243; 14.AZ.56.247; 14.AZ.157.157;
14.AZ.157.158; 14.AZ.157.196; 14.AZ.157.223; 14.AZ.157.240;
14.AZ.157.244; 14.AZ.157.243; 14.AZ.157.247; 14.AZ.196.157;
14.AZ.196.158; 14.AZ.196.196; 14.AZ.196.223; 14.AZ.196.240;
14.AZ.196.244; 14.AZ.196.243; 14.AZ.196.247; 14.AZ.223.157;
14.AZ.223.158; 14.AZ.223.196; 14.AZ.223.223; 14.AZ.223.240;
14.AZ.223.244; 14.AZ.223.243; 14.AZ.223.247; 14.AZ.240.157;
14.AZ.240.158; 14.AZ.240.196; 14.AZ.240.223; 14.AZ.240.240;
14.AZ.240.244; 14.AZ.240.243; 14.AZ.240.247; 14.AZ.244.157;
14.AZ.244.158; 14.AZ.244.196; 14.AZ.244.223; 14.AZ.244.240;
14.AZ.244.244; 14.AZ.244.243; 14.AZ.244.247; 14.AZ.247.157;
14.AZ.247.158; 14.AZ.247.196; 14.AZ.247.223; 14.AZ.247.240;
14.AZ.247.244; 14.AZ.247.243; 14.AZ 247.247;
Prodrugs of 14.BF 14.BF.4.157; 14.BF.4.158; 14.BF.4.196; 14.BF.4.223; 14.BF.4.240;
14.BF.4.244; 14.BF.4.243; 14.BF.4.247; 14.BF.5.157; 14.BF.5.158;
14.BF.5.196; 14.BF.5.223; 14.BF.5.240; 14.BF.5.244; 14.BF.5.243;
14.BF.5.247; 14.BF.7.157; 14.BF.7.158; 14.BF.7.196; 14.BF.7.223;
14.BF.7.240; 14.BF.7.244; 14.BF.7.243; 14.BF.7.247; 14.BF.15.157;
14.BF.15.158; 14.BF.15.196; 14.BF.15.223; 14.BF.15.240; 14.BF.15.244;
14.BF.15.243; 14.BF.15.247; 14.BF.16.157; 14.BF.16.158; 14.BF.16.196;
14.BF.16.223; 14.BF.16.240; 14.BF.16.244; 14.BF.16.243; 14.BF.16.247;
14.BF.18.157; 14.BF.18.158; 14.BF.18.196; 14.BF.18.223; 14.BF.18.240;
14.BF.18.244; 14.BF.18.243; 14.BF.18.247; 14.BF.26.157; 14.BF.26.158;
14.BF.26.196; 14.BF.26.223; 14.BF.26.240; 14.BF.26.244; 14.BF.26.243;
14.BF.26.247; 14.BF.27.157; 14.BF.27.158; 14.BF.27.196; 14.BF.27.223;
14.BF.27.240; 14.BF.27.244; 14.BF.27.243; 14.BF.27.247; 14.BF.29.157;
14.BF.29.158; 14.BF.29.196; 14.BF.29.223; 14.BF.29.240; 14.BF.29.244;
14.BF.29.243; 14.BF.29.247; 14.BF.54.157; 14.BF.54.158; 14.BF.54.196;
14.BF.54.223; 14.BF.54.240; 14.BF.54.244; 14.BF.54.243; 14.BF.54.247;
14.BF.55.157; 14.BF.55.158; 14.BF.55.196; 14.BF.55.223; 14.BF.55.240;
14.BF.55.244; 14.BF.55.243; 14.BF.55.247; 14.BF.56.157; 14.BF.56.158;
14.BF.56.196; 14.BF.56.223; 14.BF.56.240; 14.BF.56.244; 14.BF.56.243;
14.BF.56.247; 14.BF.157.157; 14.BF.157.158; 14.BF.157.196;
14.BF.157.223; 14.BF.157.240; 14.BF.157.244; 14.BF.157.243;
14.BF.157.247; 14.BF.196.157; 14.BF.196.158; 14.BF.196.196;
14.BF.196.223; 14.BF.196.240; 14.BF.196.244; 14.BF.196.243;
14.BF.196.247; 14.BF.223.157; 14.BF.223.158; 14.BF.223.196;
14.BF.223.223; 14.BF.223.240; 14.BF.223.244; 14.BF.223.243;

TABLE 7-continued

14.BF.223.247; 14.BF.240.157; 14.BF.240.158; 14.BF.240.196;
14.BF.240.223; 14.BF.240.240; 14.BF.240.244; 14.BF.240.243;
14.BF.240.247; 14.BF.244.157; 14.BF.244.158; 14.BF.244.196;
14.BF.244.223; 14.BF.244.240; 14.BF.244.244; 14.BF.244.243;
14.BF.244.247; 14.BF.247.157; 14.BF.247.158; 14.BF.247.196;
14.BF.247.223; 14.BF.247.240; 14.BF.247.244; 14.BF.247.243;
14.BF.247.247;

Prodrugs of 14.CI

14.CI.4.157; 14.CI.4.158; 14.CI.4.196; 14.CI.4.223; 14.CI.4.240;
14.CI.4.244; 14.CI.4.243; 14.CI.4.247; 14.CI.5.157; 14.CI.5.158;
14.CI.5.196; 14.CI.5.223; 14.CI.5.240; 14.CI.5.244; 14.CI.5.243;
14.CI.5.247; 14.CI.7.157; 14.CI.7.158; 14.CI.7.196; 14.CI.7.223;
14.CI.7.240; 14.CI.7.244; 14.CI.7.243; 14.CI.7.247; 14.CI.15.157;
14.CI.15.158; 14.CI.15.196; 14.CI.15.223; 14.CI.15.240; 14.CI.15.244;
14.CI.15.243; 14.CI.15.247; 14.CI.16.157; 14.CI.16.158; 14.CI.16.196;
14.CI.16.223; 14.CI.16.240; 14.CI.16.244; 14.CI.16.243; 14.CI.16.247;
14.CI.18.157; 14.CI.18.158; 14.CI.18.196; 14.CI.18.223; 14.CI.18.240;
14.CI.18.244; 14.CI.18.243; 14.CI.18.247; 14.CI.26.157; 14.CI.26.158;
14.CI.26.196; 14.CI.26.223; 14.CI.26.240; 14.CI.26.244; 14.CI.26.243;
14.CI.26.247; 14.CI.27.157; 14.CI.27.158; 14.CI.27.196; 14.CI.27.223;
14.CI.27.240; 14.CI.27.244; 14.CI.27.243; 14.CI.27.247; 14.CI.29.157;
14.CI.29.158; 14.CI.29.196; 14.CI.29.223; 14.CI.29.240; 14.CI.29.244;
14.CI.29.243; 14.CI.29.247; 14.CI.54.157; 14.CI.54.158; 14.CI.54.196;
14.CI.54.223; 14.CI.54.240; 14.CI.54.244; 14.CI.54.243; 14.CI.54.247;
14.CI.55.157; 14.CI.55.158; 14.CI.55.196; 14.CI.55.223; 14.CI.55.240;
14.CI.55.244; 14.CI.55.243; 14.CI.55.247; 14.CI.56.157; 14.CI.56.158;
14.CI.56.196; 14.CI.56.223; 14.CI.56.240; 14.CI.56.244; 14.CI.56.243;
14.CI.56.247; 14.CI.157.157; 14.CI.157.158; 14.CI.157.196;
14.CI.157.223; 14.CI.157.240; 14.CI.157.244; 14.CI.157.243;
14.CI.157.247; 14.CI.196.157; 14.CI.196.158; 14.CI.196.196;
14.CI.196.223; 14.CI.196.240; 14.CI.196.244; 14.CI.196.243;
14.CI.196.247; 14.CI.223.157; 14.CI.223.158; 14.CI.223.196;
14.CI.223.223; 14.CI.223.240; 14.CI.223.244; 14.CI.223.243;
14.CI.223.247; 14.CI.240.157; 14.CI.240.158; 14.CI.240.196;
14.CI.240.223; 14.CI.240.240; 14.CI.240.244; 14.CI.240.243;
14.CI.240.247; 14.CI.244.157; 14.CI.244.158; 14.CI.244.196;
14.CI.244.223; 14.CI.244.240; 14.CI.244.244; 14.CI.244.243;
14.CI.244.247; 14.CI.247.157; 14.CI.247.158; 14.CI.247.196;
14.CI.247.223; 14.CI.247.240; 14.CI.247.244; 14.CI.247.243;
14.CI.247.247;

Prodrugs of 14.CO

14.CO.4.157; 14.CO.4.158; 14.CO.4.196; 14.CO.4.223; 14.CO.4.240;
14.CO.4.244; 14.CO.4.243; 14.CO.4.247; 14.CO.5.157; 14.CO.5.158;
14.CO.5.196; 14.CO.5.223; 14.CO.5.240; 14.CO.5.244; 14.CO.5.243;
14.CO.5.247; 14.CO.7.157; 14.CO.7.158; 14.CO.7.196; 14.CO.7.223;
14.CO.7.240; 14.CO.7.244; 14.CO.7.243; 14.CO.7.247; 14.CO.15.157;
14.CO.15.158; 14.CO.15.196; 14.CO.15.223; 14.CO.15.240;
14.CO.15.244; 14.CO.15.243; 14.CO.15.247; 14.CO.16.157;
14.CO.16.158; 14.CO.16.196; 14.CO.16.223; 14.CO.16.240;
14.CO.16.244; 14.CO.16.243; 14.CO.16.247; 14.CO.18.157;
14.CO.18.158; 14.CO.18.196; 14.CO.18.223; 14.CO.18.240;
14.CO.18.244; 14.CO.18.243; 14.CO.18.247; 14.CO.26.157;
14.CO.26.158; 14.CO.26.196; 14.CO.26.223; 14.CO.26.240;
14.CO.26.244; 14.CO.26.243; 14.CO.26.247; 14.CO.27.157;
14.CO.27.158; 14.CO.27.196; 14.CO.27.223; 14.CO.27.240;
14.CO.27.244; 14.CO.27.243; 14.CO.27.247; 14.CO.29.157;
14.CO.29.158; 14.CO.29.196; 14.CO.29.223; 14.CO.29.240;
14.CO.29.244; 14.CO.29.243; 14.CO.29.247; 14.CO.54.157;
14.CO.54.158; 14.CO.54.196; 14.CO.54.223; 14.CO.54.240;
14.CO.54.244; 14.CO.54.243; 14.CO.54.247; 14.CO.55.157;
14.CO.55.158; 14.CO.55.196; 14.CO.55.223; 14.CO.55.240;
14.CO.55.244; 14.CO.55.243; 14.CO.55.247; 14.CO.56.157;
14.CO.56.158; 14.CO.56.196; 14.CO.56.223; 14.CO.56.240;
14.CO.56.244; 14.CO.56.243; 14.CO.56.247; 14.CO.157.157;
14.CO.157.158; 14.CO.157.196; 14.CO.157.223; 14.CO.157.240;
14.CO.157.244; 14.CO.157.243; 14.CO.157.247; 14.CO.196.157;
14.CO.196.158; 14.CO.196.196; 14.CO.196.223; 14.CO.196.240;
14.CO.196.244; 14.CO.196.196; 14.CO.196.247; 14.CO.223.157;
14.CO.223.158; 14.CO.223.196; 14.CO.223.223; 14.CO.223.240;
14.CO.223.244; 14.CO.223.243; 14.CO.223.247; 14.CO.240.157;
14.CO.240.158; 14.CO.240.196; 14.CO.240.223; 14.CO.240.240;
14.CO.240.244; 14.CO.240.243; 14.CO.240.247; 14.CO.244.157;
14.CO.244.158; 14.CO.244.196; 14.CO.244.223; 14.CO.244.240;
14.CO.244.244; 14.CO.244.243; 14.CO.244.247; 14.CO.4.157;
14.CO.4.158; 14.CO.4.196; 14.CO.4.223; 14.CO.4.240; 14.CO.4.244;
14.CO.4.243; 14.CO.4.247;

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the Handbook of Pharmaceutical Excipients (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations of the invention, both for veterinary and for human use, comprise at least one active ingredient, as defined above, together with one or more acceptable carriers and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

For administration to the eye or other external tissues e.g., mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid. (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl n-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for administration to the eye include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 μm (including particle sizes in a range between 0.1 and 500 μm in increments such as 0.5 μm, 1 μm, 30 μm, 35 μm, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of infections as described herein.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention can also be formulated to provide controlled release of the active ingredient to allow less frequent dosing or to improve the pharmacokinetic or toxicity profile of the active ingredient. Accordingly, the invention also provided compositions comprising one or more compounds of the invention formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 100 mg/kg body weight per day. Typically, from about 0.01 to about 10 mg/kg body weight per day. More typically, from about 0.01 to about 5 mg/kg body weight per day. More typically, from about 0.05 to about 0.5 mg/kg body weight per day. For example, the daily candidate dose for an adult human of approximately 70 kg body weight will range from 1 mg to 1000 mg, or between 5 mg and 500 mg, and may take the form of single or multiple doses.

In another embodiment, the present application provides a pharmaceutical composition comprising a therapeutically effective amount of a compound of the present invention, or a pharmaceutically acceptable salt, solvate, and/or ester thereof, and a pharmaceutically acceptable carrier.

In another embodiment, the present application provides a pharmaceutical composition comprising a therapeutically effective amount of a compound of the present invention, or a pharmaceutically acceptable salt, solvate, and/or ester thereof, in combination with at least one additional active therapeutic agent and a pharmaceutically acceptable carrier.

In another embodiment, the present application provides a pharmaceutical composition comprising a therapeutically effective amount of a compound of the present invention, or a pharmaceutically acceptable salt, solvate, and/or ester thereof, in combination with at least one additional active therapeutic agent and a pharmaceutically acceptable carrier. The at least one additional active therapeutic agent is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present application provides a pharmaceutical composition comprising a therapeutically effective amount of a compound of the present invention, or a pharmaceutically acceptable salt, solvate, and/or ester thereof, in combination with at least one additional active therapeutic agent and a pharmaceutically acceptable carrier; wherein said at least one additional active therapeutic agent is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof, wherein (1) HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859; (2) HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR 355 BS, VRX 840773, UK-453061, and RDEA806; (3) HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, amdoxovir, KP-1461, and fosalvudine tidoxil (formerly HDP 99.0003); (4) HIV nucleotide inhibitors of reverse transcriptase are selected from the group consisting of tenofovir and adefovir; (5) HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011; (6) gp41 inhibitor are selected from the group consisting of enfuvirtide, sifuvirtide, FB006M, and TRI-1144; (7) CXCR4 inhibitor is AMD-070; (8) entry inhibitor is SP01A; (9) gp120 inhibitor is BMS-488043 or BlockAide/CR; (10) G6PD and NADH-oxidase inhibitor is immunitin; (11) CCR5 inhibitors are selected from the group consisting of aplaviroc, vicriviroc, maraviroc, PRO-140, INCB15050, PF-232798 (Pfizer), and CCR5 mAb004; and (12) other drugs for treating HIV are selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDXO10 (ipilimumab), PBS119, ALG 889, and PA-1050040 (PA-040).

In another embodiment, the present application provides a pharmaceutical composition comprising a therapeutically effective amount of a compound of the present invention, or a pharmaceutically acceptable salt, solvate, and/or ester thereof, in combination with at least one additional active therapeutic agent and a pharmaceutically acceptable carrier; wherein said at least one additional active therapeutic agent is selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

More specifically, one or more compounds of the present invention may be combined with one or more compounds selected from the group consisting of (1) HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859; (2) HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR 355 BS, VRX 840773, UK-453061, and RDEA806; (3) HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, amdoxovir, KP-1461, and fosalvudine tidoxil (formerly HDP 99.0003); (4) HIV nucleotide inhibitors of reverse transcriptase are selected from the group consisting of tenofovir and adefovir; (5) HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011; (6) gp41 inhibitor are selected from the group consisting of enfuvirtide, sifuvirtide, FB006M, and TRI-1144; (7) CXCR4 inhibitor is AMD-070; (8) entry inhibitor is SP01A; (9) gp120 inhibitor is BMS-488043 or BlockAide/CR; (10) G6PD and NADH-oxidase inhibitor is immunitin; (11) CCR5 inhibitors are selected from the group consisting of aplaviroc, vicriviroc, maraviroc, PRO-140, INCB15050, PF-232798 (Pfizer), and CCR5 mAb004; and (12) other drugs for treating HIV are selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDXO10 (ipilimumab), PBS119, ALG 889, and PA-1050040 (PA-040).

In another embodiment, the present application provides a combination pharmaceutical product or kit comprising: a first pharmaceutical composition comprising a compound of the present invention, or a pharmaceutically acceptable salt, solvate, or ester thereof; and a second pharmaceutical composition comprising at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

In one embodiment, the compounds of the present invention can be administered alone, e.g., without other active therapeutic in ingredients or agents. In another embodiment, the compounds of the present invention are used in combination with other active therapeutic ingredients or agents. Preferably, the other active therapeutic ingredients or agents are HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

Combinations of the compounds of the present invention are typically selected based on the condition to be treated, cross-reactivities of ingredients and pharmaco-properties of the combination. For example, when treating and infection (e.g., HIV or HCV), the compositions of the invention are combined with therapeutic agents (such as those described herein).

Non-limiting examples of suitable therapeutic agents suitable for combining with the compounds of the present invention include (1) HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859; (2) HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR 355 BS, VRX 840773, UK-453061, and RDEA806; (3) HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, amdoxovir, KP-1461, and fosalvudine tidoxil (formerly HDP 99,0003); (4) HIV nucleotide inhibitors of reverse transcriptase are selected from the group consisting of tenofovir and adefovir; (5) HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011; (6) gp41 inhibitor are selected from the group consisting of enfuvirtide, sifuvirtide, FB006M, and TRI-1144; (7) CXCR4 inhibitor is AMD-070; (8) entry inhibitor is SP01A; (9) gp120 inhibitor is BMS-488043 or BlockAide/CR; (10) G6PD and NADH-oxidase inhibitor is immunitin; (11) CCR5 inhibitors are selected from the group consisting of aplaviroc, vicriviroc, maraviroc, PRO-140, INCB15050, PF-232798 (Pfizer), and CCR5 mAb004; and (12) other drugs for treating HIV are selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDXO10 (ipilimumab), PBS119, ALG 889, and PA-1050040 (PA-040).

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic effect", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

In another embodiment, the present invention provides a method for inhibiting HIV protease comprising administering a therapeutically effective amount of a compound of the present invention, or a pharmaceutically acceptable salt, solvate, or ester thereof, to a patient in need of such treatment.

In another embodiment, the present invention provides a method for inhibiting HIV protease, further comprising co-administering a therapeutic amount of at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present invention provides a method for treating AIDS or AIDS Related Complex comprising administering a therapeutically effective amount of a compound of the present invention, or a pharmaceutically acceptable salt, solvate, and/or ester thereof, to a patient in need of such treatment.

In another embodiment, the present invention provides a method for treating AIDS or AIDS Related Complex comprising co-administering a therapeutically effective amount of a compound of the present invention, or a pharmaceutically acceptable salt, solvate, and/or ester thereof and a therapeutic amount of at least one additional active agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof, to a patient in need of such treatment.

In yet another embodiment, the present application provides a method for treating an HIV infection comprising administering to a patient in need thereof a therapeutically effective amount of a compound of the present invention, or a pharmaceutically acceptable salt, solvate, and/or ester thereof, in combination with a therapeutically effective amount of one or more additional therapeutic agents selected from the group consisting of (1) HIV protease inhibitors are selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859; (2) HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR 355 BS, VRX 840773, UK-453061, and RDEA806; (3) HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, racivir (1-FTC), D-d4FC, emtricitabine, phosphazide, fozivudine tidoxil, apricitibine (AVX754), GS-7340, amdoxovir, KP-1461, and fosalvudine tidoxil (formerly HDP 99.0003); (4) HIV nucleotide inhibitors of reverse transcriptase are selected from the group consisting of tenofovir and adefovir; (5) HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011; (6) gp41 inhibitor are selected from the group consisting of enfuvirtide, sifuvirtide, FB006M, and TRI-1144; (7) CXCR4 inhibitor is AMD-070; (8) entry inhibitor is SP01A; (9) gp120 inhibitor is BMS-488043 or BlockAide/CR; (10) G6PD and NADH-oxidase inhibitor is immunitin; (11) CCR5 inhibitors are selected from the group consisting of aplaviroc, vicriviroc, maraviroc, PRO-140, INCB15050, PF-232798 (Pfizer), and CCR5 mAb004; and (12) other drugs for treating HIV are selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS119, ALG 889, and PA-1050040 (PA-040).

In another embodiment, the present invention provides a method of inhibiting the replication of a retrovirus comprising contacting said retrovirus with a compound of the present invention, or a pharmaceutically acceptable salt, solvate, and/or ester thereof.

In another embodiment, the present invention provides a method of inhibiting the replication of a retrovirus comprising contacting said retrovirus with a compound of the present invention, or a pharmaceutically acceptable salt, solvate, and/or ester thereof and at least one additional active agent selected from the group consisting of one or more HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

In another embodiment, the present invention provides for the use of compounds of the present invention, or pharmaceutically acceptable salts, solvates, and/or esters thereof, or phosphonate prodrugs thereof, for the preparation of a medicament for the treatment of AIDS, AIDS Related Complex, or an HIV infection.

EXAMPLES

Example 1

Scheme 1

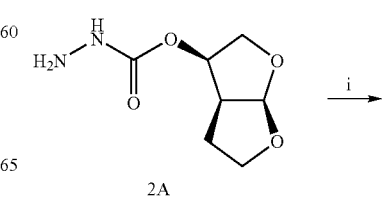

2A

-continued

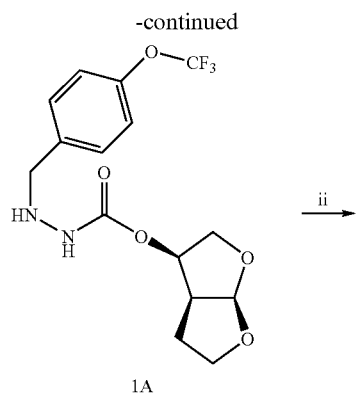

1A

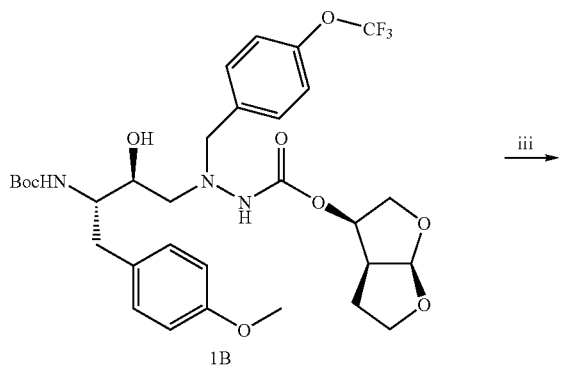

1B

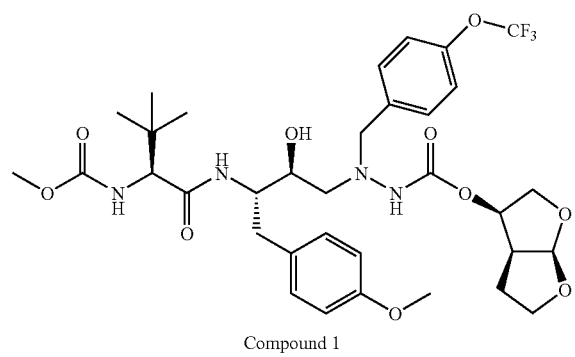

Compound 1

Reagents and conditions:
i. a. 4-trifluoromethoxy-benzaldehyde, isopropanol, 80° C.; b. Pd/C, H₂, THF;
ii. 1D, AcOH, isopropanol;
iii. a. TFA, CH₂Cl₂; b. N(methoxycarbonyl)-L-tert-leucine, TPTU, NMM, DMF.

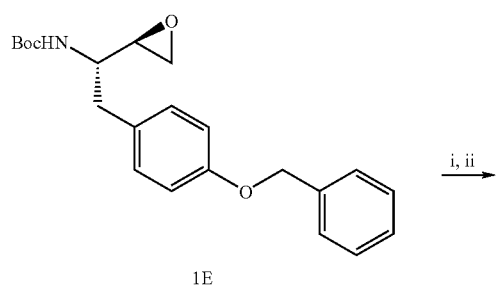

1E

-continued

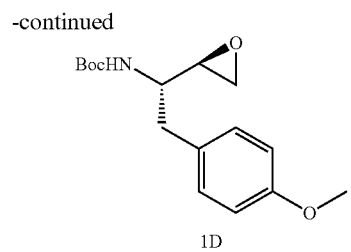

1D

Reagents and conditions:
i. H₂, Pd(OH)₂/C, EtOH/EtOAc;
ii. MeI, Cs₂CO₃, ACN, 83%.

Compound 1A

Compound 2A (245 mg, 1.30 mmol, see Example 2) in isopropanol (10 mL) was treated with commercially available 4-trifluoromethoxy-benzaldehyde (186 μL, 1.30 mmol) at 80° C. for 18 h. The reaction mixture was cooled to room temperature and purified by flash chromatography (silica gel, 0 to 100% EtOAc/Hex) to give a white solid (371 mg, 1.03 mmol, 79%). To a solution (254 mg) of the above white solid in ethanol (6 mL) was added 10% palladium/carbon (25 mg). The resulting reaction mixture was stirred under a hydrogen atmosphere at for 1.5 h. then filtered through a pad of CELITE. The filtered reaction mixture was concentrated and purified by flash chromatography (silica gel, 0 to 100% EtOAc/Hex) to give compound 1A as a white solid (231 mg, 0.638 mmol, 90%). Mass spectrum: 362.8 (M+H)⁺.

Compound 1D

A mixture of [2-(4-Benzyloxy-phenyl)-1-oxiranyl-ethyl]-carbamic acid tert-butyl ester, 1E, purchased from Acme Bioscience, Inc., (0.99 g, 2.68 mmol) and 20 wt % palladium hydroxide (0.15 g) in EtOH/EtOAc (1:4, 25 mL) was stirred under a hydrogen atmosphere for 5 h. Mixture was filtered through a pad of CELITE, concentrated and purified by flash chromatography (silica gel, 25 to 60% EtOAc/Hex) to give a white solid (0.618 g, 2.21 mmol, 83%). The above product (0.500 g, 1.79 mmol) was dissolved in acetonitrile (18 mL) and cooled to 0° C. Cesium carbonate (0.875 g, 2.685 mmol) and iodomethane (0.223 g, 3.58 mmol) was added and reaction mixture was warmed to room temperature overnight. The reaction mixture was concentrated, dissolved in EtOAc/H₂O and washed with brine. The organic layer was dried (MgSO₄), concentrated to give a while solid (0.589 g, 2.01 mmol, 83%)

Compound 1B

To a solution of compound 1D (64.0 mg, 0.218 mmol) in isopropanol (3.0 mL) were added compound 1A (65.9 mg, 0.182 mmol) and AcOH (8.7 mg). After stirring for 3 days at 80° C., the reaction mixture was concentrated and purified by flash chromatography (silica gel, 0 to 100% EtOAc/Hex) to give compound 1B as a white solid (81.6 mg, 0.124 mmol, 68%). Mass spectrum: 656.0 (M+H)⁺.

Compound 1

To a solution of compound 1B (81.6 mg, 0.124 mmol) in CH₂Cl₂ (1.6 mL) at 0° C. was added TFA (0.4 mL). The resulting reaction mixture was stirred at 0° C. for 15 min. and at room temperature for 75 min. The mixture was coevaporated with toluene (5 mL). The residue was partitioned with a saturated NaHCO₃ solution and EtOAc, and extracted with EtOAc (1×). The organic layer was washed with H₂O (1×), dried over Na₂SO₄ and concentrated to give a crude product. A solution of N-(methoxycarbonyl)-L-tert-leucine (35.3 mg, 0.186 mmol) and TPTU (O-(1,2-dihydro-2-oxo-1-pyridyl)-N,N,N',N'-tetramethyluronium tetrafluoroborate) (55.3 mg, 0.186 mmol) in DMF (2 mL) was stirred for 10 min at room temperature. The above crude product and diisopropylethylamine (64.9 μL, 0.373 mmol) in DMF (2 mL) was added to the reaction mixture dropwise and stirred for 18 h at room temperature. The reaction mixture was partitioned with saturated NaHCO₃ solution and EtOAc, extracted with EtOAc (2×) and dried over Na₂SO₄. The dried solution was concentrated and purified by flash chromatography (silica gel, 0 to 100% EtOAc/Hex and 0 to 10% MeOH/CH₂Cl₂) to give Compound 1 as a white solid (48.5 mg, 0.067 mmol, 54%). ¹H NMR (300 MHz, CDCl₃): δ 7.36-7.34 (d), 7.18-7.15 (d), 7.13-7.10 (d), 6.77-6.74 (d), 6.34-6.31 (d), 6.07 (s), 5.68-5.67 (d), 5.32-5.30 (d), 5.11-5.04 (m), 4.18-4.01 (m), 3.94-3.57 (m), 3.02-2.96 (m), 2.88-2.75 (m), 2.61-2.57 (d), 1.72-1.64 (m), 0.86 (s). Mass spectrum: 727.2 (M+H)⁺.

Example 2

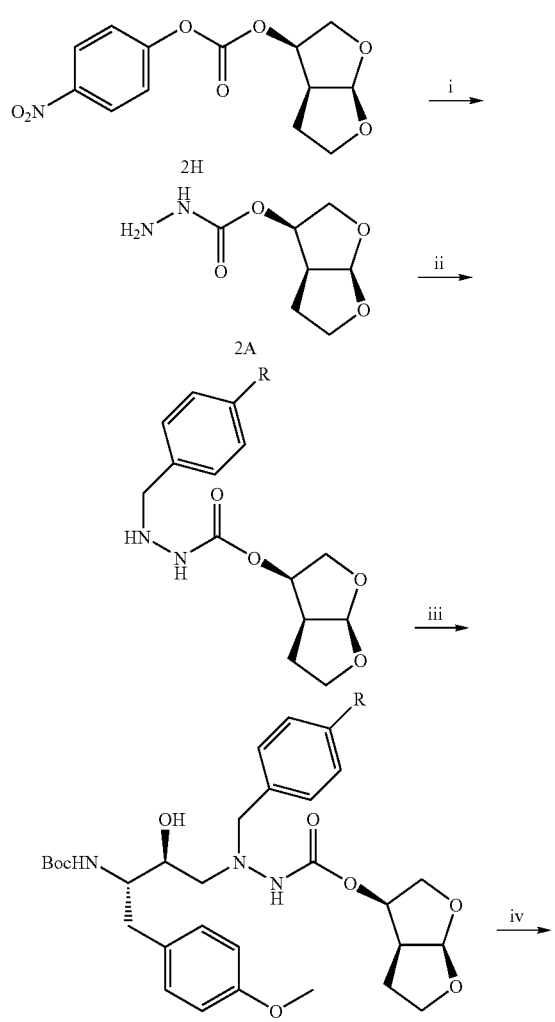

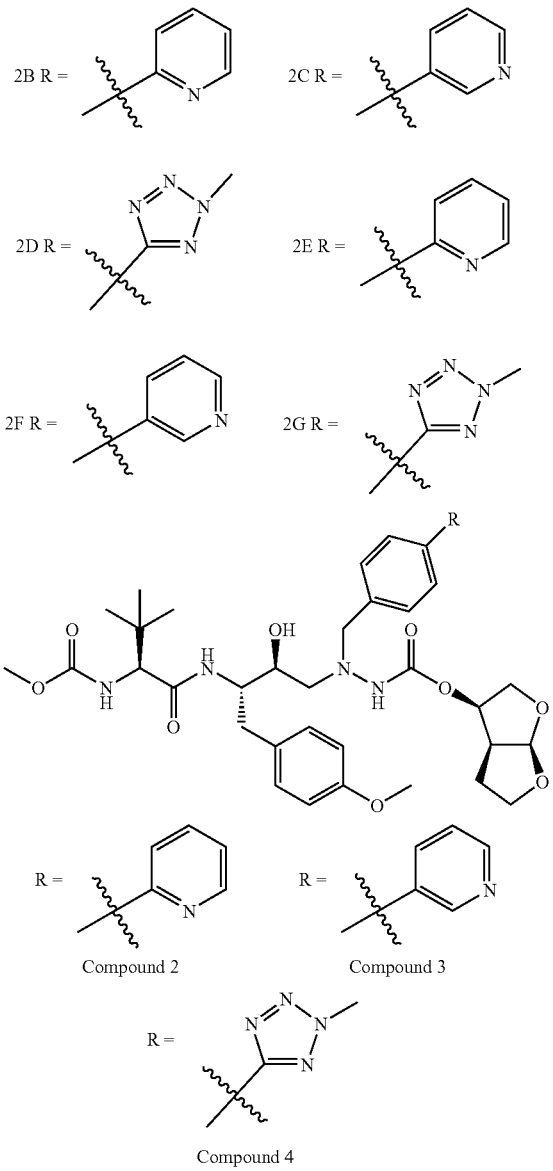

Compound 2    Compound 3

Compound 4

Reagents and conditions:
i. Hydrazine, ACN, quant.;
ii. a. aldehyde, isopropanol, 80° C. ; b. NaCNBH₃, p-TsOH, THF or H₂, Pd/C, EtOH;
iii. 2I, AcOH, isopropanol;
iv. a. TFA, CH₂Cl₂; b. N-(methoxycarbonyl)-L-tert-leucine, TPTU, NMM, DMF.

Compound 2A

To a solution of compound 2H (3.01 g, 10.19 mmol, prepared according to J. F. Miller et al, Bioorg. Med. Chem. Lett. 14, 959-963, 2004) in acetonitrile at 0° C. was added hydrazine (1.60 mL, 51.0 mmol). The reaction mixture was stirred at 0° C. for 2 h, during which an orange precipitate formed. The reaction mixture was filtered and the filtrate was concentrated. The resulting residue was suspended in acetonitrile and filtered. The residue was re-suspended in acetonitrile, filtered and concentrated to provide compound 2A as a yellow oil and 4-nitrophenol as a contaminant (2.14 g, 10.19 mmol, quant.). Mass spectrum: 189.2 (M+H)⁺.

Compound 2B

A solution of commercially available 4-(2-pyridyl)benzaldehyde (0.615 g, 3.36 mmol) and compound 2A (0.421 g, 2.24 mmol) in isopropanol (12.0 mL) was heated at 80° C. for 4 h. The reaction mixture was concentrated and purified by flash chromatography (silica gel, 50 to 100% EtOAc/Hex) to give an off-white solid (0.555 g, 1.57 mmol). The above solid was dissolved in THF (3.0 mL) and sodium cyanoborohydride (0.095 g, 1.51 mmol) was added, followed by a solution of n-toluenesulfonic acid (0.291 g, 1.53 mmol) in THF (3.0 mL). The reaction mixture was stirred overnight at room temperature and then diluted with EtOAc. The organic layer was washed with saturated $NaHCO_3$ solution, brine, dried ($MgSO_4$), and concentrated. The residue was dissolved in MeOH (2.0 mL) and THF (3.0 mL) and cooled to 0° C. A suspension of $Na_2B_4O_7 \cdot 10H_2O$ (2.4 g) in $H_2O$ (6.0 mL) was added and the mixture was stirred overnight, diluted with EtOAc and washed with saturated $NaHCO_3$ solution. The aqueous layer was back-extracted with EtOAc (3×) and the combined organic layer was dried ($MgSO_4$), concentrated and purified by flash chromatography (silica gel, 50 to 100% EtOAc/Hex) to give compound 2B as a white foam (0.4497 g, 1.27 mmol, 84%). Mass spectrum: 356.1 $(M+H)^+$.

Compound 2C

A solution of commercially available 4-(3-pyridyl)benzaldehyde (0.220 g, 1.20 mmol) and compound 2A (0.227 g, 1.20 mmol) in isopropanol (12.0 mL) was heated at 80° C. for 18 h. The reaction mixture was concentrated and purified (silica gel, 2 to 15% IPA/$CH_2Cl_2$) to give an off-white solid (0.130 g, 0.367 mmol). To a solution of the above solid in ethanol (12 mL) were added 20% palladium hydroxide/carbon (0.052 g) and acetic acid (42 µL, 0.734 mmol). The reaction mixture was stirred under a hydrogen atmosphere at 50° C. for 1 h, then filtered through a pad of CELITE. The filtered reaction mixture was concentrated and purified (silica gel, 0 to 10% IPA/EtOAc) to give compound 2C as a colorless film (0.0919 g, 0.259 mmol, 22%). Mass spectrum: 356.1 $(M+H)^+$.

Compound 2D

A solution of 4-(2-methyl-2H-tetrazol-5-yl)benzaldehyde (0.200 g, 1.06 mmol) and compound 2A (0.200 g, 1.06 mmol) in isopropanol (5.0 mL) was heated at 80° C. for 16 h. The reaction mixture was concentrated and purified (silica gel, 40 to 80% EtOAc/Hex)) to give an off-white foam. The off-white foam was dissolved in THF (3.0 mL) and sodium cyanoborohydride (0.040 g, 0.633 mmol) was added, followed by a solution of n-toluenesulfonic acid (0.123 g, 0.646 mmol) in THF (3.0 mL). The reaction mixture was stirred overnight at room temperature and then diluted with EtOAc. The organic layer was washed with saturated $NaHCO_3$ solution (2×), brine, dried ($MgSO_4$), and concentrated to give a colorless film as a residue. The residue was dissolved in MeOH (2.0 mL) and THF (1.0 mL) and cooled to 0° C. A suspension of $Na_2B_4O_7 \cdot 10H_2O$ (1.0 g) in $H_2O$ (6.0 mL) was added and the resulting mixture was stirred overnight, diluted with EtOAc and washed with saturated $NaHCO_3$ solution. The aqueous layer was back-extracted with EtOAc (3×) and the combined organic layer was dried ($MgSO_4$), concentrated and purified by flash chromatography (silica gel, 50 to 100% EtOAc/Hex) to give compound 2D as a white foam (0.151 g, 0.420 mmol, 39%). Mass spectrum: 361.1 $(M+H)^+$.

Compound 2E

A solution of compound 2B (167 mg, 0.468 mmol) and compound 1D (137 mg, 0.468 mmol) in isopropanol (4.0 mL) was stirred at 80° C. for 8 h. The reaction mixture was concentrated and purified by reversed phase HPLC (5 to 100% acetonitrile/$H_2O$+0.1% TFA) to give compound 2E as a white powder after lyophilization (97.6 mg, 0.150 mmol, 32%). Mass spectrum: 649.1 $(M+H)^+$.

Compound 2F

A solution of compound 2C (91.9 mg, 0.259 mmol), compound 1D (75.9 mg, 0.259 mmol) and acetic acid (11.8 µL, 0.207 mmol) in isopropanol (2.5 mL) was stirred at 80° C. for 7 h. The reaction mixture was concentrated and purified (silica gel, 50 to 100% EtOAc/Hex to 20% IPA/EtOAc) to give compound 2F as a white foam (26.9 mg, 0.0415 mmol, 16%). Mass spectrum: 649.1 $(M+H)^+$.

Compound 2G

A solution of compound 2D (67 mg, 0.187 mmol), compound 1D (55 mg, 0.187 mmol) and acetic acid (8.6 µL, 0.150 mmol) in isopropanol (2.0 mL) was stirred at 80° C. for 16 h. The reaction mixture was concentrated and dissolved in EtOAc. The organic layer was washed with saturated $NaHCO_3$/brine solution and dried ($MgSO_4$). The washed organic layer was concentrated and purified (silica gel, 50 to 90% EtOAc/Hex) to give compound 2G as a clear film (70 mg, 0.107 mmol, 57%). Mass spectrum: 654.2 $(M+H)^+$.

Compound 2

To a solution of compound 2E (97.6 mg, 0.150 mmol) in $CH_2Cl_2$ (2.0 mL) at 0° C. was added TFA (0.2 mL). The reaction mixture was stirred at 0° C. for 5 h, then concentrated and purified by reversed phase HPLC (5 to 100% acetonitrile/$H_2O$+0.1% TFA). The fractions containing product were pooled and concentrated. The resulting residue was stirred with saturated $NaHCO_3$ solution for 15 min and extracted with EtOAc (3×) to provide an organic phase. The organic phase was dried ($MgSO_4$), concentrated and lyophilized to give a product as white powder (50.6 mg, 0.0922 mmol).

A solution of N-(methoxycarbonyl)-L-tert-leucine (37.8 mg, 0.200 mmol) and TPTU (59.41 mg, 0.200 mmol) in DMF (0.5 mL) was stirred for 35 min at room temperature. The above product and N-methylmorpholine (40 µL, 0.364 mmol) in DMF (0.5 mL) were added to the reaction mixture and stirred for 48 h at room temperature. The reaction mixture was diluted with EtOAc and washed with saturated $NaHCO_3$ solution, brine and dried ($MgSO_4$). The washed reaction mixture was concentrated and purified by flash chromatography (silica gel, EtOAc) and purified again by reversed phase HPLC (5 to 100% acetonitrile/$H_2O$) and lyophilized to give Compound 2 as a white powder (48 mg, 0.0667 mmol, 44%). $^1H$ NMR (300 MHz, $CD_3OD$): δ 8.64 (d, J=5.4 Hz, 1H), 8.20-8.12 (m, 1H), 8.06-8.01 (m, 1H), 7.84 (d, J=8.1 Hz, 2H), 7.72-7.50 (m, 3H), 7.13 (d, J=8.7 Hz, 2H), 6.74 (d, J=8.4 Hz, 2H), 5.53 (d, j=5.1 Hz, 1H), 4.95-4.80 (m, 1H), 4.25-4.15 (m, 1H), 3.95-3.60 (m, 14H), 2.97-2.62 (m, 5H), 1.65-1.55 (m, 2H), 0.84 (s, 9H). Mass spectrum: 720.2 (M+H)+.

Compound 3

To a solution of compound 2F (26.9 mg, 0.0415 mmol) in CH$_2$Cl$_2$ (1.0 mL) at 0° C. was added TFA (0.2 mL). The reaction mixture was stirred at 0° C. for 2 h, then concentrated and diluted with EtOAc. The organic layer was washed with saturated NaHCO$_3$ solution and back-extracted with EtOAc (3×). The combined organic layer was dried (MgSO$_4$), concentrated and dried under high vacuum to give a crude product.

A solution of N-(methoxycarbonyl)-L-tert-leucine (17.3 mg, 0.0913 mmol) and TPTU (27.1 mg, 0.0913 mmol) in DMF (0.3 mL) was stirred for 45 min at room temperature. The above crude product and N-methylmorpholine (14 µL, 0.125 mmol) in DMF (0.3 mL) was added to the reaction mixture and stirred for 36 h at room temperature. The reaction mixture was diluted with EtOAc and washed with saturated NaHCO$_3$ solution, brine and dried (MgSO$_4$). The washed reaction mixture was concentrated and purified by reversed phase HPLC (5 to 100% acetonitrile/H$_2$O+0.1% TFA) and lyophilized to give Compound 3 as a white powder (20 mg, 0.0278 mmol, 67%). $^1$H NMR (300 MHz, CD$_3$OD): δ 9.10 (s, 1H), 8.84 (d, J=8.1 Hz, 1H), 8.76 (d, J=5.1 Hz, 1H), 8.12-8.05 (m, 1H), 7.72 (d, J=5.7 Hz, 2H), 7.57 (d, J=8.1 Hz, 2H), 7.12 (d, J=8.7 Hz, 2H), 6.74 (d, J=8.4 Hz, 2H), 5.54 (d, J=5.4 Hz, 1H), 4.95-4.80 (m, 1H), 4.25-4.15 (m, 1H), 3.95-3.60 (m, 14H), 2.97-2.62 (m, 5H), 1.65-1.55 (m, 2H), 0.84 (s, 9H). Mass spectrum: 720.2 (M+H)+.

Compound 4

To a solution of compound 2G (70 mg, 0.107 mmol) in CH$_2$Cl$_2$ (2.0 mL) at 0° C. was added TFA (0.4 mL). The reaction mixture was stirred at 0° C. for 2 h, then concentrated and diluted with EtOAc. The organic layer was washed with saturated NaHCO$_3$ solution and back-extracted with EtOAc (3×). The combined organic layer was dried (MgSO$_4$), concentrated and lyophilized from acetonitrile/H$_2$O to give a crude product.

A solution of N-(methoxycarbonyl)-L-tert-leucine (45 mg, 0.238 mmol) and TPTU (71 mg, 0.238 mmol) in DMF (0.3 mL) was stirred for 30 min at room temperature. The above crude product and N-methylmorpholine (48 µL, 0.432 mmol) in DMF (0.3 mL) was added to the reaction mixture and stirred for 36 h at room temperature. The reaction mixture was diluted with EtOAc and washed with saturated NaHCO$_3$ solution, brine and dried (MgSO$_4$). The washed reaction mixture was concentrated and purified by reversed phase HPLC (5 to 100% acetonitrile/H$_2$O) and lyophilized to give Compound 4 as a white powder (50 mg, 0.0690 mmol, 64%). $^1$H NMR (300 MHz, CD$_3$OD): δ 7.97 (d, J=8.4 Hz, 2H), 7.47 (d, J=8.1 Hz, 2H), 7.12 (d, J=8.4 Hz, 2H), 6.74 (d, J=8.7 Hz, 2H), 5.53 (d, J=5.4 Hz, 1H), 4.95-4.80 (m, 1H), 4.20-4.10 (m, 1H), 3.95-3.60 (m, 17H), 2.97-2.62 (m, 5H), 1.60-1.50 (m, 2H), 0.82 (s, 9H). Mass spectrum: 720.2 (M+H)+.

Example 3

Scheme 3

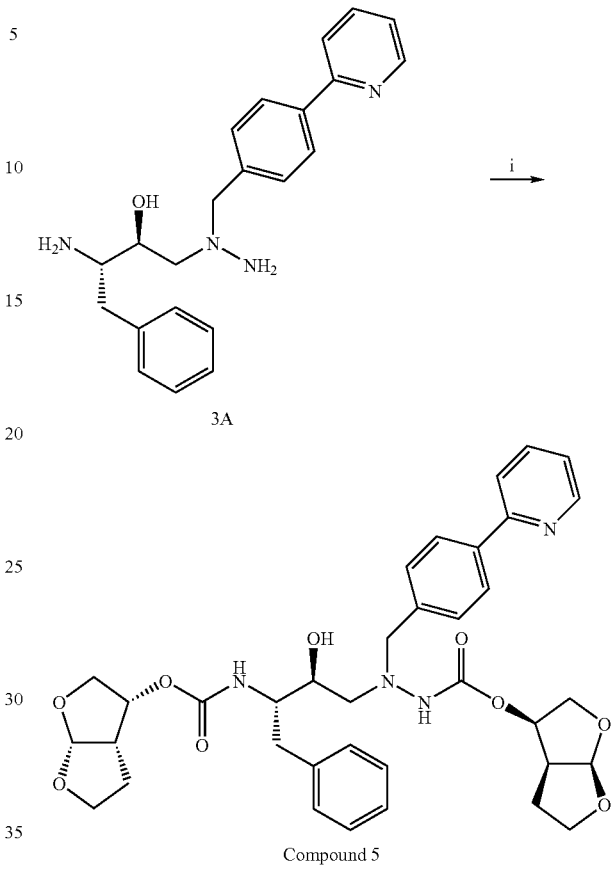

Reagents and conditions:
i. 2H, diisopropylethylamine, DMAP, ACN, 19%;

Compound 5

Compound 3A (0.120 g, 0.254 mmol), prepared according to the method of Bold et al., *J. Med. Chem.* 1998, 41, 3387-3401 (incorporated herein by reference in its entirety), was dissolved in acetonitrile (2.5 mL) and cooled to 0° C. Diisopropylethylamine (0.31 mL, 1.778 mmol) and DMAP (0.003 g, 0.0254 mmol) were added, followed by compound 2H (0.1502 g, 0.509 mmol). The reaction mixture was warmed to room temperature overnight and then diluted with EtOAc. The organic layer was washed with H$_2$O (3×), 1M NaOH (3×), brine and dried (MgSO$_4$). The washed organic layer was concentrated and purified by reversed phase HPLC (5 to 100% acetonitrile/H$_2$O+0.1% TFA) to give a white powder after lyophilization. The white powder was dissolved in EtOAc and stirred with saturated NaHCO$_3$ solution for 1 h. Brine was then added and the resulting product was extracted with EtOAc (3×). Lyophilization provided Compound 5 as a white powder (31.8 mg, 0.047 mmol, 19%). $^1$H NMR (300 MHz, CD$_3$OD): δ 8.75 (d, J=5.7 Hz, 1H), 8.60-8.50 (m, 1H), 8.27 (d, J=8.1 Hz, 1H), 7.95-7.90 (m, 1H), 7.86 (d, J=8.4 Hz, 2H), 7.67 (d, J=8.4 Hz, 2H), 7.30-7.05 (m, 5H), 5.54 (d, J=5.4 Hz, 1H), 4.98-4.80 (m, 2H), 4.10-3.40 (m, 11H), 2.95-2.68 (m, 7H), 1.65-1.45 (m, 4H). Mass spectrum: 675.2 (M+H)+.

Example 4
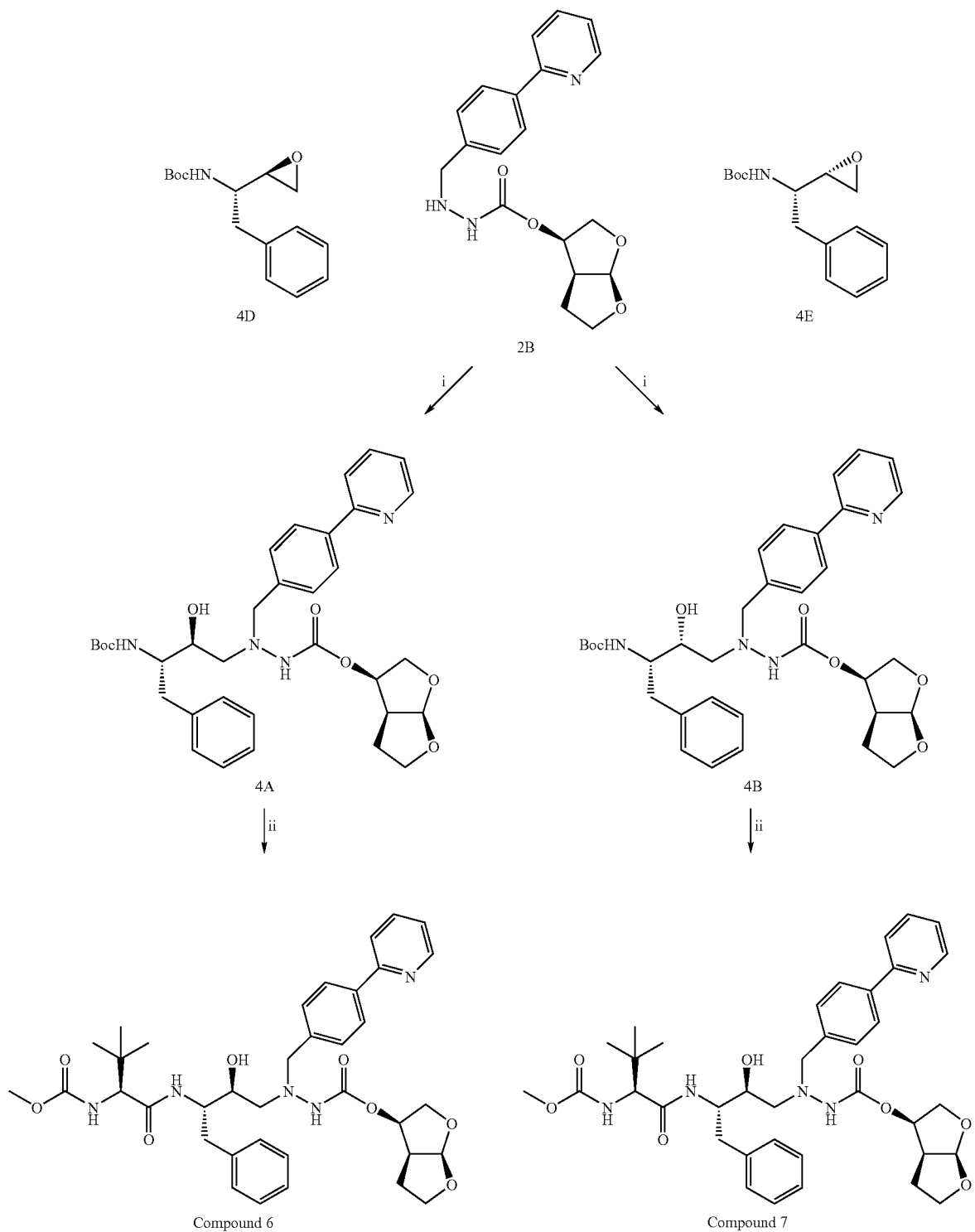
Reagents and conditions:
i. 4D or 4E, isopropanol;
iv. a. TFA, CH$_2$Cl$_2$; b. N-(methoxycarbonyl)-L-tert-leucine, TPTU, NMM, DMF.

Compound 4A

A solution of compound 2B (148 mg, 0.416 mmol) and commercially available compound 4D (148 mg, 0.562 mmol) in isopropanol (4.0 mL) was stirred at 80° C. for 18 h. The reaction mixture was concentrated and purified by flash chromatography (silica gel, 50 to 100% EtOAc/Hex) to give compound 4A as a white foam (115 mg, 0.186 mmol, 45%). Mass spectrum: 619.1 (M+H)+.

Compound 4B

A solution of compound 2B (102 mg, 0.287 mmol) and commercially available compound 4E (227 mg, 0.860 mmolin isopropanol (3.0 mL) was stirred at 80° C. for 16 h. The reaction mixture was concentrated and purified by flash chromatography (silica gel, 50 to 100% EtOAc/Hex) to give an impure product, which was purified by reversed phase HPLC (5 to 100% acetonitrile/H$_2$O+0.1% TFA) and lyophilized to give compound 4B as a white powder (21.5 mg, 0.034 mmol, 12%). Mass spectrum: 619.2 (M+H)+.

Compound 6

To a solution of compound 4A (115 mg, 0.186 mmol) in CH$_2$Cl$_2$ (2.0 mL) at 0° C. was added TFA (0.2 mL). The reaction mixture was stirred at 0° C. for 5 h, then concentrated and purified by reversed phase HPLC (5 to 100% acetonitrile/H$_2$O+0.1% TFA). The fractions containing product were pooled and concentrated to provide a residue. The residue was stirred with saturated NaHCO$_3$ solution for 15 min and extracted with EtOAc (3×). The organic layer was dried (MgSO$_4$), concentrated and lyophilized to give the product as a white powder (50.2 mg, 0.0922 mmol).

A solution of N-(methoxycarbonyl)-L-tert-leucine (32.2 mg, 0.170 mmol) and TPTU (50.7 mg, 0.170 mmol) in DMF (0.5 mL) was stirred for 15 min at room temperature. The product obtained above and N-methylmorpholine (25 µL, 0.231 mmol) in DMF (0.5 mL) was added to the reaction mixture and stirred for 36 h at room temperature. The reaction mixture was diluted with EtOAc and washed with saturated NaHCO$_3$ solution, brine and dried (MgSO$_4$). The washed reaction mixture was concentrated and purified by flash chromatography (silica gel, EtOAc) and purified again by reversed phase HPLC (5 to 100% acetonitrile/H$_2$O+0.1% TFA) and lyophilized to give Compound 6 as a white powder (45 mg, 0.0560 mmol, 61%). $^1$H NMR (300 MHz, CD$_3$OD): δ 8.64 (d, J=5.4 Hz, 1H), 8.25-8.19 (m, 1H), 8.06 (d, J=8.4 Hz, 1H), 7.84 (d, J=8.1 Hz, 2H), 7.72-7.50 (m, 3H), 7.25-7.05 (m, 5H), 5.53 (d, J=5.1 Hz, 1H), 4.95-4.80 (m, 1H), 4.30-4.20 (m, 1H), 3.95-3.40 (m, 11H), 2.97-2.62 (m, 5H), 1.65-1.55 (m, 2H), 0.83 (s, 9H). Mass spectrum: 690.2 (M+H)+.

Compound 7

To a solution of compound 4B (21 mg, 0.034 mmol) in CH$_2$Cl$_2$ (1.0 mL) at 0° C. was added TFA (0.1 mL). The reaction mixture was stirred at 0° C. for 4 h, then concentrated and diluted with EtOAc. The organic layer was washed with saturated NaHCO$_3$ solution and back-extracted with EtOAc (3×). The combined organic layer was dried (MgSO$_4$), concentrated and dried under high vacuum to give a crude product.

A solution of N-(methoxycarbonyl)-L-tert-leucine (14 mg, 0.07483 mmol) and TPTU (22 mg, 0.0748 mmol) in DMF (0.3 mL) was stirred for 35 min at room temperature. The above crude product and N-methylmorpholine (15 µL, 0.136 mmol) in DMF (0.3 mL) was added to the reaction mixture and stirred for 20 h at room temperature. The reaction mixture was diluted with EtOAc and washed with saturated NaHCO$_3$ solution, brine and dried (MgSO$_4$). The washed reaction mixture was concentrated and purified by reversed phase HPLC (5 to 100% acetonitrile/H$_2$O+0.1% TFA) and lyophilized to give Compound 7 as a white powder (15.3 mg, 0.0190 mmol, 56%). $^1$H NMR (300 MHz, CD$_3$OD): δ 8.74 (d, J=5.4 Hz, 1H), 8.535-8.42 (m, 1H), 8.24 (d, J=8.1 Hz, 1H), 7.90-7.80 (m, 3H), 7.67 (d, J=8.4 Hz, 2H), 7.25-7.05 (m, 5H), 5.53 (d, J=5.1 Hz, 1H), 5.00-4.89 (m, 1H), 4.20-3.50 (m, 12H), 3.20-2.62 (m, 5H), 1.60-1.50 (m, 2H), 0.82 (s, 9H). Mass spectrum: 690.2 (M+H)+.

Example 5

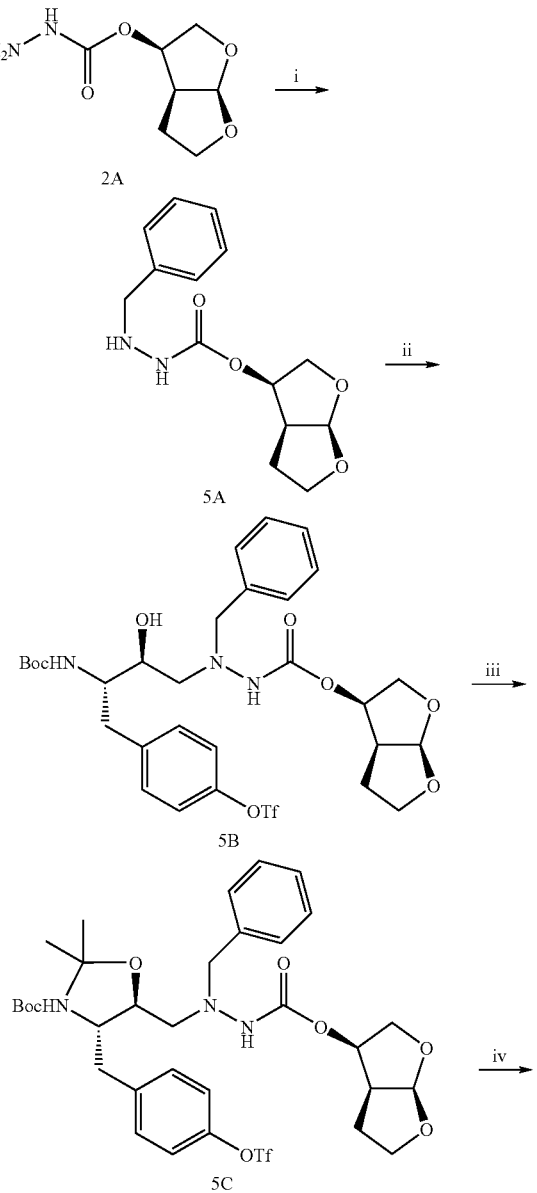

Scheme 5

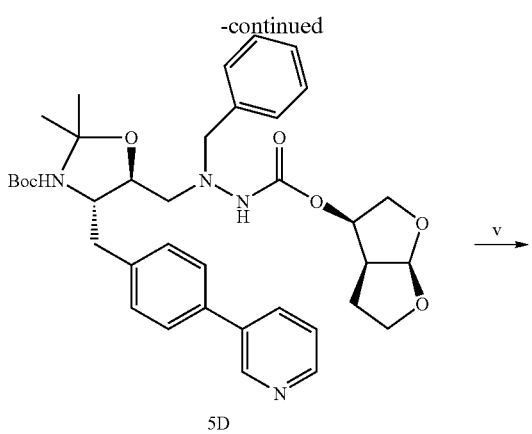

5D

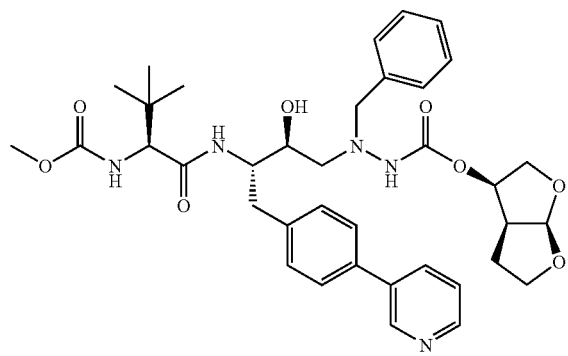

Compound 8

Reagents and conditions:
i. a. benzaldehyde, isopropanol, 80° C.; b. NaCNBH₃, p-TsOH, THF;
ii. 5E, AcOH, isopropanol;
iii. camphorsulfonic acid, dimethoxypropane, acetone;
iv. 3-pyridineboronic acid, PdCl₂(dppf), Na₂CO₃, DME;
v. a. TFA, CH₂Cl₂; b. N'(methoxycarbonyl)-L-tert-leucine, TPTU, NMM, DMF.

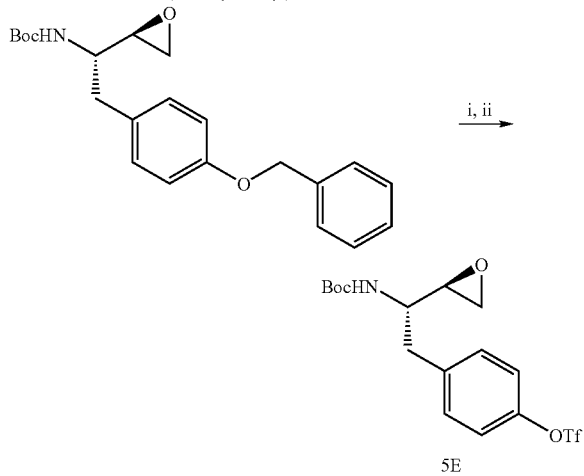

5E

Reagents and conditions:
i. H₂, Pd(OH)₂/C, EtOH/EtOAc;
ii. N-Phenyltrifluoromethanesulfonimide, Cs₂CO₃, CH₂Cl₂, 96%.

Compound 5A

A solution of benzaldehyde (0.107 mL, 1.05 mmol) and compound 2A (0.247 g, 1.05 mmol) in isopropanol (5.0 mL) was heated at 80° C. for 4 h. The reaction mixture was concentrated and purified by flash chromatography (silica gel, 30 to 80% EtOAc/Hex) to give a white foam (0.289 g, 1.05 mmol). The white foam was dissolved in THF (5.0 mL) and sodium cyanoborohydride (0.072 g, 1.14 mmol) was added, followed by a solution of n-toluenesulfonic acid (0.219 g, 1.15 mmol) in THF (5.0 mL). The resulting reaction mixture was stirred overnight at room temperature and then diluted with EtOAc. The organic layer was washed with saturated NaHCO₃ solution, brine, dried (MgSO₄), and concentrated. The resulting residue was dissolved in MeOH (5.0 mL) and THF (5.0 mL). A suspension of Na₂B₄O₇·10H₂O (0.6 g) in H₂O (10.0 mL) was added and the resulting mixture was stirred overnight, diluted with EtOAc and washed with saturated NaHCO₃ solution. The aqueous layer was back-extracted with EtOAc (3×) and the combined organic layer was dried (MgSO₄), concentrated and purified by flash chromatography (silica gel, 30 to 100% EtOAc/Hex) to give compound 5A as a white foam (0.2121 g, 0.76 mmol, 73%). Mass spectrum: 278.9 (M+H)⁺.

Compound 5E

A mixture of commercially available [2-(4-Benzyloxy-phenyl)-1-oxiranyl-ethyl]-carbamic acid tert-butyl ester (2.02 g, 5.47 mmol) and 10 wt % palladium/carbon (0.400 g) in EtOH/EtOAc (1:2, 30 mL) was stirred under a hydrogen atmosphere for 2.5 h. Mixture was filtered through a pad of CELITE, concentrated to give a white solid that was dissolved in dichloromethane (20 mL). To this solution was added N-phenyltrifluoromethanesulfonimide (2.15 g, 6.02 mmol) and cesium carbonate (1.96 g, 6.02 mmol) and reaction mixture was stirred overnight at room temperature. The reaction mixture was diluted with H₂O and CH₂Cl₂ and washed with brine. The organic layer was dried (MgSO₄), concentrated and purified by flash chromatography (silica gel, 20 to 50% EtOAc/Hex) to give a white solid (0.1.481 g, 3.60 mmol, 66%).

Compound 5B

A solution of compound 5E (0.090 g, 0.219 mmol), compound 5A (0.061 g, 0.219 mmol) and acetic acid (10 µL, 0.175 mmol) in isopropanol (2.0 mL) was heated at 80° C. overnight. The reaction mixture was concentrated and purified by flash chromatography (silica gel, 50 to 100% EtOAc/Hex) to give compound 5B as a white solid (0.099 g, 0.144 mmol, 66%). Mass spectrum: 690.1 (M+H)⁺.

Compound 5C

A solution of compound 5B (0.099 g, 0.144 mmol), camphorsulfonic acid (0.037 g, 0.158 mmol) and dimethoxypropane (0.177 mL, 1.44 mmol) in acetone was heated at reflux for 4.5 h. The reaction mixture was cooled to room temperature and quenched with solid sodium bicarbonate. The mixture was stirred for 30 min and then filtered, concentrated and purified by flash chromatography (silica gel, 20 to 50% EtOAc/Hex) to give compound 5C as a white foam (0.0767 g, 0.105 mmol, 73%). Mass spectrum: 730.0 (M+H)⁺.

Compound 5D

To a Smith process vial were added compound 5C (0.0767 g, 0.105 mmol), 3-pyridineboronic acid (0.0323 g, 0.263 mmol), PdCl₂(dppf) (9 mg, 0.011 mmol), 2M Na₂CO₃ (0.26 mL) and DME (0.6 mL). The vial was sealed and heated at 120° C. for 25 min using microwave irradiation. The reaction mixture was diluted with EtOAc and washed with saturated NaHCO₃ solution, brine and dried (MgSO₄). The washed reaction mixture was concentrated and purified by flash chromatography (silica gel, 40 to 100% EtOAc/Hex) to give a brown oil (50.6 mg, 0.0768 mmol, 73%). Mass spectrum: 659.3 (M+H)+.

Compound 8

To a solution of compound 5D (15 mg, 0.0228 mmol) in CH$_2$Cl$_2$ (0.6 mL) at 0° C. was added TFA (0.4 mL). The reaction mixture was stirred at room temperature for 3 h, then concentrated and diluted with EtOAc. The organic layer was washed with saturated NaHCO$_3$ solution and back-extracted with EtOAc (3×). The combined organic layer was dried (MgSO$_4$), concentrated and dried under high vacuum to give a crude product.

A solution of N-(methoxycarbonyl)-L-tert-leucine (9.5 mg, 0.0501 mmol) and TPTU (15 mg, 0.0501 mmol) in DMF (0.2 mL) was stirred for 30 min at room temperature. The above crude product and N-methylmorpholine (7.5 μL, 0.0684 mmol) in DMF (0.2 mL) was added to the reaction mixture and stirred for 20 h at room temperature. The reaction mixture was diluted with EtOAc and washed with saturated NaHCO$_3$ solution, brine and dried (MgSO$_4$). The washed reaction mixture was concentrated and purified by reversed phase HPLC (5 to 100% acetonitrile/H$_2$O+0.1% TFA) and lyophilized to give Compound 8 as a white powder (7.7 mg, 0.0096 mmol, 42%). $^1$H NMR (300 MHz, CD$_3$OD): δ 9.05 (s, 1H), 8.76 (d, J=8.7 Hz, 1H), 8.73 (s, 1H), 8.05 (dd, J=8.1, 5.7 Hz, 1H), 7.63 (d, J=8.1 Hz, 2H), 7.44 (d, J=8.1 Hz, 2H), 7.31-7.20 (m, 5H), 5.52 (d, J=4.8 Hz, 1H), 4.95-4.89 (m, 1H), 3.94-3.22 (m, 12H), 3.10-2.65 (m, 5H), 1.70-1.55 (m, 2H), 0.83 (s, 9H). Mass spectrum: 690.3 (M+H)+.

Example 6

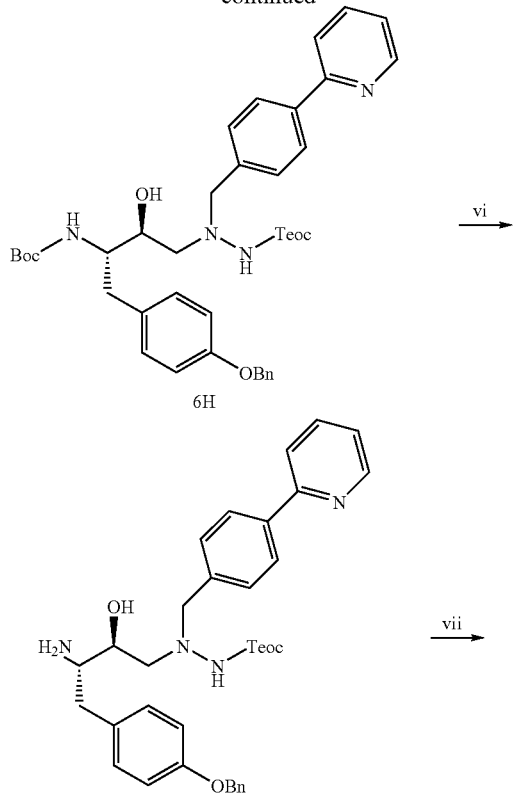

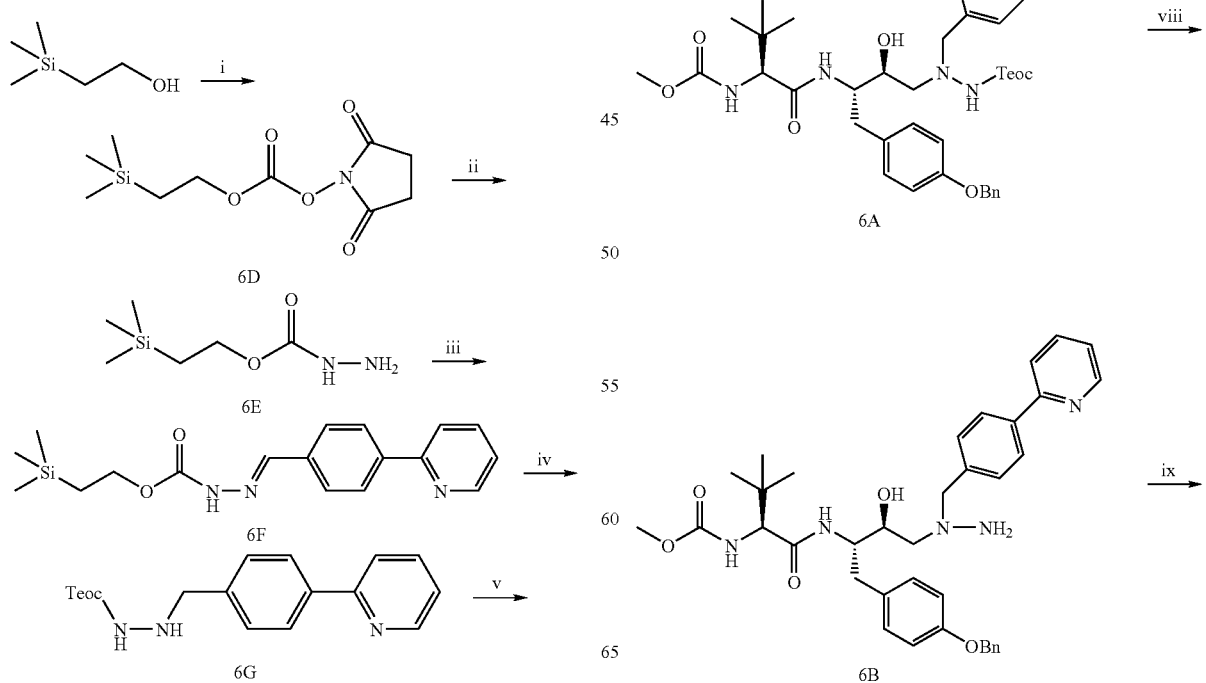

-continued

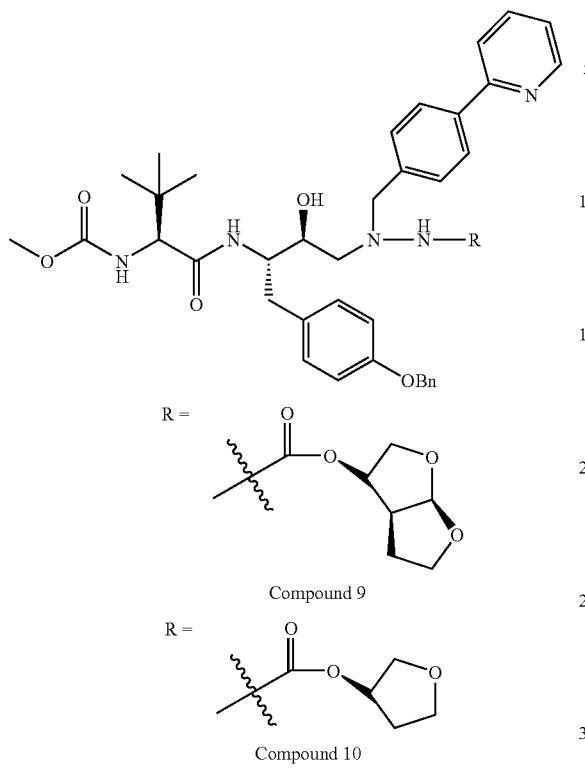

Compound 6D

Reagents and conditions:
i. Di-succinimidy carbonate, MeCN, TEA;
ii. hydrazine, THF, 0° C.;
iii. 4-pyridin-2-yl-benzaldehyde, EtOH;
iv. a. sodium cyanoborohydride, THF, toluene-4-sulfonic acid; b. 1N NaOH, THF, MeOH;
v. IPA, epoxide, 65° C.;
vi. 1N HCl, 0° C.;
vii. DMF, DIEA, TPTU, 0° C. to r.t.;
viii. 4N HCl in dioxane;
ix. MeCN, DIEA, DMAP, carbonate.

Compound 6D

TEA (21.9 mL, 155.6 mmol, 3.0 eq.) was added to 2-trimethylsilanyl-ethanol (7.4 mL, 51.88 mmol, 1.0 eq.) in 260 mL MeCN, followed by di-succinimidyl carbonate (20 g, 1.5 eq.). The reaction was stirred at room temperature for 3 hours. The reaction was concentrated and extracted using EtOAc/saturated NaHCO$_3$. The organic layer was concentrated after dried over Na$_2$SO$_4$. Ether (100 mL) was added to the residue to form precipitate. The precipitate was filtered and dried to give Compound 6D as a white solid (11.1 g, 84%). $^1$H NMR (300 MHz, CDCl$_3$): δ 4.42 (t, 3H), 2.82 (s, 4H), 1.16 (t, 2H), 0.1 (s, 9H).

Compound 6E

Hydrazine monohydrate (5.73 mL, 115.6 mmol, 5.0 eq.) was added to compound 6D (6 g, 23.13 mmol, 1.0 eq.) in 50 mL THF at 0° C. Precipitate formed. The reaction was monitored by $^1$H NMR. The reaction was complete after 2 hours. The reaction mixture was concentrated and extracted using EtOAc/saturated NaHCO$_3$ (1×), brine (1×). The organic layer was concentrated after dried over Na$_2$SO$_4$ to give Compound 6E as a white solid (3.23 g, 79%). $^1$H NMR (300 MHz, CDCl$_3$): δ 5.84 (b, 1H), 4.20 (t, 2H), 1.00 (t, 2H), 0.1 (s, 9H).

Compound 6F

4-Pyridin-2-yl-benzaldehyde (3.35 g, 18.3 mmol, 1.0 eq.) was added to compound 6E (3.23 g, 18.3 mmol, 1.0 eq.) in 30 mL EtOH at room temperature. The reaction was stirred at room temperature for 15 hours. The reaction mixture was concentrated and extracted using EtOAc/saturated NaHCO$_3$ (2×) and brine (1×). The organic layer was concentrated after dried over Na$_2$SO$_4$. The residue was re-crystallized (hexane/EtOAc) to give Compound 6F as a white solid (5.13 g, 82%). LC-MS shows 342.1 (M+H)$^+$.

Compound 6G

Sodium cyanoborohydride (990 mg, 15.75 mmol, 1.05 eq.) was added to compound 6F (5.13 g, 15.0 mmol, 1.0 eq.) in 30 mL THF at room temperature, followed by toluene-4-sulfonic acid monohydrate (2.85 g, 1.0 eq.). The reaction was stirred at room temperature for 15 hours. The reaction mixture was concentrated. THF (20 mL) and MeOH (4 mL) mixture was added to the residue. 1N NaOH (82 mL, 5.5 eq.) was added to the above suspension at 0° C. dropwise. The reaction was stirred at 0° C. for 1 hour. The reaction mixture was extracted using EtOAc/brine (2×). The organic layer was concentrated after dried over Na$_2$SO$_4$. The residue was purified by silica gel (30-60% EtOAc/hexane) to give Compound 6G as a white solid (4.4 g, 86%). LC-MS shows 343.9 (M+H)$^+$.

Compound 6H

Isopropanol (15 mL) was added to compound 6G (1.96 g, 5.72 mmol, 1.0 eq.) and the epoxide ([2-(4-benzyloxy-phenyl)-1-oxiranyl-ethyl]-carbamic acid tert-butyl ester) (2.11 g, 1.0 eq.). The reaction mixture was heated to 65° C. for 17 hours. The reaction mixture was concentrated and purified by silica gel (30-60% EtOAc/hexane) to give Compound 6H as a white solid (1.5 g, 47%). LC-MS shows 735.2 (M+Na)$^+$.

Compound 6C

1N HCl in MeCN (24 mL, excess) was added to compound 6H (360 mg, 0.505 mmol) at 0° C. The reaction was stirred at 0° C. for 2.5 hours. The reaction mixture was quenched by adding 22 mL 1N NaOH solution at 0° C. The reaction mixture was extracted using EtOAc/saturated NaHCO$_3$. The organic layer was concentrated and purified by silica gel (2-10% MeOH/DCM) to give Compound 6C as a white solid (285 mg, 92%). LC-MS shows 635.2 (M+Na)$^+$.

Compound 6A

TPTU (38 mg, 1.5 eq.) was added to N-(methoxycarbonyl)-L-tert-leucine (25 mg, 1.5 eq.) in 1.5 mL DMF at 0° C. The mixture was stirred at 0° C. for 5 minutes. Compound 6C (53 mg, 0.086 mmol, 1.0 eq.) in 1.5 mL DMF and DIEA (45 μL, 3.0 eq.) was added. The reaction was stirred at 0° C., and then warmed up to room temperature overnight. The reaction mixture was concentrated and extracted with EtOAc and brine. The organic layer was concentrated and purified by silica gel by flash chromatography (40-100% EtOAc/hexane) to give compound 6A as a white solid (61 mg, 90%). LC-MS: 784.1 (M+H)$^+$.

Compound 6B

4N HCl (0.3 mL) was added to compound 6A (60 mg, 0.076 mmol). The reaction mixture was stirred at room temperature overnight. The reaction mixture was then concentrated and purified by reversed phase HPLC (0.1% TFA in MeCN/water) to give compound 6B as a white solid (36 mg, 75%). LC-MS: 640.3 (M+H)$^+$.

Compound 9

DIEA (16 μL, 0.09 mmol, 3.0 eq.) was added to compound 6B (19 mg, 0.03 mmol) in 0.3 mL MeCN at room temperature, followed by 2H (carbonic acid hexahydro-furo[2,3-b]furan-3-yl ester 4-nitro-phenyl ester) (9.2 mg, 1.05 eq.) and DMAP (0.7 mg, 0.2 eq.). The reaction mixture was stirred at room temperature overnight. The reaction mixture was then extracted with EtOAc and brine. The organic layer was concentrated and purified by reverse phase HPLC (0.05% TFA in MeCN/water) to give Compound 9 as a white solid (4.5 mg, 19%). LC-MS: 796.3 (M+H)$^+$. $^1$H NMR (300 MHz, CD$_3$OD): δ 8.78 (d, 1H), 8.28 (m, 1H), 8.12 (d, 1H), 7.91 (d, 2H), 7.62 (m, 3H), 7.38 (m, 5H), 7.18 (d, 2H), 6.84 (d, 2H), 5.58 (d, 1H), 5.02 (s, 4H), 4.98 (m, 2H), 4.23 (m, 1H), 3.65-3.96 (m, 8H), 3.54 (m, 4H), 2.84 (m, 4H), 1.58 (m, 2H), 0.88 (s, 9H).

Compound 10

DIEA (11 μL, 0.06 mmol, 4.0 eq.) was added to compound 6B (10 mg, 0.0156 mmol) in 0.3 mL MeCN at room temperature, followed by mono-furan carbonate (Carbonic acid 4-nitro-phenyl ester tetrahydro-furan-3-yl ester, prepared according to WO 2005064008) (5 mg, 1.2 eq.) and DMAP (0.6 mg, 0.3 eq.). The reaction was concentrated and purified by reverse phase HPLC (0.05% TFA in MeCN/water) and prep TLC (silica gel); 8% MeOH/DCM) to give compound 10 as a white solid (1.6 mg, 14%). LC-MS: 754.3 (M+H)$^+$. $^1$H NMR (300 MHz, CD$_3$OD): δ 8.60 (d, 1H), 8.16 (d, 1H), 7.85 (m, 3H), 7.66 (d, 1H), 7.50 (d, 2H), 7.38 (m, 5H), 7.18 (d, 2H), 6.84 (d, 2H), 5.02 (m, 4H), 4.08 (m, 1H), 3.60-3.96 (m, 10H), 2.84 (m, 4H), 2.02 (m, 2H), 1.78 (m, 1H), 0.88 (s, 9H).

Example 7

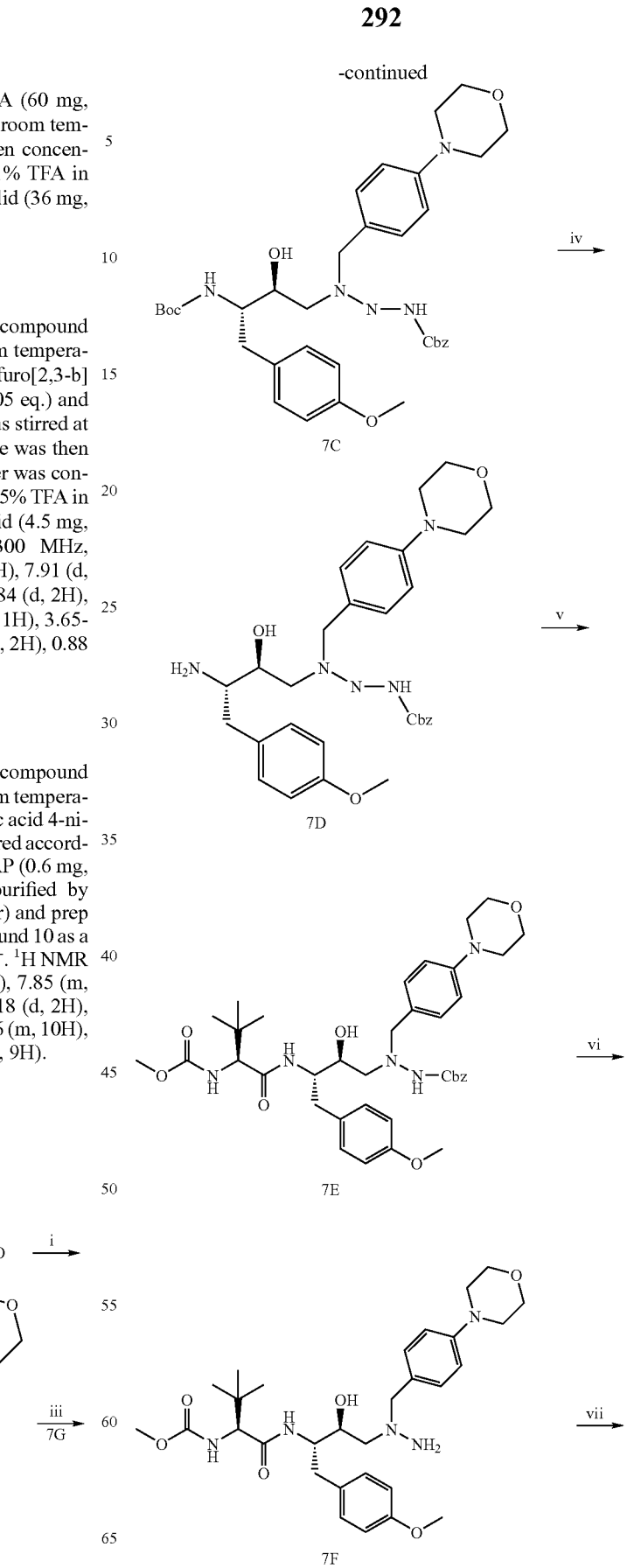

-continued

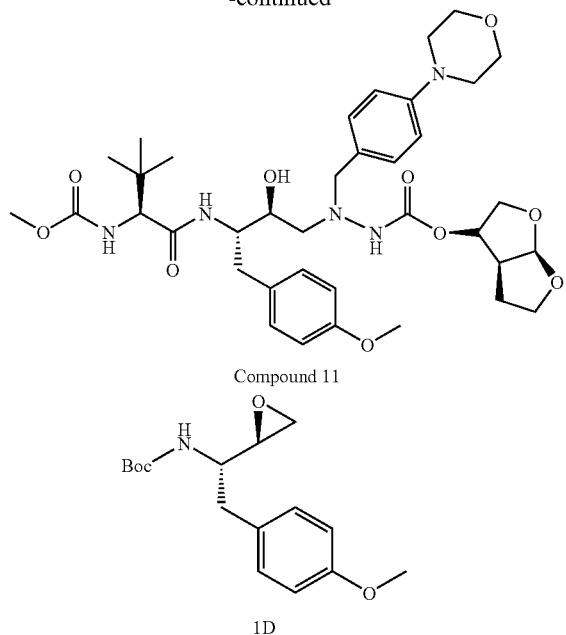

Compound 11

Reagents and conditions:
i. IPA, 80° C.;
ii. a. NaCNBH₃, p-TsOH, THF; b. Na₂B₄O₇, THF, water;
iii. 1D, IPA, 0.8 eq. HOAc;
iv. TFA, DCM;
v. N'(methoxycarbonyl)-L-leucine, TPTU, DMF, DIEA;
vi. MeSMe, TFA;
vii. DCM, DIEA, bis-furan carbonate, DMAP.

Compound 7A

Commercially available 4-morpholin-4-yl-benzaldehyde (806 mg, 4.2 mmol, 1.05 eq.) was added to tert-butyl carbazate (667 mg, 4.0 mmol, 1.0 eq.) in 25 mL of isopropanol. The reaction mixture was heated to 80° C. for 70 minutes. A precipitate formed. The reaction mixture was cooled to room temperature, and ice was added. The precipitate was removed by filtration and dried to give compound 7A as a light yellow solid (1.34 g, 98%). LC-MS: 340.1 (M+H)⁺.

Compound 7B

Sodium cyanoborohyride (260 mg, 4.14 mmol, 1.05 eq.) was added to compound 7A (1.34 g, 3.95 mmol, 1.0 eq.) in 20 mL of THF, followed by the addition of toluene-4-sulfonic acid monohydrate (751 mg, 1.0 eq.) in 10 mL of THF, dropwise. The reaction mixture was stirred at room temperature for 3 hours. The reaction mixture was filtered through a CELITE pad. The filtrate was extracted with EtOAc/sat. NaHCO₃ (1×) and brine (1×). The organic layer was concentrated. The resulting residue was dissolved in a THF (20 mL) and water (20 mL) mixture. Sodium tetraborate decahydrate (6.32 g, 4.2 eq.) was added to the solution. The solution was stirred at room temperature overnight. The solution was then extracted with EtOAc/sat. NaHCO₃ (2×) and brine (1×). The organic layer was concentrated and dried over Na₂SO₄ to give compound 7B as a white solid (1.31 g, 97%). LC-MS: 342.1 (M+H)⁺.

Compound 7C

Acetic acid (8 μL, 0.14 mmol, 0.8 eq.) was added to compound 7B (59 mg, 0.174 mmol, 1.0 eq.) and compound 1D (51 mg, 1.0 eq.) in 1.8 mL of IPA. The reaction mixture was heated to 80° C. for 19 hours. The reaction mixture was cooled to room temperature and concentrated. The resulting residue was purified with silica gel by flash chromatography (40-80% EtOAc/hexane) to give compound 7C as a white solid (82 mg, 74%). LC-MS: 657.2 (M+Na)⁺.

Compound 7D

TFA (1 mL) was added to compound 7C (82 mg, 0.129 mmol) in 2.0 mL of DCM at 0° C. The reaction mixture was stirred at 0° C. for 1 hour. The reaction mixture was concentrated and extracted with EtOAc/sat. NaHCO₃ solution (2×). The organic layer was concentrated and dried over Na₂SO₄ to give compound 7D as a white solid (48 mg, 70%). LC-MS: 557.2 (M+Na)⁺.

Compound 7E

TPTU (40 mg, 1.5 eq.) was added to N-(methoxycarbonyl)-L-tert-leucine (25 mg, 0.134 mmol, 1.5 eq.) in 2.5 mL DMF at 0° C. The reaction mixture was stirred at 0° C. for 5 minutes. Compound 7D (48 mg, 0.09 mmol, 1.0 eq.) and DIEA (47 μL, 3.0 eq.) was added. The reaction mixture was stirred at 0° C. and warmed up to room temperature overnight. The reaction mixture was extracted with EtOAc/sat. NaHCO₃ (1×) and brine (1×). The organic layer was concentrated and purified by silica gel by flash chromatography (40-80% EtOAc/hexane) to give compound 7E as a white solid (41 mg, 65%). LC-MS: 728.3 (M+Na)⁺.

Compound 7F

Dimethylsulfite (0.6 mL) and TFA (2.4 mL) mixture was added to compound 7E (41 mg, 0.058 mmol) in 2.0 mL of DCM at room temperature. The reaction mixture was stirred at room temperature for 14 hours. The reaction mixture was concentrated and extracted with EtOAc/sat. NaHCO₃ (2×) and brine (1×). The organic layer was concentrated and purified by silica gel by flash chromatography (4-8% MeOH/DCM) to give a white solid (15.5 mg, 46%). LC-MS: 572.2 (M+H)⁺.

Compound 11

DIEA (9.4 μL, 0.054 mmol, 2.0 eq.) was added to compound 7F (15.5 mg, 0.027 mmol, 1.0 eq.) and 2H (8.4 mg, 1.05 eq.) in 1.0 mL DCM, followed by DMAP (0.7 mL, 0.2 eq.). The reaction mixture was stirred at room temperature for 3 days. The reaction mixture was then concentrated and purified by silica gel by flash chromatography (4-8% MeOH/DCM) to give Compound 11 as a white solid (3.0 mg, 15%). LC-MS: 750.3 (M+Na)⁺. ¹H NMR (300 MHz, CDCl₃): δ 7.20 (m, 2H), 7.18 (d, 2H), 7.00 (m, 2H), 6.76 (d, 2H), 5.60 (d, 1H), 5.18 (m, 1H), 3.85 (m, 7H), 3.60-3.80 (m, 10H), 3.20 (s, 4H), 3.0 (m, 2H), 2.8 (m, 5H), 2.5 (m, 1H), 2.0 (m, 1H), 1.55 (m, 2H), 0.9 (s, 9H).

Example 8

Scheme 8

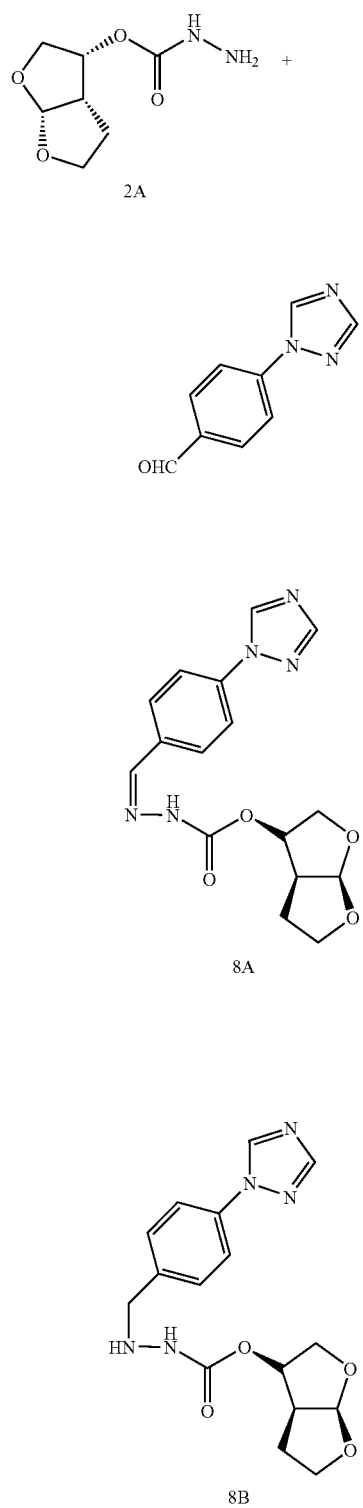

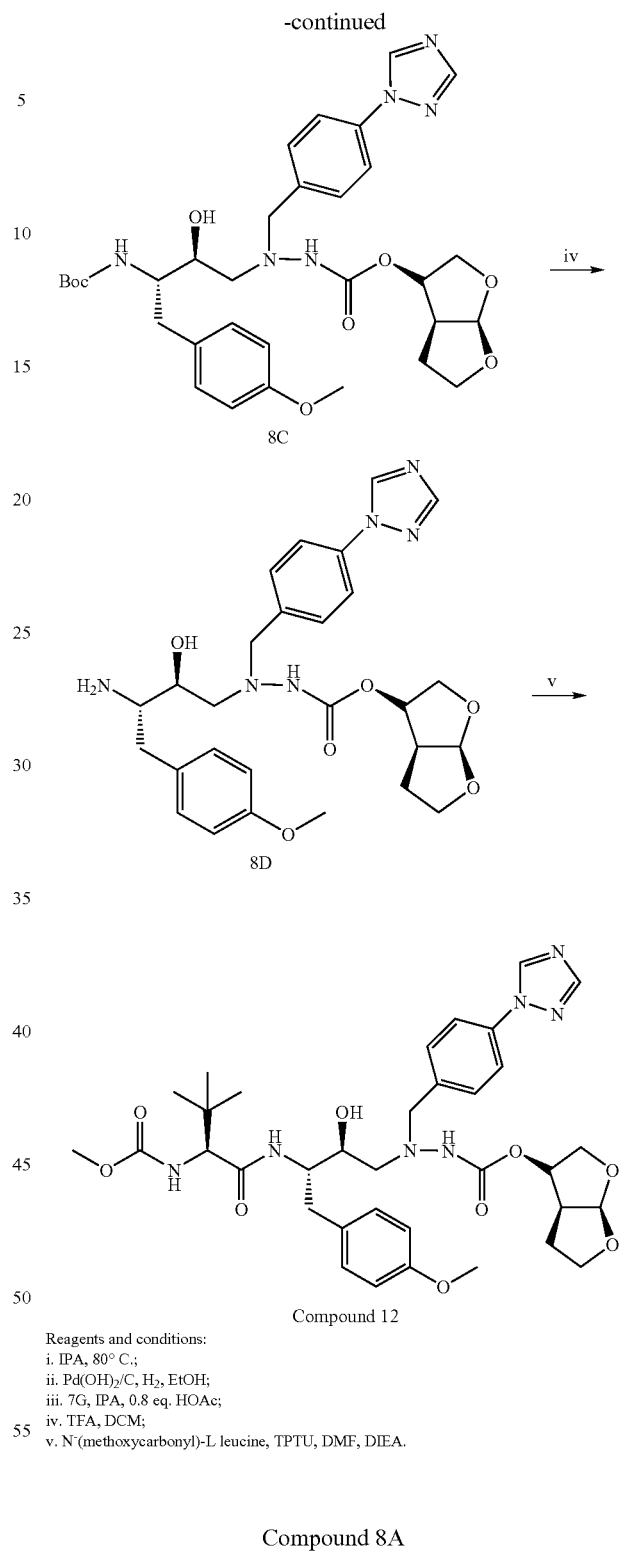

Reagents and conditions:
i. IPA, 80° C.;
ii. Pd(OH)$_2$/C, H$_2$, EtOH;
iii. 7G, IPA, 0.8 eq. HOAc;
iv. TFA, DCM;
v. N-(methoxycarbonyl)-L leucine, TPTU, DMF, DIEA.

Compound 8A

4-[1,2,4]Triazol-1-yl-benzaldehyde (commercially available) (112 mg, 0.646 mmol, 1.0 eq.) was added to compound 2A (152 mg, 1.0 eq.) in 5 mL isopropanol. The reaction mixture was heated to 80° C. for 16 hours. A light yellow precipitate formed. The reaction mixture was cooled to room temperature, and ice was added. The precipitate was filtered off and dried to give compound 8A as a light yellow solid (200 mg, 91%). LC-MS: 344.4 (M+H)+.

Compound 8B

10% Pd(OH)₂/C (20 mg) was added to compound 8A (48 mg, 0.14 mmol) in 50 mL of ethanol. A H₂ balloon was applied to the reaction vessel. The reaction was completed after 4 hours. The reaction mixture was filtered through a CELITE pad and the filtrate was concentrated. The resulting residue was purified by silica gel by flash chromatography (2-8% MeOH/DCM) to give compound 8B as a light yellow solid (32 mg, 64%). LC-MS: 346.0 (M+H)+.

Compound 8C

Acetic acid (4.2 µL, 0.07 mmol, 0.8 eq.) was added to compound 8B (32 mg, 0.093 mmol, 1.0 eq.) and compound 7G (27 mg, 1.0 eq.) in 1.8 mL of IPA. The reaction mixture was heated to 80° C. for 26 hours. The reaction mixture was then cooled to room temperature and concentrated. The resulting residue was purified by silica gel by flash chromatography (4-8% MeOH/DCM) to give compound 8C as a white solid (23 mg, 39%). LC-MS: 661.2 (M+Na)+.

Compound 8D

TFA (0.5 mL) was added to compound 8C (23 mg, 0.036 mmol) in 2.0 mL of DCM solution at 0° C. The reaction mixture was stirred at 0° C. for 90 minutes. The reaction mixture was concentrated and extracted with EtOAc/sat. NaHCO₃ (2×). The organic layer was concentrated and dried over Na₂SO₄ to give compound 8D as a white solid (11.5 mg, 60%). LC-MS: 561.2 (M+Na)+.

Compound 12

TPTU (9 mg, 1.5 eq.) was added to N-(methoxycarbonyl)-L-tert-leucine (6 mg, 0.03 mmol, 1.5 eq.) in 1.0 mL DMF at 0° C. The reaction mixture was stirred at 0° C. for 5 minutes. Compound 8D (11 mg, 0.02 mmol, 1.0 eq.) and DIEA (10.5 µL, 3.0 eq.) were added. The reaction mixture was stirred at 0° C. and warmed up to room temperature for 90 minutes. The reaction mixture was extracted with EtOAc/sat. NaHCO₃ (1×) and brine (1×). The organic layer was concentrated and purified by silica gel by flash chromatography (2-8% MeOH/DCM) to give Compound 12 as a white solid (7.4 mg, 52%). LC-MS: 710.1 (M+H)+. ¹H NMR (300 MHz, CDCl₃): δ 7.20 (m, 2H), 7.18 (d, 2H), 7.00 (m, 2H), 6.76 (d, 2H), 5.60 (d, 1H), 5.18 (m, 1H), 3.85 (m, 7H), 3.60-3.80 (m, 10H), 3.20 (s, 4H), 3.0 (m, 2H), 2.8 (m, 5H), 2.5 (m, 1H), 2.0 (m, 1H), 1.55 (m, 2H), 0.9 (s, 9H).

Example 9

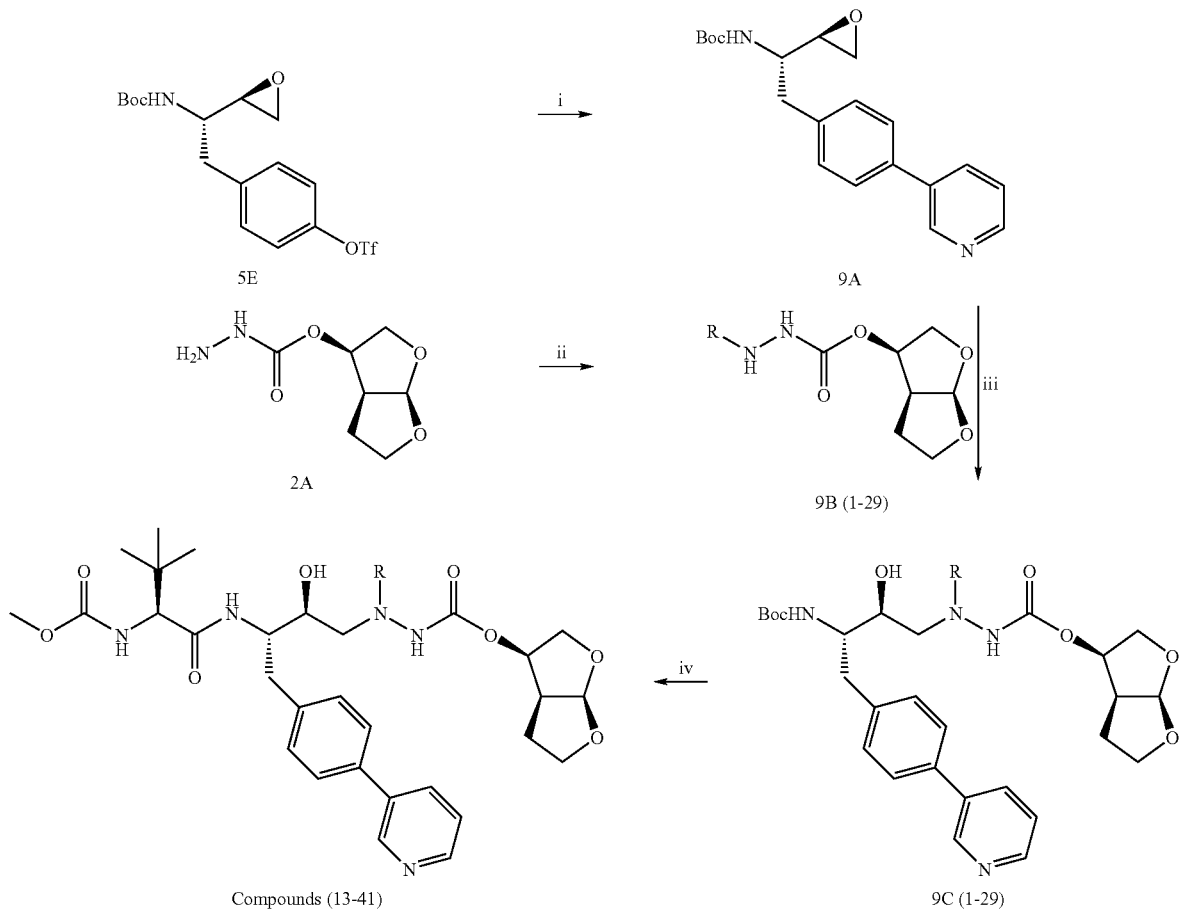

Scheme 9

-continued

Reagents and conditions;
i. 3-pyridineboronic acid, PdCl₂(dppf), DME, aq. Na₂CO₃, 78%;
ii. a. aldehyde, isopropanol, 80° C.; b. NaBH₃CN,
iii. HOAc, IPA, 80° C.;
iv. a. TFA, DCM; b. N-(methoxycarbonyl)-L-tert-leucine, TPTU, NMM, DMF.

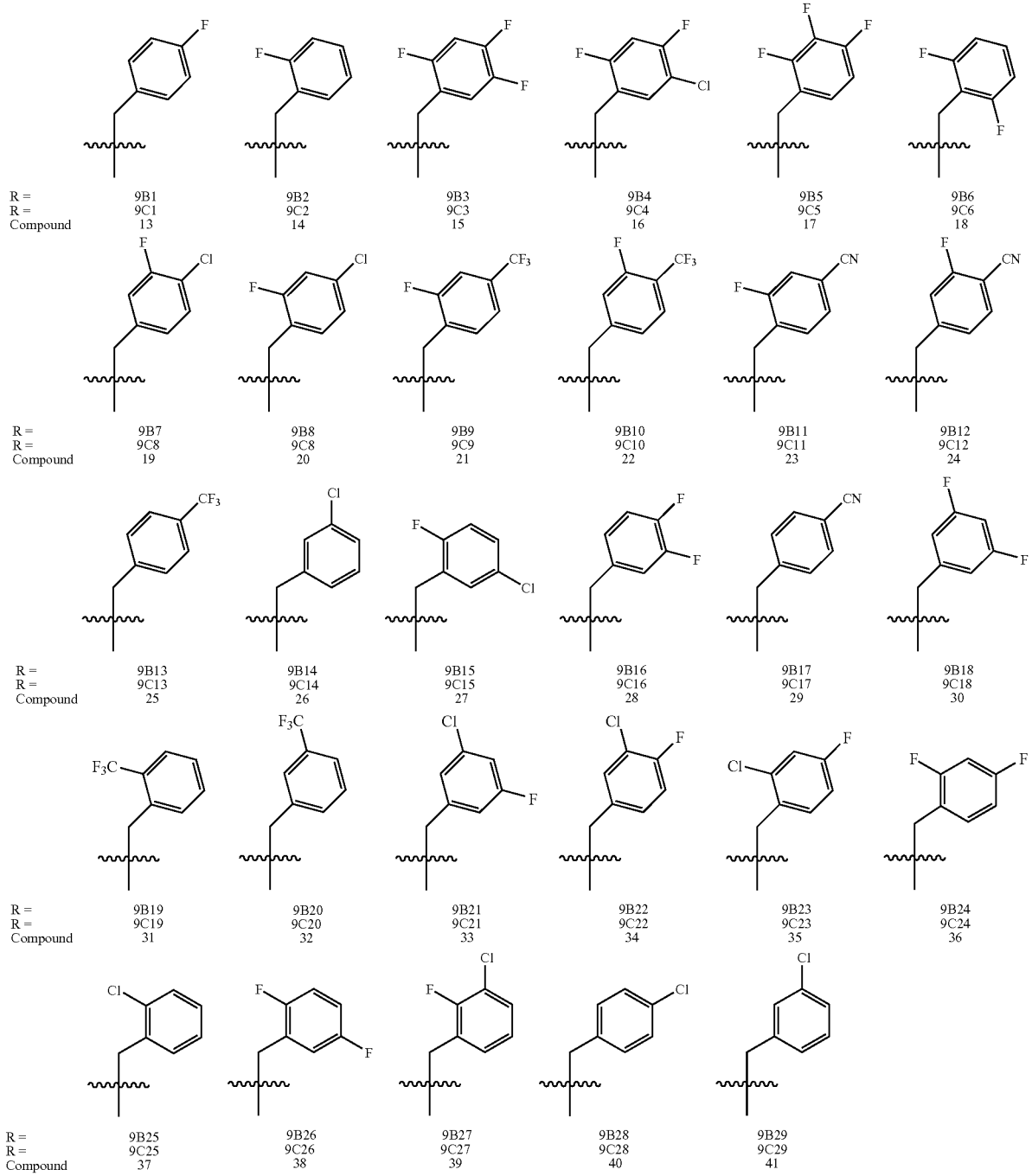

Compound 9A

A round-bottom flask was charged with compound 5E (1.24 g, 3.01 mmol), 3-pyridineboronic acid (Aldrich, 0.741 g, 6.03 mmol), and PdCl₂(dppf) (0.276 g, 0.301 mmol). A 2M aqueous sodium carbonate solution (7.5 mL, 15.05 mmol) and dimethoxyethane (30 mL) were added and reaction mixture was stirred for 45 min at 80° C. The reaction mixture was diluted with ethyl acetate and washed with brine. The organic layer was dried (MgSO₄), concentrated to 10 mL and purified by flash chromatography (silica gel, 30 to 60% isopropanol/ Hex) to give a white solid (0.7247 g, 70%). LC-MS shows 341.1 (M+H). $^1$H NMR (300 MHz, CDCl₃): δ 8.81 (s, 1H), 8.58 (m, 1H), 7.82 (m, 1H), 7.51 (m, 2H), 7.37 (m, 3H), 4.64

(m, 1H), 4.17 (m, 1H), 3.04 (m, 1H), 2.95 (m, 2H), 2.72 (t, 1H), 2.60 (s, 1H), 1.39 (s, 9H).

Compound 9B1

Compound 9B1 was prepared in a manner similar to compound 5A except 4-fluorobenzaldehyde (168 µL, 1.59 mmol) was used instead of benzaldehyde; (0.329 g, 69%). Mass spectrum: 296.8 (M+H)$^+$.

Compound 9B2

Compound 9B2 was prepared in a manner similar to compound 5A except 2-fluorobenzaldehyde (143 µL, 1.36 mmol) was used instead of benzaldehyde; (0.2867 g, 71%). Mass spectrum: 296.9 (M+H)$^+$.

Compound 9B3

Compound 9B3 was prepared in a manner similar to compound 5A except 2,4,5-trifluorobenzaldehyde (0.4052 g, 2.15 mmol) was used instead of benzaldehyde; (0.334 g, 47%). Mass spectrum: 332.9 (M+H)$^+$.

Compound 9B4

Compound 9B4 was prepared in a manner similar to compound 5A except 5-chloro, 2,4-difluorobenzaldehyde (0.160 g, 0.906 mmol) was used instead of benzaldehyde; (0.2099 g, 60%). Mass spectrum: 348.8, 350.8 (M+H)$^+$.

Compound 9B5

Compound 9B5 was prepared in a manner similar to compound 5A except 2,3,4-trifluorobenzaldehyde was used instead of benzaldehyde.

Compound 9B6

Compound 9B6 was prepared in a manner similar to compound 5A except 2,6-difluorobenzaldehyde was used instead of benzaldehyde.

Compound 9B7

Compound 9B7 was prepared in a manner similar to compound 5A except 4-chloro, 3-fluorobenzaldehyde was used instead of benzaldehyde;

Compound 9B8

Compound 9B8 was prepared in a manner similar to compound 5A except 4-chloro-2-fluorobenzaldehyde was used instead of benzaldehyde.

Compound 9B9

Compound 9B9 was prepared in a manner similar to compound 5A except 2-fluoro-4-(trifluoromethyl)benzaldehyde was used instead of benzaldehyde

Compound 9B10

Compound 9B10 was prepared in a manner similar to compound 5A except 3-fluoro-4-(trifluoromethyl)benzaldehyde (0.3077 g, 1.6 mmol) was used instead of benzaldehyde; (0.3469 g, 60%). Mass spectrum: 364.8 (M+H)$^+$.

Compound 9B11

Compound 9B11 was prepared in a manner similar to compound 5A except 4-cyano-2-fluorobenzaldehyde (0.249 g, 1.67 mmol) was used instead of benzaldehyde; (0.2808 g, 52%). Mass spectrum: 321.8, 322.81 (M+H)$^+$.

Compound 9B12

Compound 9B12 was prepared in a manner similar to compound 5A except 2-fluoro-4-formylbenzonitrile (0.254 g, 1.7 mmol) was used instead of benzaldehyde; (0.311 g, 57%). Mass spectrum: 321.8, 322.8 (M+H)$^+$.

Compound 9B13

A round-bottom flask was charged with compound 2A (201 mg, 0.918 mmol) and 4-trifluoromethyl-benzaldehyde (123 µL, 0.918 mmol) in 1.5 mL IPA. The reaction was heated to 80° C. overnight. The reaction was cooled to room temperature, and poured into ice, and a precipitate formed. The precipitate was filtered and dried to a white solid (309 mg, 98%). LC-MS shows 344.8 (M+H). $^1$H NMR (300 MHz, CD$_3$OD): δ 8.12 (s, 1H), 7.90 (m, 2H), 7.68 (m, 2H), 5.72 (d, 1H), 5.34 (m, 1H), 4.08 (m, 1H), 3.96 (m, 2H), 3.84 (m, 1H), 3.19 (m, 2H), 2.17 (m, 1H), 1.97 (m, 1H). Sodium cyanoborohydride (68 mg, 1.07 mmol, 1.2 eq.) was added to the above compound in 20 mL THF, followed by toluene-4-sulfonic acid monohydrate (204 mg, 1.07 mmol, 1.2 eq.). The reaction was stirred at room overnight, then concentrated. Ethyl acetate was added, followed by washing with saturated sodium bicarbonate solution. The organic layer was concentrated. The residue was re-dissolved in a THF/water mixture (10 mL: 10 mL). Sodium tetraborate decahydrate (1.44 g, 4.2 eq.) was added to the solution. The reaction was stirred at room temperature overnight. The reaction mixture was extracted with EtOAc/sat. NaHCO$_3$ (2×) and brine (1×). The organic layer was concentrated and purified by silica gel (40-80% EtOAc/hexane) to give white solid (206 mg, 67%). $^1$H NMR (300 MHz, CD$_3$OD): δ 7.60 (m, 4H), 5.62 (d, 1H), 5.10 (q, 1H), 4.08 (m, 2H), 3.80 (m, 2H), 3.70 (m, 1H), 3.03 (m, 1H), 1.82 (m, 2H).

Compound 9B14

Compound 2A (401 mg, 2.13 mmol) in isopropanol (13 mL) was treated with commercially available 3-chlorobenzaldehyde (364 µL, 3.20 mmol) at 80° C. for 4 h. The reaction mixture was cooled to room temperature and purified (silica gel, 30 to 90% EtOAc/Hex) to give a white foam (662 mg, 2.13 mmol, 99%). To a solution of the above foam in ethanol (15 mL) was added 10% palladium/carbon (66 mg). The reaction mixture was stirred under a hydrogen atmosphere at for 1 h. then filtered through a pad of Celite. Concentrated and purified (silica gel, 20 to 100% EtOAc/Hex) to give a clear yellow oil (222 mg, 0.709 mmol, 33%). Mass spectrum: 312.9 (M+H)$^+$.

Compound 9B15

Compound 9B15 was prepared in a manner similar to compound 9B13 except 3-chloro-6-fluoro-benzaldehyde was used instead of 4-trifluoromethyl-benzaldehyde. LC-MS shows: 330.9 (M+H)$^+$.

Compound 9B16

Compound 9B16 was prepared in a manner similar to compound 9B13 except 3,4-difluorobenzaldehyde was used instead of 4-trifluoromethyl-benzaldehyde. LC-MS shows: 314.8 $(M+H)^+$.

Compound 9B17

Compound 9B17 was prepared in a manner similar to compound 9B13 except 4-cyanobenzaldehyde was used instead of 4-trifluoromethyl-benzaldehyde. LC-MS shows: 301.9 $(M+H)^+$.

Compound 9B18

Compound 9B18 was prepared in a manner similar to compound 9B13 except 3,5-difluorobenzaldehyde was used instead of 4-trifluoromethyl-benzaldehyde. LC-MS shows: 314.9 $(M+H)^+$.

Compound 9B19

Compound 9B19 was prepared in a manner similar to compound 9B13 except 2-trifluoromethylbenzaldehyde was used instead of 4-trifluoromethyl-benzaldehyde. LC-MS shows: 346.9 $(M+H)^+$.

Compound 9B20

Compound 9B20 was prepared in a manner similar to compound 9B13 except 3-trifluoromethylbenzaldehyde was used instead of 4-trifluoromethyl-benzaldehyde. LC-MS shows: 346.9 $(M+H)^+$.

Compound 9B21

Compound 9B21 was prepared in a manner similar to compound 9B13 except 3-chloro-5-fluoro-benzaldehyde was used instead of 4-trifluoromethyl-benzaldehyde. LC-MS shows: 330.9 $(M+H)^+$.

Compound 9B22

Compound 9B22 was prepared in a manner similar to compound 9B13 except 3-chloro-4-fluoro-benzaldehyde was used instead of 4-trifluoromethyl-benzaldehyde. LC-MS shows: 330.9 $(M+H)^+$.

Compound 9B23

Compound 9B23 was prepared in a manner similar to compound 9B13 except 2-chloro-3-fluoro-benzaldehyde was used instead of 4-trifluoromethyl-benzaldehyde. LC-MS shows: 330.9 $(M+H)^+$.

Compound 9B24

Compound 2A (380 mg, 2.02 mmol) in isopropanol (12 mL) was treated with commercially available 2,4-difluorobenzaldehyde (331 µL, 3.03 mmol) at 80° C. for 4 h. The reaction mixture was cooled to room temperature and purified (silica gel, 30 to 100% EtOAc/Hex) to give a white foam (617 mg, 1.97 mmol, 98%). To a solution of the above foam in ethanol (15 mL) was added 10% palladium/carbon (62 mg). The reaction mixture was stirred under a hydrogen atmosphere at for 1 h. then filtered through a pad of Celite. Concentrated and purified (silica gel, 0 to 100% EtOAc/Hex) to give a white solid (476 mg, 1.51 mmol, 77%). Mass spectrum: 314.8 $(M+H)^+$.

Compound 9B25

Compound 9B25 was prepared in a manner similar to compound 9B24 except that 2-chlorobenzaldehyde was used instead of 2,4-difluorobenzaldehyde.

Compound 9B26

Compound 2A (380 mg, 2.02 mmol) in isopropanol (12 mL) was treated with commercially available 2,4-difluorobenzaldehyde (331 µL, 3.03 mmol) at 80° C. for 4 h. The reaction mixture was cooled to room temperature and purified (silica gel, 30 to 100% EtOAc/Hex) to give a white foam (617 mg, 1.97 mmol, 98%). To a solution of the above foam in ethanol (15 mL) were added 10% palladium/carbon (62 mg). The reaction mixture was stirred under a hydrogen atmosphere at for 1 h. then filtered through a pad of Celite. Concentrated and purified (silica gel, 0 to 100% EtOAc/Hex) to give a white solid (476 mg, 1.51 mmol, 77%). Mass spectrum: 314.8 $(M+H)^+$.

Compound 9B27

Compound 9B27 was prepared in a manner similar to compound 9B24 except that 3-chloro-2-fluoro-benzaldehyde was used instead of 2,4-difluorobenzaldehyde.

Compound 9B28

Compound 9B28 was prepared in a manner similar to compound 9B24 except that 4-chlorobenzaldehyde was used instead of 2,4-difluorobenzaldehyde.

Compound 9B29

Compound 2A (381 mg, 2.02 mmol) in isopropanol (12 mL) was treated with commercially available 3-fluorobenzaldehyde (332 µL, 3.04 mmol) at 80° C. for 4 h. The reaction mixture was cooled to room temperature and purified (silica gel, 30 to 90% EtOAc/Hex) to give a white foam (558 mg, 1.90 mmol, 94%). To a solution of the above foam in ethanol (15 mL) were added 10% palladium/carbon (56 mg). The reaction mixture was stirred under a hydrogen atmosphere at for 1 h. then filtered through a pad of Celite. Concentrated and purified (silica gel, 20 to 100% EtOAc/Hex) to give a white solid (485 mg, 1.64 mmol, 86%). Mass spectrum: 296.8 $(M+H)^+$.

Compound 9C1

Compound 9C1 was prepared in a manner similar to compound 5B by reacting compound 9A (0.1 M solution in isopropanol) with compound 9B1.

Compound 9C2

Compound 9C2 was prepared in a manner similar to compound 5B by reacting compound 9A (0.1 M solution in isopropanol) with compound 9B2.

Compound 9C3

Compound 9C3 was prepared in a manner similar to compound 5B by reacting compound 9A (2.5 mL of 0.1 M solution in isopropanol, 0.25 mmol) with compound 9B3 (0.334 g, 1.0 mmol); (0.025 g, 15%). Mass spectrum: 673.2 (M+H)$^+$.

Compound 9C4

Compound 9C4 was prepared in a manner similar to compound 5B by reacting compound 9A (1.5 mL of 0.1 M solution in isopropanol, 0.15 mmol) with compound 9B4 (0.2099 g, 0.602 mmol); (0.024 g, 24%). Mass spectrum: 689.2, 691.2 (M+H)$^+$.

Compound 9C5

Compound 9C5 was prepared in a manner similar to compound 5B by reacting compound 9A (0.1 M solution in isopropanol) with compound 9B5.

Compound 9C6

Compound 9C6 was prepared in a manner similar to compound 5B by reacting compound 9A (0.1 M solution in isopropanol) with compound 9B6.

Compound 9C7

Compound 9C7 was prepared in a manner similar to compound 5B by reacting compound 9A (0.1 M solution in isopropanol) with compound 9B7. Compound 9C8.

Compound 9C8 was prepared in a manner similar to compound 5B by reacting compound 9A (0.1 M solution in isopropanol) with compound 9B8.

Compound 9C9

Compound 9C9 was prepared in a manner similar to compound 5B by reacting compound 9A (0.1 M solution in isopropanol) with compound 9B9.

Compound 9C10

Compound 9C10 was prepared in a manner similar to compound 5B by reacting compound 9A (2.38 mL of 0.1M solution in isopropanol, 0.238 mmol) with compound 9B10 (0.3469 g, 0.602 mmol); (0.0308 g, 18%). Mass spectrum: 705.3, 706.2 (M+H)$^+$.

Compound 9C11

Compound 9C11 was prepared in a manner similar to compound 5B by reacting compound 9A (2.18 mL of 0.1 M solution in isopropanol, 0.218 mmol) with compound 9B11 (0.2808 g, 0.698 mmol); (0.0249 g, 17%). Mass spectrum: 662.3 (M+H)$^+$.

Compound 9C12

Compound 9C12 was prepared in a manner similar to compound 5B by reacting compound 9A (2.42 mL of 0.1 M solution in isopropanol, 0.242 mmol) with compound 9B12 (0.311 g, 0.774 mmol); (0.0295 g, 20%). Mass spectrum: 662.3 (M+H)$^+$.

Compound 9C13

A round-bottom flask was charged with compound 9A (0.1 M in IPA, 1.49 mL, 0.149 mmol), compound 9B13 (206 mg, 0.595 mmol, 4.0 eq.) and acetic acid (27 μL, 0.476 mmol, 3.2 eq.). The reaction mixture was heated at 80° C. for 18 hours. The reaction mixture was concentrated and purified by flash chromatography (silica gel, 30 to 100% ethyl acetate/hexane) to give a white solid (30 mg, 30%). LC-MS shows 687.3 (M+H). $^1$H NMR (300 MHz, CDCl$_3$): δ 8.80 (s, 1H), 8.58 (s, 1H), 7.84 (d, 1H), 7.60-7.42 (m, 3H), 7.40 (m, 3H), 5.62 (m, 1H), 5.01 (m, 2H), 4.12-3.49 (m, 10H), 3.02-2.83 (m, 4H), 1.36 (s, 9H).

Compound 9C14

To a solution of compound 9A (85 mg, 0.250 mmol) in isopropanol (2.5 mL) were added compound 9B14 (222 mg, 0.709 mmol) and AcOH (32 μL). After stirring for 18 h at 80° C., the reaction mixture was concentrated and purified (silica gel, 2 to 10% MeOH/CH$_2$Cl$_2$) to give a white foam (48.6 mg, 0.0744 mmol, 30%). Mass spectrum: 653.3 (M+H)$^+$.

Compound 9C15

Compound 9C15 was prepared in a manner similar to compound 9C13 except compound 9B15 was used instead of compound 9B13. LC-MS shows: 671.2 (M+H)$^+$.

Compound 9C16

Compound 9C16 was prepared in a manner similar to compound 9C13 except compound 9B16 was used instead of compound 9B13. LC-MS shows: 655.3 (M+H)$^+$.

Compound 9C17

Compound 9C17 was prepared in a manner similar to compound 9C13 except compound 9B17 was used instead of compound 9B13. LC-MS shows: 644.2 (M+H)$^+$.

Compound 9C18

Compound 9C18 was prepared in a manner similar to compound 9C13 except compound 9B18 was used instead of compound 9B13. LC-MS shows: 655.3 (M+H)$^+$.

Compound 9C19

Compound 9C19 was prepared in a manner similar to compound 9C13 except compound 9B19 was used instead of compound 9B13. LC-MS shows: 687.3 (M+H)$^+$.

Compound 9C20

Compound 9C20 was prepared in a manner similar to compound 9C13 except compound 9B20 was used instead of compound 9B13. LC-MS shows: 687.3 (M+H)$^+$.

Compound 9C21

Compound 9C21 was prepared in a manner similar to compound 9C13 except compound 9B21 was used instead of compound 9B13. LC-MS shows: 671.2 (M+H)$^+$.

Compound 9C22

Compound 9C22 was prepared in a manner similar to compound 9C13 except compound 9B22 was used instead of compound 9B13. LC-MS shows: 671.2 (M+H)$^+$.

Compound 9C23

Compound 9C23 was prepared in a manner similar to compound 9C13 except compound 9B23 was used instead of compound 9B13. LC-MS shows: 671.2 (M+H)$^+$.

Compound 9C24

To a solution of compound 9A (50 mg, 0.147 mmol) in isopropanol (1.5 mL) were added compound 9B24 (185 mg, 0.588 mmol) and AcOH (28 mg). After stirring for 18 h at 80° C., the reaction mixture was concentrated and purified (silica gel, 0 to 100% EtOAc/Hex) to give a clear film (28.1 mg, 0.0429 mmol, 29%). Mass spectrum: 655.2 (M+H)$^+$.

Compound 9C25

To a solution of compound 9A (50 mg, 0.147 mmol) in isopropanol (1.5 mL) were added compound 9B25 (184 mg, 0.588 mmol) and AcOH (28 mg). After stirring for 18 h at 80° C., the reaction mixture was concentrated and purified (silica gel, 0 to 100% EtOAc/Hex) to give a white foam (30 mg, 0.045 mmol, 31%). Mass spectrum: 653.2 (M+H)$^+$.

Compound 9C26

To a solution of compound 9A (50 mg, 0.147 mmol) in isopropanol (1.5 mL) were added compound 9B26 (185 mg, 0.588 mmol) and AcOH (28 mg). After stirring for 18 h at 80° C., the reaction mixture was concentrated and purified (silica gel, 0 to 100% EtOAc/Hex) to give a yellow clear film (16.6 mg, 0.025 mmol, 17%). Mass spectrum: 655.2 (M+H)$^+$.

Compound 9C27

To a solution of compound 9A (50 mg, 0.147 mmol) in isopropanol (1.5 mL) were added compound 9B27 (194 mg, 0.588 mmol) and AcOH (28 mg). After stirring for 18 h at 80° C., the reaction mixture was concentrated and purified (silica gel, 10 to 100% EtOAc/Hex) to give a slightly yellow film (19 mg, 0.028 mmol, 19%). Mass spectrum: 671.3 (M+H)$^+$.

Compound 9C28

To a solution of compound 9A (50 mg, 0.147 mmol) in isopropanol (1.5 mL) were added compound 9B28 (183 mg, 0.588 mmol) and AcOH (28 mg). After stirring for 18 h at 80° C., the reaction mixture was concentrated and purified (silica gel, 10 to 100% EtOAc/Hex) to give a crude product (102 mg). Mass spectrum: 653.2 (M+H)$^+$.

Compound 9C29

To a solution of compound 9A (102 mg, 0.300 mmol) in isopropanol (3 mL) were added compound 9B29 (485 mg, 1.64 mmol) and AcOH (74 µL). After stirring for 18 h at 80° C., the reaction mixture was concentrated and purified (silica gel, 2 to 10% MeOH/CH$_2$Cl$_2$) to give a clear film (76.6 mg, 0.120 mmol, 40%). Mass spectrum: 637.3 (M+H)$^+$.

Compound 13

Compound 13 was prepared in a manner similar to compound 8 except compound 9C1 was used instead of compound 5D. Mass spectrum: (M+H)$^+$. LC-MS shows: 708.3 (M+1). $^1$H NMR (300 MHz, CD$_3$OD): δ 9.08 (s, 1H), 8.79 (m, 2H), 8.08 (m, 1H), 7.68 (m, 3H), 7.51 (d, 2H), 7.39 (m, 2H), 7.01 (m, 1H), 7.18-7.01 (m, 1H), 5.58 (d, 1H), 4.97 (m, 1H), 4.36 (m, 1H), 3.97-3.50 (m, 8H), 3.56 (s, 3H), 3.09-2.82 (m, 5H), 1.71 (m, 2H), 0.92 (s, 9H)

Compound 14

Compound 14 was prepared in a manner similar to compound 8 except compound 9C2 was used instead of compound 5D; Mass spectrum: (M+H)$^+$. LC-MS shows: 708.3 (M+1). $^1$H NMR (300 MHz, CD$_3$OD): δ 9.12 (s, 1H), 8.79 (d, 2H), 8.05 (d, 1H), 7.78 (d, 1H), 7.66 (d, 2H), 7.52 (m, 3H), 7.31 (m, 1H), 7.18-7.01 (m, 1H), 5.58 (d, 1H), 4.97 (m, 1H), 4.36 (m, 1H), 3.97-3.50 (m, 8H), 3.56 (s, 3H), 3.09-2.82 (m, 5H), 1.71 (m, 2H), 0.92 (s, 9H).

Compound 15

Compound 15 was prepared in a manner similar to compound 8 except compound 9C3 (0.025 g, 0.037 mmol) was used instead of compound 5D; (0.013 g, 48%). $^1$H NMR (300 MHz, CD$_3$OD): δ 8.72 (s, 1H), 8.45 (s, 1H), 8.01 (d, J=7.8 Hz, 1H), 7.4-7.25 (m, 6H), 7.2-7.0 (m, 1H), 5.52 (d, J=5.4 Hz, 1H), 4.95-4.89 (m, 1H), 4.3-4.2 (m, 1H), 3.94-3.22 (m, 11H), 3.0-2.65 (m, 5H), 1.70-1.55 (m, 2H), 0.843 (s, 9H). Mass spectrum: 744.3 (M+H)$^+$.

Compound 16

Compound 16 was prepared in a manner similar to compound 8 except compound 9C4 (0.0244 g, 0.0354 mmol) was used instead of compound 5D; (0.013 g, 50%). $^1$H NMR (300 MHz, CD$_3$OD): δ 8.72 (s, 1H), 8.45 (d, J=3.9 Hz, 1H), 8.02 (d, J=7.5 Hz, 1H) 7.64 (dd, J=7.5, 7.5 Hz, 1H), 7.5-7.25 (m, 5H), 7.06 (dd, J=9.0, 9.0 Hz, 1H), 5.53 (d, J=5.4 Hz, 1H), 4.95-4.89 (m, 1H), 4.3-4.2 (m, 1H), 3.94-3.22 (m, 11H), 3.0-2.65 (m, 5H), 1.70-1.55 (m, 2H), 0.85 (s, 9H). Mass spectrum: 760.3, 761.3 (M+H)$^+$.

Compound 17

Compound 17 was prepared in a manner similar to compound 8 except compound 9C5 (0.0176 g, 0.0262 mmol) was used instead of compound 5D; (0.010 g, 52%). $^1$H NMR (300 MHz, CD$_3$OD): δ 8.72 (s, 1H), 8.45 (d, J=3.9 Hz, 1H), 8.02 (d, J=7.5 Hz, 1H) 7.6-7.2 (m, 6H), 7.1-7.0 (m, 1H), 5.53 (d, J=5.1 Hz, 1H), 4.95-4.89 (m, 1H), 4.3-4.2 (m, 1H), 3.95-3.20 (m, 11H), 3.0-2.65 (m, 5H), 1.70-1.55 (m, 2H), 0.85 (s, 9H). Mass spectrum: 744.3, 745.3 (M+H)$^+$.

Compound 18

Compound 18 was prepared in a manner similar to compound 8 except compound 9C6 (0.0576 g, 0.0866 mmol) was used instead of compound 5D; (0.0356 g, 57%). $^1$H NMR (300 MHz, CD$_3$OD): δ 8.72 (s, 1H), 8.45 (d, J=4.8 Hz, 1H), 8.01 (d, J=8.1 Hz, 1H) 7.6-7.2 (m, 7H), 7.0-6.8 (m, 1H), 5.53 (d, J=5.7 Hz, 1H), 4.95-4.89 (m, 1H), 4.2-4.1 (m, 1H), 3.95-3.20 (m, 11H), 3.0-2.65 (m, 5H), 1.80-1.60 (m, 2H), 0.88 (s, 9H). Mass spectrum: 726.3, 727.3 (M+H)$^+$.

Compound 19

Compound 19 was prepared in a manner similar to compound 8 except compound 9C7 (0.0505 g, 0.0753 mmol) was used instead of compound 5D; (0.0261 g, 47%). $^1$H NMR (300 MHz, CD$_3$OD): δ 8.72 (s, 1H), 8.45 (d, J=3.6 Hz, 1H), 8.02 (d, J=7.8 Hz, 1H) 7.6-7.2 (m, 7H), 7.13 (d, J=8.1, 1H),

Compound 20

Compound 20 was prepared in a manner similar to compound 8 except compound 9C8 (0.0470 g, 0.070 mmol) was used instead of compound 5D; (0.0283 g, 54%). $^1$H NMR (300 MHz, CD$_3$OD): δ 8.72 (s, 1H), 8.45 (d, J=3.9 Hz, 1H), 8.02 (d, J=7.5 Hz, 1H) 7.6-7.3 (m, 7H), 7.15-7.0 (m, 1H), 5.52 (d, J=4.8 Hz, 1H), 4.95-4.89 (m, 1H), 4.3-4.2 (m, 1H), 3.95-3.20 (m, 11H), 3.0-2.65 (m, 5H), 1.85-1.65 (m, 2H), 0.84 (s, 9H). Mass spectrum: 742.2, 743.3 (M+H)$^+$.

Compound 21

Compound 21 was prepared in a manner similar to compound 8 except compound 9C9 (0.0315 g, 0.0447 mmol) was used instead of compound 5D; (0.0208 g, 60%). $^1$H NMR (300 MHz, CD$_3$OD): δ 8.72 (s, 1H), 8.45 (d, J=3.6 Hz, 1H), 8.02 (d, J=8.1 Hz, 1H) 7.73 (dd, J=8.1 Hz, 8.1 Hz, 1H), 7.6-7.3 (m, 7H), 5.51 (d, J=5.1 Hz, 1H), 4.95-4.89 (m, 1H), 4.3-4.2 (m, 1H), 4.0-3.20 (m, 11H), 3.0-2.65 (m, 5H), 1.85-1.75 (m, 2H), 0.83 (s, 9H). Mass spectrum: 776.3, 777.3 (M+H)$^+$.

Compound 22

Compound 22 was prepared in a manner similar to compound 8 except compound 9C10 (0.0308 g, 0.0437 mmol) was used instead of compound 5D; (0.0198 g, 58%). $^1$H NMR (300 MHz, CD$_3$OD): δ 8.72 (s, 1H), 8.45 (d, J=5.1 Hz, 1H), 8.02 (d, J=8.7 Hz, 1H), 7.6-7.3 (m, 8H), 5.51 (d, J=5.1 Hz, 1H), 4.95-4.89 (m, 1H), 4.3-4.2 (m, 1H), 4.0-3.20 (m, 11H), 3.0-2.65 (m, 5H), 1.80-1.6 (m, 2H), 0.81 (s, 9H). Mass spectrum: 776.3, 777.3 (M+H)$^+$.

Compound 23

Compound 23 was prepared in a manner similar to compound 8 except compound 9C11 (0.0249 g, 0.0376 mmol) was used instead of compound 5D; (0.0127 g, 46%). $^1$H NMR (300 MHz, CD$_3$OD): δ 8.72 (s, 1H), 8.45 (d, J=4.5 Hz, 1H), 8.02 (d, J=8.1 Hz, 1H), 7.75-7.65 (m, 1H), 7.55-7.30 (m, 7H), 5.51 (d, J=5.1 5 Hz, 1H), 4.95-4.89 (m, 1H), 4.3-4.2 (m, 1H), 4.0-3.20 (m, 11H), 3.0-2.65 (m, 5H), 1.80-1.6 (m, 2H), 0.84 (s, 9H). Mass spectrum: 733.4, 734.3 (M+H)$^+$.

Compound 24

Compound 24 was prepared in a manner similar to compound 8 except compound 9C12 (0.0295 g, 0.0446 mmol) was used instead of compound 5D; (0.0112 g, 34%). $^1$H NMR (300 MHz, CD$_3$OD): δ 8.72 (s, 1H), 8.45 (d, J=4.5 Hz, 1H), 8.02 (d, J=8.1 Hz, 1H), 7.64 (dd, J=7.5, 6.6 Hz, 1H), 7.55-7.30 (m, 7H), 5.52 (d, J=5.1 Hz, 1H), 4.95-4.89 (m, 1H), 4.4-4.3 (m, 1H), 4.0-3.20 (m, 11H), 3.0-2.65 (m, 5H), 1.80-1.6 (m, 2H), 0.82 (s, 9H). Mass spectrum: 733.4, 734.3 (M+H)$^+$.

Compound 25

TFA (1 mL) was added to compound 9C13 (30 mg, 0.0437 mmol) in 2 mL DCM. The reaction was stirred at room temperature for 90 minutes. The reaction mixture was concentrated. Ethyl acetate was added to the reaction crude and washed with saturated sodium bicarbonate aqueous solution. The organic layer was concentrated after drying over anhydrous sodium sulfate to give pale solid (23 mg, 90%). LC-MS shows 587.2 (M+H). TPTU (53 mg, 0.176 mmol, 4.5 eq.) was added to N-(methoxycarbonyl)-L-tert-leucine (34 mg, 0.176 mmol, 4.5 eq.) in 1.4 mL DMF at 0° C. Mixture was stirred at 0° C. for 5 minutes. The above compound (23 mg, 0.039 mmol, 1.0 eq.) and NMM (26 µL, 0.235 mmol, 6.0 eq.) was added. The reaction was stirred at 0° C. and warmed up to room temperature overnight. The reaction mixture was extracted by EtOAc/sat. NaHCO$_3$ (1×) and brine (1×). The organic layer was concentrated and purified by silica gel (2-8% MeOH/DCM) followed by reverse phase HPLC (0.5% TFA in MeCN/water) to give a white solid (11.9 mg, 40%). LC-MS shows 758.3 (M+H)$^+$. $^1$H NMR (300 MHz, CD$_3$OD): δ 8.82 (m, 1H), 8.51 (d, 1H), 8.07 (d, 1H), 7.74 (d, 1H), 7.56 (m, 7H), 7.40 (m, 2H), 5.58 (m, 1H), 4.97 (m, 1H), 4.39 (m, 1H), 4.08-3.50 (m, 8H), 3.36 (s, 3H), 3.02-2.72 (m, 5H), 1.53 (m, 1H), 0.82 (s, 9H).

Compound 26

Compound 26 was prepared in a manner similar to compound 25 except compound 9C14 was used instead of compound 9C13. $^1$H NMR (300 MHz, CDCl$_3$): δ 8.79 (s), 8.57 (s), 7.84-7.82 (d), 7.47-7.45 (d), 7.34-7.26 (m), 6.38-6.35 (d), 6.04 (s), 5.65-5.63 (d), 5.26-5.23 (d), 5.11-5.04 (m), 4.27 (s), 4.21-4.09 (m), 3.96-3.61 (m), 3.01-2.98 (m), 2.85-2.78 (m), 2.67-2.64 (d), 1.85 (s), 1.70-1.68 (m), 0.87 (s). Mass spectrum: 724.3 (M+H)$^+$.

Compound 27

Compound 27 was prepared in a manner similar to compound 25 except compound 9C15 was used instead of compound 9C13. LC-MS shows: 742.4 (M+H)$^+$. $^1$H NMR (300 MHz, CD$_3$OD): δ 8.78 (s, 1H), 8.50 (m, 1H), 8.08 (m, 1H), 7.98 (m, 1H), 7.55 (m, 3H), 7.40 (m, 2H), 7.28 (m, 1H), 7.05 (m, 1H), 5.58 (d, 1H), 4.96 (m, 1H), 4.31 (m, 1H), 3.96-3.52 (m, 8H), 3.56-2.92 (m, 3H), 2.79 (m, 2H), 1.66 (m, 2H), 0.92 (s, 9H).

Compound 28

Compound 28 was prepared in a manner similar to compound 25 except compound 9C16 was used instead of compound 9C13. LC-MS shows: 726.3 (M+H)$^+$. $^1$H NMR (300 MHz, CD$_3$OD): δ 8.79 (s, 1H), 8.50 (d, 1H), 8.06 (d, 1H), 7.50 (m, 3H), 7.40 (m, 3H), 7.17 (m, 2H), 5.58 (d, 1H), 4.97 (m, 1H), 4.36 (m, 1H), 3.97-3.50 (m, 8H), 3.56 (s, 3H), 3.09-2.82 (m, 3H), 2.74 (m, 2H), 1.63 (m, 2H), 0.92 (s, 9H).

Compound 29

Compound 29 was prepared in a manner similar to compound 25 except compound 9C17 was used instead of compound 9C13 LC-MS shows: 715.4 (M+H)$^+$. $^1$H NMR (300 MHz, CD$_3$OD): δ 8.79 (s, 1H), 8.52 (d, 1H), 8.06 (d, 1H), 7.72-7.49 (m, 6H), 7.40 (m, 2H), 5.58 (d, 1H), 4.97 (m, 1H), 4.36 (m, 1H), 3.97-3.50 (m, 8H), 3.56 (s, 3H), 3.09-2.82 (m, 3H), 2.78 (m, 2H), 1.60 (m, 2H), 0.92 (s, 9H).

Compound 30

Compound 30 was prepared in a manner similar to compound 25 except compound 9C18 was used instead of compound 9C13. LC-MS shows: 726.3 (M+H)$^+$. $^1$H NMR (300 MHz, CD$_3$OD): δ 8.79 (s, 1H), 8.52 (d, 1H), 8.06 (d, 1H), 7.74

(m, 1H), 7.57 (m, 3H), 7.40 (m, 2H), 7.0 (m, 2H), 6.82 (t, 1H), 6.62 (d, 1H), 5.58 (d, 1H), 4.97 (m, 1H), 4.36 (m, 1H), 3.97-3.50 (m, 8H), 3.56 (s, 3H), 3.09-2.82 (m, 3H), 2.78 (m, 2H), 1.60 (m, 2H), 0.92 (s, 9H).

Compound 31

Compound 31 was prepared in a manner similar to compound 25 except compound 9C19 was used instead of compound 9C13. LC-MS shows: 758.3 (M+H)$^+$. $^1$H NMR (300 MHz, CD$_3$OD): δ 9.06 (s, 1H), 8.76 (m, 2H), 8.04 (m, 1H), 7.96 (m, 1H), 7.76 (m, 1H), 7.67 (m, 3H), 7.60 (m, 1H), 7.50 (m, 2H), 7.42 (m, 1H), 5.58 (d, 1H), 4.99 (m, 1H), 4.38 (m, 1H), 4.16 (m, 2H), 3.90 (m, 2H), 3.76 (m, 2H), 3.69 (m, 2H), 3.56 (s, 3H), 30.3 (m, 1H), 2.92 (m, 2H), 2.83 (m, 2H), 1.70 (m, 2H), 0.92 (s, 9H).

Compound 32

Compound 32 was prepared in a manner similar to compound 25 except compound 9C20 was used instead of compound 9C13. LC-MS shows: 758.3 (M+H)$^+$. $^1$H NMR (300 MHz, CD$_3$OD): δ 9.06 (s, 1H), 8.72 (m, 1H), 8.52 (m, 1H), 8.00 (m, 1H), 7.86 (m, 2H), 7.64 (m, 3H), 7.58 (m, 1H), 7.50 (m, 3H), 5.58 (d, 1H), 4.96 (m, 1H), 4.38 (m, 1H), 4.16-3.49 (m, 8H), 3.56 (s, 3H), 3.09-2.82 (m, 5H), 1.60 (m, 2H), 0.92 (s, 9H).

Compound 33

Compound 33 was prepared in a manner similar to compound 25 except compound 9C21 was used instead of compound 9C13. LC-MS shows: 742.3 (M+H)$^+$. $^1$H NMR (300 MHz, CD$_3$OD): δ 9.06 (s, 1H), 8.72 (m, 2H), 8.04 (m, 1H), 7.76 (m, 1H), 7.68 (m, 2H), 7.51 (m, 2H), 7.27 (m, 1H), 7.19 (m, 1H), 7.09 (m, 1H), 5.58 (d, 1H), 4.96 (m, 1H), 4.41 (m, 1H), 3.96-3.52 (m, 8H), 3.56 (s, 3H), 3.09-2.92 (m, 3H), 2.81 (m, 2H), 1.62 (m, 2H), 0.92 (s, 9H).

Compound 34

Compound 34 was prepared in a manner similar to compound 25 except compound 9C22 was used instead of compound 9C13. LC-MS shows: 742.3 (M+H)$^+$. $^1$H NMR (300 MHz, CD$_3$OD): δ 9.06 (s, 1H), 8.72 (m, 3H), 8.02 (m, 1H), 7.70 (m, 3H), 7.51 (m, 3H), 7.37 (m, 1H), 7.18 (m, 1H), 5.58 (d, 1H), 4.96 (m, 1H), 4.41 (m, 1H), 3.96-3.52 (m, 8H), 3.56 (s, 3H), 3.09-2.92 (m, 3H), 2.79 (m, 2H), 1.60 (m, 2H), 0.92 (s, 9H).

Compound 35

Compound 35 was prepared in a manner similar to compound 25 except compound 9C23 was used instead of compound 9C13. LC-MS shows: 742.4 (M+H)$^+$. $^1$H NMR (300 MHz, CD$_3$OD): δ 8.78 (s, 1H), 8.50 (m, 1H), 8.08 (m, 1H), 7.98 (m, 1H), 7.55 (m, 3H), 7.40 (m, 2H), 7.28 (m, 1H), 7.05 (m, 1H), 5.58 (d, 1H), 4.96 (m, 1H), 4.31 (m, 1H), 3.96-3.52 (m, 8H), 3.56-2.92 (m, 3H), 2.79 (m, 2H), 1.66 (m, 2H), 0.92 (s, 9H).

Compound 36

A solution of compound 9C24 (28 mg, 0.043 mmol) in 20% TFA/CH$_2$Cl$_2$ (2 mL) was stirred for 1 h and concentrated. The mixture was partitioned with saturated NaHCO$_3$ solution and EtOAc, extracted with EtOAc (1×). The organic layer was dried over Na$_2$SO$_4$ and concentrated. A solution of N-(methoxycarbonyl)-L-tert-leucine (21 mg, 0.11 mmol) and TPTU (33 mg, 0.11 mmol) in DMF (1 mL) was stirred for 10 min at room temperature. The above amine and diisopropylethylamine (38 µL, 0.22 mmol) in DMF (1 mL) was added to the reaction mixture dropwise and stirred for 18 h at room temperature. The reaction mixture was partitioned with saturated NaHCO$_3$ solution and EtOAc, extracted with EtOAc (1×) washed with water and dried over Na$_2$SO$_4$. Concentrated and purified (prep TLC, 5% MeOH/CH$_2$Cl$_2$) to give a desired compound (17 mg, 0.023 mmol, 53%). $^1$H NMR (300 MHz, CDCl$_3$): δ 8.79 (s), 8.57-8.56 (d), 7.84-7.81 (d), 7.47-7.44 (d), 7.37-7.31 (m), 6.89-6.77 (m), 6.39-6.36 (d), 5.99 (s), 5.65-5.64 (d), 5.27-5.24 (d), 5.07-5.05 (m), 4.19-4.11 (m), 3.96-3.89 (m), 3.78-3.55 (m), 3.01-2.98 (m), 2.86-2.79 (m), 2.67-2.63 (d), 1.86 (s), 1.72 (m), 1.28-1.23 (m), 0.91 (s). Mass spectrum: 726.3 (M+H)$^+$.

Compound 37

Compound 37 was prepared in a manner similar to compound 36 except compound 9C25 was used instead of compound 9C24. $^1$H NMR (300 MHz, CDCl$_3$): δ 8.80 (s), 8.57-8.56 (d), 7.85-7.82 (d), 7.47-7.45 (d), 7.35-7.33 (m), 7.26-7.24 (m), 6.39-6.36 (d), 6.02 (s), 5.64-5.63 (d), 5.27-5.24 (d), 5.04-5.00 (m), 4.23-4.13 (m), 4.08-4.02 (m), 3.93-3.49 (m), 3.01-2.81 (m), 2.17 (s), 1.83 (s), 1.72-1.70 (m), 1.31-1.26 (m), 0.90 (s). Mass spectrum: 724.3 (M+H)$^+$.

Compound 38

Compound 38 was prepared in a manner similar to compound 36 except compound 9C26 was used instead of compound 9C24. $^1$H NMR (300 MHz, CDCl$_3$): δ 8.81 (s), 8.57-8.56 (d), 7.85-7.83 (d), 7.48-7.46 (d), 7.38-7.35 (m), 7.11 (s), 7.02-6.99 (m), 6.31 (d), 5.87 (s), 5.66 (d), 5.22-5.20 (d), 5.09-5.06 (m), 4.20-4.17 (m), 3.99-3.89 (m), 3.82-3.79 (m), 3.70-3.63 (m), 3.01-2.98 (m), 2.84-2.81 (m), 2.71-2.68 (d), 1.72-1.66 (m), 1.32-1.26 (m), 0.91 (s). Mass spectrum: 726.3 (M+H)$^+$.

Compound 39

Compound 39 was prepared in a manner similar to compound 36 except compound 9C27 was used instead of compound 9C24. $^1$H NMR (300 MHz, CDCl$_3$): δ 8.79 (s), 8.57-8.56 (d), 7.85-7.82 (d), 7.47-7.45 (d), 7.37-7.32 (m), 7.10-7.05 (m), 6.43-6.40 (d), 6.06 (s), 5.65-5.64 (d), 5.27-5.24 (d), 5.07-5.05 (m), 4.23-4.13 (m), 4.08-4.02 (m), 3.93-3.49 (m), 3.01-2.81 (m), 2.17 (s), 1.83 (s), 1.72-1.70 (m), 1.32-1.26 (m), 0.91 (s). Mass spectrum: 742.3 (M+H)$^+$.

Compound 40

Compound 40 was prepared in a manner similar to compound 36 except compound 9C28 was used instead of compound 9C24. $^1$H NMR (300 MHz, CDCl$_3$): δ 8.80 (s), 8.58-8.56 (d), 7.85-7.82 (d), 7.48-7.45 (d), 7.37-7.27 (m), 6.31 (d), 5.91 (s), 5.65-5.64 (d), 5.24-5.21 (d), 5.12-5.05 (m), 4.17-4.11 (m), 3.97-3.90 (m), 3.79-3.49 (m), 3.00-2.98 (m), 2.80-2.76 (m), 2.62-2.58 (m), 2.18 (s), 1.82 (s), 1.67 (m), 1.27-1.25 (m), 0.86 (s). Mass spectrum: 724.4 (M+H)$^+$.

Compound 41

Compound 41 was prepared in a manner similar to compound 36 except compound 9C29 was used instead of compound 9C24. $^1$H NMR (300 MHz, CDCl$_3$): δ 8.77 (s), 8.54 (s), 7.82-7.80 (d), 7.45-7.43 (d), 7.35-7.23 (m), 7.09-7.03 (m), 6.99-6.93 (m), 6.50-6.47 (d), 6.47-6.35 (s), 5.63-5.61 (d), 5.35-5.32 (d), 5.11-5.04 (m), 4.35 (s), 4.19-4.11 (m), 3.96-3.54 (m), 3.00-2.95 (m), 2.87-2.78 (m), 2.69-2.66 (d), 1.68-1.66 (d), 0.86 (s). Mass spectrum: 708.4 (M+H)$^+$.

Scheme 10
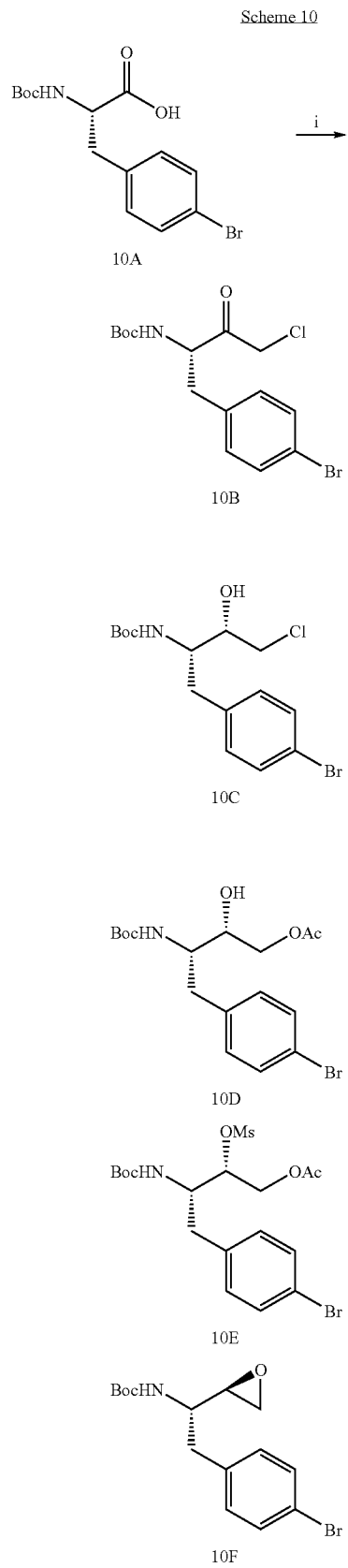
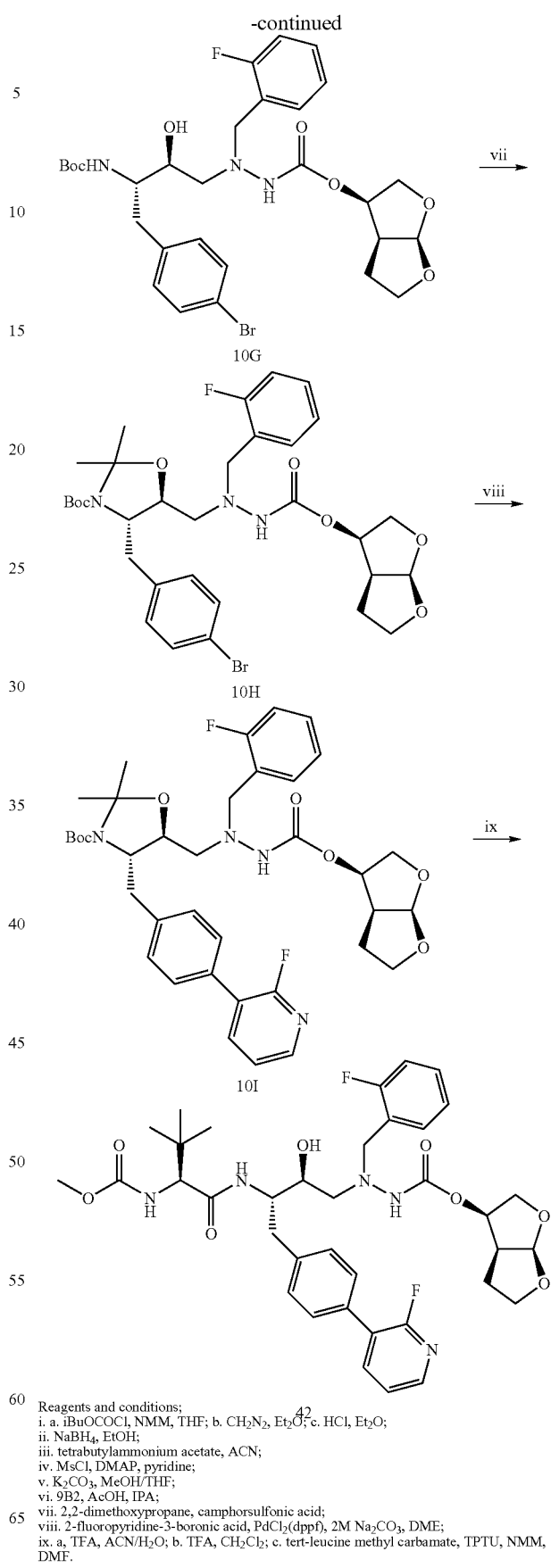
Reagents and conditions;
i. a. iBuOCOCl, NMM, THF; b. CH2N2, Et2O; c. HCl, Et2O;
ii. NaBH4, EtOH;
iii. tetrabutylammonium acetate, ACN;
iv. MsCl, DMAP, pyridine;
v. K2CO3, MeOH/THF;
vi. 9B2, AcOH, IPA;
vii. 2,2-dimethoxypropane, camphorsulfonic acid;
viii. 2-fluoropyridine-3-boronic acid, PdCl2(dppf), 2M Na2CO3, DME;
ix. a, TFA, ACN/H2O; b. TFA, CH2Cl2; c. tert-leucine methyl carbamate, TPTU, NMM, DMF.

Example 10

Compound 10B

A solution of commercially available Boc-4-bromo-L-phenylalanine (5.9 g, 17.14 mmol) and N-methylmorpholine (1.98 mL, 18.00 mmol) in THF (29 mL) at −78° C. was treated with isobutyl chloroformate (2.33 mL, 18.00 mmol). The reaction mixture was then stirred at room temperature for 1 h, filtered, washed with dry THF (15 mL) to give the crude mixed anhydride.

To a separate flask in a sodium chloride/ice bath were added 40% potassium hydroxide (16.5 mL), ether (69 mL) followed by 1-methyl-3-nitro-1-nitrosoguanidine portion-wise (5.29 g, 35.99 mmol). The yellow ether layer was added above mixed anhydride at −20° C. and reaction mixture was stirred at this temperature for 1 h. The reaction mixture was purged with nitrogen gas for 30 min, concentrated and partitioned between ether/ethyl acetate and water, washed with saturated $NaHCO_3$ solution, brine and dried ($MgSO_4$). Concentration gave a yellow residue that was dissolved in ether (30 mL) and cooled to −20° C. Concentrated hydrochloric acid (3.82 mL) was added and reaction mixture was stirred for 30 min at room temperature. The reaction mixture was quenched with saturated $NaHCO_3$ solution and extracted with ethyl acetate, washed with brine and dried ($MgSO_4$). Concentration and recrystallization from ethanol gave a white solid (2.75 g, 42%).

Compound 10C

To a solution of compound 10B (3.69 g, 9.81 mmol) in toluene (6 mL), ethanol (43 mL) and ethyl acetate (5 mL) at −10° C. was added sodium borohydride (0.185 g, 4.91 mmol) portion-wise. The reaction mixture was stirred at −10° C. for 1 h, and quenched with acetic acid (0.57 mL). The reaction mixture was heated to 60° C. over 40 min and then heated at reflux to give a cloudy solution. The reaction mixture was cooled to −10° C. over 2 h and stirred at −10° C. for 3 h, giving a white precipitate. Product was collected by filtration, washed with cold water and dried under high vacuum to give a white solid (1.70 g, 46%).

Compound 10D

A mixture of compound 10C (1.70 g, 4.49 mmol), tetrabutylammonium acetate (1.62 g, 5.39 mmol) in acetonitrile (22 mL) was heated at reflux for 18 h. The reaction mixture was cooled, concentrated and portioned between water (40 mL) and ethyl acetate (40 mL). The organic layer was separated, dried ($MgSO_4$) and concentrated. The resulting reside was dissolved in refluxing methanol (20 mL) and allowed to cool, giving a white precipitate. Product was collected by filtration and dried under high vacuum to give a white solid (0.5229 g, 28%).

Compound 10E

To a solution of compound 10D (0.7194 g, 1.72 mmol) in pyridine (3.0 mL) at 0° C. was added methanesulfonyl chloride (0.27 mL, 3.44 mmol). The reaction mixture was stirred at −20° C. for 48 h. DMAP (25 mg) and methanesulfonyl chloride (0.5 mL) was added and reaction continued for 24 h. The reaction mixture was diluted with ethyl acetate, washed with 1N HCl (3×60 mL), water and dried ($MgSO_4$). Concentration and treatment with hexane (60 mL) gave a white solid after standing for 2 h. Product was collected by filtration and dried under vacuum to give a white solid (0.7781 g, 94%).

Compound 10F

A mixture of compound 10E (0.7392 g, 1.54 mmol) and potassium carbonate (0.468 g, 3.89 mmol) in methanol (15 mL) and THF (15 mL) was stirred 24 h at room temperature. Ethyl acetate (15 mL) and water (15 mL) were added and organic layer was separated, dried ($MgSO_4$) and concentrated. Residue was purified by flash column chromatography (silica gel, 10 to 50% ethyl acetate/hexane) to give a white solid (0.4176 g, 79%). $^1$H NMR (300 MHz, CD3OD): • 7.37 (d, J=8.4 Hz, 2H), 7.13 (d, J=8.1 Hz, 2H), 3.72 (br s, 1H), 2.96 (br d, J=2.7 Hz, 1H), 2.9-2.6 (m, 3H), 2.45 (br s, 1H), 1.31 (s, 9H).

Compound 10G

A solution of compound 10F (0.099 g, 0.29 mmol), compound 9B2 (0.172 g, 0.580 mmol) acetic acid (10 μL, 0.174 mmol) in isopropanol (3.0 mL) was heated at 80° C. for 12 h. The reaction mixture was concentrated and purified by flash column chromatography (silica gel, 20 to 50% ethyl acetate/hexane) to give a white solid (0.110 g, 59%). Mass spectrum: 637.8 $(M+H)^+$.

Compound 10H

Compound 10H was prepared in a manner similar to compound 5C except compound 10G (0.110 g, 0.173 mmol) was used instead of compound 5B (0.0869 g, 74%). Mass spectrum: 700.2, 703.2 $(M+Na)^+$.

Compound 10I

Compound 10I was prepared in a manner similar to compound 5D except compound 10H (0.489 g, 0.072 mmol) was reacted with 2-fluoropyridine-3-boronic acid (0.025 g, 0.18 mmol) to give compound 10I (0.0423 g, 85%). Mass spectrum: 695.1 $(M+H)^+$.

Compound 42

Compound 42 was prepared in a manner similar to compound 8 except compound 10I (0.0423 g, 0.0609 mmol) was used instead of compound 5D to give compound 42 (0.0165 g, 37%). $^1$H NMR (300 MHz, $CD_3OD$): δ 8.11 (d, J=4.4 Hz, 1H), 8.00 (dd, J=7.8, 9.0 Hz, 1H), 7.5-7.2 (m, 7H), 7.15-6.90 (m, 2H), 5.52 (d, J=5.4 Hz, 1H), 4.95-4.89 (m, 1H), 4.3-4.2 (m, 1H), 4.0-3.20 (m, 11H), 3.0-2.65 (m, 5H), 1.80-1.6 (m, 2H), 0.85 (s, 9H). Mass spectrum: 726.3 $(M+H)^+$.

Example 11

Scheme 11

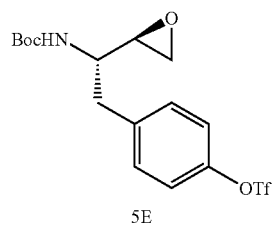

5E

+

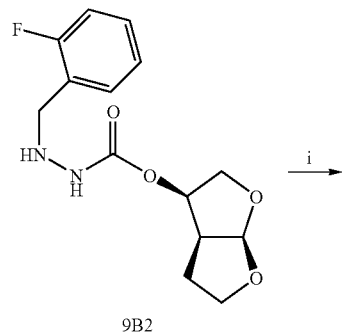

9B2

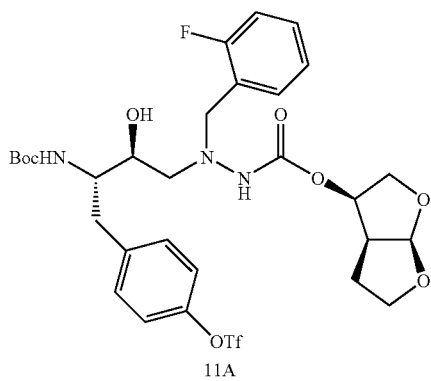

11A

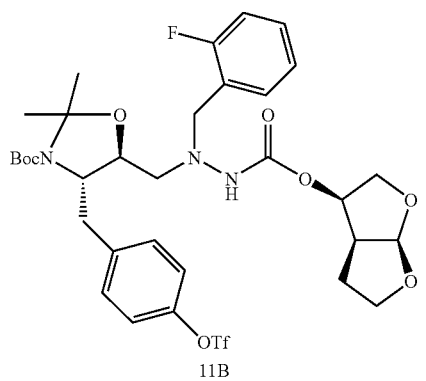

11B

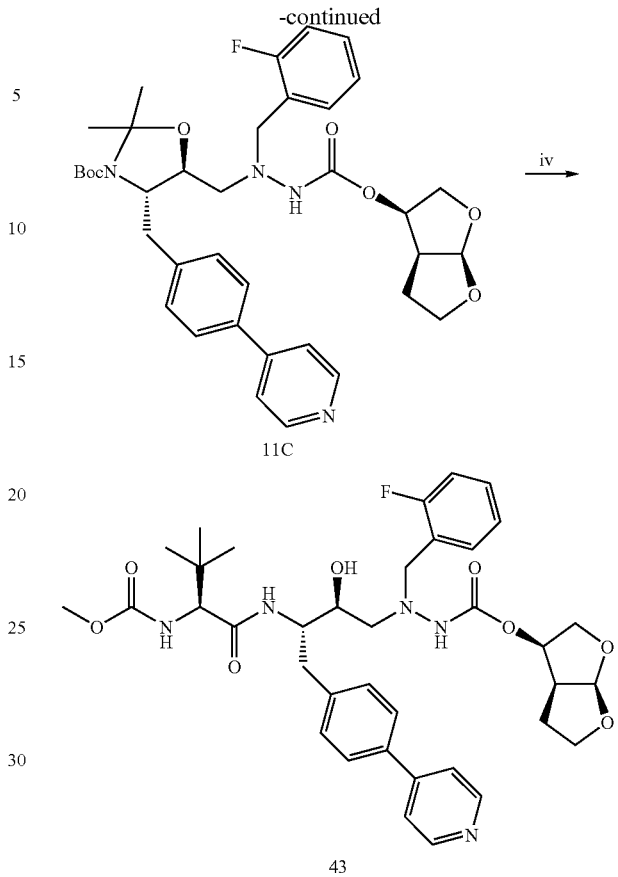

11C

43

Reagents and conditions:
i. AcOH, IPA;
ii. 2,2-dimethoxypropane, camphorsulfonic acid;
iii. 4-pyridine boronic acid, PdCl$_2$(dpf), 2M Na$_2$CO$_3$, DME;
iv. a. TFA, ACN/H$_2$O; b. TFA, CH$_2$Cl$_2$; c. tert-leucine methyl carbamate, TPTU, NMM, DMF.

Compound 11A

Compound 11A was prepared in a manner similar to compound 5B except compound 9B2 (g, mmol) was used instead of compound 5A to give compound 11A (g, %). Mass spectrum: (M+H)$^+$.

Compound 11B

Compound 11B was prepared in a manner similar to compound 5C except compound 11A (g, mmol) was used instead of compound 5B to give compound 11B (g, %). Mass spectrum: (M+H)$^+$.

Compound 11C

Compound 11C was prepared in a manner similar to compound 5D except compound 11B (0.0792 g, 0.106 mmol) was reacted with 4-pyridine boronic acid (0.0255 g, 0.208 mmol) to give compound 11C (0.0609 g, 85%). Mass spectrum: 677.2 (M+H)$^+$.

Compound 43

Compound 43 was prepared in a manner similar to compound 8 except compound 11C (0.0584 g, 0.0863 mmol) was used instead of compound 5D give compound 43 (0.0281 g, 46%). ¹H NMR (300 MHz, CD₃OD): δ 8.53 (br s, 2H), 7.67-6.9 (m, 9H), 6.60 (d, J=9.0 Hz, 1H), 5.52 (d, J=5.1 Hz, 1H), 4.95-4.89 (m, 1H), 4.3-4.2 (m, 1H), 4.0-3.20 (m, 11H), 3.0-2.65 (m, 5H), 1.80-1.6 (m, 2H), 0.85 (s, 9H). Mass spectrum: 708.4 (M+H)⁺.

Example 12

Scheme 12

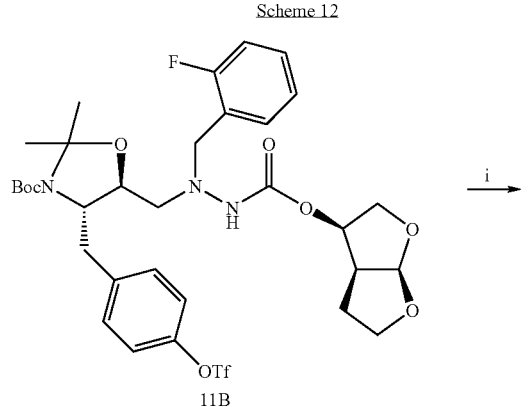

11B

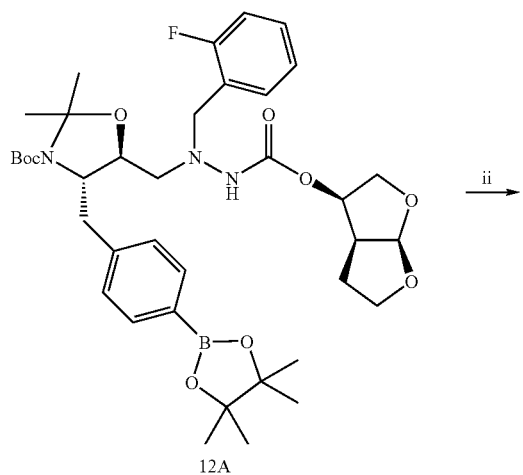

12A

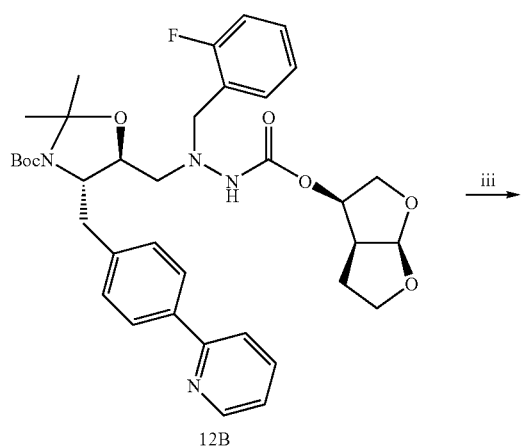

12B

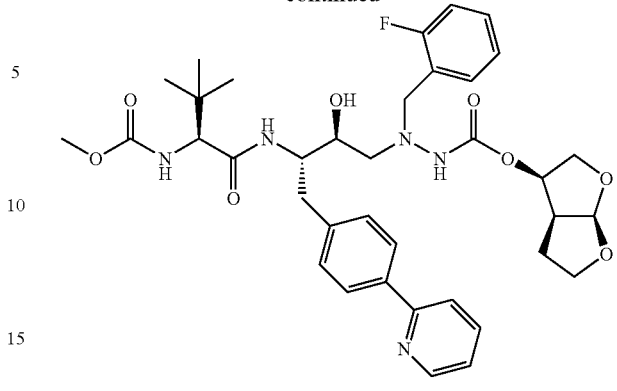

44

Reagents and conditions:
i. 4,4,5,5-tetramethyl-1,3,2-dioxaborolane, PdCl₂(dppf), triethylamine, dioxane;
ii. 2-bromopyridine, PdCl₂(dppf), 2M Na₂CO₃, DME;
iii. a. TFA, ACN/H₂O; b. TFA, CH₂Cl₂; c. tert-leucine methyl carbamate, TPTU, NMM, DMF.

Compound 12A

Compound 11B (0.1226 g, 0.164 mmol) was dissolved in freshly distilled dioxane (3 mL) and to this solution was added PdCl₂(dppf) (0.008 g, 0.0098 mmol), triethylamine (0.137 mL, 0.984 mmol) and 4,4,5,5-tetramethyl-1,3,2-dioxaborolane (0.14 mL, 0.984 mmol). The reaction mixture was stirred at reflux for 6.5 h, cooled and diluted with ethyl acetate. Organic layer was washed with saturated NaHCO₃ solution/brine, dried (MgSO₄), and concentrated. The resulting residue was purified flash column chromatography (silica gel, 10 to 50% ethyl acetate) to give a colorless film (0.050 g, 42%). Mass spectrum: 726.2 (M+H)⁺.

Compound 12B

A mixture of compound 12A (0.050 g, 0.0685 mmol), 2-bromopyridine (13 μL, 0.137 mmol) and PdCl₂(dppf) (0.0056 g, 0.00685 mmol) in 2M Na₂CO₃ (0.14 mL, 0.274 mmol) and dimethoxyethane (0.5 mL) was stirred at 90° C. for 6 h, cooled and diluted with ethyl acetate. Organic layer was washed with saturated NaHCO₃ solution/brine, dried (MgSO₄), and concentrated. The resulting residue was purified flash column chromatography (silica gel, 60 to 100% ethyl acetate) to give a foam (0.032 g, 69%). Mass spectrum: 677.3 (M+H)⁺.

Compound 44

Compound 44 was prepared in a manner similar to compound 8 except compound 12B (0.032 g, 0.0476 mmol) was used instead of compound 5D give compound 44 (0.0281 g, 46%). ¹H NMR (300 MHz, CD₃OD): δ 8.53 (d, J=4.8 Hz, 1H), 7.8-7.7 (m, 4H), 7.5-6.9 (m, 7H), 5.49 (d, J=5.4 Hz, 1H), 4.95-4.89 (m, 1H), 4.25-4.15 (m, 1H), 4.0-3.20 (m, 11H), 3.0-2.65 (m, 5H), 1.70-1.5 (m, 2H), 0.86 (s, 9H). Mass spectrum: 708.4 (M+H)⁺.

Example 13

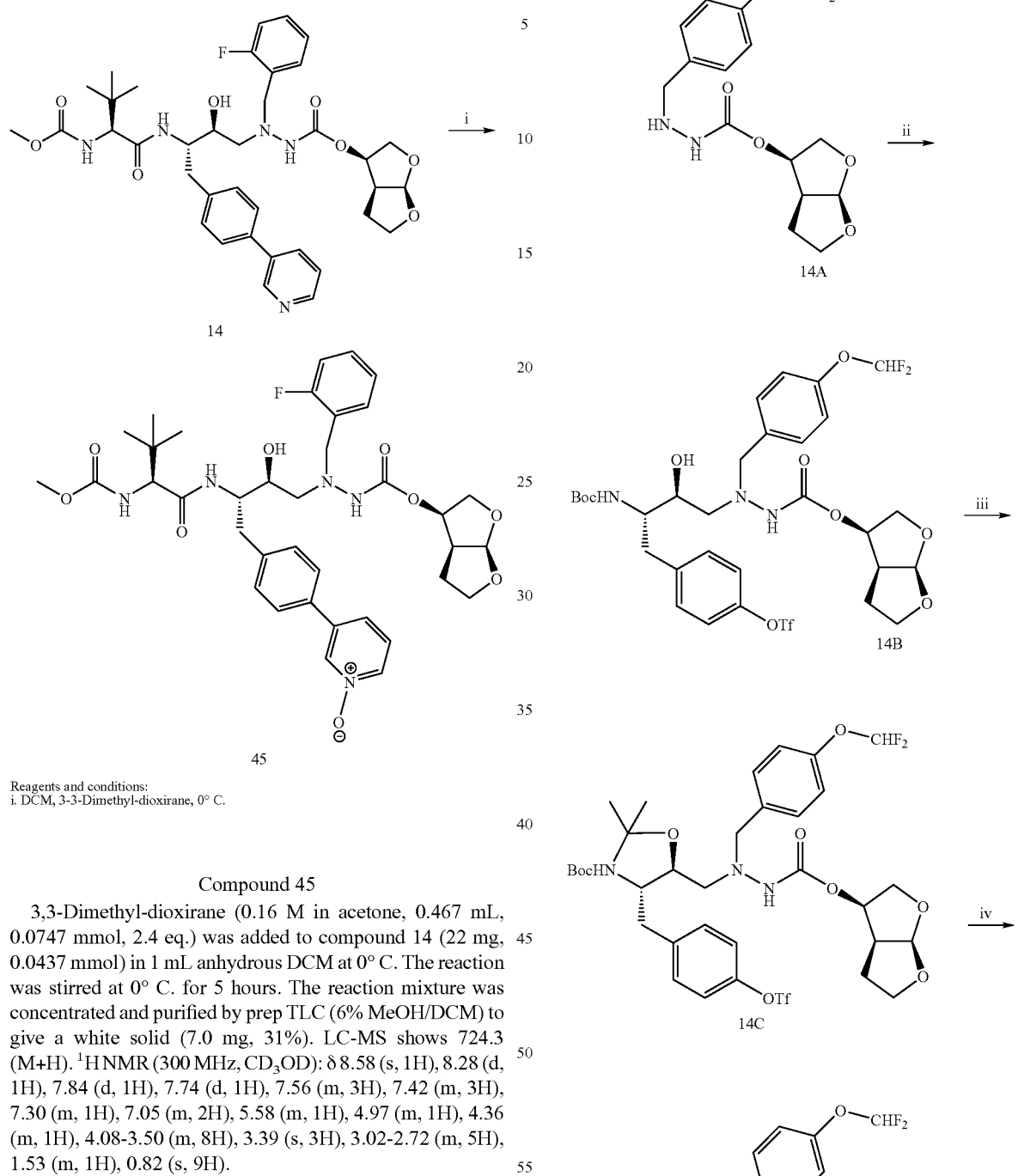

Reagents and conditions:
i. DCM, 3-3-Dimethyl-dioxirane, 0° C.

Compound 45

3,3-Dimethyl-dioxirane (0.16 M in acetone, 0.467 mL, 0.0747 mmol, 2.4 eq.) was added to compound 14 (22 mg, 0.0437 mmol) in 1 mL anhydrous DCM at 0° C. The reaction was stirred at 0° C. for 5 hours. The reaction mixture was concentrated and purified by prep TLC (6% MeOH/DCM) to give a white solid (7.0 mg, 31%). LC-MS shows 724.3 (M+H). $^1$H NMR (300 MHz, CD$_3$OD): δ 8.58 (s, 1H), 8.28 (d, 1H), 7.84 (d, 1H), 7.74 (d, 1H), 7.56 (m, 3H), 7.42 (m, 3H), 7.30 (m, 1H), 7.05 (m, 2H), 5.58 (m, 1H), 4.97 (m, 1H), 4.36 (m, 1H), 4.08-3.50 (m, 8H), 3.39 (s, 3H), 3.02-2.72 (m, 5H), 1.53 (m, 1H), 0.82 (s, 9H).

Example 14

Scheme 14

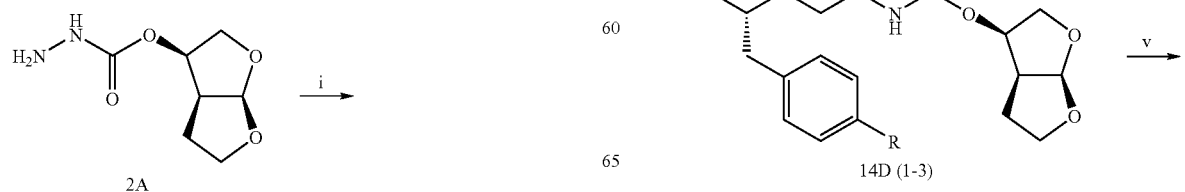

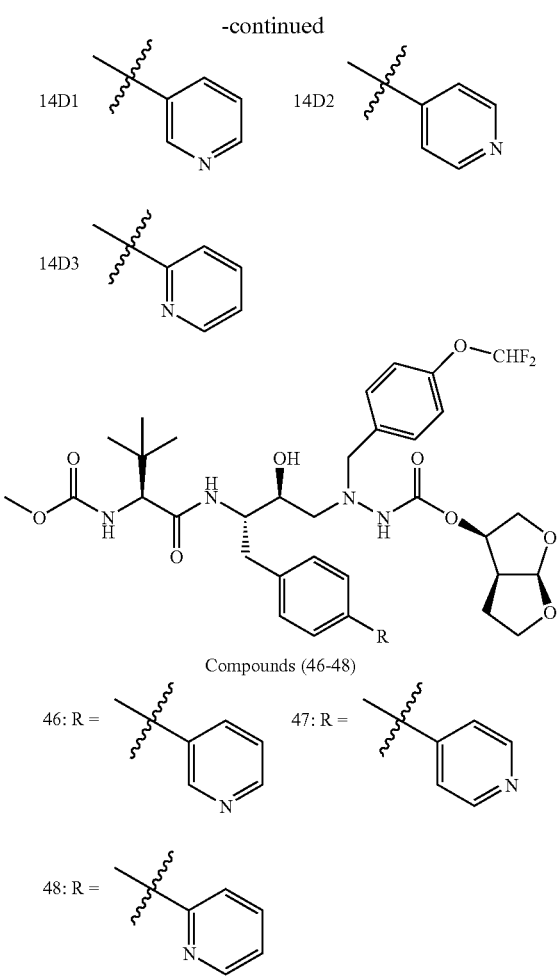

Compounds (46-48)

46: R = 3-pyridyl
47: R = 4-pyridyl
48: R = 2-pyridyl

Reagents and conditions:
i. a. 4-difluoromethoxy-benzaldehyde, isopropanol, 80° C.; b. Pd/C, H₂, EtOH;
ii. 5E, AcOH, isopropanol;
iii. camphorsulfonic acid, dimethoxypropane, acetone;
iv. pyridineboronic acid, PdCl₂(dppf), Na₂CO₃, DME;
v. a. TFA, CH₂Cl₂; b. N'(methoxycarbonal)-L-tert-leucine, TPTU, NMM, DMF.

Compound 14A

Compound 2A (296 mg, 1.58 mmol) in isopropanol (9 mL) was treated with commercially available 4-difluoromethoxy-benzaldehyde (263 µL, 1.99 mmol) at 80° C. for 4.5 h. The reaction mixture was cooled to room temperature and purified (silica gel, 30 to 100% EtOAc/Hex) to give a white foam (491 mg, 1.43 mmol, 91%). To a solution of the above foam in ethanol (12 mL) were added 10% palladium/carbon (49 mg). The reaction mixture was stirred under a hydrogen atmosphere at for 1 h. then filtered through a pad of Celite. Concentrated and purified (silica gel, 30 to 100% EtOAc/Hex) to give a clear thick oil (376 mg, 1.09 mmol, 76%). Mass spectrum: 344.9 (M+H)⁺.

Compound 14B

To a solution of compound 5E (424 mg, 1.03 mmol) in isopropanol (15 mL) were added compound 14A (323 mg, 0.937 mmol) and AcOH (45 mg). After stirring for 3 days at 80° C., the reaction mixture was concentrated and purified (silica gel, 10 to 100% EtOAc/Hex) to give a desired compound (480 mg, 0.636 mmol, 68%). Mass spectrum: 756.2 (M+H)⁺.

Compound 14C

A solution of compound 14B (480 mg, 0.636 mmol), camphorsulfonic acid (155 mg, 0.667 mmol) and dimethoxypropane (780 mL, 6.36 mmol) in acetone (8 mL) was heated at reflux for 4.5 h. The reaction mixture was cooled to room temperature, partitioned with saturated NaHCO₃ solution and EtOAc, extracted with EtOAc (1×), washed with H₂O (1×) and dried over Na₂SO₄. Concentrated and purified (silica gel, 0 to 100% EtOAc/Hex) to give a white foam (354 mg, 0.445 mmol, 70%). Mass spectrum: 796.2 (M+H)⁺.

Compound 14D1

To a Smith process vial were added compound 14C (70 mg, 0.088 mmol), 3-pyridineboronic acid (27 mg, 0.22 mmol), PdCl₂(dppf) (10 mg, 0.009 mmol), 2M Na₂CO₃ (0.22 mL) and DME (1.5 mL). Vial was sealed and heated at 120° C. for 25 min via microwave irradiation. The reaction mixture was diluted with EtOAc and washed with saturated NaHCO₃ solution, H₂O and dried over Na₂SO₄. Concentrated and purified (silica gel, 20 to 90% EtOAc/Hex) to give a white solid (49 mg, 0.067 mmol, 77%). Mass spectrum: 725.3 (M+H)⁺.

Compound 14D2

To a Smith process vial were added compound 14C (53 mg, 0.064 mmol), 4-pyridineboronic acid (20 mg, 0.16 mmol), PdCl₂(dppf) (7.5 mg, 0.009 mmol), 2M Na₂CO₃ (0.16 mL) and DME (1.0 mL). Vial was sealed and heated at 120° C. for 25 min via microwave irradiation. The reaction mixture was diluted with EtOAc and washed with saturated NaHCO₃ solution, H₂O and dried over Na₂SO₄. Concentrated and purified (silica gel, 20 to 90% EtOAc/Hex) to give a white solid (42 mg, 0.058 mmol, 66%). Mass spectrum: 725.3 (M+H)⁺.

Compound 14D3

To a Smith process vial were added compound 14C (70 mg, 0.064 mmol), 2-Pyridineboronic acid N-phenyldiethanolamine ester (89 mg, 0.22 mmol), PdCl₂(dppf) (8.6 mg, 0.009 mmol), 2M Na₂CO₃ (0.22 mL) and DME (1.5 mL). Vial was sealed and heated at 120° C. for 25 min via microwave irradiation. The reaction mixture was diluted with EtOAc and washed with saturated NaHCO₃ solution, H₂O and dried over Na₂SO₄. Concentrated and purified (silica gel, 20 to 90% EtOAc/Hex) to give a clear film (10 mg, 0.014 mmol, 16%). Mass spectrum: 725.2 (M+H)⁺.

Compound 46

A solution of compound 14D1 (49 mg, 0.067 mmol) in 2% TFA/CH₂Cl₂ (2 mL) was stirred for overnight and 400 µL of TFA was added then stirred for 40 min. The mixture was partitioned with saturated NaHCO₃ solution and EtOAc, extracted with EtOAc (1×). The organic layer was dried over Na₂SO₄ and concentrated. A solution of N-(methoxycarbonyl)-L-tert-leucine (19 mg, 0.10 mmol) and TPTU (30 mg, 0.10 mmol) in DMF (0.5 mL) was stirred for 10 min at room temperature. The above amine and diisopropylethylamine (26 mg, 0.20 mmol) in DMF (0.5 mL) was added to the reaction mixture dropwise and stirred for 2 h at room temperature. The reaction mixture was partitioned with saturated NaHCO₃ solution and EtOAc, extracted with EtOAc (2×) and dried over Na₂SO₄. Concentrated and purified (silica gel, 0 to 100% EtOAc/Hex and 0 to 5% MeOH/CH₂Cl₂ and prepTLC with 5% MeOH/CH₂Cl₂) to give a desired compound (19 mg, 0.025 mmol, 37%). ¹H NMR (300 MHz, CDCl₃): δ 8.79 (s), 8.58-8.56 (d), 7.85-7.82 (d), 7.49-7.44 (m), 7.37-7.30 (m), 7.09-7.06 (m), 6.76 (s), 6.51 (s), 6.39-6.26 (m), 6.02 (s), 5.59 (s), 5.65-5.64 (m), 5.43-5.40 (d), 5.24-5.21 (d), 5.11-5.04 (m), 4.41 (s), 4.28-3.08 (m), 3.93-3.57 (m), 3.06-2.78 (m), 2.64-2.60 (d), 1.91 (s), 1.67-1.65 (m), 1.32-1.26 (m), 0.86-0.85 (d). Mass spectrum: 756.3 (M+H)⁺.

Compound 47

A solution of compound 14D2 (42 mg, 0.058 mmol) in 2% TFA/CH₂Cl₂ (2 mL) was stirred for overnight and 400 μL of TFA was added then stirred for 40 min. The mixture was partitioned with saturated NaHCO₃ solution and EtOAc, extracted with EtOAc (1×). The organic layer was dried over Na₂SO₄ and concentrated. A solution of N-(methoxycarbonyl)-L-tert-leucine (16 mg, 0.09 mmol) and TPTU (26 mg, 0.09 mmol) in DMF (0.5 mL) was stirred for 10 min at room temperature. The above amine and diisopropylethylamine (22 mg, 0.17 mmol) in DMF (0.5 mL) was added to the reaction mixture dropwise and stirred for 2 h at room temperature. The reaction mixture was partitioned with saturated NaHCO₃ solution and EtOAc, extracted with EtOAc (2×) and dried over Na₂SO₄. Concentrated and purified (prepTLC with 6% MeOH/CH₂Cl₂) to give a desired compound (20 mg, 0.026 mmol, 46%). ¹H NMR (300 MHz, CDCl₃): δ 8.62-8.60 (d), 7.55-7.50 (m), 7.47-7.45 (m), 7.38-7.30 (m), 7.09-7.06 (m), 6.76 (s), 6.51 (s), 6.39-6.26 (m), 6.02 (s), 5.59 (s), 5.65-5.64 (m), 5.43-5.40 (d), 5.24-5.21 (d), 5.11-5.04 (m), 4.41 (s), 4.28-3.08 (m), 3.93-3.57 (m), 3.06-2.78 (m), 2.64-2.60 (d), 1.91 (s), 1.67-1.65 (m), 1.32-1.26 (m), 0.86-0.85 (d). Mass spectrum: 756.4 (M+H)⁺.

Compound 48

A solution of compound 14D3 (10 mg, 0.014 mmol) in 2% TFA/CH₂Cl₂ (2 mL) was stirred for overnight and 400 μL of TFA was added then stirred for 40 min. The mixture was partitioned with saturated NaHCO₃ solution and EtOAc, extracted with EtOAc (1×). The organic layer was dried over Na₂SO₄ and concentrated. A solution of N-(methoxycarbonyl)-L-tert-leucine (4.1 mg, 0.02 mmol) and TPTU (6.4 mg, 0.02 mmol) in DMF (0.5 mL) was stirred for 10 min at room temperature. The above amine and diisopropylethylamine (5.6 mg, 0.04 mmol) in DMF (0.5 mL) was added to the reaction mixture dropwise and stirred for 2 h at room temperature. The reaction mixture was partitioned with saturated NaHCO₃ solution and EtOAc, extracted with EtOAc (2×) and dried over Na₂SO₄. Concentrated and purified (prepTLC with 6% MeOH/CH₂Cl₂) to give a desired compound (5.1 mg, 0.007 mmol, 47%). ¹H NMR (300 MHz, CDCl₃): 8.67-8.65 (d), 7.91-7.87 (m), 7.77-7.68 (m), 7.38-7.20 (m), 7.10-7.07 (m), 6.76 (s), 6.51 (s), 6.39-6.26 (m), 6.02 (s), 5.59 (s), 5.65-5.64 (m), 5.43-5.40 (d), 5.24-5.21 (d), 5.11-5.04 (m), 4.41 (s), 4.28-3.08 (m), 3.93-3.57 (m), 3.06-2.78 (m), 2.64-2.60 (d), 1.91 (s), 1.67-1.65 (m), 1.32-1.26 (m), 0.86-0.85 (d). Mass spectrum: 756.3 (M+H)⁺.

Example 15

Scheme 15

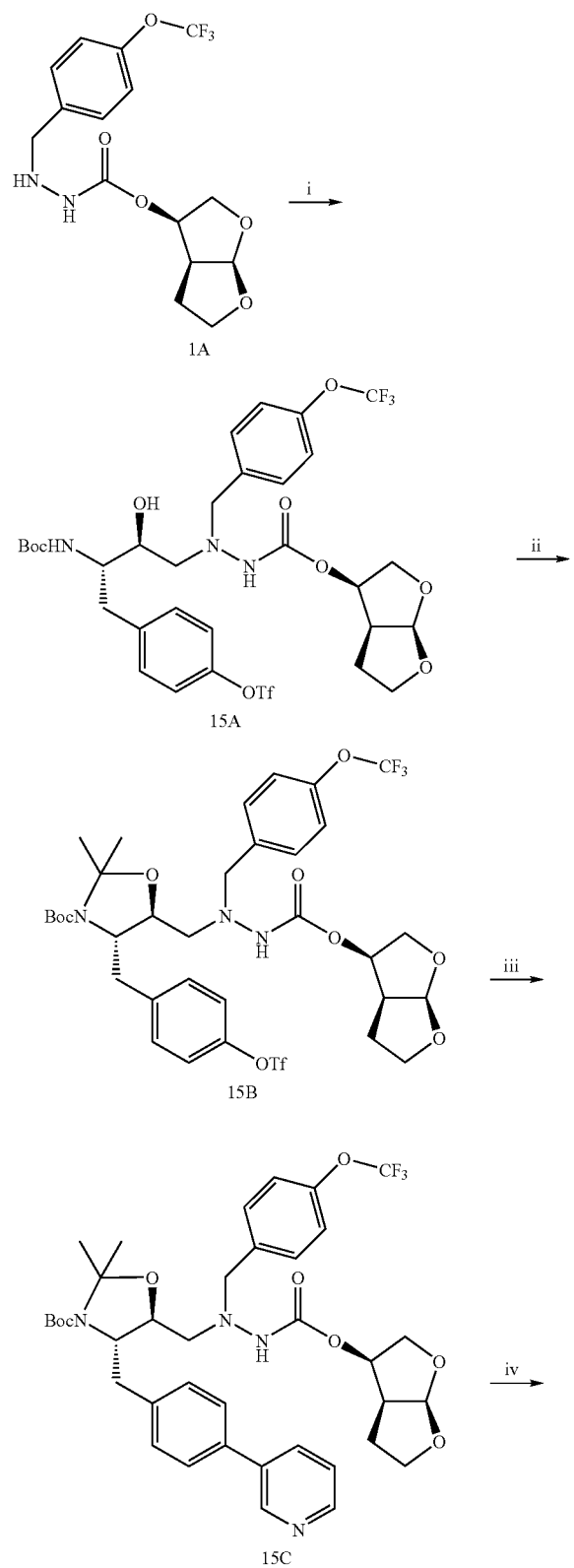

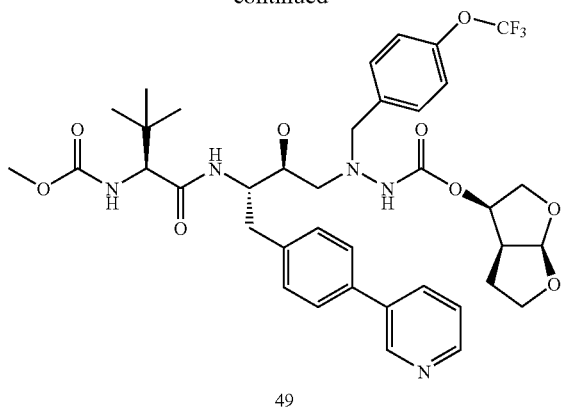

49

Reagents and conditions;
i. 5E, AcOH, isopropanol;
ii. camphorsulfonic acid, dimethoxypropane, acetone;
iii. 3-pyridineboronic acid, PdCl₂(dppf), Na₂CO₃, DME;
iv. a. TFA, CH₂Cl₂; b. N-(methoxycarbonyl)-L-tert-leucine, TPTU, NMM, DMF.

Compound 15A

To a solution of compound 5E (225 mg, 0.455 mmol) in isopropanol (4 mL) were added compound 1A (165 mg, 0.546 mmol) and AcOH (22 mg). After stirring for 3 days at 80° C., the reaction mixture was concentrated and purified (silica gel, 0 to 100% EtOAc/Hex) to give a white solid (249 mg, 0.322 mmol, 71%). Mass spectrum: 773.9 (M+H)$^+$.

Compound 15B

A solution of compound 15A (249 mg, 0.322 mmol), camphorsulfonic acid (82 mg, 0.354 mmol) and dimethoxypropane (395 mL, 3.22 mmol) in acetone (4 mL) was heated at reflux for 4.5 h. The reaction mixture was cooled to room temperature, partitioned with saturated NaHCO₃ solution and EtOAc, extracted with EtOAc (1×), washed with H₂O (1×) and dried over Na₂SO₄. Concentrated and purified (silica gel, 0 to 100% EtOAc/Hex) to give a clear thick oil (164 mg, 0.201 mmol, 63%). Mass spectrum: 814.3 (M+H)$^+$.

Compound 15C

To a Smith process vial were added compound 15B (62 mg, 0.076 mmol), 3-pyridineboronic acid (23 mg, 0.19 mmol), PdCl₂(dppf) (7.4 mg, 0.009 mmol), 2M Na₂CO₃ (0.19 mL) and DME (1.5 mL). Vial was sealed and heated at 120° C. for 25 min via microwave irradiation. The reaction mixture was diluted with EtOAc and washed with saturated NaHCO₃ solution, H₂O and dried over Na₂SO₄. Concentrated and purified (silica gel, 20 to 90% EtOAc/Hex) to give a clear thick oil (45 mg, 0.061 mmol, 80%). Mass spectrum: 743.2 (M+H)$^+$.

Compound 49

A solution of compound 15C (45 mg, 0.061 mmol) in 3% TFA/CH₂Cl₂ (2 mL) was stirred for overnight and 400 µL of TFA was added then stirred for 40 min. The mixture was partitioned with saturated NaHCO₃ solution and EtOAc, extracted with EtOAc (1×). The organic layer was dried over Na₂SO₄ and concentrated. A solution of N-(methoxycarbonyl)-L-tert-leucine (17 mg, 0.091 mmol) and TPTU (27 mg, 0.091 mmol) in DMF (0.5 mL) was stirred for 10 min at room temperature. The above amine and diisopropylethylamine (24 mg, 0.18 mmol) in DMF (0.5 mL) was added to the reaction mixture dropwise and stirred for 18 h at room temperature. The reaction mixture was partitioned with saturated NaHCO₃ solution and EtOAc, extracted with EtOAc (1×) washed with water and dried over Na₂SO₄. Concentrated and purified (6% MeOH/CH₂Cl₂) to give a desired compound (26 mg, 0.034 mmol, 55%). $^1$H NMR (300 MHz, CDCl₃): δ 8.78 (s), 8.57-8.55 (d), 7.84-7.81 (d), 7.47-7.44 (d), 7.37-7.31 (m), 7.18-7.15 (d), 6.39-6.36 (d), 6.12 (s), 5.64-5.62 (d), 5.27-5.24 (d), 5.11-5.04 (m), 4.29 (s), 4.22-4.14 (m), 3.96-3.89 (m), 3.78-3.55 (m), 3.01-2.98 (m), 2.86-2.79 (m), 2.67-2.63 (d), 1.96 (s), 1.67-1.65 (m), 1.31-1.26 (m), 0.85 (s). Mass spectrum: 774.3 (M+H)$^+$.

Biological Assays Used for the Characterization of HIV Protease Inhibitors HIV-1 Protease Enzyme Assay (Ki)

The assay is based on the fluorimetric detection of synthetic hexapeptide substrate cleavage by HIV-1 protease in a defined reaction buffer as initially described by M. V. Toth and G. R. Marshall, Int. J. Peptide Protein Res. 36, 544 (1990)

Substrate: (2-aminobenzoyl)Thr-Ile-Nle-(n-nitro)Phe-Gln-Arg

Substrate supplied by Bachem California, Inc. (Torrance, Calif.; Cat. no. H-2992)

Enzyme: recombinant HIV-1 protease expressed in *E. Coli*

Enzyme supplied by Bachem California, Inc. (Torrance, Calif.; Cat. no. H-9040)

Reaction buffer:
100 mM ammonium acetate, pH 5.3
1 M sodium chloride
1 mM ethylendiaminetetraacetic acid
1 mM dithiothreitol
10% dimethylsulfoxide Assay Protocol for the Determination of Inhibition Constant Ki:
1. Prepare series of solutions containing identical amount of the enzyme (1 to 2.5 nM) and a tested inhibitor at different concentrations in the reaction buffer
2. Transfer the solutions (190 µL each) into a white 96-well plate
3. Preincubate for 15 min at 37° C.
4. Solubilize the substrate in 100% dimethylsulfoxide at a concentration of 800 µM. Start the reaction by adding 10 µL of 800 µM substrate into each well (final substrate concentration of 40 µM)
5. Measure the real-time reaction kinetics at 37° C. by using Gemini 96-well plate fluorimeter (Molecular Devices, Sunnyvale, Calif.) at λ(Ex)=330 nm and λ(Em)=420 nm
6. Determine initial velocities of the reactions with different inhibitor concentrations and calculate Ki (in picomolar concentration units) value by using EnzFitter program (Biosoft, Cambridge, U.K.) according to an algorithm for tight-binding competitive inhibition described by Ermolieff J., Lin X., and Tang J., Biochemistry 36, 12364 (1997)

Anti-HIV-1 Cell Culture Assay (EC₅₀)

The assay is based on quantification of the HIV-1-associated cytopathic effect by a calorimetric detection of the viability of virus-infected cells in the presence or absence of tested inhibitors. The HIV-1-induced cell death is determined using a metabolic substrate 2,3-bis(2-methoxy-4-nitro-5-sulfophenyl)-2H-tetrazolium-5-carboxanilide (XTT) which is converted only by intact cells into a product with specific absorption characterisitics as described by Weislow O S, Kiser R, Fine D L, Bader J, Shoemaker R H and Boyd M R, J. Natl. Cancer Inst. 81, 577 (1989).

Assay Protocol for Determination of $EC_{50}$:
1. Maintain MT2 cells in RPMI-1640 medium supplemented with 5% fetal bovine serum and antibiotics.
2. Infect the cells with the wild-type HIV-1 strain IIIB (Advanced Biotechnologies, Columbia, Md.) for 3 hours at 37° C. using the virus inoculum corresponding to a multiplicity of infection equal to 0.01.
3. Prepare a set of solutions containing various concentrations of the tested inhibitor by making 5-fold serial dilutions in 96-well plate (100 μL/well). Distribute the infected cells into the 96-well plate (20,000 cells in 100 μL/well). Include samples with untreated infected and untreated mock-infected control cells.
4. Incubate the cells for 5 days at 37° C.
5. Prepare XTT solution (6 mL per assay plate) at a concentration of 2 mg/mL in a phosphate-buffered saline pH 7.4. Heat the solution in water-bath for 5 min at 55° C. Add 50 μL of N-methylphenazonium methasulfate (5 μg/mL) per 6 mL of XTT solution.
6. Remove 100 μL media from each well on the assay plate.
7. Add 100 μL of the XTT substrate solution per well and incubate at 37° C. for 45 to 60 min in a $CO_2$ incubator.
8. Add 20 μL of 2% Triton X-100 per well to inactivate the virus.
9. Read the absorbance at 450 nm with subtracting off the background absorbance at 650 nm.
10. Plot the percentage absorbance relative to untreated control and estimate the $EC_{50}$ value as drug concentration resulting in a 50% protection of the infected cells.

Cytotoxicity Cell Culture Assay ($CC_{50}$):

The assay is based on the evaluation of cytotoxic effect of tested compounds using a metabolic substrate 2,3-bis(2-methoxy-4-nitro-5-sulfophenyl)-2H-tetrazolium-5-carboxanilide (XTT) as described by Weislow O S, Kiser R, Fine D L, Bader J, Shoemaker R H and Boyd M R, J. Natl. Cancer Inst. 81, 577 (1989).

Assay Protocol for Determination of $CC_{50}$:
1. Maintain MT-2 cells in RPMI-1640 medium supplemented with 5% fetal bovine serum and antibiotics.
2. Prepare a set of solutions containing various concentrations of the tested inhibitor by making 5-fold serial dilutions in 96-well plate (100 μL/well). Distribute cells into the 96-well plate (20,000 cells in 100 μL/well). Include samples with untreated cells as a control.
3. Incubate the cells for 5 days at 37° C.
4. Prepare XTT solution (6 mL per assay plate) in dark at a concentration of 2 mg/mL in a phosphate-buffered saline pH 7.4. Heat the solution in a water-bath at 55° C. for 5 min. Add 50 μL of N-methylphenazonium methasulfate (5 μg/mL) per 6 mL of XTT solution.
5. Remove 100 μL media from each well on the assay plate and add 100 μL of the XTT substrate solution per well. Incubate at 37° C. for 45 to 60 min in a $CO_2$ incubator.
6. Add 20 μL of 2% Triton X-100 per well to stop the metabolic conversion of XTT.
7. Read the absorbance at 450 nm with subtracting off the background at 650 nm.

Plot the percentage absorbance relative to untreated control and estimate the CC50 value as drug concentration resulting in a 50% inhibition of the cell growth. Consider the absorbance being directly proportional to the cell growth.

Representative compounds of the present invention have $K_i$ values (pM) in the range of about 1-1300, or about 1-1000, about 1-500, about 1-200, or less than about 30.

What is claimed:
1. A compound of formula (I),

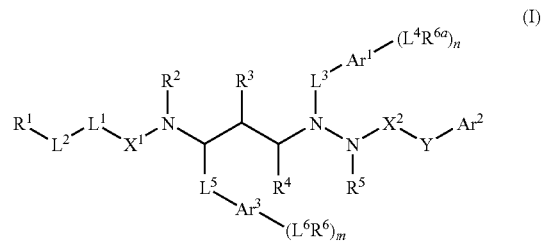

wherein, $X^1$ and $X^2$ are each independently —C(O)—;

Y is —O—;

$L^1$ is —O—, alkylene, substituted alkylene, alkenylene, substituted alkenylene, alkynylene, or substituted alkynylene;

$L^2$ is a covalent bond or —$NR^8$—;

with the proviso that when $L^1$ is alkylene and $L^2$ is a covalent bond, $R^1$ is not a substituted heterocyclyl selected from the group of heterocyclyls consisting of:

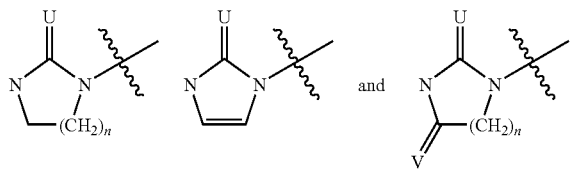

wherein U and V are independently O, S, or NH; n is 1 or 2;

$L^3$ and $L^5$ are each independently a covalent bond, alkylene or substituted alkylene;

$L^4$ and $L^6$ are each independently a bond, or —O—;

$Ar^1$ and $Ar^3$ are each independently aryl or substituted aryl;

$Ar^2$ is heterocyclyl or sybstituted heterocyclyl;

$R^1$ is cycloalkyl, substituted cycloalkyl, cycloalkenyl, substituted cycloalkenyl, heterocyclyl, substituted heterocyclyl, or —C(O)$OR^9$;

$R^2$, $R^4$ and $R^5$ are H;

$R^3$ is —OH;

$R^6$ and $R^{6a}$ are each independently H, halo, cyano, alkyl, substituted alkyl, haloalkyl, substituted haloalkyl, alkenyl, substituted alkenyl, alkynyl, substituted alkynyl, heterocyclyl, substituted heterocyclyl, aryl, substituted aryl, heteroaryl, or substituted heteroaryl;

$R^8$ is H, alkyl, or substituted alkyl;

$R^9$ is H, alkyl, substituted alkyl, alkenyl, substituted alkenyl, alkynyl, or substituted alkynyl;

m is 0 or 1;

n is 0, 1 or 2;

or a pharmaceutically acceptable salt, and/or ester thereof.

2. The compound of claim 1, wherein each $L^3$ and $L^5$ is independently methylene, ethylene, or propylene.

3. The compound of claim 1, wherein $Ar^1$ and $Ar^3$ are phenyl or naphthyl.

4. The compound of claim 1, wherein -L$^5$-Ar$^3$ is

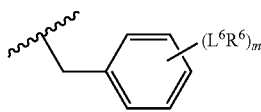

wherein,
L$^6$ is a covalent bond, or —O—;
R$^6$ is H, alkyl, substituted alkyl, alkenyl, substituted alkenyl, alkynyl, substituted alkynyl, alkoxy, substituted alkoxy, heterocyclyl, substituted heterocyclyl, aryl, substituted aryl, heteroaryl or substituted heteroaryl;
m is 0, or 1.

5. The compound of claim 4, wherein R$^6$ is phenyl or pyridine.

6. The compound of claim 4, wherein L$^6$ is —O—; R$^6$ is alkyl or substituted alkyl.

7. The compound of claim 1, wherein L$^3$ is alkylene; Ar$^1$ is aryl or substituted aryl.

8. The compound of claim 5, wherein R$^{6a}$ is

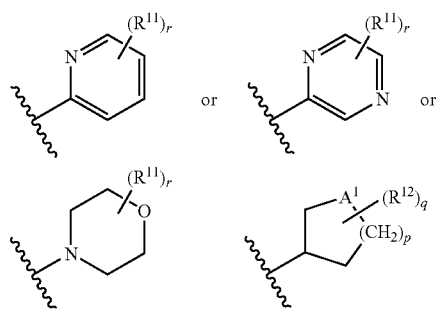

wherein A$^1$ is O, S, S(O), or S(O)$_2$;
R$^{12}$ is H, alkyl, substituted haloalkyl, substituted haloalkyl, hydroxyalkyl, substituted hydroxyalkyl, alkoxyalkyl or substituted alkoxyalkyl;
p is 1 or 2; and
q is 0, 1, 2, or 3.

9. The compound of 1, wherein Ar$^2$ is bicyclic-heterocyclyl having from 1 to 3 heteroatoms selected from O, S, and N.

10. The compound of claim 9, wherein Ar$^2$ is

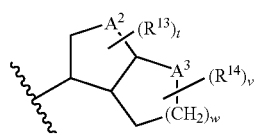

wherein,
A$^2$ and A$^3$ are each independently O or S;
R$^{13}$ and R$^{14}$ are each independently H, alkyl, substituted haloalkyl, substituted haloalkyl, hydroxyalkyl, substituted hydroxyalkyl, alkoxyalkyl or substituted alkoxyalkyl;
t is 1, 2, or 3;
v is 1, 2, 3, or 4; and
w is 1 or 2.

11. The compound of claim 1, wherein L$^1$ is substituted alkylene, L$^2$ is N(R$^8$) wherein R$^8$ is H or alkyl; R$^1$ is —C(O)OR$^9$ wherein R$^9$ is alkyl.

12. The compound of claim 11, wherein R$^1$-L$^2$-L$^1$- is

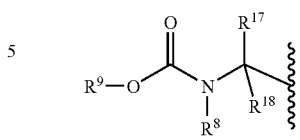

wherein R$^9$ is alkyl; R$^8$, R$^{17}$, and R$^{18}$ are independently H, alkyl, or substituted alkyl.

13. The compound of claim 1, wherein,
X$^1$ is —C(O)—;
X$^2$ is —C(O)—;
Y is —O—;
L$^1$ is —O—;
L$^2$ is a covalent bond;
L$^3$ and L$^5$ are each independently alkylene;
L$^4$ is a covalent bond;
Ar$^1$ and Ar$^3$ are each independently aryl, substituted aryl;
R$^{6a}$ is heteroaryl or substituted heteroaryl;
Ar$^2$ is heterocyclyl or substituted heterocyclyl;
R$^1$ is heterocyclyl or substituted heterocyclyl;
R$^3$ is —OH or —O-PG wherein PG is a protecting group;
m is 0; and
n is 1.

14. The compound of claim 1, wherein,
X$^1$ is —C(O)—;
X$^2$ is —C(O)—;
Y is —O—;
L is alkylene;
L$^2$ is N(R$^8$);
L$^3$ and L$^5$ are each independently alkylene;
L$^4$ is a covalent bond;
L$^6$ is a bond or —O—;
Ar$^1$ and Ar$^3$ are each independently aryl, substituted aryl;
R$^6$ is alkyl or substituted alkyl;
R$^{6a}$ is heteroaryl or substituted heteroaryl;
Ar$^2$ is heterocyclyl or substituted heterocyclyl;
R$^1$ is CO(O)R$^9$;
R$^2$, R$^4$ and R$^5$ are H;
R$^3$ is —OH;
R$^8$ is H;
R$^9$ is methyl;
m is 1;
n is 1.

15. The compound of claim 1, selected from the group consisting of

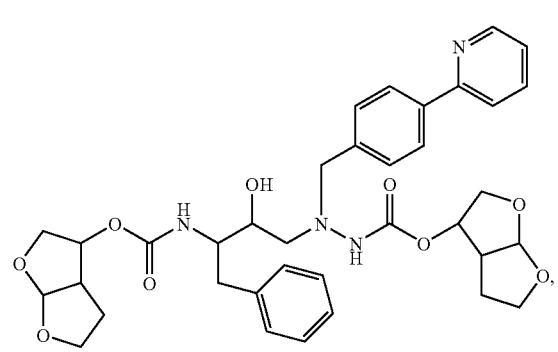

333
-continued
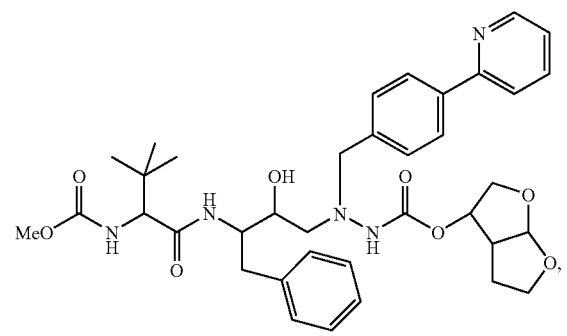
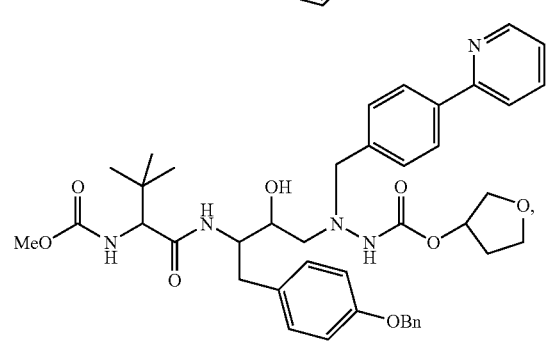
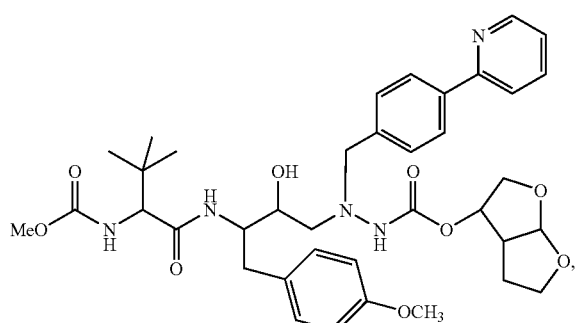
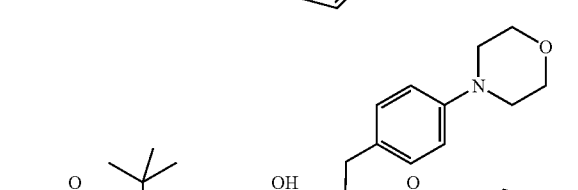
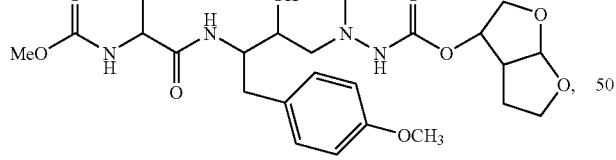
334
-continued
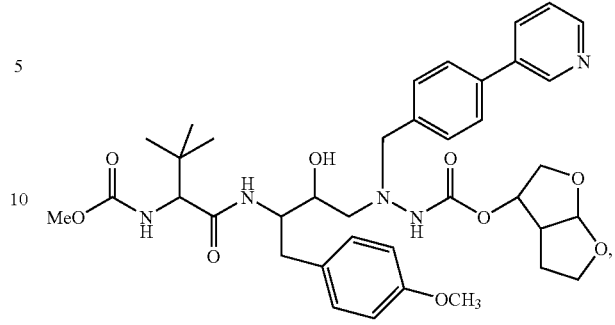
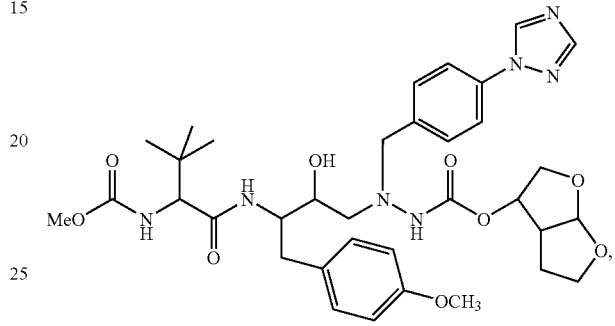
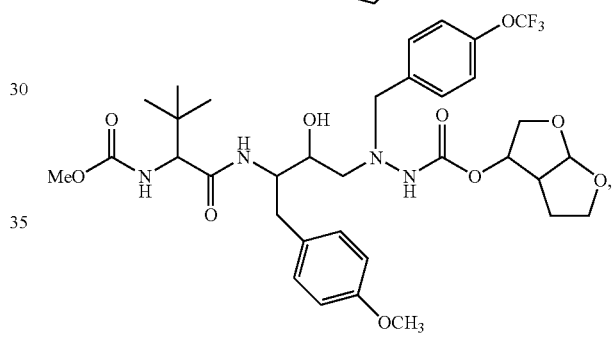
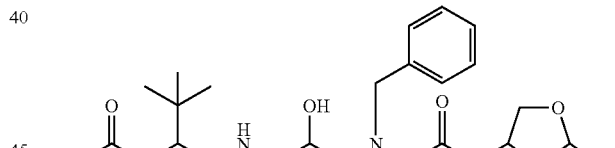
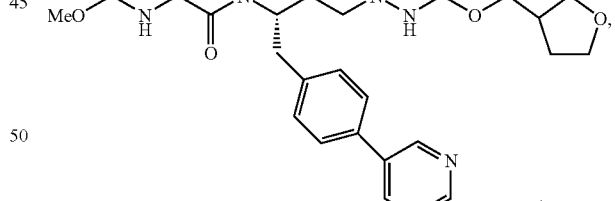

335
-continued
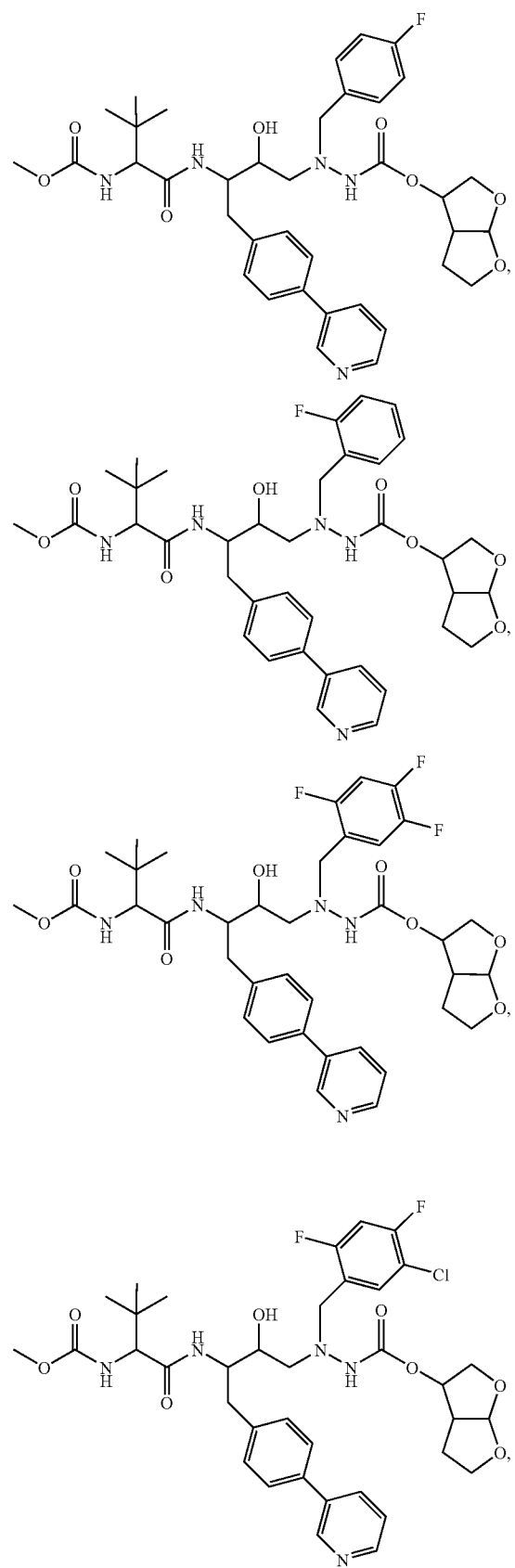
336
-continued
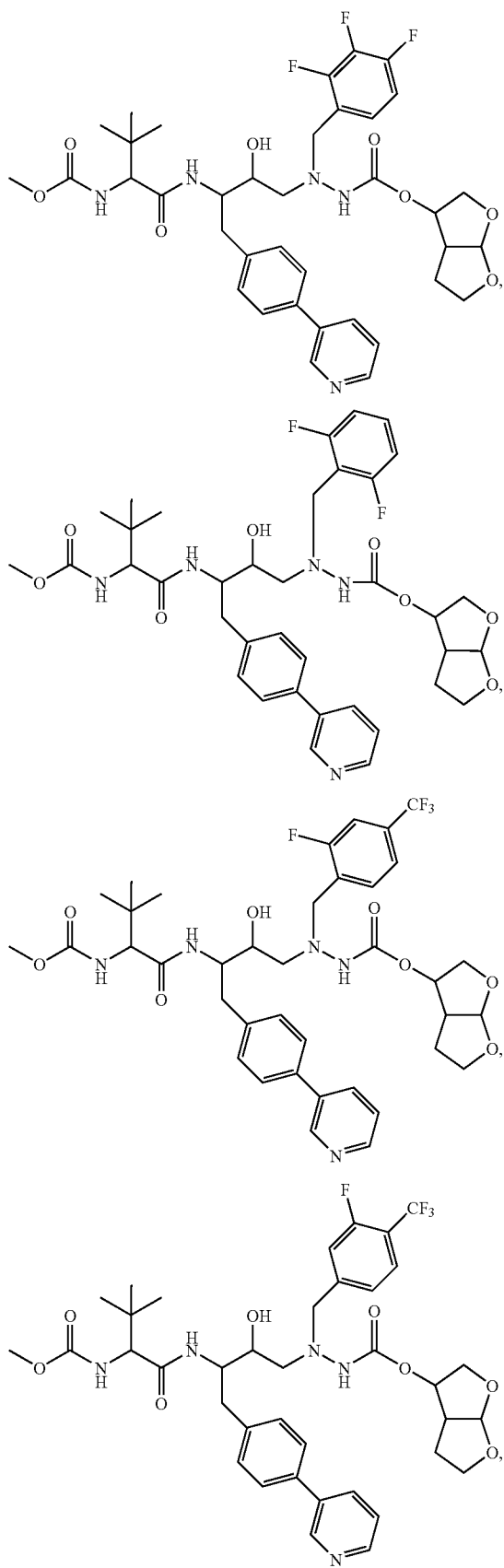

337
-continued
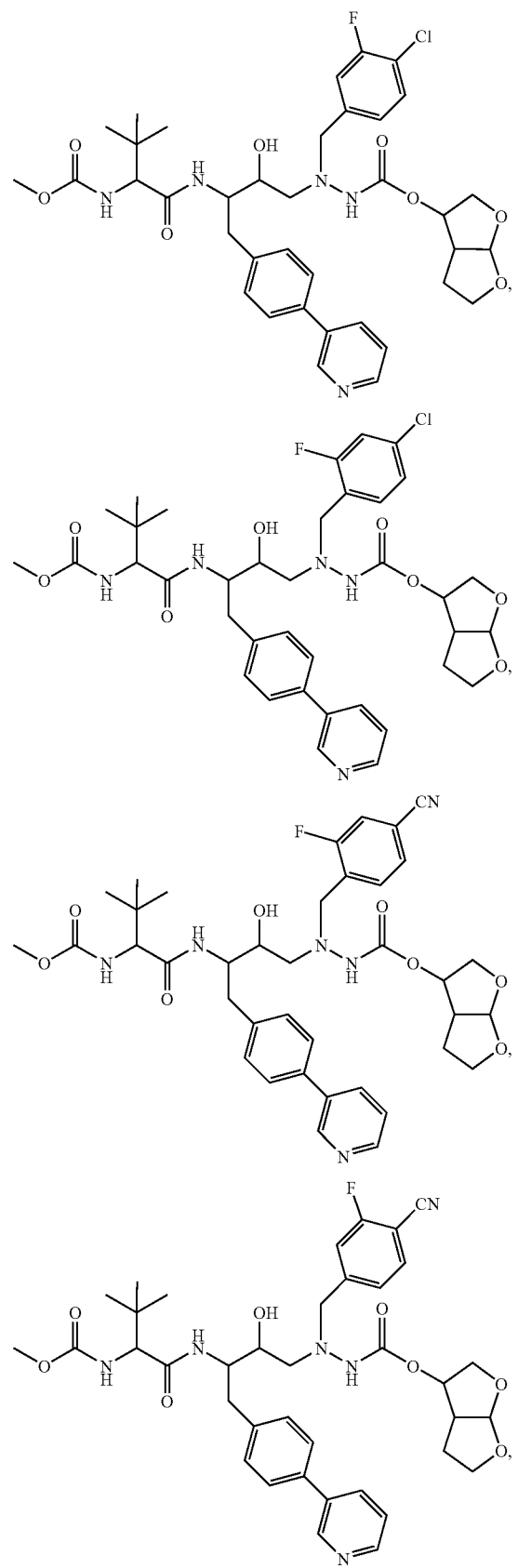
338
-continued
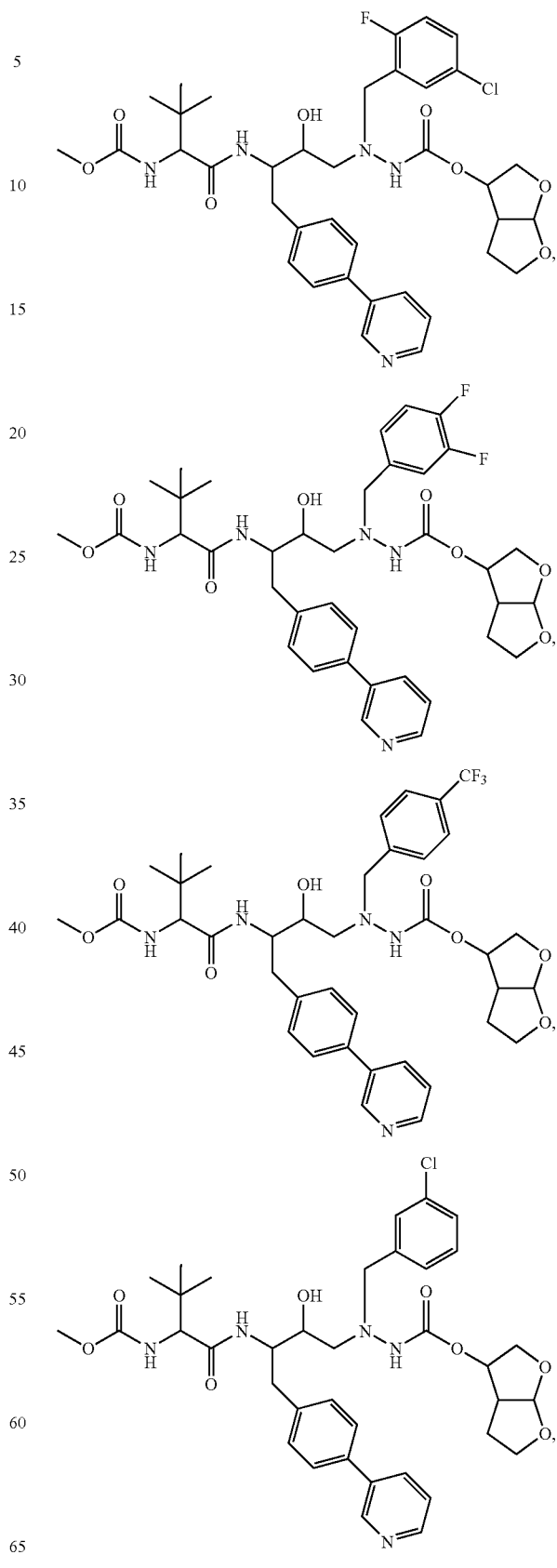

339
-continued
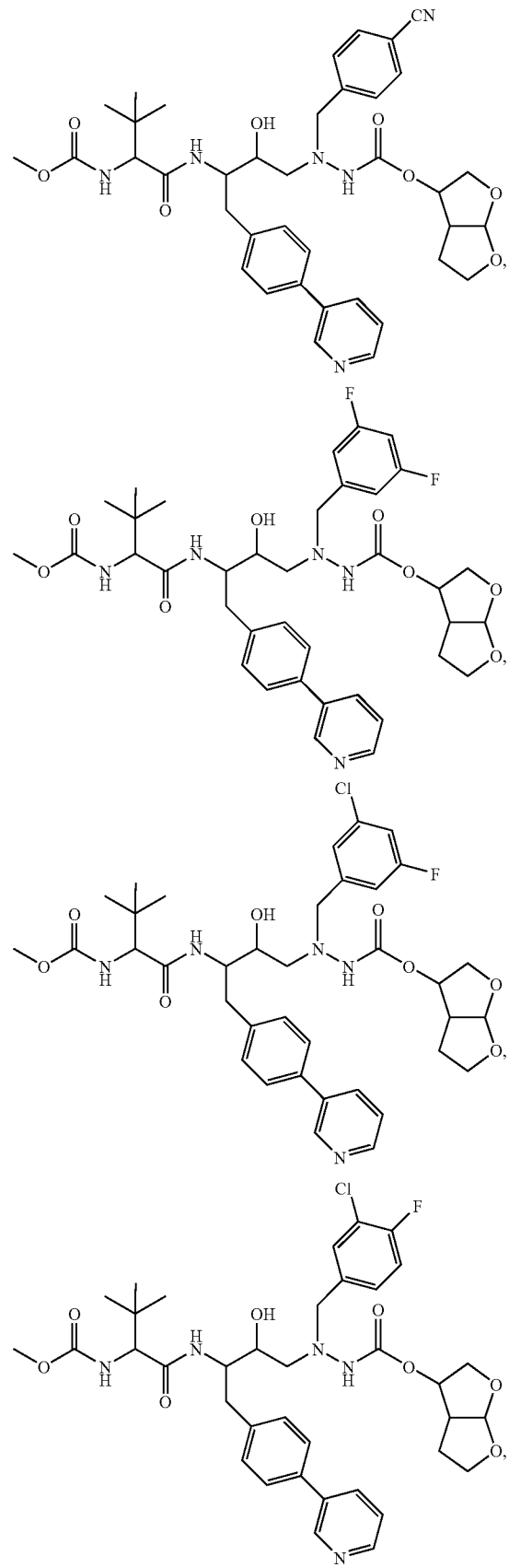
340
-continued
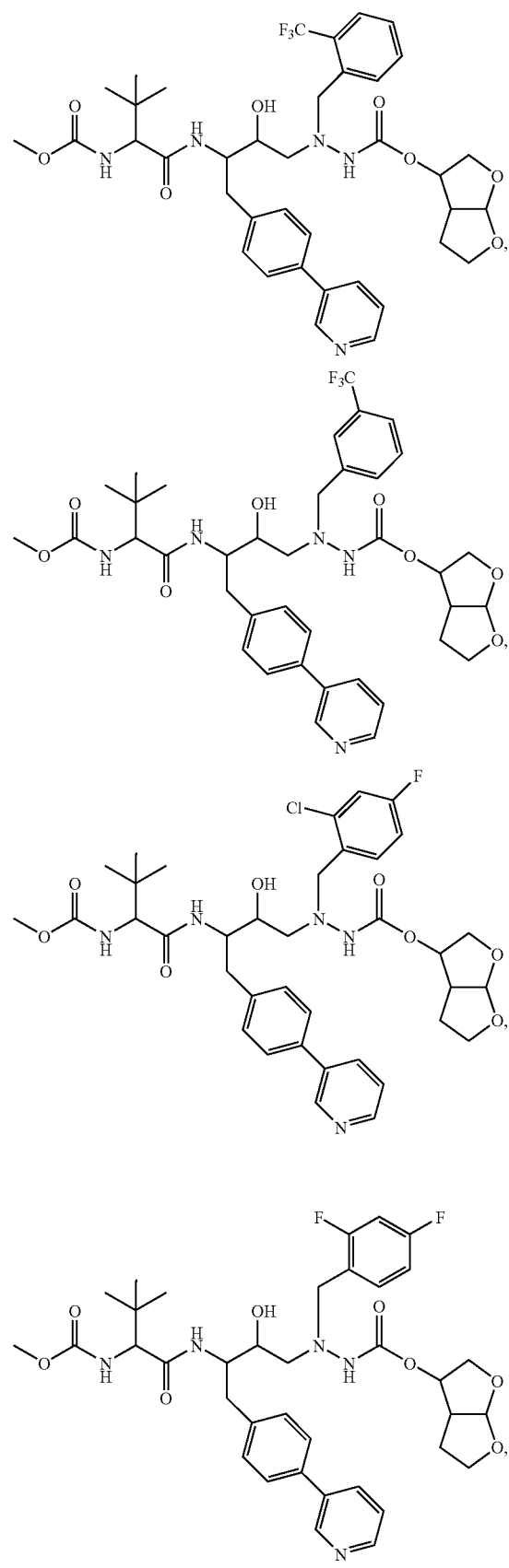

341
-continued
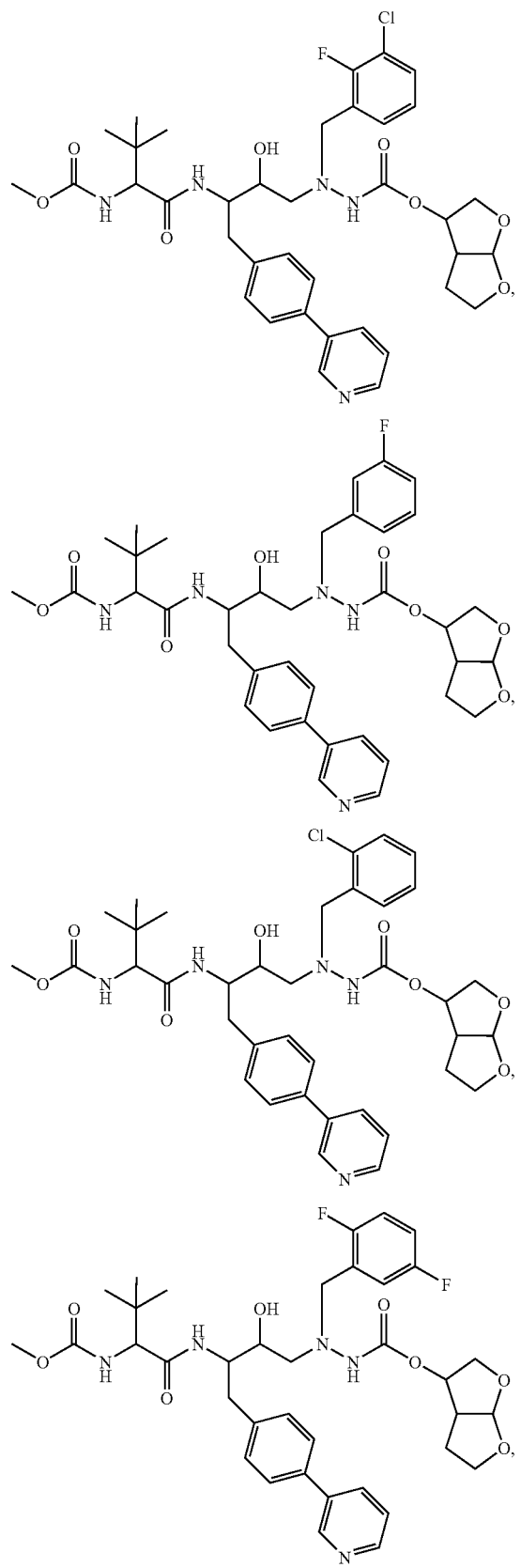
342
-continued
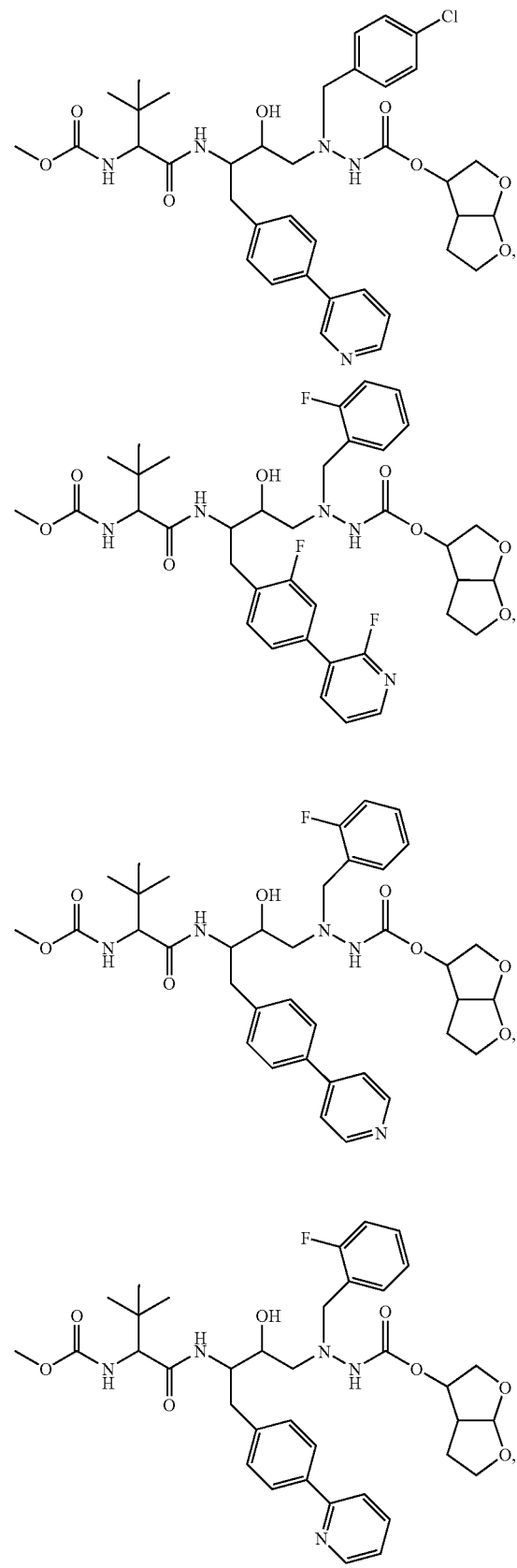

-continued

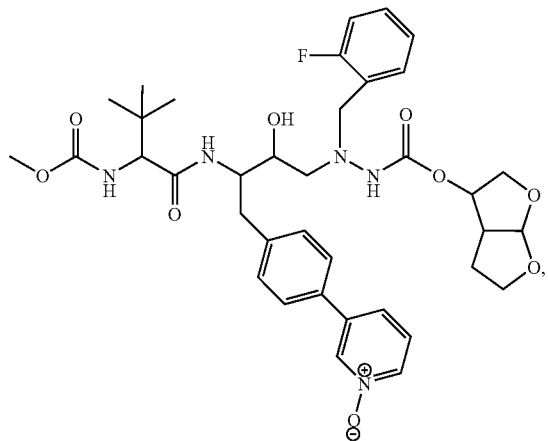

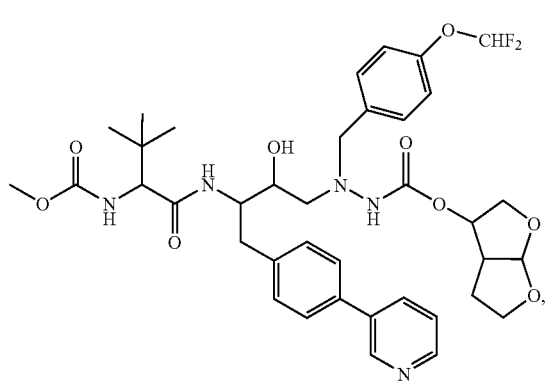

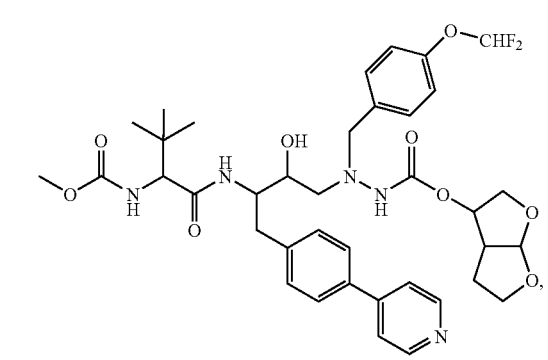

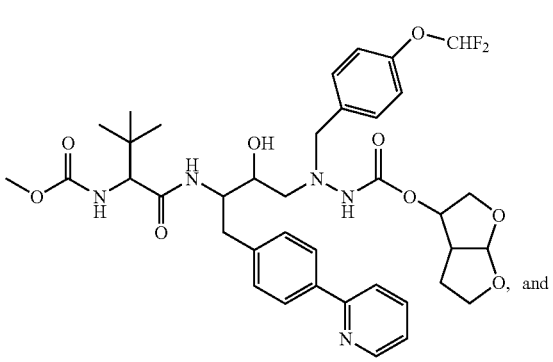

-continued

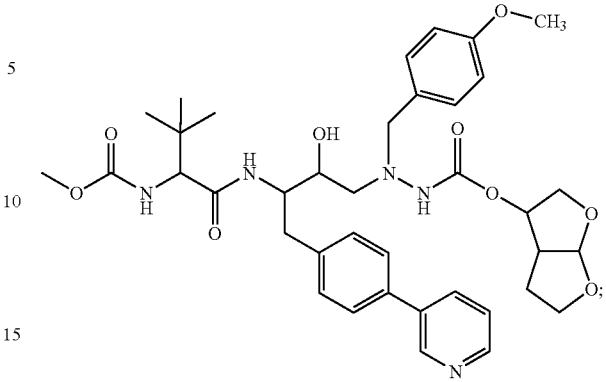

or a pharmaceutically acceptable salt, solvate and/or ester thereof.

16. A pharmaceutical composition comprising:
   a therapeutically effective amount of at least one compound of claim 1, or a pharmaceutically acceptable salt, colvate, and/or ester thereof, and a pharmaceutically acceptable carrier or exipient.

17. The pharmaceutical composition of claim 16, further comprising:
   at least one additional active agent, wherein said at least one additional active agent is selected from the group consisting of: HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, entry inhibitors, gp120 inhibitors, G6PD and NADH-oxidase inhibitors, CCR5 inhibitors, other drugs for treating HIV, and mixtures thereof.

18. The pharmaceutical composition of claim 17, wherein:
   (1) said HIV protease inhibitors are selected from the group consisting of: amprenavir, atazanavir, fosamprenavir, indinavir, lopiriavir, ritonavir, nelfinavir, saquinavir, tipranavir, brecanavir, darunavir, TMC-126, TMC-114, mozenavir (DMP-450), JE-2147 (AG1776), L-756423, 800334649, KNI-272, DPC-681, DPC-684, GW640385X, DG17, PPL-100, DG35, and AG 1859;
   (2) said HIV non-nucleoside inhibitors of reverse transcriptase are selected from the group consisting of capravirine, emivirine, delaviridine, efavirenz, nevirapine, (+) calanolide A, etravirine, GW5634, DPC-083, DPC-961, DPC-963, MIV-150, TMC-120, TMC-278 (rilpivirene), efavirenz, BILR 355 BS, VRX 840773, UK-453061, and RDEA806;
   (3) said HIV nucleoside inhibitors of reverse transcriptase are selected from the group consisting of zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, apricitibine (AVX754), GS-7340, amdoxovir, KP-1461, and fosalvudine tidoxil (formerly HDP 99.0003);
   (4) said HIV nucleotide inhibitors of reverse transcriptase are selected from the group consisting of tenofovir and adefovir;
   (5) said HIV integrase inhibitors are selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), elvitegravir, L-870812, and L-870810, MK-0518 (raltegravir), BMS-538158, GSK364735C, BMS-707035, MK-2048, and BA 011;

(6) said gp41 inhibitor are selected from the group consisting of enfuvirtide, sifuvirtide, FB006M, and TRI-1144;

(7) said CXCR4 inhibitor is AMD-070;

(8) said entry inhibitor is SP01A;

(9) said gp120 inhibitor is BMS-488043 or BlockAide/CR;

(10) said G6PD and NADH-oxidase inhibitor is immunitin;

(11) said CCR5 inhibitors are selected from the group consisting of aplaviroc, vicriviroc, maraviroc, PRO-140, INCB15050, PF-232798 (Pfizer), and CCR5 mAb004; and

(12) said other drugs for treating HIV are selected from the group consisting of BAS-100, SPI-452, REP 9, SP-01A, TNX-355, DES6, ODN-93, ODN-112, VGV-1, PA-457 (bevirimat), Ampligen, HRG214, Cytolin, VGX-410, KD-247, AMZ 0026, CYT 99007A-221 HIV, DEBIO-025, BAY 50-4798, MDX010 (ipilimumab), PBS119, ALG 889, and PA-1050040 (PA-040).

19. The compound of claim 1 having structure of formula Ia:

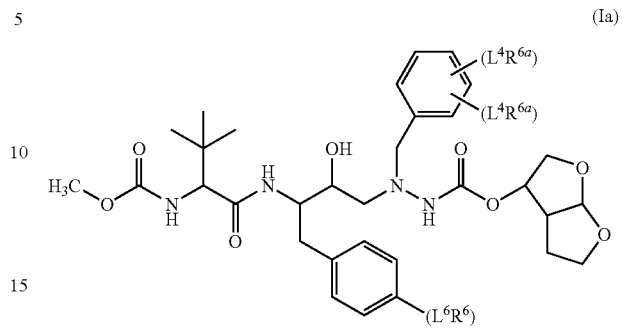

(Ia)

wherein $L^4$ is independently a bond or —O—; $L^6$ is a bond; $R^6$ is heteroaryl; $R^{6a}$ is independently hydrogen, halo, cyano, alkyl or haloalkyl.

20. The compound of claim 19, wherein $R^6$ is pyridine.

21. The compound of claim 19, wherein $L^4$ is independently a bond or —O—; $L^6$ is a bond; $R^6$ is pyridine; $R^{6a}$ is independently hydrogen, halo, cyano, $(C_1\text{-}C_6)$alkyl or $(C_1\text{-}C_6)$haloalkyl.

* * * * *